US012582641B2

(12) United States Patent
Yang et al.

(10) Patent No.: US 12,582,641 B2
(45) Date of Patent: Mar. 24, 2026

(54) SULFUR-CONTAINING COMPOUND BASED ON GLUTARIMIDE SKELETON AND APPLICATION THEREOF

(71) Applicant: SHANGHAITECH UNIVERSITY, Shanghai (CN)

(72) Inventors: Xiaobao Yang, Shanghai (CN); Biao Jiang, Shanghai (CN); Xing Qiu, Shanghai (CN); Ning Sun, Shanghai (CN); Renhong Sun, Shanghai (CN); Linyi Liu, Shanghai (CN); Chaowei Ren, Shanghai (CN)

(73) Assignee: SHANGHAITECH UNIVERSITY, Shanghai (CN)

( * ) Notice: Subject to any disclaimer, the term of this patent is extended or adjusted under 35 U.S.C. 154(b) by 1098 days.

(21) Appl. No.: 17/433,462

(22) PCT Filed: Feb. 25, 2020

(86) PCT No.: PCT/CN2020/076578
§ 371 (c)(1),
(2) Date: Aug. 24, 2021

(87) PCT Pub. No.: WO2020/173426
PCT Pub. Date: Sep. 3, 2020

(65) Prior Publication Data

US 2022/0143002 A1 May 12, 2022

(30) Foreign Application Priority Data

Feb. 25, 2019 (CN) ........................ 201910138460.3

(51) Int. Cl.
*A61K 31/4545* (2006.01)
*A61K 31/454* (2006.01)
(Continued)

(52) U.S. Cl.
CPC ........ *A61K 31/4545* (2013.01); *A61K 31/454* (2013.01); *A61K 31/4709* (2013.01);
(Continued)

(58) Field of Classification Search
CPC .............. A61K 31/4545; A61K 31/454; A61K 31/4709; A61K 31/496; A61K 31/506;
(Continued)

(56) References Cited

U.S. PATENT DOCUMENTS 9,938,264 B2 4/2018 Crews et al.
9,993,514 B2 6/2018 Campos
(Continued)

FOREIGN PATENT DOCUMENTS

CN 1867331 11/2006
CN 101679380 3/2010
(Continued)

OTHER PUBLICATIONS

Steinebach "A MedChem toolbox for cereblon-directed PROTACs" Med. Chem. Commun., 2019, 10, 1037-1041 (Year: 2019).*
(Continued)

*Primary Examiner* — Renee Claytor
(74) *Attorney, Agent, or Firm* — NIXON & VANDERHYE, PC

(57) ABSTRACT

The present disclosure relates to a compound of Formula (I) or a salt, a solvate, an isotopically enriched analog, a tautomer, a polymorph, a stereoisomer thereof, or a mixture of stereoisomers thereof, and their use for treating a tumor. The present disclosure also relates to a compound of Formula (I') or a pharmaceutically acceptable salt, a solvate, an isotopically enriched analog, a tautomer, a polymorph, a stereoisomer thereof, or a mixture of stereoisomers thereof, and their use for treating a tumor.
(Continued)

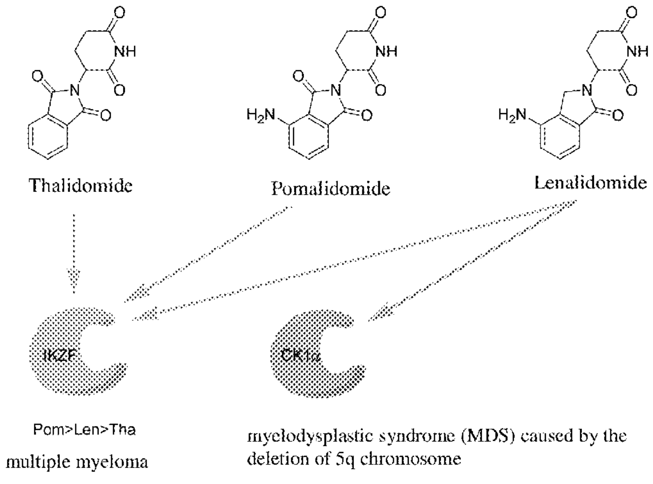

Thalidomide
Pomalidomide
Lenalidomide

Formula (I)

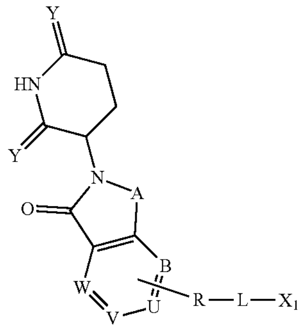

53 Claims, 3 Drawing Sheets

(51) Int. Cl.

| | |
|---|---|
| *A61K 31/4709* | (2006.01) |
| *A61K 31/496* | (2006.01) |
| *A61K 31/506* | (2006.01) |
| *A61K 31/517* | (2006.01) |
| *A61K 31/5377* | (2006.01) |
| *A61K 31/541* | (2006.01) |
| *A61K 31/55* | (2006.01) |
| *A61K 31/551* | (2006.01) |
| *A61K 45/06* | (2006.01) |
| *A61P 35/00* | (2006.01) |
| *C07D 401/04* | (2006.01) |
| *C07D 401/14* | (2006.01) |
| *C07D 405/14* | (2006.01) |
| *C07D 409/14* | (2006.01) |
| *C07D 413/14* | (2006.01) |
| *C07D 471/04* | (2006.01) |
| *C07D 471/08* | (2006.01) |
| *C07D 491/107* | (2006.01) |

(52) U.S. Cl.
CPC .......... *A61K 31/496* (2013.01); *A61K 31/506* (2013.01); *A61K 31/517* (2013.01); *A61K 31/5377* (2013.01); *A61K 31/541* (2013.01); *A61K 31/55* (2013.01); *A61K 31/551* (2013.01); *A61K 45/06* (2013.01); *A61P 35/00* (2018.01); *C07D 401/04* (2013.01); *C07D 401/14* (2013.01); *C07D 405/14* (2013.01); *C07D 409/14* (2013.01); *C07D 413/14* (2013.01); *C07D 471/04* (2013.01); *C07D 471/08* (2013.01); *C07D 491/107* (2013.01)

(58) Field of Classification Search
CPC .............. A61K 31/517; A61K 31/5377; A61K 31/541; A61K 31/55; A61K 31/551; A61K 45/06; A61P 35/00; A61P 7/06; A61P 35/02; C07D 401/04; C07D 401/14; C07D 405/14; C07D 409/14; C07D 413/14; C07D 471/04; C07D 471/08; C07D 491/107; C07D 417/14; C07D 453/02; C07D 487/08; C07F 9/65583; C07F 9/6558
See application file for complete search history.

(56) References Cited

U.S. PATENT DOCUMENTS

| | | | | |
|---|---|---|---|---|
| 10,385,037 | B2 | 8/2019 | Ruchelman et al. | |
| 10,450,310 | B2 | 10/2019 | Gray et al. | |
| 10,759,808 | B2 | 9/2020 | Wang et al. | |
| 11,104,666 | B2 | 8/2021 | Crew et al. | |
| 11,771,709 | B2 | 10/2023 | Yang et al. | |
| 12,226,424 | B2 | 2/2025 | Yang et al. | |
| 2006/0063926 | A1 | 3/2006 | Ma et al. | |
| 2006/0211728 | A1 | 9/2006 | Greig et al. | |
| 2008/0167345 | A1 | 7/2008 | Jones et al. | |
| 2010/0099658 | A1 | 4/2010 | Kondoh et al. | |
| 2010/0204196 | A1 | 8/2010 | Chamberlain et al. | |
| 2012/0028924 | A1 | 2/2012 | Aquila et al. | |
| 2012/0083488 | A1 | 4/2012 | Kinoshita et al. | |
| 2012/0202776 | A1 | 8/2012 | Wang et al. | |
| 2013/0143922 | A1 | 6/2013 | Greig et al. | |
| 2013/0190298 | A1 | 7/2013 | Liang et al. | |
| 2015/0291562 | A1 | 10/2015 | Crew et al. | |
| 2016/0022642 | A1 | 1/2016 | Crews | |
| 2018/0099940 | A1* | 4/2018 | Crew | A61K 31/506 |
| 2022/0041576 | A1 | 2/2022 | Chen et al. | |
| 2022/0041578 | A1 | 2/2022 | Chen et al. | |
| 2022/0117982 | A1* | 4/2022 | Yang | A61K 31/675 |
| 2022/0143002 | A1 | 5/2022 | Yang et al. | |
| 2022/0313829 | A1* | 10/2022 | Yang | A61K 47/545 |
| 2023/0096517 | A1* | 3/2023 | Yang | A61K 31/454 514/323 |
| 2023/0203022 | A1* | 6/2023 | Yang | A61K 45/06 514/218 |

FOREIGN PATENT DOCUMENTS

| | | |
|---|---|---|
| CN | 102822165 | 12/2012 |
| CN | 103396397 | 11/2013 |
| CN | 103787802 | 5/2014 |
| CN | 106432104 | 2/2017 |
| CN | 106458993 A | 2/2017 |
| CN | 108136044 | 6/2018 |
| CN | 108366992 | 8/2018 |
| CN | 109311900 | 2/2019 |
| CN | 109475528 | 3/2019 |
| CN | 105566290 | 5/2019 |
| CN | 109912655 | 6/2019 |
| CN | 109928956 | 6/2019 |
| CN | 110204532 | 9/2019 |
| CN | 110291087 | 9/2019 |
| CN | 110357889 | 10/2019 |
| CN | 110506039 | 11/2019 |
| CN | 11051298 | 4/2020 |
| CN | 110963994 | 4/2020 |
| CN | 111606883 | 9/2020 |
| JP | H02-184659 | 7/1990 |
| JP | 2006519827 | 8/2006 |
| JP | 2008513538 | 5/2008 |
| JP | 2010515715 | 5/2010 |
| JP | 2010522170 | 7/2010 |
| JP | 2010535798 | 11/2010 |
| JP | 2011523646 | 8/2011 |
| JP | 2013534221 | 9/2013 |
| JP | 2013539765 | 10/2013 |
| JP | 2017513862 | 6/2017 |
| JP | 2019513746 | 5/2019 |
| JP | 2020504089 | 2/2020 |
| JP | 2022503942 | 1/2022 |
| JP | 2022521746 | 4/2022 |
| WO | 2004080976 | 9/2004 |
| WO | 2008115516 | 9/2008 |
| WO | 2009008371 | 1/2009 |
| WO | 2010143664 | 12/2010 |
| WO | 2016065980 | 5/2016 |
| WO | 2016197032 | 12/2016 |
| WO | 2017079267 | 5/2017 |
| WO | 2017/117474/ | 7/2017 |
| WO | 2017/185036 | 10/2017 |
| WO | 2017176957 | 10/2017 |

(56) References Cited

FOREIGN PATENT DOCUMENTS

| | | | |
|---|---|---|---|
| WO | 2017176958 | | 10/2017 |
| WO | 2017185031 | | 10/2017 |
| WO | 2017197051 | | 11/2017 |
| WO | 2017197056 | | 11/2017 |
| WO | 2018052945 | | 3/2018 |
| WO | 2018052949 | | 3/2018 |
| WO | 2018071606 | | 4/2018 |
| WO | 2018/098288 | | 5/2018 |
| WO | 2018102067 | | 6/2018 |
| WO | 2018102725 | | 6/2018 |
| WO | 2018119441 | | 6/2018 |
| WO | 2018119448 | | 6/2018 |
| WO | 2018140809 | | 8/2018 |
| WO | 2019038717 | | 2/2019 |
| WO | 2019079569 | | 4/2019 |
| WO | 2019133531 | | 7/2019 |
| WO | 2019195609 | | 10/2019 |
| WO | 2019196812 | A1 | 10/2019 |
| WO | 2020006264 | | 1/2020 |
| WO | 2020114482 | | 6/2020 |
| WO | 2020173426 | | 9/2020 |
| WO | 2020198435 | | 10/2020 |
| WO | 2021113557 | | 6/2021 |
| WO | 2021118629 | | 6/2021 |

OTHER PUBLICATIONS

International Search Report for PCT/CN2020/076578 mailed Mar. 30, 2020, 9 pages.

Written Opinion of the ISA for PCT/CN2020/076578 mailed Mar. 30, 2020, 6 pages.

Yiming Li et al., "Selective Late-Stage Oxygenation of Sulfides with Ground-State Oxygen by Uranyl Photocatalysis", Angewandte Chem. Int. Ed. 2019, first published Jul. 2019, 58, pp. 13499-13506, DOI: 10.1002/anie.201906080, Wiley Online Library (8 pages).

Yiming Li et al., "A Highly Efficient Cu-Catalyzed S-Transfer Reaction: From Amine to Sulfide", Organic Letters, pubs.acs.org/OrgLett, ASC Publications, 2014 American Chemical Society, dx.doi.org/10.1021/015009747, pp. 2692-2695, Downloaded via Shanghai Advanced Research Inst on Aug. 30, 2021 at 00:30:59 (UTC). See https://pubs.acs.org/sharingguidelines for options on how to legitimately share published articles. (4 pages).

Donghuai Xiao et al., "Design, synthesis and biological evaluation of the thioether-containing lenalidomide analogs with anti-proliferative activities", Science Direct, European Journal of Medicinal Chemistry 176 (available on line May 15, 2019), pp. 419-430 (12 pages).

Yamazoe et al (Heterobifunctional molecules induce dephosphorylation of kinases-a proof of concept study, ChemRxiv, Jul. 31, 2019, doi.org/10.26434/chemrxiv.9177878.v1).

International Search Report for PCT/CN2021/077793, mailed May 26, 2021, 14 pages.

Written Opinion of the ISA for PCT/CN2021/077793, mailed May 26, 2021, 19 pages.

U.S. Appl. No. 17/922,124, filed Oct. 28, 2022, 89 pages.

U.S. Appl. No. 17/632,612, filed Aug. 24, 2022, 287 pages.

U.S. Appl. No. 17/801,953, filed Aug. 24, 2022, 103 pages.

Lai, Ashton C., Modular PROTAC Design for the Degradation of Oncogenic BCR-ABL, Angewandte Chemie, International Edition, 2016, 55(2), 807-810.

Zhang, Chengwei, Proteolysis Targeting Chimeras (PROTACs) of Anaplastic Lymphoma Kinase (ALK), European Journal of Medicinal Chemistry, 2018, 151, 304-314.

Turk, et. al., Proceedings of the National Academy of Sciences of the United States of America (1996), 93(15), 7552-7556.

Ishoey, Mette, Translation Termination Factor GSPT1 is a Phenotypically Relevant Off-Target of Heterobifunctional Phthalimide Degraders, A CS Chemical Biology , 2018, 13(3), 553-560.

Restriction Requirement issued in U.S. Appl. No. 17/801,953 dated Feb. 5, 2025, 11 pages.

Non-Final Office Action issued in U.S. Appl. No. 17/632,612 dated Nov. 27, 2024, 27 pages.

Non-Final Office Action issued in U.S. Appl. No. 17/046,690 dated Mar. 25, 2024, 21 pages.

Non-Final Office Action issued in U.S. Appl. No. 17/046,690 dated May 24, 2023, 19 pages.

Restriction Requirement issued in U.S. Appl. No. 17/046,690 dated May 24, 2022, 11 pages.

Non-Final Office Action issued in U.S. Appl. No. 17/046,690 dated Sep. 14, 2022, 31 pages.

* cited by examiner

SULFUR-CONTAINING COMPOUND BASED ON GLUTARIMIDE SKELETON AND APPLICATION THEREOF

This application is the U.S. national phase of International Application No. PCT/CN2020/076578 filed Feb. 25, 2020 which designated the U.S. and claims priority to CN Patent Application No. 201910138460.3 filed Feb. 25, 2019, the entire contents of each of which are hereby incorporated by reference.

TECHNICAL FIELD

The present disclosure relates generally to a compound of Formula (I) or salts, solvates, isotopically enriched analogs, tautomers, polymorphs, stereoisomers (including enantiomers), or a mixture of stereoisomers thereof, and their use in anti-tumor therapy.

Formula (I)

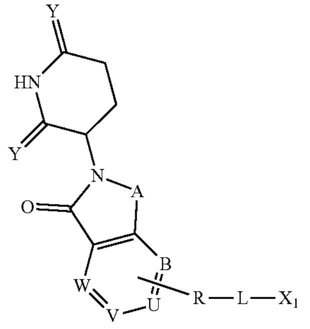

BACKGROUND

Multiple myeloma (MM) is a malignant hematological cancer, accounting for 1% of all cancer types and 10% of hematological malignancies. MM patients have symptoms clinically like anemia, impaired renal function, repeated infections, osteolytic bone destruction, etc, which usually occur in middle-aged and elderly people. The most important treatments for MM are chemotherapy and early autologous stem cell transplantation. However, these treatments have poor recovery and a high recurrence rate. Recent research results show that immunomodulatory drugs are an important cornerstone in the treatment of multiple myeloma, and they have an important impact on the improvement of the clinical remission rate and the prolongation of survival.

Thalidomide is the first generation immunomodulatory drug. It was used to relieve morning sickness in pregnant women in the 1950s and 1960s. However, the use of thalidomide was forbidden because it can cause severe fetal malformations. However, as Singhal et al. used thalidomide as a single agent for the treatment of patients with refractory multiple myeloma for the first time, it showed good clinical effectiveness. Later, researchers did a large number of clinical trials of thalidomide alone or in combination with dexamethasone in the treatment of refractory or relapsed multiple myeloma. Thalidomide has been found to have immunomodulatory function and anti-tumor activities, and has attracted widespread attention.

In order to increase its immunomodulatory function and anti-cancer activity and reduce toxic and side effects, scientists have used thalidomide as a lead compound to synthesize a series of phthalimide-replaced derivatives pomalidomide and lenalidomide. Lenalidomide is a derivative with lower toxic but higher activity, and approved by the FDA in 2006 in combination with dexamethasone for the treatment of relapsed or refractory multiple myeloma. In 2013, the third-generation immunomodulatory drug pomalidomide was approved for patients with relapsed/refractory multiple myeloma who have been treated with at least two drugs including lenalidomide and bortezomib. The detailed mechanism of action has not been clear until a study in 2010 using biochemical methods to affinity purify proteins that interact with thalidomide identified that Cereblon was the main target of thalidomide and its analogs; and research in related fields was becoming more and more active. Subsequently, the mechanism of these drugs in the treatment of multiple myeloma was revealed: immunomodulatory drugs can bind to the CRBN protein in cells, so that $CRL4A^{CRBN}$ ubiquitin ligase ubiquitinylates and degradate transcription factors IKZF1 and IKZF3 which are essential in the development and survival of B cells. In 2014, Professor Harper discovered five endogenous ligase substrates through ubiquitination analysis using protein chips: GRINL1A, MBOAT7, OTUD7B, C6orf141 and MEIS2. MEIS2, as a transcription factor, plays an important role in the normal development of the human body, and its increased expression can cause the toe tip of chicken embryos to become shorter, indicating that this molecule is a potential downstream molecule for thalidomide-induced embryo malformation. The binding site of MEIS2 molecule in CRBN is the same as that of thalidomide, so thalidomide and MEIS2 competitively bind to CRBN. In 2015, Professor Krönke discovered that lenalidomide is also a highly effective method for the treatment of myelodysplastic syndrome (MDS) caused by the deletion of 5q chromosome. Through using stable isotope labeling by amino acids in cell culture (SILAC) quantitative mass spectrometry to evaluate the global changes in ubiquitination and protein levels in del (5q) bone marrow cell line KG-1, it was found that lenalidomide can uniquely degrade CK1α protein, while neither pomalidomide nor thalidomide has any effect in CK1α (see FIG. 1).

In summary, thalidomide and their derivatives play a vital role in the treatment of multiple related malignancies such as multiple myeloma. However, due to the fact that there are few reports on this kind of compounds having heteroatom substitutions and their biological activity needs to be further improved, there is an urgent need to design and synthesize a series of new high-activity thalidomide derivatives in order to achieve better therapeutic effects.

SUMMARY OF INVENTION

In one aspect, the present disclosure provides a compound of Formula (I):

Formula (I)

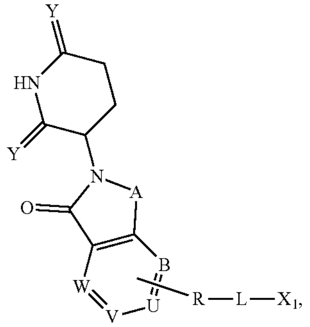

or a salt, a solvate, an isotopically enriched analog, a tautomer, a polymorph, a stereoisomer (including an enantiomer) thereof, or a mixture of stereoisomers thereof, in which A represents $CH_2$ or C(O);

B, U, V, and W are the same or different and each independently represent CH or N, where B, U, V, and W are not N at the same time;

Y represents O or S;

R represents SH, and L and $X_1$ are absent; or

R represents S, L represents an optionally substituted linear or branched alkyl, and $X_1$ is absent; or R represents S(O) or $S(O)_2$, L represents an optionally substituted linear or branched alkyl, or amino group, and $X_1$ is absent; or R represents S, S(O) or $S(O)_2$, and L represents an optionally substituted linear or branched alkylene group, wherein the linear or branched alkylene group is optionally interrupted one or more times by one or more groups selected from O, C(O), S, S(O), $S(O)_2$, $C(O)N(R_1)$, $N(R_2)C(O)$, $N(R_3)$, $N(R_4)C(O)N(R_5)$, optionally substituted cycloalkylene, optionally substituted arylene, optionally substituted heterocyclene, optionally substituted heteroarylene, or any combination thereof, wherein $R_1$, $R_2$, $R_3$, $R_4$, and $R_5$ each independently represent H or $C_{1-3}$ alkyl; and $X_1$ represents $NR_6R_7$, $C(O)NR_eR_f$, $NHC(O)R_8$, $NHC(O)NR_9R_{10}$, quaternary ammonium salt group, $OR_h$, SH, optionally substituted (especially optionally substituted with one or more fluorine) linear or branched alkyl, optionally substituted cycloalkyl, optionally substituted aryl, optionally substituted heterocyclyl, or optionally substituted heteroaryl, where $R_6$, $R_7$, $R_e$, $R_f$, $R_h$, $R_9$, and $R_{10}$ each independently represent H, optionally substituted linear or branched alkyl, optionally substituted cycloalkyl, optionally substituted aryl, optionally substituted heterocyclyl, or optionally substituted heteroaryl, wherein $R_6$ and $R_7$ are not H at the same time; and where $R_8$ represents a linear or branched alkyl, aryl, heteroaryl, or heterocyclyl; or where $R_e$ and $R_f$ together with the nitrogen atom to which they are attached form a 5- to 8-membered heterocyclyl; or $X_1$ represents a group of Formula ($G_1$):

Formula ($G_1$)

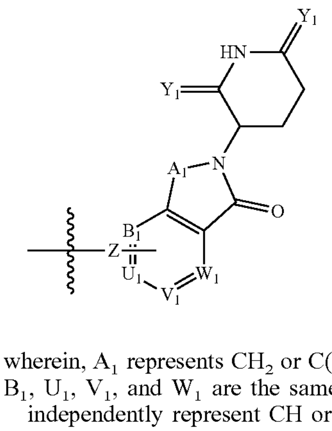

wherein, $A_1$ represents $CH_2$ or C(O);

$B_1$, $U_1$, $V_1$, and $W_1$ are the same or different and each independently represent CH or N, where $B_1$, $U_1$, $V_1$, and $W_1$ are not N at the same time;

$Y_1$ represents O or S; and

Z represents S, S(O), or $S(O)_2$; and provided that the following compounds are excluded:

2-(2,6-dioxopiperidin-3-yl)-4-mercaptoisoindoline-1,3-dione;

3-(4-mercapto-1-oxoisoindolin-2-yl)piperidine-2,6-dione;

2-(2,6-dioxopiperidin-3-yl)-4-(methylsulfinyl)isoindoline-1,3-dione;

3-(4-(methylsulfinyl)-1-oxoisoindolin-2-yl)piperidine-2,6-dione;

2-(2,6-dioxopiperidin-3-yl)-4-(methylsulfonyl)isoindoline-1,3-dione; and 3-(4-(methylsulfonyl)-1-oxoisoindolin-2-yl)piperidine-2,6-dione.

A further object of the present invention is to provide a compound of Formula (I') or a salt, a solvate, an isotopically enriched analog, a tautomer, a polymorph, a stereoisomer (including an enantiomer) thereof, or a mixture of stereoisomers thereof, Formula (I')

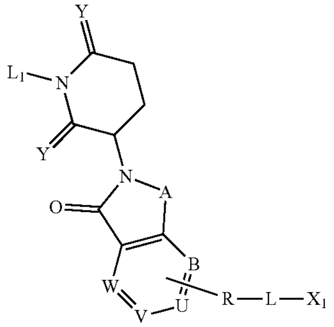

wherein,

A, B, U, V, W, and Y are as defined in Formula (I) herein;

R represents S, S(O), or $S(O)_2$;

L represents an optionally substituted linear or branched alkylene group optionally interrupted one or more times by one or more groups selected from O, C(O), S, S(O), $S(O)_2$, $S(O)_2N(R_1)$, $N(R_2)S(O)_2$, $C(O)N(R_1)$, $N(R_2)C(O)$, $N(R_3)$, $N(R_4)C(O)N(R_5)$, optionally substituted cycloalkylene, optionally substituted arylene, optionally substituted heterocyclylene, optionally substituted heteroarylene, or any combination thereof, wherein $R_1$, $R_2$, $R_3$, $R_4$, and $R_5$ each independently represent H or $C_{1-3}$ alkyl; and when $L_1$ represents H, $X_1$ represents $NHC(O)R_i$ or $SR_j$, wherein $R_i$ and $R_j$ each independently represent cycloalkyl optionally substituted with a substituent(s) selected from $C_{1-6}$ alkyl, oxo, halogen, cyano, trifluoromethyl, amino, hydroxy, $C_{1-3}$ alkoxy, halogenated $C_{1-3}$ alkoxy, methanesulfonyloxy, trifluoromethanesulfonyloxy, p-toluenesulfonyloxy, or any combination thereof, or $X_1$ represents cycloalkyl optionally substituted with a substituent(s) selected from $C_{1-6}$ alkyl, oxo, halogen, cyano, trifluoromethyl, amino, hydroxy, $C_{1-3}$alkoxy, halogenated $C_{1-3}$ alkoxy, methanesulfonyloxy, trifluoromethanesulfonyloxy, p-toluenesulfonyloxy, or any combination thereof, or when $L_1$ represents $C_{1-3}$ alkyl, $X_1$ represents:

$NR_6R_7$, wherein $R_6$ represents H or $C_{1-6}$ alkyl, and $R_7$ represents cycloalkyl optionally substituted with a substituent(s) selected from $C_{1-6}$ alkyl, oxo, halogen, cyano, trifluoromethyl, amino, hydroxyl, $C_{1-3}$ alkoxy, halogenated $C_{1-3}$ alkoxy, methanesulfonyloxy, trifluoromethanesulfonyloxy, p-toluenesulfonyloxy, or any combination thereof; or heterocyclyl, optionally substituted with a substituent (s) selected from $C_{1-6}$ alkyl, oxo, halogen, cyano, trifluoromethyl, amino, hydroxy, $C_{1-3}$ alkoxy, halogenated $C_{1-3}$ alkoxy, methanesulfonyloxy, trifluoromethanesulfonyloxy, p-toluenesulfonyloxy, or any combination thereof.

In some embodiments, the present invention also provides:

a pharmaceutical composition comprising:

the compound of Formula (I), or a pharmaceutically acceptable salt, a solvate, an isotopically enriched analog, a tautomer, a polymorph, a stereoisomer (including enantiomers) thereof, or a mixture of stereoisomers thereof; or the compound of Formula (I'), or a pharmaceutically acceptable salt, a solvate, an isotopically enriched analog, a tautomer, a polymorph, a stereoisomer (including enantiomers) thereof, or a mixture of stereoisomers thereof;

and at least one pharmaceutically acceptable carrier.

In some embodiments, the present invention also provides:

a kit comprising:

the compound of Formula (I), or a pharmaceutically acceptable salt, a solvate, an isotopically enriched analog, a tautomer, a polymorph, a stereoisomer (including enantiomers) thereof, or a mixture of stereoisomers thereof; or the compound of Formula (I'), or a pharmaceutically acceptable salt, a solvate, an isotopically enriched analog, a tautomer, a polymorph, a stereoisomer (including enantiomers) thereof, or a mixture of stereoisomers thereof, or the pharmaceutical composition of the present invention.

In some embodiments, the present invention also provides the compound of Formula (I) or a pharmaceutically acceptable salt, a solvate, an isotopically enriched analog, a tautomer, a polymorph, a stereoisomer (including enantiomers) thereof, or mixtures of stereoisomers thereof, or the compound of Formula (I'), or a pharmaceutically acceptable salt, a solvate, an isotopically enriched analog, a tautomer, a polymorph, a stereoisomer (including enantiomers) thereof, or a mixture of stereoisomers thereof, for use as a medicament.

In some embodiments, the present invention also provides the compound of Formula (I) or a pharmaceutically acceptable salt, a solvate, an isotopically enriched analog, a tautomer, a polymorph, a stereoisomer (including enantiomers) thereof, or mixtures of stereoisomers thereof; or the compound of Formula (I'), or a pharmaceutically acceptable salt, a solvate, an isotopically enriched analog, a tautomer, a polymorph, a stereoisomer (including enantiomers) thereof, or a mixture of stereoisomers thereof, or the pharmaceutical composition of the present disclosure, which are useful to treat a cancer or tumor.

In some embodiments, the present invention also provides the use of the compound of Formula (I) or a pharmaceutically acceptable salt, a solvate, an isotopically enriched analog, a tautomer, a polymorph, a stereoisomer (including enantiomers) thereof, or a mixture of stereoisomers thereof; or the compound of Formula (I'), or a pharmaceutically acceptable salt, a solvate, an isotopically enriched analog, a tautomer, a polymorph, a stereoisomer (including enantiomers) thereof, or a mixture of stereoisomers thereof; or the pharmaceutical composition of the present invention, in the manufacture of a medicament for treating a cancer or a tumor.

In some embodiments, the present invention also provides a method for treating a cancer or tumor, comprising administering to a subject a therapeutically effective amount of the compound of Formula (I), or a pharmaceutically acceptable salt, a solvate, an isotopically enriched analog, a tautomer, a polymorph, a stereoisomer (including enantiomers) thereof, or a mixture of stereoisomers thereof; or the compound of Formula (I'), or a pharmaceutically acceptable salt, a solvate, an isotopically enriched analog, a tautomer, a polymorph, a stereoisomer (including enantiomers) thereof, or a mixture of stereoisomers thereof; or the pharmaceutical composition of the present invention.

DETAILED DESCRIPTION OF THE INVENTION

Figure 1:
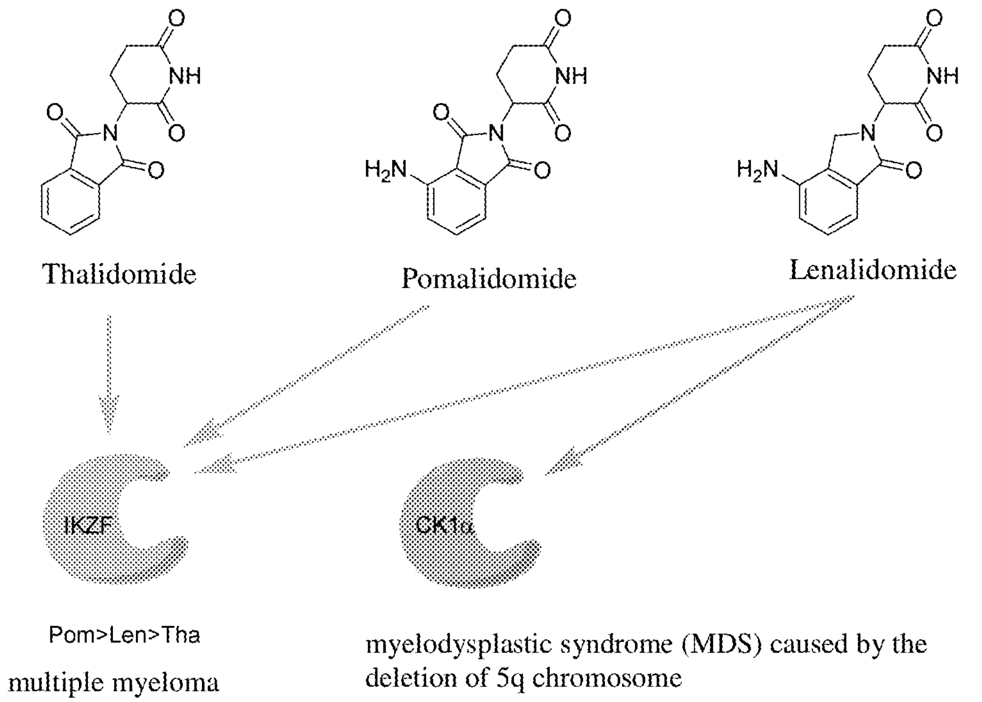
FIG. 1 shows target proteins of reported immunomodulatory small molecules and their indications.

Therefore, in one aspect, the present disclosure provides, in embodiment 1), the compound of Formula (I):

Formula (I)

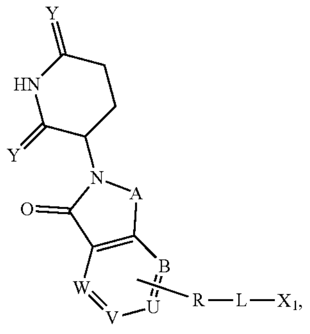

or a salt, a solvate, an isotopically enriched analog, a tautomer, a polymorph, a stereoisomer (including an enantiomer) thereof, or a mixture of stereoisomers thereof, in which A represents $CH_2$ or C(O);

B, U, V, and W are the same or different and each independently represent CH or N, where B, U, V, and W are not N at the same time;

Y represents O or S;

R represents SH, and L and $X_1$ are absent; or

R represents S, L represents an optionally substituted linear or branched alkyl, and $X_1$ is absent; or R represents S(O) or $S(O)_2$, L represents an optionally substituted linear or branched alkyl or amino group, and $X_1$ is absent; or R represents S, S(O), or $S(O)_2$, and L represents an optionally substituted linear or branched alkylene group, wherein the linear or branched alkylene group is optionally interrupted one or more times by one or more groups selected from O, C(O), S, S(O), $S(O)_2$, $C(O)N(R_1)$, $N(R_2)C(O)$, $N(R_3)$, $N(R_4)C(O)N(R_5)$, optionally substituted cycloalkylene, optionally substituted arylene, optionally substituted heterocyclylene, optionally substituted heteroarylene, or any combination thereof, wherein $R_1$, $R_2$, $R_3$, $R_4$, and $R_5$ each independently represent H or $C_{1-3}$ alkyl; and $X_1$ represents $NR_6R_7$, $C(O)NR_eR_f$, $NHC(O)R_8$, $NHC(O)NR_9R_{10}$, quaternary ammonium salt group, $OR_h$, SH, optionally substituted (especially optionally substituted with one or more fluorine) linear or branched alkyl, optionally substituted cycloalkyl, optionally substituted aryl, optionally substituted heterocyclyl, or optionally substituted heteroaryl, where $R_6$, $R_7$, $R_e$, $R_f$, $R_h$, $R_9$, and $R_{10}$ each independently represent H, optionally substituted linear or branched alkyl, optionally substituted cycloalkyl, optionally substituted aryl, optionally substituted heterocyclyl, or optionally substituted heteroaryl, wherein $R_6$ and $R_7$ are not H at the same time; and where $R_8$ represents a linear or branched alkyl, aryl, heteroaryl, or heterocyclyl; or where $R_e$ and $R_f$ together with the nitrogen atom to which they are attached form a 5- to 8-membered heterocyclyl; or $X_1$ represents a group of Formula ($G_1$):

Formula ($G_1$)

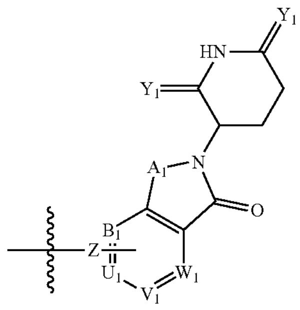

wherein, $A_1$ represents $CH_2$ or C(O);

$B_1$, $U_1$, $V_1$, and $W_1$ are the same or different and each independently represent CH or N, where $B_1$, $U_1$, $V_1$, and $W_1$ are not N at the same time;

$Y_1$ represents O or S; and

Z represents S, S(O), or $S(O)_2$; and provided that the following compounds are excluded:

2-(2,6-dioxopiperidin-3-yl)-4-mercaptoisoindoline-1,3-dione;

3-(4-mercapto-1-oxoisoindolin-2-yl)piperidine-2,6-dione;

2-(2,6-dioxopiperidin-3-yl)-4-(methylsulfinyl)isoindoline-1,3-dione;

3-(4-(methylsulfinyl)-1-oxoisoindolin-2-yl)piperidine-2,6-dione;

2-(2,6-dioxopiperidin-3-yl)-4-(methylsulfonyl)isoindoline-1,3-dione; and 3-(4-(methylsulfonyl)-1-oxoisoindolin-2-yl)piperidine-2,6-dione.

Embodiment 2) relates to the compound of Formula (I) or a salt, a solvate, an isotopically enriched analog, a tautomer, a polymorph, a stereoisomer thereof, or a mixture of stereoisomers thereof as described in embodiment 1), wherein the ring atoms B, U, V, and W in Formula (I) are the same and are all CH.

Embodiment 3) relates to the compound of Formula (I) or a salt, a solvate, an isotopically enriched analog, a tautomer, a polymorph, a stereoisomer thereof, or a mixture of stereoisomers thereof as described in embodiment 1), wherein one of the ring atoms B, U, V, and W in Formula (I) is N, and the rest are CH.

Embodiment 4) relates to the compound of Formula (I) or a salt, a solvate, an isotopically enriched analog, a tautomer, a polymorph, a stereoisomer thereof, or a mixture of stereoisomers thereof as described in embodiment 1), wherein two of the ring atoms B, U, V, and W in Formula (I) are N, and the rest are CH.

Embodiment 5) relates to the compound of Formula (I) or a salt, a solvate, an isotopically enriched analog, a tautomer, a polymorph, a stereoisomer thereof, or a mixture of stereoisomers thereof as described in embodiment 1), wherein three of the ring atoms B, U, V, and W in Formula (I) are N, and the rest is CH.

Embodiment 6) relates to the compound of Formula (I) or a salt, a solvate, an isotopically enriched analog, a tautomer, a polymorph, a stereoisomer thereof, or a mixture of stereoisomers thereof as described in embodiment 1), which is also compound of Formula (Ia):

Formula (Ia)

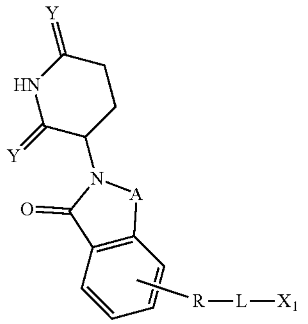

wherein A, R, L, $X_1$, and Y are as defined in embodiment 1).

Embodiment 7) relates to the compound of Formula (I) or a salt, a solvate, an isotopically enriched analog, a tautomer, a polymorph, a stereoisomer thereof, or a mixture of stereoisomers thereof as described in embodiment 1), which is also compound of Formula (Ib):

Formula (Ib)

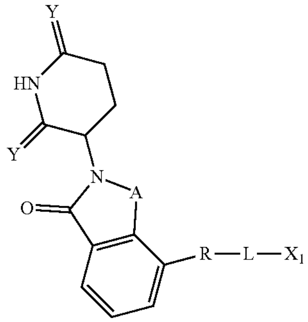

wherein A, R, L, $X_1$, and Y are as defined in embodiment 1).

Embodiment 8) relates to the compound of Formula (I) or a salt, a solvate, an isotopically enriched analog, a tautomer, a polymorph, a stereoisomer thereof, or a mixture of stereoisomers thereof as described in embodiment 1), which is also compound of Formula (Ic):

Formula (Ic)

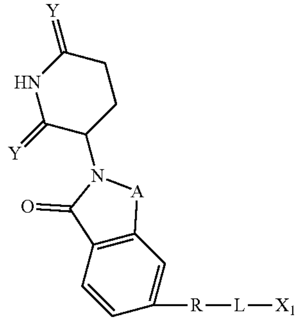

wherein A, R, L, $X_1$, and Y are as defined in embodiment 1).

Embodiment 9) relates to the compound of Formula (I) or a salt, a solvate, an isotopically enriched analog, a tautomer, a polymorph, a stereoisomer thereof, or a mixture of stereoisomers thereof as described in embodiment 1), which is also compound of Formula (Id):

Formula (Id)

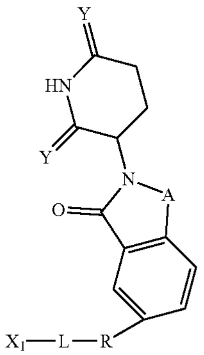

wherein A, R, L, $X_1$, and Y are as defined in embodiment 1).

Embodiment 10) relates to the compound of Formula (I) or a salt, a solvate, an isotopically enriched analog, a tautomer, a polymorph, a stereoisomer thereof, or a mixture of stereoisomers thereof as described in embodiment 1), which is also compound of Formula (Ie):

Formula (Ie)

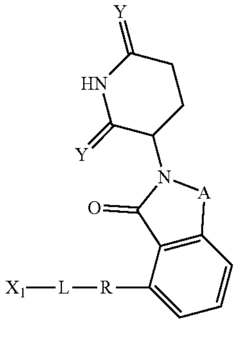

wherein A, R, L, $X_1$, and Y are as defined in embodiment 1).

Embodiment 11) relates to the compound of Formula (I) or a salt, a solvate, an isotopically enriched analog, a tautomer, a polymorph, a stereoisomer thereof, or a mixture of stereoisomers thereof as described in any one of embodiments 1) to 10), wherein Y represents O.

Embodiment 12) relates to the compound of Formula (I) or a salt, a solvate, an isotopically enriched analog, a tautomer, a polymorph, a stereoisomer thereof, or a mixture of stereoisomers thereof as described in any one of embodiments 1) to 10), wherein Y in Formula (I) represents S.

Embodiment 13) relates to the compound of Formula (I) or a salt, a solvate, an isotopically enriched analog, a tautomer, a polymorph, a stereoisomer thereof, or a mixture of stereoisomers thereof as described in any one of embodiments 1) to 11), wherein A in Formula (I) represents C(O).

Embodiment 14) relates to the compound of Formula (I) or a salt, a solvate, an isotopically enriched analog, a tautomer, a polymorph, a stereoisomer thereof, or a mixture of stereoisomers thereof as described in any one of embodiments 1) to 11), wherein A in Formula (I) represents $CH_2$.

Embodiment 15) relates to the compound of Formula (I) or a salt, a solvate, an isotopically enriched analog, a tautomer, a polymorph, a stereoisomer thereof, or a mixture of stereoisomers thereof as described in any one of embodiments 1) to 14), wherein R in Formula (I) represents S, L represents an optionally substituted linear or branched alkyl group, and $X_1$ is absent. In a sub-embodiment, R represents S, L represents an optionally substituted linear or branched $C_{1-40}$ alkyl (especially $C_{1-30}$ alkyl), and $X_1$ is absent. In a sub-embodiment, R represents S, L represents methyl, ethyl, n-propyl, isopropyl, n-butyl, isobutyl, sec-butyl, tert-butyl, pentyl, isopentyl, neopentyl, tert-amyl, hexyl, heptyl, octyl, nonyl, decyl, undecyl, dodecyl, tridecyl, tetradecyl, or pentadecyl, and $X_1$ is absent.

Embodiment 16) relates to the compound of Formula (I) or a salt, a solvate, an isotopically enriched analog, a tautomer, a polymorph, a stereoisomer thereof, or a mixture of stereoisomers thereof as described in any one of embodiments 1) to 14), wherein R in Formula (I) represents S(O) or $S(O)_2$, L represents an optionally substituted linear or branched alkyl or amino group, and $X_1$ is absent. In a sub-embodiment, R represents S(O) or $S(O)_2$, L represents optionally substituted linear or branched $C_{1-40}$ alkyl (especially $C_{1-30}$ alkyl) or amino group, and $X_1$ is absent. In a sub-embodiment, R represents S(O) or $S(O)_2$, L represents methyl, ethyl, n-propyl, isopropyl, n-butyl, isobutyl, sec-butyl, tert-butyl, pentyl, isopentyl, neopentyl, tert-amyl, hexyl, heptyl, octyl, nonyl, decyl, undecyl, dodecyl, tridecyl, tetradecyl, pentadecyl, or amino group, and $X_1$ is absent.

Embodiment 17) relates to the compound of Formula (I) or a salt, a solvate, an isotopically enriched analog, a tautomer, a polymorph, a stereoisomer thereof, or a mixture of stereoisomers thereof as described in any one of embodiments 1) to 14), wherein R represents SH, L and $X_1$ are absent.

Embodiment 18) relates to the compound of Formula (I) or a salt, a solvate, an isotopically enriched analog, a tautomer, a polymorph, a stereoisomer thereof, or a mixture of stereoisomers thereof as described in any one of embodiments 1) to 14), wherein R represents S, S(O) or $S(O)_2$;

L represents an optionally substituted linear or branched $C_{1-40}$ alkylene group, wherein the linear or branched $C_{1-40}$ alkylene group is optionally interrupted one or more times by one or more groups selected from O, C(O), S, S(O), $S(O)_2$, $C(O)N(R_1)$, $N(R_2)C(O)$, $N(R_3)$, $N(R_4)C(O)N(R_5)$, optionally substituted cycloalkylene, optionally substituted arylene, optionally substituted heterocyclylene, optionally substituted heteroarylene, or any combination thereof, wherein $R_1$, $R_2$, $R_3$, $R_4$, and $R_5$ each independently represent H or $C_{1-3}$ alkyl; and $X_1$ represents $NR_6R_7$, $C(O)NR_eR_f$, $NHC(O)R_8$, $NHC(O)NR_9R_{10}$, $OR_h$, SH, quaternary ammonium salt group, optionally substituted (especially optionally substituted with one or more fluorine) linear or branched $C_{1-10}$ alkyl, optionally substituted cycloalkyl, optionally substituted aryl, optionally substituted heterocyclyl, or optionally substituted heteroaryl, where $R_6$, $R_7$, $R_e$, $R_f$, $R_h$, $R_9$, and $R_{10}$ each independently represent H, optionally substituted linear or branched $C_{1-10}$ alkyl, optionally substituted cycloalkyl, optionally substituted aryl, optionally substituted heterocyclyl, or optionally substituted heteroaryl, wherein $R_6$ and $R_7$ are not H at the same time; and where $R_8$ represents a linear or branched $C_{1-8}$ alkyl, aryl, heteroaryl, or heterocyclyl, or where $R_e$ and $R_f$ together with the nitrogen atom to which they are attached form 5- to 8-membered heterocyclyl; or $X_1$ represents a group of Formula ($G_1$):

Formula ($G_1$)

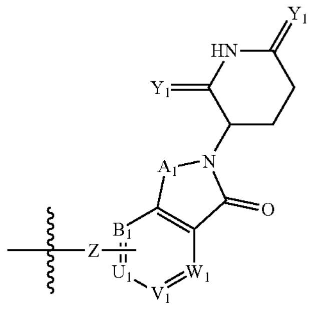

wherein, $A_1$ represents $CH_2$ or C(O);

$B_1$, $U_1$, $V_1$, and $W_1$ are the same or different and each independently represent CH or N, where $B_1$, $U_1$, $V_1$ and $W_1$ are not N at the same time;

$Y_1$ represents O or S; and

Z represents S, S(O), or $S(O)_2$.

Embodiment 19) relates to the compound of Formula (I) or a salt, a solvate, an isotopically enriched analog, a tautomer, a polymorph, a stereoisomer thereof, or a mixture of stereoisomers thereof as described in any one of embodiments 1) to 14), wherein R represents S, S(O), or $S(O)_2$;

L represents an optionally substituted linear or branched $C_{1-40}$ alkylene group, wherein the linear or branched $C_{1-40}$ alkylene group is optionally interrupted one or more times by one or more groups selected from:

O; C(O); S; S(O); $S(O)_2$; $C(O)N(R_1)$; $N(R_2)C(O)$; $N(R_3)$; $N(R_4)C(O)N(R_5)$;

arylene group optionally substituted with substituent (s) selected from halogen, methanesulfonyloxy, trifluoromethanesulfonyloxy, p-toluenesulfonyloxy, or $C_{1-5}$ alkyl;

heterocyclylene group optionally substituted with substituent(s) selected from halogen, methanesulfonyloxy, trifluoromethanesulfonyloxy, p-toluenesulfonyloxy, oxo, or $C_{1-5}$ alkyl;

heteroarylene group optionally substituted with substituent(s) selected from halogen, methanesulfonyloxy, trifluoromethanesulfonyloxy, p-toluenesulfonyloxy, or $C_{1-5}$ alkyl;

cycloalkylene group optionally substituted with substituent(s) selected from halogen, methanesulfonyloxy, trifluoromethanesulfonyloxy, p-toluenesulfonyloxy, or $C_{1-5}$ alkyl, or any combination thereof, wherein $R_1$, $R_2$, $R_3$, $R_4$, and $R_5$ each independently represent H or $C_{1-3}$ alkyl; and $X_1$ represents:

$NR_6R_7$; $C(O)NR_eR_f$; $NHC(O)R_8$; $NHC(O)NR_9R_{10}$; $OR_h$; SH; quaternary ammonium salt group;

a linear or branched $C_{1-10}$ alkyl optionally substituted with one or more fluorine;

cycloalkyl optionally substituted with substituent(s) selected from halogen, oxo, cyano, trifluoromethyl, amino, hydroxy, $C_{1-3}$ alkoxy, halogenated $C_{1-3}$ alkoxy, methanesulfonyloxy, trifluoromethanesulfonyloxy, p-toluenesulfonyloxy, $C_{1-6}$ alkyl, or any combination thereof;

aryl optionally substituted with substituent(s) selected from halogen, oxo, cyano, trifluoromethyl, amino, hydroxy, $C_{1-3}$ alkoxy, halogenated $C_{1-3}$ alkoxy, methanesulfonyloxy, trifluoromethanesulfonyloxy, p-toluenesulfonyloxy, $C_{1-6}$ alkyl, or any combination thereof;

heterocyclyl optionally substituted with substituent(s) selected from halogen, cyano, trifluoromethyl, amino, hydroxy, $C_{1-3}$ alkoxy, halogenated $C_{1-3}$ alkoxy, $C_{1-6}$ alkylsulfonyl, bis($C_{1-6}$ alkyl) phosphono, methanesulfonyloxy, trifluoromethanesulfonyloxy, p-toluenesulfonyloxy, oxo, optionally substituted 6-membered aryl, optionally substituted 5- or 6-membered heterocyclyl, optionally substituted 5- or 6-membered heteroaryl, $C_{1-6}$ alkyl, or any combination thereof; or heteroaryl optionally substituted with substituent(s) selected from halogen, cyano, trifluoromethyl, amino, hydroxy, $C_{1-3}$ alkoxy, halogenated $C_{1-3}$ alkoxy, bis($C_{1-6}$ alkyl)phosphono, $C_{1-6}$ alkylsulfonyl, methanesulfonyloxy, trifluoromethanesulfonyloxy, p-toluenesulfonyloxy, $C_{1-6}$ alkyl, optionally substituted 6-membered aryl, optionally substituted 5- or 6-membered heterocyclyl, optionally substituted 5- or 6-membered heteroaryl, or any combination thereof;

wherein $R_6$, $R_7$, $R_e$, $R_f$, $R_h$, $R_9$, and $R_{10}$ each independently represent H, optionally substituted linear or branched $C_{1-10}$ alkyl, optionally substituted cycloalkyl, optionally substituted aryl, optionally substituted heterocyclyl, or optionally substituted heteroaryl, wherein $R_6$ and $R_7$ are not H at the same time, and wherein $R_8$ represents a linear or branched $C_{1-6}$ alkyl, optionally substituted aryl, optionally substituted heteroaryl or optionally substituted heterocyclyl, or wherein $R_e$ and $R_f$ together with the nitrogen atom to which they are attached form a 5- to 8-membered heterocyclyl.

Embodiment 20) relates to the compound of Formula (I) or a salt, a solvate, an isotopically enriched analog, a tautomer, a polymorph, a stereoisomer thereof, or a mixture of stereoisomers thereof as described in embodiments 1) or 19), wherein L represents the following groups (which are optionally further substituted, e.g., by substituent(s) selected from halogen, $C_{1-5}$ alkyl, methanesulfonyloxy, trifluoromethanesulfonyloxy, p-toluenesulfonyloxy, or any combination thereof):

linear or branched $C_1$-$C_{40}$ alkylene; $*-((CH_2)_{n1}O)_{m1}-(CH_2)_{n2}-$; $*-((CH_2)_{n1}O)_{m1}-(CH_2)_{n2}-O-(CH_2)_{n3}-$; $*-(CH_2)_{n1}-O-(CH_2)_{n2}-$; $*-((CR_{11}R_{12})_{n1}O)_{m1}-(CR_{13}R_{14})_{n2}-$; $*-((CR_{15}R_{16})_{n1}O)_{m1}-(CR_{17}R_{18})_{n2}-O-(CR_{19}R_{20})_{n3}-$; $*-(CH_2)_{n1}-S-(CH_2)_{n2}-$; $*-(CH_2)_{n1}-S(O)-(CH_2)_{n2}-$; $*-(CH_2)_{n1}-S(O)_2-(CH_2)_{n2}-$; $*-(CH_2)_{n1}-N(R_{21})-(CH_2)_{n2}-$; $*-(CH_2)_{n1}-N(R_{22})C(O)-(CH_2)_{n2}-$; $*-(CH_2)_{n1}-C(O)N(R_{23})-(CH_2)_{n2}-$; $*-(CH_2)_{n1}-N(R_{24})C(O)N(R_{25})-(CH_2)_{n2}-$; $*-(CH_2)_{n1}-(N(R_{26})C(O)-(CH_2)_{n2})_{m1}-$; $*-(CH_2)_{n1}$-piperazinylene-$(CH_2)_{n2}-$; $*-(CH_2)_{n1}$-phenylene-$(CH_2)_{n2}-$; $*-(CH_2)_{n1}$-phenylene-$(CH_2)_{n2}-N(R_{21})-(CH_2)_{n3}-$; $*-(CH_2)_{n1}$-furanylene-$(CH_2)_{n2}-$; $*-(CH_2)_{n1}$-furanylene-$(CH_2)_{n2}-N(R_{21})-(CH_2)_{n3}-$; $*-(CH_2)_{n1}$-thiazolylene-$(CH_2)_{n2}-$; $*-(CH_2)_{n1}$-thiazolylene-$C(O)N(R_{23})-(CH_2)_{n2}-$; $*-(CH_2)_{n1}$-thiazolylene-$(CH_2)_{n2}-N(R_{21})-(CH_2)_{n3}-$;

linear or branched alkylene group optionally interrupted one or more times by one or more groups selected from C(O), $N(R_{21})$, $C(O)N(R_{23})$, $N(R_{22})C(O)$, optionally substituted cycloalkylene, optionally substituted arylene, optionally substituted heterocyclylene, or optionally substituted heteroarylene, or any combination thereof; or $*-((CH_2)_{n1}O)_{m1}-(CH_2)_{n2}-$, in which the backbone carbon chain is interrupted one or more times by one or more groups selected from C(O), optionally substituted cycloalkylene, optionally substituted arylene, optionally substituted heterocyclylene, optionally substituted heteroarylene, or any combination thereof, wherein * indicates the point of attachment to R;

$R_{21}$, $R_{22}$, $R_{23}$, $R_{24}$, $R_{25}$, and $R_{26}$ are each independently selected from H and $C_{1-3}$ alkyl;

$R_{11}$, $R_{12}$, $R_{13}$, $R_{14}$, $R_{15}$, $R_{16}$, $R_{17}$, $R_{18}$, $R_{19}$, and $R_{20}$ each independently represent H, a linear or branched $C_1$-$C_{10}$ alkyl, or $C_3$-$C_{10}$ cycloalkyl group, wherein in the same group L, $R_{11}$, $R_{12}$, $R_{13}$, and $R_{14}$, or $R_{15}$, $R_{16}$, $R_{17}$, $R_{18}$, $R_{19}$, and $R_{20}$ are not H at the same time; and n1, n2, n3, and m1 each independently represent an integer of 1, 2, 3, 4, 5, 6, 7, 8, 9, 10, 11, 12, 13, 14, 15, 16, 17, 18, 19, or 20.

Embodiment 21) relates to the compound of Formula (I) or a salt, a solvate, an isotopically enriched analog, a tautomer, a polymorph, a stereoisomer thereof, or a mixture of stereoisomers thereof as described in embodiment 20), wherein L represents an optionally substituted linear or branched $C_1$-$C_{40}$ alkylene group. In a sub-embodiment, L represents a linear or branched $C_1$-$C_{40}$ alkylene optionally substituted with substituent(s) selected from halogen, $C_{1-5}$ alkyl, methanesulfonyloxy, trifluoromethanesulfonyloxy, p-toluenesulfonyloxy, or any combination thereof.

Embodiment 22) relates to the compound of Formula (I) or a salt, a solvate, an isotopically enriched analog, a tautomer, a polymorph, a stereoisomer thereof, or a mixture of stereoisomers thereof as described in embodiment 20) or 21), wherein L represents the following groups: $-CH_2-$; $-(CH_2)_2-$; $-(CH_2)_3-$; $-(CH_2)_4-$; $-(CH_2)_5-$; $-(CH_2)_6-$; $-(CH_2)_7-$; $-(CH_2)_8-$; $-(CH_2)_9-$; $-(CH_2)_{10}-$; $-(CH_2)_{11}-$; $-(CH_2)_{12}-$; $-(CH_2)_{13}-$; $-(CH_2)_{14}-$; $-(CH_2)_{15}-$; $-(CH_2)_{16}-$; $-(CH_2)_{17}-$; $-(CH_2)_{18}-$; $-(CH_2)_{19}-$; or $-(CH_2)_{20}-$. In a sub-embodiment, L represents $-CH_2-$; $-(CH_2)_2-$; $-(CH_2)_3-$; $-(CH_2)_4-$; $-(CH_2)_5-$; $-(CH_2)_6-$; $-(CH_2)_7-$; $-(CH_2)_8-$; $-(CH_2)_9-$; $-(CH_2)_{10}-$; $-(CH_2)_{11}-$; $-(CH_2)_{12}-$; $-(CH_2)_{13}-$; $-(CH_2)_{14}-$; $-(CH_2)_{15}-$; $-(CH_2)_{16}-$; $-(CH_2)_{17}-$; $-(CH_2)_{18}-$; $-(CH_2)_{19}-$; or $-(CH_2)_{20}-$; wherein the groups are optionally substituted with substituent(s) selected from halogen, $C_{1-5}$ alkyl, methanesulfonyloxy, trifluoromethanesulfonyloxy, p-toluenesulfonyloxy, or any combination thereof.

Embodiment 23) relates to the compound of Formula (I) or a salt, a solvate, an isotopically enriched analog, a tautomer, a polymorph, a stereoisomer thereof, or a mixture of stereoisomers thereof as described in embodiment 20), wherein L represents the following groups: $*-((CH_2)_{n1}O)_{m1}-(CH_2)_{n2}-$, $*-((CH_2)_{n1}O)_{m1}-(CH_2)_{n2}-O-(CH_2)_{n3}-$, $*-(CH_2)_{n1}-O-(CH_2)_{n2}-$, $*-((CR_{11}R_{12})_{n1}O)_{m1}-(CR_{13}R_{14})_{n2}-$, $*-((CR_{15}R_{16})_{n1}O)_{m1}-(CR_{17}R_{18})_{n2}-O-(CR_{19}R_{20})_{n3}-$, wherein * indicates the point of attachment to R;

$R_{11}$, $R_{12}$, $R_{13}$, $R_{14}$, $R_{15}$, $R_{16}$, $R_{17}$, $R_{18}$, $R_{19}$, and $R_{20}$ each independently represent H, a linear or branched $C_1$-$C_{10}$ alkyl group, or a $C_3$-$C_{10}$ cycloalkyl group, wherein in the same group L, $R_{11}$, $R_{12}$, $R_{13}$, and $R_{14}$, or $R_{15}$, $R_{16}$, $R_{17}$, $R_{18}$, $R_{19}$, and $R_{20}$ are not H at the same time; and n1, n2, n3, and m1 each independently represent an integer of 1, 2, 3, 4, 5, 6, 7, 8, 9, 10, 11, 12, 13, 14, 15, 16, 17, 18, 19, or 20; and the groups are optionally substituted, e.g., by substituent (s) selected from halogen, $C_{1-5}$ alkyl, methanesulfonyloxy, trifluoromethanesulfonyloxy, p-toluenesulfonyloxy, or any combination thereof.

Embodiment 24) relates to the compound of Formula (I) or a salt, a solvate, an isotopically enriched analog, a tautomer, a polymorph, a stereoisomer thereof, or a mixture of stereoisomers thereof as described in embodiment 20) or 23), wherein L represents the following groups: $*-CH_2CH_2O(CH_2)_2-$; $*-(CH_2CH_2O)_2-(CH_2)_2-$; $*-(CH_2CH_2O)_3-(CH_2)_2-$; $*-(CH_2CH_2O)_4-(CH_2)_2-$; $*-(CH_2CH_2O)_5-(CH_2)_2-$; $*-(CH_2CH_2O)_6-(CH_2)_2-$; $*-(CH_2CH_2O)_7-(CH_2)_2-$; $*-(CH_2CH_2O)_8-(CH_2)_2-$; $*-(CH_2CH_2O)_9(CH_2)_2-$; $*-(CH_2CH_2O)_{10}(CH_2)_2-$; $*-CH_2CH_2OCH_2-$; $*-(CH_2CH_2O)_2-CH_2-$; $*-(CH_2CH_2O)_3-CH_2-$; $*-(CH_2CH_2O)_4-CH_2-$; $*-(CH_2CH_2O)_5-CH_2-$; $*-(CH_2CH_2O)_6-CH_2-$; $*-(CH_2CH_2O)_7-CH_2-$; $*-(CH_2CH_2O)_8-CH_2-$; $*-(CH_2CH_2O)_9-CH_2-$; $*-(CH_2CH_2O)_{10}-CH_2-$; $*-CH_2CH_2O(CH_2)_3-$; $*-(CH_2CH_2O)_2-(CH_2)_3-$; $*-(CH_2CH_2O)_3-(CH_2)_3-$; $*-(CH_2CH_2O)_4-(CH_2)_3-$; $*-(CH_2CH_2O)_5-(CH_2)_3-$; $*-(CH_2CH_2O)_6-(CH_2)_3-$; $*-(CH_2CH_2O)_7-(CH_2)_3-$; $*-(CH_2CH_2O)_8-(CH_2)_3-$; $*-(CH_2CH_2O)_9(CH_2)_3-$; $*-(CH_2CH_2O)_{10}(CH_2)_3-$; $*-CH_2CH_2OCH_2CH_2CH_2OCH_2-$; $*-CH_2CH_2OCH_2CH_2CH_2O-(CH_2)_2-$; $*-CH_2CH_2OCH_2CH_2CH_2O-(CH_2)_3-$; $*-(CH_2CH_2O)_2(CH_2CH_2CH_2O)(CH_2)_3-$; $*-(CH_2CH_2O)_2(CH_2CH_2CH_2O)_2(CH_2)_3-$; $*-(CH_2)_1O(CH_2)_1-$; $*-(CH_2)_1O(CH_2)_2-$; $*-(CH_2)_2O(CH_2)_2-$; $*-(CH_2)_2O(CH_2)_1-$; $*-(CH_2)_2O(CH_2)_3-$; $*-(CH_2)_2O(CH_2)_4-$; $*-(CH_2)_2O(CH_2)_5-$; $*-(CH_2)_2O(CH_2)_6-$; $*-(CH_2)_3O(CH_2)_1-$; $*-(CH_2)_3O(CH_2)_2-$; $*-(CH_2)_3O(CH_2)_3-$; $*-(CH_2)_4O(CH_2)_1-$; $*-(CH_2)_4O(CH_2)_2-$; $*-(CH_2)_4O$ $(CH_2)_3$—; *—$(CH_2)_5O(CH_2)_1$—; *—$(CH_2)_5O(CH_2)_2$—; *—$(CH_2)_5O(CH_2)_3$—; *—$(CH_2)_5O(CH_2)_4$—; or *—$(CH_2)_5$ $O(CH_2)_5$—; wherein * indicates the point of attachment to R, and the groups are optionally substituted, e.g., by substituent(s) selected from halogen, $C_{1-5}$ alkyl, methanesulfonyloxy, trifluoromethanesulfonyloxy, p-toluenesulfonyloxy, or any combination thereof.

Embodiment 25) relates to the compound of Formula (I) or a salt, a solvate, an isotopically enriched analog, a tautomer, a polymorph, a stereoisomer thereof, or a mixture of stereoisomers thereof as described in embodiment 20), wherein L represents the following group:

*—$(CH_2)_{n1}$—$N(R_{21})$—$(CH_2)_{n2}$—,

- wherein * indicates the point of attachment to R;
- $R_{21}$ is selected from H and $C_{1-3}$ alkyl;
- n1 and n2 each independently represent an integer of 1, 2, 3, 4, 5, 6, 7, 8, 9, 10, 11, 12, 13, 14, 15, 16, 17, 18, 19, or 20; and
- the group is optionally substituted, e.g., by substituent(s) selected from halogen, $C_{1-5}$ alkyl, methanesulfonyloxy, trifluoromethanesulfonyloxy, p-toluenesulfonyloxy, or any combination thereof.

Embodiment 26) relates to the compound of Formula (I) or a salt, a solvate, an isotopically enriched analog, a tautomer, a polymorph, a stereoisomer thereof, or a mixture of stereoisomers thereof as described in embodiment 20) or 25), wherein L represents the following groups: *—$(CH_2)_1$—NH—$(CH_2)_1$—; *—$(CH_2)_2$—NH—$(CH_2)_1$—; *—$(CH_2)_2$ —NH—$(CH_2)_2$—; *—$(CH_2)_2$—NH—$(CH_2)_3$—; *—$(CH_2)_2$—NH—$(CH_2)_4$—; *—$(CH_2)_2$—NH—$(CH_2)_5$—; *—$(CH_2)_2$—NH—$(CH_2)_6$—; *—$(CH_2)_2$ —NH—$(CH_2)_7$—; *—$(CH_2)_2$—NH—$(CH_2)_8$—; *—$(CH_2)_2$ —NH—$(CH_2)_9$—; *—$(CH_2)_2$—NH—$(CH_2)_{10}$—; *—$(CH_2)_2$—NH—$(CH_2)_{11}$—; *—$(CH_2)_2$—NH—$(CH_2)_{12}$—; *—$(CH_2)_3$—NH—$(CH_2)_1$—; *—$(CH_2)_3$ —NH—$(CH_2)_2$—; *—$(CH_2)_3$—NH—$(CH_2)_3$—; *—$(CH_2)_4$ —NH—$(CH_2)_1$—; *—$(CH_2)_4$—NH—$(CH_2)_2$—; *—$(CH_2)_5$—NH—$(CH_2)_3$—; *—$(CH_2)_5$—NH—$(CH_2)_1$—; *—$(CH_2)_5$—NH—$(CH_2)_2$—; *—$(CH_2)_8$ —NH—$(CH_2)_2$—; *—$(CH_2)_5$—NH—$(CH_2)_3$—; *—$(CH_2)_5$ —NH—$(CH_2)_4$—; *—$(CH_2)_5$—NH—$(CH_2)_5$—; *—$(CH_2)_1$—$N(CH_3)$—$(CH_2)_8$—; *—$(CH_2)_2$—$N(CH_3)$—$(CH_2)_1$—; *—$(CH_2)_3$—$N(CH_3)$—$(CH_2)_1$—; *—$(CH_2)_4$—$N(CH_3)$—$(CH_2)_1$—; *—$(CH_2)_5$—$N(CH_3)$—$(CH_2)_1$—; *—$(CH_2)_6$—$N(CH_3)$—$(CH_2)_1$—; *—$(CH_2)_2$—$N(CH_3)$—$(CH_2)_2$—; *—$(CH_2)_2$—$N(CH_3)$—$(CH_2)_3$—; *—$(CH_2)_2$—$N(CH_3)$—$(CH_2)_4$—; *—$(CH_2)_2$—$N(CH_3)$—$(CH_2)_5$—; *—$(CH_2)_2$—$N(CH_3)$—$(CH_2)_6$—; *—$(CH_2)_2$—$N(CH_3)$—$(CH_2)_7$—; *—$(CH_2)_2$—$N(CH_3)$—$(CH_2)_8$—; *—$(CH_2)_2$—$N(CH_3)$—$(CH_2)_9$—; *—$(CH_2)_2$—$N(CH_3)$—$(CH_2)_{10}$—; *—$(CH_2)_2$—$N(CH_3)$—$(CH_2)_{n1}$—; or *—$(CH_2)_2$ —$N(CH_3)$—$(CH_2)_{12}$—, wherein * indicates the point of attachment to R, and the groups are optionally substituted, e.g., by substituent(s) selected from halogen, $C_{1-5}$ alkyl, methanesulfonyloxy, trifluoromethanesulfonyloxy, p-toluenesulfonyloxy, or any combination thereof.

Embodiment 27) relates to the compound of Formula (I) or a salt, a solvate, an isotopically enriched analog, a tautomer, a polymorph, a stereoisomer thereof, or a mixture of stereoisomers thereof as described in embodiment 20), wherein L represents the following group:

*—$(CH_2)_{n1}$—$N(R_{22})C(O)$—$(CH_2)_{n2}$—,

- wherein * indicates the point of attachment to R;
- $R_{22}$ is selected from H and $C_{1-3}$ alkyl; and
- n1 and n2 each independently represent an integer of 1, 2, 3, 4, 5, 6, 7, 8, 9, 10, 11, 12, 13, 14, 15, 16, 17, 18, 19, or 20; and
- the group is optionally substituted, e.g., by substituent(s) selected from halogen, $C_{1-5}$ alkyl, methanesulfonyloxy, trifluoromethanesulfonyloxy, p-toluenesulfonyloxy, or any combination thereof.

Embodiment 28) relates to the compound of Formula (I) or a salt, a solvate, an isotopically enriched analog, a tautomer, a polymorph, a stereoisomer thereof, or a mixture of stereoisomers thereof as described in embodiment 20) or 27), wherein L represents the following groups: *—$(CH_2)_2$ —NHC(O)—$CH_2$—; *—$(CH_2)_2$—NHC(O)—$(CH_2)_2$—; *—$(CH_2)_2$—NHC(O)—$(CH_2)_3$—; *—$(CH_2)_2$—NHC(O)—$(CH_2)_4$—; *—$(CH_2)_2$—NHC(O)—$(CH_2)_5$—; *—$(CH_2)_2$—NHC(O)—$(CH_2)_6$—; *—$(CH_2)_2$—NHC(O)—$(CH_2)_7$—; *—$(CH_2)_2$—NHC(O)—$(CH_2)_8$—; *—$(CH_2)_2$—NHC(O)—$(CH_2)_9$—; *—$(CH_2)_2$—NHC(O)—$(CH_2)_{10}$—; *—$(CH_2)_2$ —NHC(O)—$(CH_2)_{11}$—; *—$(CH_2)_2$—NHC(O)—$(CH_2)_{12}$—; *—$(CH_2)_2$—NHC(O)—$(CH_2)_{13}$—; *—$(CH_2)_2$ —NHC(O)—$(CH_2)_{14}$—; *—$(CH_2)_2$—NHC(O)—$(CH_2)_{15}$—; *—$(CH_2)_3$—NHC(O)—$CH_2$—; *—$(CH_2)_3$—NHC(O)—$(CH_2)_2$—; *—$(CH_2)_3$—NHC(O)—$(CH_2)_3$—; *—$(CH_2)_3$—NHC(O)—$(CH_2)_4$—; *—$(CH_2)_3$—NHC(O)—$(CH_2)_5$—; *—$(CH_2)_3$—NHC(O)—$(CH_2)_6$—; *—$(CH_2)_3$—NHC(O)—$(CH_2)_7$—; *—$(CH_2)_3$—NHC(O)—$(CH_2)_8$—; *—$(CH_2)_3$—NHC(O)—$(CH_2)_9$—; *—$(CH_2)_3$—NHC(O)—$(CH_2)_{10}$—; *—$(CH_2)_3$—NHC(O)—$(CH_2)_{11}$—; *—$(CH_2)_3$ —NHC(O)—$(CH_2)_{12}$—; *—$(CH_2)_3$—NHC(O)—$(CH_2)_{13}$—; *—$(CH_2)_3$—NHC(O)—$(CH_2)_{14}$—; *—$(CH_2)_3$ —NHC(O)—$(CH_2)_{15}$—; *—$(CH_2)_4NHC(O)(CH_2)_1$—; *—$(CH_2)_4NHC(O)(CH_2)_2$—; *—$(CH_2)_4NHC(O)(CH_2)_3$—; *—$(CH_2)_4NHC(O)(CH_2)_4$—; *—$(CH_2)_4NHC(O)(CH_2)_5$—; *—$(CH_2)_4NHC(O)(CH_2)_6$—; *—$(CH_2)_4$ $NHC(O)(CH_2)_7$—; *—$(CH_2)_4NHC(O)(CH_2)_8$—; *—$(CH_2)_4$ $NHC(O)(CH_2)_9$—; *—$(CH_2)_4NHC(O)(CH_2)_{10}$—; *—$(CH_2)_5NHC(O)(CH_2)_1$—; *—$(CH_2)_5NHC(O)(CH_2)_2$—; *—$(CH_2)_2$—$N(CH_3)C(O)$—$CH_2$—; *—$(CH_2)_2$—$N(CH_3)C(O)$—$(CH_2)_2$—; *—$(CH_2)_2$—$N(CH_3)C(O)$—$(CH_2)_3$—; *—$(CH_2)_2$—$N(CH_3)C(O)$—$(CH_2)_4$—; *—$(CH_2)_2$—$N(CH_3)C(O)$—$(CH_2)_5$—; *—$(CH_2)_2$—$N(CH_3)C(O)$—$(CH_2)_6$—; *—$(CH_2)_2$—$N(CH_3)C(O)$—$(CH_2)_7$—; *—$(CH_2)_2$—$N(CH_3)C(O)$—$(CH_2)_8$—; *—$(CH_2)_2$—$N(CH_3)C(O)$—$(CH_2)_9$—; *—$(CH_2)_2$—$N(CH_3)C(O)$—$(CH_2)_{10}$—; *—$(CH_2)_2$—$N(CH_3)C(O)$—$(CH_2)_{n1}$—; *—$(CH_2)_2$—$N(CH_3)C(O)$—$(CH_2)_{12}$—; *—$(CH_2)_2$—$N(CH_3)C(O)$—$(CH_2)_{13}$—; *—$(CH_2)_2$—$N(CH_3)C(O)$—$(CH_2)_{14}$—; or *—$(CH_2)_2$—$N(CH_3)C(O)$—$(CH_2)_{15}$—, wherein * indicates the point of attachment to R, and the groups are optionally substituted, e.g., by substituent(s) selected from halogen, $C_{1-5}$ alkyl, methanesulfonyloxy, trifluoromethanesulfonyloxy, p-toluenesulfonyloxy, or any combination thereof.

Embodiment 29) relates to the compound of Formula (I) or a salt, a solvate, an isotopically enriched analog, a tautomer, a polymorph, a stereoisomer thereof, or a mixture of stereoisomers thereof as described in embodiment 20), wherein L represents the following group:

*—$(CH_2)_{n1}$—$C(O)N(R_{23})$—$(CH_2)_{n2}$—,

- wherein * indicates the point of attachment to R;
- $R_{23}$ is selected from H and $C_{1-3}$ alkyl;
- n1 and n2 each independently represent an integer of 1, 2, 3, 4, 5, 6, 7, 8, 9, 10, 11, 12, 13, 14, 15, 16, 17, 18, 19, or 20; and
- the group is optionally substituted, e.g., by substituent(s) selected from halogen, $C_{1-5}$ alkyl, methanesulfonyloxy, trifluoromethanesulfonyloxy, p-toluenesulfonyloxy, or any combination thereof.

Embodiment 30) relates to the compound of Formula (I) or a salt, a solvate, an isotopically enriched analog, a tautomer, a polymorph, a stereoisomer thereof, or a mixture of stereoisomers thereof as described in embodiment 20) or 29), wherein L represents the following groups: *—$(CH_2)_2$—C(O)NH—$CH_2$—; *—$(CH_2)_2$—C(O)NH—$(CH_2)_2$—; *—$(CH_2)_2$—C(O)NH—$(CH_2)_3$—; *—$(CH_2)_2$—C(O)NH—$(CH_2)_4$—; *—$(CH_2)_2$—C(O)NH—$(CH_2)_5$—; *—$(CH_2)_2$—C(O)NH—$(CH_2)_6$—; *—$(CH_2)_2$—C(O)NH—$(CH_2)_7$—; *—$(CH_2)_2$—C(O)NH—$(CH_2)_8$—; *—$(CH_2)_2$—C(O)NH—$(CH_2)_9$—; *—$(CH_2)_2$—C(O)NH—$(CH_2)_{10}$—; *—$(CH_2)_2$—C(O)NH—$(CH_2)_{n1}$—; *—$(CH_2)_2$—C(O)NH—$(CH_2)_{12}$—; *—$(CH_2)_2$—C(O)NH—$(CH_2)_{13}$—; *—$(CH_2)_2$—C(O)NH—$(CH_2)_{14}$—; *—$(CH_2)_2$—C(O)NH—$(CH_2)_{15}$—; *—$(CH_2)_3$—C(O)NH—$CH_2$—; *—$(CH_2)_3$—C(O)NH—$(CH_2)_2$—; *—$(CH_2)_3$—C(O)NH—$(CH_2)_3$—; *—$(CH_2)_3$—C(O)NH—$(CH_2)_4$—; *—$(CH_2)_3$—C(O)NH—$(CH_2)_5$—; *—$(CH_2)_3$—C(O)NH—$(CH_2)_6$—; *—$(CH_2)_3$—C(O)NH—$(CH_2)_7$—; *—$(CH_2)_3$—C(O)NH—$(CH_2)_8$—; *—$(CH_2)_3$—C(O)NH—$(CH_2)_9$—; *—$(CH_2)_3$—C(O)NH—$(CH_2)_{10}$—; *—$(CH_2)_3$—C(O)NH—$(CH_2)_{11}$—; *—$(CH_2)_3$—C(O)NH—$(CH_2)_{12}$—; *—$(CH_2)_3$—C(O)NH—; *—$(CH_2)_{13}$—; *—$(CH_2)_3$—C(O)NH—$(CH_2)_{14}$—; *—$(CH_2)_3$—C(O)NH—$(CH_2)_{15}$—; *—$(CH_2)_4$C(O)NH$(CH_2)_1$—; *—$(CH_2)_4$C(O)NH$(CH_2)_2$—; *—$(CH_2)_4$C(O)NH$(CH_2)_3$—; *—$(CH_2)_4$C(O)NH$(CH_2)_4$—; *—$(CH_2)_4$C(O)NH$(CH_2)_5$—; *—$(CH_2)_4$C(O)NH$(CH_2)_6$—; *—$(CH_2)_4$C(O)NH$(CH_2)_7$—; *—$(CH_2)_4$C(O)NH$(CH_2)_8$—; *—$(CH_2)_4$ C(O)NH$(CH_2)_9$—; *—$(CH_2)_4$C(O)NH$(CH_2)_{10}$—; *—$(CH_2)_2$—C(O)N$(CH_3)$—$CH_2$—; *—$(CH_2)_2$—C(O)N$(CH_3)$—$(CH_2)_2$—; *—$(CH_2)_2$—C(O)N$(CH_3)$—$(CH_2)_3$—; *—$(CH_2)_2$—C(O)N$(CH_3)$—$(CH_2)_4$—; *—$(CH_2)_2$—C(O)N$(CH_3)$—$(CH_2)$—; *—$(CH_2)_2$—C(O)N$(CH_3)$—$(CH_2)_6$—; *—$(CH_2)_2$—C(O)N$(CH_3)$—$(CH_2)_7$—; *—$(CH_2)_2$—C(O)N$(CH_3)$—$(CH_2)_8$—; *—$(CH_2)_2$—C(O)N$(CH_3)$—$(CH_2)_9$—; *—$(CH_2)_2$—C(O)N$(CH_3)$—$(CH_2)_{10}$—; *—$(CH_2)_2$—C(O)N$(CH_3)$—$(CH_2)_{11}$—; *—$(CH_2)_2$—C(O)N$(CH_3)$—$(CH_2)_{12}$—; *—$(CH_2)_2$—C(O)N$(CH_3)$—$(CH_2)_{13}$—; *—$(CH_2)_2$—C(O)N$(CH_3)$—$(CH_2)_{14}$—; or *—$(CH_2)_2$—C(O)N$(CH_3)$—$(CH_2)_{15}$—, wherein * indicates the point of attachment to R, and the groups are optionally substituted, e.g., by substituent(s) selected from halogen, $C_{1-5}$ alkyl, methanesulfonyloxy, trifluoromethanesulfonyloxy, p-toluenesulfonyloxy, or any combination thereof.

Embodiment 31) relates to the compound of Formula (I) or a salt, a solvate, an isotopically enriched analog, a tautomer, a polymorph, a stereoisomer thereof, or a mixture of stereoisomers thereof as described in embodiment 20), wherein L represents the following group:

*—$(CH_2)_{n1}$—N$(R_{24})$C(O)N$(R_{25})$—$(CH_2)_{n2}$—, wherein * indicates the point of attachment to R;

$R_{24}$ and $R_{25}$ are each independently selected from H and $C_{1-3}$ alkyl; and n1 and n2 each independently represent an integer of 1, 2, 3, 4, 5, 6, 7, 8, 9, 10, 11, 12, 13, 14, 15, 16, 17, 18, 19, or 20; and the group is optionally substituted, e.g., by substituent(s) selected from halogen, $C_{1-5}$ alkyl, methanesulfonyloxy, trifluoromethanesulfonyloxy, p-toluenesulfonyloxy, or any combination thereof.

Embodiment 32) relates to the compound of Formula (I) or a salt, a solvate, an isotopically enriched analog, a tautomer, a polymorph, a stereoisomer thereof, or a mixture of stereoisomers thereof as described in embodiment 20) or 31), wherein L represents the following groups: *—$(CH_2)_2$—NHC(O)NH—$(CH_2)_4$—; *—$(CH_2)_4$—NHC(O)NH—$(CH_2)_2$—; *—$CH_2$—NHC(O)NH—$(CH_2)_2$—; *—$(CH_2)_2$—NHC(O)NH—$CH_2$—; *—$(CH_2)_2$—NHC(O)NH—$(CH_2)_2$—; *—$(CH_2)_2$—NHC(O)NH—$(CH_2)_3$—; or *—$(CH_2)_3$—NHC(O)NH—$(CH_2)_2$—; wherein the groups are optionally substituted, e.g., by substituent(s) selected from halogen, $C_{1-5}$ alkyl, methanesulfonyloxy, trifluoromethanesulfonyloxy, p-toluenesulfonyloxy, or any combination thereof.

Embodiment 33) relates to the compound of Formula (I) or a salt, a solvate, an isotopically enriched analog, a tautomer, a polymorph, a stereoisomer thereof, or a mixture of stereoisomers thereof as described in embodiment 20), wherein L represents:

*—$(CH_2)_{n1}$-piperazinylene-$(CH_2)_{n2}$—, wherein * indicates the point of attachment to R;

the piperazinylene group is optionally substituted with halogen, methanesulfonyloxy, trifluoromethanesulfonyloxy, p-toluenesulfonyloxy, or $C_{1-5}$ alkyl (especially methyl, ethyl, propyl, isopropyl, butyl, sec-butyl or tert-butyl) or any combination thereof; and n1 and n2 each independently represent an integer of 1, 2, 3, 4, 5, 6, 7, 8, 9, 10, 11, 12, 13, 14, 15, 16, 17, 18, 19, or 20.

Embodiment 34) relates to the compound of Formula (I) a salt, a solvate, an isotopically enriched analog, a tautomer, a polymorph, a stereoisomer thereof, or a mixture of stereoisomers thereof as described in embodiment 20) or 33), wherein L represents: *—$CH_2$-piperazinylene-$CH_2$—; *—$(CH_2)_2$-piperazinylene-$(CH_2)_2$—; *—$(CH_2)_2$-piperazinylene-$(CH_2)_3$—; *—$(CH_2)_2$-piperazinylene-$(CH_2)_4$—; *—$(CH_2)_2$-piperazinylene-$(CH_2)_5$—; *—$(CH_2)_3$-piperazinylene-$CH_2$—; *—$(CH_2)_3$-piperazinylene-$(CH_2)_2$—; *—$(CH_2)_3$-piperazinylene-$(CH_2)_3$—; *—$(CH_2)_4$-piperazinylene-$CH_2$—; *—$(CH_2)_4$-piperazinylene-$(CH_2)_2$—; *—$(CH_2)_4$-piperazinylene-$(CH_2)_3$—; *—$(CH_2)_8$-piperazinylene-$CH_2$—; *—$(CH_2)_8$-piperazinylene-$(CH_2)_2$—; *—$(CH_2)_8$-piperazinylene-$(CH_2)_3$—; *—$(CH_2)_8$-piperazinylene-$(CH_2)_4$—; *—$(CH_2)_8$-piperazinylene-$(CH_2)_8$—; *—$(CH_2)_8$-piperazinylene-$(CH_2)_6$—; *—$(CH_2)_8$-piperazinylene-$(CH_2)_7$—; *—$(CH_2)_8$-piperazinylene-$(CH_2)_8$—; *—$CH_2$-piperazinylene-$(CH_2)_8$—; *—$(CH_2)_2$-piperazinylene-$(CH_2)_8$—; *—$(CH_2)_3$-piperazinylene-$(CH_2)_8$—; *—$(CH_2)_4$-piperazinylene-$(CH_2)_8$—; *—$(CH_2)_5$-piperazinylene-$(CH_2)_8$—; *—$(CH_2)_6$-piperazinylene-$(CH_2)_8$—; or *—$(CH_2)_7$-piperazinylene-$(CH_2)_8$—; wherein * indicates the point of attachment to R; and the piperazinylene group is optionally substituted with halogen, methanesulfonyloxy, trifluoromethanesulfonyloxy, p-toluenesulfonyloxy, or $C_{1-5}$ alkyl (especially methyl, ethyl, propyl, isopropyl, butyl, sec-butyl, or tert-butyl) or any combination thereof. In a sub-embodiment, L represents: *—$CH_2$-piperazinylene-$CH_2$—; *—$(CH_2)_2$-piperazinylene-$(CH_2)_2$—; *—$(CH_2)_2$-piperazinylene-$(CH_2)_3$—; *—$(CH_2)_2$-piperazinylene-$(CH_2)_4$—; *—$(CH_2)_2$-piperazinylene-$(CH_2)_5$—; *—$(CH_2)_3$-piperazinylene-$CH_2$—; *—$(CH_2)_3$-piperazinylene-$(CH_2)_2$—; *—$(CH_2)_3$-piperazinylene-$(CH_2)_3$—; *—$(CH_2)_4$-piperazinylene-$CH_2$—; *—$(CH_2)_4$-piperazinylene-$(CH_2)_2$—; *—$(CH_2)_4$-piperazinylene-$(CH_2)_3$—; *—$(CH_2)_8$-piperazinylene-$CH_2$—; *—$(CH_2)_8$-piperazinylene-$(CH_2)_2$—; *—$(CH_2)_8$-piperazinylene-$(CH_2)_3$—; *—$(CH_2)_8$-piperazinylene-$(CH_2)_4$—; *—$(CH_2)_8$-piperazinylene-$(CH_2)_5$—; *—$(CH_2)_8$-piperazinylene-$(CH_2)_6$—; *—$(CH_2)_8$-piperazinylene-$(CH_2)_7$—; *—$(CH_2)_8$-piperazinylene-$(CH_2)_8$—; *—$CH_2$-piperazinylene-$(CH_2)_8$—; *—$(CH_2)_2$-piperazinylene-$(CH_2)_8$—; *—$(CH_2)_3$-piperazinylene-$(CH_2)_8$—; *—$(CH_2)_4$-piperazinylene-$(CH_2)_8$—; *—$(CH_2)_5$-piperazinylene-$(CH_2)_8$—; *—$(CH_2)_6$-piperazinylene-$(CH_2)_8$—; or *—$(CH_2)_7$-piperazinylene-$(CH_2)_8$—; wherein * indicates the point of attachment to R.

Embodiment 35) relates to the compound of Formula (I) or a salt, a solvate, an isotopically enriched analog, a tautomer, a polymorph, a stereoisomer thereof, or a mixture of stereoisomers thereof as described in embodiment 20), wherein L represents:

*—$(CH_2)_{n1}$-phenylene-$(CH_2)_{n2}$—, wherein * indicates the point of attachment to R;

the phenylene group is optionally substituted with halogen, methanesulfonyloxy, trifluoromethanesulfonyloxy, p-toluenesulfonyloxy, or $C_{1-5}$ alkyl (especially methyl, ethyl, propyl, isopropyl, butyl, sec-butyl, or tert-butyl) or any combination thereof; and n1 and n2 each independently represent an integer of 1, 2, 3, 4, 5, 6, 7, 8, 9, 10, 11, 12, 13, 14, 15, 16, 17, 18, 19, or 20.

Embodiment 36) relates to the compound of Formula (I) or a salt, a solvate, an isotopically enriched analog, a tautomer, a polymorph, a stereoisomer thereof, or a mixture of stereoisomers thereof as described in embodiment 20) or 35), wherein L represents: *—$CH_2$-phenylene-$CH_2$—; *—$(CH_2)_2$-phenylene-$(CH_2)_2$—; *—$(CH_2)_2$-phenylene-$(CH_2)_3$—; *—$(CH_2)_2$-phenylene-$(CH_2)_4$—; *—$(CH_2)_2$-phenylene-$(CH_2)_5$—; *—$(CH_2)_3$-phenylene-$CH_2$—; *—$(CH_2)_3$-phenylene-$(CH_2)_2$—; *—$(CH_2)_3$-phenylene-$(CH_2)_3$—; *—$(CH_2)_4$-phenylene-$CH_2$—; *—$(CH_2)_4$-phenylene-$(CH_2)_2$—; *—$(CH_2)_4$-phenylene-$(CH_2)_3$—; *—$(CH_2)_5$-phenylene-$(CH_2)_3$—; *—$(CH_2)_6$-phenylene-$(CH_2)_3$—; *—$(CH_2)_7$-phenylene-$(CH_2)_3$—; *—$(CH_2)_8$-phenylene-$CH_2$—; *—$(CH_2)_8$-phenylene-$(CH_2)_2$—; *—$(CH_2)_8$-phenylene-$(CH_2)_3$—; *—$(CH_2)_8$-phenylene-$(CH_2)_4$—; *—$(CH_2)_8$-phenylene-$(CH_2)_8$—; *—$(CH_2)_8$-phenylene-$(CH_2)_6$—; *—$(CH_2)_8$-phenylene-$(CH_2)_7$—; *—$(CH_2)_8$-phenylene-$(CH_2)_8$—; *—$CH_2$-phenylene-$(CH_2)_8$—; *—$(CH_2)_2$-phenylene-$(CH_2)_8$—; *—$(CH_2)_3$-phenylene-$(CH_2)_8$—; *—$(CH_2)_4$-phenylene-$(CH_2)_8$—; *—$(CH_2)_8$-phenylene-$(CH_2)_8$—; *—$(CH_2)_6$-phenylene-$(CH_2)_8$—; or *—$(CH_2)_7$-phenylene-$(CH_2)_8$—; wherein * indicates the point of attachment to R; and the phenylene group is optionally substituted with halogen, methanesulfonyloxy, trifluoromethanesulfonyloxy, p-toluenesulfonyloxy, or $C_{1-5}$ alkyl (especially methyl, ethyl, propyl, isopropyl, butyl, sec-butyl, or tert-butyl) or any combination thereof. In a sub-embodiment, L represents: *—$CH_2$-phenylene-$CH_2$—; *—$(CH_2)_2$-phenylene-$(CH_2)_2$—; *—$(CH_2)_2$-phenylene-$(CH_2)_3$—; *—$(CH_2)_2$-phenylene-$(CH_2)_4$—; *—$(CH_2)_2$-phenylene-$(CH_2)_5$—; *—$(CH_2)_3$-phenylene-$CH_2$—; *—$(CH_2)_3$-phenylene-$(CH_2)_2$—; *—$(CH_2)_3$-phenylene-$(CH_2)_3$—; *—$(CH_2)_4$-phenylene-$CH_2$—; *—$(CH_2)_4$ -phenylene-$(CH_2)_2$—; *—$(CH_2)_4$-phenylene-$(CH_2)_3$—; *—$(CH_2)_5$-phenylene-$(CH_2)_3$—; *—$(CH_2)_6$-phenylene-$(CH_2)_3$—; *—$(CH_2)_7$-phenylene-$(CH_2)_3$—; *—$(CH_2)_8$-phenylene-$CH_2$—; *—$(CH_2)_8$-phenylene-$(CH_2)_2$—; *—$(CH_2)_8$-phenylene-$(CH_2)_3$—; *—$(CH_2)_8$-phenylene-$(CH_2)_4$—; *—$(CH_2)_8$-phenylene-$(CH_2)_5$—; *—$(CH_2)_8$-phenylene-$(CH_2)_6$—; *—$(CH_2)_8$-phenylene-$(CH_2)_7$—; *—$(CH_2)_8$-phenylene-$(CH_2)_8$—; *—$CH_2$-phenylene-$(CH_2)_8$—; *—$(CH_2)_2$-phenylene-$(CH_2)_8$—; *—$(CH_2)_3$-phenylene-$(CH_2)_8$—; *—$(CH_2)_4$-phenylene-$(CH_2)_8$—; *—$(CH_2)_5$-phenylene-$(CH_2)_8$—; *—$(CH_2)_6$-phenylene-$(CH_2)_8$—; or *—$(CH_2)_7$-phenylene-$(CH_2)_8$—, wherein * indicates the point of attachment to R.

Embodiment 37) relates to the compound of Formula (I) or a salt, a solvate, an isotopically enriched analog, a tautomer, a polymorph, a stereoisomer thereof, or a mixture of stereoisomers thereof as described in embodiment 20), wherein L represents the following group: *—$(CH_2)_{n1}$—S—$(CH_2)_{n2}$—, where * indicates the point of attachment to R; n1 and n2 each independently represent an integer of 1, 2, 3, 4, 5, 6, 7, 8, 9, 10, 11, 12, 13, 14, 15, 16, 17, 18, 19, or 20; and the group is optionally substituted, e.g., by substituent(s) selected from halogen, $C_{1-5}$ alkyl, methanesulfonyloxy, trifluoromethanesulfonyloxy, p-toluenesulfonyloxy, or any combination thereof.

Embodiment 38) relates to the compound of Formula (I) or a salt, a solvate, an isotopically enriched analog, a tautomer, a polymorph, a stereoisomer thereof, or a mixture of stereoisomers thereof as described in embodiment 20) or 37), wherein L represents the following groups: *—$(CH_2)_1$S$(CH_2)_1$—, *—$(CH_2)_2$S$(CH_2)_2$—, *—$(CH_2)_2$S$(CH_2)_1$—, *—$(CH_2)_1$S$(CH_2)_2$—, *—$(CH_2)_1$S$(CH_2)_3$—, *—$(CH_2)_1$S$(CH_2)_4$—, *—$(CH_2)_2$S$(CH_2)_3$—, *—$(CH_2)_2$S$(CH_2)_4$—, *—$(CH_2)_2$S$(CH_2)_5$—, *—$(CH_2)_3$S$(CH_2)_1$—, *—$(CH_2)_3$S$(CH_2)_2$—, *—$(CH_2)_3$S$(CH_2)_3$—, *—$(CH_2)_4$S$(CH_2)_1$—, *—$(CH_2)_4$S$(CH_2)_2$—, *—$(CH_2)_4$S$(CH_2)_3$—, *—$(CH_2)_5$S$(CH_2)_1$—, *—$(CH_2)_5$S$(CH_2)_2$—, *—$(CH_2)_5$S$(CH_2)_3$—, *—$(CH_2)_6$S$(CH_2)_1$—, *—$(CH_2)_6$S$(CH_2)_2$—, *—$(CH_2)_6$S$(CH_2)_3$—, *—$(CH_2)_7$S$(CH_2)_1$—, *—$(CH_2)_7$S$(CH_2)_2$—, *—$(CH_2)_7$S$(CH_2)_3$—, *—$(CH_2)_8$S$(CH_2)_1$—, *—$(CH_2)_8$S$(CH_2)_2$—, *—$(CH_2)_8$S$(CH_2)_3$—, *—$(CH_2)_9$S$(CH_2)_1$—, *—$(CH_2)_9$S$(CH_2)_2$—, or *—$(CH_2)_9$S$(CH_2)_3$—, where * indicates the point of attachment to R, and the groups are optionally substituted, e.g., by substituent(s) selected from halogen, $C_{1-5}$ alkyl, methanesulfonyloxy, trifluoromethanesulfonyloxy, p-toluenesulfonyloxy, or any combination thereof.

Embodiment 39) relates to the compound of Formula (I) or a salt, a solvate, an isotopically enriched analog, a tautomer, a polymorph, a stereoisomer thereof, or a mixture of stereoisomers thereof as described in embodiment 20), wherein L represents the following group: *—$(CH_2)_{n1}$—S(O)—$(CH_2)_{n2}$—, where * indicates the point of attachment to R; n1 and n2 each independently represent an integer of 1, 2, 3, 4, 5, 6, 7, 8, 9, 10, 11, 12, 13, 14, 15, 16, 17, 18, 19, or 20; and the group is optionally substituted, e.g., by substituent(s) selected from halogen, $C_{1-5}$ alkyl, methanesulfonyloxy, trifluoromethanesulfonyloxy, p-toluenesulfonyloxy, or any combination thereof.

Embodiment 40) relates to the compound of Formula (I) or a salt, a solvate, an isotopically enriched analog, a tautomer, a polymorph, a stereoisomer thereof, or a mixture of stereoisomers thereof as described in embodiment 20) or 39), wherein L represents the following groups: *—$(CH_2)_1$S(O)$(CH_2)_1$—; *—$(CH_2)_2$S(O)$(CH_2)_2$—; *—$(CH_2)_2$S(O)$(CH_2)_1$—; *—$(CH_2)_1$S(O)$(CH_2)_2$—; $(CH_2)_1$S(O)$(CH_2)_3$—; *—$(CH_2)_1$S(O)$(CH_2)_4$—; *—$(CH_2)_2$S(O)$(CH_2)_3$—; *—$(CH_2)_2$S(O)$(CH_2)_4$—; *—$(CH_2)_2$S(O)$(CH_2)_5$—; *—$(CH_2)_3$S(O)$(CH_2)_1$—; *—$(CH_2)_3$S(O)$(CH_2)_2$—; *—$(CH_2)_3$S(O)$(CH_2)_3$; *—$(CH_2)_4$S(O)$(CH_2)_1$—; *—$(CH_2)_4$S(O)$(CH_2)_2$—; *—$(CH_2)_4$S(O)$(CH_2)_3$—; *—$(CH_2)_5$S(O)$(CH_2)_1$—; *—$(CH_2)_5$S(O)$(CH_2)_2$—; *—$(CH_2)_5$S(O)$(CH_2)_3$—; *—$(CH_2)_6$S(O)$(CH_2)_1$—; *—$(CH_2)_6$S(O)$(CH_2)_2$—; *—$(CH_2)_6$S(O)$(CH_2)_3$—; *—$(CH_2)_7$S(O)$(CH_2)_1$—; *—$(CH_2)_7$S(O)$(CH_2)_2$—; *—$(CH_2)_7$S(O)$(CH_2)_3$—; *—$(CH_2)_8$S(O)$(CH_2)_1$—; *—$(CH_2)_8$S(O)$(CH_2)_2$—; *—$(CH_2)_8$S(O)$(CH_2)_3$—; *—$(CH_2)_9$S(O)$(CH_2)_1$—; *—$(CH_2)_9$S(O)$(CH_2)_2$—; or *—$(CH_2)_9$S(O)$(CH_2)_3$—, wherein * indicates the point of attachment to R; and the groups are optionally substituted, e.g., by substituent(s) selected from halogen, $C_{1-5}$ alkyl, methanesulfonyloxy, trifluoromethanesulfonyloxy, p-toluenesulfonyloxy, or any combination thereof.

Embodiment 41) relates to the compound of Formula (I) or a salt, a solvate, an isotopically enriched analog, a tautomer, a polymorph, a stereoisomer thereof, or a mixture of stereoisomers thereof as described in embodiment 20), wherein L represents the following group: *—$(CH_2)_{n1}$—S$(O)_2$—$(CH_2)_{n2}$—, where * indicates the point of attachment to R; n1 and n2 each independently represent an integer of 1, 2, 3, 4, 5, 6, 7, 8, 9, 10, 11, 12, 13, 14, 15, 16, 17, 18, 19, or 20; and the group is optionally substituted, e.g., by substituent(s) selected from halogen, $C_{1-5}$ alkyl, methanesulfonyloxy, trifluoromethanesulfonyloxy, p-toluenesulfonyloxy, or any combination thereof.

Embodiment 42) relates to the compound of Formula (I) or a salt, a solvate, an isotopically enriched analog, a tautomer, a polymorph, a stereoisomer thereof, or a mixture of stereoisomers thereof as described in embodiment 20) or 41), wherein L represents the following groups: *—$(CH_2)_1S(O)_2(CH_2)_1$—; *—$(CH_2)_2S(O)_2(CH_2)_2$—; *—$(CH_2)_2S(O)_2$ $(CH_2)_1$—; *—$(CH_2)_1S(O)_2(CH_2)_2$—; *—$(CH_2)_1S(O)_2(CH_2)_3$—; *—$(CH_2)_1S(O)_2(CH_2)_4$—; *—$(CH_2)_2S(O)_2(CH_2)_3$—; *—$(CH_2)_2S(O)_2(CH_2)_4$—; *—$(CH_2)_2S(O)_2(CH_2)_5$—; *—$(CH_2)_3S(O)_2(CH_2)_1$—; *—$(CH_2)_3S(O)_2(CH_2)_2$—; *—$(CH_2)_3S(O)_2(CH_2)_3$—; *—$(CH_2)_4S(O)_2(CH_2)_1$—; *—$(CH_2)_4S(O)_2(CH_2)_2$—; *—$(CH_2)_4S(O)_2(CH_2)_3$—; *—$(CH_2)_5S(O)_2(CH_2)_1$—; *—$(CH_2)_5S(O)_2(CH_2)_2$—; *—$(CH_2)_5S(O)(CH_2)_3$—; *—$(CH_2)_6S(O)_2(CH_2)_1$—; *—$(CH_2)_6S(O)_2(CH_2)_2$—; *—$(CH_2)_6S(O)_2(CH_2)_3$—; *—$(CH_2)_7S(O)_2(CH_2)_1$—; *—$(CH_2)_7S(O)_2(CH_2)_2$—; *—$(CH_2)_7S(O)_2(CH_2)_3$—; *—$(CH_2)_8S(O)_2(CH_2)_1$—; *—$(CH_2)_8S(O)_2(CH_2)_2$—; *—$(CH_2)_8S(O)_2(CH_2)_3$—; *—$(CH_2)_9S(O)_2(CH_2)_1$—; *—$(CH_2)_9S(O)_2(CH_2)_2$—; or *—$(CH_2)_9S(O)_2(CH_2)_3$—, wherein * indicates the point of attachment to R; and the groups are optionally substituted, e.g., by substituent(s) selected from halogen, $C_{1-5}$ alkyl, methanesulfonyloxy, trifluoromethanesulfonyloxy, p-toluenesulfonyloxy, or any combination thereof.

Embodiment 43) relates to the compound of Formula (I) or a salt, a solvate, an isotopically enriched analog, a tautomer, a polymorph, a stereoisomer thereof, or a mixture of stereoisomers thereof as described in embodiment 20), wherein L represents the following groups: *—$(CH_2)_1$—NH—$(CH_2)_1$—; *—$(CH_2)_2$—NH—$(CH_2)_1$—; *—$(CH_2)_2$—NH—$(CH_2)_2$—; *—$(CH_2)_2$—NH—$(CH_2)_3$—; *—$(CH_2)_2$ —NH—$(CH_2)_4$—; *—$(CH_2)_2$—NH—$(CH_2)_5$—; *—$(CH_2)_2$—NH—$(CH_2)_6$—; *—$(CH_2)_2$—NH—$(CH_2)_7$—; *—$(CH_2)_2$—NH—$(CH_2)_8$—; *—$(CH_2)_2$—NH—$(CH_2)_9$—; *—$(CH_2)_2$—NH—$(CH_2)_{10}$—; *—$(CH_2)_2$ —NH—$(CH_2)_{11}$—; *—$(CH_2)_2$—NH—$(CH_2)_{12}$—; *—$(CH_2)_3$—NH—$(CH_2)_1$—; *—$(CH_2)_3$—NH—$(CH_2)_2$—; *—$(CH_2)_3$—NH—$(CH_2)_3$—; *—$(CH_2)_4$—NH—$(CH_2)_1$—; *—$(CH_2)_4$—NH—$(CH_2)_2$—; *—$(CH_2)_5$ —NH—$(CH_2)_3$—; *—$(CH_2)_5$—NH—$(CH_2)_1$—; *—$(CH_2)_5$—NH—$(CH_2)_2$—; *—$(CH_2)_8$—NH—$(CH_2)_2$—; *—$(CH_2)_5$—NH—$(CH_2)_3$—; *—$(CH_2)_5$—NH—$(CH_2)_4$—; *—$(CH_2)_5$—NH—$(CH_2)_5$—; *—$(CH_2)_1$ —N($CH_3$)—$(CH_2)_8$—; *—$(CH_2)_2$—N($CH_3$)—$(CH_2)_1$—; *—$(CH_2)_3$—N($CH_3$)—$(CH_2)_1$—; *—$(CH_2)_4$—N($CH_3$)—$(CH_2)_1$—; *—$(CH_2)_5$—N($CH_3$)—$(CH_2)_1$—; *—$(CH_2)_6$—N($CH_3$)—$(CH_2)_1$—; *—$(CH_2)_2$—N($CH_3$)—$(CH_2)_2$—; *—$(CH_2)_2$—N($CH_3$)—$(CH_2)_3$—; *—$(CH_2)_2$—N($CH_3$)—$(CH_2)_4$—; *—$(CH_2)_2$—N($CH_3$)—$(CH_2)_5$—; *—$(CH_2)_2$—N($CH_3$)—$(CH_2)_6$—; *—$(CH_2)_2$—N($CH_3$)—$(CH_2)_7$—; *—$(CH_2)_2$—N($CH_3$)—$(CH_2)_8$—; *—$(CH_2)_2$—N($CH_3$)—$(CH_2)_9$—; *—$(CH_2)_2$—N($CH_3$)—$(CH_2)_{10}$—; *—$(CH_2)_2$—N($CH_3$)—$(CH_2)_{11}$—; *—$(CH_2)_2$—N($CH_3$)—$(CH_2)_{12}$—; *—$(CH_2)_2$—NHC(O)—$CH_2$—; *—$(CH_2)_2$—NHC(O)—$(CH_2)_2$—; *—$(CH_2)_2$—NHC(O)—$(CH_2)_3$—; *—$(CH_2)_2$—NHC(O)—$(CH_2)_4$—; *—$(CH_2)_2$—NHC(O)—$(CH_2)_5$—; *—$(CH_2)_2$—NHC(O)—$(CH_2)_6$—; *—$(CH_2)_2$—NHC(O)—$(CH_2)_7$—; *—$(CH_2)_2$—NHC(O)—$(CH_2)_8$—; *—$(CH_2)_2$—NHC(O)—$(CH_2)_9$—; *—$(CH_2)_2$—NHC(O)—$(CH_2)_{10}$—; *—$(CH_2)_2$—NHC(O)—$(CH_2)_1$—; *—$(CH_2)_2$ —NHC(O)—$(CH_2)_{12}$—; *—$(CH_2)_2$—NHC(O)—$(CH_2)_{13}$—; *—$(CH_2)_2$—NHC(O)—$(CH_2)_{14}$—; *—$(CH_2)_2$ —NHC(O)—$(CH_2)_{15}$—; *—$(CH_2)_3$—NHC(O)—$CH_2$—; *—$(CH_2)_3$—NHC(O)—$(CH_2)_2$—; *—$(CH_2)_3$—NHC(O)—$(CH_2)_3$—; *—$(CH_2)_3$—NHC(O)—$(CH_2)_4$—; *—$(CH_2)_3$—NHC(O)—$(CH_2)_5$—; *—$(CH_2)_3$—NHC(O)—$(CH_2)_6$—; *—$(CH_2)_3$—NHC(O)—$(CH_2)_7$—; *—$(CH_2)_3$—NHC(O)—$(CH_2)_8$—; *—$(CH_2)_3$—NHC(O)—$(CH_2)_9$—; *—$(CH_2)_3$—NHC(O)—$(CH_2)_{10}$—; *—$(CH_2)_3$—NHC(O)—$(CH_2)_{11}$—; *—$(CH_2)_3$—NHC(O)—$(CH_2)_{12}$—; *—$(CH_2)_3$—NHC (O)—$(CH_2)_{13}$—; *—$(CH_2)_3$—NHC(O)—$(CH_2)_{14}$—; *—$(CH_2)_3$—NHC(O)—$(CH_2)_{15}$—; *—$(CH_2)_4$NHC(O) $(CH_2)_1$—; *—$(CH_2)_4$NHC(O)$(CH_2)_2$—; *—$(CH_2)_4$NHC (O)$(CH_2)_3$—; *—$(CH_2)_4$NHC(O)$(CH_2)_4$—; *—$(CH_2)_4$ NHC(O)$(CH_2)_5$—; *—$(CH_2)_4$NHC(O)$(CH_2)_6$—; *—$(CH_2)_4$ NHC(O)$(CH_2)_7$—; *—$(CH_2)_4$NHC(O) $(CH_2)_8$—; *—$(CH_2)_4$NHC(O)$(CH_2)_9$—; *—$(CH_2)_4$NHC (O)$(CH_2)_{10}$—; *—$(CH_2)_5$NHC(O)$(CH_2)_1$—; *—$(CH_2)_5$ NHC(O)$(CH_2)_2$—; *—$(CH_2)_2$—N($CH_3$)C(O)—$CH_2$—; *—$(CH_2)_2$—N($CH_3$)C(O)—$(CH_2)_2$—; *—$(CH_2)_2$—N ($CH_3$)C(O)—$(CH_2)_3$—; *—$(CH_2)_2$—N($CH_3$)C(O) —$(CH_2)_4$—; *—$(CH_2)_2$—N($CH_3$)C(O)—$(CH_2)_5$—; *—$(CH_2)_2$—N($CH_3$)C(O)—$(CH_2)_6$—; *—$(CH_2)_2$—N ($CH_3$)C(O)—$(CH_2)_7$—; *—$(CH_2)_2$—N($CH_3$)C(O) —$(CH_2)_8$—; *—$(CH_2)_2$—N($CH_3$)C(O)—$(CH_2)_9$—; *—$(CH_2)_2$—N($CH_3$)C(O)—$(CH_2)_{10}$—; *—$(CH_2)_2$—N ($CH_3$)C(O)—$(CH_2)_{n1}$—; *—$(CH_2)_2$—N($CH_3$)C(O)—$(CH_2)_{12}$—; *—$(CH_2)_2$—N($CH_3$)C(O)—$(CH_2)_{13}$—; *—$(CH_2)_2$—N($CH_3$)C(O)—$(CH_2)_{14}$—; *—$(CH_2)_2$—N ($CH_3$)C(O)—$(CH_2)_{15}$—; *—$(CH_2)_2$—C(O)NH—$CH_2$—; *—$(CH_2)_2$—C(O)NH—$(CH_2)_2$—; *—$(CH_2)_2$—C(O)NH—$(CH_2)_3$—; *—$(CH_2)_2$—C(O)NH—$(CH_2)_4$—; *—$(CH_2)_2$—C(O)NH—$(CH_2)_5$—; *—$(CH_2)_2$—C(O)NH—$(CH_2)_6$—; *—$(CH_2)_2$—C(O)NH—$(CH_2)_7$—; *—$(CH_2)_2$—C(O)NH—$(CH_2)_8$—; *—$(CH_2)_2$—C(O)NH—$(CH_2)_9$—; *—$(CH_2)_2$—C(O)NH—$(CH_2)_{10}$—; *—$(CH_2)_2$—C(O)NH—$(CH_2)_{11}$—; *—$(CH_2)_2$—C(O)NH—$(CH_2)_{12}$—; *—$(CH_2)_2$—C(O) NH—$(CH_2)_{13}$—; *—$(CH_2)_2$—C(O)NH—$(CH_2)_{14}$—; *—$(CH_2)_2$—C(O)NH—$(CH_2)_{15}$—; *—$(CH_2)_3$—$(CH_2)$ NH—$CH_2$; *—$(CH_2)_3$—C(O)NH—$(CH_2)_2)_2$—; *—$(CH_2)_3$ —C(O)NH—$(CH_2)_3$—; *—$(CH_2)_3$—C(O)NH—$(CH_2)_4$—; *—$(CH_2)_3$—C(O)NH—$(CH_2)_5$—; *—$(CH_2)_3$—C(O)NH—$(CH_2)_6$—; *—$(CH_2)_3$—C(O)NH—$(CH_2)_7$—; *—$(CH_2)_3$—C(O)NH—$(CH_2)_8$—; *—$(CH_2)_3$—C(O)NH—$(CH_2)_9$—; *—$(CH_2)_3$—C(O)NH—$(CH_2)_{10}$—; *—$(CH_2)_3$—C(O) NH—$(CH_2)_{n1}$—; *—$(CH_2)_3$—C(O)NH—$(CH_2)_{12}$—; *—$(CH_2)_3$—C(O)NH—$(CH_2)_{13}$—; *—$(CH_2)_3$—C(O) NH—$(CH_2)_{43}$—C(O)NH—$(CH_2)_{15}$—; *—$(CH_2)_4$C(O)NH $(CH_2)_1$—; *—$(CH_2)_4$C(O)NH$(CH_2)_2$—; *—$(CH_2)_4$C(O) NH$(CH_2)_3$—; *—$(CH_2)_4$C(O)NH$(CH_2)_4$—; *—$(CH_2)_4$C (O)NH$(CH_2)_5$—; *—$(CH_2)_4$C(O)NH$(CH_2)_6$—; *—$(CH_2)_4$ C(O)NH$(CH_2)_7$—; *—$(CH_2)_4$C(O)NH$(CH_2)_8$—; *—$(CH_2)_4$ C(O)NH$(CH_2)_9$—; *—$(CH_2)_4$C(O)NH $(CH_2)_{10}$—; *—$(CH_2)_2$—C(O)N($CH_3$)—$CH_2$—; *—$(CH_2)_2$ —C(O)N($CH_3$)—$(CH_2)_2$—; *—$(CH_2)_2$—C(O)N($CH_3$)—$(CH_2)_3$—; *—$(CH_2)_2$—C(O)N($CH_3$)—$(CH_2)_4$—; *—$(CH_2)_2$—C(O)N($CH_3$)—$(CH_2)_5$—; *—$(CH_2)_2$—C(O)N ($CH_3$)—$(CH_2)_6$—; *—$(CH_2)_2$—C(O)N($CH_3$)—$(CH_2)_7$—; *—$(CH_2)_2$—C(O)N($CH_3$)—$(CH_2)_8$—; *—$(CH_2)_2$—C(O)N $(CH_3)$—$(CH_2)_9$—; *—$(CH_2)_2$—C(O)N$(CH_3)$—$(CH_2)_{10}$—; *—$(CH_2)_2$—C(O)N$(CH_3)$—$(CH_2)_{14}$—; *—$(CH_2)_2$—C(O)N$(CH_3)$—$(CH_2)_{12}$—; *—$(CH_2)_2$—C(O)N$(CH_3)$—$(CH_2)_{13}$—; *—$(CH_2)_2$—C(O)N$(CH_3)$—$(CH_2)_{14}$—; *—$(CH_2)_2$—C(O)N$(CH_3)$—$(CH_2)_{15}$—; *—$(CH_2)_2$—NHC(O)NH—$(CH_2)_4$—; *—$(CH_2)_4$—NHC(O)NH—$(CH_2)_2$—; *—$CH_2$—NHC(O)NH—$(CH_2)_2$—; *—$(CH_2)_2$—NHC(O)NH—$CH_2$—; *—$(CH_2)_2$—NHC(O)NH—$(CH_2)_2$—; *—$(CH_2)_2$—NHC(O)NH—$(CH_2)_3$—; *—$(CH_2)_3$—NHC(O)NH—$(CH_2)_2$—; *—$CH_2$-piperazinylene-$CH_2$—; *—$(CH_2)_2$-piperazinylene-$(CH_2)_2$—; *—$(CH_2)_2$-piperazinylene-$(CH_2)_3$—; *—$(CH_2)_2$-piperazinylene-$(CH_2)_4$—; *—$(CH_2)_2$-piperazinylene-$(CH_2)_5$—; *—$(CH_2)_3$-piperazinylene-$CH_2$—; *—$(CH_2)_3$-piperazinylene-$(CH_2)_2$—; *—$(CH_2)_3$-piperazinylene-$(CH_2)_3$—; *—$(CH_2)_4$-piperazinylene-$CH_2$—; *—$(CH_2)_4$-piperazinylene-$(CH_2)_2$—; *—$(CH_2)_4$-piperazinylene-$(CH_2)_3$—; *—$(CH_2)$-piperazinylene-$CH_2$—; *—$(CH_2)_8$-piperazinylene-$(CH_2)_2$—; *—$(CH_2)_8$-piperazinylene-$(CH_2)_3$—; *—$(CH_2)_8$-piperazinylene-$(CH_2)_4$—; *—$(CH_2)_8$-piperazinylene-$(CH_2)_5$—; *—$(CH_2)_8$-piperazinylene-$(CH_2)$—; *—$(CH_2)_8$-piperazinylene-$(CH_2)_7$—; *—$(CH_2)_8$-piperazinylene-$(CH_2)$—; *—$CH_2$-piperazinylene-$(CH_2)_8$—; *—$(CH_2)_2$-piperazinylene-$(CH_2)$—; *—$(CH_2)_3$-piperazinylene-$(CH_2)$—; *—$(CH_2)_4$-piperazinylene-$(CH_2)$—; *—$(CH_2)_8$-piperazinylene-$(CH_2)_8$—; *—$(CH_2)_6$-piperazinylene-$(CH_2)_8$—; *—$(CH_2)_7$-piperazinylene-$(CH_2)_8$—; *—$CH_2$-phenylene-$CH_2$—; *—$(CH_2)_2$-phenylene-$(CH_2)_2$—; *—$(CH_2)_2$-phenylene-$(CH_2)_3$—; *—$(CH_2)_2$-phenylene-$(CH_2)_4$—; *—$(CH_2)_2$-phenylene-$(CH_2)_5$—; *—$(CH_2)_3$-phenylene-$CH_2$—; *—$(CH_2)_3$-phenylene-$(CH_2)_2$—; *—$(CH_2)_3$-phenylene-$(CH_2)_3$—; *—$(CH_2)_4$-phenylene-$CH_2$—; *—$(CH_2)_4$ -phenylene-$(CH_2)_2$—; *—$(CH_2)_4$-phenylene-$(CH_2)_3$—; *—$(CH_2)_5$-phenylene-$(CH_2)_3$—; *—$(CH_2)_6$-phenylene-$(CH_2)_3$—; *—$(CH_2)_7$-phenylene-$(CH_2)_3$—; *—$(CH_2)_8$-phenylene-$CH_2$—; *—$(CH_2)_8$-phenylene-$(CH_2)_2$—; *—$(CH_2)_8$-phenylene-$(CH_2)_3$—; *—$(CH_2)_8$-phenylene-$(CH_2)_4$—; *—$(CH_2)_8$-phenylene-$(CH_2)_8$—; *—$(CH_2)_5$-phenylene-$(CH_2)_6$—; *—$(CH_2)_8$-phenylene-$(CH_2)_7$—; *—$(CH_2)_8$-phenylene-$(CH_2)_8$—; *—$CH_2$-phenylene-$(CH_2)_8$—; *—$(CH_2)_2$-phenylene-$(CH_2)_8$—; *—$(CH_2)_3$-phenylene-$(CH_2)_8$—; *—$(CH_2)_4$-phenylene-$(CH_2)_8$—; *—$(CH_2)_5$-phenylene-$(CH_2)_8$—; *—$(CH_2)_6$-phenylene-$(CH_2)_8$—; *—$(CH_2)_7$-phenylene-$(CH_2)_8$—; *—$(CH_2)_1S(CH_2)_1$—; *—$(CH_2)_2S(CH_2)_2$—; *—$(CH_2)_2S(CH_2)_1$—; *—$(CH_2)_1S(CH_2)_2$—; *—$(CH_2)_1S(CH_2)_3$—; *—$(CH_2)_1S(CH_2)_4$—; *—$(CH_2)_2S(CH_2)_3$—; *—$(CH_2)_2S(CH_2)_4$—; *—$(CH_2)_2S(CH_2)_5$—; *—$(CH_2)_3S(CH_2)_1$—; *—$(CH_2)_3S(CH_2)_2$—; *—$(CH_2)_3S(CH_2)_3$—; *—$(CH_2)_4S(CH_2)_1$—; *—$(CH_2)_4S(CH_2)_2$—; *—$(CH_2)_4S(CH_2)_3$—; *—$(CH_2)_5S(CH_2)_1$—; *—$(CH_2)_5S(CH_2)_2$—; *—$(CH_2)_5S(CH_2)_3$—; *—$(CH_2)_6S(CH_2)_1$—; *—$(CH_2)_6S(CH_2)_2$—; *—$(CH_2)_6S(CH_2)_3$—; *—$(CH_2)_7S(CH_2)_1$—; *—$(CH_2)_7S(CH_2)_2$—; *—$(CH_2)_7S(CH_2)_3$—; *—$(CH_2)_8S(CH_2)_1$—; *—$(CH_2)_8S(CH_2)_2$—; *—$(CH_2)_8S(CH_2)_3$—; *—$(CH_2)_9S(CH_2)_1$—; *—$(CH_2)_9S(CH_2)_2$—; *—$(CH_2)_9S(CH_2)_3$—; *—$(CH_2)_1S(O)(CH_2)_1$—; *—$(CH_2)_2S(O)(CH_2)_2$—; *—$(CH_2)_2S(O)(CH_2)_1$—; *—$(CH_2)_1S(O)(CH_2)_2$—; *—$(CH_2)_1S(O)(CH_2)_3$—; *—$(CH_2)_1S(O)(CH_2)_4$—; *—$(CH_2)_2S(O)(CH_2)_3$—; *—$(CH_2)_2S(O)(CH_2)_4$—; *—$(CH_2)_2S(O)(CH_2)_5$—; *—$(CH_2)_3S(O)(CH_2)_1$—; *—$(CH_2)_3S(O)(CH_2)_2$—; *—$(CH_2)_3S(O)(CH_2)_3$—; *—$(CH_2)_4S(O)(CH_2)_1$—; *—$(CH_2)_4S(O)(CH_2)_2$—; *—$(CH_2)_4S(O)(CH_2)_3$—; *—$(CH_2)_5S(O)(CH_2)_1$—; *—$(CH_2)_5S(O)(CH_2)_2$—; *—$(CH_2)_5S(O)(CH_2)_3$; *—$(CH_2)_6S(O)(CH_2)_1$—; *—$(CH_2)_6S(O)(CH_2)_2$—; *—$(CH_2)_6S(O)(CH_2)_3$—; *—$(CH_2)_7S(O)(CH_2)_1$—; *—$(CH_2)_7S(O)(CH_2)_2$—; *—$(CH_2)_7S(O)(CH_2)_3$—; *—$(CH_2)_8S(O)(CH_2)_1$—; *—$(CH_2)_8S(O)(CH_2)_2$—; *—$(CH_2)_8S(O)(CH_2)_3$—; *—$(CH_2)_9S(O)(CH_2)_1$—; *—$(CH_2)_9S(O)(CH_2)_2$—; *—$(CH_2)_9S(O)(CH_2)_3$—; *—$(CH_2)_1S(O)_2(CH_2)_1$—; *—$(CH_2)_2S(O)_2(CH_2)_2$—; *—$(CH_2)_2S(O)_2(CH_2)_1$—; *—$(CH_2)_1S(O)_2(CH_2)_2$—; *—$(CH_2)_1S(O)_2(CH_2)_3$—; *—$(CH_2)_1S(O)_2(CH_2)_4$—; *—$(CH_2)_2S(O)_2(CH_2)_3$—; *—$(CH_2)_2S(O)_2(CH_2)_4$—; *—$(CH_2)_2S(O)_2(CH_2)_5$—; *—$(CH_2)_3S(O)_2(CH_2)_1$—; *—$(CH_2)_3S(O)_2(CH_2)_2$—; *—$(CH_2)_3S(O)_2(CH_2)_3$—; *—$(CH_2)_4S(O)_2(CH_2)_1$—; *—$(CH_2)_4S(O)_2(CH_2)_2$—; *—$(CH_2)_4S(O)_2(CH_2)_3$—; *—$(CH_2)_5S(O)_2(CH_2)_1$—; *—$(CH_2)_5S(O)_2(CH_2)_2$—; *—$(CH_2)_5S(O)(CH_2)_3$—; *—$(CH_2)_6S(O)_2(CH_2)_1$—; *—$(CH_2)_6S(O)_2(CH_2)_2$—; *—$(CH_2)_6S(O)_2(CH_2)_3$—; *—$(CH_2)_7S(O)_2(CH_2)_1$—; *—$(CH_2)_7S(O)_2(CH_2)_2$—; *—$(CH_2)_7S(O)_2(CH_2)_3$—; *—$(CH_2)_8S(O)_2(CH_2)_1$—; *—$(CH_2)_8S(O)_2(CH_2)_2$—; *—$(CH_2)_8S(O)_2(CH_2)_3$—; *—$(CH_2)_9S(O)_2(CH_2)_1$—; *—$(CH_2)_9S(O)_2(CH_2)_2$—; or*—$(CH_2)_9S(O)_2(CH_2)_3$—, wherein * indicates the point of attachment to R; and the groups are optionally substituted, e.g., by substituent(s) selected from halogen, $C_{1-5}$ alkyl, methanesulfonyloxy, trifluoromethanesulfonyloxy, p-toluenesulfonyloxy, or any combination thereof.

Embodiment 44) relates to the compound of Formula (I) or a salt, a solvate, an isotopically enriched analog, a tautomer, a polymorph, a stereoisomer thereof, or a mixture of stereoisomers thereof as described in embodiment 20), wherein L represents the following groups: *—$(CH_2)_6$—NH—$(CH_2)_1$—; *—$(CH_2)_6$—NH—$(CH_2)_3$—; *—$(CH_2)_6$—NH—$(CH_2)_4$—; *—$(CH_2)_6$—NH—$(CH_2)_5$—; *—$(CH_2)_7$ —NH—$(CH_2)_1$—; *—$(CH_2)_7$—NH—$(CH_2)_2$—; *—$(CH_2)_7$—NH—$(CH_2)_3$—; *—$(CH_2)_7$—NH—$(CH_2)_4$—; *—$(CH_2)_6$—NH—CH$(CH_3)$—; *—$(CH_2)_5$ —NH—CH$(CH_3)$—; *—$(CH_2)_4$—NH—CH$(CH_3)$—; *—$(CH_2)_3$—NH—CH$(CH_3)$—; *—$(CH_2)_2$—NH—CH$(CH_3)$—; *—$(CH_2)_7$—NH—CH$(CH_3)$—; *—$(CH_2)_5$—NH—CH$(CH_3)$—; *—$(CH_2)_7$—NH—CH$(CF_3)$—; *—$(CH_2)_6$—NH—CH$(CF_3)$—; *—$(CH_2)_5$—NH—CH$(CF_3)$—; *—$(CH_2)_4$—NH—CH$(CF_3)$—; *—$(CH_2)_3$—NH—CH$(CF_3)$—; *—$(CH_2)_2$—NH—CH$(CF_3)$—; *—$(CH_2)_8$—NH—CH$(CF_3)$—; *—$CH_2$—C(O)NH—$(CH_2)_4$—; *—$CH_2$—C(O)NH—$(CH_2)_2$—; *—$CH_2$—C(O)NH—$(CH_2)_3$—; *—$CH_2$—C(O)NH—$(CH_2)_5$—; *—$(CH_2)_1$-phenylene-$(CH_2)_1$—; *—$(CH_2)_2$-phenylene-$(CH_2)_1$—; *—$(CH_2)_1$-phenylene-$(CH_2)_2$—; *—$(CH_2)_1$-phenylene-$(CH_2)_3$—; *—$(CH_2)_3$-phenylene-$(CH_2)_1$—; *—$(CH_2)_4$-phenylene-$(CH_2)_1$—; *—$(CH_2)_1$-phenylene-$(CH_2)_4$—; *—$(CH_2)_2$-phenylene-$(CH_2)_2$—; *—$CH_2$-phenylene-$CH_2$—NH—CH$(CH_3)$—; *—$CH_2$-phenylene-$(CH_2)_2$—NH—CH$(CH_3)$—; *—$CH_2$-phenylene-$CH_2$—NH—$CH_2$—; *—$CH_2$-phenylene-$(CH_2)_2$—NH—$CH_2$—; *—$(CH_2)_1$—C(O)NH—$(CH_2)_4$—; *—$(CH_2)_1$-furanylene-$(CH_2)_1$—; *—$(CH_2)_1$-furanylene-$(CH_2)_2$—; *—$(CH_2)_1$-furanylene-$(CH_2)_3$—; *—$(CH_2)_2$-furanylene-$(CH_2)_1$—; *—$(CH_2)_2$-furanylene-$(CH_2)_2$—; *—$(CH_2)_3$-furanylene-$(CH_2)_1$—; *—$(CH_2)_3$-furanylene-$(CH_2)_2$—; *—$(CH_2)_1$-thiazolylene-$(CH_2)_1$—; *—$(CH_2)_1$-thiazolylene-$(CH_2)_2$—; *—$(CH_2)_1$-thiazolylene-$(CH_2)_3$—; *—$(CH_2)_2$-thiazolylene-$(CH_2)_1$—; *—$(CH_2)_2$-thiazolylene-$(CH_2)_2$—; *—$(CH_2)_3$-thiazolylene-$(CH_2)_1$—; *—$(CH_2)_3$-thiazolylene-$(CH_2)_2$—; or *—$CH_2$-thiazolylene-$CH_2$—NH—$CH_2$—, wherein * indicates the point of attachment to R; and the groups are optionally substituted, e.g., by substituent(s) selected from halogen, $C_{1-5}$ alkyl, methanesulfonyloxy, trifluoromethanesulfonyloxy, p-toluenesulfonyloxy, or any combination thereof.

Embodiment 45) relates to the compound of Formula (I) or a salt, a solvate, an isotopically enriched analog, a tautomer, a polymorph, a stereoisomer thereof, or a mixture of stereoisomers thereof as described in embodiment 20), wherein L represents the following groups:
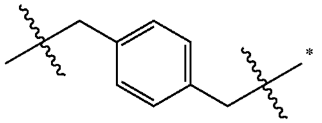
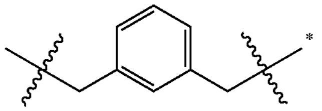
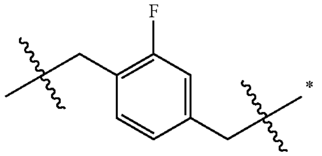
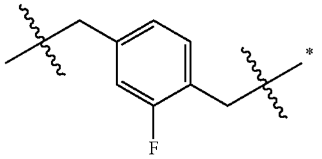
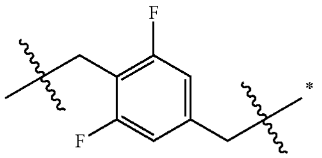
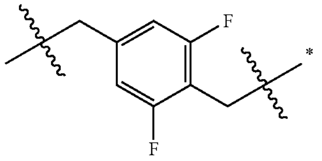
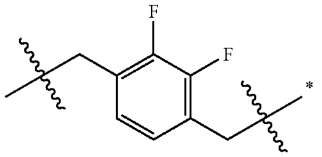
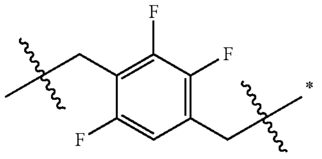
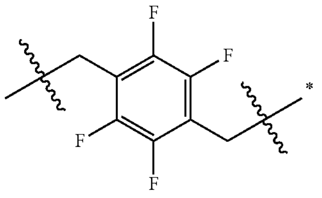
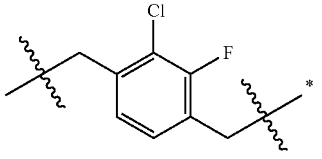
-continued
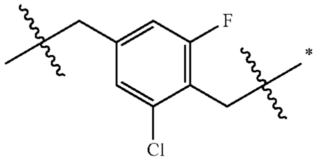
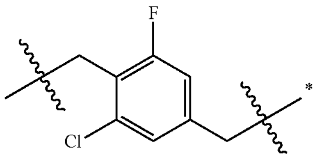
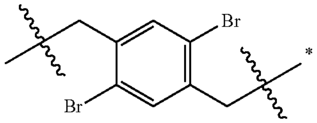
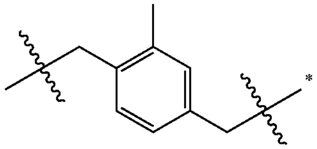
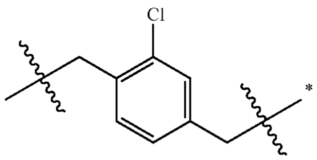
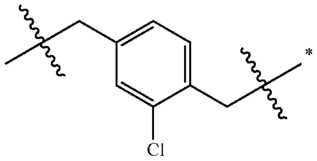
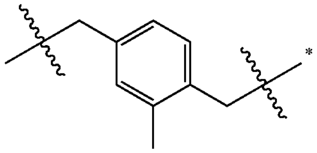
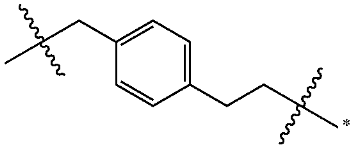
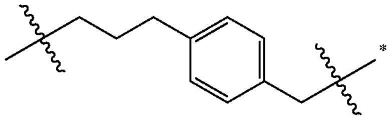
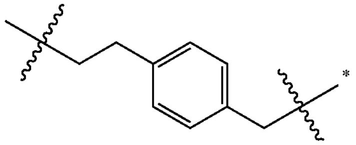
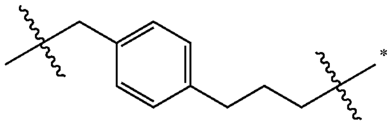

-continued

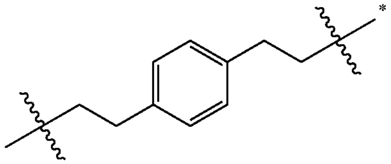

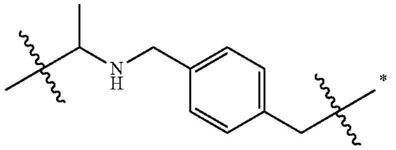

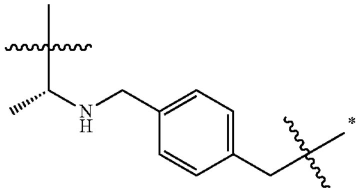

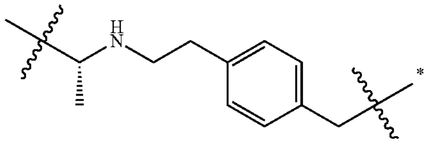

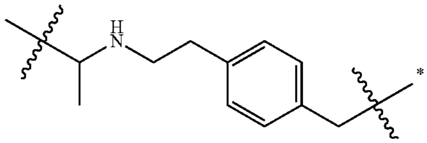

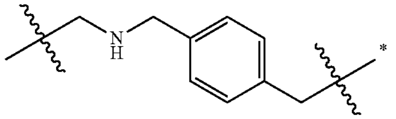

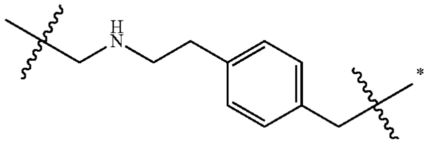

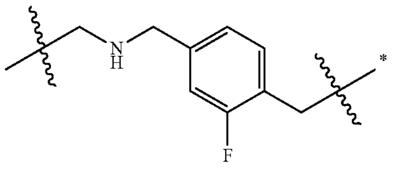

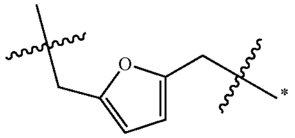

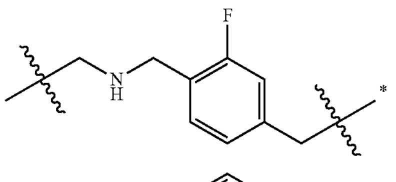

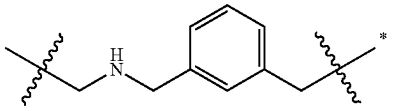

-continued

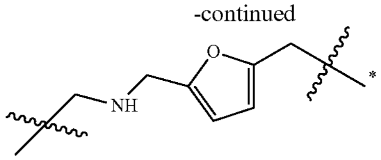

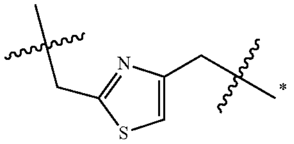

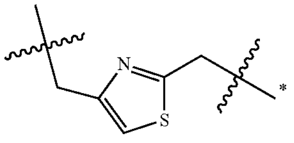

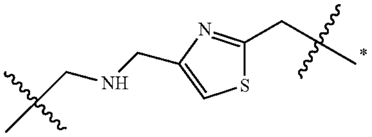

or

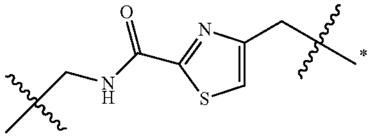

wherein * indicates the point of attachment to R; and the groups are optionally substituted, e.g., by substituent (s) selected from halogen, $C_{1-5}$ alkyl, methanesulfonyloxy, trifluoromethanesulfonyloxy, p-toluenesulfonyloxy, or any combination thereof.

Embodiment 46) relates to the compound of Formula (I) or a salt, a solvate, an isotopically enriched analog, a tautomer, a polymorph, a stereoisomer thereof, or a mixture of stereoisomers thereof as described in any one of embodiments 18) to 45), wherein $X_1$ represents $C(O)NH_2$, piperidine-1-carbonyl, N,N-diisopropylcarbamoyl, $NHC(O)CH_3$, SH, adamantanyl-O— (especially adamantan-1-yl-O—, or adamantan-2-yl-O—), norcamphanyl-O—, 1,7,7-trimethylbicyclo[2.2.1]heptanyl-O— (i.e., bornyl, especially (1S,2R,4S)-1,7,7-trimethylbicyclo[2.2.1]heptan-2-yl-O—), or OH.

Embodiment 47) relates to the compound of Formula (I) or a salt, a solvate, an isotopically enriched analog, a tautomer, a polymorph, a stereoisomer thereof, or a mixture of stereoisomers thereof as described in any one of embodiments 18) to 45), wherein $X_1$ represents cyclohexyl-O— (for example, 2-isopropyl-5-methylcyclohexyl-O—), adamantan-1-yl-O—, adamantan-2-yl-O—, adamantanyl-NH—C(O)—, 3,5-dimethyladamantan-1-yl-NHC(O)—, adamantan-2-yl-NHC(O)—, or $NHC(O)CH_3$.

Embodiment 48) relates to the compound of Formula (I) or a salt, a solvate, an isotopically enriched analog, a tautomer, a polymorph, a stereoisomer thereof, or a mixture of stereoisomers thereof as described in any one of embodiments 18) to 45), wherein $X_1$ represents a linear or branched $C_{1-10}$ alkyl group optionally substituted with one or more fluorine.

Embodiment 49) relates to the compound of Formula (I) or a salt, a solvate, an isotopically enriched analog, a tautomer, a polymorph, a stereoisomer thereof, or a mixture of stereoisomers thereof as described in embodiment 48), wherein $X_1$ represents $CF_2CF_3$, or $CF_3$.

Embodiment 50) relates to the compound of Formula (I) or a salt, a solvate, an isotopically enriched analog, a tautomer, a polymorph, a stereoisomer thereof, or a mixture of stereoisomers thereof as described in any one of embodiments 18) to 45), wherein $X_1$ represents cycloalkyl group optionally substituted with substituent(s) selected from halogen, cyano, $C_{1-3}$ alkyl, $C_{1-3}$ alkoxy, trifluoromethyl, methanesulfonyloxy, trifluoromethanesulfonyloxy, p-toluenesulfonyloxy, $C_{1-5}$ alkyl, or any combination thereof.

Embodiment 51) relates to the compound of Formula (I) or a salt, a solvate, an isotopically enriched analog, a tautomer, a polymorph, a stereoisomer thereof, or a mixture of stereoisomers thereof as described in embodiment 50), wherein $X_1$ represents cyclobutyl, 3,3-difluorocyclobutyl, cyclopentyl, cyclohexyl, cycloheptyl, bicyclo[2.2.1]heptan-2-yl, or adamantanyl.

Embodiment 52) relates to the compound of Formula (I) or a salt, a solvate, an isotopically enriched analog, a tautomer, a polymorph, a stereoisomer thereof, or a mixture of stereoisomers thereof as described in embodiment 50), wherein $X_1$ represents cyclopropyl, 2,3-dihydro-1H-indenyl, or 4-cyano-2,3-dihydro-1H-indenyl.

Embodiment 53) relates to the compound of Formula (I) or a salt, a solvate, an isotopically enriched analog, a tautomer, a polymorph, a stereoisomer thereof, or a mixture of stereoisomers thereof as described in embodiment 50), wherein $X_1$ represents adamantan-1-yl, adamantan-2-yl, 3,5-dimethyladamantan-1-yl, or (1S,2R,4S)-1,7,7-trimethylbicyclo[2.2.1]heptan-2-yl.

Embodiment 54) relates to the compound of Formula (I) or a salt, a solvate, an isotopically enriched analog, a tautomer, a polymorph, a stereoisomer thereof, or a mixture of stereoisomers thereof as described in any one of embodiments 18) to 45), wherein $X_1$ represents a quaternary ammonium salt group of the Formula $N^+R_aR_bR_cX^-$, where $R_a$, $R_b$, and $R_c$ each independently represent $C_{1-20}$ alkyl group, and $X^-$ represents $F^-$, $Cl^-$, $Br^-$, or $I^-$; or where $R_a$ and $R_b$ together with the nitrogen atom to which they are attached form 5- to 8-membered heterocyclyl, and the ring atoms of the 5- to 8-membered heterocyclyl optionally further comprise a heteroatom selected from oxygen, nitrogen, and sulfur, and $R_c$ represents $C_{1-20}$ alkyl; and $X^-$ represents $F^-$, $Cl^-$, $Br^-$, or $I^-$.

Embodiment 55) relates to the compound of Formula (I) or a salt, a solvate, an isotopically enriched analog, a tautomer, a polymorph, a stereoisomer thereof, or a mixture of stereoisomers thereof as described in embodiment 54), wherein $R_a$, $R_b$, and $R_c$ each independently represent a $C_{1-10}$ alkyl group (for example, methyl, ethyl, n-propyl, isopropyl, n-butyl, isobutyl, sec-butyl, tert-butyl, pentyl, isopentyl, neopentyl, tert-amyl, hexyl, heptyl, octyl, nonyl, or decyl).

Embodiment 56) relates to the compound of Formula (I) or a salt, a solvate, an isotopically enriched analog, a tautomer, a polymorph, a stereoisomer thereof, or a mixture of stereoisomers thereof as described in embodiment 54), wherein $R_a$ and $R_b$ each independently represent methyl, ethyl, propyl, isopropyl or butyl; R, represents ethyl; and $X^-$ represents $Cl^-$.

Embodiment 57) relates to the compound of Formula (I) or a salt, a solvate, an isotopically enriched analog, a tautomer, a polymorph, a stereoisomer thereof, or a mixture of stereoisomers thereof as described in embodiment 54), wherein $R_a$, $R_b$, and $R_c$ all represent ethyl, and $X^-$ represents $Cl^-$; or wherein $R_a$, $R_b$ and $R_c$ all represent methyl, and $X^-$ represents $Cl^-$.

Embodiment 58) relates to the compound of Formula (I) or a salt, a solvate, an isotopically enriched analog, a tautomer, a polymorph, a stereoisomer thereof, or a mixture of stereoisomers thereof as described in any one of embodiments 18) to 45), wherein $X_1$ represents a quaternary ammonium salt group of the Formula $N^+R_aR_bR_cX^-$, where $R_a$ and $R_b$ together with the nitrogen atom to which they are attached form 5- to 8-membered heterocyclyl, and the ring atoms of the 5- to 8-membered heterocyclyl optionally further comprise a heteroatom selected from oxygen, nitrogen, and sulfur, and $R_c$ represents $C_{1-20}$ alkyl; and $X^-$ represents $F^-$, $Cl^-$, $Br^-$, or $I^-$.

Embodiment 59) relates to the compound of Formula (I) or a salt, a solvate, an isotopically enriched analog, a tautomer, a polymorph, a stereoisomer thereof, or a mixture of stereoisomers thereof as described in embodiment 58), wherein $X_1$ represents:

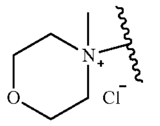

or

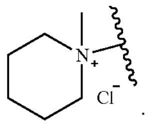

.

Embodiment 60) relates to the compound of Formula (I) or a salt, a solvate, an isotopically enriched analog, a tautomer, a polymorph, a stereoisomer thereof, or a mixture of stereoisomers thereof as described in any one of embodiments 18) to 45), wherein $X_1$ represents aryl group optionally substituted with substituent(s) selected from halogen, halogenated $C_{1-3}$ alkyl, methanesulfonyloxy, trifluoromethanesulfonyloxy, p-toluenesulfonyloxy, $C_{1-5}$ alkyl, or any combination thereof.

Embodiment 61) relates to the compound of Formula (I) or a salt, a solvate, an isotopically enriched analog, a tautomer, a polymorph, a stereoisomer thereof, or a mixture of stereoisomers thereof as described in embodiment 60), wherein $X_1$ represents optionally substituted phenyl or naphthyl.

Embodiment 62) relates to the compound of Formula (I) or a salt, a solvate, an isotopically enriched analog, a tautomer, a polymorph, a stereoisomer thereof, or a mixture of stereoisomers thereof as described in embodiment 60), wherein $X_1$ represents phenyl, 4-fluorophenyl, 4-chlorophenyl, 3,5-difluorophenyl, 4-(bromomethyl)-2-fluorophenyl, or 3,4,5-trifluorophenyl.

Embodiment 63) relates to the compound of Formula (I) or a salt, a solvate, an isotopically enriched analog, a tautomer, a polymorph, a stereoisomer thereof, or a mixture of stereoisomers thereof as described in any one of embodiments 18) to 45), wherein $X_1$ represents optionally substituted heterocyclyl, or optionally substituted heteroaryl, wherein said optionally substituted heterocyclyl is optionally substituted with substituent(s) selected from: $C_{1-6}$ alkyl (for example $C_{1-3}$ alkyl), halogen, oxo, cyano, amino, hydroxy, $C_{1-3}$ alkoxy, halogenated $C_{1-3}$ alkoxy, halogenated $C_{1-3}$ alkyl, di($C_{1-6}$ alkyl)phosphono, $C_{1-6}$ alkylsulfonyl, optionally substituted 6-membered aryl, optionally substituted 5- or 6-membered heterocyclyl, or optionally substituted 5- or 6-membered heteroaryl group, or any combination thereof; and said optionally substituted heteroaryl is optionally substituted with substituent(s) selected from: $C_{1-6}$ alkyl (for example $C_{1-3}$ alkyl), halogen, cyano, amino, hydroxy, $C_{1-3}$ alkoxy, halogenated $C_{1-3}$ alkoxy, halogenated $C_{1-3}$ alkyl, di($C_{1-6}$ alkyl)phosphono, $C_{1-6}$ alkylsulfonyl, optionally substituted 6-membered aryl, optionally substituted 5- or 6-membered heterocyclyl, or optionally substituted 5- or 6-membered heteroaryl group, or any combination thereof.

Embodiment 64) relates to the compound of Formula (I) or a salt, a solvate, an isotopically enriched analog, a tautomer, a polymorph, a stereoisomer thereof, or a mixture of stereoisomers thereof as described in embodiment 63), wherein said optionally substituted 5- or 6-membered heterocyclyl is optionally substituted with substituent(s) selected from: $C_{1-6}$ alkyl (for example $C_{1-3}$ alkyl), cyano, halogenated $C_{1-3}$ alkyl, amino, hydroxyl, halogen, or any combination thereof; and said optionally substituted 6-membered aryl is optionally substituted with substituent(s) selected from $C_{1-6}$ alkyl (e.g., $C_{1-3}$ alkyl), halogenated $C_{1-3}$ alkyl, amino, hydroxyl, halogen, or any combination thereof; and said optionally substituted 5- or 6-membered heteroaryl is optionally substituted with substituent(s) selected from: $C_{1-6}$ alkyl (e.g., $C_{1-3}$ alkyl), halogenated $C_{1-3}$ alkyl, amino, hydroxyl, halogen, or any combination thereof.

Embodiment 65) relates to the compound of Formula (I) or a salt, a solvate, an isotopically enriched analog, a tautomer, a polymorph, a stereoisomer thereof, or a mixture of stereoisomers thereof as described in embodiment 63) or 64), wherein $X_1$ represents:

- optionally substituted morpholinyl, which is optionally substituted with, e.g., $C_{1-6}$ alkyl (for example $C_{1-3}$ alkyl), halogen, oxo, cyano, amino, hydroxy, $C_{1-3}$ alkoxy, halogenated $C_{1-3}$ alkoxy, halogenated $C_{1-3}$ alkyl, di($C_{1-6}$ alkyl)phosphono, $C_{1-6}$ alkylsulfonyl, optionally substituted 6-membered aryl, optionally substituted 5- or 6-membered heterocyclyl, optionally substituted 5- or 6-membered heteroaryl group, or any combination thereof;
- optionally substituted piperidinyl, which is optionally substituted with, e.g., $C_{1-6}$ alkyl (for example $C_{1-3}$ alkyl), halogen, oxo, cyano, amino, hydroxy, $C_{1-3}$ alkoxy, halogenated $C_{1-3}$ alkoxy, halogenated $C_{1-3}$ alkyl, di($C_{1-6}$ alkyl)phosphono, $C_{1-6}$ alkylsulfonyl, optionally substituted 6-membered aryl, optionally substituted 5- or 6-membered heterocyclyl, optionally substituted 5- or 6-membered heteroaryl group, or any combination thereof;
- optionally substituted piperazinyl, which is optionally substituted with, e.g., $C_{1-6}$ alkyl (for example $C_{1-3}$ alkyl), halogen, oxo, cyano, amino, hydroxy, $C_{1-3}$ alkoxy, halogenated $C_{1-3}$ alkoxy, halogenated $C_{1-3}$ alkyl, di($C_{1-6}$ alkyl)phosphono, $C_{1-6}$ alkylsulfonyl, optionally substituted 6-membered aryl, optionally substituted 5- or 6-membered heterocyclyl, optionally substituted 5- or 6-membered heteroaryl group, or any combination thereof;
- optionally substituted 1,4-diazepan-1-yl, which is optionally substituted with, e.g., $C_{1-6}$ alkyl (for example $C_{1-3}$ alkyl), halogen, oxo, cyano, amino, hydroxy, $C_{1-3}$ alkoxy, halogenated $C_{1-3}$ alkoxy, halogenated $C_{1-3}$ alkyl, di($C_{1-6}$ alkyl)phosphono, $C_{1-6}$ alkylsulfonyl, optionally substituted 6-membered aryl, optionally substituted 5- or 6-membered heterocyclyl, optionally substituted 5- or 6-membered heteroaryl group, or any combination thereof;
- optionally substituted 3,8-diazabicyclo[3.2.1]octan-3-yl, which is optionally substituted with, e.g., $C_{1-6}$ alkyl (for example $C_{1-3}$ alkyl), halogen, oxo, cyano, amino, hydroxy, $C_{1-3}$ alkoxy, halogenated $C_{1-3}$ alkoxy, halogenated $C_{1-3}$ alkyl, di($C_{1-6}$ alkyl)phosphono, $C_{1-6}$ alkylsulfonyl, optionally substituted 6-membered aryl, optionally substituted 5- or 6-membered heterocyclyl, optionally substituted 5- or 6-membered heteroaryl group, or any combination thereof;
- optionally substituted 2,5-diazabicyclo[2.2.2]octan-2-yl, which is optionally substituted with, e.g., $C_{1-6}$ alkyl (for example $C_{1-3}$ alkyl), halogen, oxo, cyano, amino, hydroxy, $C_{1-3}$ alkoxy, halogenated $C_{1-3}$ alkoxy, halogenated $C_{1-3}$ alkyl, di($C_{1-6}$ alkyl)phosphono, $C_{1-6}$ alkylsulfonyl, optionally substituted 6-membered aryl, optionally substituted 5- or 6-membered heterocyclyl, optionally substituted 5- or 6-membered heteroaryl group, or any combination thereof;
- optionally substituted pyrrolidinyl, which is optionally substituted with, e.g., $C_{1-6}$ alkyl (for example $C_{1-3}$ alkyl), halogen, cyano, amino, hydroxy, $C_{1-3}$ alkoxy, halogenated $C_{1-3}$ alkoxy, halogenated $C_{1-3}$ alkyl, di($C_{1-6}$ alkyl)phosphono, $C_{1-6}$ alkylsulfonyl, optionally substituted 6-membered aryl, optionally substituted 5- or 6-membered heterocyclyl, or optionally substituted 5- or 6-membered heteroaryl group, or any combination thereof;
- optionally substituted quinazolinyl, which is optionally substituted with, e.g., $C_{1-6}$ alkyl (for example $C_{1-3}$ alkyl), halogen, cyano, amino, hydroxy, $C_{1-3}$ alkoxy, halogenated $C_{1-3}$ alkoxy, halogenated $C_{1-3}$ alkyl, di($C_{1-6}$ alkyl)phosphono, $C_{1-6}$ alkylsulfonyl, optionally substituted 6-membered aryl, optionally substituted 5- or 6-membered heterocyclyl, optionally substituted 5- or 6-membered heteroaryl group, or any combination thereof;
- optionally substituted pyridyl, which is optionally substituted with, e.g., $C_{1-6}$ alkyl (for example $C_{1-3}$ alkyl), halogen, cyano, amino, hydroxy, $C_{1-3}$ alkoxy, halogenated $C_{1-3}$ alkoxy, halogenated $C_{1-3}$ alkyl, di($C_{1-6}$ alkyl)phosphono, $C_{1-6}$ alkylsulfonyl, optionally substituted 6-membered aryl, optionally substituted 5- or 6-membered heterocyclyl, optionally substituted 5- or 6-membered heteroaryl group, or any combination thereof;
- optionally substituted pyrimidinyl, which is optionally substituted with, e.g., $C_{1-6}$ alkyl (for example $C_{1-3}$ alkyl), halogen, cyano, amino, hydroxy, $C_{1-3}$ alkoxy, halogenated $C_{1-3}$ alkoxy, halogenated $C_{1-3}$ alkyl, di($C_{1-6}$ alkyl)phosphono, $C_{1-6}$ alkylsulfonyl, optionally substituted 6-membered aryl, optionally substituted 5- or 6-membered heterocyclyl, optionally substituted 5- or 6-membered heteroaryl group, or any combination thereof;
- optionally substituted thiazolyl, which is optionally substituted with, e.g., $C_{1-6}$ alkyl (for example $C_{1-3}$ alkyl), halogen, cyano, amino, hydroxy, $C_{1-3}$ alkoxy, halogenated $C_{1-3}$ alkoxy, halogenated $C_{1-3}$ alkyl, di($C_{1-6}$ alkyl)phosphono, $C_{1-6}$ alkylsulfonyl, optionally substituted 6-membered aryl, optionally substituted 5- or 6-membered heterocyclyl, optionally substituted 5- or 6-membered heteroaryl group, or any combination thereof;
- optionally substituted quinolyl, which is optionally substituted with, e.g., $C_{1-6}$ alkyl (for example $C_{1-3}$ alkyl), halogen, cyano, amino, hydroxy, $C_{1-3}$ alkoxy, halogenated $C_{1-3}$ alkoxy, halogenated $C_{1-3}$ alkyl, di($C_{1-6}$ alkyl)phosphono, $C_{1-6}$ alkylsulfonyl, optionally substituted 6-membered aryl, optionally substituted 5- or 6-membered heterocyclyl, optionally substituted 5- or 6-membered heteroaryl group, or any combination thereof;
- optionally substituted indolyl, which is optionally substituted with, e.g., $C_{1-6}$ alkyl (for example $C_{1-3}$ alkyl), halogen, cyano, amino, hydroxy, $C_{1-3}$ alkoxy, halogenated $C_{1-3}$ alkoxy, halogenated $C_{1-3}$ alkyl, di($C_{1-6}$ alkyl)phosphono, $C_{1-6}$ alkylsulfonyl, optionally substituted 6-membered aryl, optionally substituted 5- or 6-membered heterocyclyl, or optionally substituted 5- or 6-membered heteroaryl group, or any combination thereof;

optionally substituted benzothienyl, which is optionally substituted with, e.g., $C_{1-6}$ alkyl (for example $C_{1-3}$ alkyl), halogen, cyano, amino, hydroxy, $C_{1-3}$ alkoxy, halogenated $C_{1-3}$ alkoxy, halogenated $C_{1-3}$ alkyl, di($C_{1-6}$ alkyl)phosphono, $C_{1-6}$ alkylsulfonyl, optionally substituted 6-membered aryl, optionally substituted 5- or 6-membered heterocyclyl, optionally substituted 5- or 6-membered heteroaryl group, or any combination thereof;

optionally substituted benzofuranyl, which is optionally substituted with, e.g., $C_{1-6}$ alkyl (for example $C_{1-3}$ alkyl), halogen, cyano, amino, hydroxy, $C_{1-3}$ alkoxy, halogenated $C_{1-3}$ alkoxy, halogenated $C_{1-3}$ alkyl, di($C_{1-6}$ alkyl)phosphono, $C_{1-6}$ alkylsulfonyl, optionally substituted 6-membered aryl, optionally substituted 5- or 6-membered heterocyclyl, optionally substituted 5- or 6-membered heteroaryl group, or any combination thereof.

Embodiment 66) relates to the compound of Formula (I) or a salt, a solvate, an isotopically enriched analog, a tautomer, a polymorph, a stereoisomer thereof, or a mixture of stereoisomers thereof as described in embodiment 63) or 64), wherein $X_1$ represents the following optionally substituted groups: 2-azabicyclo[3.2.1]octyl; 1,4-diazabicyclo [3.2.1]octyl; tetrahydro-2H-pyranyl; azacycloheptyl; azacyclooctyl; isoindolyl; thiomorpholino; 5-azaspiro[2.4]heptyl; 6-azaspiro[2.5]octyl; 2-oxa-7-azaspiro[3.5]nonyl; 3-azabicyclo[3.1.0]hexyl; 3-azabicyclo[4.1.0]heptyl; 5,7-dihydro-6H-pyrrolo[3,4-b]pyridyl; 3-azaspiro[5.5]undecan-3-yl; hexahydro-1H-isoindol-2(3H)-yl; (3aR,7aS)-hexahydro-1H-isoindol-2(3H)-yl; (3aR,7aS)-octahydro-2H-isoindol-2-yl; azetidinyl; or [1,4'-dipiperidin]-1'-yl; wherein the groups are optionally substituted with substituent(s) selected from: $C_{1-6}$ alkyl (for example $C_{1-3}$ alkyl), halogen, cyano, amino, hydroxy, oxo, $C_{1-3}$ alkoxy, halogenated $C_{1-3}$ alkoxy, halogenated $C_{1-3}$ alkyl, di($C_{1-6}$ alkyl)phosphono, $C_{1-6}$ alkylsulfonyl, optionally substituted 6-membered aryl, optionally substituted 5- or 6-membered heterocyclyl, optionally substituted 5- or 6-membered heteroaryl group, or any combination thereof.

Embodiment 67) relates to the compound of Formula (I) or a salt, a solvate, an isotopically enriched analog, a tautomer, a polymorph, a stereoisomer thereof, or a mixture of stereoisomers thereof as described in embodiment 65), wherein $X_1$ represents: morpholinyl; piperidinyl; piperazinyl; N-methylpiperazinyl; (N-methylpiperazinyl)piperidinyl; 3,5-dimethylpiperazinyl; 1,4-diazepan-1-yl; 4-methyl-1,4-diazepan-1-yl; 1-methyl-1,4-diazepan-1-yl; 8-methyl-3,8-diazabicyclo[3.2.1]octan-3-yl; 5-methyl-2,5-diazabicyclo [2.2.2]octan-2-yl; 4-(4-fluorophenyl)piperazin-1-yl; 4-(3,4-difluorophenyl)piperazin-1-yl; 2-oxopiperidin-1-yl; 2-oxopyrrolidin-1-yl; 2,6-dioxopiperidin-3-yl; pyridyl; pyrimidinyl; thiazolyl; quinolyl; 6,7-difluoroquinazolin-4-yl; 3-cyano-quinolyl; indolyl; 1-methyl-1H-indol-7-yl; benzothienyl; benzofuranyl; quinazolinyl; 6,7-difluoroquinazolin-4-yl; pyrrolidinyl; 4-(pyridin-3-yl)pyrimidin-2-yl; or 4,4-difluoropiperidinyl.

Embodiment 68) relates to the compound of Formula (I) or a salt, a solvate, an isotopically enriched analog, a tautomer, a polymorph, a stereoisomer thereof, or a mixture of stereoisomers thereof as described in embodiment 65) or 66), wherein $X_1$ represents: 2-oxopiperidin-1-yl; 4-(methylsulfonyl)piperazin-1-yl; 4-(ethylsulfonyl)piperazin-1-yl; 1,4-diazabicyclo[3.2.1]octan-4-yl; 8,8-difluoro-2-azabicyclo[3.2.1]octan-2-yl; 3-fluoro-4-hydroxypyrrolidin-1-yl; 3-methyl-4-(trifluoromethyl)pyrrolidin-1-yl; 4,4-dimethylpiperidin-1-yl; 3,5-dimethylpiperidin-1-yl; 4,4-difluoropiperidin-1-yl; 4-methylpiperazin-1-yl; tetrahydro-2H-pyran-2-yl; pyrrolidin-1-yl; 3-cyanoazetidinyl; 3-hydroxyazetidinyl; 3-hydroxy-3-methylazetidinyl; 3-hydroxy-2-methylazetidin-1-yl; 3-(trifluoromethoxy)azetidin-1-yl; azepan-1-yl; azacyclooctan-1-yl; 7-fluoro-5-azaspiro [2.4]heptan-5-yl; 1,1-difluoro-5-azaspiro[2.4]heptan-5-yl; 1,1-difluoro-6-azaspiro[2.5]octan-6-yl; 6-azaspiro[2.5]octan-6-yl; 2-oxa-7-azaspiro[3.5]nonan-7-yl; 3-azabicyclo [3.1.0]hexan-3-yl; 6-(difluoromethyl)-3-azabicyclo[4.1.0] heptan-3-yl; 3-fluoro-5,7-dihydro-6H-pyrrolo[3,4-b] pyridin-6-yl; 3-(trifluoromethyl)-5,7-dihydro-6H-pyrrolo[3,4-b]pyridin-6-yl; isoindol-2-yl; thiomorpholino; [1,4'-dipiperidin]-1'-yl;

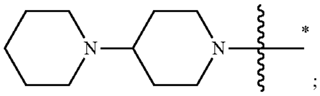

; or

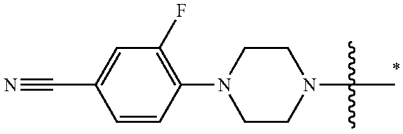

;

wherein * indicates the point of attachment to R.

Embodiment 69) relates to the compound of Formula (I) or a salt, a solvate, an isotopically enriched analog, a tautomer, a polymorph, a stereoisomer thereof, or a mixture of stereoisomers thereof as described in any one of embodiments 18) to 45), wherein $X_1$ represents an optionally substituted cycloalkyl or optionally substituted aryl, wherein said optionally substituted cycloalkyl is optionally substituted with substituent(s) selected from: $C_{1-6}$ alkyl, halogen, $C_{1-3}$ alkoxycarbonyl, or any combination thereof; and wherein said optionally substituted aryl is optionally substituted with substituent(s) selected from: halogenated $C_{2-4}$ alkenyl, halogen, or any combination thereof.

Embodiment 70) relates to the compound of Formula (I) or a salt, a solvate, an isotopically enriched analog, a tautomer, a polymorph, a stereoisomer thereof, or a mixture of stereoisomers thereof as described in embodiment 69), wherein $X_1$ represents (2-bromovinyl)phenyl, or

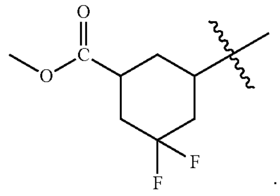 [SMILES: *C1CC(C(=O)OC)CC(F)(F)C1]

.

Embodiment 71) relates to the compound of Formula (I) or a salt, a solvate, an isotopically enriched analog, a tautomer, a polymorph, a stereoisomer thereof, or a mixture of stereoisomers thereof as described in any one of embodiments 18) to 45), wherein $X_1$ represents $NR_6R_7$, wherein $R_6$ and $R_7$ each independently represent H or an optionally substituted linear or branched $C_{1-10}$ alkyl group, provided that $R_6$ and $R_7$ are not H at the same time.

Embodiment 72) relates to the compound of Formula (I) or a salt, a solvate, an isotopically enriched analog, a tautomer, a polymorph, a stereoisomer thereof, or a mixture of stereoisomers thereof as described in embodiment 71), wherein $X_1$ represents $NHCH_3$, $N(CH_3)_2$, $N(CH_2CH_3)_2$, or $N(CH(CH_3)_2)_2$.

Embodiment 73) relates to the compound of Formula (I) or a salt, a solvate, an isotopically enriched analog, a tautomer, a polymorph, a stereoisomer thereof, or a mixture of stereoisomers thereof as described in any one of embodiments 18) to 45), wherein $X_1$ represents $NR_6R_7$, wherein $R_6$ represents H and $R_7$ represents substituted ethyl, wherein the substituent of said substituted ethyl is 2,6-dichloro-3-fluorophenyl.

Embodiment 74) relates to the compound of Formula (I) or a salt, a solvate, an isotopically enriched analog, a tautomer, a polymorph, a stereoisomer thereof, or a mixture of stereoisomers thereof as described in any one of embodiments 18) to 45), wherein $X_1$ represents $NR_6R_7$, wherein $R_6$ represents H or methyl; and $R_7$ represents the following groups: optional substituted cycloalkyl; optionally substituted aryl; optionally substituted heterocyclyl; or optionally substituted heteroaryl; wherein the groups are optionally substituted with substituent(s) selected from: halogen; $C_{1-5}$ alkyl, di($C_{1-6}$ alkyl)phosphono; $C_{1-6}$ alkylsulfonyl; oxo; optionally substituted 6-membered aryl; optionally substituted 5- or 6-membered heterocyclyl; optionally substituted 5- or 6-membered heteroaryl; or cyano; wherein said optionally substituted 5- or 6-membered heterocyclyl is optionally substituted with substituent (s) selected from $C_{1-6}$ alkyl or halogen; said optionally substituted 6-membered aryl is optionally substituted with substituent(s) selected from $C_{1-6}$ alkyl or halogen; and said optionally substituted 5- or 6-membered heteroaryl is optionally substituted with substituent(s) selected from $C_{1-6}$ alkyl or halogen.

Embodiment 75) relates to the compound of Formula (I) or a salt, a solvate, an isotopically enriched analog, a tautomer, a polymorph, a stereoisomer thereof, or a mixture of stereoisomers thereof as described in embodiment 74), wherein $X_1$ represents $NR_6R_7$, wherein $R_6$ represents H or methyl; and $R_7$ represents pyrimidinyl, pyrrolidinyl (especially pyrrolidin-1-yl), pyridyl, quinazolinyl, 6,7-difluoroquinazolin-4-yl, phenyl, 3-chloro-4-methylphenyl, 4-fluorophenyl, 3,5-difluorophenyl, 3,4,5-trifluorophenyl, 2-(dimethylphosphono)phenyl, 2-(isopropylsulfonyl) phenyl, 4-(pyridin-3-yl)pyrimidin-2-yl, indolyl, 1-methyl-1H-indol-7-yl, benzothienyl, benzo[b]thien-7-yl, benzofuran-7-yl, benzofuranyl, 3-cyano-quinol-4-yl, quinolyl, thiazolyl, adamantanyl, adamantan-1-yl, adamantan-2-yl, 3,5-dimethyladamantan-1-yl, 1,7,7-trimethylbicyclo[2.2.1]heptan-2-yl, 4-(4-methylpiperazin-1-yl)piperidin-1-yl, cyclohexyl, dimethylcyclohexyl (for example, 4,4-dimethylcyclohexyl), $C_{7-12}$ spiro-cycloalkyl (for example, spiro[5.5]undec-3-yl, spiro[3.3]heptyl, spiro[3.3]hept-2-yl), azepanyl (for example, azepan-1-yl), azacyclooctanyl (for example, azacyclooctan-1-yl), piperidinyl, dimethylpiperidinyl (for example, 4,4-dimethylpiperidinyl, 3,5-dimethylpiperidinyl), or azaspirocycloalkyl (for example, 3-azaspiro[5.5]undec-3-yl).

Embodiment 76) relates to the compound of Formula (I) or a salt, a solvate, an isotopically enriched analog, a tautomer, a polymorph, a stereoisomer thereof, or a mixture of stereoisomers thereof as described in any one of embodiments 18) to 45), wherein $X_1$ represents $NR_6R_7$, wherein $R_6$ represents H, methyl, ethyl, isopropyl, or cyclohexyl; and $R_7$ represents the following optionally substituted groups: adamantanyl, noradamantanyl, norcamphanyl, cyclohexyl, cyclopentyl, cyclopropyl, cyclobutyl, ethyl, isopropyl, tert-butyl, methyl, 2,4-dimethylpent-3-yl, dicyclopropylmethyl, spiro[3.3]heptyl, bicyclo[1.1.1]pentyl, bicyclo[2.2.2]octyl, 4,4-dimethylcyclohexyl, oxetanyl, oxazolyl, 2,3-dihydro-1H-indenyl, quinuclidinyl, 1,7,7-trimethylbicyclo[2.2.1]heptyl, 7,7-dimethylbicyclo[2.2.1]heptyl, bicyclo[2.2.1]heptyl, or 1-cyclopropylethyl.

Embodiment 77) relates to the compound of Formula (I) or a salt, a solvate, an isotopically enriched analog, a tautomer, a polymorph, a stereoisomer thereof, or a mixture of stereoisomers thereof as described in embodiment 76), wherein $R_7$ represents bicyclo[1.1.1]pent-1-yl, 4,4-dimethylcyclohexyl, 2-methoxycyclopropyl, 3-fluorocyclobutyl, 3,3-difluorocyclobutyl, 3,3-difluoro-1-(2-(trifluoromethyl) phenyl)cyclobutyl, 3-(2-(trifluoromethyl)phenyl)oxetan-3-yl, 3,3-difluorocyclopentyl, 3-hydroxycyclohexyl, (1S,3S)-3-hydroxycyclohexyl, 3-cyano-bicyclo[1.1.1]pent-1-yl, bicyclo[2.2.2]octan-1-yl, 4-hydroxybicyclo[2.2.2]octan-1-yl, 2-isopropyl-5-methylcyclohexyl, 5-methyloxazol-2-yl , 4-cyano-2,3-dihydro-1H-inden-1-yl, 2,4-dimethylpentan-3-yl, dicyclopropylmethyl, quinuclidin-3-yl, (S)-quinuclidin-3-yl, (R)-quinuclidin-3-yl, adamantan-1-yl, 3-hydroxyadamantanyl, 3-hydroxyadamantan-1-yl, 3-chloroadamantan-1-yl, 4-chloroadamantan-1-yl, 2-chloroadamantan-1-yl, adamantan-2-yl, 1,7,7-trimethylbicyclo[2.2.1]heptan-2-yl, 7,7-dimethylbicyclo[2.2.1]heptan-1-yl, 7,7-dimethyl-2-oxo-bicyclo[2.2.1]heptan-1-yl, 3,5-dimethyladamantanyl, 3,5-dimethyladamantan-1-yl, hexahydro-2,5-methanopentalen-3a(1H)-yl, bicyclo[2.2.1]heptyl, bicyclo[2.2.1]heptan-2-yl, 1-cyclopropylethyl, or

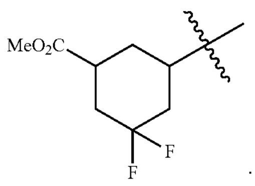 [SMILES: *C1CC(C(=O)OC)CC(F)(F)C1]

.

Embodiment 78) relates to the compound of Formula (I) or a salt, a solvate, an isotopically enriched analog, a tautomer, a polymorph, a stereoisomer thereof, or a mixture of stereoisomers thereof as described in any one of embodiments 18) to 45), wherein $X_1$ represents $NR_6R_7$, where $R_6$ represents H, and $R_7$ represents thiazolyl which is substituted with the group of the Formula C(O)NHR$_d$, where $R_d$ represents a $C_{1-5}$ alkyl or 2-chloro-6-methylphenyl.

Embodiment 79) relates to the compound of Formula (I) or a salt, a solvate, an isotopically enriched analog, a tautomer, a polymorph, a stereoisomer thereof, or a mixture of stereoisomers thereof as described in any one of embodiments 18) to 45), wherein $X_1$ represents $NR_6R_7$, where $R_6$ represents H and $R_7$ represents pyrimidin-4-yl, pyridin-4-yl, or quinazolin-4-yl; or wherein $X_1$ represents $NR_6R_7$, where $R_6$ and $R_7$ represent phenyl.

Embodiment 80) relates to the compound of Formula (I) or a salt, a solvate, an isotopically enriched analog, a tautomer, a polymorph, a stereoisomer thereof, or a mixture of stereoisomers thereof as described in any one of embodiments 18) to 45), wherein $X_1$ represents $NHC(O)NR_9R_{10}$, where $R_9$ represents H, and $R_{10}$ represents adamantanyl, adamantan-1-yl, adamantan-2-yl, 3,5-dimethyladamantan-1-yl, phenyl, or 3-chloro-4-methylphenyl.

Embodiment 81) relates to the compound of Formula (I) or a salt, a solvate, an isotopically enriched analog, a tautomer, a polymorph, a stereoisomer thereof, or a mixture of stereoisomers thereof as described in any one of embodiments 18) to 45), wherein $X_1$ represents $C(O)NH_2$, piperidin-1-carbonyl, N,N-diisopropylcarbamoyl.

Embodiment 82) relates to the compound of Formula (I) or a salt, a solvate, an isotopically enriched analog, a tautomer, a polymorph, a stereoisomer thereof, or a mixture of stereoisomers thereof as described in any one of embodiments 18) to 45), wherein $X_1$ represents OH, adamantanyl-O—, norcamphanyl-O—, or 1,7,7-trimethyl-bicyclo[2.2.1]heptanyl-O— (for example, (1S,2R,4S)-1,7,7-trimethyl-bicyclo[2.2.1]heptanyl-O—).

Embodiment 83) relates to the compound of Formula (I) or a salt, a solvate, an isotopically enriched analog, a tautomer, a polymorph, a stereoisomer thereof, or a mixture of stereoisomers thereof as described in any one of embodiments 18) to 45), wherein $X_1$ represents a optionally substituted linear or branched $C_{1-10}$ alkyl, which is optionally substituted, for example, by one or more fluorine. In a sub-embodiment, $X_1$ represents methyl, ethyl, propyl, isopropyl, n-butyl, isobutyl, sec-butyl, tert-butyl, pentyl, isopentyl, neopentyl, tert-amyl, hexyl, heptyl, octyl, nonyl, decyl, $CF_2CF_3$ or $CF_3$.

Embodiment 84) relates to the compound of Formula (I) or a salt, a solvate, an isotopically enriched analog, a tautomer, a polymorph, a stereoisomer thereof, or a mixture of stereoisomers thereof as described in any one of embodiments 18) to 45), wherein $X_1$ represents $NHC(O)R_8$, where $R_8$ represents a linear or branched $C_{1-6}$ alkyl, aryl, heteroaryl or heterocyclyl. In a sub-embodiment, $X_1$ represents $NHC(O)CH_3$.

Embodiment 85) relates to the compound of Formula (I) or a salt, a solvate, an isotopically enriched analog, a tautomer, a polymorph, a stereoisomer thereof, or a mixture of stereoisomers thereof as described in any one of embodiments 18) to 45), wherein $X_1$ represents $NHC(O)NR_9R_{10}$, where $R_9$ and $R_{10}$ each independently represent H, an optionally substituted linear or branched $C_{1-10}$ alkyl group, an optionally substituted cycloalkyl group, an optionally substituted aryl group, an optionally substituted heterocyclyl, or a an optionally substituted heteroaryl, wherein $R_9$ and $R_{10}$ are optionally not H at the same time.

Embodiment 86) relates to the compound of Formula (I) or a salt, a solvate, an isotopically enriched analog, a tautomer, a polymorph, a stereoisomer thereof, or a mixture of stereoisomers thereof as described in any one of embodiments 18) to 45) or 85), wherein $X_1$ represents $NHC(O)NR_9R_{10}$, where $R_9$ and $R_{10}$ each independently represent H, or the following optionally substituted groups: methyl, ethyl, propyl, isopropyl, n-butyl, isobutyl, sec-butyl, tert-butyl, pentyl, isopentyl, neopentyl, tert-amyl, hexyl, heptyl, octyl, nonyl, decyl, phenyl, naphthyl, pyrimidinyl, pyridyl, quinazolinyl, quinolinyl, isoquinolinyl, pyrrolyl, imidazolyl, pyrazolyl, triazolyl, pyridyl, pyrimidinyl, pyridazinyl, pyrazinyl, indolyl, isoindolyl, indazolyl, benzimidazolyl, benzotriazolyl, naphthyridinyl, cinnolinyl, quinoxalinyl, phthalazinyl, pyrazolo[1,5-a]pyridinyl, pyrazolo[1,5-a]pyrimidinyl, imidazo[1,2-a]pyridinyl, 1H-pyrrolo[3,2-b]pyridyl, 1H-pyrrolo[2,3-b]pyridyl, 4H-fluoro[3,2-b]pyrrolyl, adamantanyl, adamantan-1-yl, adamantan-2-yl, 3,5-dimethyladamantan-1-yl, phenyl, or 3-chloro-4-methylphenyl.

Embodiment 87) relates to the compound of Formula (I) or a salt, a solvate, an isotopically enriched analog, a tautomer, a polymorph, a stereoisomer thereof, or a mixture of stereoisomers thereof as described in any one of embodiments 18) to 45), 85), or 86), wherein $X_1$ represents $NHC(O)NR_9R_{10}$, where $R_9$ represents H, and $R_{10}$ represents adamantanyl, adamantan-1-yl, adamantan-2-yl, 3,5-dimethyladamantan-1-yl, phenyl, or 3-chloro-4-methylphenyl.

Embodiment 88) relates to the compound of Formula (I) or a salt, a solvate, an isotopically enriched analog, a tautomer, a polymorph, a stereoisomer thereof, or a mixture of stereoisomers thereof as described in any one of embodiments 18) to 45), wherein $X_1$ represents optionally substituted cycloalkyl (for example, $C_3$-$C_{12}$ cycloalkyl or $C_3$-$C_{10}$ cycloalkyl). In a sub-embodiment, the cycloalkyl group is optionally substituted with halogen, methanesulfonyloxy, trifluoromethanesulfonyloxy, p-toluenesulfonyloxy, oxo, $C_{1-3}$ alkyl, $C_{1-3}$ alkoxy, cyano, or trifluoromethyl. In a sub-embodiment, $X_1$ represents cyclobutyl, 3,3-difluorocyclobutyl, cyclopentyl, cyclohexyl, cycloheptyl, bicyclo[2.2.1]heptan-2-yl, or adamantantanyl. In a sub-embodiment, $X_1$ represents adamantan-1-yl, adamantan-2-yl, 3,5-dimethyladamantan-1-yl, or (1S,2R,4S)-1,7,7-trimethylbicyclo[2.2.1]heptan-2-yl.

Embodiment 89) relates to the compound of Formula (I) or a salt, a solvate, an isotopically enriched analog, a tautomer, a polymorph, a stereoisomer thereof, or a mixture of stereoisomers thereof as described in any one of embodiments 18) to 45), wherein $X_1$ represents optionally substituted aryl (for example, 5- to 14-numbered aryl). In a sub-embodiment, the aryl group is optionally substituted with halogen, methanesulfonyloxy, trifluoromethanesulfonyloxy, p-toluenesulfonyloxy, or $C_{1-3}$ alkyl. In a sub-embodiment, $X_1$ represents phenyl, 3-chloro-4-methylphenyl, naphthyl, or fluorenyl. In a sub-embodiment, $X_1$ represents phenyl, 4-fluorophenyl, 3,5-difluorophenyl, or 3,4,5-trifluorophenyl.

Embodiment 90) relates to the compound of Formula (I) or a salt, a solvate, an isotopically enriched analog, a tautomer, a polymorph, a stereoisomer thereof, or a mixture of stereoisomers thereof as described in any one of embodiments 18) to 45), wherein $X_1$ represents optionally substituted heterocyclyl (for example, 3- to 12-numbered heterocyclyl). In a sub-embodiment, the heterocyclyl is optionally substituted with $C_{1-6}$ alkyl, oxo, bis($C_{1-6}$ alkyl)phosphono, $C_{1-6}$ alkylsulfonyl, optionally substituted 5- or 6-membered heteroaryl, halogen, methanesulfonyloxy, trifluoromethanesulfonyloxy, or p-toluenesulfonyloxy, oxo, $C_{1-3}$ alkoxy, cyano, trifluoromethyl, optionally substituted aryl (for example, optionally substituted 6-membered aryl group, such as phenyl, or 4-fluorophenyl), optionally substituted heterocyclyl (such as optionally substituted 5- or 6-membered heterocyclyl, such as piperazinyl, N-methylpiperazinyl), amino, or hydroxy. In a sub-embodiment, the optional substituent(s) of the optionally substituted 5- or 6-membered heterocyclyl is selected from $C_{1-6}$ alkyl or halogen, and the optional substituent(s) of the optionally substituted 6-membered aryl group is selected from $C_{1-6}$ alkyl or halogen, and the substituents of the optionally substituted 5- or 6-membered heteroaryl are selected from $C_{1-6}$ alkyl or halogen. In a sub-embodiment, $X_1$ represents the following optionally substituted heterocyclyl: azetidinyl, oxetanyl, pyrrolidinyl, imidazolidinyl, pyrazolidinyl, piperidinyl, triazolyl, tetrahydrofuranyl, tetrahydropyranyl, tetrahydrothienyl, tetrahydrothiopyranyl, oxazolidinyl, thiazolidinyl, piperidinyl, piperazinyl, morpholinyl, thiomorpholinyl, dioxacyclohexyl, 1,4-diazacycloheptan-1-yl, 3,8-diazabicyclo[3.2.1]octan-3-yl, or 2,5-diazabicyclo[2.2.2]octan-2-yl, wherein the substituents of said optionally substituted heterocyclyl may be selected from halogen, methanesulfonyloxy, trifluoromethanesulfonyloxy, or p-toluenesulfonyloxy, oxo, $C_{1-3}$ alkyl, $C_{1-3}$ alkoxy, cyano, trifluoromethyl, optionally substituted aryl (especially phenyl, 4-fluorophenyl), optionally substituted heterocyclyl (for example, piperazinyl, N-methylpiperazinyl), amino, or hydroxyl. In a sub-embodiment, $X_1$ represents morpholinyl, piperidinyl, piperazinyl, N-methylpiperazinyl, (N-methylpiperazinyl)piperidinyl, 3,5-dimethylpiperazin-1-yl, 1,4-diazepan-1-yl, 4-methyl-1,4-diazepan-1-yl, 1-methyl-1,4-diazepan-1-yl, 4-(4-fluorophenyl) piperazin-1-yl, 4-(3,4-difluorophenyl)piperazin-1-yl, 4,4-difluoropiperidin-1-yl, 2-oxopiperidin-1-yl, pyrrolidinyl, 2-oxopyrrolidin-1-yl, 2,6-dioxopiperidin-3-yl, 1-methyl-1,4-diazepan-1-yl, 8-methyl-3,8-diazabicyclo[3.2.1]octan-3-yl, or 5-methyl-2,5-diazabicyclo[2.2.2]octan-2-yl.

Embodiment 91) relates to the compound of Formula (I) or a salt, a solvate, an isotopically enriched analog, a tautomer, a polymorph, a stereoisomer thereof, or a mixture of stereoisomers thereof as described in any one of embodiments 18) to 45), wherein $X_1$ represents optionally substituted heteroaryl (for example, 5- to 10-numbered heteroaryl). In a sub-embodiment, the heteroaryl group is optionally substituted with $C_{1-6}$ alkyl, oxo, bis($C_{1-6}$ alkyl) phosphono, $C_{1-6}$ alkylsulfonyl, optionally substituted 6-membered aryl, optionally substituted 5- or 6-membered heterocyclyl, or optionally substituted 5- or 6-membered heteroaryl, halogen, methanesulfonyloxy, trifluoromethanesulfonyloxy, or p-toluenesulfonyloxy, oxo, $C_{1-3}$ alkoxy, cyano, or trifluoromethyl. In a sub-embodiment, the optional substituent(s) of the optionally substituted 5- or 6-membered heterocyclyl is selected from $C_{1-6}$ alkyl or halogen, and the optional substituent(s) of the optionally substituted 6-membered aryl is selected from $C_{1-6}$ alkyl or halogen, and the optional substituent(s) of the optionally substituted 5- or 6-membered heteroaryl is selected from $C_{1-6}$ alkyl or halogen. In a sub-embodiment, $X_1$ represents optionally substituted quinazolinyl, optionally substituted pyridyl, optionally substituted pyrimidinyl, optionally substituted thiazolyl, optionally substituted quinolinyl, optionally substituted indolyl, optionally substituted benzothienyl, or optionally substituted benzofuryl, wherein the optional substituents are as defined above. In a sub-embodiment, $X_1$ represents pyridyl, pyrimidinyl, thiazolyl, quinolinyl, 6,7-difluoroquinazolin-4-yl, 3-cyano-quinolinyl, indolyl, 1-methyl-1H-indol-7-yl, benzothienyl, benzofuranyl, quinazolinyl, 6,7-difluoroquinazolin-4-yl, or 4-(pyridin-3-yl)pyrimidin-2-yl.

Embodiment 92) relates to the compound of Formula (I) or a salt, a solvate, an isotopically enriched analog, a tautomer, a polymorph, a stereoisomer thereof, or a mixture of stereoisomers thereof as described in any one of embodiments 18) to 45), wherein $X_1$ represents a group of Formula ($G_1$):

Formula ($G_1$)

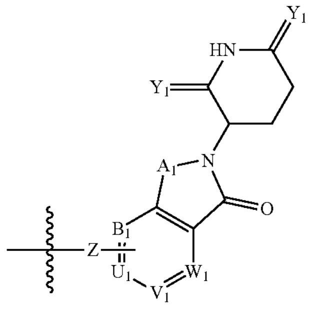

wherein, $A_1$ represents $CH_2$ or C(O);

$B_1$, $U_1$, $V_1$, and $W_1$ are the same and all represent CH; or one of $B_1$, $U_1$, $V_1$, $W_1$ is N, and the rest are CH; or two of $B_1$, $U_1$, $V_1$, $W_1$ are N, and the rest are CH; or three of $B_1$, $U_1$, $V_1$, $W_1$ are N, and the rest is CH; or $Y_1$ represents O or S; and Z represents S, S(O), or $S(O)_2$;

Embodiment 93) relates to the compound of Formula (I) or a salt, a solvate, an isotopically enriched analog, a tautomer, a polymorph, a stereoisomer thereof, or a mixture of stereoisomers thereof as described in any one of embodiments 18) to 45) or 92), wherein $X_1$ represents a group of Formula ($G_2$):

Formula ($G_2$)

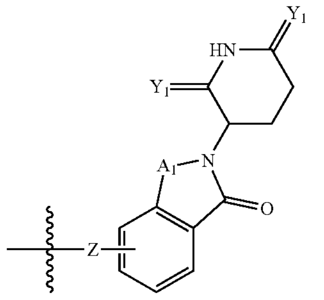

wherein, $A_1$ represents $CH_2$ or C(O), $Y_i$ represents O or S, and Z represents S, S(O), or $S(O)_2$.

Embodiment 94) relates to the compound of Formula (I) or a salt, a solvate, an isotopically enriched analog, a tautomer, a polymorph, a stereoisomer thereof, or a mixture of stereoisomers thereof as described in any one of embodiments 18) to 45) or 92), wherein $X_1$ represents a group of Formula ($G_3$):

Formula ($G_3$)

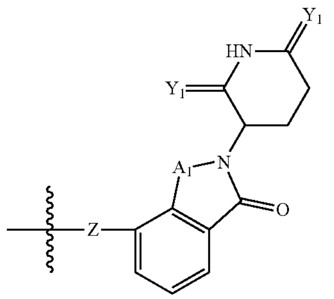

wherein, $A_1$ represents $CH_2$ or C(O), $Y_i$ represents O or S, and Z represents S, S(O), or $S(O)_2$.

Embodiment 95) relates to the compound of Formula (I) or a salt, a solvate, an isotopically enriched analog, a tautomer, a polymorph, a stereoisomer thereof, or a mixture of stereoisomers thereof as described in any one of embodiments 18) to 45) or 92), wherein $X_1$ represents a group of Formula ($G_4$):

Formula ($G_4$)

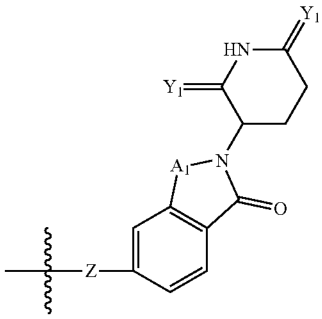

wherein, $A_1$ represents $CH_2$ or C(O), $Y_1$ represents O or S, and Z represents S, S(O), or $S(O)_2$.

Embodiment 96) relates to the compound of Formula (I) or a salt, a solvate, an isotopically enriched analog, a tautomer, a polymorph, a stereoisomer thereof, or a mixture of stereoisomers thereof as described in any one of embodiments 18) to 45) or 92), wherein $X_1$ represents a group of Formula ($G_5$):

Formula ($G_5$)

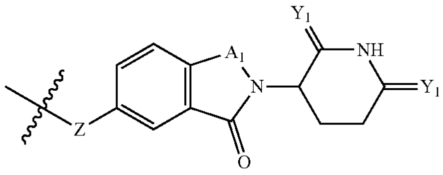

wherein, $A_1$ represents $CH_2$ or C(O), $Y_i$ represents O or S, and Z represents S, S(O), or $S(O)_2$.

Embodiment 97) relates to the compound of Formula (I) or a salt, a solvate, an isotopically enriched analog, a tautomer, a polymorph, a stereoisomer thereof, or a mixture of stereoisomers thereof as described in any one of embodiments 18) to 45) or 92), wherein $X_1$ represents a group of Formula ($G_6$):

Formula ($G_6$)

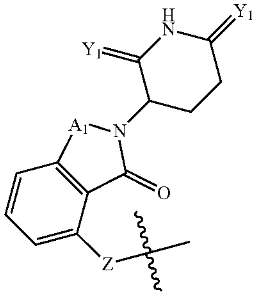

wherein, $A_1$ represents $CH_2$ or C(O), $Y_1$ represents O or S, and Z represents S, S(O), or $S(O)_2$.

Embodiment 98) relates to the compound of Formula (I) or a salt, a solvate, an isotopically enriched analog, a tautomer, a polymorph, a stereoisomer thereof, or a mixture of stereoisomers thereof as described in any one of embodiments 92) to 97), wherein $A_1$ represents $CH_2$ or C(O), $Y_1$ represents O, and Z represents S.

In another aspect, the present disclosure provides, in embodiment A1), the compound of Formula (I'):

Formula (I')

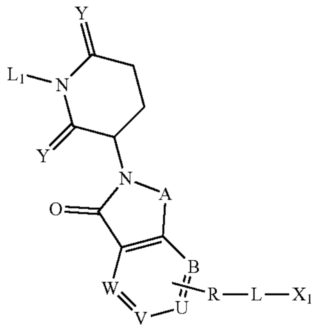

or a salt, a solvate, an isotopically enriched analog, a tautomer, a polymorph, a stereoisomer (including an enantiomer) thereof, or a mixture of stereoisomers thereof, in which A, B, U, V, W, Y are as defined in any one of Embodiments 1) to 14);

R represents S, S(O), or $S(O)_2$;

L represents an optionally substituted linear or branched alkylene group, wherein the linear or branched alkylene group is optionally interrupted one or more times by one or more groups selected from: O, C(O), S, S(O), $S(O)_2$, $S(O)_2N(R_1)$, $N(R_2)S(O)_2$, $C(O)N(R_1)$, $N(R_2)C(O)$, $N(R_3)$, $N(R_4)C(O)N(R_5)$, optionally substituted cycloalkylene, optionally substituted arylene, optionally substituted heterocyclylene, optionally substituted heteroarylene, or any combination thereof, wherein $R_1$, $R_2$, $R_3$, $R_4$, and $R_5$ each independently represent H or $C_{1-3}$ alkyl; and when $L_1$ represents H, $X_1$ represents $NHC(O)R_i$ or $SR_j$, wherein $R_i$ and $R_j$ each independently represent cycloalkyl optionally substituted with substituent(s) selected from $C_{1-6}$ alkyl, oxo, halogen, cyano, trifluoromethyl, amino, hydroxy, $C_{1-3}$ alkoxy, halogenated $C_{1-3}$ alkoxy, methanesulfonyloxy, trifluoromethanesulfonyloxy, p-toluenesulfonyloxy, or any combination thereof, or $X_1$ represents cycloalkyl optionally substituted with substituent(s) selected from $C_{1-6}$ alkyl, oxo, halogen, cyano, trifluoromethyl, amino, hydroxy, $C_{1-3}$ alkoxy, halogenated $C_{1-3}$ alkoxy, methanesulfonyloxy, trifluoromethanesulfonyloxy, p-toluenesulfonyloxy, or any combination thereof; or when $L_1$ represents $C_{1-3}$ alkyl, $X_1$ represents:

$NR_6R_7$, where $R_6$ represents H or $C_{1-6}$ alkyl, and $R_7$ represents cycloalkyl optionally substituted with substituent(s) selected from $C_{1-6}$ alkyl, oxo, halogen, cyano, trifluoromethyl, amino, hydroxy, $C_{1-3}$ alkoxy, halogenated $C_{1-3}$ alkoxy, methanesulfonyloxy, trifluoromethanesulfonyloxy, p-toluenesulfonyloxy, or any combination thereof; or heterocyclyl, optionally substituted with substituent(s) selected from $C_{1-6}$ alkyl, oxo, halogen, cyano, trifluoromethyl, amino, hydroxy, $C_{1-3}$ alkoxy, halogenated $C_{1-3}$ alkoxy, methanesulfonyloxy, trifluoromethanesulfonyloxy, p-toluenesulfonyloxy, or any combination thereof.

Embodiment A2) relates to the compound of Formula (I') or a salt, a solvate, an isotopically enriched analog, a tautomer, a polymorph, a stereoisomer thereof, or a mixture of stereoisomers thereof as described in embodiment A1), wherein A represents $CH_2$ or C(O), and B, U, V and W all represent CH.

Embodiment A3) relates to the compound of Formula (I') or a salt, a solvate, an isotopically enriched analog, a tautomer, a polymorph, a stereoisomer thereof, or a mixture of stereoisomers thereof as described in embodiment A1), wherein L represents an optionally substituted linear or branched $C_{1-40}$ alkylene group, wherein the linear or branched $C_{1-40}$ alkylene group is optionally interrupted one or more times by one or more groups selected from:

O; C(O); S; S(O); $S(O)_2$; $S(O)_2N(R_1)$; $N(R_2)S(O)_2$; $C(O)N(R_1)$; $N(R_2)C(O)$; $N(R_3)$; $N(R_4)C(O)N(R_5)$;

arylene group optionally substituted with substituent(s) selected from halogen, methanesulfonyloxy, trifluoromethanesulfonyloxy, p-toluenesulfonyloxy, or $C_{1-5}$ alkyl, heterocyclylene group optionally substituted with substituent(s) selected from halogen, methanesulfonyloxy, trifluoromethanesulfonyloxy, p-toluenesulfonyloxy, oxo, or $C_{1-5}$ alkyl;

heteroarylene group optionally substituted with substituent(s) selected from halogen, methanesulfonyloxy, trifluoromethanesulfonyloxy, p-toluenesulfonyloxy, or $C_{1-5}$ alkyl;

cycloalkylene group optionally substituted with substituent(s) selected from halogen, methanesulfonyloxy, trifluoromethanesulfonyloxy, p-toluenesulfonyloxy, oxo, or $C_{1-5}$ alkyl, or any combination thereof, wherein $R_1$, $R_2$, $R_3$, $R_4$, and $R_5$ each independently represent H or $C_{1-3}$ alkyl.

Embodiment A4) relates to the compound of Formula (I') or a salt, a solvate, an isotopically enriched analog, a tautomer, a polymorph, a stereoisomer thereof, or a mixture of stereoisomers thereof as described in embodiment A1), wherein L represents the following optionally substituted groups:

linear or branched $C_1$-$C_{40}$ alkylene; $*—(CH_2)_{n1}—N(R_{22})S(O)_2—(CH_2)_{n2}—$; $*—(CH_2)_{n1}—S(O)_2N(R_{23})—(CH_2)_{n2}—$; or $*—(CH_2)_{n1}$-phenylene-$(CH_2)_{n2}—$;

wherein * indicates the point of attachment to R;

$R_{22}$ and $R_{23}$ are each independently selected from H and $C_{1-3}$ alkyl;

n1 and n2 each independently represent an integer of 1, 2, 3, 4, 5, 6, 7, 8, 9, 10, 11, 12, 13, 14, 15, 16, 17, 18, 19, or 20.

Embodiment A5) relates to the compound of Formula (I') or a salt, a solvate, an isotopically enriched analog, a tautomer, a polymorph, a stereoisomer thereof, or a mixture of stereoisomers thereof as described in embodiment A1), wherein L represents the following optionally substituted groups:

$—CH_2—$; $—(CH_2)_2—$; $—(CH_2)_3—$; $—(CH_2)_4—$; $—(CH_2)_5—$; $—(CH_2)_6—$; $—(CH_2)_7—$; $—(CH_2)_8—$; $—(CH_2)_9—$; $—(CH_2)_{10}—$; $—(CH_2)_{11}—$; $—(CH_2)_{12}—$; $—(CH_2)_{13}—$; $—(CH_2)_{14}—$; $—(CH_2)_{15}—$; $—(CH_2)_{16}—$; $—(CH_2)_{17}—$; $—(CH_2)_{18}—$; $—(CH_2)_{19}—$; $—(CH_2)_{20}—$; $*—(CH_2)_2—NHS(O)_2—CH_2—$; $*—(CH_2)_2—NHS(O)_2—(CH_2)_2—$; $*—(CH_2)_2—NHS(O)_2—(CH_2)_3—$; $*—(CH_2)_2—NHS(O)_2—(CH_2)_4—$; $*—(CH_2)_2—NHS(O)_2—(CH_2)_5—$; $*—(CH_2)_2—NHS(O)_2—(CH_2)_6—$; $*—(CH_2)_2—NHS(O)_2—(CH_2)_7—$; $*—(CH_2)_2—NHS(O)_2—(CH_2)_8—$; $*—(CH_2)_2—NHS(O)_2—(CH_2)_9—$; $*—(CH_2)_2—NHS(O)_2—(CH_2)_{10}—$; $*—(CH_2)_2—NHS(O)_2—(CH_2)_{11}—$; $*—(CH_2)_2—NHS(O)_2—(CH_2)_{12}—$; $*—(CH_2)_2—NHS(O)_2—(CH_2)_{13}—$; $*—(CH_2)_2—NHS(O)_2—(CH_2)_{14}—$; $*—(CH_2)_2—NHS(O)_2—(CH_2)_{15}—$; $*—(CH_2)_3—NHS(O)_2—CH_2—$; $*—(CH_2)_3—NHS(O)_2—(CH_2)_2—$; $*—(CH_2)_3—NHS(O)_2—(CH_2)_3—$; $*—(CH_2)_3—NHS(O)_2—(CH_2)_4—$; $*—(CH_2)_3—NHS(O)_2—(CH_2)_5—$; $*—(CH_2)_3—NHS(O)_2—(CH_2)_6—$; $*—(CH_2)_3—NHS(O)_2—(CH_2)_7—$; $*—(CH_2)_3—NHS(O)_2—(CH_2)_8—$; $*—(CH_2)_3—NHS(O)_2—(CH_2)_9—$; $*—(CH_2)_3—NHS(O)_2—(CH_2)_{10}—$; $*—(CH_2)_3—NHS(O)_2—(CH_2)_{11}—$; $*—(CH_2)_3—NHS(O)_2—(CH_2)_{12}—$; $*—(CH_2)_3—NHS(O)_2—(CH_2)_{13}—$; $*—(CH_2)_3—NHS(O)_2—(CH_2)_{14}—$; $*—(CH_2)_3—NHS(O)_2—(CH_2)_{15}—$; $*—(CH_2)_4—NHS(O)_2—(CH_2)_1—$; $*—(CH_2)_4NHS(O)_2(CH_2)_2—$; $*—(CH_2)_4—NHS(O)_2—(CH_2)_3—$; $*—(CH_2)_4—NHS(O)_2—(CH_2)_4—$; $*—(CH_2)_4NHS(O)_2—(CH_2)_5—$; $*—(CH_2)_4—NHS(O)_2—(CH_2)_6—$; $*—(CH_2)_4—NHS(O)_2—(CH_2)_7—$; $*—(CH_2)_4—NHS(O)_2—(CH_2)_8—$; $*—(CH_2)_4—NHS(O)_2—(CH_2)_9—$; $*—(CH_2)_4—NHS(O)_2—(CH_2)_{10}—$; $*—(CH_2)_5—NHS(O)_2—(CH_2)_1—$; $*—(CH_2)_6—NHS(O)_2—(CH_2)_1—$; $*—(CH_2)_7—NHS(O)_2—(CH_2)_1—$; $*—(CH_2)_8—NHS(O)_2—(CH_2)_1—$; $*—(CH_2)_8—NHS(O)_2—(CH_2)_2—$; $*—(CH_2)_9—NHS(O)_2—(CH_2)_1—$; $*—(CH_2)_{10}—NHS(O)_2—(CH_2)_1—$; $*—(CH_2)_5—NHS(O)_2—(CH_2)_2—$; $*—(CH_2)_6—NHS(O)_2—(CH_2)_2—$; $*—(CH_2)_7—NHS(O)_2—(CH_2)_2—$; $*—(CH_2)_8—NHS(O)_2—(CH_2)_3—$; $*—(CH_2)_9—NHS(O)_2—(CH_2)_2—$; $*—(CH_2)_{10}—NHS(O)_2—(CH_2)_2—$; $*—CH_2$-phenylene-$CH_2—$; $*—(CH_2)_1$-phenylene-$(CH_2)_2—$; $*—(CH_2)_1$-phenylene-$(CH_2)_3—$; $*—(CH_2)_1$-phenylene-$(CH_2)_4—$; $*—(CH_2)_2$-phenylene-$(CH_2)_1—$; $*—(CH_2)_2$-phenylene-$(CH_2)_2—$; $*—(CH_2)_2$-phenylene-$(CH_2)_3—$; $*—(CH_2)_2$-phenylene-$(CH_2)_4—$; $*—(CH_2)_2$-phenylene-$(CH_2)_5—$; $*—(CH_2)_3$-phenylene-$(CH_2)_1—$; $*—(CH_2)_3$-phenylene-$CH_2—$; $*—(CH_2)_3$-phenylene-$(CH_2)_2—$; $*—(CH_2)_3$-phenylene-$(CH_2)_3—$; $*—(CH_2)_4$-phenylene-$CH_2—$; $*—(CH_2)_4$-phenylene-$(CH_2)_2—$; $*—(CH_2)_4$-phenylene-$(CH_2)_3—$; $*—(CH_2)_5$-phenylene-$(CH_2)_3—$; $*—(CH_2)_6$-phenylene-$(CH_2)_3—$; $*—(CH_2)_7$-phenylene-$(CH_2)_3—$; $*—(CH_2)_8$-phenylene-$CH_2—$; $*—(CH_2)_8$-phenylene-$(CH_2)_2—$; $*—(CH_2)_8$-phenylene-$(CH_2)_3—$; $*—(CH_2)_8$-phenylene-$(CH_2)_4—$; $*—(CH_2)_8$-phenylene-$(CH_2)_5—$; $*—(CH_2)_8$-phenylene-$(CH_2)_6—$; $*—(CH_2)_8$-phenylene-$(CH_2)_7—$; $*—(CH_2)_8$-phenylene-$(CH_2)_8—$; $*—CH_2$-phenylene-$(CH_2)_8—$; $*—(CH_2)_2$-phenylene-$(CH_2)_8—$; $*—(CH_2)_3$-phenylene-$(CH_2)_8—$; $*—(CH_2)_4$-phenylene-$(CH_2)_8—$; $*—(CH_2)_8$-phenylene-$(CH_2)_8—$; $*—(CH_2)_6$-phenylene-$(CH_2)_8—$; or $*—(CH_2)_7$-phenylene-$(CH_2)_8—$;

wherein * indicates the point of attachment to R.

Embodiment A6) relates to the compound of Formula (I') or a salt, a solvate, an isotopically enriched analog, a tautomer, a polymorph, a stereoisomer thereof, or a mixture of stereoisomers thereof as described in embodiment A1), wherein L represents the following optionally substituted groups:

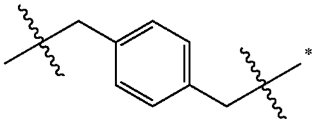
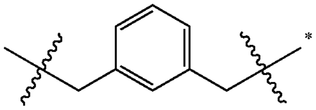
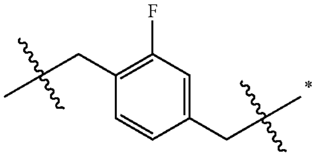
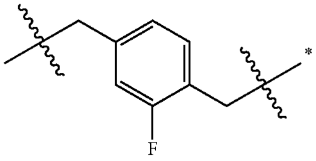
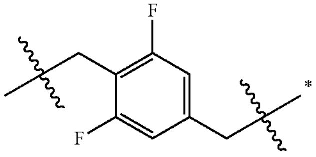
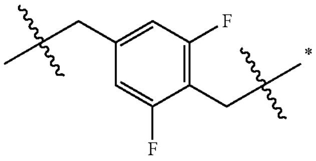
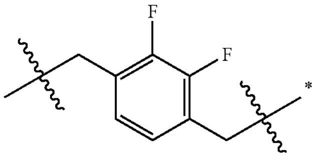
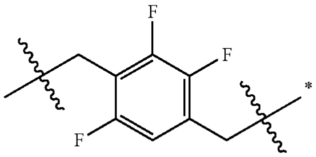
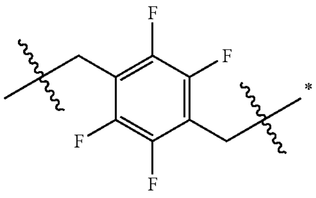
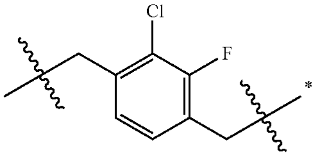
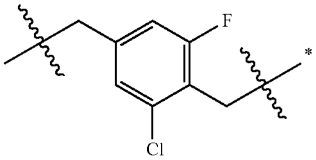
-continued
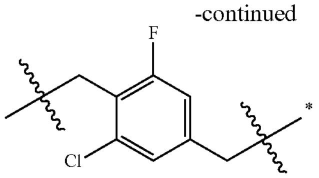
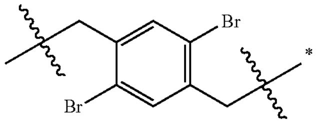
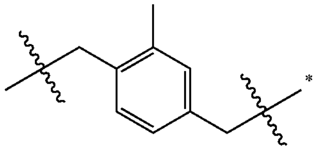
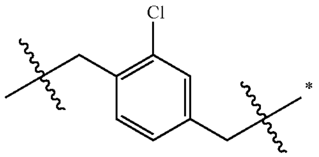
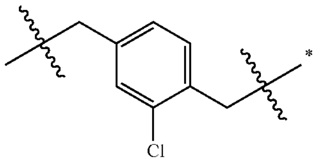
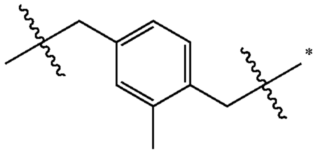
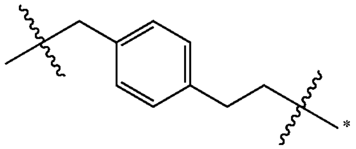
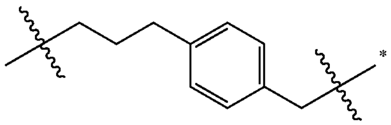
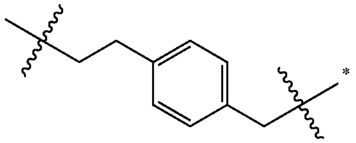
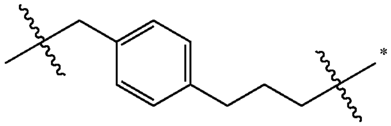
or
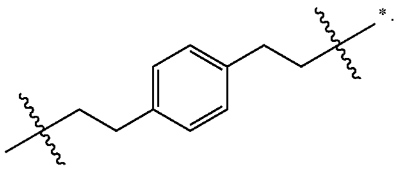
Embodiment A7) relates to the compound of Formula (I') or a salt, a solvate, an isotopically enriched analog, a tautomer, a polymorph, a stereoisomer thereof, or a mixture of stereoisomers thereof as described in any one of embodiments A1) to A6), wherein $L_1$ represents H, and $X_1$ represents the following optionally substituted groups:

adamantanyl-C(O)NH—, adamantanyl-S—, or norcamphanyl, wherein the optional substituent(s) of the optionally substituted group is selected from $C_{1-6}$ alkyl (for example $C_{1-3}$ alkyl), oxo, halogen, cyano, trifluoromethyl, amino, hydroxy, $C_{1-3}$ alkoxy, halogenated $C_{1-3}$ alkoxy, methanesulfonyloxy, trifluoromethanesulfonyloxy, p-toluenesulfonyloxy, or any combination thereof.

Embodiment A8) relates to the compound of Formula (I') or a salt, a solvate, an isotopically enriched analog, a tautomer, a polymorph, a stereoisomer thereof, or a mixture of stereoisomers thereof as described in embodiment A7), wherein $X_1$ represents adamantan-1-yl-C(O)NH—, 3-hydroxyadamantanyl-C(O)NH—, 3-hydroxyadamantan-1-yl-C(O)NH—, 3-chloro-adamantan-1-yl-C(O)NH—, 4-chloro-adamantan-1-yl-C(O)NH—, 2-chloroadamantan-1-yl-C(O)NH—, adamantan-2-yl-C(O)NH—, adamantan-1-yl-S—, 3-hydroxyadamantanyl-S—, 3-hydroxyadamantan-1-yl-S—, 3-chloroadamantan-1-yl-S—, 4-chloroadamantan-1-yl-S—, 2-chloroadamantan-1-yl-S—, adamantan-2-yl-S—, bicyclo[2.2.1]heptan-2-yl, 1,7,7-trimethylbicyclo[2.2.1]heptan-2-yl, 7,7-dimethylbicyclo[2.2.1]heptan-1-yl, or 7,7-dimethyl-2-oxobicyclo[2.2.1]heptan-1-yl.

Embodiment A9) relates to the compound of Formula (I') or a salt, a solvate, an isotopically enriched analog, a tautomer, a polymorph, a stereoisomer thereof, or a mixture of stereoisomers thereof as described in any one of embodiments A1) to A6), wherein:

when $L_1$ represents $C_{1-3}$ alkyl, $X_1$ represents $NR_6R_7$, where $R_6$ represents H or $C_{1-3}$ alkyl, and $R_7$ represents the following optionally substituted groups:

adamantanyl; cyclohexyl; spiro-cycloalkyl; or norcamphanyl; wherein the optional substituents of said optionally substituted groups are selected from $C_{1-6}$ alkyl (for example $C_{1-3}$ alkyl), oxo, halogen, cyano, trifluoromethyl, amino, hydroxy, $C_{1-3}$ alkoxy, halogenated $C_{1-3}$ alkoxy, methanesulfonyloxy, trifluoromethanesulfonyloxy, p-toluenesulfonyloxy, or any combination thereof.

Embodiment A10) relates to the compound of Formula (I') or a salt, a solvate, an isotopically enriched analog, a tautomer, a polymorph, a stereoisomer thereof, or a mixture of stereoisomers thereof as described in any one of embodiments A1) to A6), wherein $R_7$ represents adamantan-1-yl, 3-hydroxyadamantanyl, 3-hydroxyadamantan-1-yl, 3-chloroadamantan-1-yl, 4-chloroadamantan-1-yl, 2-chloroadamantan-1-yl, adamantan-2-yl, bicyclo[2.2.1]heptan-2-yl, 1,7,7-trimethylbicyclo[2.2.1]heptan-2-yl, 7,7-dimethylbicyclo[2.2.1]heptan-1-yl, or 7,7-dimethyl-2-oxobicyclo[2.2.1]heptan-1-yl.

Embodiment A11) relates to the compound of Formula (I') or a salt, a solvate, an isotopically enriched analog, a tautomer, a polymorph, a stereoisomer thereof, or a mixture of stereoisomers thereof as described in any one of embodiments A1) to A6), wherein when $L_1$ represents $C_{1-3}$ alkyl, $X_1$ represents an optionally substituted piperidinyl, wherein the optional substituent(s) of said optionally substituted piperidinyl is selected from: $C_{1-6}$ alkyl (for example $C_{1-3}$ alkyl), halogen, oxo, cyano, amino, hydroxy, $C_{1-3}$ alkoxy, halogenated $C_{1-3}$ alkoxy, halogenated $C_{1-3}$ alkyl, di($C_{1-6}$ alkyl) phosphono, $C_{1-6}$ alkylsulfonyl, or any combination thereof.

Particularly preferred are the compounds of the present disclosure and their salts (especially pharmaceutically acceptable salts, such as hydrochloride, etc.), enantiomers, diastereomers, solvates, polymorphs in Table 1:

TABLE 1

The compounds of the present invention

| Compound No. | Structure of the compounds | The compound's name |
|---|---|---|
| SIAIS12100-73 | 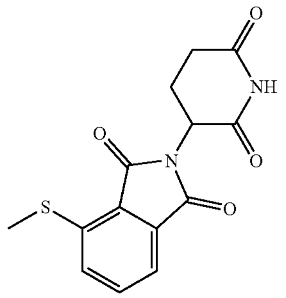 [SMILES: CSc1cccc2c1C(=O)N(C1CCC(=O)NC1=O)C2=O] | 2-(2,6-dioxopiperidin-3-yl)-4-(methylthio)isoindoline-1,3-dione |
| SIAIS16407-4 | 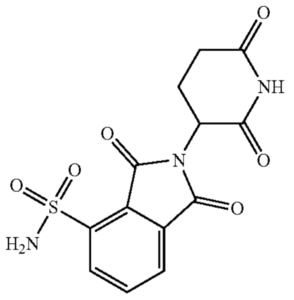 [SMILES: NS(=O)(=O)c1cccc2c1C(=O)N(C1CCC(=O)NC1=O)C2=O] | 2-(2,6-dioxopiperidin-3-yl)-1,3-dioxoisoindoline-4-sulfonamide |

TABLE 1-continued

| The compounds of the present invention | | |
|---|---|---|
| Compound No. | Structure of the compounds | The compound's name |
| | 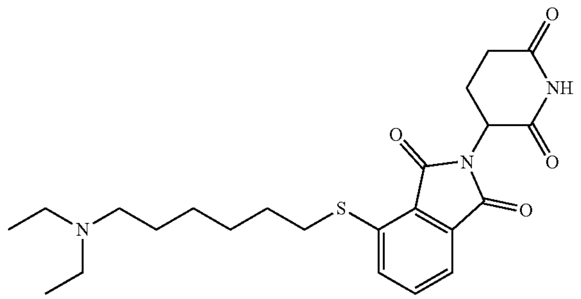 [SMILES: CCN(CC)CCCCCCSc1cccc2c1C(=O)N(C1CCC(=O)NC1=O)C2=O] | 4-((6-(diethylamino)hexyl)thio)-2-(2,6-dioxopiperidin-3-yl)isoindoline-1,3-dione |
| | 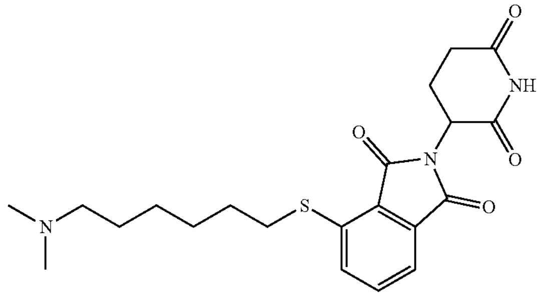 [SMILES: CN(C)CCCCCCSc1cccc2c1C(=O)N(C1CCC(=O)NC1=O)C2=O] | 4-((6-(dimethylamino)hexyl)thio)-2-(2,6-dioxopiperidin-3-yl)isoindoline-1,3-dione |
| | 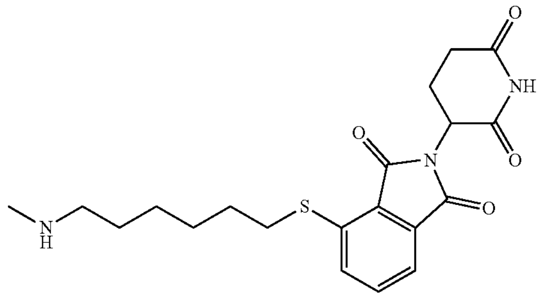 [SMILES: CNCCCCCCSc1cccc2c1C(=O)N(C1CCC(=O)NC1=O)C2=O] | 2-(2,6-dioxopiperidin-3-yl)-4-((6-(methylamino)hexyl)thio)isoindoline-1,3-dione |
| SIAIS12210-33 | 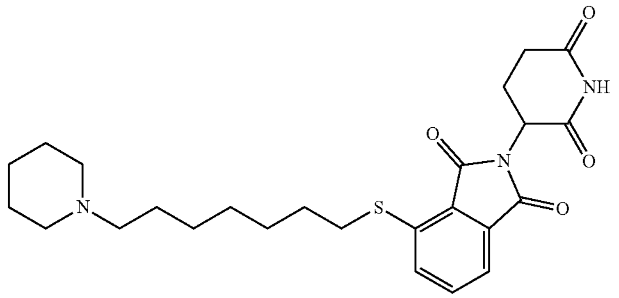 [SMILES: O=C1CCC(N2C(=O)c3cccc(SCCCCCCCN4CCCCC4)c3C2=O)C(=O)N1] | 2-(2,6-dioxopiperidin-3-yl)-4-((7-(piperidin-1-yl)heptyl)thio)isoindoline-1,3-dione |
| SIAIS12220-97 | 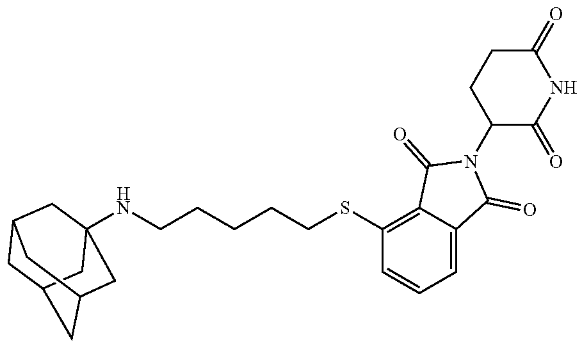 [SMILES: O=C1CCC(N2C(=O)c3cccc(SCCCCCNC45CC6CC(CC(C6)C4)C5)c3C2=O)C(=O)N1] | 4-((5-((adamantan-1-yl)amino)pentyl)thio)-2-(2,6-dioxopiperidin-3-yl)isoindoline-1,3-dione |

TABLE 1-continued
| The compounds of the present invention | | |
|---|---|---|
| Compound No. | Structure of the compounds | The compound's name |
| SIAIS12221-09 | 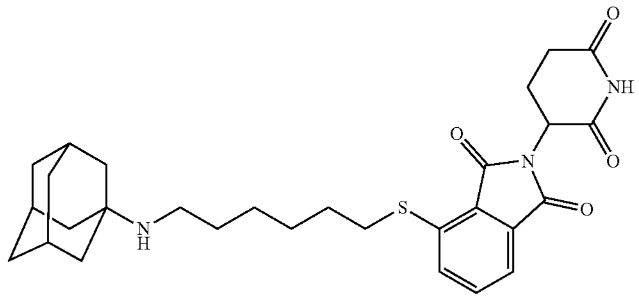 [SMILES: O=C1CCC(N2C(=O)c3cccc(SCCCCCCNC45CC6CC(CC(C6)C4)C5)c3C2=O)C(=O)N1] | 4-((6-((adamantan-1-yl)amino)hexyl)thio)-2-(2,6-dioxopiperidin-3-yl)isoindoline-1,3-dione |
| SIAIS12210-69 | 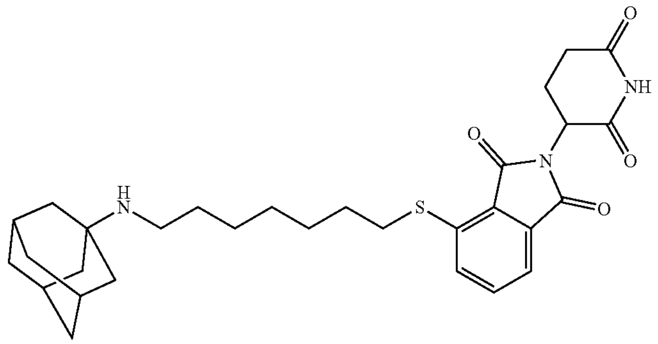 [SMILES: O=C1CCC(N2C(=O)c3cccc(SCCCCCCCNC45CC6CC(CC(C6)C4)C5)c3C2=O)C(=O)N1] | 4-((7-((adamantan-1-yl)amino)heptyl)thio)-2-(2,6-dioxopiperidin-3-yl)isoindoline-1,3-dione |
| SIAIS12220-29 | 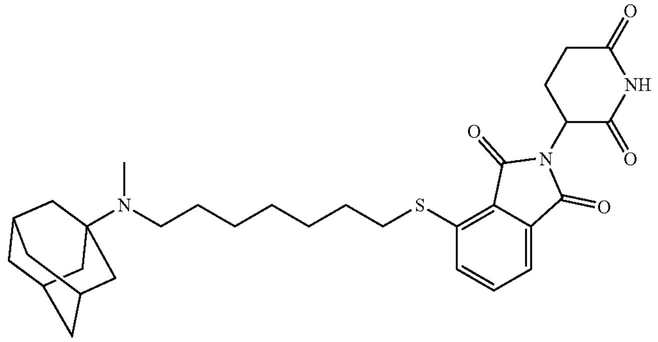 [SMILES: CN(CCCCCCCSc1cccc2c1C(=O)N(C1CCC(=O)NC1=O)C2=O)C12CC3CC(CC(C3)C1)C2] | 4-((7-((adamantan-1-yl)(methyl)amino)heptyl)thio)-2-(2,6-dioxopiperidin-3-yl)isoindoline-1,3-dione |

TABLE 1-continued

| Compound No. | Structure of the compounds | The compound's name |
|---|---|---|
| | The compounds of the present invention | |
| SIAIS12220-71 | 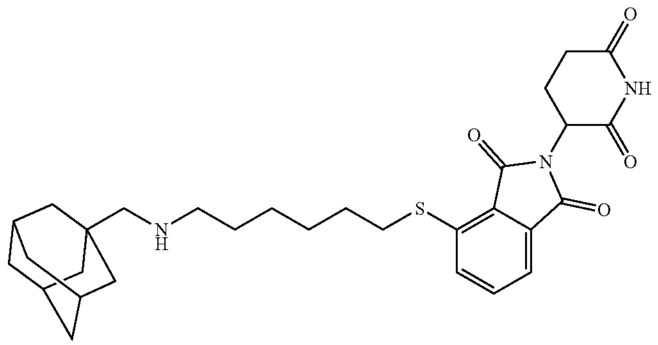 [SMILES: O=C1CCC(N2C(=O)c3cccc(SCCCCCCNCC45CC6CC(CC(C6)C4)C5)c3C2=O)C(=O)N1] | 4-((6-(((adamantan-1-yl)methyl)amino)hexyl)thio)-2-(2,6-dioxopiperidin-3-yl)isoindoline-1,3-dione |
| SIAIS12220-13 | 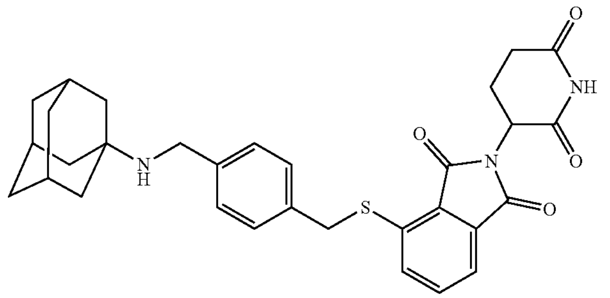 [SMILES: O=C1CCC(N2C(=O)c3cccc(SCc4ccc(CNC56CC7CC(CC(C7)C5)C6)cc4)c3C2=O)C(=O)N1] | 4-((4-(((adamantan-1-yl)amino)methyl)benzyl)thio)-2-(2,6-dioxopiperidin-3-yl)isoindoline-1,3-dione |
| SIAIS12211-77 | 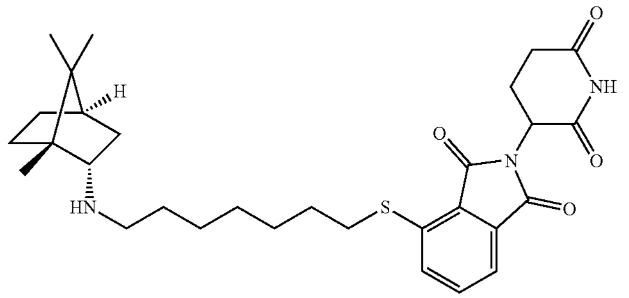 [SMILES: CC1(C)[C@@H]2CC[C@@]1(C)[C@@H](NCCCCCCCSc1cccc3c1C(=O)N(C1CCC(=O)NC1=O)C3=O)C2] | 2-(2,6-dioxopiperidin-3-yl)-4-((7-(((1R,2S,4R)-1,7,7-trimethylbicyclo[2.2.1]heptan-2-yl)amino)heptyl)thio)isoindoline-1,3-dione |
| SIAIS12211-47 | 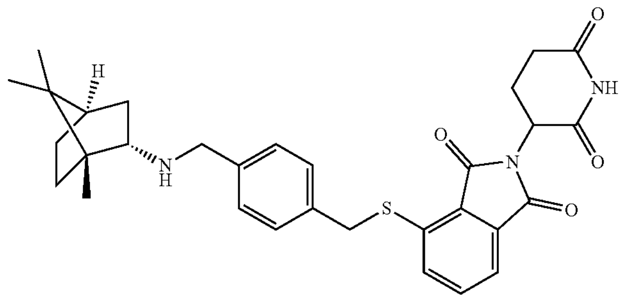 [SMILES: CC1(C)[C@@H]2CC[C@@]1(C)[C@@H](NCc1ccc(CSc3cccc4c3C(=O)N(C3CCC(=O)NC3=O)C4=O)cc1)C2] | 2-(2,6-dioxopiperidin-3-yl)-4-((4-((((1R,2S,4R)-1,7,7-trimethylbicyclo[2.2.1]heptan-2-yl)amino)methyl)benzyl)thio) isoindoline-1,3-dione |
| SIAIS12211-75 | 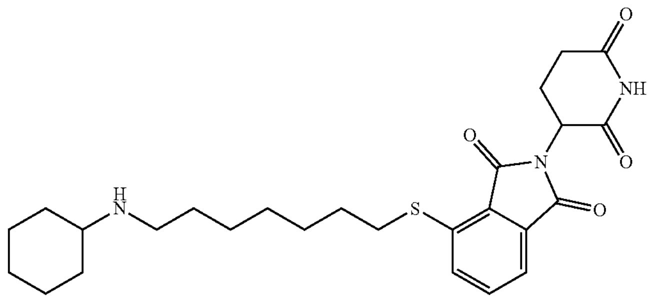 [SMILES: O=C1CCC(N2C(=O)c3cccc(SCCCCCCCNC4CCCCC4)c3C2=O)C(=O)N1] | 4-((7-(cyclohexylamino)heptyl)thio)-2-(2,6-dioxopiperidin-3-yl)isoindoline-1,3-dione |

TABLE 1-continued

| The compounds of the present invention | | |
|---|---|---|
| Compound No. | Structure of the compounds | The compound's name |
| | 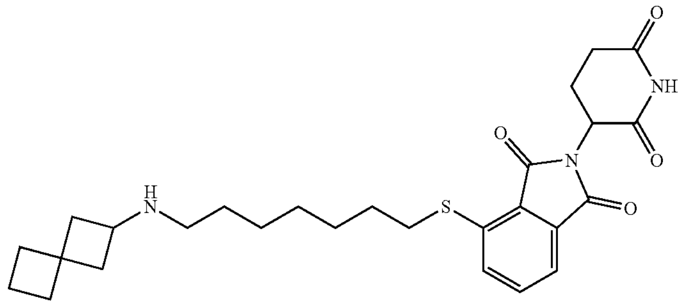 [SMILES: O=C1CCC(N2C(=O)c3cccc(SCCCCCCCNC4CC5(CCC5)C4)c3C2=O)C(=O)N1] | 2-(2,6-dioxopiperidin-3-yl)-4-((7-(spiro[3.3]heptan-2-ylamino)heptyl)thio)isoindoline-1,3-dione |
| SIAIS12241-51 | 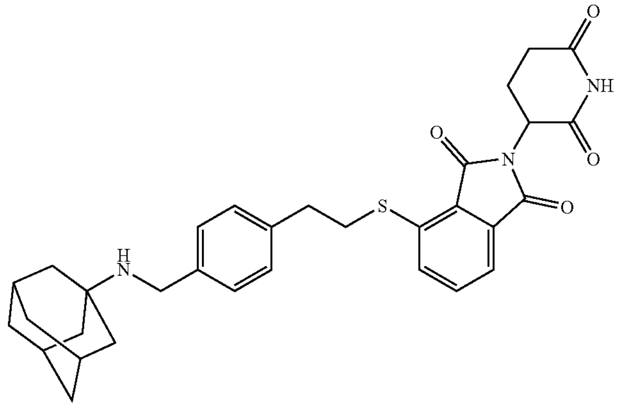 [SMILES: O=C1CCC(N2C(=O)c3cccc(SCCc4ccc(CNC56CC7CC(CC(C7)C5)C6)cc4)c3C2=O)C(=O)N1] | 4-((4-(((adamantan-1-yl)amino)methyl)phenethyl)thio)-2-(2,6-dioxopiperidin-3-yl)isoindoline-1,3-dione |
| SIAIS12241-63 | 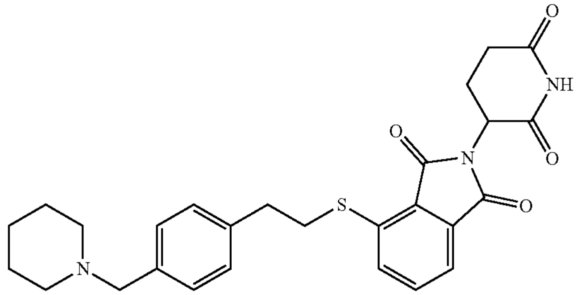 [SMILES: O=C1CCC(N2C(=O)c3cccc(SCCc4ccc(CN5CCCCC5)cc4)c3C2=O)C(=O)N1] | 2-(2,6-dioxopiperidin-3-yl)-4-((4-(piperidin-1-ylmethyl)phenethyl)thio) isoindoline-1,3-dione |
| SIAIS12270-19 | 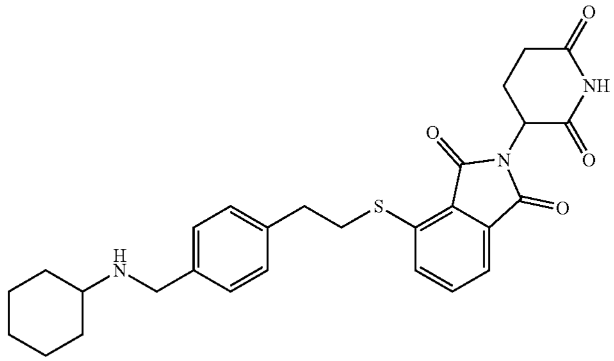 [SMILES: O=C1CCC(N2C(=O)c3cccc(SCCc4ccc(CNC5CCCCC5)cc4)c3C2=O)C(=O)N1] | 4-((4-((cyclohexylamino)methyl)phenethyl)thio)-2-(2,6-dioxopiperidin-3-yl)isoindoline-1,3-dione |

TABLE 1-continued

| The compounds of the present invention | | |
|---|---|---|
| Compound No. | Structure of the compounds | The compound's name |
| SIAIS12270-85 | 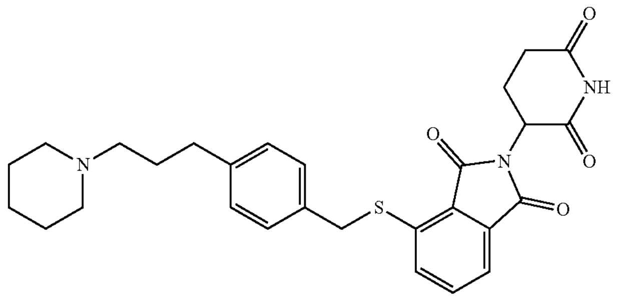 [SMILES: O=C1CCC(N2C(=O)c3cccc(SCc4ccc(CCCN5CCCCC5)cc4)c3C2=O)C(=O)N1] | 2-(2,6-dioxopiperidin-3-yl)-4-((4-(3-(piperidin-1-yl)propyl)benzyl)thio)isoindoline-1,3-dione |
| SIAIS12270-87 | 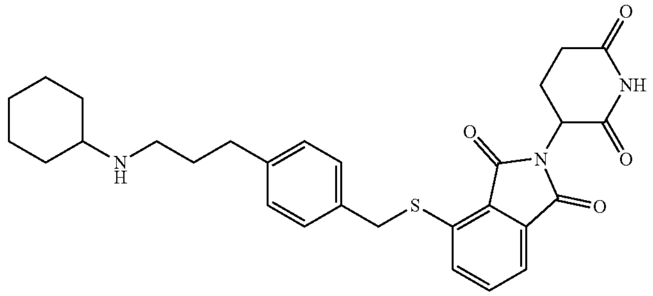 [SMILES: O=C1CCC(N2C(=O)c3cccc(SCc4ccc(CCCNC5CCCCC5)cc4)c3C2=O)C(=O)N1] | 4-((4-(3-(cyclohexylamino)propyl)benzyl)thio)-2-(2,6-dioxopiperidin-3-yl)isoindoline-1,3-dione |
| SIAIS12270-91 | 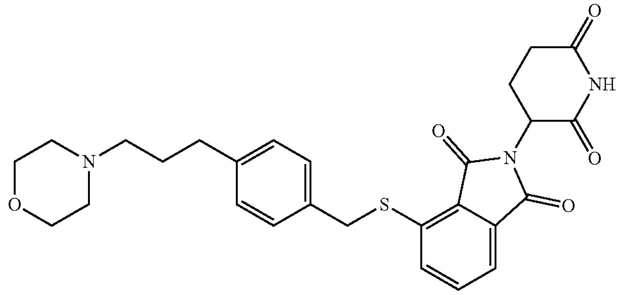 [SMILES: O=C1CCC(N2C(=O)c3cccc(SCc4ccc(CCCN5CCOCC5)cc4)c3C2=O)C(=O)N1] | 2-(2,6-dioxopiperidin-3-yl)-4-((4-(3-morpholinopropyl)benzyl)thio)isoindoline-1,3-dione |
| SIAIS12270-39 | 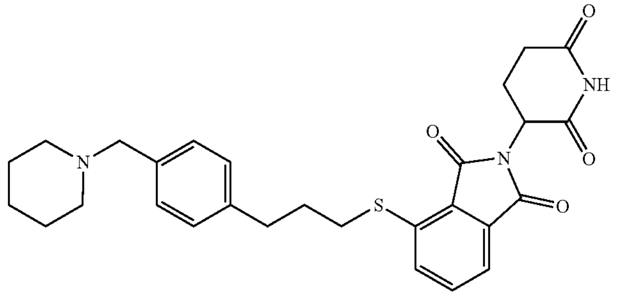 [SMILES: O=C1CCC(N2C(=O)c3cccc(SCCCc4ccc(CN5CCCCC5)cc4)c3C2=O)C(=O)N1] | 2-(2,6-dioxopiperidin-3-yl)-4-((3-(4-(piperidin-1-ylmethyl)phenyl)propyl)thio)isoindoline-1,3-dione |
| SIAIS12270-69 | 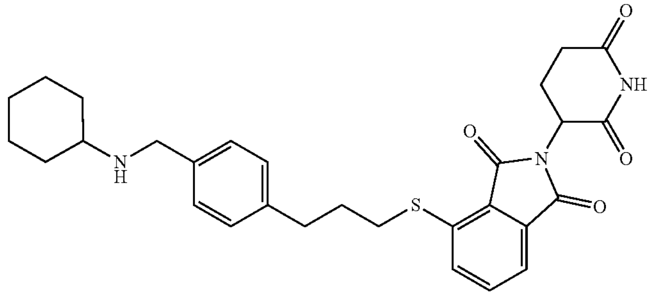 [SMILES: O=C1CCC(N2C(=O)c3cccc(SCCCc4ccc(CNC5CCCCC5)cc4)c3C2=O)C(=O)N1] | 4-((3-(4-((cyclohexylamino)methyl)phenyl)propyl)thio)-2-(2,6-dioxopiperidin-3-yl)isoindoline-1,3-dione |

TABLE 1-continued

The compounds of the present invention

| Compound No. | Structure of the compounds | The compound's name |
|---|---|---|
| SIAIS12270-41 | 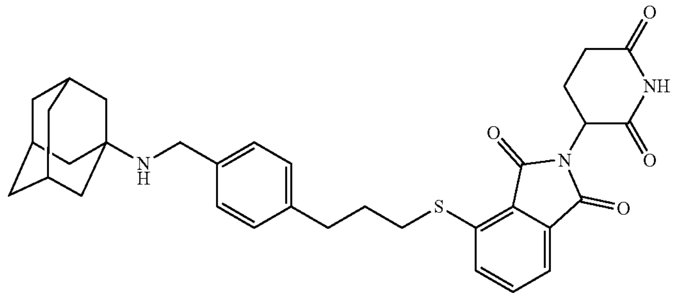 [SMILES: O=C1CCC(N2C(=O)c3cccc(SCCCc4ccc(CNC56CC7CC(CC(C7)C5)C6)cc4)c3C2=O)C(=O)N1] | 4-((3-(4-(((adamantan-1-yl)amino)methyl)phenyl)propyl)thio)-2-(2,6-dioxopiperidin-3-yl)isoindoline-1,3-dione |
| SIAIS12240-11 | 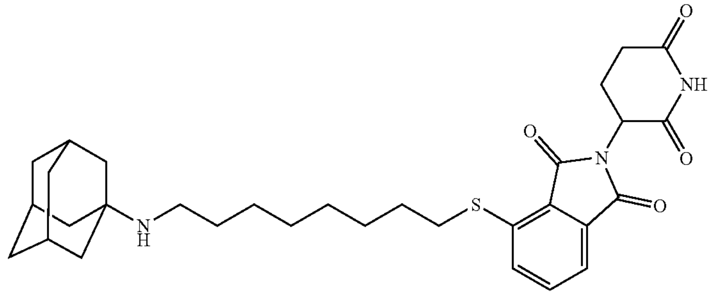 [SMILES: O=C1CCC(N2C(=O)c3cccc(SCCCCCCCCNC45CC6CC(CC(C6)C4)C5)c3C2=O)C(=O)N1] | 4-((8-((adamantan-1-yl)amino)octyl)thio)-2-(2,6-dioxopiperidin-3-yl)isoindoline-1,3-dione |
| SIAIS12240-76 | 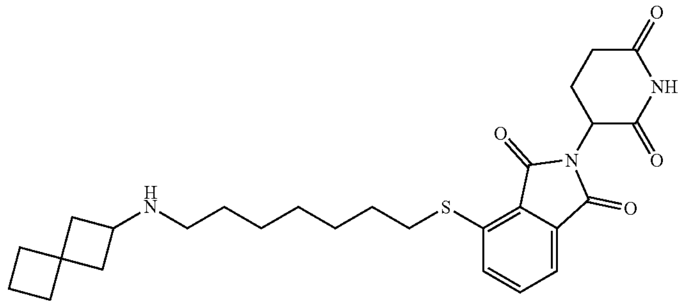 [SMILES: O=C1CCC(N2C(=O)c3cccc(SCCCCCCCNC4CC5(CCC5)C4)c3C2=O)C(=O)N1] | 2-(2,6-dioxopiperidin-3-yl)-4-((7-(spiro[3.3]heptan-2-ylamino)heptyl)thio)isoindoline-1,3-dione |
| SIAIS17108-8 | 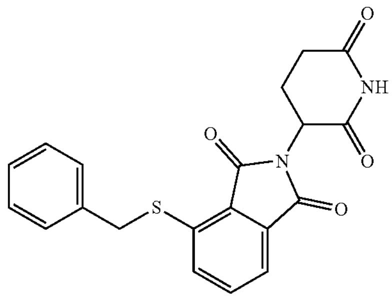 [SMILES: O=C1CCC(N2C(=O)c3cccc(SCc4ccccc4)c3C2=O)C(=O)N1] | 3-(4-(benzylthio)-1-oxoisoindolin-2-yl)piperidine-2,6-dione |
| SIAIS12100-83 | 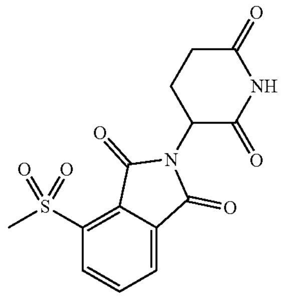 [SMILES: CS(=O)(=O)c1cccc2c1C(=O)N(C1CCC(=O)NC1=O)C2=O] | 3-(4-(methylsulfonyl)-1-oxoisoindolin-2-yl)piperidine-2,6-dione |

TABLE 1-continued

| The compounds of the present invention | | |
|---|---|---|
| Compound No. | Structure of the compounds | The compound's name |
| SIAIS12100-71 | 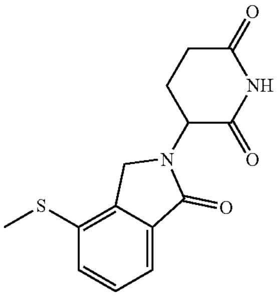 [SMILES: CSc1cccc2c1CN(C1CCC(=O)NC1=O)C2=O] | 3-(4-(methylthio)-1-oxoisoindolin-2-yl)piperidine-2,6-dione |
| SIAIS12130-73 | 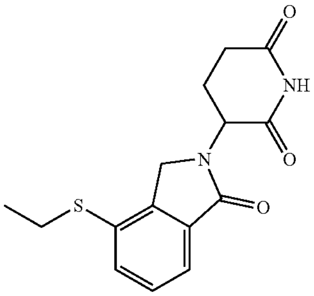 [SMILES: CCSc1cccc2c1CN(C1CCC(=O)NC1=O)C2=O] | 3-(4-(ethylthio)-1-oxoisoindolin-2-yl)piperidine-2,6-dione |
| SIAIS12130-71 | 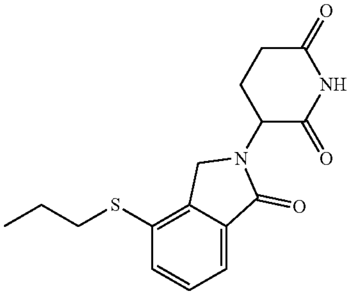 [SMILES: CCCSc1cccc2c1CN(C1CCC(=O)NC1=O)C2=O] | 3-(1-oxo-4-(propylthio)isoindolin-2-yl)piperidine-2,6-dione |
| SIAIS12130-75 | 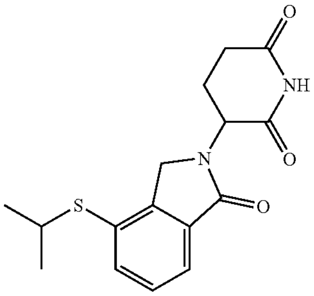 [SMILES: CC(C)Sc1cccc2c1CN(C1CCC(=O)NC1=O)C2=O] | 3-(4-(isopropylthio)-1-oxoisoindolin-2-yl)piperidine-2,6-dione |
| SIAIS12131-67 | 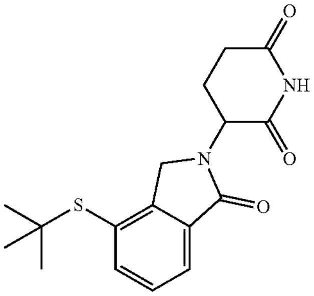 [SMILES: CC(C)(C)Sc1cccc2c1CN(C1CCC(=O)NC1=O)C2=O] | 3-(4-(tert-butylthio)-1-oxoisoindolin-2-yl)piperidine-2,6-dione |

TABLE 1-continued

| The compounds of the present invention | | |
|---|---|---|
| Compound No. | Structure of the compounds | The compound's name |
| SIAIS12131-95 | 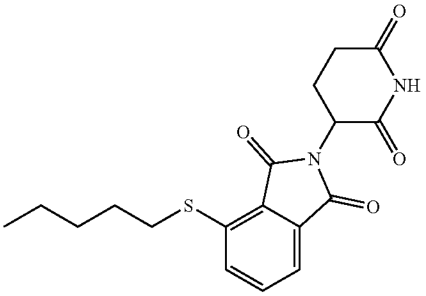 [SMILES: CCCCCSc1cccc2c1C(=O)N(C1CCC(=O)NC1=O)C2=O] | 3-(1-oxo-4-(pentylthio)isoindolin-2-yl)piperidine-2,6-dione |
| SIAIS12160-25 | 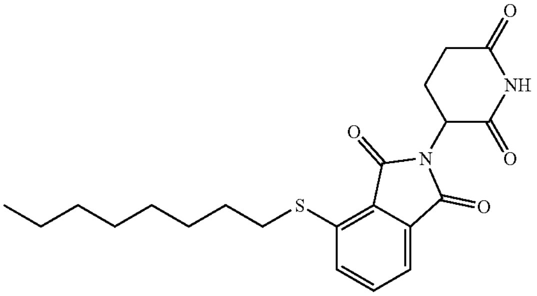 [SMILES: CCCCCCCCSc1cccc2c1C(=O)N(C1CCC(=O)NC1=O)C2=O] | 3-(4-(octylthio)-1-oxoisoindolin-2-yl)piperidine-2,6-dione |
| SIAIS12161-89 | 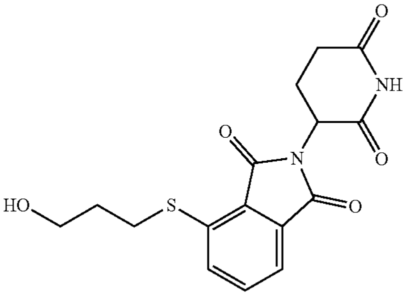 [SMILES: O=C1CCC(N2C(=O)c3cccc(SCCCO)c3C2=O)C(=O)N1] | 3-(4-((3-hydroxypropyl)thio)-1-oxoisoindolin-2-yl)piperidine-2,6-dione |
| SIAIS12200-69 | 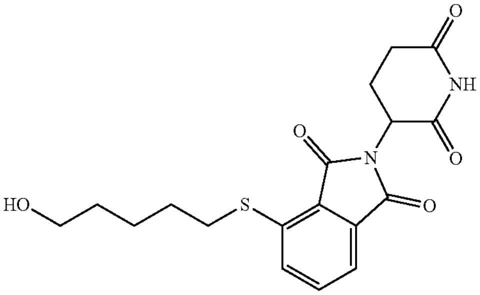 [SMILES: O=C1CCC(N2C(=O)c3cccc(SCCCCCO)c3C2=O)C(=O)N1] | 3-(4-((5-hydroxypentyl)thio)-1-oxoisoindolin-2-yl)piperidine-2,6-dione |
| SIAIS26400-6 | 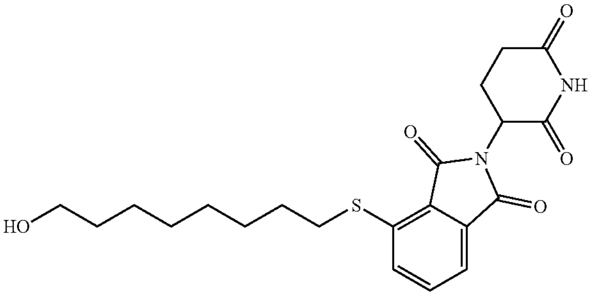 [SMILES: O=C1CCC(N2C(=O)c3cccc(SCCCCCCCCS)c3C2=O)C(=O)N1] | 3-(4-((8-hydroxyoctyl)thio)-1-oxoisoindolin-2-yl)piperidine-2,6-dione |

TABLE 1-continued

| The compounds of the present invention | | |
|---|---|---|
| Compound No. | Structure of the compounds | The compound's name |
| SIAIS12201-43 | 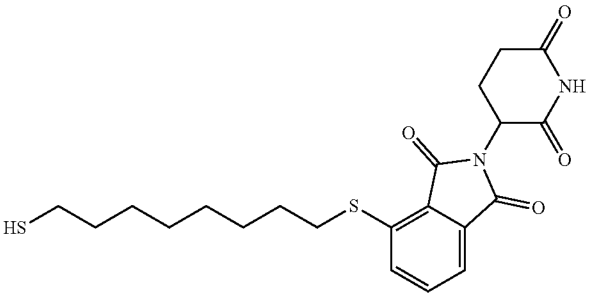 | 3-(4-((8-mercaptooctyl)thio)-1-oxoisoindolin-2-yl)piperidine-2,6-dione |
| SIAIS12271-27 | 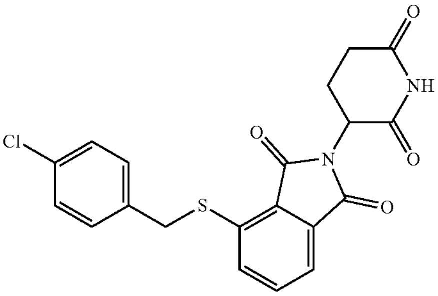 [SMILES: O=C1CCC(N2C(=O)c3cccc(SCc4ccc(Cl)cc4)c3C2=O)C(=O)N1] | 3-(4-((4-chlorobenzyl)thio)-1-oxoisoindolin-2-yl)piperidine-2,6-dione |
| SIAIS12131-45 | 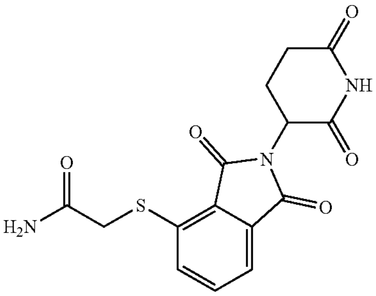 [SMILES: NC(=O)CSc1cccc2c1C(=O)N(C1CCC(=O)NC1=O)C2=O] | 2-((2-(2,6-dioxopiperidin-3-yl)-1-oxoisoindolin-4-yl)thio)acetamide |
| SIAIS12201-33 | 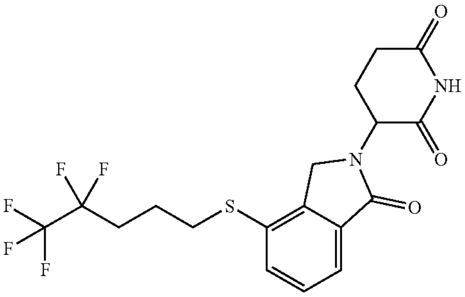 [SMILES: O=C1CCC(N2Cc3c(SCCCC(F)(F)C(F)(F)F)cccc3C2=O)C(=O)N1] | 3-(1-oxo-4-((4,4,5,5,5-pentafluoropentyl)thio)isoindolin-2-yl)piperidine-2,6-dione |
| SIAIS12201-31 | 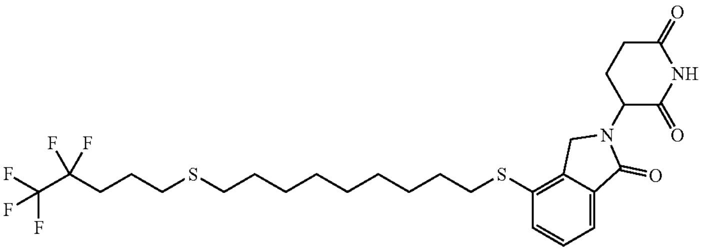 [SMILES: O=C1CCC(N2Cc3c(SCCCCCCCCCSCCCC(F)(F)C(F)(F)F)cccc3C2=O)C(=O)N1] | 3-(1-oxo-4-((9-((4,4,5,5,5-pentafluoropentyl)thio)nonyl)thio)isoindolin-2-yl)piperidine-2,6-dione |

TABLE 1-continued

| Compound No. | Structure of the compounds | The compound's name |
|---|---|---|
| SIAIS12201-45 | 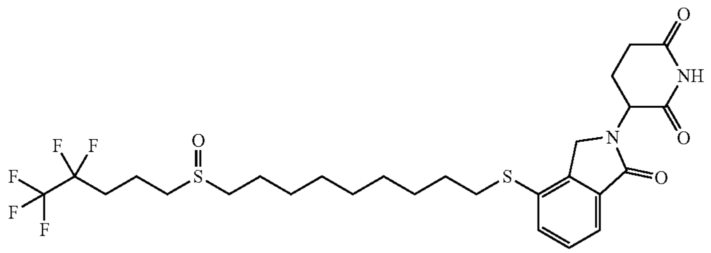 [SMILES: O=C1CCC(N2Cc3c(SCCCCCCCCCS(=O)CCCC(F)(F)C(F)(F)F)cccc3C2=O)C(=O)N1] | 3-(1-oxo-4-((9-((4,4,5,5,5-pentafluoropentyl)sulfinyl)nonyl) thio)isoindolin-2-yl)piperidine-2,6-dione |
| SIAIS12201-47 | 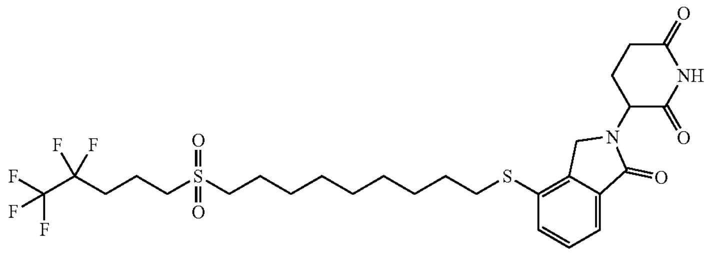 [SMILES: O=C1CCC(N2Cc3c(SCCCCCCCCCS(=O)(=O)CCCC(F)(F)C(F)(F)F)cccc3C2=O)C(=O)N1] | 3-(1-oxo-4-((9-((4,4,5,5,5-pentafluoropentyl)sulfonyl)nonyl) thio)isoindolin-2-yl)piperidine-2,6-dione |
| | 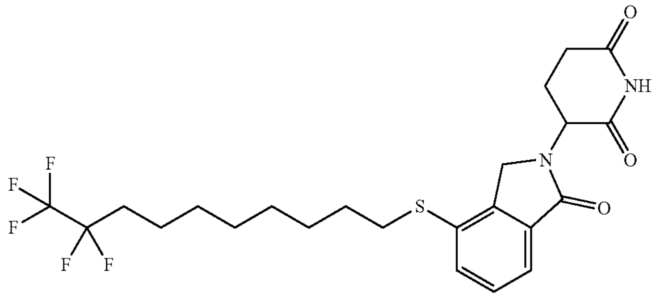 [SMILES: O=C1CCC(N2Cc3c(SCCCCCCCCC(F)(F)C(F)(F)F)cccc3C2=O)C(=O)N1] | 3-(1-oxo-4-((9,9,10,10,10-pentafluorodecyl)thio)isoindolin-2-yl)piperidine-2,6-dione |
| | 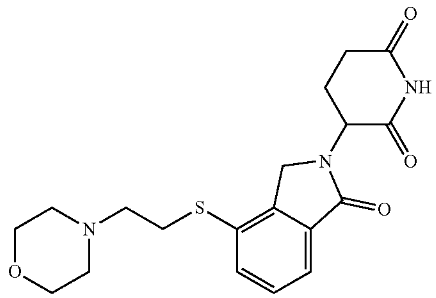 [SMILES: O=C1CCC(N2Cc3c(SCCN4CCOCC4)cccc3C2=O)C(=O)N1] | 3-(4-((2-morpholinoethyl)thio)-1-oxoisoindolin-2-yl)piperidine-2,6-dione |
| | 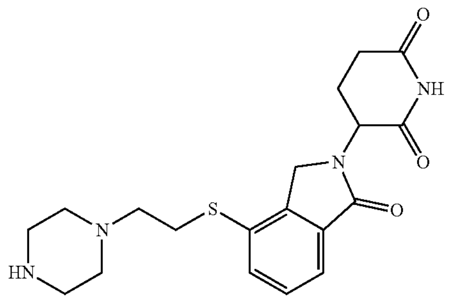 [SMILES: O=C1CCC(N2Cc3c(SCCN4CCNCC4)cccc3C2=O)C(=O)N1] | 3-(1-oxo-4-((2-(piperazin-1-yl)ethyl)thio)isoindolin-2-yl)piperidine-2,6-dione |

The compounds of the present invention

TABLE 1-continued

The compounds of the present invention

| Compound No. | Structure of the compounds | The compound's name |
| --- | --- | --- |
| | 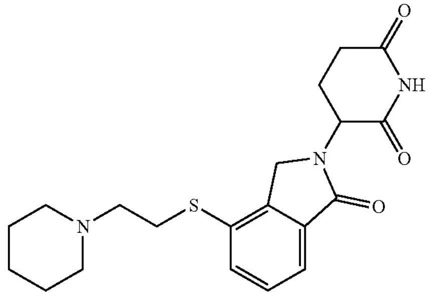 [SMILES: O=C1CCC(N2Cc3c(SCCN4CCCCC4)cccc3C2=O)C(=O)N1] | 3-(1-oxo-4-((2-(piperidin-1-yl)ethyl)thio)isoindolin-2-yl)piperidine-2,6-dione |
| | 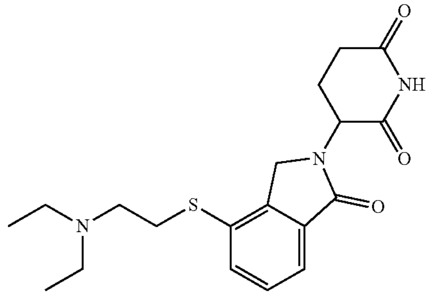 [SMILES: CCN(CC)CCSc1cccc2c1CN(C1CCC(=O)NC1=O)C2=O] | 3-(4-((2-(diethylamino)ethyl)thio)-1-oxoisoindolin-2-yl)piperidine-2,6-dione |
| | 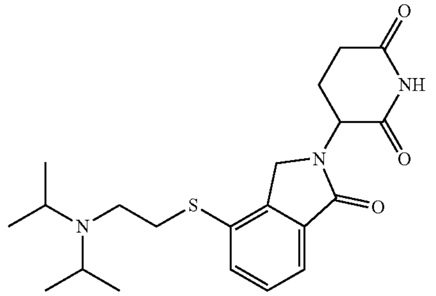 [SMILES: CC(C)N(CCSc1cccc2c1CN(C1CCC(=O)NC1=O)C2=O)C(C)C] | 3-(4-((2-(diisopropylamino)ethyl)thio)-1-oxoisoindolin-2-yl)piperidine-2,6-dione |
| | 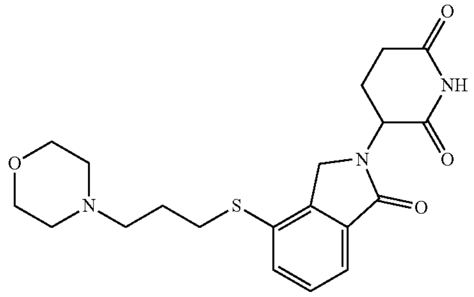 [SMILES: O=C1CCC(N2Cc3c(SCCCN4CCOCC4)cccc3C2=O)C(=O)N1] | 3-(4-((3-morpholinopropyl)thio)-1-oxoisoindolin-2-yl)piperidine-2,6-dione |
| | 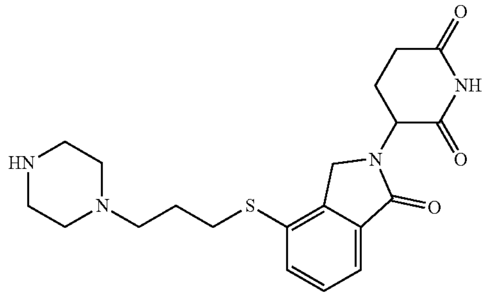 [SMILES: O=C1CCC(N2Cc3c(SCCCN4CCNCC4)cccc3C2=O)C(=O)N1] | 3-(1-oxo-4-((3-(piperazin-1-yl)propyl)thio)isoindolin-2-yl)piperidine-2,6-dione |

TABLE 1-continued

| The compounds of the present invention | | |
|---|---|---|
| Compound No. | Structure of the compounds | The compound's name |
| | 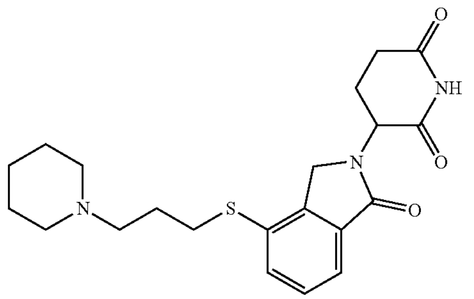 [SMILES: O=C1CCC(N2Cc3c(SCCCN4CCCCC4)cccc3C2=O)C(=O)N1] | 3-(1-oxo-4-((3-(piperidin-1-yl)propyl)thio)isoindolin-2-yl)piperidine-2,6-dione |
| | 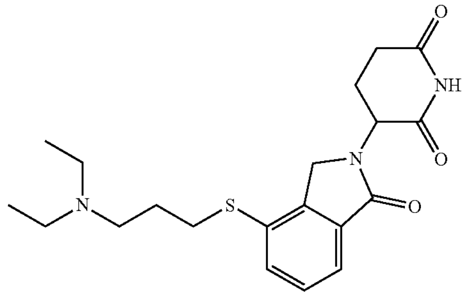 [SMILES: CCN(CC)CCCSc1cccc2c1CN(C1CCC(=O)NC1=O)C2=O] | 3-(4-((3-(diethylamino)propyl)thio)-1-oxoisoindolin-2-yl)piperidine-2,6-dione |
| | 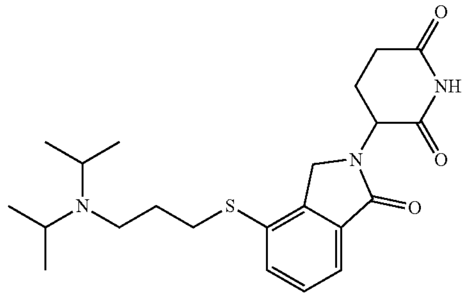 [SMILES: CC(C)N(CCCSc1cccc2c1CN(C1CCC(=O)NC1=O)C2=O)C(C)C] | 3-(4-((3-(diisopropylamino)propyl)thio)-1-oxoisoindolin-2-yl)piperidine-2,6-dione |
| | 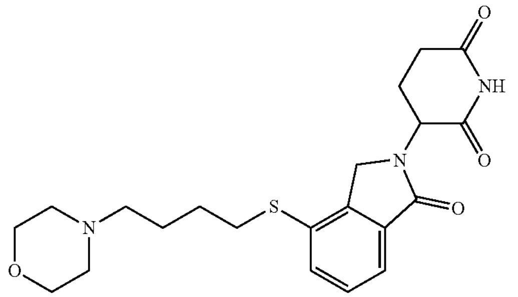 [SMILES: O=C1CCC(N2Cc3c(SCCCCN4CCOCC4)cccc3C2=O)C(=O)N1] | 3-(4-((4-morpholinobutyl)thio)-1-oxoisoindolin-2-yl)piperidine-2,6-dione |
| | 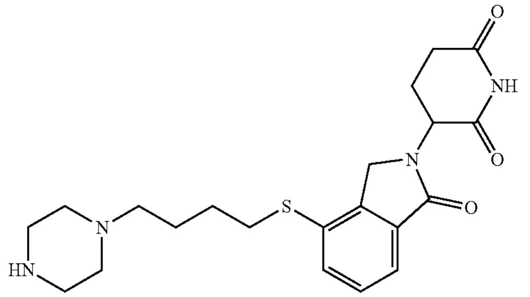 [SMILES: O=C1CCC(N2Cc3c(SCCCCN4CCNCC4)cccc3C2=O)C(=O)N1] | 3-(1-oxo-4-((4-(piperazin-1-yl)butyl)thio)isoindolin-2-yl)piperidine-2,6-dione |

TABLE 1-continued

The compounds of the present invention

| Compound No. | Structure of the compounds | The compound's name |
|---|---|---|
| | 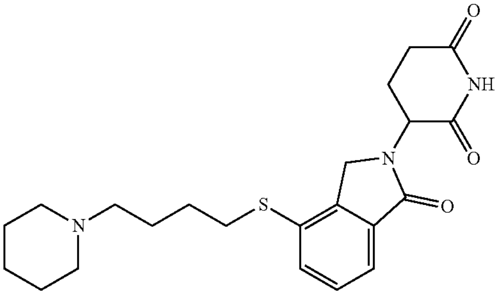 [SMILES: O=C1CCC(N2Cc3c(SCCCCN4CCCCC4)cccc3C2=O)C(=O)N1] | 3-(1-oxo-4-((4-(piperidin-1-yl)butyl)thio)isoindolin-2-yl)piperidine-2,6-dione |
| | 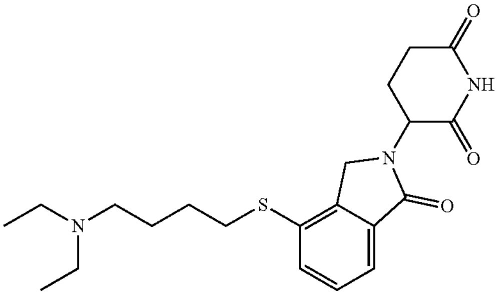 [SMILES: CCN(CC)CCCCSc1cccc2c1CN(C1CCC(=O)NC1=O)C2=O] | 3-(4-((4-(diethylamino)butyl)thio)-1-oxoisoindolin-2-yl)piperidine-2,6-dione |
| | 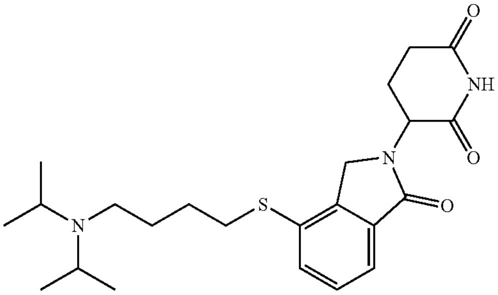 [SMILES: CC(C)N(CCCCSc1cccc2c1CN(C1CCC(=O)NC1=O)C2=O)C(C)C] | 3-(4-((4-(diisopropylamino)butyl)thio)-1-oxoisoindolin-2-yl)piperidine-2,6-dione |
| SIAIS12160-61 | 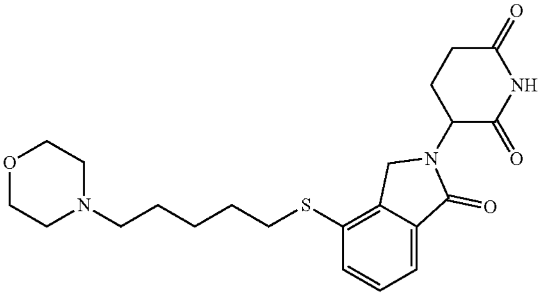 | 3-(4-((5-morpholinopentyl)thio)-1-oxoisoindolin-2-yl)piperidine-2,6-dione |
| SIAIS12160-63 | 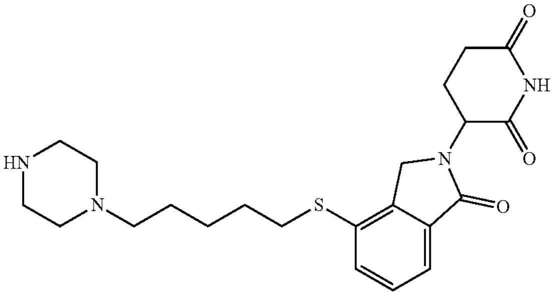 [SMILES: O=C1CCC(N2Cc3c(SCCCCCN4CCNCC4)cccc3C2=O)C(=O)N1] | 3-(1-oxo-4-((5-(piperazin-1-yl)pentyl)thio)isoindolin-2-yl)piperidine-2,6-dione |

TABLE 1-continued

| The compounds of the present invention | | |
|---|---|---|
| Compound No. | Structure of the compounds | The compound's name |
| | 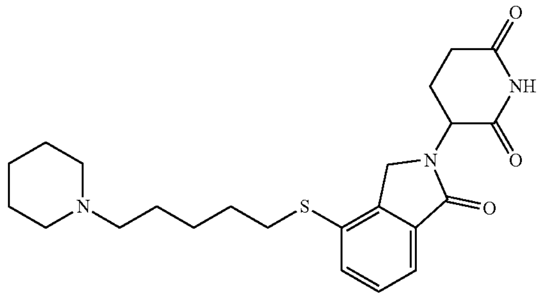 [SMILES: O=C1CCC(N2Cc3c(SCCCCCN4CCCCC4)cccc3C2=O)C(=O)N1] | 3-(1-oxo-4-((5-(piperidin-1-yl)pentyl)thio)isoindolin-2-yl)piperidine-2,6-dione |
| SIAIS12161-39 | 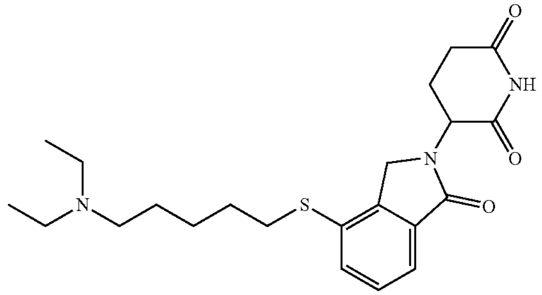 | 3-(4-((5-(diethylamino)pentyl)thio)-1-oxoisoindolin-2-yl)piperidine-2,6-dione |
| | 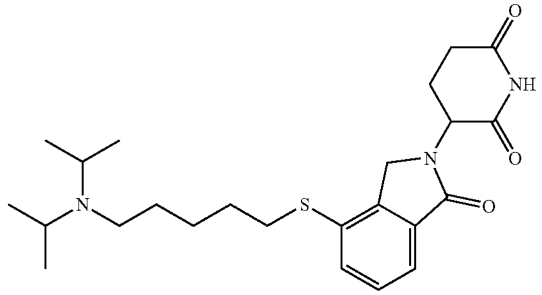 [SMILES: CC(C)N(CCCCCSc1cccc2c1CN(C1CCC(=O)NC1=O)C2=O)C(C)C] | 3-(4-((5-(diisopropylamino)pentyl)thio)-1-oxoisoindolin-2-yl)piperidine-2,6-dione |
| SIAIS12160-89 | 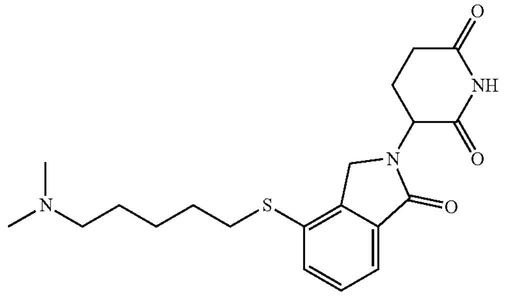 | 3-(4-((5-(dimethylamino)pentyl)thio)-1-oxoisoindolin-2-yl)piperidine-2,6-dione |
| SIAIS12161-41 | 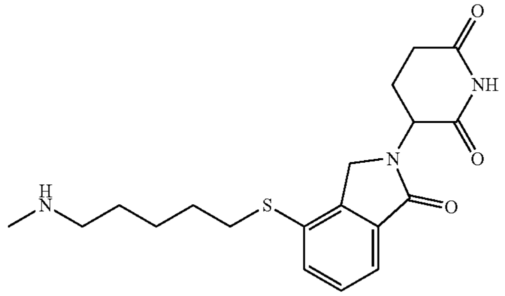 [SMILES: CNCCCCCSc1cccc2c1CN(C1CCC(=O)NC1=O)C2=O] | 3-(4-((5-(methylamino)pentyl)thio)-1-oxoisoindolin-2-yl)piperidine-2,6-dione |

TABLE 1-continued

| The compounds of the present invention | | |
|---|---|---|
| Compound No. | Structure of the compounds | The compound's name |
| SIAIS12160-95 | 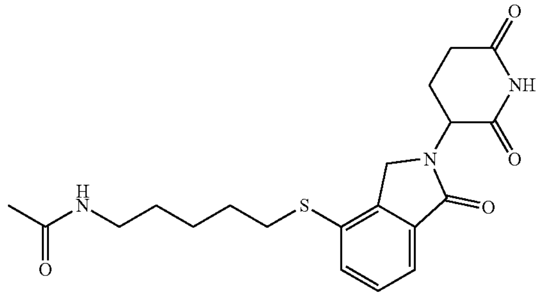 [SMILES: CC(=O)NCCCCCSc1cccc2c1CN(C1CCC(=O)NC1=O)C2=O] | N-(5-((2-(2,6-dioxopiperidin-3-yl)-1-oxoisoindolin-4-yl)thio)pentyl)acetamide |
| SIAIS12211-23 | 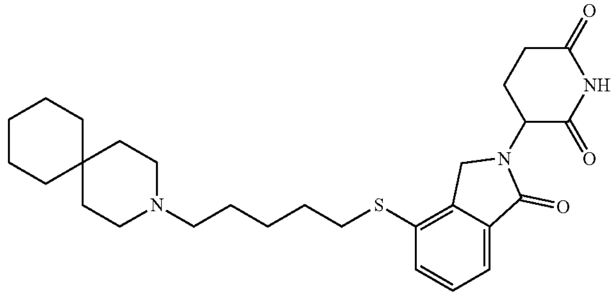 [SMILES: O=C1CCC(N2Cc3c(SCCCCCN4CCC5(CCCCC5)CC4)cccc3C2=O)C(=O)N1] | 3-(4-((5-(3-azaspiro[5.5]undecan-3-yl)pentyl)thio)-1-oxoisoindolin-2-yl)piperidine-2,6-dione |
| SIAIS12200-27 | 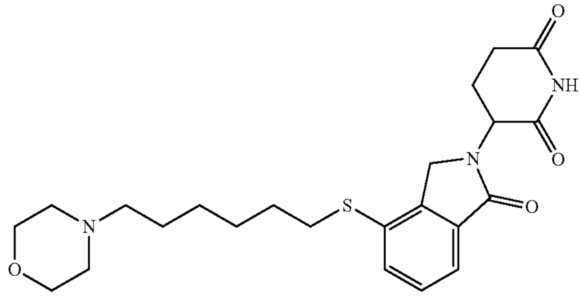 | 3-(4-((6-morpholinohexyl)thio)-1-oxoisoindolin-2-yl)piperidine-2,6-dione |
| | 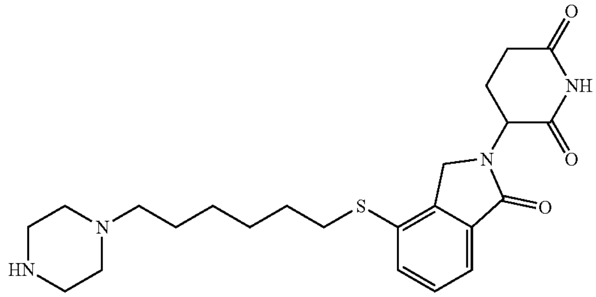 [SMILES: O=C1CCC(N2Cc3c(SCCCCCCN4CCNCC4)cccc3C2=O)C(=O)N1] | 3-(1-oxo-4-((6-(piperazin-1-yl)hexyl)thio)isoindolin-2-yl)piperidine-2,6-dione |
| | 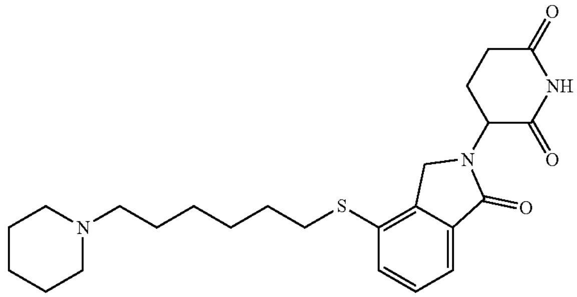 [SMILES: O=C1CCC(N2Cc3c(SCCCCCCN4CCCCC4)cccc3C2=O)C(=O)N1] | 3-(1-oxo-4-((6-(piperidin-1-yl)hexyl)thio)isoindolin-2-yl)piperidine-2,6-dione |

TABLE 1-continued

| The compounds of the present invention | | |
|---|---|---|
| Compound No. | Structure of the compounds | The compound's name |
| SIAIS12200-29 | 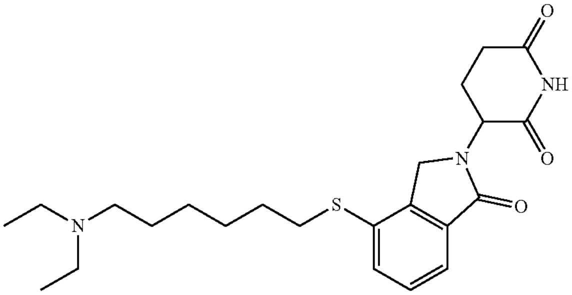 [SMILES: CCN(CC)CCCCCCSc1cccc2c1CN(C1CCC(=O)NC1=O)C2=O] | 3-(4-((6-(diethylamino)hexyl)thio)-1-oxoisoindolin-2-yl)piperidine-2,6-dione |
| | 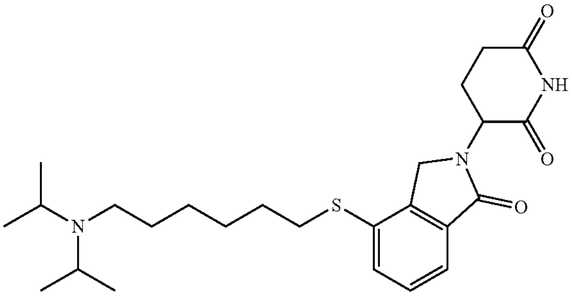 [SMILES: CC(C)N(CCCCCCSc1cccc2c1CN(C1CCC(=O)NC1=O)C2=O)C(C)C] | 3-(4-((6-(diisopropylamino)hexyl)thio)-1-oxoisoindolin-2-yl)piperidine-2,6-dione |
| | 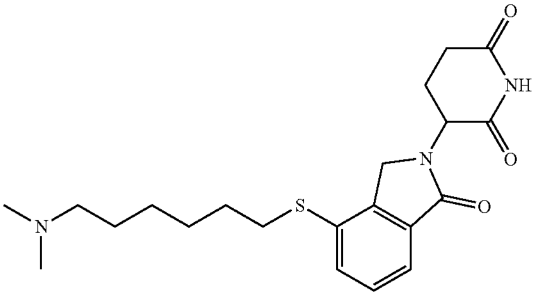 [SMILES: CN(C)CCCCCCSc1cccc2c1CN(C1CCC(=O)NC1=O)C2=O] | 3-(4-((6-(dimethylamino)hexyl)thio)-1-oxoisoindolin-2-yl)piperidine-2,6-dione |
| | 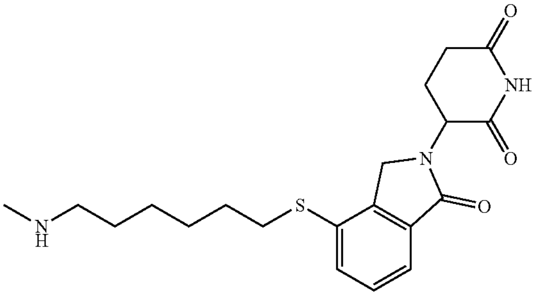 [SMILES: CNCCCCCCSc1cccc2c1CN(C1CCC(=O)NC1=O)C2=O] | 3-(4-((6-(methylamino)hexyl)thio)-1-oxoisoindolin-2-yl)piperidine-2,6-dione |
| SIAIS12201-83 | 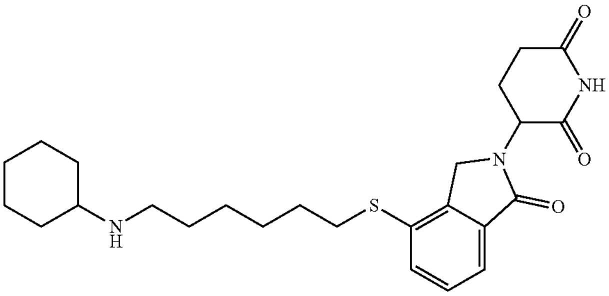 [SMILES: O=C1CCC(N2Cc3c(SCCCCCCNC4CCCCC4)cccc3C2=O)C(=O)N1] | 3-(4-((6-(cyclohexylamino)hexyl)thio)-1-oxoisoindolin-2-yl)piperidine-2,6-dione |

TABLE 1-continued

| The compounds of the present invention | | |
|---|---|---|
| Compound No. | Structure of the compounds | The compound's name |
| | 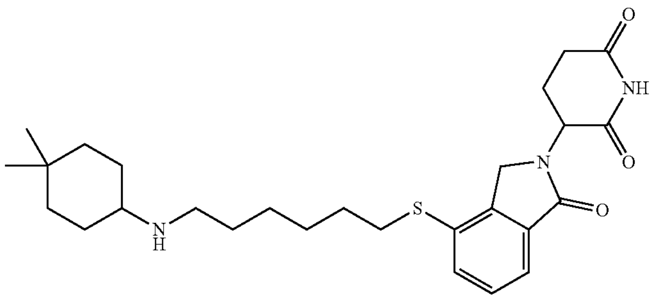 [SMILES: CC1(C)CCC(NCCCCCCSc2cccc3c2CN(C2CCC(=O)NC2=O)C3=O)CC1] | 3-(4-((6-((4,4-dimethylcyclohexyl)amino)hexyl)thio)-1-oxoisoindolin-2-yl)piperidine-2,6-dione |
| | 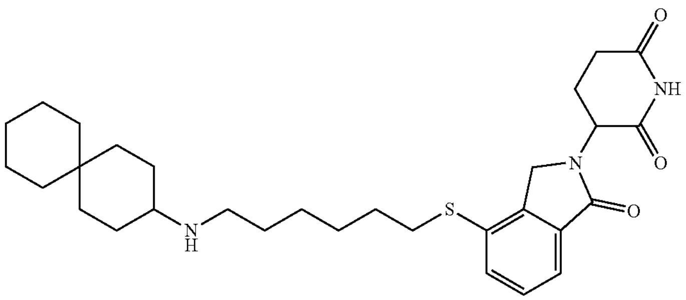 [SMILES: O=C1CCC(N2Cc3c(SCCCCCCNC4CCC5(CCCCC5)CC4)cccc3C2=O)C(=O)N1] | 3-(1-oxo-4-((6-(spiro[5.5]undecan-3-ylamino)hexyl)thio)isoindolin-2-yl)piperidine-2,6-dione |
| | 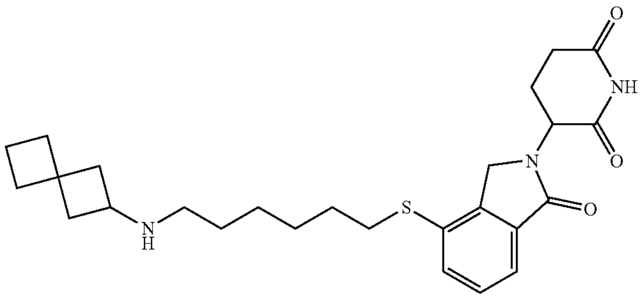 [SMILES: O=C1CCC(N2Cc3c(SCCCCCCNC4CC5(CCC5)C4)cccc3C2=O)C(=O)N1] | 3-(1-oxo-4-((6-(spiro[3.3]heptan-2-ylamino)hexyl)thio)isoindolin-2-yl)piperidine-2,6-dione |
| SIAIS12211-21 | 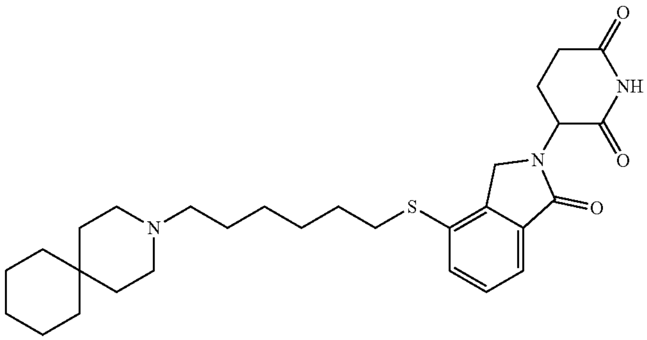 [SMILES: O=C1CCC(N2Cc3c(SCCCCCCN4CCC5(CCCCC5)CC4)cccc3C2=O)C(=O)N1] | 3-(4-((6-(3-azaspiro[5.5]undecan-3-yl)hexyl)thio)-1-oxoisoindolin-2-yl)piperidine-2,6-dione |

TABLE 1-continued

The compounds of the present invention

| Compound No. | Structure of the compounds | The compound's name |
| --- | --- | --- |
| SIAIS12221-99 | 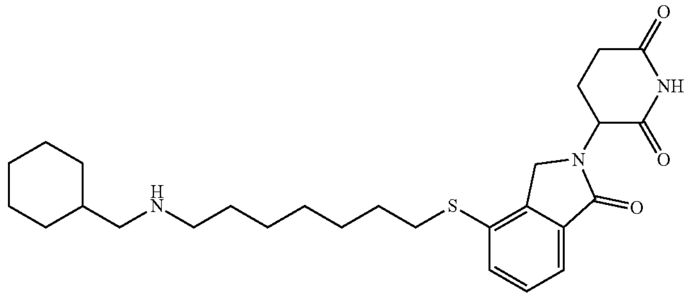 [SMILES: O=C1CCC(N2Cc3c(SCCCCCCCNCC4CCCCC4)cccc3C2=O)C(=O)N1] | 3-(4-((7-((cyclohexylmethyl)amino)heptyl)thio)-1-oxoisoindolin-2-yl)piperidine-2,6-dione |
| SIAIS12200-31 | 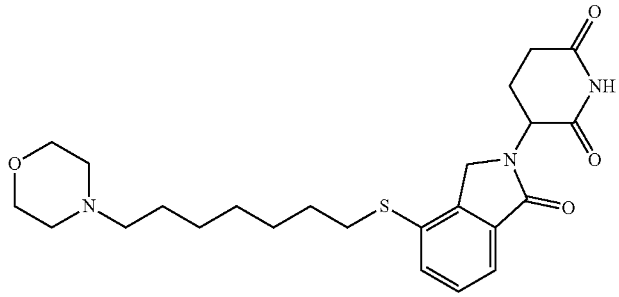 [SMILES: O=C1CCC(N2Cc3c(SCCCCCCCN4CCOCC4)cccc3C2=O)C(=O)N1] | 3-(4-((7-morpholinoheptyl)thio)-1-oxoisoindolin-2-yl)piperidine-2,6-dione |
| SIAIS12221-97 | 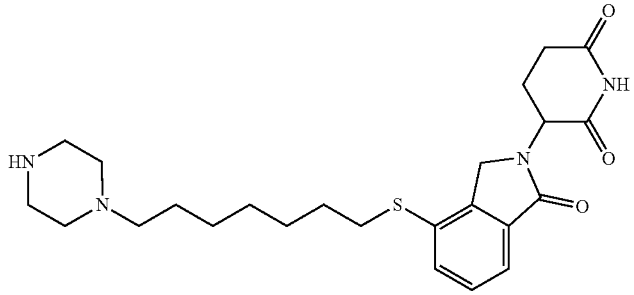 [SMILES: O=C1CCC(N2Cc3c(SCCCCCCCN4CCNCC4)cccc3C2=O)C(=O)N1] | 3-(1-oxo-4-((7-(piperazin-1-yl)heptyl)thio)isoindolin-2-yl)piperidine-2,6-dione |
| SIAIS12201-61 | 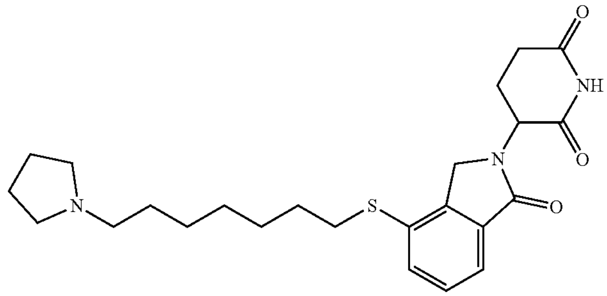 [SMILES: O=C1CCC(N2Cc3c(SCCCCCCCN4CCCC4)cccc3C2=O)C(=O)N1] | 3-(1-oxo-4-((7-(pyrrolidin-1-yl)heptyl)thio)isoindolin-2-yl)piperidine-2,6-dione |
| SIAIS12201-05 | 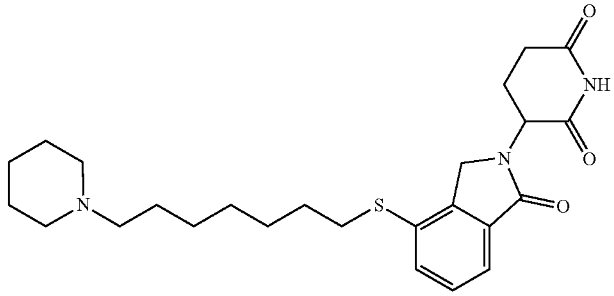 [SMILES: O=C1CCC(N2Cc3c(SCCCCCCCN4CCCCC4)cccc3C2=O)C(=O)N1] | 3-(1-oxo-4-((7-(piperidin-1-yl)heptyl)thio)isoindolin-2-yl)piperidine-2,6-dione |

TABLE 1-continued

The compounds of the present invention

| Compound No. | Structure of the compounds | The compound's name |
|---|---|---|
| SIAIS12201-63 | 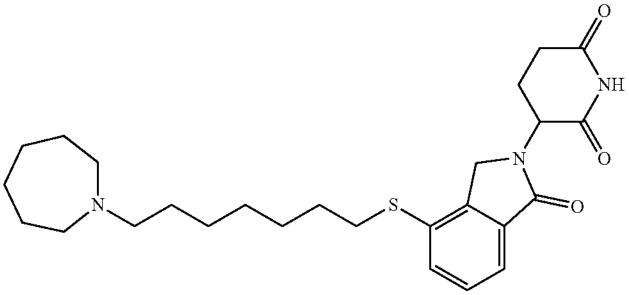 [SMILES: O=C1CCC(N2Cc3c(SCCCCCCCN4CCCCCC4)cccc3C2=O)C(=O)N1] | 3-(4-((7-(azepan-1-yl)heptyl)thio)-1-oxoisoindolin-2-yl)piperidine-2,6-dione |
| SIAIS12201-93 | 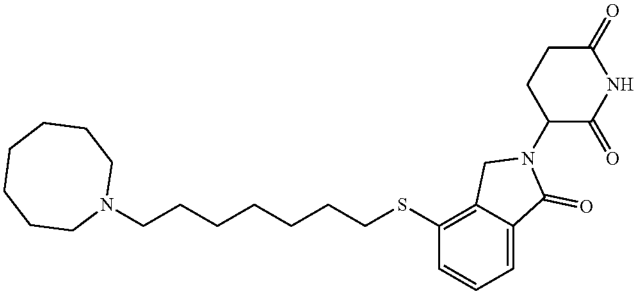 [SMILES: O=C1CCC(N2Cc3c(SCCCCCCCN4CCCCCCC4)cccc3C2=O)C(=O)N1] | 3-(4-((7-(azocan-1-yl)heptyl)thio)-1-oxoisoindolin-2-yl)piperidine-2,6-dione |
| SIAIS12210-27 | 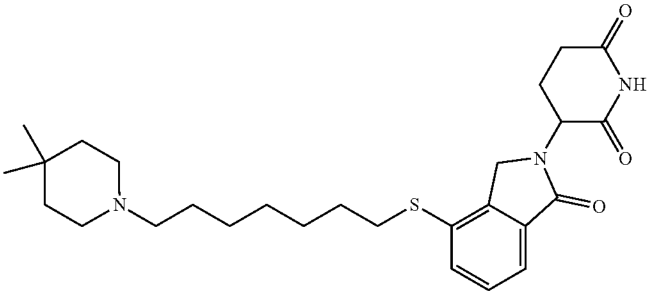 [SMILES: CC1(C)CCN(CCCCCCCSc2cccc3c2CN(C2CCC(=O)NC2=O)C3=O)CC1] | 3-(4-((7-(4,4-dimethylpiperidin-1-yl)heptyl)thio)-1-oxoisoindolin-2-yl)piperidine-2,6-dione |
| SIAIS12210-21 | 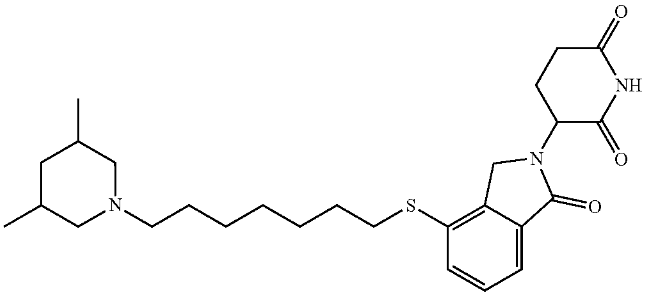 [SMILES: CC1CC(C)CN(CCCCCCCSc2cccc3c2CN(C2CCC(=O)NC2=O)C3=O)C1] | 3-(4-((7-(3,5-dimethylpiperidin-1-yl)heptyl)thio)-1-oxoisoindolin-2-yl)piperidine-2,6-dione |
| SIAIS12210-15 | 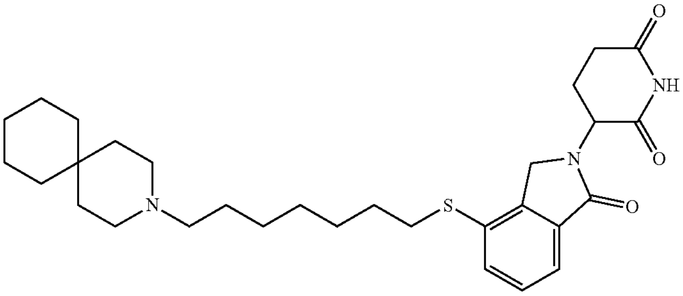 [SMILES: O=C1CCC(N2Cc3c(SCCCCCCCN4CCC5(CCCCC5)CC4)cccc3C2=O)C(=O)N1] | 3-(4-((7-(3-azaspiro[5.5]undecan-3-yl)heptyl)thio)-1-oxoisoindolin-2-yl)piperidine-2,6-dione |

TABLE 1-continued

| The compounds of the present invention | | |
|---|---|---|
| Compound No. | Structure of the compounds | The compound's name |
| SIAIS12221-05 | 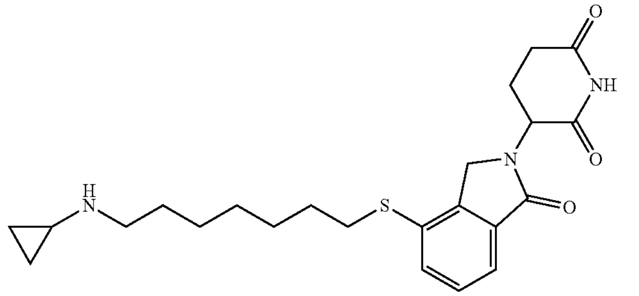 [SMILES: O=C1CCC(N2Cc3c(SCCCCCCCNC4CC4)cccc3C2=O)C(=O)N1] | 3-(4-((7-(cyclopropylamino)heptyl)thio)-1-oxoisoindolin-2-yl)piperidine-2,6-dione |
| SIAIS12221-03 | 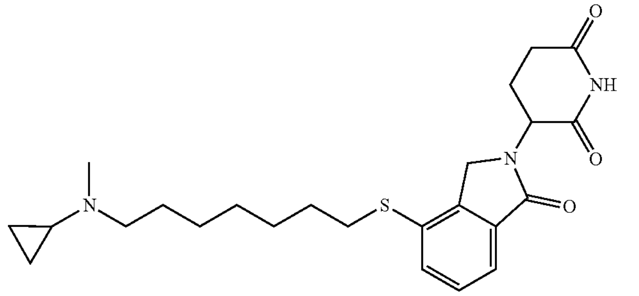 [SMILES: CN(CCCCCCCSc1cccc2c1CN(C1CCC(=O)NC1=O)C2=O)C1CC1] | 3-(4-((7-(cyclopropyl(methyl)amino)heptyl)thio)-1-oxoisoindolin-2-yl)piperidine-2,6-dione |
| SIAIS12221-15 | 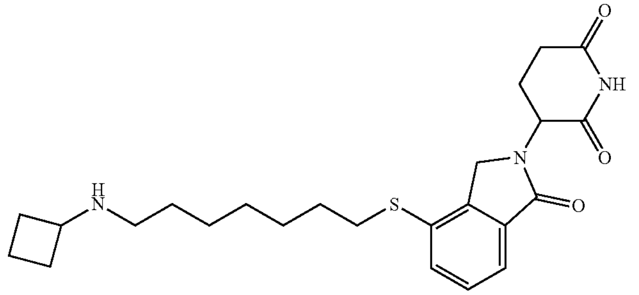 [SMILES: O=C1CCC(N2Cc3c(SCCCCCCCNC4CCC4)cccc3C2=O)C(=O)N1] | 3-(4-((7-(cyclobutylamino)heptyl)thio)-1-oxoisoindolin-2-yl)piperidine-2,6-dione |
| SIAIS12221-23 | 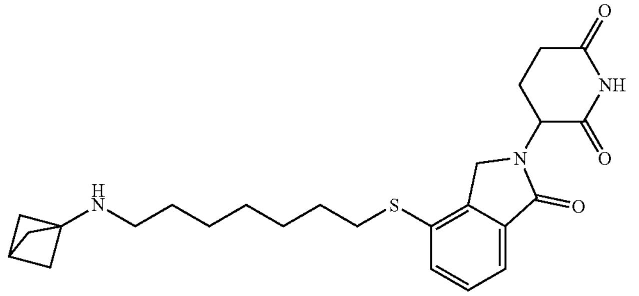 [SMILES: O=C1CCC(N2Cc3c(SCCCCCCCNC45CC(C4)C5)cccc3C2=O)C(=O)N1] | 3-(4-((7-(bicyclo[1.1.1]pentan-1-ylamino)heptyl)thio)-1-oxoisoindolin-2-yl)piperidine-2,6-dione |
| SIAIS12221-17 | 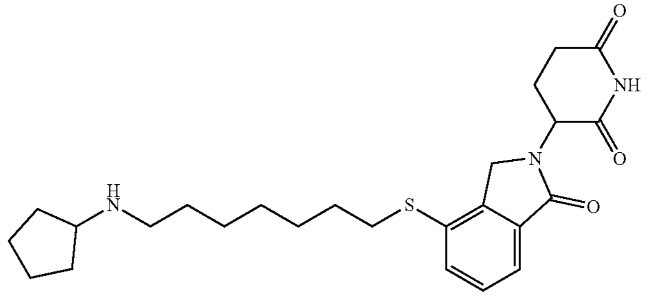 [SMILES: O=C1CCC(N2Cc3c(SCCCCCCCNC4CCCC4)cccc3C2=O)C(=O)N1] | 3-(4-((7-(cyclopentylamino)heptyl)thio)-1-oxoisoindolin-2-yl)piperidine-2,6-dione |

TABLE 1-continued

| Compound No. | Structure of the compounds | The compound's name |
|---|---|---|
| SIAIS12201-85 | 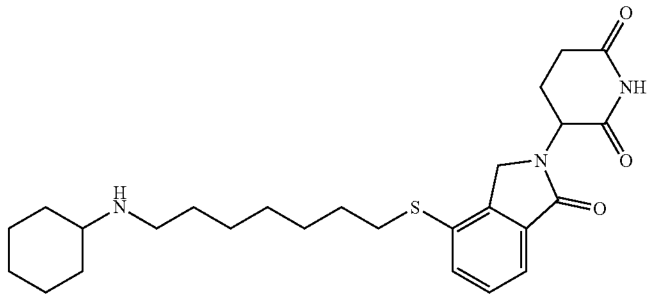 [SMILES: O=C1CCC(N2Cc3c(SCCCCCCCNC4CCCCC4)cccc3C2=O)C(=O)N1] | 3-(4-((7-(cyclohexylamino)heptyl)thio)-1-oxoisoindolin-2-yl)piperidine-2,6-dione |
| SIAIS12210-29 | 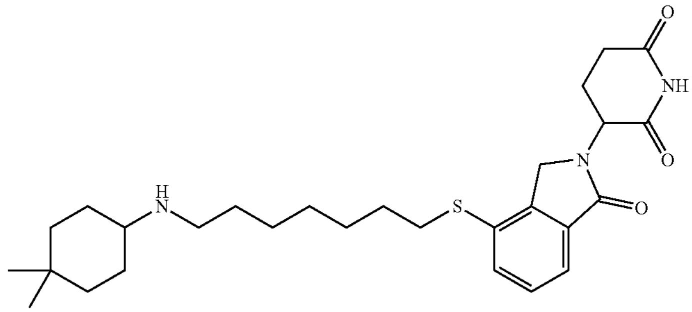 [SMILES: CC1(C)CCC(NCCCCCCCSc2cccc3c2CN(C2CCC(=O)NC2=O)C3=O)CC1] | 3-(4-((7-((4,4-dimethylcyclohexyl)amino)heptyl)thio)-1-oxoisoindolin-2-yl)piperidine-2,6-dione |
| SIAIS12211-25 | 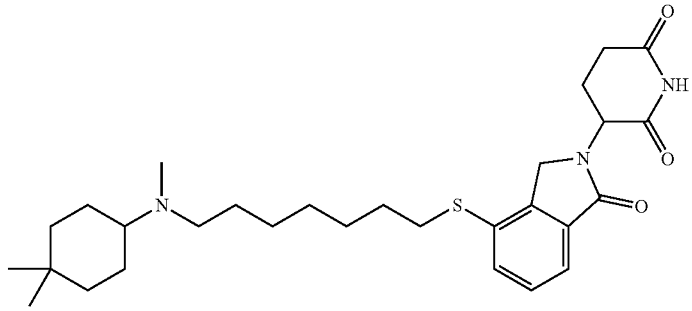 [SMILES: CN(CCCCCCCSc1cccc2c1CN(C1CCC(=O)NC1=O)C2=O)C1CCC(C)(C)CC1] | 3-(4-((7-((4,4-dimethylcyclohexyl)(methyl)amino)heptyl)thio)-1-oxoisoindolin-2-yl)piperidine-2,6-dione |
| SIAIS12221-47 | 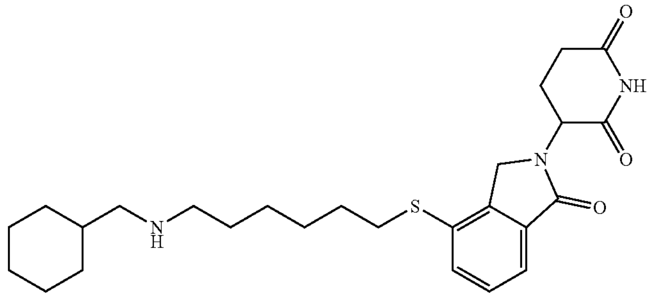 [SMILES: O=C1CCC(N2Cc3c(SCCCCCCNCC4CCCCC4)cccc3C2=O)C(=O)N1] | 3-(4-((6-((cyclohexylmethyl)amino)hexyl)thio)-1-oxoisoindolin-2-yl)piperidine-2,6-dione |
| SIAIS12221-07 | 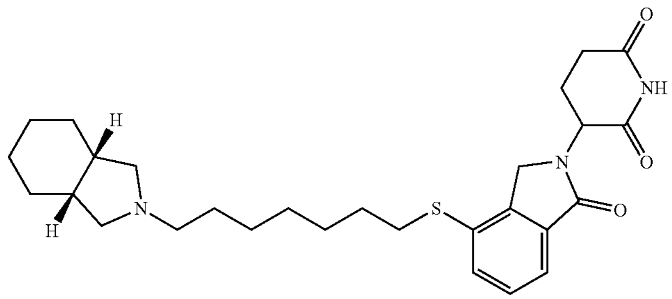 [SMILES: O=C1CCC(N2Cc3c(SCCCCCCCN4C[C@H]5CCCC[C@H]5C4)cccc3C2=O)C(=O)N1] | 3-(4-((7-((3aR,7aS)-hexahydro-1H-isoindol-2(3H)-yl)heptyl)thio)-1-oxoisoindolin-2-yl)piperidine-2,6-dione |

The compounds of the present invention

TABLE 1-continued

| Compound No. | Structure of the compounds | The compound's name |
|---|---|---|
| SIAIS12220-77 | 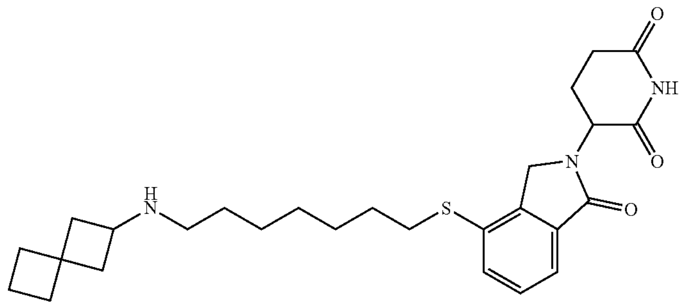 [SMILES: O=C1CCC(N2Cc3c(SCCCCCCCNC4CC5(CCC5)C4)cccc3C2=O)C(=O)N1] | 3-(1-oxo-4-((7-(spiro[3.3]heptan-2-ylamino)heptyl)thio)isoindolin-2-yl)piperidine-2,6-dione |
| SIAIS12220-79 | 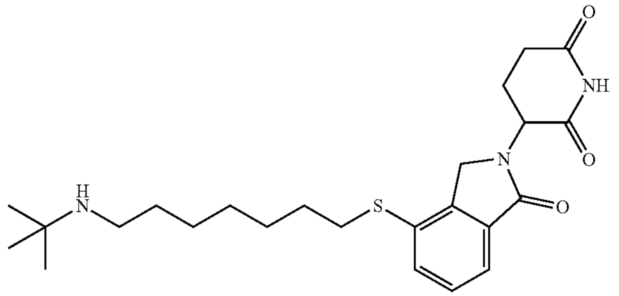 [SMILES: CC(C)(C)NCCCCCCCSc1cccc2c1CN(C1CCC(=O)NC1=O)C2=O] | 3-(4-((7-(tert-butylamino)heptyl)thio)-1-oxoisoindolin-2-yl)piperidine-2,6-dione |
| | 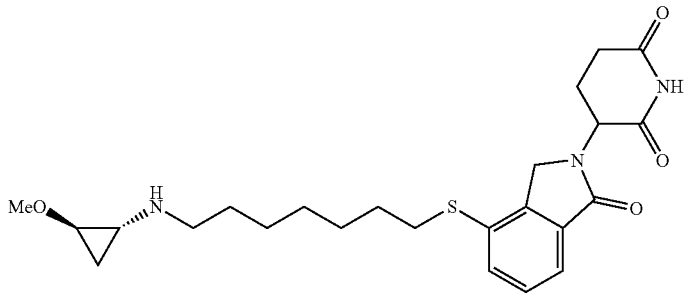 [SMILES: CO[C@@H]1C[C@H]1NCCCCCCCSc1cccc2c1CN(C1CCC(=O)NC1=O)C2=O] | 3-(4-((7-(((1R,2R)-2-methoxycyclopropyl)amino)heptyl)thio)-1-oxoisoindolin-2-yl)piperidine-2,6-dione |
| | 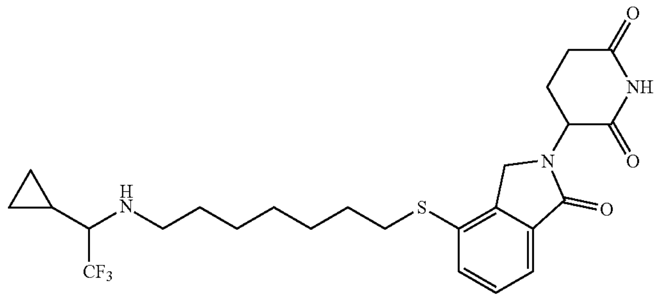 [SMILES: O=C1CCC(N2Cc3c(SCCCCCCCNC(C4CC4)C(F)(F)F)cccc3C2=O)C(=O)N1] | 3-(4-((7-((1-cyclopropyl-2,2,2-trifluoroethyl)amino)heptyl)thio)-1-oxoisoindolin-2-yl)piperidine-2,6-dione |
| | 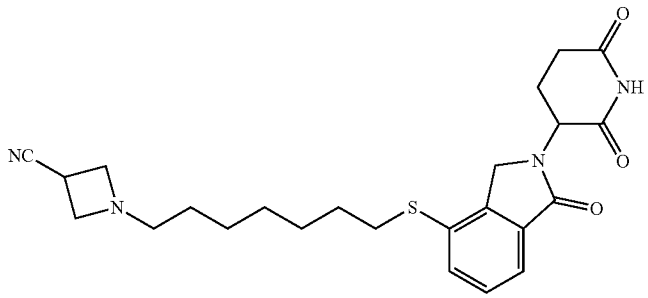 | 1-(7-((2-(2,6-dioxopiperidin-3-yl)-1-oxoisoindolin-4-yl)thio)heptyl)azetidine-3-carbonitrile |

TABLE 1-continued

The compounds of the present invention

| Compound No. | Structure of the compounds | The compound's name |
|---|---|---|
| | 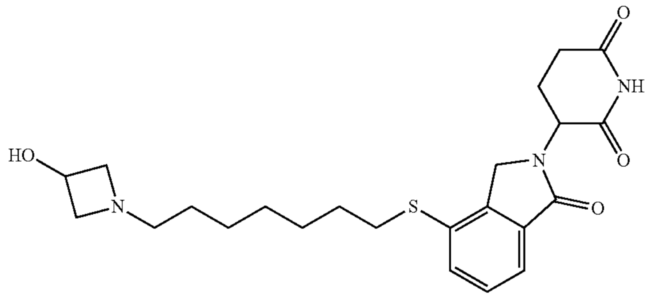 [SMILES: N#CC1CN(CCCCCCCSc2cccc3c2CN(C2CCC(=O)NC2=O)C3=O)C1] | 3-(4-((7-(3-hydroxyazetidin-1-yl)heptyl)thio)-1-oxoisoindolin-2-yl)piperidine-2,6-dione |
| | 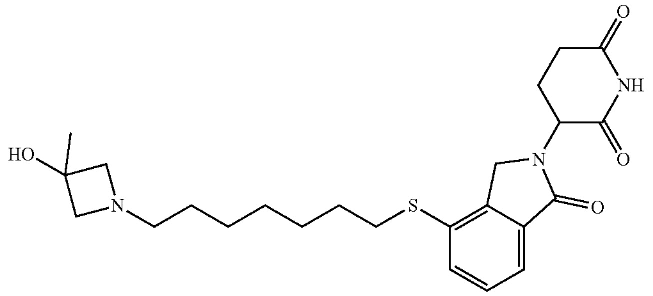 [SMILES: CC1(O)CN(CCCCCCCSc2cccc3c2CN(C2CCC(=O)NC2=O)C3=O)C1] | 3-(4-((7-(3-hydroxy-3-methylazetidin-1-yl)heptyl)thio)-1-oxoisoindolin-2-yl)piperidine-2,6-dione |
| | 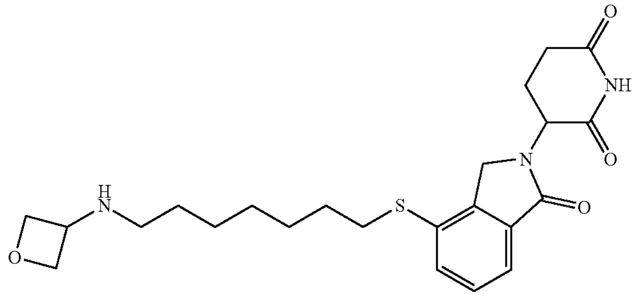 [SMILES: O=C1CCC(N2Cc3c(SCCCCCCCNC4COC4)cccc3C2=O)C(=O)N1] | 3-(4-((7-(oxetan-3-ylamino)heptyl)thio)-1-oxoisoindolin-2-yl)piperidine-2,6-dione |
| | 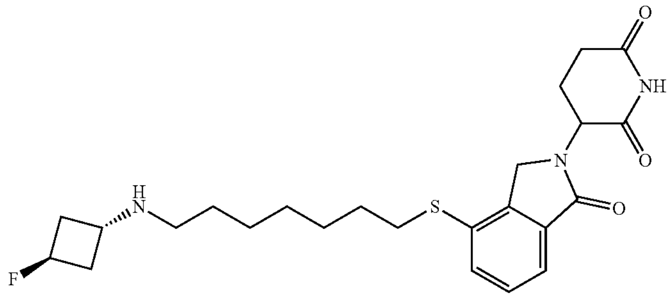 [SMILES: O=C1CCC(N2Cc3c(SCCCCCCCN[C@H]4C[C@H](F)C4)cccc3C2=O)C(=O)N1] | 3-(4-((7-(((1r,3r)-3-fluorocyclobutyl)amino)heptyl)thio)-1-oxoisoindolin-2-yl)piperidine-2,6-dione |
| | 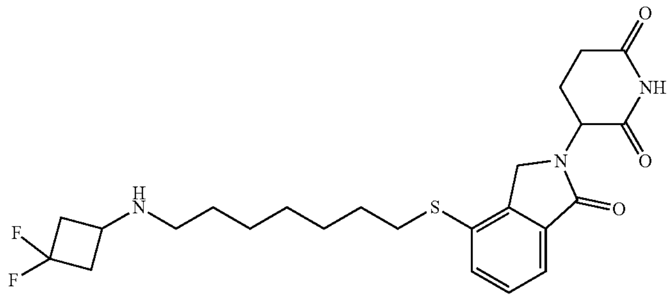 [SMILES: O=C1CCC(N2Cc3c(SCCCCCCCNC4CC(F)(F)C4)cccc3C2=O)C(=O)N1] | 3-(4-((7-((3,3-difluorocyclobutyl)amino)heptyl)thio)-1-oxoisoindolin-2-yl)piperidine-2,6-dione |

TABLE 1-continued

| The compounds of the present invention | | |
|---|---|---|
| Compound No. | Structure of the compounds | The compound's name |
| | 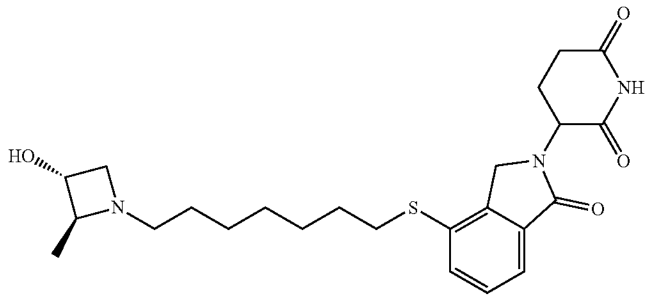 [SMILES: C[C@H]1[C@H](O)CN1CCCCCCCSc1cccc2c1CN(C1CCC(=O)NC1=O)C2=O] | 3-(4-((7-((2S,3R)-3-hydroxy-2-methylazetidin-1-yl)heptyl)thio)-oxoisoindolin-2-yl)piperidine-2,6-dione |
| | 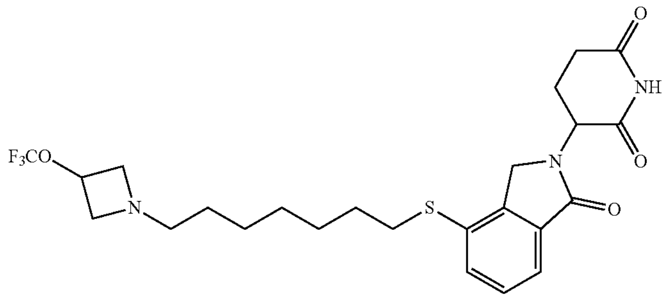 [SMILES: O=C1CCC(N2Cc3c(SCCCCCCCN4CC(OC(F)(F)F)C4)cccc3C2=O)C(=O)N1] | 3-(1-oxo-4-((7-(3-(trifluoromethoxy)azetidin-yl)heptyl)thio)isoindolin-2-yl)piperidine-2,6-dione |
| | 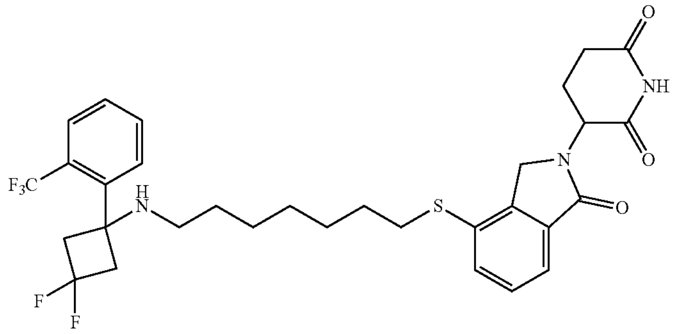 [SMILES: O=C1CCC(N2Cc3c(SCCCCCCCNC4(c5ccccc5C(F)(F)F)CC(F)(F)C4)cccc3C2=O)C(=O)N1] | 3-(4-((7-((3,3-difluoro-1-(2-(trifluoromethyl)phenyl)cyclobutyl)amino)heptyl)thio)-1-oxoisoindolin-2-yl)piperidine-2,6-dione |
| | 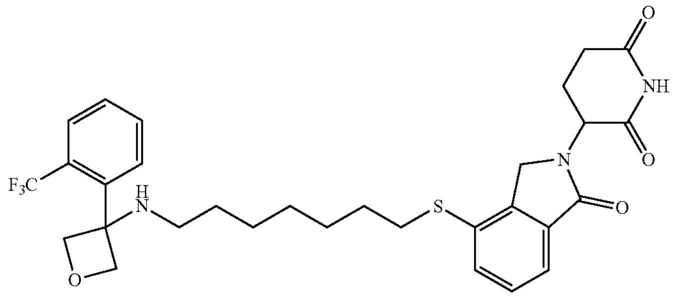 [SMILES: O=C1CCC(N2Cc3c(SCCCCCCCNC4(c5ccccc5C(F)(F)F)COC4)cccc3C2=O)C(=O)N1] | 3-(1-oxo-4-((7-((3-(2-(trifluoromethyl)phenyl)oxetan-3-yl)amino)heptyl)thio)isoindolin-2-yl)piperidine-2,6-dione |

TABLE 1-continued

The compounds of the present invention

| Compound No. | Structure of the compounds | The compound's name |
|---|---|---|
| | 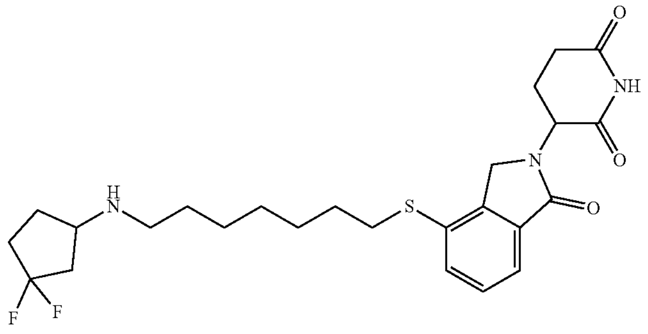 [SMILES: O=C1CCC(N2Cc3c(SCCCCCCCNC4CCC(F)(F)C4)cccc3C2=O)C(=O)N1] | 3-(4-((7-((3,3-difluorocyclopentyl)amino)heptyl)thio)-1-oxoisoindolin-2-yl)piperidine-2,6-dione |
| | 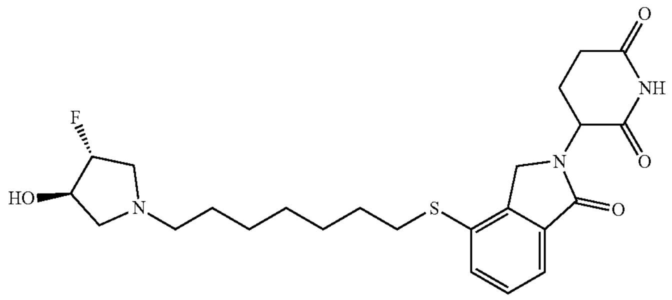 [SMILES: O=C1CCC(N2Cc3c(SCCCCCCCN4C[C@@H](O)[C@H](F)C4)cccc3C2=O)C(=O)N1] | 3-(4-((7-((3R,4R)-3-fluoro-4-hydroxypyrrolidin-1-yl)heptyl)thio)-1-oxoisoindolin-2-yl)piperidine-2,6-dione |
| | 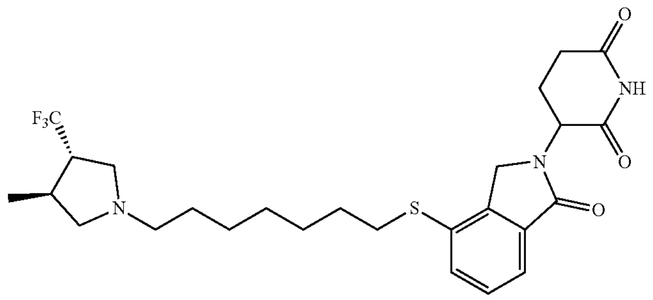 [SMILES: C[C@@H]1CN(CCCCCCCSc2cccc3c2CN(C2CCC(=O)NC2=O)C3=O)C[C@H]1C(F)(F)F] | 3-(4-((7-((3S,4S)-3-methyl-4-(trifluoromethyl)pyrrolidin-1-yl)heptyl)thio)-1-oxoisoindolin-2-yl)piperidine-2,6-dione |
| | 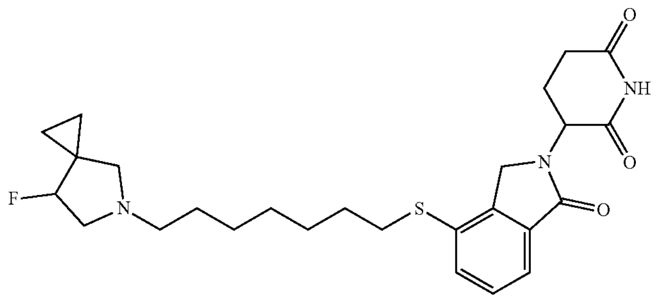 [SMILES: O=C1CCC(N2Cc3c(SCCCCCCCN4CC(F)C5(CC5)C4)cccc3C2=O)C(=O)N1] | 3-(4-((7-(7-fluoro-5-azaspiro[2.4]heptan-5-yl)heptyl)thio)-1-oxoisoindolin-2-yl)piperidine-2,6-dione |
| | 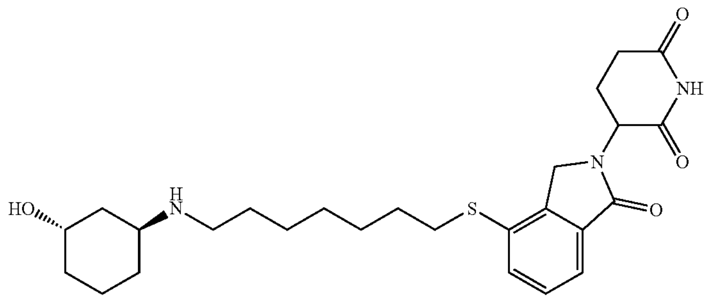 [SMILES: O=C1CCC(N2Cc3c(SCCCCCCCN[C@H]4CCC[C@H](O)C4)cccc3C2=O)C(=O)N1] | 3-(4-((7-(((1S,3S)-3-hydroxycyclohexyl)amino)heptyl)thio)-1-oxoisoindolin-2-yl)piperidine-2,6-dione |

TABLE 1-continued

| The compounds of the present invention | | |
|---|---|---|
| Compound No. | Structure of the compounds | The compound's name |
| | 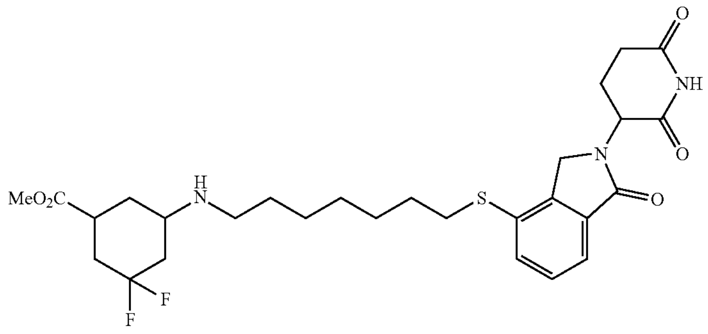 [SMILES: COC(=O)C1CC(NCCCCCCCSc2cccc3c2CN(C2CCC(=O)NC2=O)C3=O)CC(F)(F)C1] | methyl 5-((7-((2-(2,6-dioxopiperidin-3-yl)-1-oxoisoindolin-4-yl)thio)heptyl)amino)-3,3-difluorocyclohexane-1-carboxylate |
| | 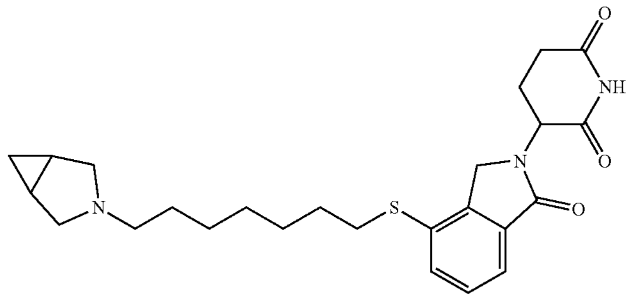 [SMILES: O=C1CCC(N2Cc3c(SCCCCCCCN4CC5CC5C4)cccc3C2=O)C(=O)N1] | 3-(4-((7-(3-azabicyclo[3.1.0]hexan-3-yl)heptyl)thio)-1-oxoisoindolin-2-yl)piperidine-2,6-dione |
| | 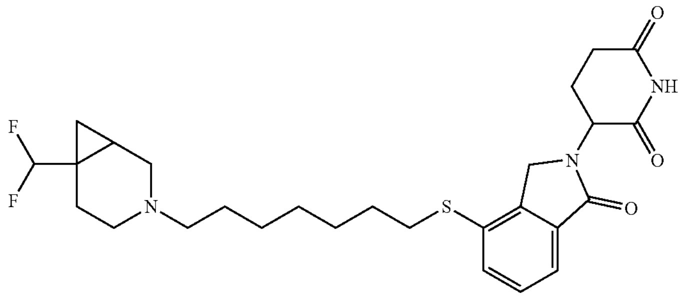 [SMILES: O=C1CCC(N2Cc3c(SCCCCCCCN4CCC5(C(F)F)CC5C4)cccc3C2=O)C(=O)N1] | 3-(4-((7-(6-(difluoromethyl)-3-azabicyclo[4.1.0]heptan-3-yl)heptyl)thio)-1-oxoisoindolin-2-yl)piperidine-2,6-dione |
| | 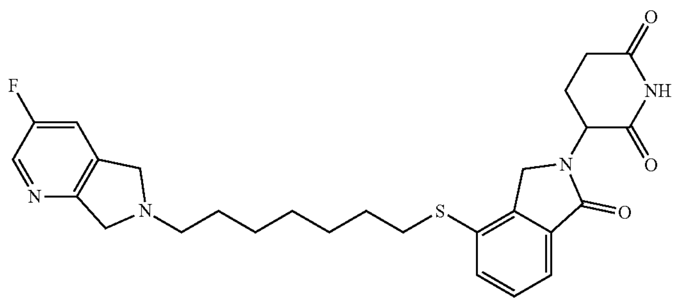 [SMILES: O=C1CCC(N2Cc3c(SCCCCCCCN4Cc5cc(F)cnc5C4)cccc3C2=O)C(=O)N1] | 3-(4-((7-(3-fluoro-5,7-dihydro-6H-pyrrolo[3,4-b]pyridin-6-yl)heptyl)thio)-1-oxoisoindolin-2-yl)piperidine-2,6-dione |

TABLE 1-continued

The compounds of the present invention

| Compound No. | Structure of the compounds | The compound's name |
| --- | --- | --- |
| | 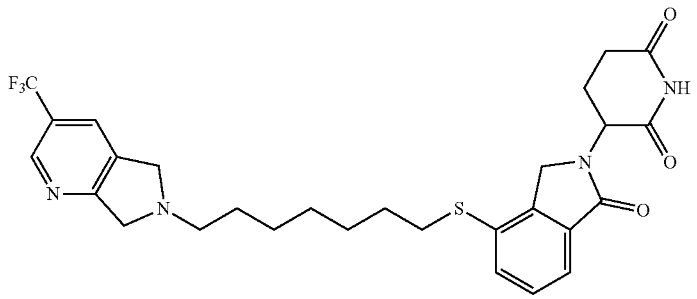 [SMILES: O=C1CCC(N2Cc3c(SCCCCCCCN4Cc5cc(C(F)(F)F)cnc5C4)cccc3C2=O)C(=O)N1] | 3-(1-oxo-4-((7-(3-(trifluoromethyl)-5,7-dihydro-6H-pyrrolo[3,4-b]pyridin-6-yl)heptyl)thio)isoindolin-2-yl)piperidine-2,6-dione |
| | 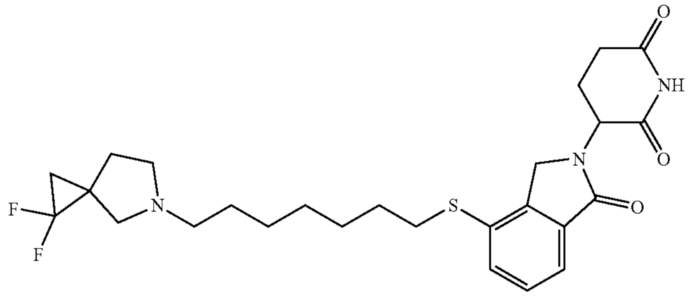 [SMILES: O=C1CCC(N2Cc3c(SCCCCCCCN4CCC5(C4)CC5(F)F)cccc3C2=O)C(=O)N1] | 3-(4-((7-(1,1-difluoro-5-azaspiro[2.4]heptan-5-yl)heptyl)thio)-1-oxoisoindolin-2-yl)piperidine-2,6-dione |
| | 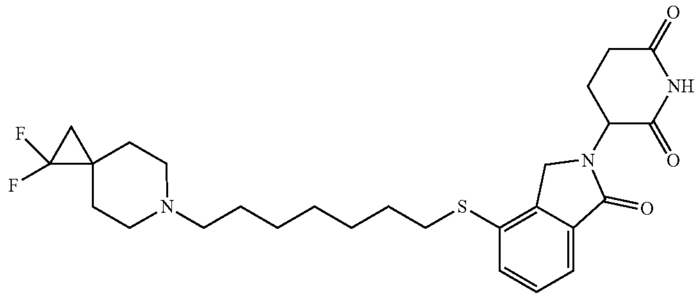 [SMILES: O=C1CCC(N2Cc3c(SCCCCCCCN4CCC5(CC4)CC5(F)F)cccc3C2=O)C(=O)N1] | 3-(4-((7-(1,1-difluoro-6-azaspiro[2.5]octan-6-yl)heptyl)thio)-1-oxoisoindolin-2-yl)piperidine-2,6-dione |
| | 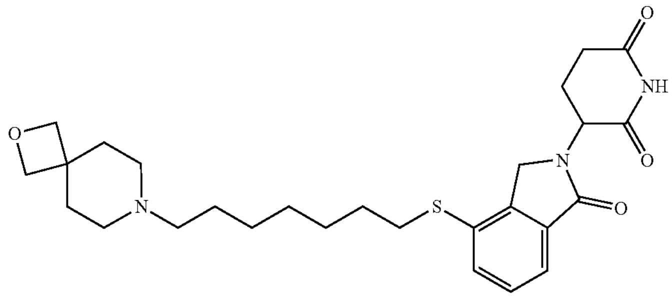 [SMILES: O=C1CCC(N2Cc3c(SCCCCCCCN4CCC5(CC4)COC5)cccc3C2=O)C(=O)N1] | 3-(4-((7-(2-oxa-7-azaspiro[3.5]nonan-7-yl)heptyl)thio)-1-oxoisoindolin-2-yl)piperidine-2,6-dione |
| | 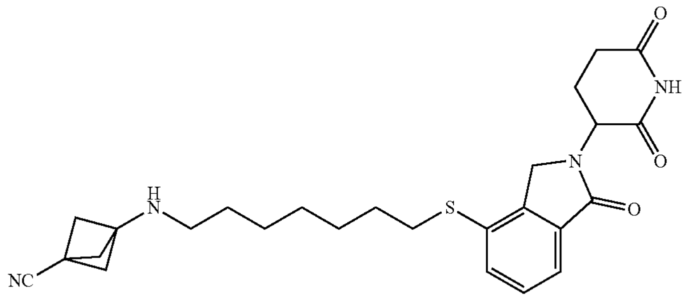 [SMILES: N#CC12CC(NCCCCCCCSc3cccc4c3CN(C3CCC(=O)NC3=O)C4=O)(C1)C2] | 3-((7-((2-(2,6-dioxopiperidin-3-yl)-1-oxoisoindolin-4-yl)thio)heptyl)amino)bicyclo[1.1.1]pentane-1-carbonitrile |

TABLE 1-continued

| The compounds of the present invention | | |
|---|---|---|
| Compound No. | Structure of the compounds | The compound's name |
| | 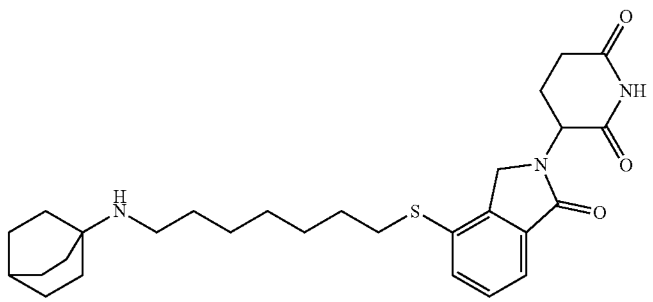 [SMILES: O=C1CCC(N2Cc3c(SCCCCCCCNC45CCC(CC4)CC5)cccc3C2=O)C(=O)N1] | 3-(4-((7-(bicyclo[2.2.2]octan-1-ylamino)heptyl)thio)-1-oxoisoindolin-2-yl)piperidine-2,6-dione |
| | 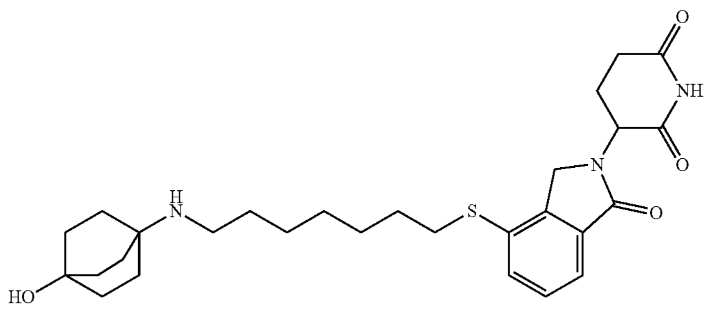 [SMILES: O=C1CCC(N2Cc3c(SCCCCCCCNC45CCC(O)(CC4)CC5)cccc3C2=O)C(=O)N1] | 3-(4-((7-((4-hydroxybicyclo[2.2.2]octan-1-yl)amino)heptyl)thio)-1-oxoisoindolin-2-yl)piperidine-2,6-dione |
| | 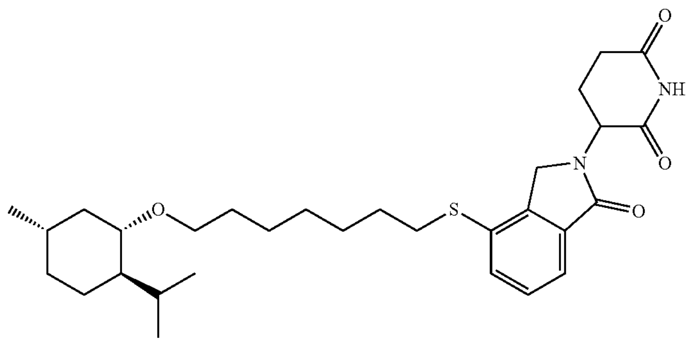 [SMILES: CC(C)[C@H]1CC[C@H](C)C[C@@H]1OCCCCCCCSc1cccc2c1CN(C1CCC(=O)NC1=O)C2=O] | 3-(4-((7-(((1S,2R,5S)-2-isopropyl-5-methylcyclohexyl)oxy)heptyl)thio)-1-oxoisoindolin-2-yl)piperidine-2,6-dione |
| | 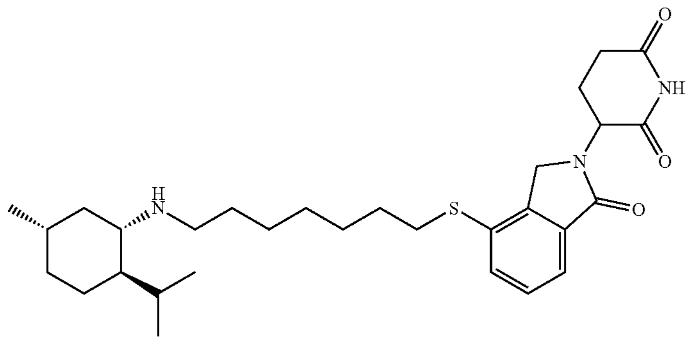 [SMILES: CC(C)[C@H]1CC[C@H](C)C[C@@H]1NCCCCCCCSc1cccc2c1CN(C1CCC(=O)NC1=O)C2=O] | 3-(4-((7-(((1S,2R,5S)-2-isopropyl-5-methylcyclohexyl)amino)heptyl)thio)-1-oxoisoindolin-2-yl)piperidine-2,6-dione |

TABLE 1-continued

| The compounds of the present invention | | |
|---|---|---|
| Compound No. | Structure of the compounds | The compound's name |
| | 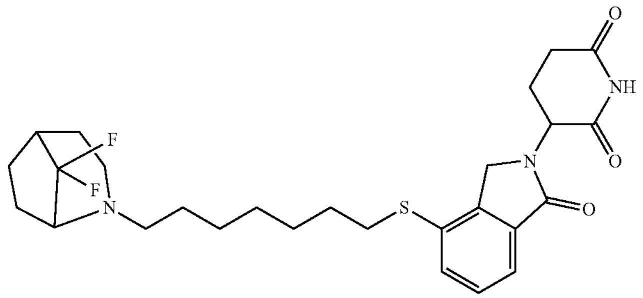 [SMILES: O=C1CCC(N2Cc3c(SCCCCCCCN4CCC5CCC4C5(F)F)cccc3C2=O)C(=O)N1] | 3-(4-((7-(8,8-difluoro-2-azabicyclo[3.2.1]octan-2-yl)heptyl)thio)-1-oxoisoindolin-2-yl)piperidine-2,6-dione |
| | 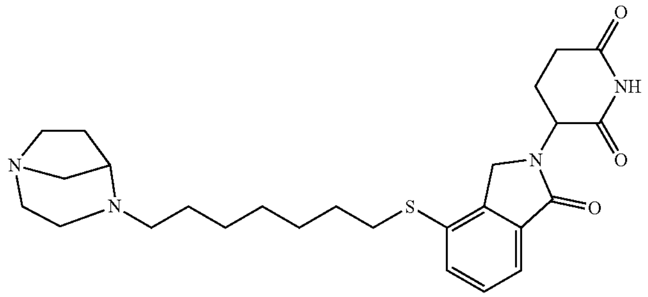 [SMILES: O=C1CCC(N2Cc3c(SCCCCCCCN4CCN5CCC4C5)cccc3C2=O)C(=O)N1] | 3-(4-((7-(1,4-diazabicyclo[3.2.1]octan-4-yl)heptyl)thio)-1-oxoisoindolin-2-yl)piperidine-2,6-dione |
| | 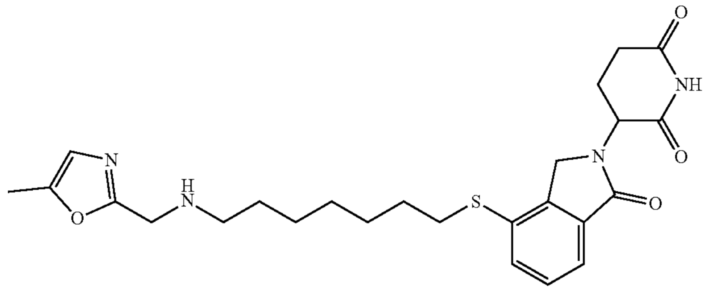 [SMILES: Cc1cnc(CNCCCCCCCSc2cccc3c2CN(C2CCC(=O)NC2=O)C3=O)o1] | 3-(4-((7-(((5-methyloxazol-2-yl)methyl)amino)heptyl)thio)-1-oxoisoindolin-2-yl)piperidine-2,6-dione |
| | 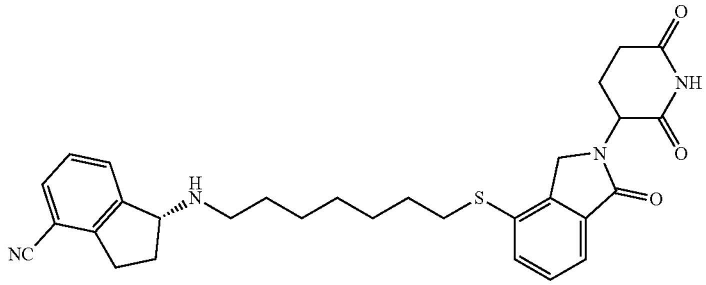 [SMILES: N#Cc1cccc2c1CC[C@H]2NCCCCCCCSc1cccc2c1CN(C1CCC(=O)NC1=O)C2=O] | (1R)-1-((7-((2-(2,6-dioxopiperidin-3-yl)-1-oxoisoindolin-4-yl)thio)heptyl)amino)-2,3-dihydro-1H-indene-4-carbonitrile |
| | 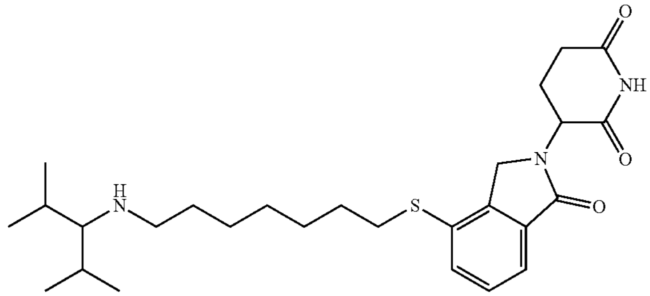 [SMILES: CC(C)C(NCCCCCCCSc1cccc2c1CN(C1CCC(=O)NC1=O)C2=O)C(C)C] | 3-(4-((7-((2,4-dimethylpentan-3-yl)amino)heptyl)thio)-1-oxoisoindolin-2-yl)piperidine-2,6-dione |

TABLE 1-continued

The compounds of the present invention

| Compound No. | Structure of the compounds | The compound's name |
| --- | --- | --- |
| SIAIS12240-31 | 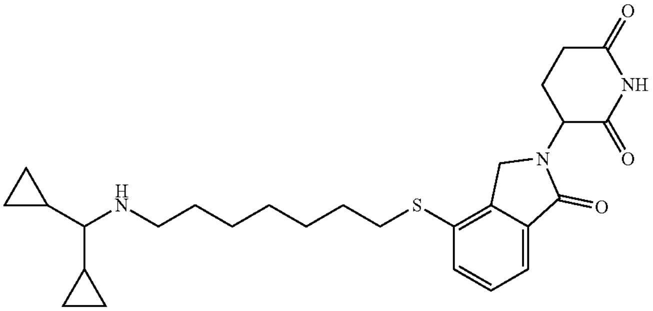 [SMILES: O=C1CCC(N2Cc3c(SCCCCCCCNC(C4CC4)C4CC4)cccc3C2=O)C(=O)N1] | 3-(4-((7-((dicyclopropylmethyl)amino)hept-yl)thio)-1-oxoisoindolin-2-yl)piperidine-2,6-dione |
| SIAIS12241-27 | 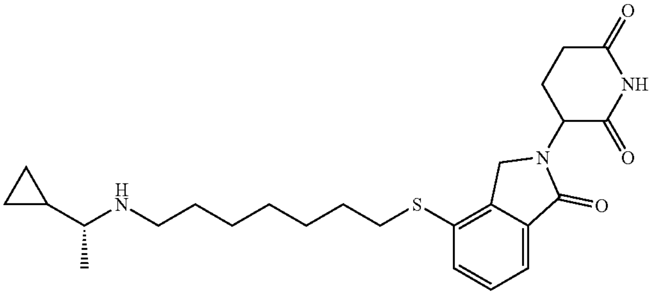 [SMILES: C[C@@H](NCCCCCCCSc1cccc2c1CN(C1CCC(=O)NC1=O)C2=O)C1CC1] | 3-(4-((7-(((R)-1-cyclopropylethyl)amino)heptyl)thio)-1-oxoisoindolin-2-yl)piperidine-2,6-dione |
| SIAIS12221-95 | 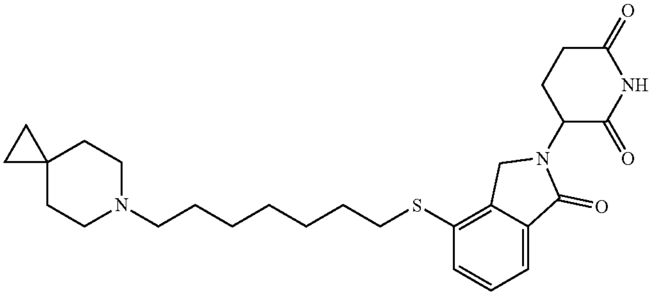 [SMILES: O=C1CCC(N2Cc3c(SCCCCCCCN4CCC5(CC4)CC5)cccc3C2=O)C(=O)N1] | 3-(4-((7-(6-azaspiro[2.5]octan-6-yl)heptyl)thio)-1-oxoisoindolin-2-yl)piperidine-2,6-dione |
| SIAIS12240-33 | 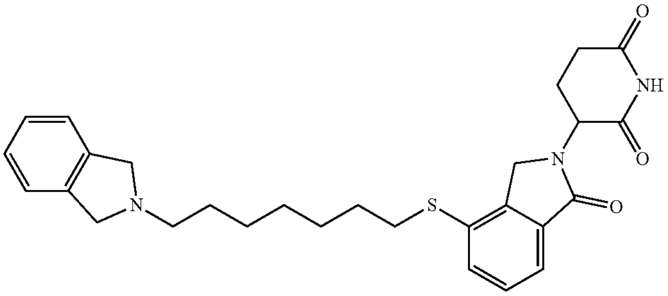 [SMILES: O=C1CCC(N2Cc3c(SCCCCCCCN4Cc5ccccc5C4)cccc3C2=O)C(=O)N1] | 3-(4-((7-(isoindolin-2-yl)heptyl)thio)-1-oxoisoindolin-2-yl)piperidine-2,6-dione |
| SIAIS12240-35 | 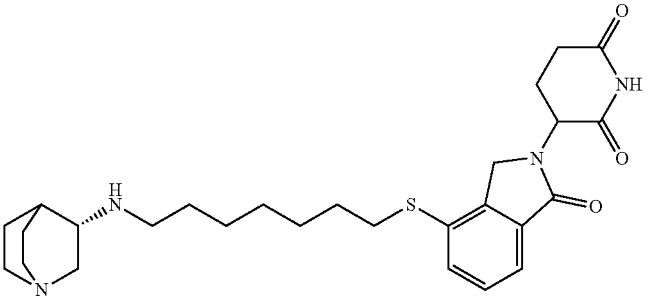 [SMILES: O=C1CCC(N2Cc3c(SCCCCCCCN[C@@H]4CN5CCC4CC5)cccc3C2=O)C(=O)N1] | 3-(1-oxo-4-((7-(((S)-quinuclidin-3-yl)amino)heptyl)thio)isoindolin-2-yl)piperidine-2,6-dione |

TABLE 1-continued

The compounds of the present invention

| Compound No. | Structure of the compounds | The compound's name |
|---|---|---|
| SIAIS12240-37 | 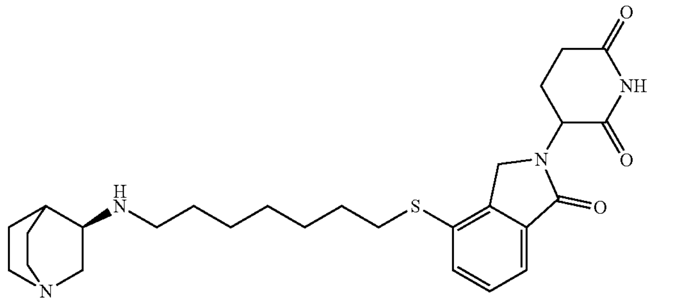 [SMILES: O=C1CCC(N2Cc3c(SCCCCCCCN[C@H]4CN5CCC4CC5)cccc3C2=O)C(=O)N1] | 3-(1-oxo-4-((7-(((R)-quinuclidin-3-yl)amino)heptyl)thio)isoindolin-2-yl)piperidine-2,6-dione |
| SIAIS12241-25 | 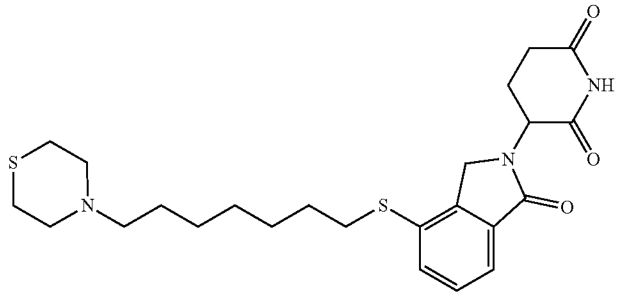 [SMILES: O=C1CCC(N2Cc3c(SCCCCCCCN4CCSCC4)cccc3C2=O)C(=O)N1] | 3-(1-oxo-4-((7-thiomorpholinoheptyl)thio)isoindolin-2-yl)piperidine-2,6-dione |
| SIAIS12240-39 | 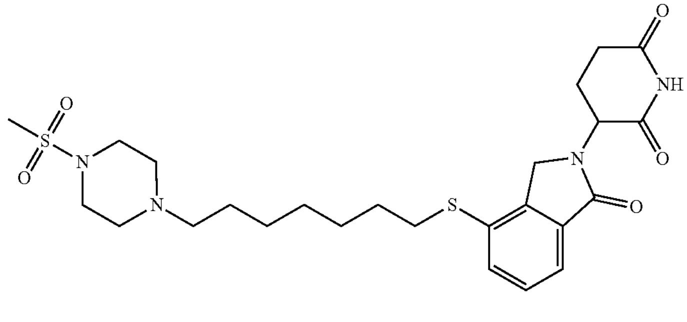 [SMILES: CS(=O)(=O)N1CCN(CCCCCCCSc2cccc3c2CN(C2CCC(=O)NC2=O)C3=O)CC1] | 3-(4-((7-(4-(methylsulfonyl)piperazin-1-yl)heptyl)thio)-1-oxoisoindolin-2-yl)piperidine-2,6-dione |
| | 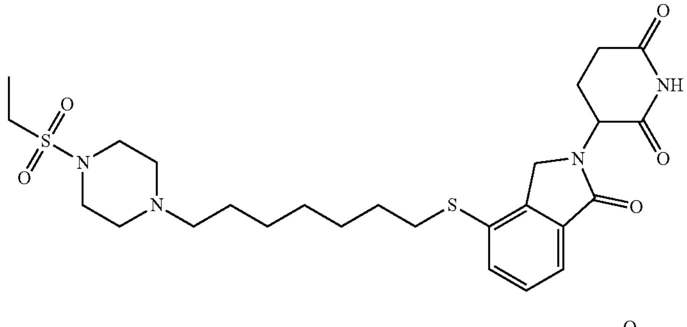 | 3-(4-((7-(4-(ethylsulfonyl)piperazin-1-yl)heptyl)thio)-1-oxoisoindolin-2-yl)piperidine-2,6-dione |
| | 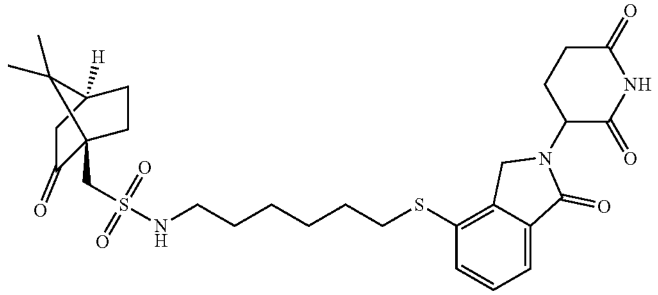 [SMILES: CC1(C)[C@H]2CC[C@]1(CS(=O)(=O)NCCCCCCSc1cccc3c1CN(C1CCC(=O)NC1=O)C3=O)C(=O)C2] | 1-((1R,4S)-7,7-dimethyl-2-oxobicyclo[2.2.1]heptan-1-yl)-N-(6-((2-(2,6-dioxopiperidin-3-yl)-1-oxoisoindolin-4-yl)thio)hexyl)methanesulfonamide |

TABLE 1-continued

The compounds of the present invention

| Compound No. | Structure of the compounds | The compound's name |
| --- | --- | --- |
| | 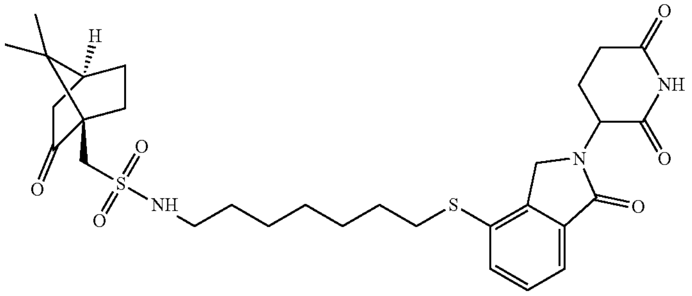 [SMILES: CC1(C)[C@H]2CC[C@]1(CS(=O)(=O)NCCCCCCCSc1cccc3c1CN(C1CCC(=O)NC1=O)C3=O)C(=O)C2] | 1-((1R,4S)-7,7-dimethyl-2-oxobicyclo[2.2.1]heptan-1-yl)-N-(7-((2-(2,6-dioxopiperidin-3-yl)-1-oxoisoindolin-4-yl)thio)heptyl)methanesulfonamide |
| SIAIS12201-15 | 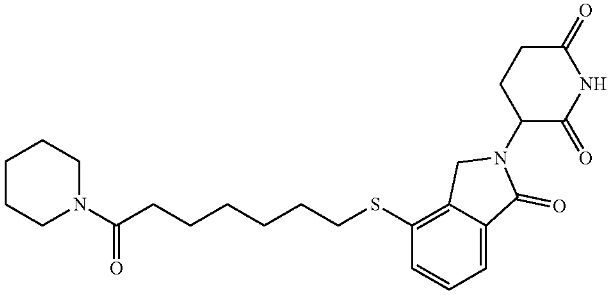 [SMILES: O=C1CCC(N2Cc3c(SCCCCCCC(=O)N4CCCCC4)cccc3C2=O)C(=O)N1] | 3-(1-oxo-4-((7-oxo-7-(piperidin-1-yl)heptyl)thio)isoindolin-2-yl)piperidine-2,6-dione |
| SIAIS12200-33 | 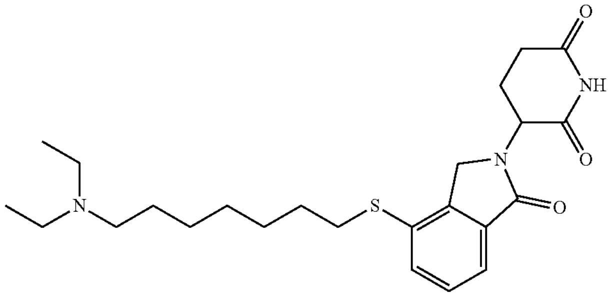 [SMILES: CCN(CC)CCCCCCCSc1cccc2c1CN(C1CCC(=O)NC1=O)C2=O] | 3-(4-((7-(diethylamino)heptyl)thio)-1-oxoisoindolin-2-yl)piperidine-2,6-dione |
| SIAIS12201-07 | 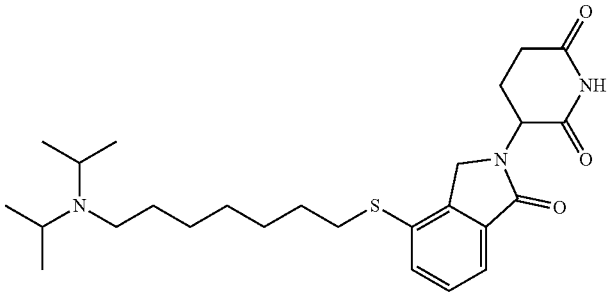 [SMILES: CC(C)N(CCCCCCCSc1cccc2c1CN(C1CCC(=O)NC1=O)C2=O)C(C)C] | 3-(4-((7-(diisopropylamino)heptyl)thio)-1-oxoisoindolin-2-yl)piperidine-2,6-dione |
| SIAIS12201-17 | 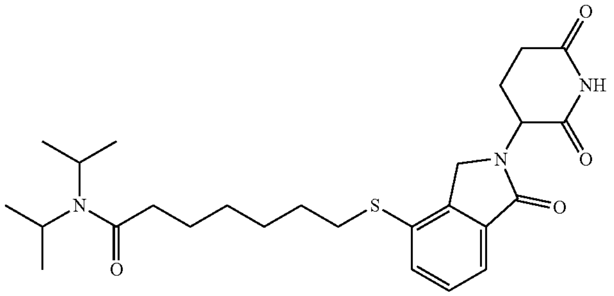 [SMILES: CC(C)N(C(=O)CCCCCCSc1cccc2c1CN(C1CCC(=O)NC1=O)C2=O)C(C)C] | 7-((2-(2,6-dioxopiperidin-3-yl)-1-oxoisoindolin-4-yl)thio)-N,N-diisopropylheptanamide |

TABLE 1-continued

The compounds of the present invention

| Compound No. | Structure of the compounds | The compound's name |
| --- | --- | --- |
| SIAIS12201-87 | 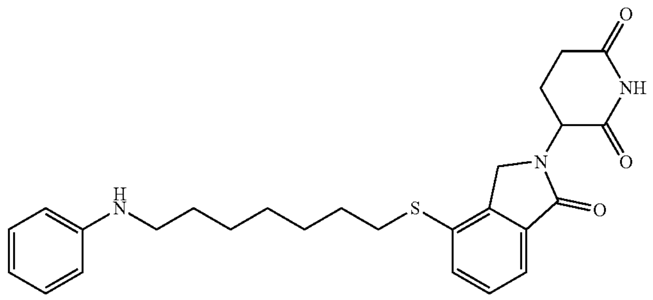 [SMILES: O=C1CCC(N2Cc3c(SCCCCCCCNc4ccccc4)cccc3C2=O)C(=O)N1] | 3-(1-oxo-4-((7-(phenylamino)heptyl)thio)isoindolin-2-yl)piperidine-2,6-dione |
| SIAIS12201-89 | 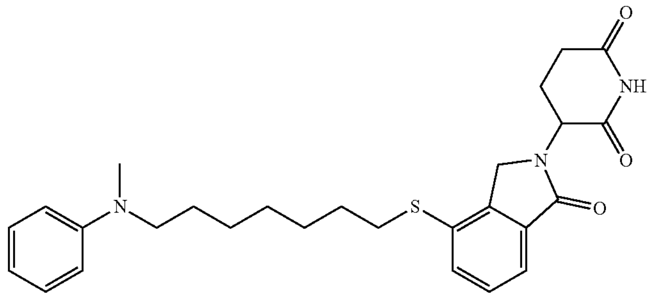 [SMILES: CN(CCCCCCCSc1cccc2c1CN(C1CCC(=O)NC1=O)C2=O)c1ccccc1] | 3-(4-((7-(methyl(phenyl)amino)heptyl)thio)-1-oxoisoindolin-2-yl)piperidine-2,6-dione |
| SIAIS12201-93 | 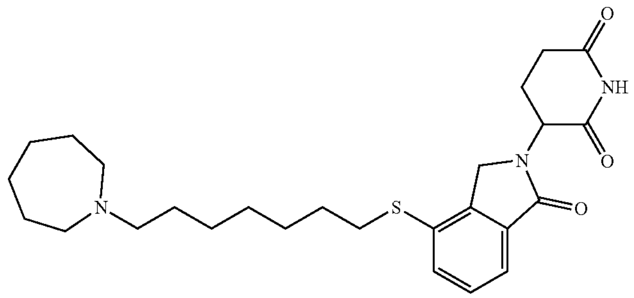 [SMILES: O=C1CCC(N2Cc3c(SCCCCCCCN4CCCCCC4)cccc3C2=O)C(=O)N1] | 3-(4-((7-(azocan-1-yl)heptyl)thio)-1-oxoisoindolin-2-yl)piperidine-2,6-dione |
| | 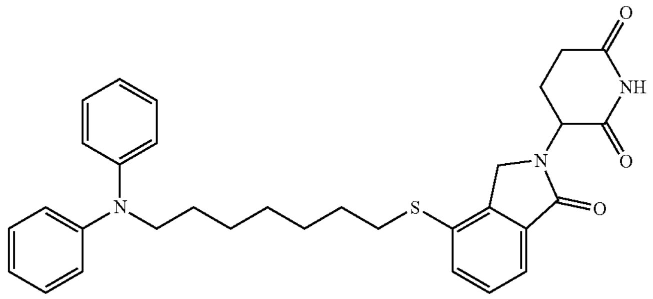 [SMILES: O=C1CCC(N2Cc3c(SCCCCCCCN(c4ccccc4)c4ccccc4)cccc3C2=O)C(=O)N1] | 3-(4-((7-(diphenylamino)heptyl)thio)-1-oxoisoindolin-2-yl)piperidine-2,6-dione |
| | 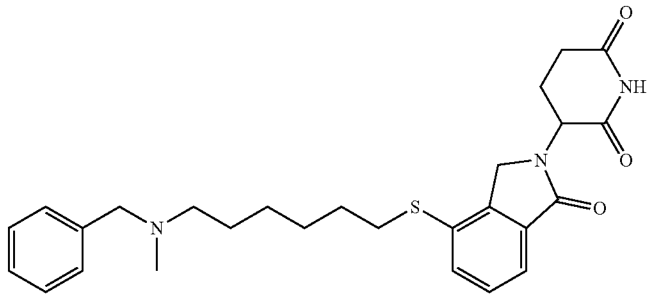 [SMILES: CN(CCCCCCSc1cccc2c1CN(C1CCC(=O)NC1=O)C2=O)Cc1ccccc1] | 3-(4-((6-(benzyl(methyl)amino)hexyl)thio)-1-oxoisoindolin-2-yl)piperidine-2,6-dione |

TABLE 1-continued

| The compounds of the present invention | | |
|---|---|---|
| Compound No. | Structure of the compounds | The compound's name |
| SIAIS12161-43 | 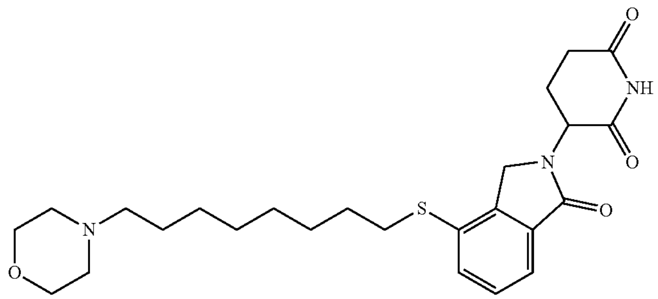 [SMILES: O=C1CCC(N2Cc3c(SCCCCCCCCN4CCOCC4)cccc3C2=O)C(=O)N1] | 3-(4-((8-morpholinooctyl)thio)-1-oxoisoindolin-2-yl)piperidine-2,6-dione |
| SIAIS12161-45 | 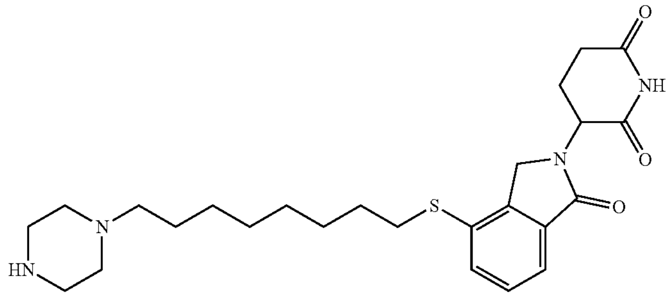 [SMILES: O=C1CCC(N2Cc3c(SCCCCCCCCN4CCNCC4)cccc3C2=O)C(=O)N1] | 3-(1-oxo-4-((8-(piperazin-1-yl)octyl)thio)isoindolin-2-yl)piperidine-2,6-dione |
| SIAIS12200-11 | 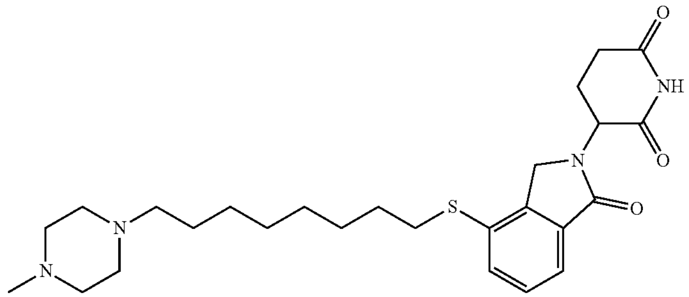 [SMILES: CN1CCN(CCCCCCCCSc2cccc3c2CN(C2CCC(=O)NC2=O)C3=O)CC1] | 3-(4-((8-(4-methylpiperazin-1-yl)octyl)thio)-1-oxoisoindolin-2-yl)piperidine-2,6-dione |
| SIAIS12200-57 | 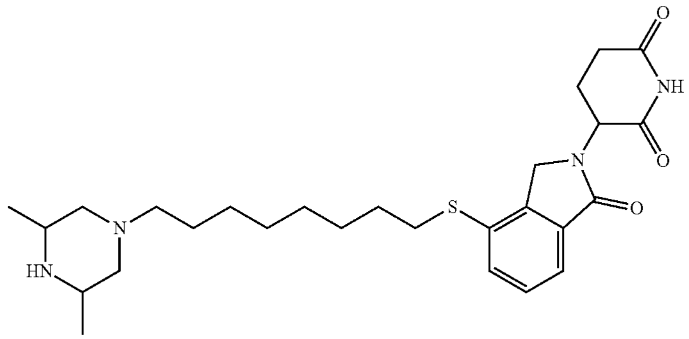 [SMILES: CC1CN(CCCCCCCCSc2cccc3c2CN(C2CCC(=O)NC2=O)C3=O)CC(C)N1] | 3-(4-((8-(3,5-dimethylpiperazin-1-yl)octyl)thio)-1-oxoisoindolin-2-yl)piperidine-2,6-dione |
| SIAIS12200-09 | 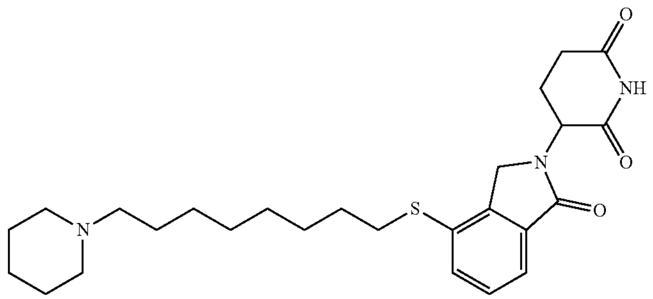 [SMILES: O=C1CCC(N2Cc3c(SCCCCCCCCN4CCCCC4)cccc3C2=O)C(=O)N1] | 3-(1-oxo-4-((8-(piperidin-1-yl)octyl)thio)isoindolin-2-yl)piperidine-2,6-dione |

TABLE 1-continued

| The compounds of the present invention | | |
|---|---|---|
| Compound No. | Structure of the compounds | The compound's name |
| SIAIS12200-55 | 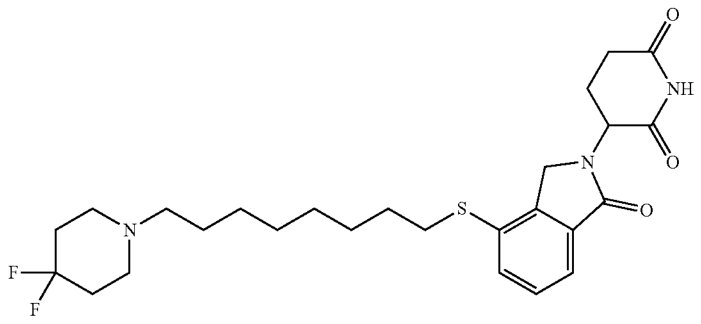 [SMILES: O=C1CCC(N2Cc3c(SCCCCCCCCN4CCC(F)(F)CC4)cccc3C2=O)C(=O)N1] | 3-(4-((8-(4,4-difluoropiperidin-1-yl)octyl)thio)-1-oxoisoindolin-2-yl)piperidine-2,6-dione |
| SIAIS12201-69 | 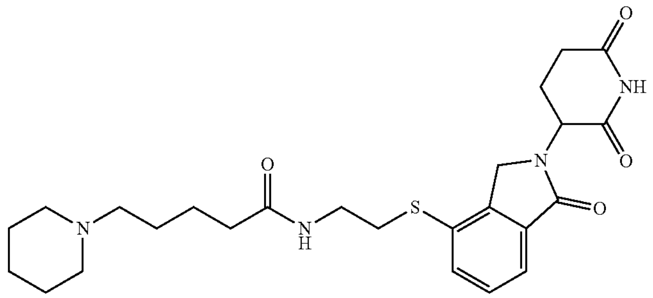 [SMILES: O=C(CCCCN1CCCCC1)NCCSc1cccc2c1CN(C1CCC(=O)NC1=O)C2=O] | N-(2-((2-(2,6-dioxopiperidin-3-yl)-1-oxoisoindolin-4-yl)thio)ethyl)-5-(piperidin-1-yl)pentanamide |
| SIAIS26401-9 | 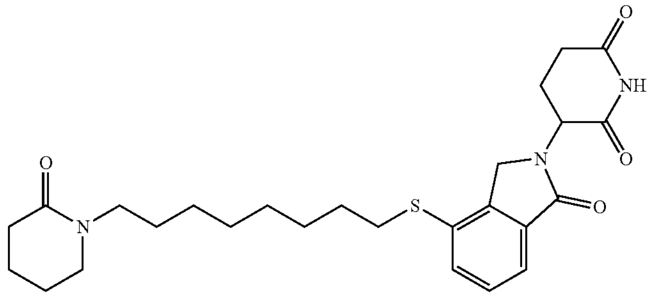 [SMILES: O=C1CCC(N2Cc3c(SCCCCCCCCN4CCCCC4=O)cccc3C2=O)C(=O)N1] | 3-(1-oxo-4-((8-(2-oxopiperidin-1-yl)octyl)thio)isoindolin-2-yl)piperidine-2,6-dione |
| | 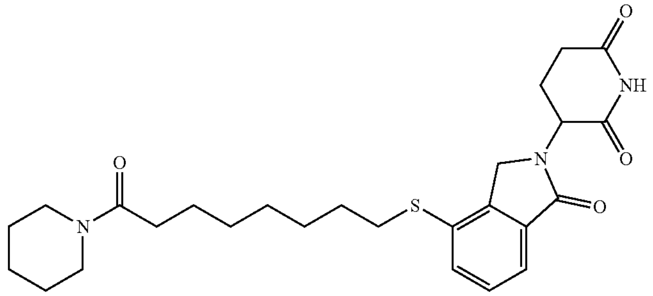 [SMILES: O=C1CCC(N2Cc3c(SCCCCCCCC(=O)N4CCCCC4)cccc3C2=O)C(=O)N1] | 3-(1-oxo-4-((8-oxo-8-(piperidin-1-yl)octyl)thio)isoindolin-2-yl)piperidine-2,6-dione |

TABLE 1-continued

| The compounds of the present invention | | |
|---|---|---|
| Compound No. | Structure of the compounds | The compound's name |
| SIAIS12200-17 | 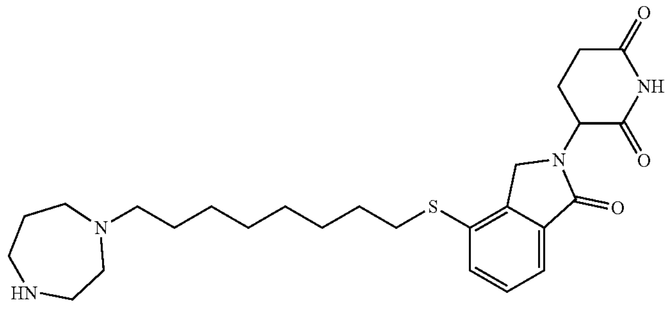 [SMILES: O=C1CCC(N2Cc3c(SCCCCCCCCN4CCCNCC4)cccc3C2=O)C(=O)N1] | 3-(4-((8-(1,4-diazepan-1-yl)octyl)thio)-1-oxoisoindolin-2-yl)piperidine-2,6-dione |
| SIAIS12200-51 | 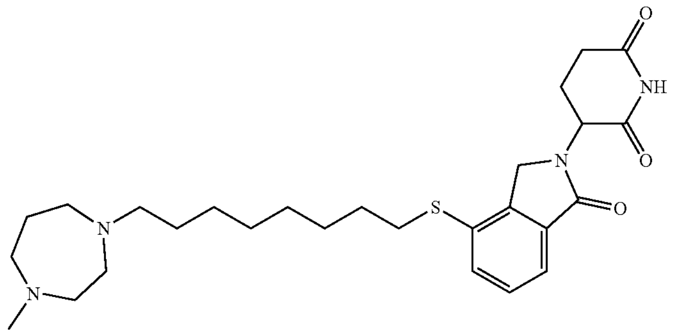 [SMILES: CN1CCCN(CCCCCCCCSc2cccc3c2CN(C2CCC(=O)NC2=O)C3=O)CC1] | 3-(4-((8-(4-methyl-1,4-diazepan-1-yl)octyl)thio)-1-oxoisoindolin-2-yl)piperidine-2,6-dione |
| SIAIS12200-19 | 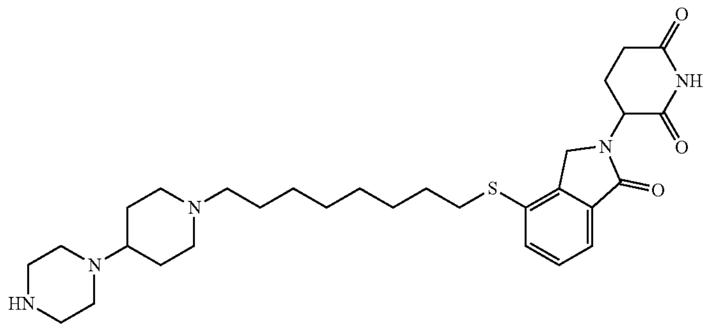 [SMILES: O=C1CCC(N2Cc3c(SCCCCCCCCN4CCC(N5CCNCC5)CC4)cccc3C2=O)C(=O)N1] | 3-(1-oxo-4-((8-(4-(piperazin-1-yl)piperidin-1-yl)octyl)thio)isoindolin-2-yl) piperidine-2,6-dione |
| SIAIS12200-49 | 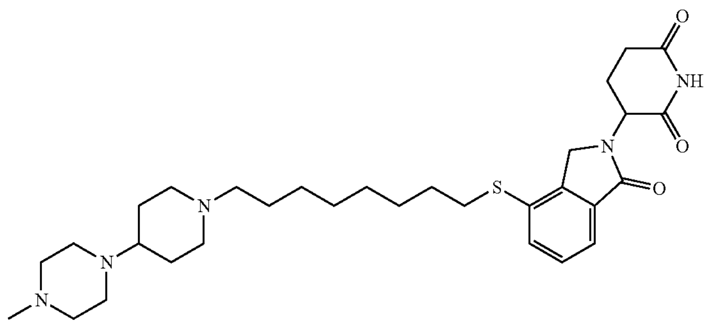 [SMILES: CN1CCN(C2CCN(CCCCCCCCSc3cccc4c3CN(C3CCC(=O)NC3=O)C4=O)CC2)CC1] | 3-(4-((8-(4-(4-methylpiperazin-1-yl)piperidin-1-yl)octyl)thio)-1-oxoisoindolin-2-yl)piperidine-2,6-dione |

TABLE 1-continued

| The compounds of the present invention | | |
|---|---|---|
| Compound No. | Structure of the compounds | The compound's name |
| SIAIS12200-21 | 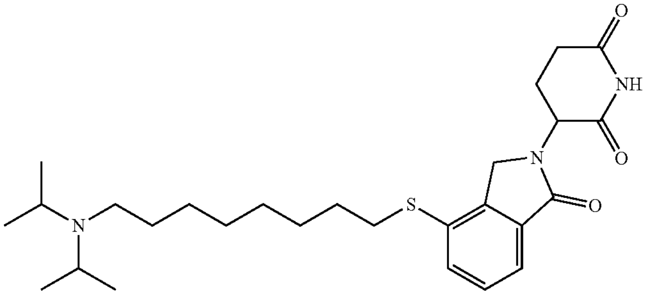 [SMILES: CC(C)N(CCCCCCCCSc1cccc2c1CN(C1CCC(=O)NC1=O)C2=O)C(C)C] | 3-(4-((8-(diisopropylamino)octyl)thio)-1-oxoisoindolin-2-yl)piperidine-2,6-dione |
| | 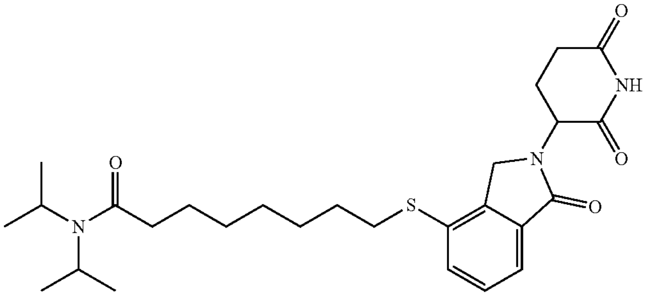 [SMILES: CC(C)N(C(=O)CCCCCCCSc1cccc2c1CN(C1CCC(=O)NC1=O)C2=O)C(C)C] | 8-((2-(2,6-dioxopiperidin-3-yl)-1-oxoisoindolin-4-yl)thio)-N,N-diisopropyloctanamide |
| SIAIS12200-35 | 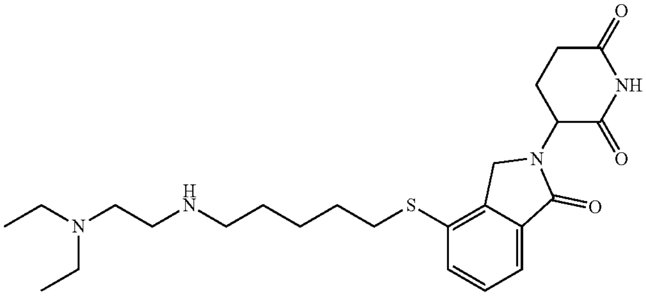 [SMILES: CCN(CC)CCNCCCCCSc1cccc2c1CN(C1CCC(=O)NC1=O)C2=O] | 3-(4-((5-((2-(diethylamino)ethyl)amino)pentyl)thio)-1-oxoisoindolin-2-yl)piperidine-2,6-dione |
| | 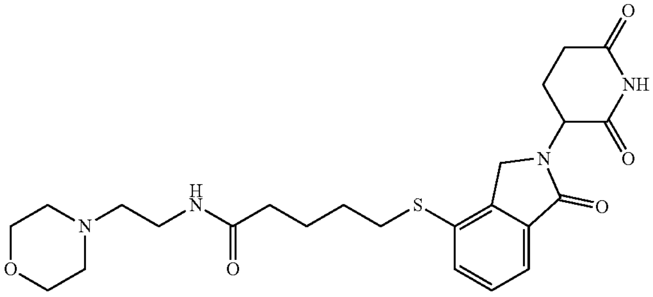 [SMILES: O=C(CCCCSc1cccc2c1CN(C1CCC(=O)NC1=O)C2=O)NCCN1CCOCC1] | 5-((2-(2,6-dioxopiperidin-3-yl)-1-oxoisoindolin-4-yl)thio)-N-(2-morpholinoethyl)pentanamide |
| | 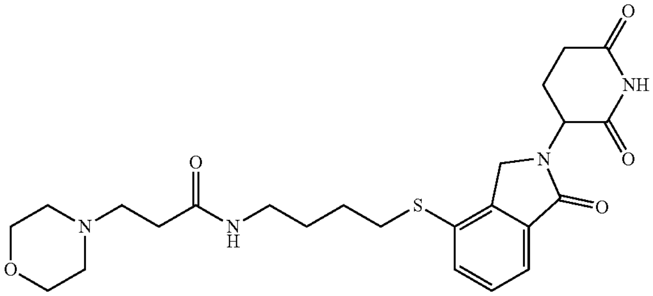 [SMILES: O=C(CCN1CCOCC1)NCCCCSc1cccc2c1CN(C1CCC(=O)NC1=O)C2=O] | N-(4-((2-(2,6-dioxopiperidin-3-yl)-1-oxoisoindolin-4-yl)thio)butyl)-3-morpholinopropanamide |

TABLE 1-continued

| The compounds of the present invention | | |
|---|---|---|
| Compound No. | Structure of the compounds | The compound's name |
| SIAIS12161-47 | 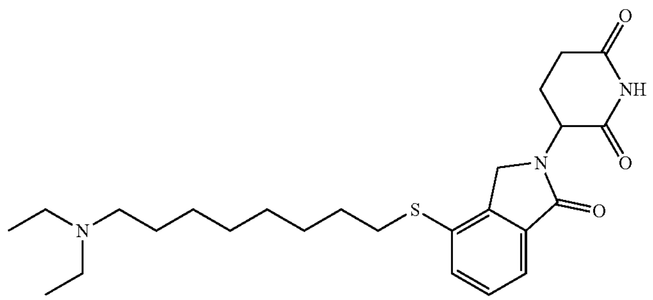 [SMILES: CCN(CC)CCCCCCCCSc1cccc2c1CN(C1CCC(=O)NC1=O)C2=O] | 3-(4-((8-(diethylamino)octyl)thio)-1-oxoisoindolin-2-yl)piperidine-2,6-dione |
| SIAIS12161-49 | 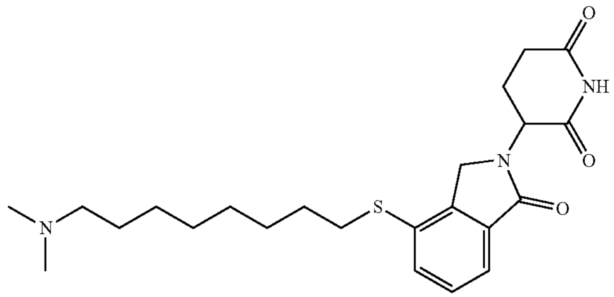 [SMILES: CN(C)CCCCCCCCSc1cccc2c1CN(C1CCC(=O)NC1=O)C2=O] | 3-(4-((8-(dimethylamino)octyl)thio)-1-oxoisoindolin-2-yl)piperidine-2,6-dione |
| SIAIS12161-51 | 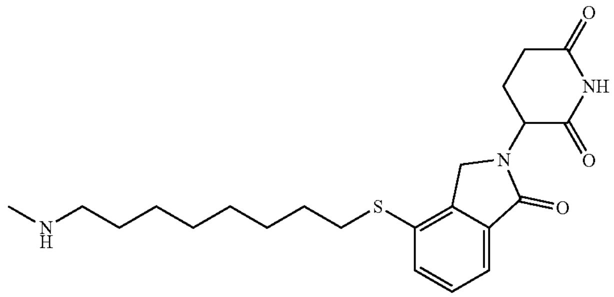 [SMILES: CNCCCCCCCCSc1cccc2c1CN(C1CCC(=O)NC1=O)C2=O] | 3-(4-((8-(methylamino)octyl)thio)-1-oxoisoindolin-2-yl)piperidine-2,6-dione |
| SIAIS26401-1 | 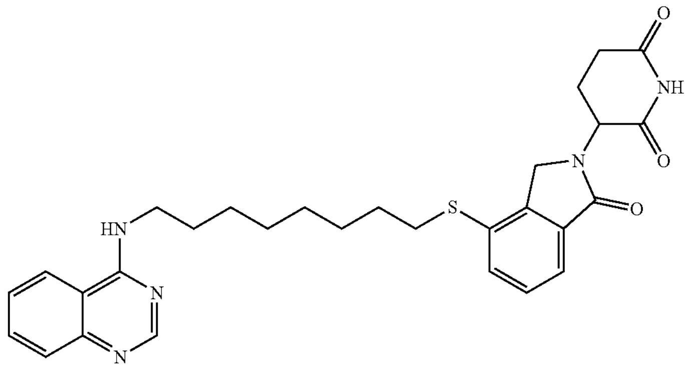 [SMILES: O=C1CCC(N2Cc3c(SCCCCCCCCNc4ncnc5ccccc45)cccc3C2=O)C(=O)N1] | 3-(1-oxo-4-((8-(quinazolin-4-ylamino)octypthio)isoindolin-2-yl)piperidine-2,6-dione |

TABLE 1-continued

| Compound No. | Structure of the compounds | The compound's name |
| --- | --- | --- |
| The compounds of the present invention | | |
| SIAIS26404-2 | 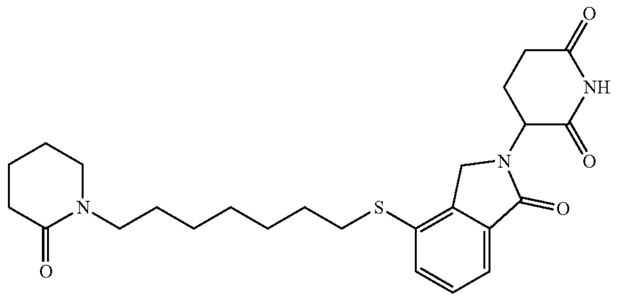 [SMILES: O=C1CCC(N2Cc3c(SCCCCCCCN4CCCCC4=O)cccc3C2=O)C(=O)N1] | 3-(1-oxo-4-((7-(2-oxopiperidin-1-yl)heptyl)thio)isoindolin-2-yl)piperidine-2,6-dione |
| SIAIS12200-65 | 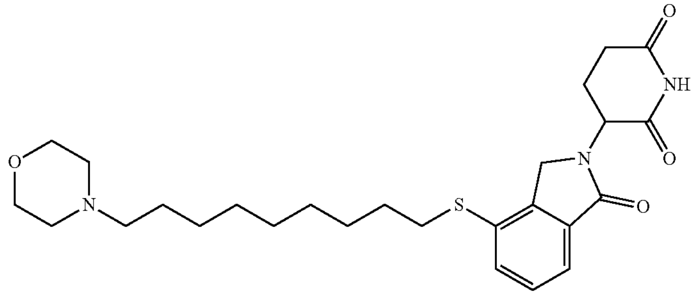 [SMILES: O=C1CCC(N2Cc3c(SCCCCCCCCCN4CCOCC4)cccc3C2=O)C(=O)N1] | 3-(4-((9-morpholinononyl)thio)-1-oxoisoindolin-2-yl)piperidine-2,6-dione |
| | 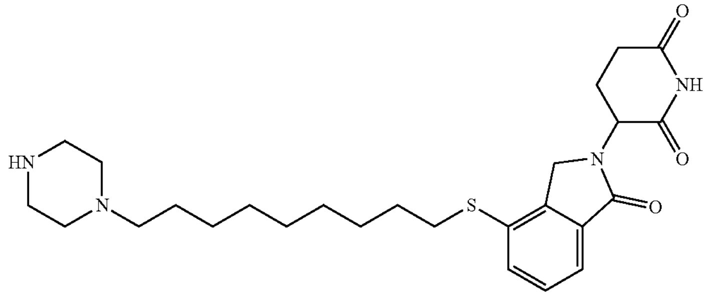 [SMILES: O=C1CCC(N2Cc3c(SCCCCCCCCCN4CCNCC4)cccc3C2=O)C(=O)N1] | 3-(1-oxo-4-((9-(piperazin-1-yl)nonyl)thio)isoindolin-2-yl)piperidine-2,6-dione |
| | 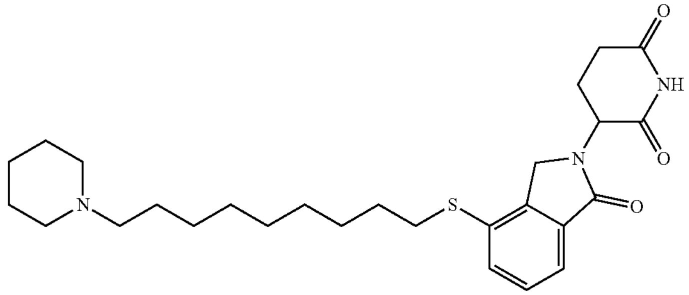 [SMILES: O=C1CCC(N2Cc3c(SCCCCCCCCCN4CCCCC4)cccc3C2=O)C(=O)N1] | 3-(1-oxo-4-((9-(piperidin-1-yl)nonyl)thio)isoindolin-2-yl)piperidine-2,6-dione |
| SIAIS12200-67 | 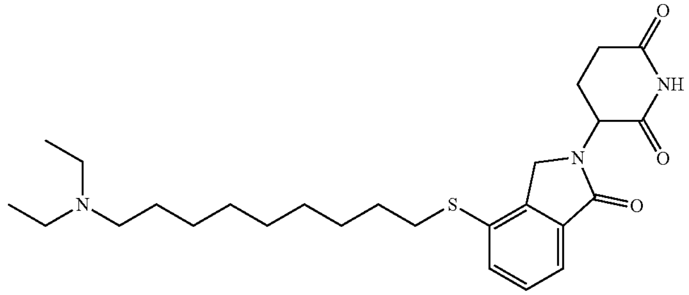 [SMILES: CCN(CC)CCCCCCCCCSc1cccc2c1CN(C1CCC(=O)NC1=O)C2=O] | 3-(4-((9-(diethylamino)nonyl)thio)-1-oxoisoindolin-2-yl)piperidine-2,6-dione |

TABLE 1-continued

The compounds of the present invention

| Compound No. | Structure of the compounds | The compound's name |
|---|---|---|
| | 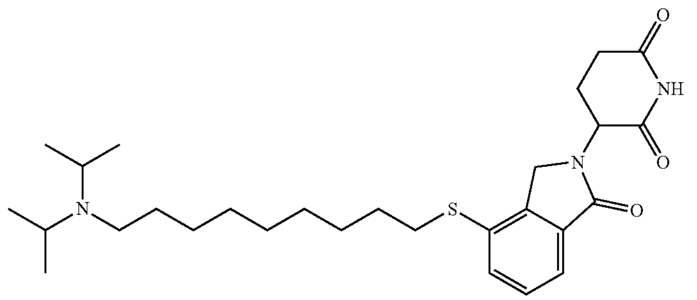 [SMILES: CC(C)N(CCCCCCCCCSc1cccc2c1CN(C1CCC(=O)NC1=O)C2=O)C(C)C] | 3-(4-((9-(diisopropylamino)nonyl)thio)-1-oxoisoindolin-2-yl)piperidine-2,6-dione |
| SIAIS12200-23 | 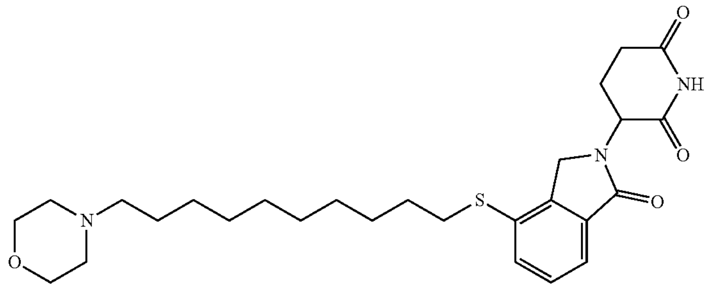 [SMILES: O=C1CCC(N2Cc3c(SCCCCCCCCCCN4CCOCC4)cccc3C2=O)C(=O)N1] | 3-(4-((10-morpholinodecyl)thio)-1-oxoisoindolin-2-yl)piperidine-2,6-dione |
| | 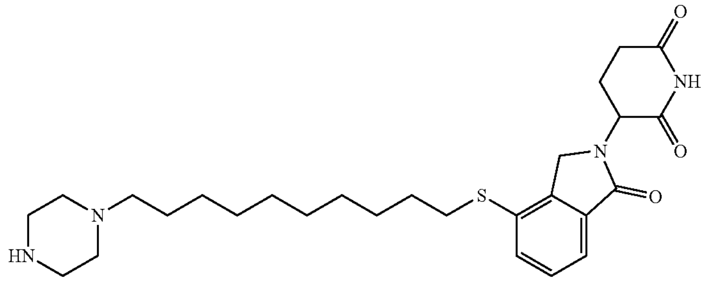 [SMILES: O=C1CCC(N2Cc3c(SCCCCCCCCCCN4CCNCC4)cccc3C2=O)C(=O)N1] | 3-(1-oxo-4-((10-(piperazin-1-yl)decyl)thio)isoindolin-2-yl)piperidine-2,6-dione |
| | 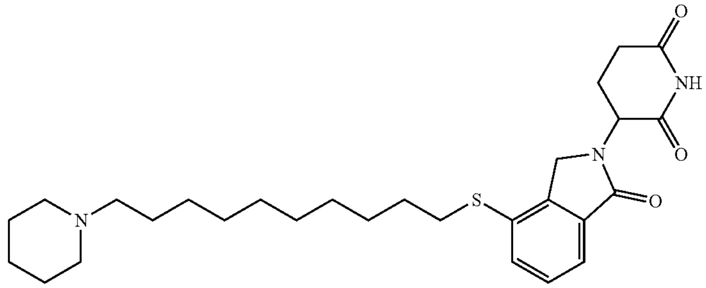 [SMILES: O=C1CCC(N2Cc3c(SCCCCCCCCCCN4CCCCC4)cccc3C2=O)C(=O)N1] | 3-(1-oxo-4-((10-(piperidin-1-yl)decyl)thio)isoindolin-2-yl)piperidine-2,6-dione |
| SIAIS12200-25 | 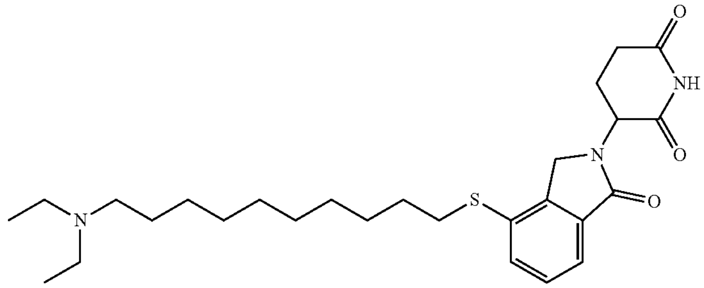 [SMILES: CCN(CC)CCCCCCCCCCSc1cccc2c1CN(C1CCC(=O)NC1=O)C2=O] | 3-(4-((10-(diethylamino)decyl)thio)-1-oxoisoindolin-2-yl)piperidine-2,6-dione |

TABLE 1-continued

The compounds of the present invention

| Compound No. | Structure of the compounds | The compound's name |
|---|---|---|
| | 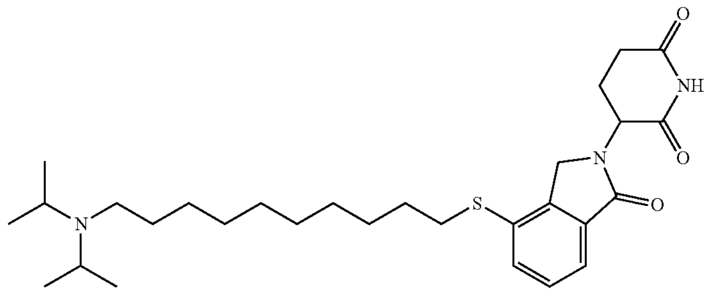 [SMILES: CC(C)N(CCCCCCCCCCSc1cccc2c1CN(C1CCC(=O)NC1=O)C2=O)C(C)C] | 3-(4-((10-(diisopropylamino)decyl)thio)-1-oxoisoindolin-2-yl)piperidine-2,6-dione |
| SIAIS12200-45 | 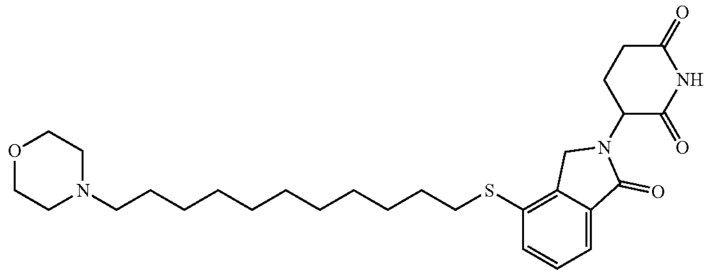 [SMILES: O=C1CCC(N2Cc3c(SCCCCCCCCCCCN4CCOCC4)cccc3C2=O)C(=O)N1] | 3-(4-((11-morpholinoundecyl)thio)-1-oxoisoindolin-2-yl)piperidine-2,6-dione |
| | 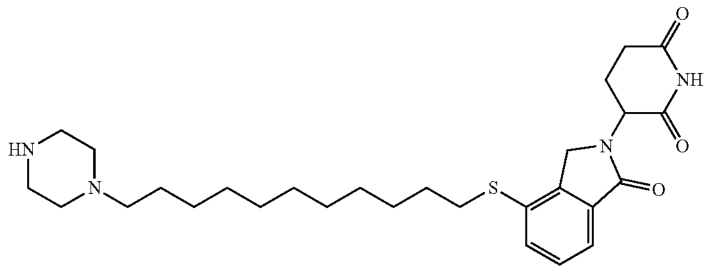 [SMILES: O=C1CCC(N2Cc3c(SCCCCCCCCCCCN4CCNCC4)cccc3C2=O)C(=O)N1] | 3-(1-oxo-4-((11-(piperazin-1-yl)undecyl)thio)isoindolin-2-yl)piperidine-2,6-dione |
| | 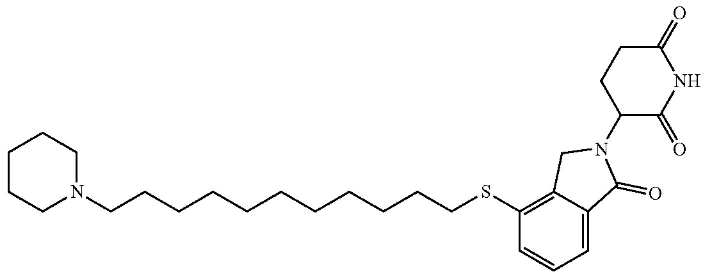 [SMILES: O=C1CCC(N2Cc3c(SCCCCCCCCCCCN4CCCCC4)cccc3C2=O)C(=O)N1] | 3-(1-oxo-4-((11-(piperidin-1-yl)undecyl)thio)isoindolin-2-yl)piperidine-2,6-dione |
| SIAIS12200-47 | 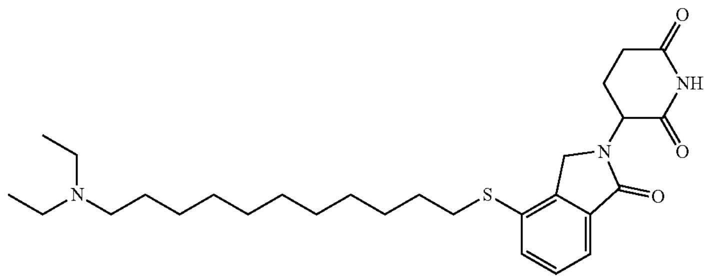 [SMILES: CCN(CC)CCCCCCCCCCCSc1cccc2c1CN(C1CCC(=O)NC1=O)C2=O] | 3-(4-((11-(diethylamino)undecyl)thio)-1-oxoisoindolin-2-yl)piperidine-2,6-dione |

TABLE 1-continued

| The compounds of the present invention | | |
|---|---|---|
| Compound No. | Structure of the compounds | The compound's name |
| | 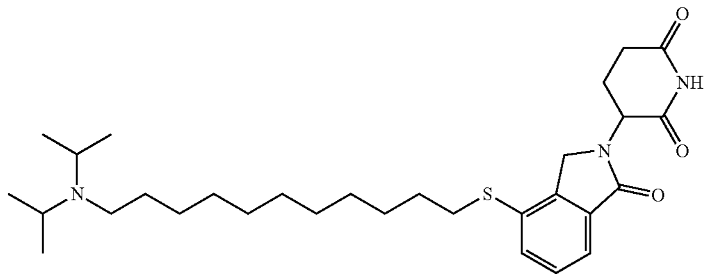 [SMILES: CC(C)N(CCCCCCCCCCCSc1cccc2c1CN(C1CCC(=O)NC1=O)C2=O)C(C)C] | 3-(4-((11-(diisopropylamino)undecyl)thio)-1-oxoisoindolin-2-yl)piperidine-2,6-dione |
| SIAIS12200-37 | 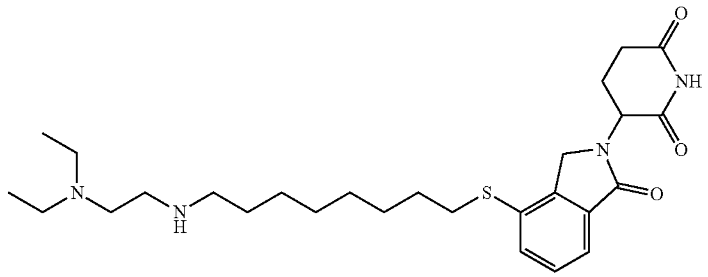 [SMILES: CCN(CC)CCNCCCCCCCCSc1cccc2c1CN(C1CCC(=O)NC1=O)C2=O] | 3-(4-((8-((2-(diethylamino)ethyl)amino)octyl)thio)-1-oxoisoindolin-2-yl)piperidine-2,6-dione |
| | 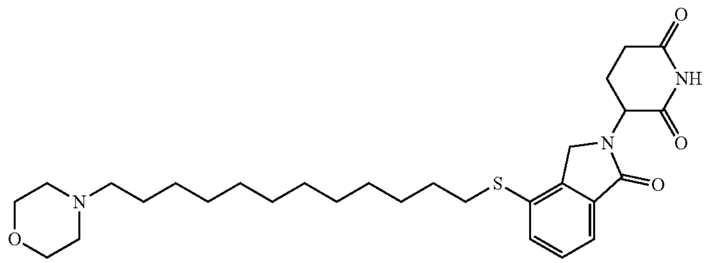 [SMILES: O=C1CCC(N2Cc3c(SCCCCCCCCCCCCN4CCOCC4)cccc3C2=O)C(=O)N1] | 3-(4-((12-morpholinododecyl)thio)-1-oxoisoindolin-2-yl)piperidine-2,6-dione |
| | 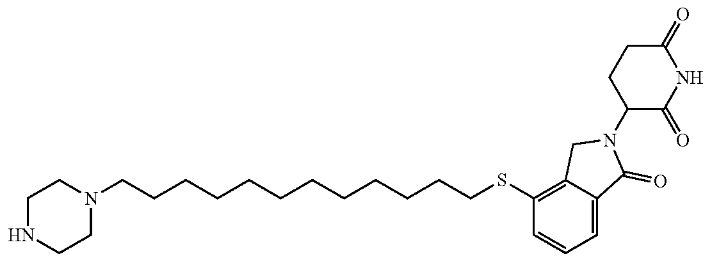 [SMILES: O=C1CCC(N2Cc3c(SCCCCCCCCCCCCN4CCNCC4)cccc3C2=O)C(=O)N1] | 3-(1-oxo-4-((12-(piperazin-1-yl)dodecyl)thio)isoindolin-2-yl)piperidine-2,6-dione |
| | 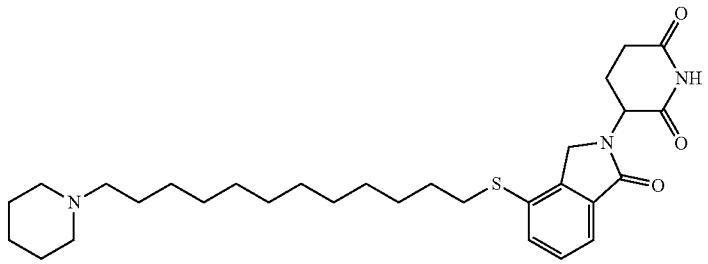 [SMILES: O=C1CCC(N2Cc3c(SCCCCCCCCCCCCN4CCCCC4)cccc3C2=O)C(=O)N1] | 3-(1-oxo-4-((12-(piperidin-1-yl)dodecyl)thio)isoindolin-2-yl)piperidine-2,6-dione |

TABLE 1-continued

| The compounds of the present invention | | |
|---|---|---|
| Compound No. | Structure of the compounds | The compound's name |
| | 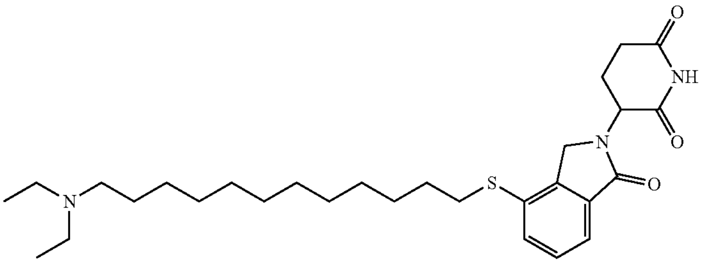 [SMILES: CCN(CC)CCCCCCCCCCCCSc1cccc2c1CN(C1CCC(=O)NC1=O)C2=O] | 3-(4-((12-(diethylamino)dodecyl)thio)-1-oxoisoindolin-2-yl)piperidine-2,6-dione |
| | 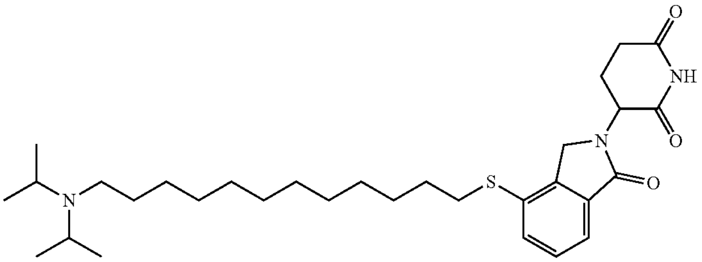 [SMILES: CC(C)N(CCCCCCCCCCCCSc1cccc2c1CN(C1CCC(=O)NC1=O)C2=O)C(C)C] | 3-(4-((12-(diisopropylamino)dodecyl)thio)-1-oxoisoindolin-2-yl)piperidine-2,6-dione |
| | 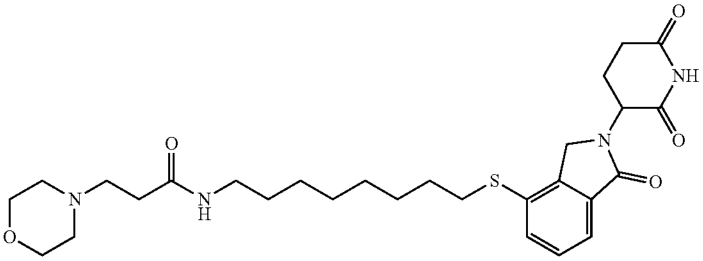 [SMILES: O=C(CCN1CCOCC1)NCCCCCCCCSc1cccc2c1CN(C1CCC(=O)NC1=O)C2=O] | N-(8-((2-(2,6-dioxopiperidin-3-yl)-1-oxoisoindolin-4-yl)thio)octyl)-3-morpholinopropanamide |
| | 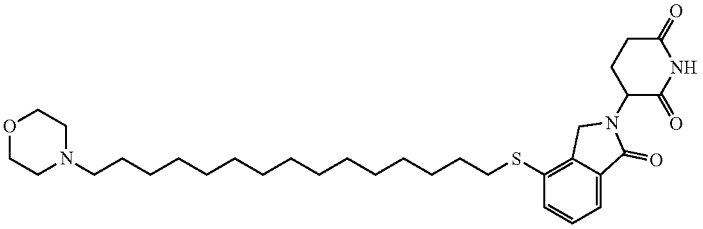 [SMILES: O=C1CCC(N2Cc3c(SCCCCCCCCCCCCCCCN4CCOCC4)cccc3C2=O)C(=O)N1] | 3-(4-((15-morpholinopentadecyl)thio)-1-oxoisoindolin-2-yl)piperidine-2,6-dione |
| | 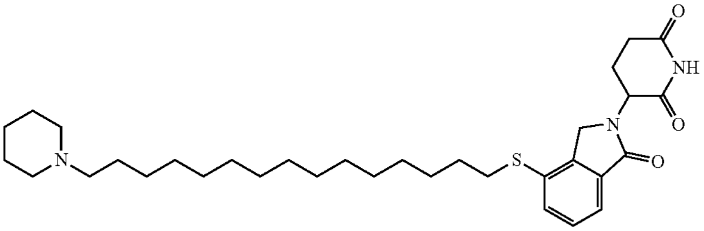 [SMILES: O=C1CCC(N2Cc3c(SCCCCCCCCCCCCCCCN4CCCCC4)cccc3C2=O)C(=O)N1] | 3-(1-oxo-4-((15-(piperidin-1-yl)pentadecyl)thio)isoindolin-2-yl)piperidine-2,6-dione |

TABLE 1-continued

| The compounds of the present invention | | |
|---|---|---|
| Compound No. | Structure of the compounds | The compound's name |
| | 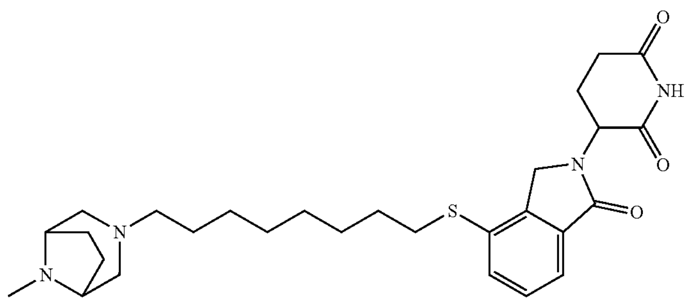 [SMILES: CN1C2CCC1CN(CCCCCCCCSc1cccc3c1CN(C1CCC(=O)NC1=O)C3=O)C2] | 3-(4-((8-(8-methyl-3,8-diazabicyclo[3.2.1]octan-3-yl)octyl)thio)-1-oxoisoindolin-2-yl)piperidine-2,6-dione |
| | 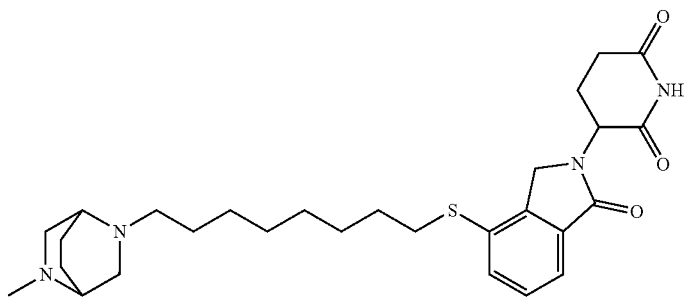 [SMILES: CN1CC2CCC1CN2CCCCCCCCSc1cccc2c1CN(C1CCC(=O)NC1=O)C2=O] | 3-(4-((8-(5-methyl-2,5-diazabicyclo[2.2.2]octan-2-yl)octyl)thio)-1-oxoisoindolin-2-yl)piperidine-2,6-dione |
| | 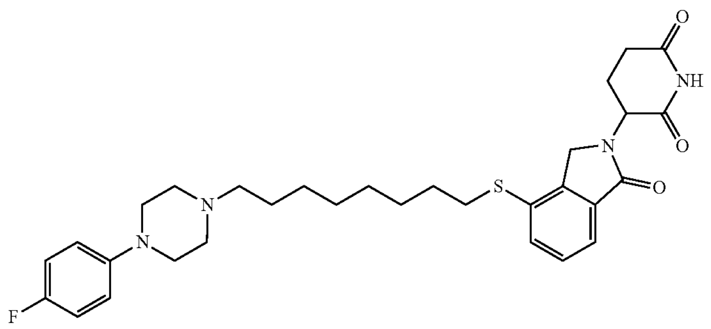 [SMILES: O=C1CCC(N2Cc3c(SCCCCCCCCN4CCN(c5ccc(F)cc5)CC4)cccc3C2=O)C(=O)N1] | 3-(4-((8-(4-(4-fluorophenyl)piperazin-1-yl)octyl)thio)-1-oxoisoindolin-2-yl)piperidine-2,6-dione |
| | 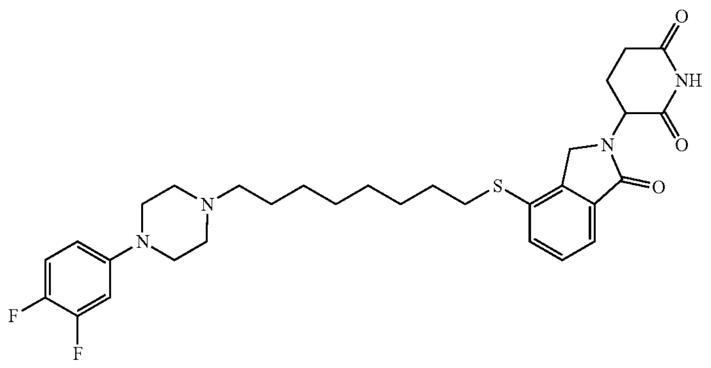 [SMILES: O=C1CCC(N2Cc3c(SCCCCCCCCN4CCN(c5ccc(F)c(F)c5)CC4)cccc3C2=O)C(=O)N1] | 3-(4-((8-(4-(3,4-difluorophenyl)piperazin-1-yl)octyl)thio)-1-oxoisoindolin-2-yl)piperidine-2,6-dione |

TABLE 1-continued

The compounds of the present invention

| Compound No. | Structure of the compounds | The compound's name |
|---|---|---|
| | 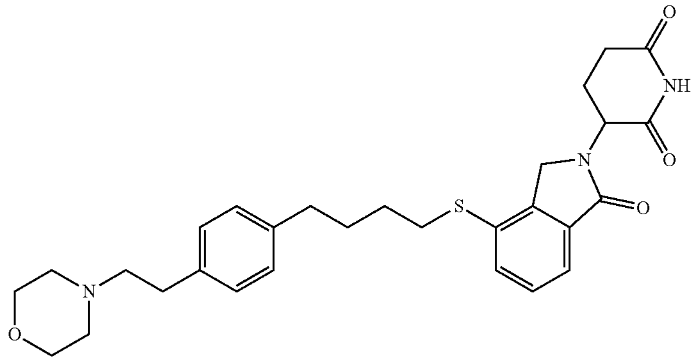 [SMILES: O=C1CCC(N2Cc3c(SCCCCc4ccc(CCN5CCOCC5)cc4)cccc3C2=O)C(=O)N1] | 3-(4-((4-(4-(2-morpholinoethyl)phenyl)butyl)thio)-1-oxoisoindolin-2-yl)piperidine-2,6-dione |
| | 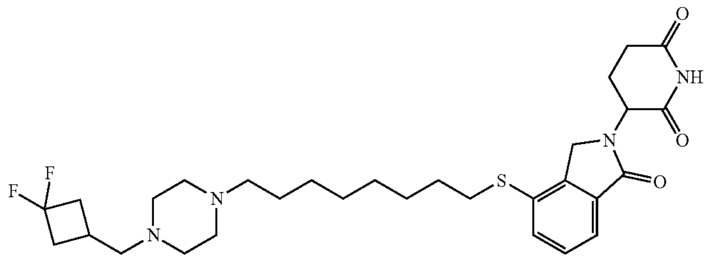 [SMILES: O=C1CCC(N2Cc3c(SCCCCCCCCN4CCN(CC5CC(F)(F)C5)CC4)cccc3C2=O)C(=O)N1] | 3-(4-((8-(4-((3,3-difluorocyclobutyl)methyl)piperazin-1-yl)octyl)thio)-1-oxoisoindolin-2-yl)piperidine-2,6-dione |
| | 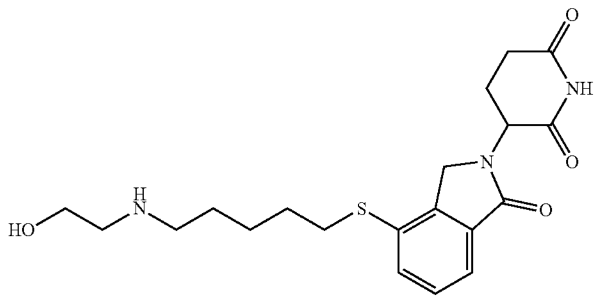 [SMILES: O=C1CCC(N2Cc3c(SCCCCCNCCO)cccc3C2=O)C(=O)N1] | 3-(4-((5-((2-hydroxyethyl)amino)pentyl)thio)-1-oxoisoindolin-2-yl)piperidine-2,6-dione |
| | 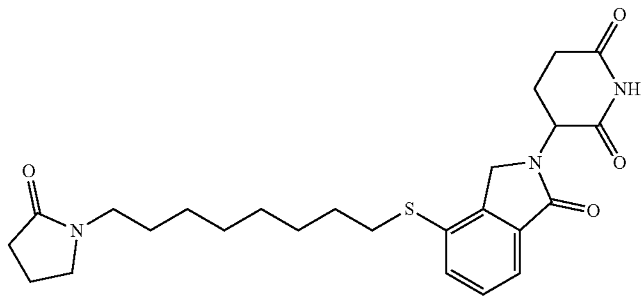 [SMILES: O=C1CCC(N2Cc3c(SCCCCCCCCN4CCCC4=O)cccc3C2=O)C(=O)N1] | 3-(1-oxo-4-((8-(2-oxopyrrolidin-1-yl)octyl)thio)isoindolin-2-yl)piperidine-2,6-dione |
| | 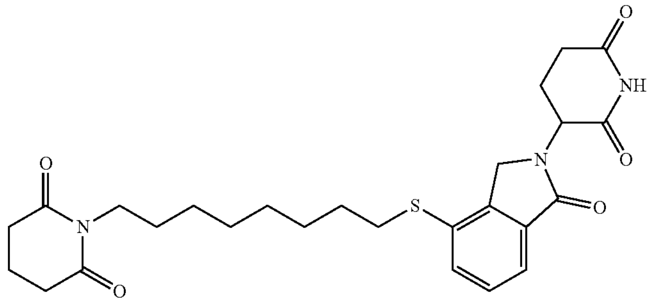 [SMILES: O=C1CCC(N2Cc3c(SCCCCCCCCN4C(=O)CCCC4=O)cccc3C2=O)C(=O)N1] | 1-(8-((2-(2,6-dioxopiperidin-3-yl)-1-oxoisoindolin-4-yl)thio)octyl)piperidine-2,6-dione |

TABLE 1-continued

The compounds of the present invention

| Compound No. | Structure of the compounds | The compound's name |
|---|---|---|
| | 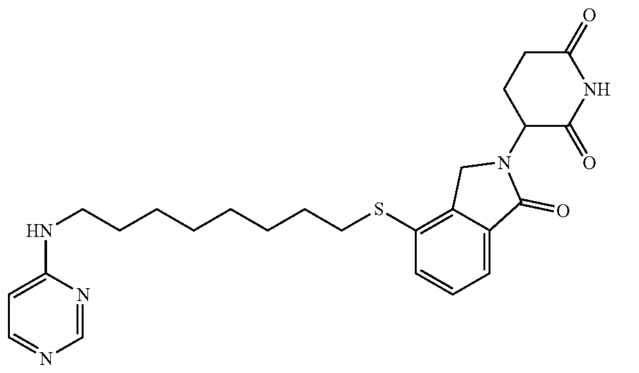 [SMILES: O=C1CCC(N2Cc3c(SCCCCCCCCNc4ccncn4)cccc3C2=O)C(=O)N1] | 3-(1-oxo-4-((8-(pyrimidin-4-ylamino)octyl)thio)isoindolin-2-yl)piperidine-2,6-dione |
| | 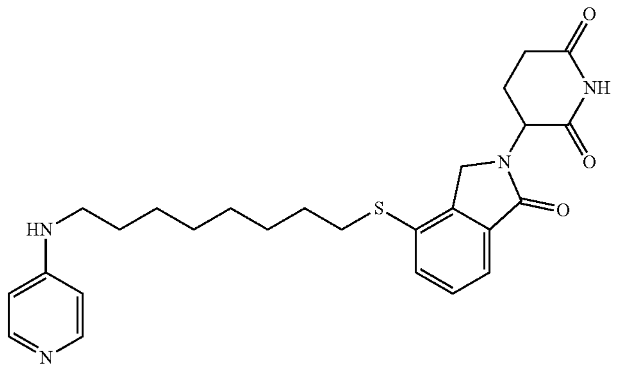 [SMILES: O=C1CCC(N2Cc3c(SCCCCCCCCNc4ccncc4)cccc3C2=O)C(=O)N1] | 3-(1-oxo-4-((8-(pyridin-4-ylamino)octyl)thio)isoindolin-2-yl)piperidine-2,6-dione |
| | 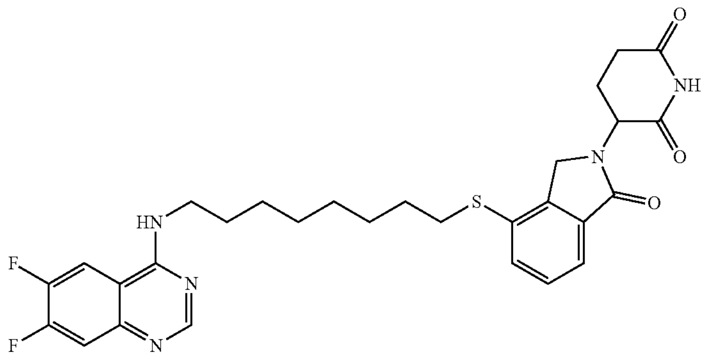 [SMILES: O=C1CCC(N2Cc3c(SCCCCCCCCNc4ncnc5cc(F)c(F)cc45)cccc3C2=O)C(=O)N1] | 3-(4-((8-((6,7-difluoroquinazolin-4-yl)amino)octyl)thio)-1-oxoisoindolin-2-yl)piperidine-2,6-dione |
| | 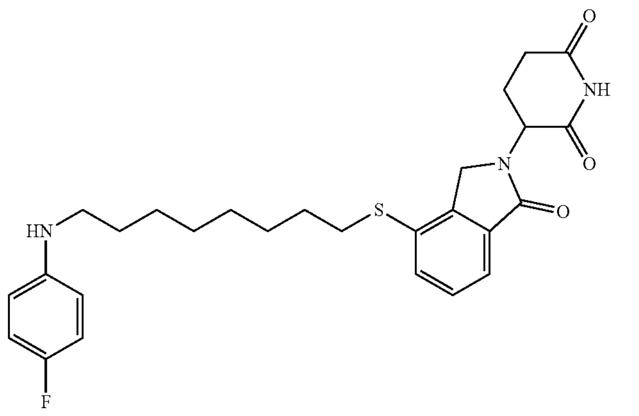 [SMILES: O=C1CCC(N2Cc3c(SCCCCCCCCNc4ccc(F)cc4)cccc3C2=O)C(=O)N1] | 3-(4-((8-((4-fluorophenyl)amino)octyl)thio)-1-oxoisoindolin-2-yl)piperidine-2,6-dione |

TABLE 1-continued

The compounds of the present invention

| Compound No. | Structure of the compounds | The compound's name |
|---|---|---|
| | 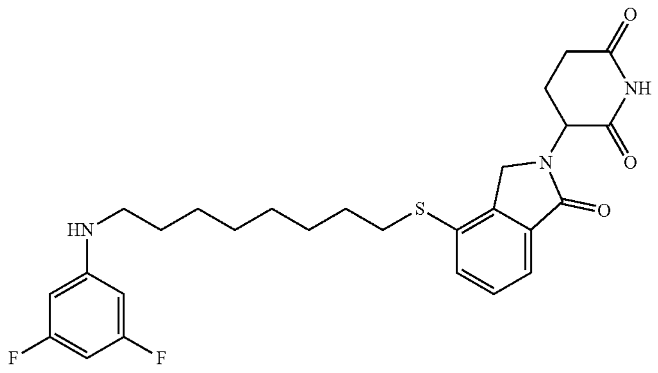 [SMILES: O=C1CCC(N2Cc3c(SCCCCCCCCNc4cc(F)cc(F)c4)cccc3C2=O)C(=O)N1] | 3-(4-((8-((3,5-difluorophenyl)amino)octyl)thio)-1-oxoisoindolin-2-yl)piperidine-2,6-dione |
| | 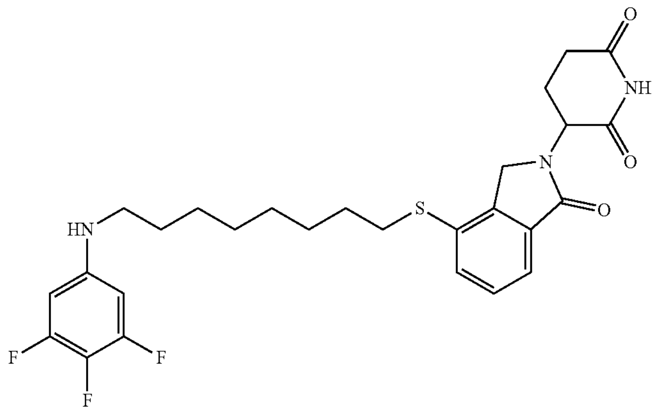 [SMILES: O=C1CCC(N2Cc3c(SCCCCCCCCNc4cc(F)c(F)c(F)c4)cccc3C2=O)C(=O)N1] | 3-(1-oxo-4-((8-((3,4,5-trifluorophenyl)amino)octyl)thio) isoindolin-2-yl)piperidine-2,6-dione |
| | 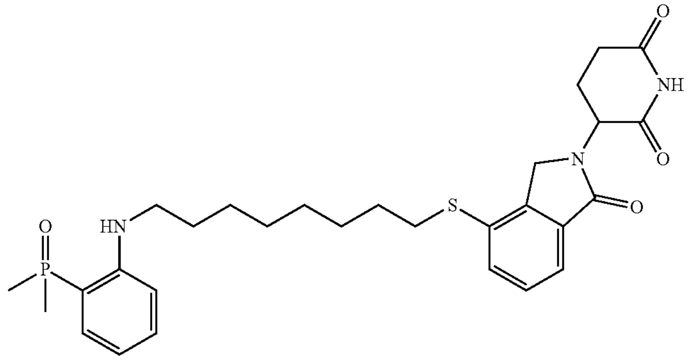 [SMILES: CP(C)(=O)c1ccccc1NCCCCCCCCSc1cccc2c1CN(C1CCC(=O)NC1=O)C2=O] | 3-(4-((8-((2-(dimethylphosphoryl)phenyl)amino) octyl)thio)-1-oxoisoindolin-2-yl)piperidine-2,6-dione |
| | 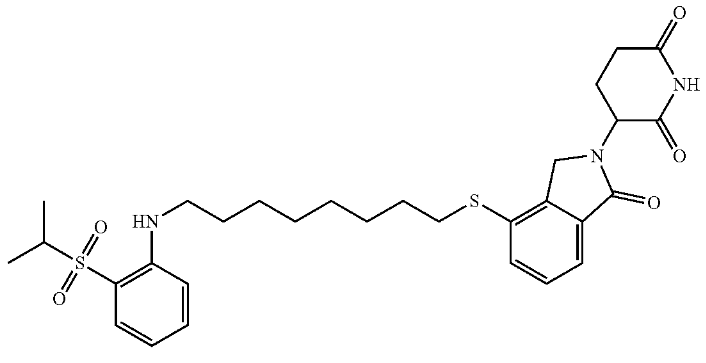 [SMILES: CC(C)S(=O)(=O)c1ccccc1NCCCCCCCCSc1cccc2c1CN(C1CCC(=O)NC1=O)C2=O] | 3-(4-((8-((2-(isopropylsulfonyl)phenyl)amino) octyl)thio)-1-oxoisoindolin-2-yl)piperidine-2,6-dione |

TABLE 1-continued

The compounds of the present invention

| Compound No. | Structure of the compounds | The compound's name |
|---|---|---|
| | 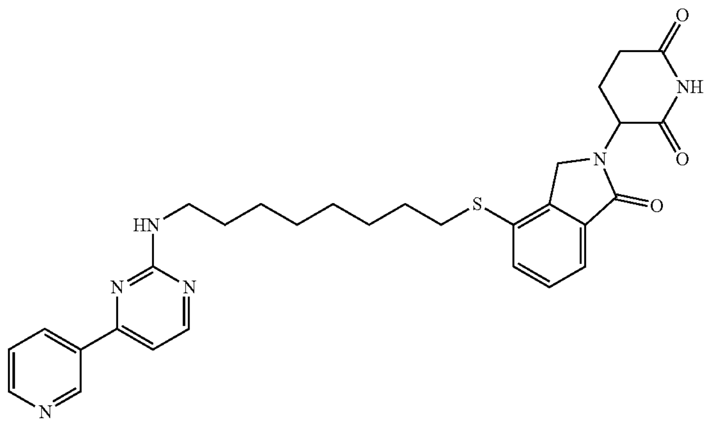 [SMILES: O=C1CCC(N2Cc3c(SCCCCCCCCNc4nccc(-c5cccnc5)n4)cccc3C2=O)C(=O)N1] | 3-(1-oxo-4-((8-((4-(pyridin-3-yl)pyrimidin-2-yl)amino)octyl)thio)isoindolin-2-yl)piperidine-2,6-dione |
| | 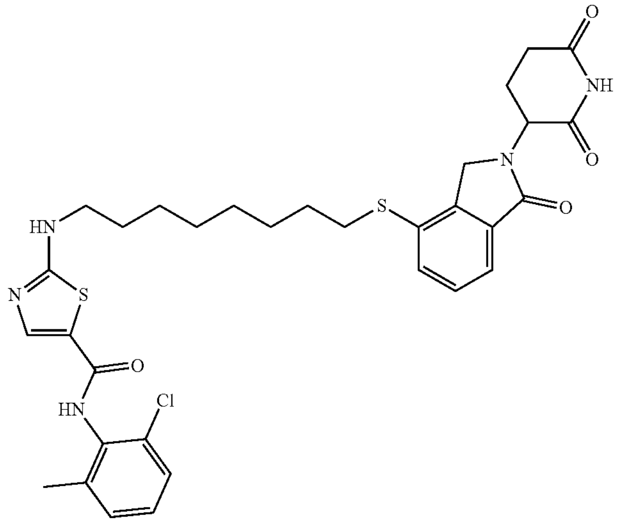 [SMILES: Cc1cccc(Cl)c1NC(=O)c1cnc(NCCCCCCCCSc2cccc3c2CN(C2CCC(=O)NC2=O)C3=O)s1] | N-(2-chloro-6-methylphenyl)-2-((8-((2-(2,6-dioxopiperidin-3-yl)-1-oxoisoindolin-4-yl)thio)octyl)amino)thiazole-5-carboxamide |
| | 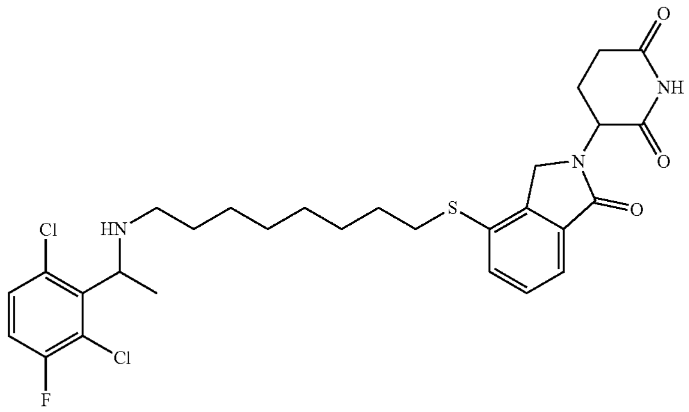 [SMILES: CC(NCCCCCCCCSc1cccc2c1CN(C1CCC(=O)NC1=O)C2=O)c1c(Cl)ccc(F)c1Cl] | 3-(4-((8-((1-(2,6-dichloro-3-fluorophenyl)ethyl)amino)octyl)thio)-1-oxoisoindolin-2-yl)piperidine-2,6-dione |

TABLE 1-continued

The compounds of the present invention

| Compound No. | Structure of the compounds | The compound's name |
| --- | --- | --- |
| | 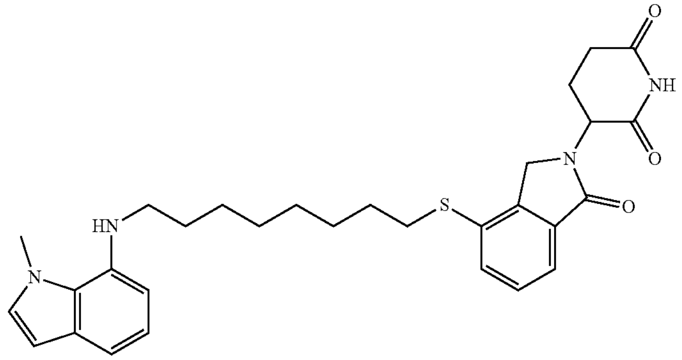 [SMILES: Cn1ccc2cccc(NCCCCCCCCSc3cccc4c3CN(C3CCC(=O)NC3=O)C4=O)c21] | 3-(4-((8-((1-methyl-1H-indol-7-yl)amino)octyl)thio)-1-oxoisoindolin-2-yl)piperidine-2,6-dione |
| | 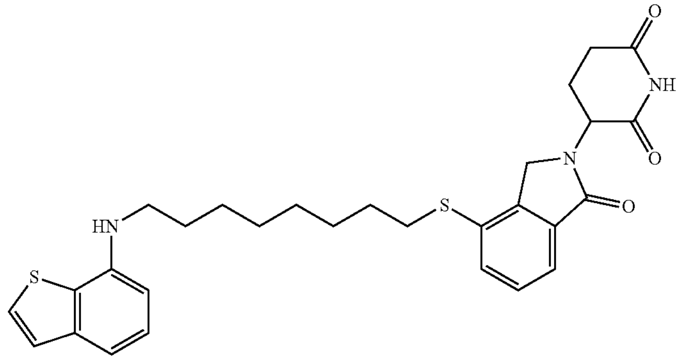 | 3-(4-((8-(benzo[b]thiophen-7-ylamino)octyl)thio)-1-oxoisoindolin-2-yl)piperidine-2,6-dione |
| | 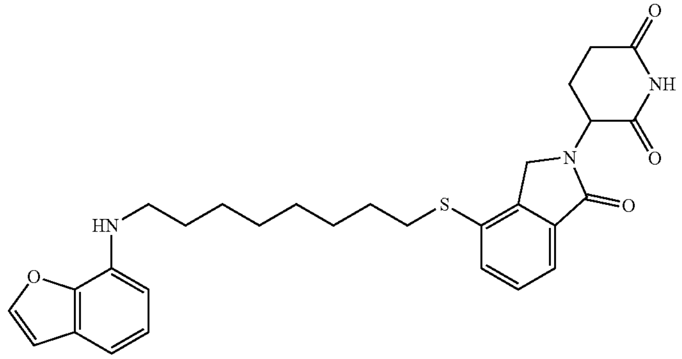 [SMILES: O=C1CCC(N2Cc3c(SCCCCCCCCNc4cccc5ccoc45)cccc3C2=O)C(=O)N1] | 3-(4-((8-(benzofuran-7-ylamino)octyl)thio)-1-oxoisoindolin-2-yl)piperidine-2,6-dione |
| | 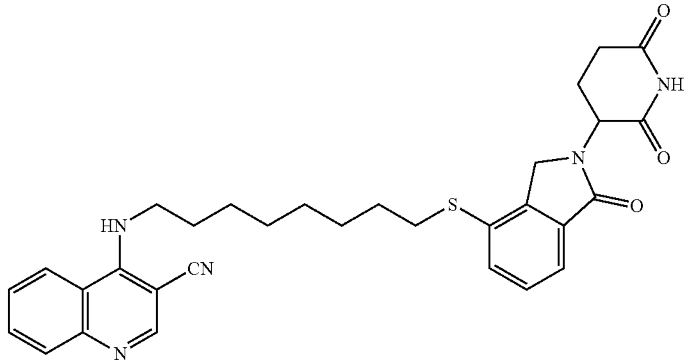 [SMILES: N#Cc1cnc2ccccc2c1NCCCCCCCCSc1cccc2c1CN(C1CCC(=O)NC1=O)C2=O] | 4-((8-((2-(2,6-dioxopiperidin-3-yl)-1-oxoisoindolin-4-yl)thio)octyl)amino)quinoline-3-carbonitrile |

TABLE 1-continued

| Compound No. | Structure of the compounds | The compound's name |
|---|---|---|
| | 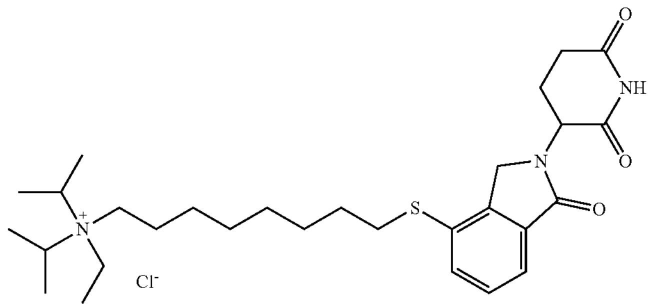 | 8-((2-(2,6-dioxopiperidin-3-yl)-1-oxoisoindolin-4-yl)thio)-N-ethyl-N,N-diisopropyloctan-1-aminium chloride |
| SIAIS12200-93 | 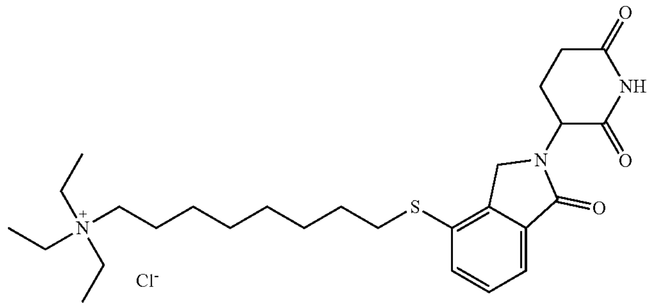 | 8-((2-(2,6-dioxopiperidin-3-yl)-1-oxoisoindolin-4-yl)thio)-N,N,N-triethyloctan-1-aminium chloride |
| | 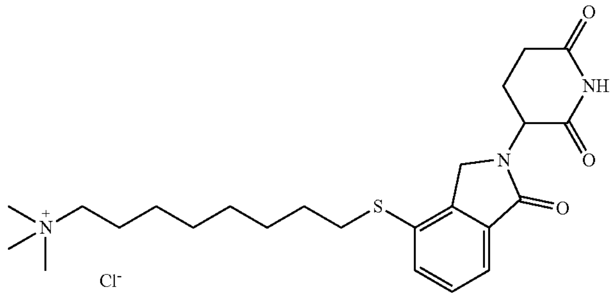 | 8-((2-(2,6-dioxopiperidin-3-yl)-1-oxoisoindolin-4-yl)thio)-N,N,N-trimethyloctan-1-aminium chloride |
| | 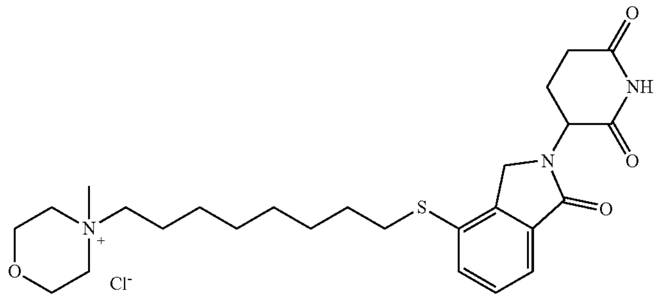 | 4-(8-((2-(2,6-dioxopiperidin-3-yl)-1-oxoisoindolin-4-yl)thio)octyl)-4-methylmorpholin-4-ium chloride |
| | 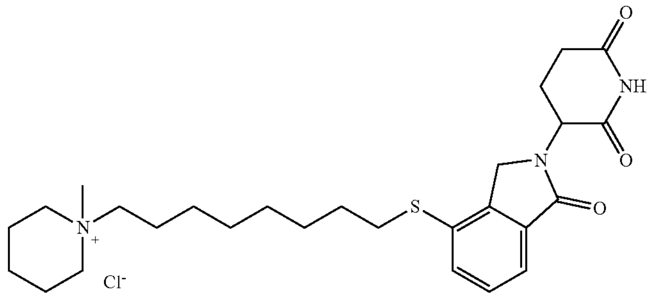 | 1-(8-((2-(2,6-dioxopiperidin-3-yl)-1-oxoisoindolin-4-yl)thio)octyl)-1-methylpiperidin-1-ium chloride |

TABLE 1-continued

The compounds of the present invention

| Compound No. | Structure of the compounds | The compound's name |
|---|---|---|
| SIAIS12221-73 | 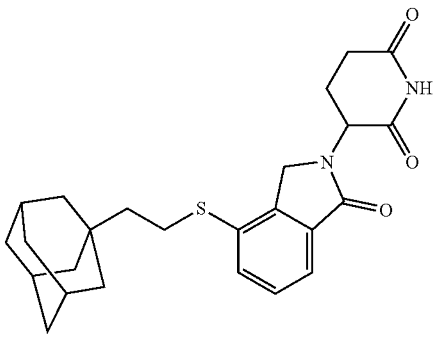 [SMILES: O=C1CCC(N2Cc3c(SCCC45CC6CC(CC(C6)C4)C5)cccc3C2=O)C(=O)N1] | 3-(4-((2-(adamantan-1-yl)ethyl)thio)-1-oxoisoindolin-2-yl)piperidine-2,6-dione |
| | 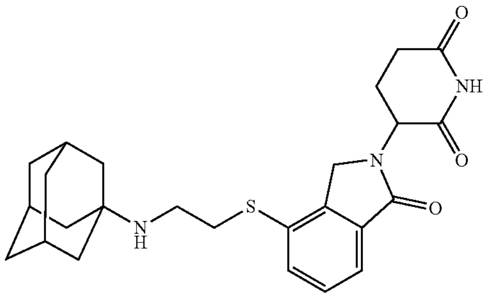 [SMILES: O=C1CCC(N2Cc3c(SCCNC45CC6CC(CC(C6)C4)C5)cccc3C2=O)C(=O)N1] | 3-(4-((2-(adamantan-1-ylamino)ethyl)thio)-1-oxoisoindolin-2-yl)piperidine-2,6-dione |
| SIAIS12221-77 | 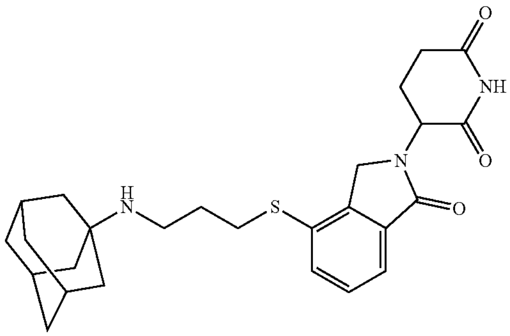 [SMILES: O=C1CCC(N2Cc3c(SCCCNC45CC6CC(CC(C6)C4)C5)cccc3C2=O)C(=O)N1] | 3-(4-((3-(adamantan-1-ylamino)propyl)thio)-1-oxoisoindolin-2-yl)piperidine-2,6-dione |
| SIAIS12221-79 | 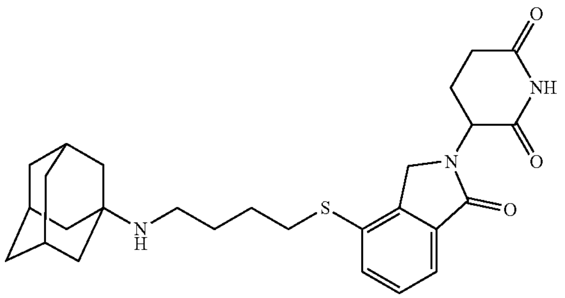 [SMILES: O=C1CCC(N2Cc3c(SCCCCNC45CC6CC(CC(C6)C4)C5)cccc3C2=O)C(=O)N1] | 3-(4-((4-((adamantan-1-yl)amino)butyl)thio)-1-oxoisoindolin-2-yl)piperidine-2,6-dione |

TABLE 1-continued

| The compounds of the present invention | | |
|---|---|---|
| Compound No. | Structure of the compounds | The compound's name |
| SIAIS12211-17 | 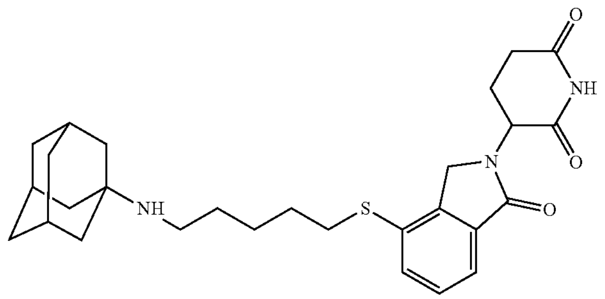 [SMILES: O=C1CCC(N2Cc3c(SCCCCCNC45CC6CC(CC(C6)C4)C5)cccc3C2=O)C(=O)N1] | 3-(4-((5-((adamantan-1-yl)amino)pentyl)thio)-1-oxoisoindolin-2-yl)piperidine-2,6-dione |
| SIAIS12201-77 | 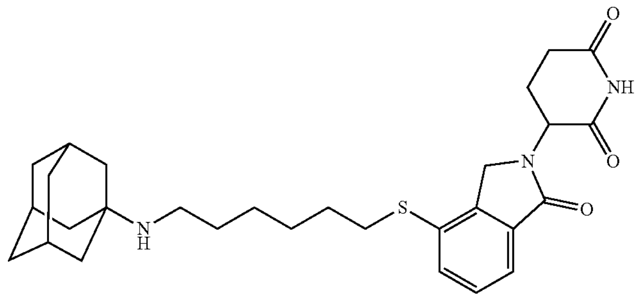 [SMILES: O=C1CCC(N2Cc3c(SCCCCCCNC45CC6CC(CC(C6)C4)C5)cccc3C2=O)C(=O)N1] | 3-(4-((6-((adamantan-1-yl)amino)hexyl)thio)-1-oxoisoindolin-2-yl)piperidine-2,6-dione |
| SIAIS12201-55 | 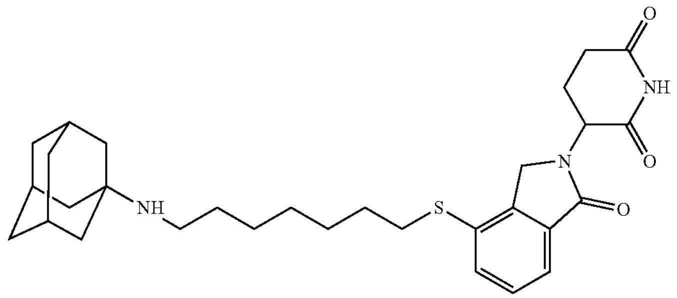 [SMILES: O=C1CCC(N2Cc3c(SCCCCCCCNC45CC6CC(CC(C6)C4)C5)cccc3C2=O)C(=O)N1] | 3-(4-((7-((adamantan-1-yl)amino)heptyl)thio)-1-oxoisoindolin-2-yl)piperidine-2,6-dione |
| | 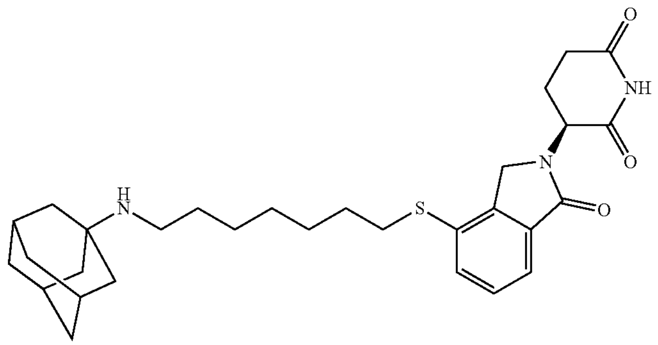 [SMILES: O=C1CC[C@H](N2Cc3c(SCCCCCCCNC45CC6CC(CC(C6)C4)C5)cccc3C2=O)C(=O)N1] | (3S)-3-(4-((7-((adamantan-1-yl)amino)heptyl)thio)-1-oxoisoindolin-2-yl)piperidine-2,6-dione |

TABLE 1-continued

| The compounds of the present invention | | |
|---|---|---|
| Compound No. | Structure of the compounds | The compound's name |
| | 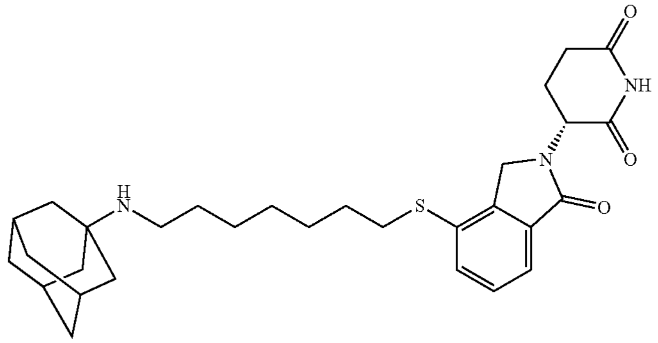 [SMILES: O=C1CC[C@@H](N2Cc3c(SCCCCCCCNC45CC6CC(CC(C6)C4)C5)cccc3C2=O)C(=O)N1] | (3R)-3-(4-((7-((adamantan-1-yl)amino)heptyl)thio)-1-oxoisoindolin-2-yl)piperidine-2,6-dione |
| SIAIS12211-49 | 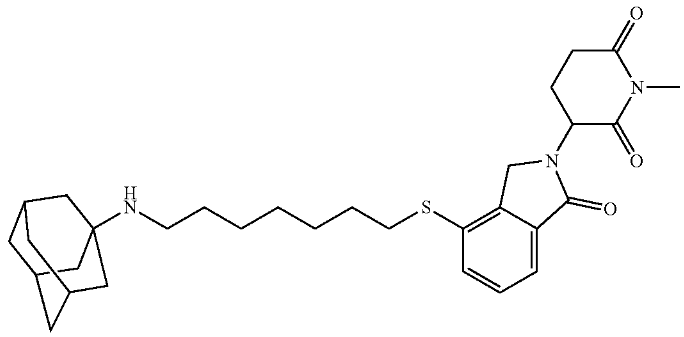 [SMILES: CN1C(=O)CCC(N2Cc3c(SCCCCCCCNC45CC6CC(CC(C6)C4)C5)cccc3C2=O)C1=O] | 3-(4-((7-(adamantan-1-ylamino)heptyl)thio)-1-oxoisoindolin-2-yl)-1-methylpiperidine-2,6-dione |
| SIAIS12200-87 | 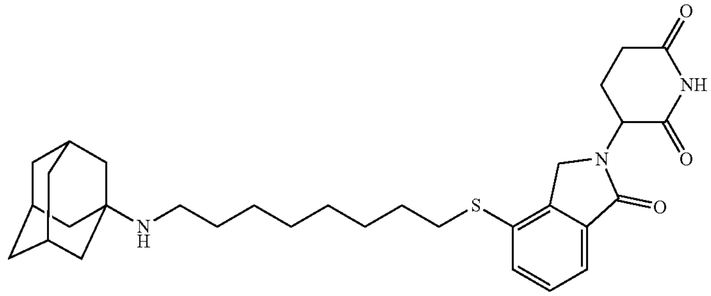 [SMILES: O=C1CCC(N2Cc3c(SCCCCCCCCNC45CC6CC(CC(C6)C4)C5)cccc3C2=O)C(=O)N1] | 3-(4-((8-((adamantan-1-yl)amino)octyl)thio)-1-oxoisoindolin-2-yl)piperidine-2,6-dione |
| | 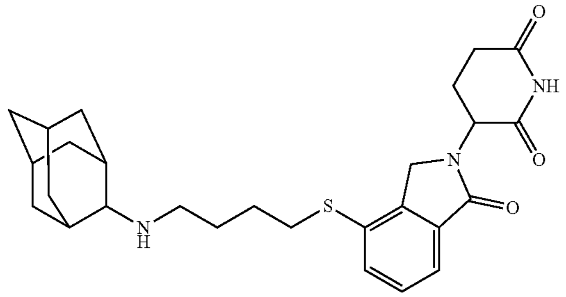 [SMILES: O=C1CCC(N2Cc3c(SCCCCNC4C5CC6CC(C5)CC4C6)cccc3C2=O)C(=O)N1] | 3-(4-((4-((adamantan-2-yl)amino)butyl)thio)-1-oxoisoindolin-2-yl)piperidine-2,6-dione |

TABLE 1-continued

| The compounds of the present invention | | |
|---|---|---|
| Compound No. | Structure of the compounds | The compound's name |
| | 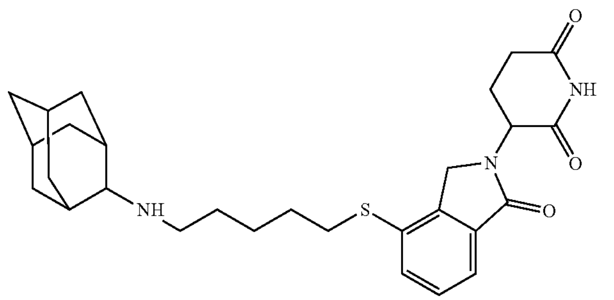 [SMILES: O=C1CCC(N2Cc3c(SCCCCCNC4C5CC6CC(C5)CC4C6)cccc3C2=O)C(=O)N1] | 3-(4-((5-((adamantan-2-yl)amino)pentyl)thio)-1-oxoisoindolin-2-yl)piperidine-2,6-dione |
| SIAIS12201-79 | 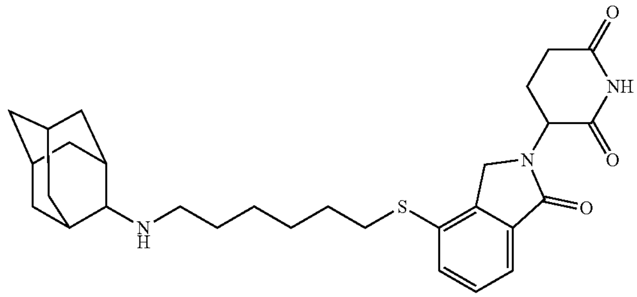 [SMILES: O=C1CCC(N2Cc3c(SCCCCCCNC4C5CC6CC(C5)CC4C6)cccc3C2=O)C(=O)N1] | 3-(4-((6-((adamantan-2-yl)amino)hexyl)thio)-1-oxoisoindolin-2-yl)piperidine-2,6-dione |
| SIAIS12201-59 | 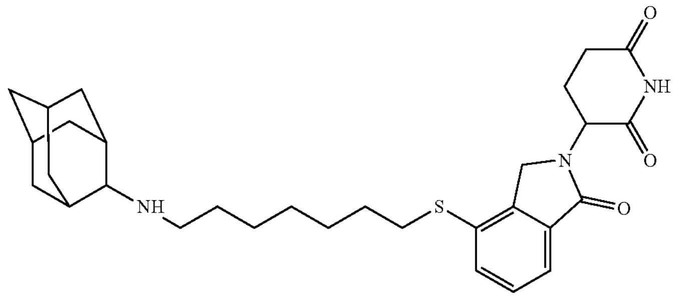 [SMILES: O=C1CCC(N2Cc3c(SCCCCCCCNC4C5CC6CC(C5)CC4C6)cccc3C2=O)C(=O)N1] | 3-(4-((7-((adamantan-2-yl)amino)heptyl)thio)-1-oxoisoindolin-2-yl)piperidine-2,6-dione |
| SIAIS12210-31 | 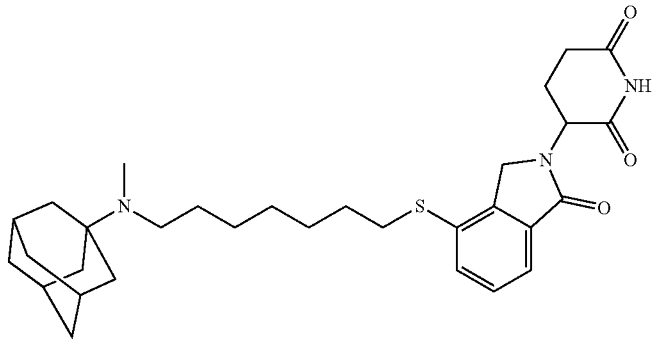 [SMILES: CN(CCCCCCCSc1cccc2c1CN(C1CCC(=O)NC1=O)C2=O)C12CC3CC(CC(C3)C1)C2] | 3-(4-((7-((adamantan-1-yl)(methyl)amino)heptyl)thio)-1-oxoisoindolin-2-yl)piperidine-2,6-dione |

TABLE 1-continued

| The compounds of the present invention | | |
|---|---|---|
| Compound No. | Structure of the compounds | The compound's name |
| | 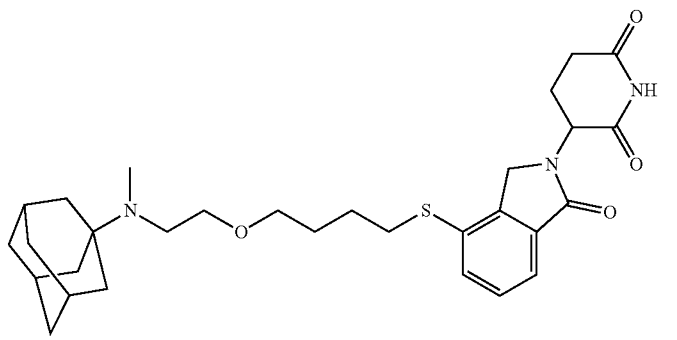 [SMILES: CN(CCOCCCCSc1cccc2c1CN(C1CCC(=O)NC1=O)C2=O)C12CC3CC(CC(C3)C1)C2] | 3-(4-((4-(2-(adamantan-1-yl(methyl)amino)ethoxy)butyl)thio)-1-oxoisoindolin-2-yl)piperidine-2,6-dione |
| SIAIS12221-41 | 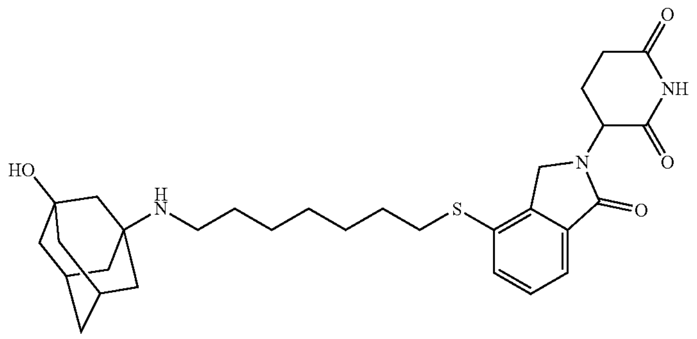 [SMILES: O=C1CCC(N2Cc3c(SCCCCCCCNC45CC6CC(CC(O)(C6)C4)C5)cccc3C2=O)C(=O)N1] | 3-(4-((7-(3-hydroxyadamantan-1-yl)amino)heptyl)thio)-1-oxoisoindolin-2-yl)piperidine-2,6-dione |
| SIAIS12210-13 | 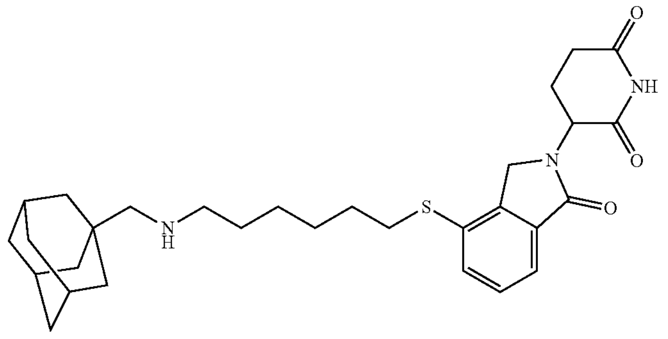 [SMILES: O=C1CCC(N2Cc3c(SCCCCCCNCC45CC6CC(CC(C6)C4)C5)cccc3C2=O)C(=O)N1] | 3-(4-((6-((adamantan-1-ylmethyl)amino)hexyl)thio)-1-oxoisoindolin-2-yl)piperidine-2,6-dione |
| SIAIS12211-27 | 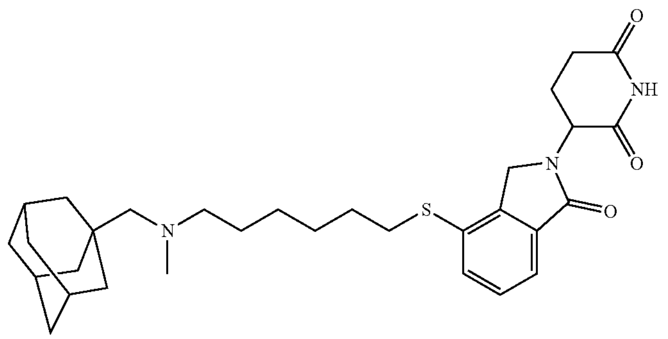 [SMILES: CN(CCCCCCSc1cccc2c1CN(C1CCC(=O)NC1=O)C2=O)CC12CC3CC(CC(C3)C1)C2] | 3-(4-((6-((adamantan-1-ylmethyl)(methyl)amino)hexyl)thio)-1-oxoisoindolin-2-yl)piperidine-2,6-dione |

TABLE 1-continued

| The compounds of the present invention | | |
|---|---|---|
| Compound No. | Structure of the compounds | The compound's name |
| SIAIS12221-39 | 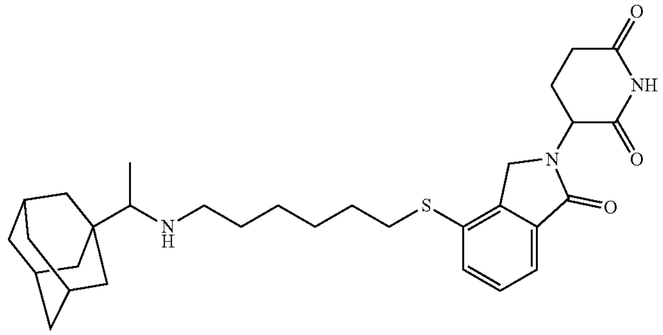 [SMILES: CC(NCCCCCCSc1cccc2c1CN(C1CCC(=O)NC1=O)C2=O)C12CC3CC(CC(C3)C1)C2] | 3-(4-((6-((1-(adamantan-1-yl)ethyl)amino)hexyl)thio)-1-oxoisoindolin-2-yl)piperidine-2,6-dione |
| | 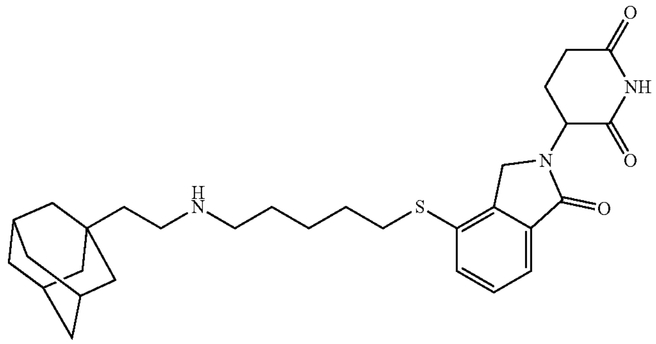 [SMILES: O=C1CCC(N2Cc3c(SCCCCCNCCC45CC6CC(CC(C6)C4)C5)cccc3C2=O)C(=O)N1] | 3-(4-((5-((2-(adamantan-1-yl)ethyl)amino)pentyl)thio)-1-oxoisoindolin-2-yl)piperidine-2,6-dione |
| SIAIS12200-89 | 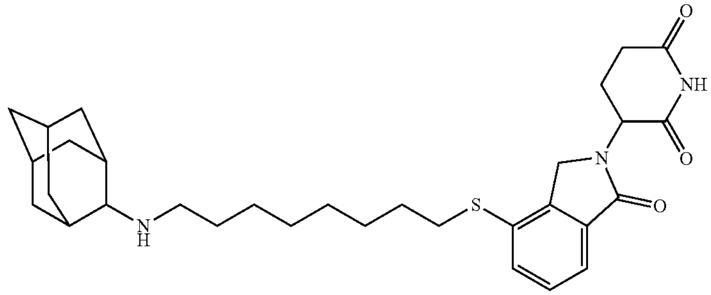 [SMILES: O=C1CCC(N2Cc3c(SCCCCCCCCNC4C5CC6CC(C5)CC4C6)cccc3C2=O)C(=O)N1] | 3-(4-((8-((adamantan-2-yl)amino)octyl)thio)-1-oxoisoindolin-2-yl)piperidine-2,6-dione |
| | 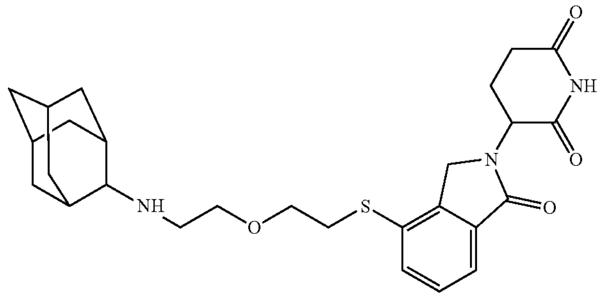 [SMILES: O=C1CCC(N2Cc3c(SCCOCCNC4C5CC6CC(C5)CC4C6)cccc3C2=O)C(=O)N1] | 3-(4-((2-(2-((adamantan-2-yl)amino)ethoxy)ethyl)thio)-1-oxoisoindolin-2-yl)piperidine-2,6-dione |

TABLE 1-continued

| The compounds of the present invention | | |
|---|---|---|
| Compound No. | Structure of the compounds | The compound's name |
| | 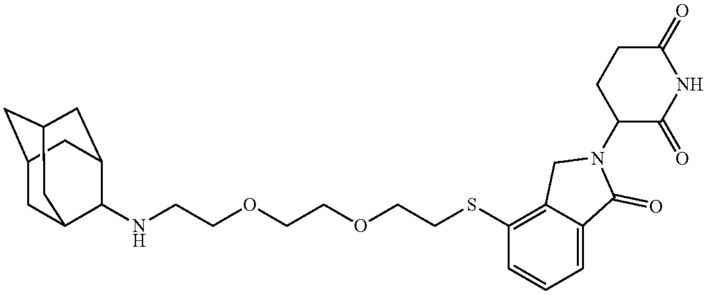 [SMILES: O=C1CCC(N2Cc3c(SCCOCCOCCNC4C5CC6CC(C5)CC4C6)cccc3C2=O)C(=O)N1] | 3-(4-((2-(2-(2-((adamantan-2-yl)amino)ethoxy)ethoxy)ethyl)thio)-1-oxoisoindolin-2-yl)piperidine-2,6-dione |
| | 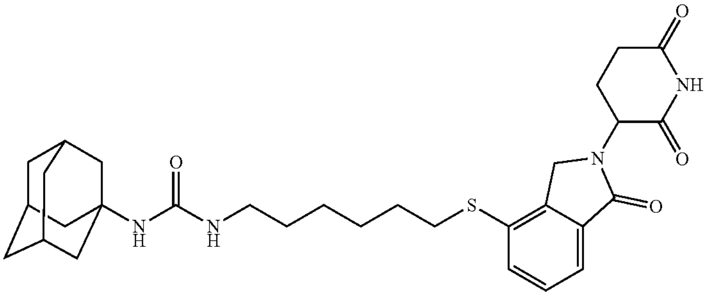 [SMILES: O=C1CCC(N2Cc3c(SCCCCCCNC(=O)NC45CC6CC(CC(C6)C4)C5)cccc3C2=O)C(=O)N1] | 1-(adamantan-1-yl)-3-(6-((2-(2,6-dioxopiperidin-3-yl)-1-oxoisoindolin-4-yl)thio)hexyl)urea |
| | 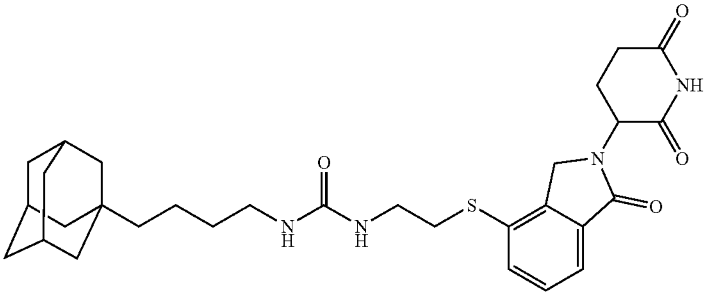 [SMILES: O=C1CCC(N2Cc3c(SCCNC(=O)NCCCCC45CC6CC(CC(C6)C4)C5)cccc3C2=O)C(=O)N1] | 1-(4-(adamantan-1-yl)butyl)-3-(2-((2-(2,6-dioxopiperidin-3-yl)-1-oxoisoindolin-4-yl)thio)ethyl)urea |
| | 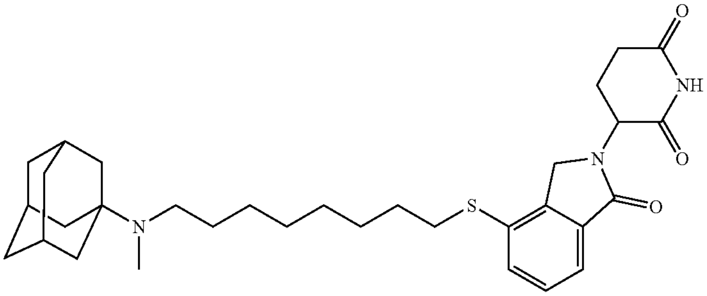 [SMILES: CN(CCCCCCCCSc1cccc2c1CN(C1CCC(=O)NC1=O)C2=O)C12CC3CC(CC(C3)C1)C2] | 3-(4-((8-((adamantan-1-yl)(methyl)amino)octyl)thio)-1-oxoisoindolin-2-yl)piperidine-2,6-dione |
| SIAIS12201-71 | 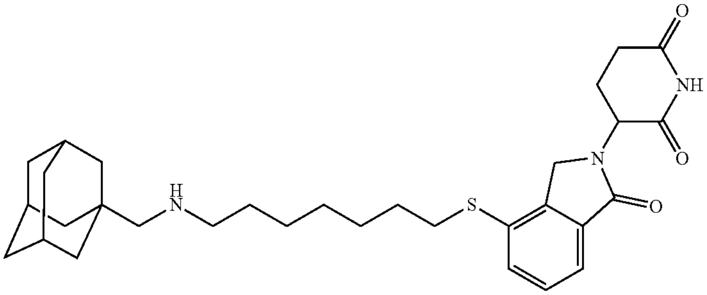 [SMILES: O=C1CCC(N2Cc3c(SCCCCCCCNCC45CC6CC(CC(C6)C4)C5)cccc3C2=O)C(=O)N1] | 3-(4-((7-(((adamantan-1-yl)methyl)amino)heptyl)thio)-1-oxoisoindolin-2-yl)piperidine-2,6-dione |

TABLE 1-continued

| The compounds of the present invention | | |
|---|---|---|
| Compound No. | Structure of the compounds | The compound's name |
| SIAIS12201-57 | 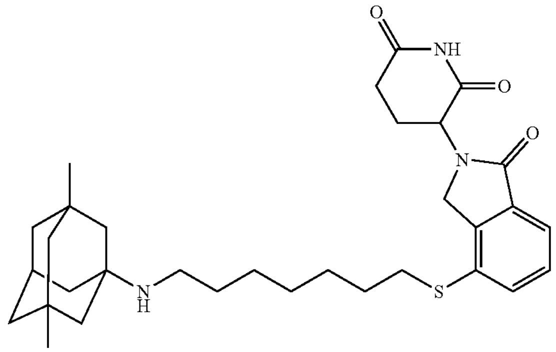 [SMILES: CC12CC3CC(C)(C1)CC(NCCCCCCCSc1cccc4c1CN(C1CCC(=O)NC1=O)C4=O)(C3)C2] | 3-(4-((7-((3,5-dimethyladamantan-1-yl)amino)heptyl)thio)-1-oxoisoindolin-2-yl)piperidine-2,6-dione |
| | 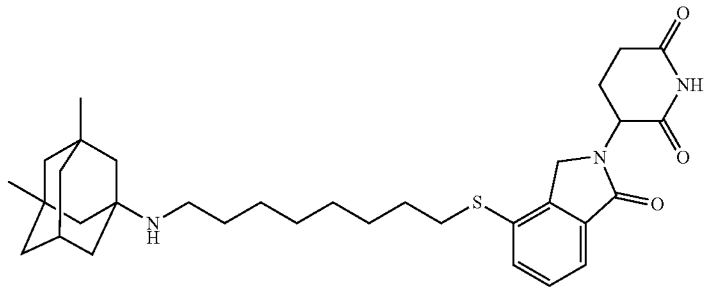 [SMILES: CC12CC3CC(C)(C1)CC(NCCCCCCCCSc1cccc4c1CN(C1CCC(=O)NC1=O)C4=O)(C3)C2] | 3-(4-((8-((3,5-dimethyladamantan-1-yl)amino)octyl)thio)-1-oxoisoindolin-2-yl)piperidine-2,6-dione |
| | 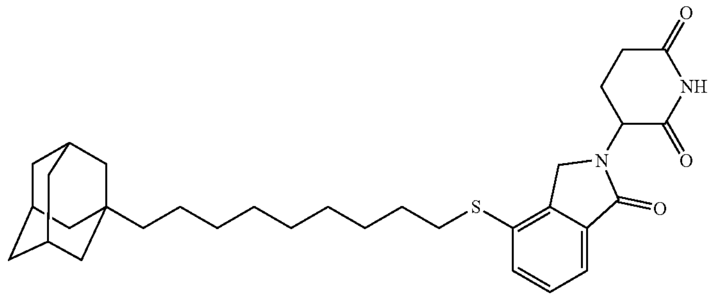 [SMILES: O=C1CCC(N2Cc3c(SCCCCCCCCCC45CC6CC(CC(C6)C4)C5)cccc3C2=O)C(=O)N1] | 3-(4-((9-(adamantan-1-yl)nonyl)thio)-1-oxoisoindolin-2-yl)piperidine-2,6-dione |
| | 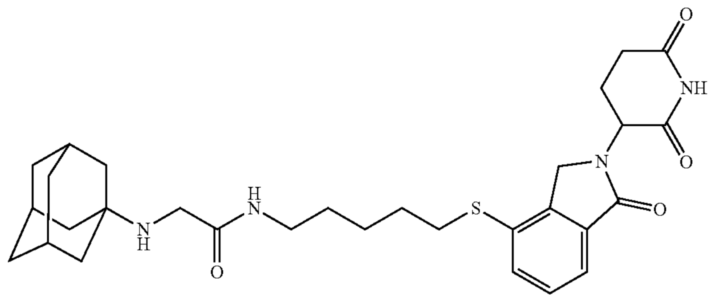 [SMILES: O=C(CNC12CC3CC(CC(C3)C1)C2)NCCCCCSc1cccc2c1CN(C1CCC(=O)NC1=O)C2=O] | 2-((adamantan-1-yl)amino)-N-(5-((2-(2,6-dioxopiperidin-3-yl)-1-oxoisoindolin-4-yl)thio)pentyl)acetamide |

TABLE 1-continued

| The compounds of the present invention | | |
|---|---|---|
| Compound No. | Structure of the compounds | The compound's name |
| SIAIS12201-95 | 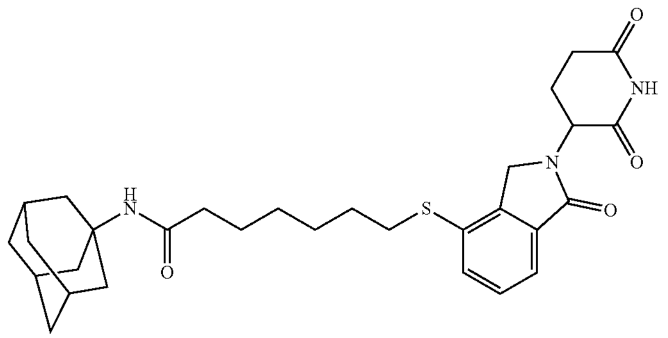 [SMILES: O=C1CCC(N2Cc3c(SCCCCCCC(=O)NC45CC6CC(CC(C6)C4)C5)cccc3C2=O)C(=O)N1] | N-(adamantan-1-yl)-7-((2-(2,6-dioxopiperidin-3-yl)-1-oxoisoindolin-4-yl)thio)heptanamide |
| SIAIS12201-97 | 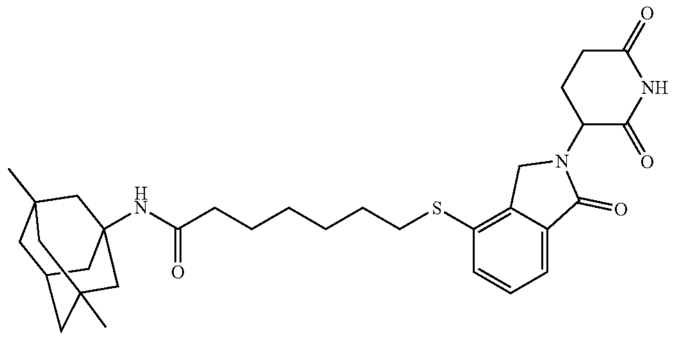 [SMILES: CC12CC3CC(C)(C1)CC(NC(=O)CCCCCCSc1cccc4c1CN(C1CCC(=O)NC1=O)C4=O)(C3)C2] | N-(3,5-dimethyladamantan-1-yl)-7-((2-(2,6-dioxopiperidin-3-yl)-1-oxoisoindolin-4-yl)thio)heptanamide |
| SIAIS12201-99 | 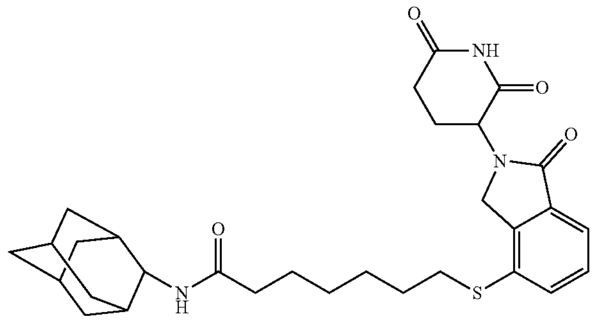 [SMILES: O=C1CCC(N2Cc3c(SCCCCCCC(=O)NC4C5CC6CC(C5)CC4C6)cccc3C2=O)C(=O)N1] | N-(adamantan-2-yl)-7-((2-(2,6-dioxopiperidin-3-yl)-1-oxoisoindolin-4-yl)thio)heptanamide |
| SIAIS12221-43 | 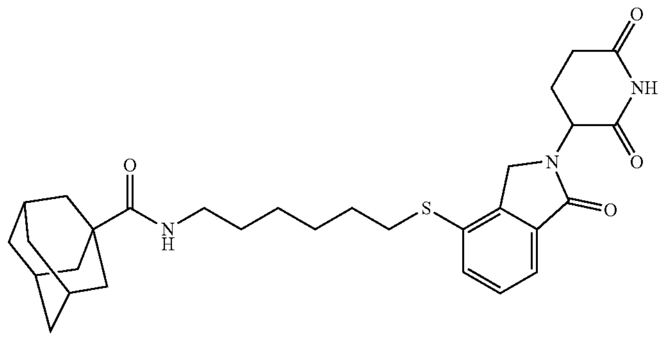 [SMILES: O=C1CCC(N2Cc3c(SCCCCCCNC(=O)C45CC6CC(CC(C6)C4)C5)cccc3C2=O)C(=O)N1] | N-(6-((2-(2,6-dioxopiperidin-3-yl)-1-oxoisoindolin-4-yl)thio)hexyl)adamantane-1-carboxamide |

TABLE 1-continued

| The compounds of the present invention | | |
|---|---|---|
| Compound No. | Structure of the compounds | The compound's name |
| SIAIS12221-45 | 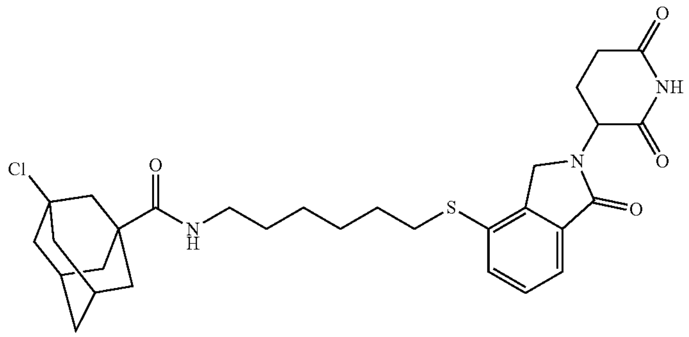 [SMILES: O=C1CCC(N2Cc3c(SCCCCCCNC(=O)C45CC6CC(CC(Cl)(C6)C4)C5)cccc3C2=O)C(=O)N1] | 3-chloro-N-(6-((2-(2,6-dioxopiperidin-3-yl)-1-oxoisoindolin-4-yl)thio)hexyl)adamantane-1-carboxamide |
| | 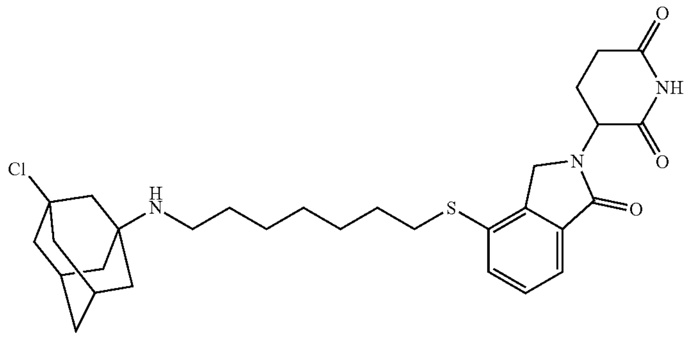 [SMILES: O=C1CCC(N2Cc3c(SCCCCCCCNC45CC6CC(CC(Cl)(C6)C4)C5)cccc3C2=O)C(=O)N1] | 3-(4-((7-((3-chloroadamantan-1-yl)amino)heptyl)thio)-1-oxoisoindolin-2-yl)piperidine-2,6-dione |
| | 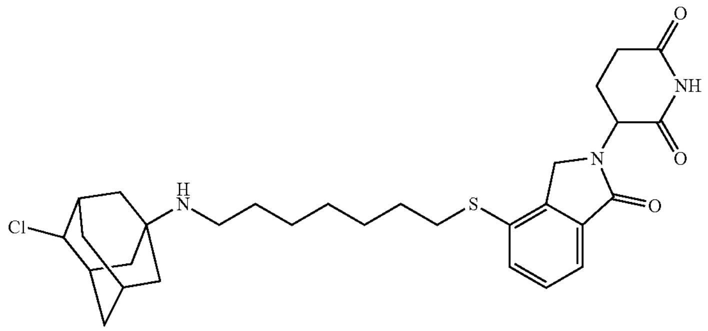 [SMILES: O=C1CCC(N2Cc3c(SCCCCCCCNC45CC6CC(C4)C(Cl)C(C6)C5)cccc3C2=O)C(=O)N1] | 3-(4-((7-((4-chloroadamantan-1-yl)amino)heptyl)thio)-1-oxoisoindolin-2-yl)piperidine-2,6-dione |
| | 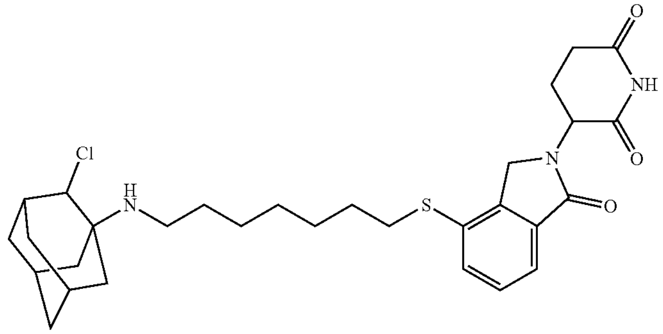 [SMILES: O=C1CCC(N2Cc3c(SCCCCCCCNC45CC6CC(CC(C6)C4Cl)C5)cccc3C2=O)C(=O)N1] | 3-(4-((7-((2-chloroadamantan-1-yl)amino)heptyl)thio)-1-oxoisoindolin-2-yl)piperidine-2,6-dione |

TABLE 1-continued

The compounds of the present invention

| Compound No. | Structure of the compounds | The compound's name |
| --- | --- | --- |
| | 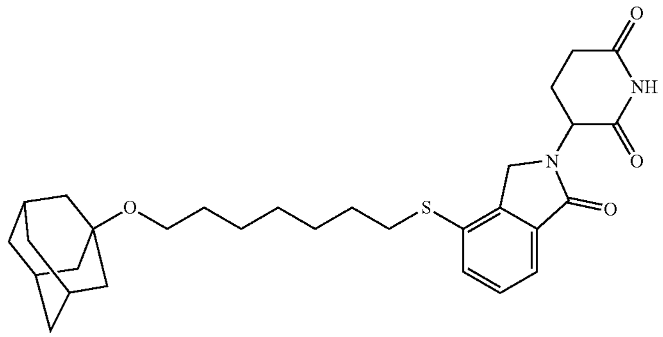 [SMILES: O=C1CCC(N2Cc3c(SCCCCCCCOC45CC6CC(CC(C6)C4)C5)cccc3C2=O)C(=O)N1] | 3-(4-((7-(adamantan-1-yloxy)heptyl)thio)-1-oxoisoindolin-2-yl)piperidine-2,6-dione |
| SIAIS26915-9 | 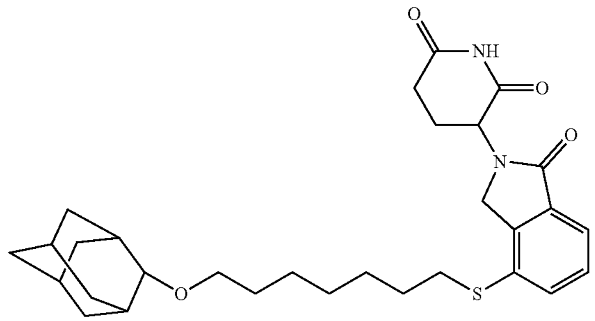 [SMILES: O=C1CCC(N2Cc3c(SCCCCCCCOC4C5CC6CC(C5)CC4C6)cccc3C2=O)C(=O)N1] | 3-(4-((7-(adamantan-2-yloxy)heptyl)thio)-1-oxoisoindolin-2-yl)piperidine-2,6-dione |
| SIAIS12210-25 | 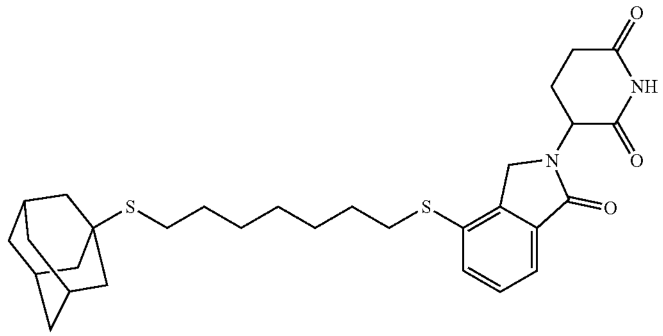 [SMILES: O=C1CCC(N2Cc3c(SCCCCCCCSC45CC6CC(CC(C6)C4)C5)cccc3C2=O)C(=O)N1] | 3-(4-((7-(adamantan-1-ylthio)heptyl)thio)-1-oxoisoindolin-2-yl)piperidine-2,6-dione |
| SIAIS12210-03 | 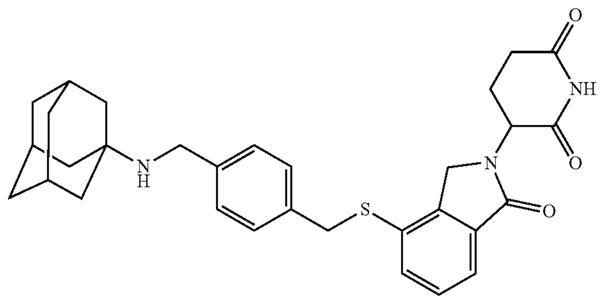 [SMILES: O=C1CCC(N2Cc3c(SCc4ccc(CNC56CC7CC(CC(C7)C5)C6)cc4)cccc3C2=O)C(=O)N1] | 3-(4-((4-(((adamantan-1-yl)amino)methyl)benzyl)thio)-1-oxoisoindolin-2-yl)piperidine-2,6-dione |

TABLE 1-continued

| The compounds of the present invention | | |
|---|---|---|
| Compound No. | Structure of the compounds | The compound's name |
| SIAIS12210-05 | 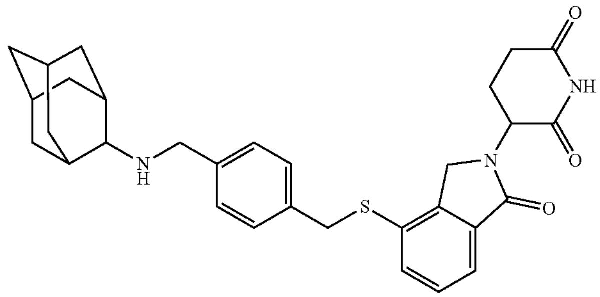 [SMILES: O=C1CCC(N2Cc3c(SCc4ccc(CNC5C6CC7CC(C6)CC5C7)cc4)cccc3C2=O)C(=O)N1] | 3-(4-((4-((adamantan-2-ylamino)methyl)benzyl)thio)-1-oxoisoindolin-2-yl)piperidine-2,6-dione |
| SIAIS12221-57 | 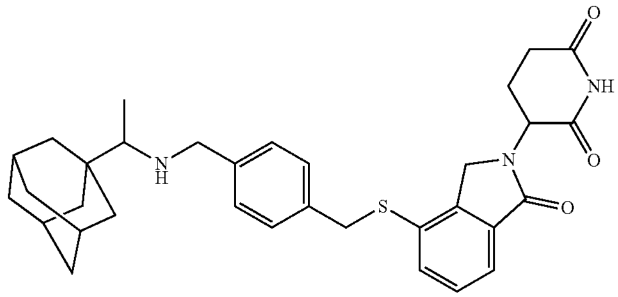 [SMILES: CC(NCc1ccc(CSc2cccc3c2CN(C2CCC(=O)NC2=O)C3=O)cc1)C12CC3CC(CC(C3)C1)C2] | 3-(4-((4-(((1-(adamantan-1-yl)ethyl)amino)methyl)benzyl)thio)-1-oxoisoindolin-2-yl)piperidine-2,6-dione |
| SIAIS12220-85 | 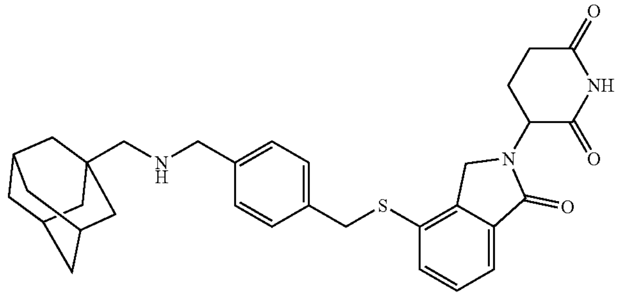 [SMILES: O=C1CCC(N2Cc3c(SCc4ccc(CNCC56CC7CC(CC(C7)C5)C6)cc4)cccc3C2=O)C(=O)N1] | 3-(4-((4-(((adamantan-1-ylmethyl)amino)methyl)benzyl)thio)-1-oxoisoindolin-2-yl)piperidine-2,6-dione |
| SIAIS28712-8 | 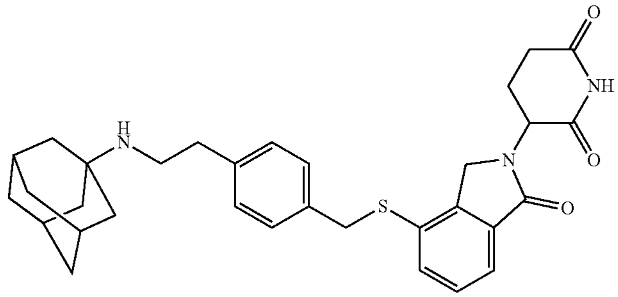 [SMILES: O=C1CCC(N2Cc3c(SCc4ccc(CCNC56CC7CC(CC(C7)C5)C6)cc4)cccc3C2=O)C(=O)N1] | 3-(4-((4-(2-(adamantan-1-ylamino)ethyl)benzyl)thio)-1-oxoisoindolin-2-yl)piperidine-2,6-dione |
| SIAIS28710-5 | 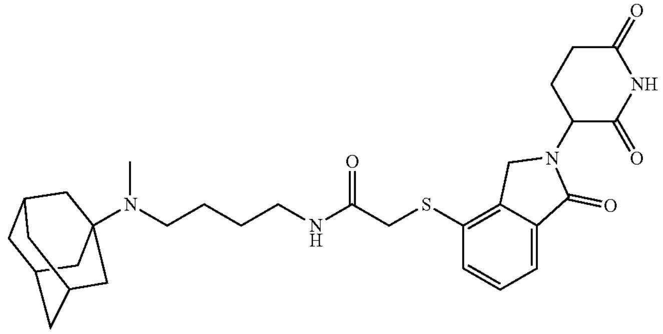 [SMILES: CN(CCCCNC(=O)CSc1cccc2c1CN(C1CCC(=O)NC1=O)C2=O)C12CC3CC(CC(C3)C1)C2] | N-(4-(adamantan-1-yl(methyl)amino)butyl)-2-((2-(2,6-dioxopiperidin-3-yl)-1-oxoisoindolin-4-yl)thio)acetamide |

TABLE 1-continued

| The compounds of the present invention | | |
|---|---|---|
| Compound No. | Structure of the compounds | The compound's name |
| | 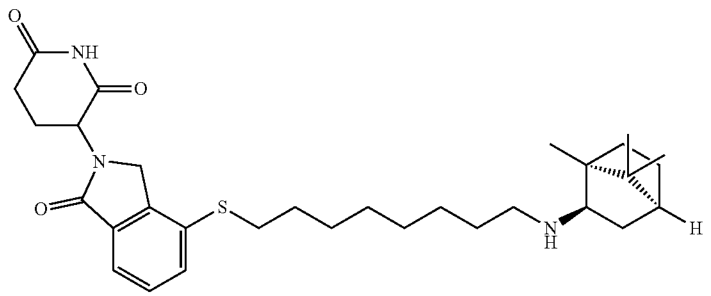 [SMILES: CC1(C)[C@H]2CC[C@]1(C)[C@H](NCCCCCCCCSc1cccc3c1CN(C1CCC(=O)NC1=O)C3=O)C2] | 3-(1-oxo-4-((8-(((1S,2R,4S)-1,7,7-trimethylbicyclo[2.2.1]heptan-2-yl)amino)octypthio)isoindolin-2-yl)piperidine-2,6-dione |
| | 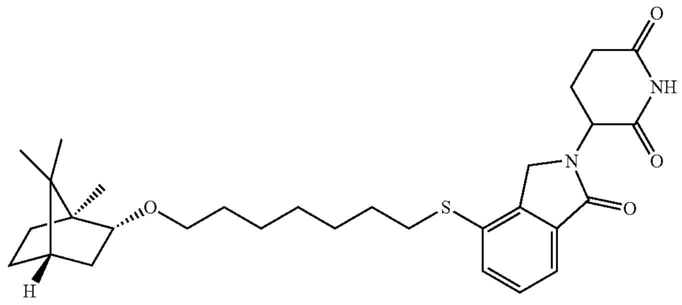 [SMILES: CC1(C)[C@H]2CC[C@]1(C)[C@H](OCCCCCCCSc1cccc3c1CN(C1CCC(=O)NC1=O)C3=O)C2] | 3-(1-oxo-4-((7-(((1S,2R,4S)-1,7,7-trimethylbicyclo[2.2.1]heptan-2-yl)oxy)heptyl)thio)isoindolin-2-yl)piperidine-2,6-dione |
| SIAIS12211-13 | 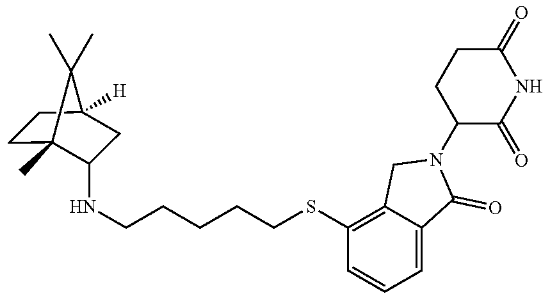 [SMILES: CC1(C)[C@@H]2CC[C@@]1(C)C(NCCCCCSc1cccc3c1CN(C1CCC(=O)NC1=O)C3=O)C2] | 3-(1-oxo-4-((5-(((1R,2S,4R)-1,7,7-trimethylbicyclo[2.2.1]heptan-2-yl)amino)pentyl)thio)isoindolin-2-yl)piperidine-2,6-dione |
| SIAIS12211-15 | 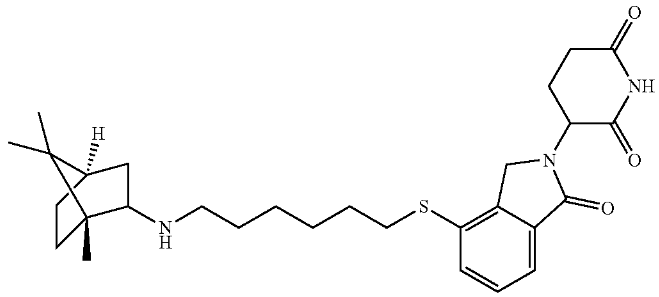 [SMILES: CC1(C)[C@@H]2CC[C@@]1(C)C(NCCCCCCSc1cccc3c1CN(C1CCC(=O)NC1=O)C3=O)C2] | 3-(1-oxo-4-((6-(((1R,2S,4R)-1,7,7-trimethylbicyclo[2.2.1]heptan-2-yl)amino)hexyl)thio)isoindolin-2-yl)piperidine-2,6-dione |
| SIAIS12210-19 | 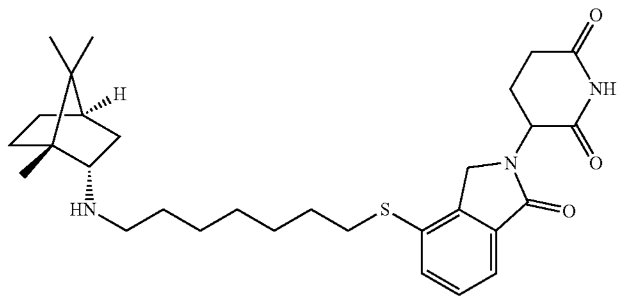 [SMILES: CC1(C)[C@@H]2CC[C@@]1(C)[C@@H](NCCCCCCCSc1cccc3c1CN(C1CCC(=O)NC1=O)C3=O)C2] | 3-(1-oxo-4-((7-(((1R,2S,4R)-1,7,7-trimethylbicyclo[2.2.1]heptan-2-yl)amino)heptyl)thio)isoindolin-2-yl)piperidine-2,6-dione |

TABLE 1-continued

| The compounds of the present invention | | |
|---|---|---|
| Compound No. | Structure of the compounds | The compound's name |
| SIAIS12211-29 | 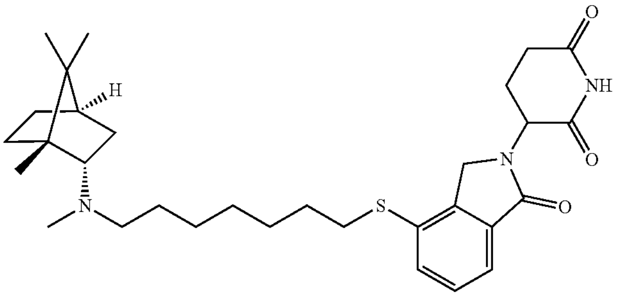 [SMILES: CN(CCCCCCCSc1cccc2c1CN(C1CCC(=O)NC1=O)C2=O)[C@H]1C[C@H]2CC[C@]1(C)C2(C)C] | 3-(4-((7-(methyl((1R,2S,4R)-1,7,7-trimethylbicyclo[2.2.1]heptan-2-yl)amino)heptyl)thio)-1-oxoisoindolin-2-yl)piperidine-2,6-dione |
| SIAIS12210-73 | 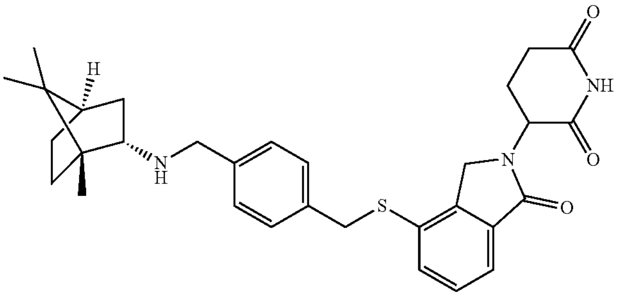 [SMILES: CC1(C)[C@@H]2CC[C@@]1(C)[C@@H](NCc1ccc(CSc3cccc4c3CN(C3CCC(=O)NC3=O)C4=O)cc1)C2] | 3-(1-oxo-4-((4-((((1R,2S,4R)-1,7,7-trimethylbicyclo[2.2.1]heptan-2-yl)amino)methyl)benzyl)thio)isoindolin-2-yl)piperidine-2,6-dione |
| | 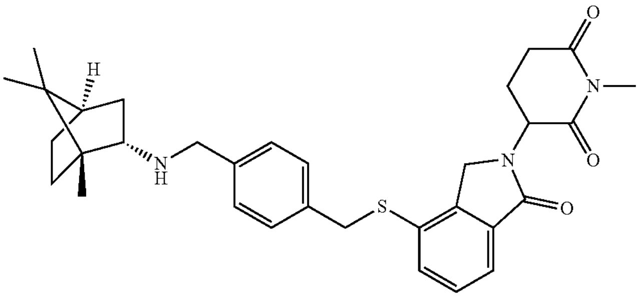 | 1-methyl-3-(1-oxo-4-((4-((((1R,2S,4R)-1,7,7-trimethylbicyclo[2.2.1]heptan-2-yl)amino)methyl)benzyl)thio)isoindolin-2-yl)piperidine-2,6-dione |
| SIAIS12201-67 | 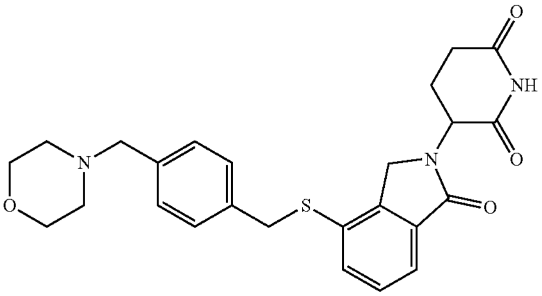 [SMILES: O=C1CCC(N2Cc3c(SCc4ccc(CN5CCOCC5)cc4)cccc3C2=O)C(=O)N1] | 3-(4-((4-(morpholinomethyl)benzyl)thio)-1-oxoisoindolin-2-yl)piperidine-2,6-dione |
| SIAIS12201-65 | 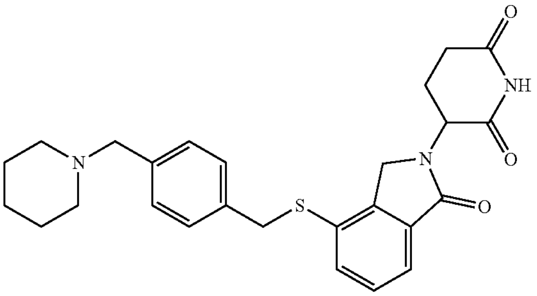 [SMILES: O=C1CCC(N2Cc3c(SCc4ccc(CN5CCCCC5)cc4)cccc3C2=O)C(=O)N1] | 3-(1-oxo-4-((4-(piperidin-1-ylmethyl)benzyl)thio)isoindolin-2-yl)piperidine-2,6-dione |

TABLE 1-continued

| The compounds of the present invention | | |
|---|---|---|
| Compound No. | Structure of the compounds | The compound's name |
| | 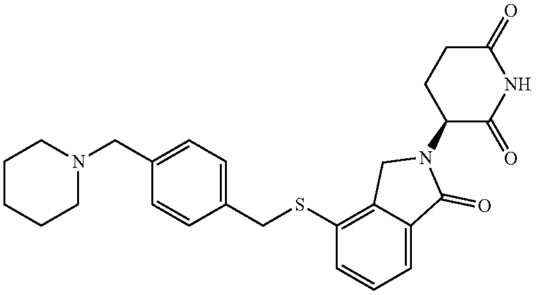 [SMILES: O=C1CC[C@H](N2Cc3c(SCc4ccc(CN5CCCCC5)cc4)cccc3C2=O)C(=O)N1] | (S)-3-(1-oxo-4-((4-(piperidin-1-ylmethyl)benzyl)thio)isoindolin-2-yl)piperidine-2,6-dione |
| | 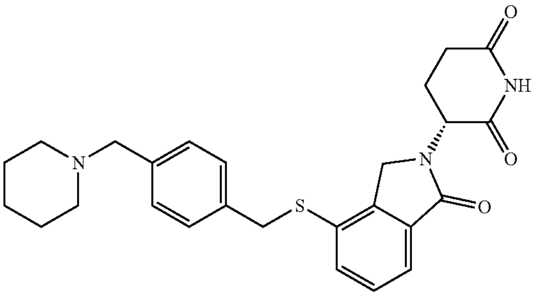 [SMILES: O=C1CC[C@@H](N2Cc3c(SCc4ccc(CN5CCCCC5)cc4)cccc3C2=O)C(=O)N1] | (R)-3-(1-oxo-4-((4-(piperidin-1-ylmethyl)benzyl)thio)isoindolin-2-yl)piperidine-2,6-dione |
| SIAIS12271-31 | 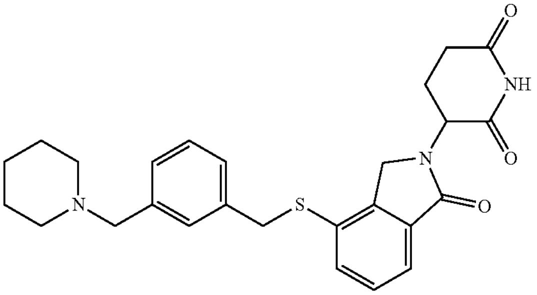 [SMILES: O=C1CCC(N2Cc3c(SCc4cccc(CN5CCCCC5)c4)cccc3C2=O)C(=O)N1] | 3-(1-oxo-4-((3-(piperidin-1-ylmethyl)benzyl)thio)isoindolin-2-yl)piperidine-2,6-dione |
| SIAIS12271-33 | 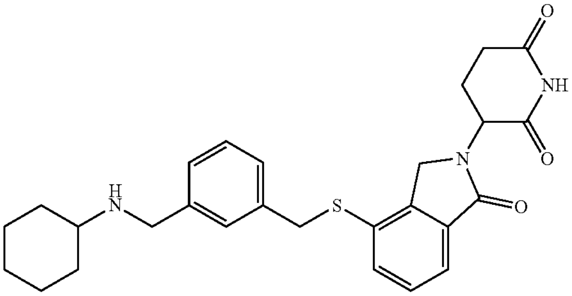 [SMILES: O=C1CCC(N2Cc3c(SCc4cccc(CNC5CCCCC5)c4)cccc3C2=O)C(=O)N1] | 3-(4-((3-((cyclohexylamino)methyl)benzyl)thio)-1-oxoisoindolin-2-yl)piperidine-2,6-dione |
| SIAIS12271-35 | 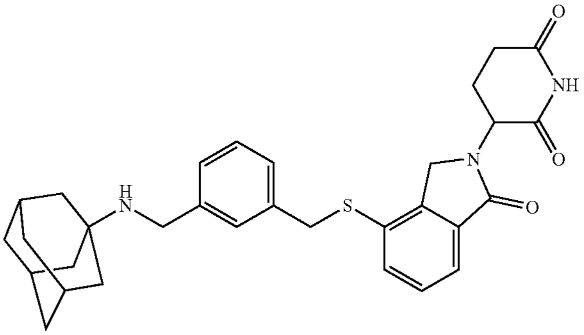 [SMILES: O=C1CCC(N2Cc3c(SCc4cccc(CNC56CC7CC(CC(C7)C5)C6)c4)cccc3C2=O)C(=O)N1] | 3-(4-((3-(((adamantan-1-yl)amino)methyl)benzyl)thio)-1-oxoisoindolin-2-yl)piperidine-2,6-dione |

TABLE 1-continued

| The compounds of the present invention | | |
|---|---|---|
| Compound No. | Structure of the compounds | The compound's name |
| SIAIS12271-37 | 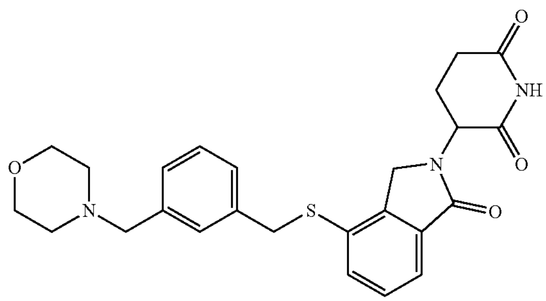 [SMILES: O=C1CCC(N2Cc3c(SCc4cccc(CN5CCOCC5)c4)cccc3C2=O)C(=O)N1] | 3-(4-((3-(morpholinomethyl)benzyl)thio)-1-oxoisoindolin-2-yl)piperidine-2,6-dione |
| SIAIS12271-39 | 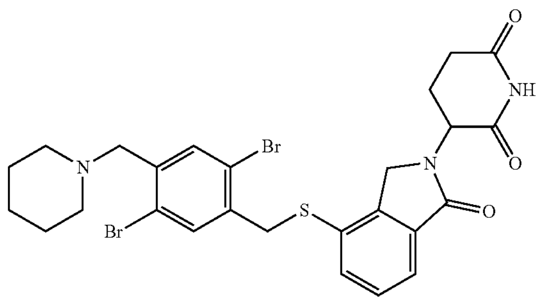 [SMILES: O=C1CCC(N2Cc3c(SCc4cc(Br)c(CN5CCCCC5)cc4Br)cccc3C2=O)C(=O)N1] | 3-(4-((2,5-dibromo-4-(piperidin-1-ylmethyl)benzyl)thio)-1-oxoisoindolin-2-yl)piperidine-2,6-dione |
| SIAIS12271-41 | 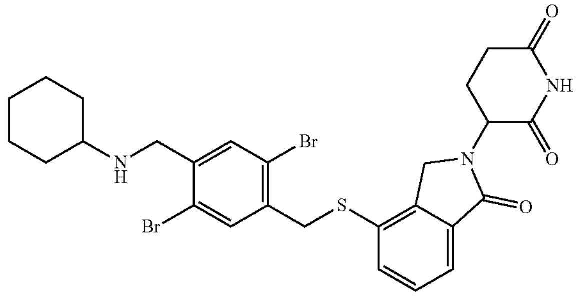 [SMILES: O=C1CCC(N2Cc3c(SCc4cc(Br)c(CNC5CCCCC5)cc4Br)cccc3C2=O)C(=O)N1] | 3-(4-((2,5-dibromo-4-((cyclohexylamino)methyl)benzyl)thio)-1-oxoisoindolin-2-yl)piperidine-2,6-dione |
| SIAIS12271-43 | 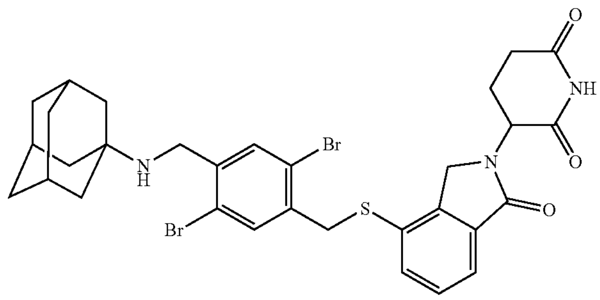 [SMILES: O=C1CCC(N2Cc3c(SCc4cc(Br)c(CNC56CC7CC(CC(C7)C5)C6)cc4Br)cccc3C2=O)C(=O)N1] | 3-(4-((4-(((adamantan-1-yl)amino)methyl)-2,5-dibromobenzyl)thio)-1-oxoisoindolin-2-yl)piperidine-2,6-dione |
| SIAIS12271-59 | 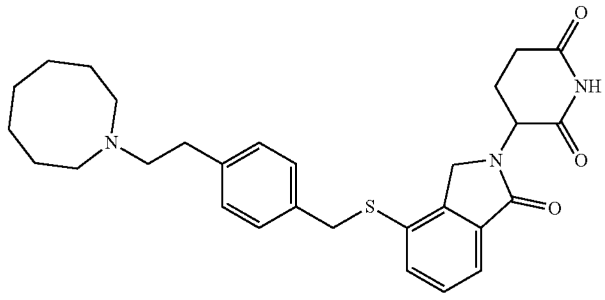 [SMILES: O=C1CCC(N2Cc3c(SCc4ccc(CCN5CCCCCCC5)cc4)cccc3C2=O)C(=O)N1] | 3-(4-((4-(2-(azocan-1-yl)ethyl)benzyl)thio)-1-oxoisoindolin-2-yl)piperidine-2,6-dione |

TABLE 1-continued

The compounds of the present invention

| Compound No. | Structure of the compounds | The compound's name |
|---|---|---|
| SIAIS12271-61 | 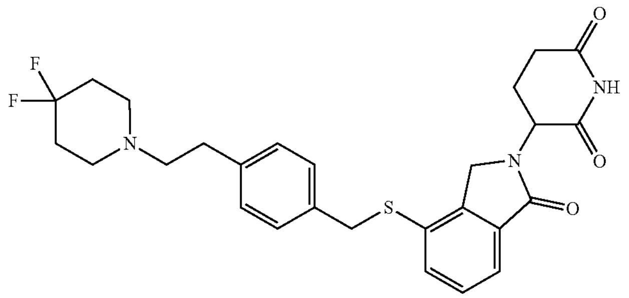 [SMILES: O=C1CCC(N2Cc3c(SCc4ccc(CCN5CCC(F)(F)CC5)cc4)cccc3C2=O)C(=O)N1] | 3-(4-((4-(2-(4,4-difluoropiperidin-1-yl)ethyl)benzyl)thio)-1-oxoisoindolin-2-yl)piperidine-2,6-dione |
| SIAIS12271-63 | 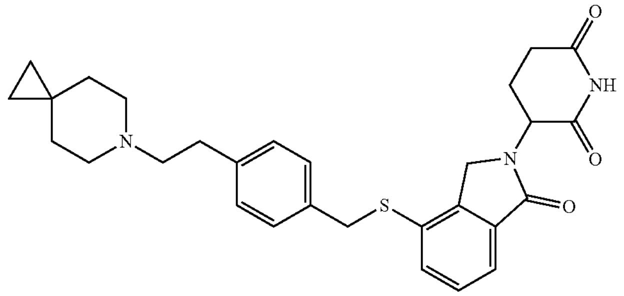 [SMILES: O=C1CCC(N2Cc3c(SCc4ccc(CCN5CCC6(CC5)CC6)cc4)cccc3C2=O)C(=O)N1] | 3-(4-((4-(2-(6-azaspiro[2.5]octan-6-yl)ethyl)benzyl)thio)-1-oxoisoindolin-2-yl)piperidine-2,6-dione |
| SIAIS12271-65 | 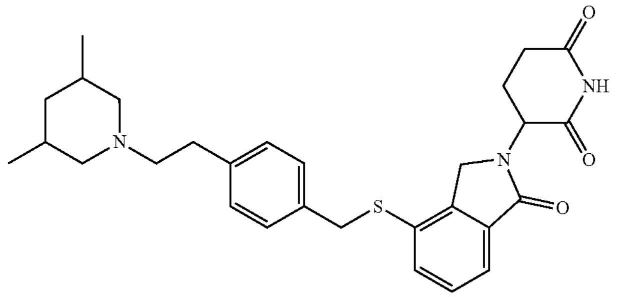 [SMILES: CC1CC(C)CN(CCc2ccc(CSc3cccc4c3CN(C3CCC(=O)NC3=O)C4=O)cc2)C1] | 3-(4-((4-(2-(3,5-dimethylpiperidin-1-yl)ethyl)benzyl)thio)-1-oxoisoindolin-2-yl)piperidine-2,6-dione |
| SIAIS12271-67 | 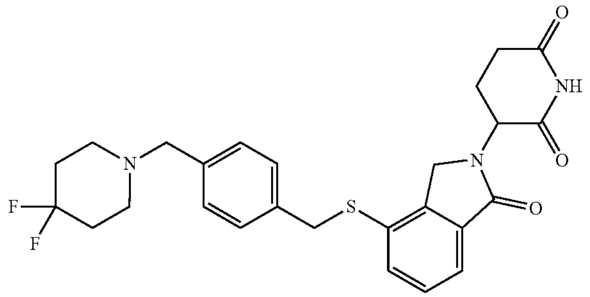 [SMILES: O=C1CCC(N2Cc3c(SCc4ccc(CN5CCC(F)(F)CC5)cc4)cccc3C2=O)C(=O)N1] | 3-(4-((4-((4,4-difluoropiperidin-1-yl)methyl)benzyl)thio)-1-oxoisoindolin-2-yl)piperidine-2,6-dione |
| SIAIS12271-69 | 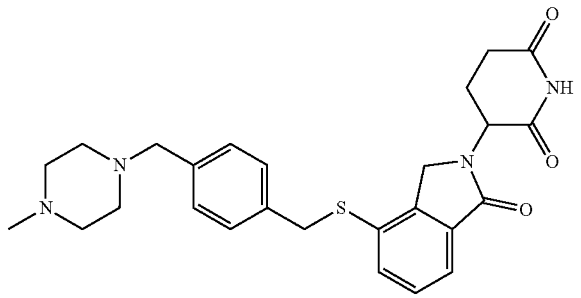 [SMILES: CN1CCN(Cc2ccc(CSc3cccc4c3CN(C3CCC(=O)NC3=O)C4=O)cc2)CC1] | 3-(4-((4-((4-methylpiperazin-1-yl)methyl)benzyl)thio)-1-oxoisoindolin-2-yl)piperidine-2,6-dione |

TABLE 1-continued

| The compounds of the present invention | | |
|---|---|---|
| Compound No. | Structure of the compounds | The compound's name |
| SIAIS12271-71 | 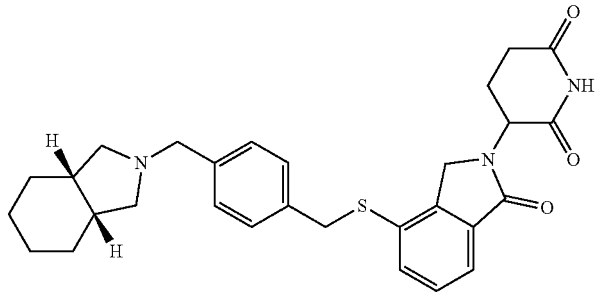 [SMILES: O=C1CCC(N2Cc3c(SCc4ccc(CN5C[C@H]6CCCC[C@H]6C5)cc4)cccc3C2=O)C(=O)N1] | 3-(4-((4-(((3aR,7aS)-octahydro-2H-isoindol-2-yl)methyl)benzyl)thio)-1-oxoisoindolin-2-yl)piperidine-2,6-dione |
| SIAIS12271-73 | 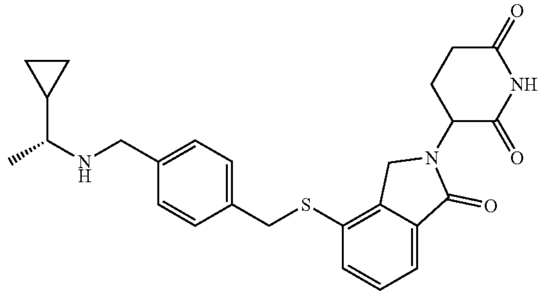 [SMILES: C[C@@H](NCc1ccc(CSc2cccc3c2CN(C2CCC(=O)NC2=O)C3=O)cc1)C1CC1] | 3-(4-((4-((((R)-1-cyclopropylethyl)amino)methyl)benzyl)thio)-1-oxoisoindolin-2-yl)piperidine-2,6-dione |
| SIAIS12271-57 | 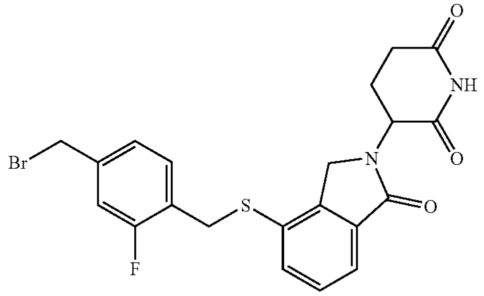 [SMILES: O=C1CCC(N2Cc3c(SCc4ccc(CBr)cc4F)cccc3C2=O)C(=O)N1] | 3-(4-((4-(bromomethyl)-2-fluorobenzyl)thio)-1-oxoisoindolin-2-yl)piperidine-2,6-dione |
| | 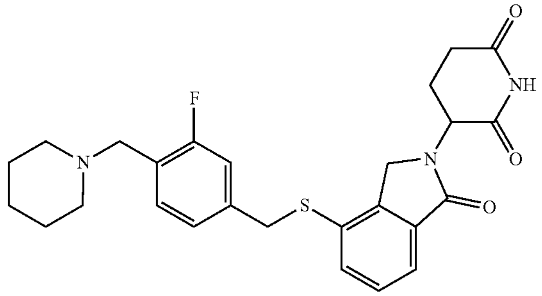 [SMILES: O=C1CCC(N2Cc3c(SCc4ccc(CN5CCCCC5)c(F)c4)cccc3C2=O)C(=O)N1] | 3-(4-((3-fluoro-4-(piperidin-1-ylmethyl)benzyl)thio)-1-oxoisoindolin-2-yl)piperidine-2,6-dione |
| | 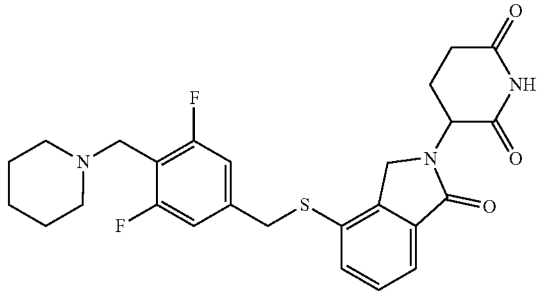 [SMILES: O=C1CCC(N2Cc3c(SCc4cc(F)c(CN5CCCCC5)c(F)c4)cccc3C2=O)C(=O)N1] | 3-(4-((3,5-difluoro-4-(piperidin-1-ylmethyl)benzyl)thio)-1-oxoisoindolin-2-yl)piperidine-2,6-dione |

TABLE 1-continued

| The compounds of the present invention | | |
|---|---|---|
| Compound No. | Structure of the compounds | The compound's name |
| SIAIS12271-75 | 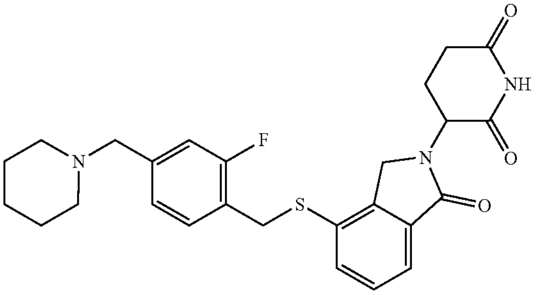 | 3-(4-((2-fluoro-4-(piperidin-1-ylmethyl)benzyl)thio)-1-oxoisoindolin-2-yl)piperidine-2,6-dione |
| | 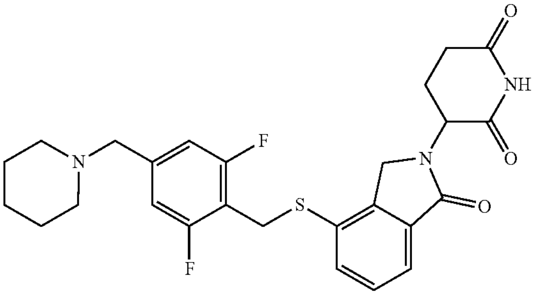 [SMILES: O=C1CCC(N2Cc3c(SCc4c(F)cc(CN5CCCCC5)cc4F)cccc3C2=O)C(=O)N1] | 3-(4-((2,6-difluoro-4-(piperidin-1-ylmethyl)benzyl)thio)-1-oxoisoindolin-2-yl)piperidine-2,6-dione |
| | 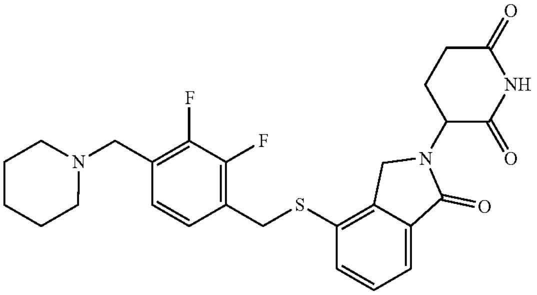 [SMILES: O=C1CCC(N2Cc3c(SCc4ccc(CN5CCCCC5)c(F)c4F)cccc3C2=O)C(=O)N1] | 3-(4-((2,3-difluoro-4-(piperidin-1-ylmethyl)benzyl)thio)-1-oxoisoindolin-2-yl)piperidine-2,6-dione |
| | 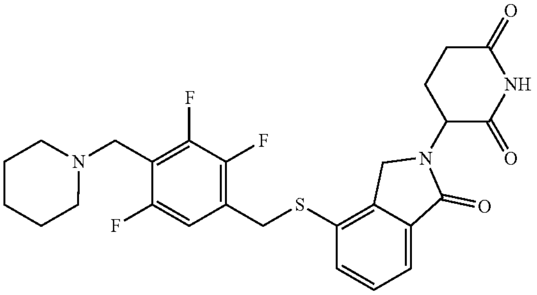 [SMILES: O=C1CCC(N2Cc3c(SCc4cc(F)c(CN5CCCCC5)c(F)c4F)cccc3C2=O)C(=O)N1] | 3-(1-oxo-4-((2,3,5-trifluoro-4-(piperidin-1-ylmethyl)benzyl)thio)isoindolin-2-yl)piperidine-2,6-dione |
| | 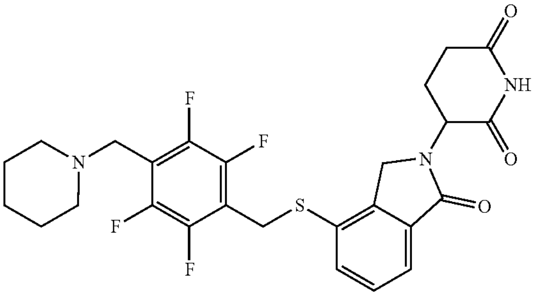 [SMILES: O=C1CCC(N2Cc3c(SCc4c(F)c(F)c(CN5CCCCC5)c(F)c4F)cccc3C2=O)C(=O)N1] | 3-(1-oxo-4-((2,3,5,6-tetrafluoro-4-(piperidin-1-ylmethyl)benzyl)thio)isoindolin-2-yl)piperidine-2,6-dione |

TABLE 1-continued

| Compound No. | Structure of the compounds | The compound's name |
| --- | --- | --- |
| | The compounds of the present invention | |
| | 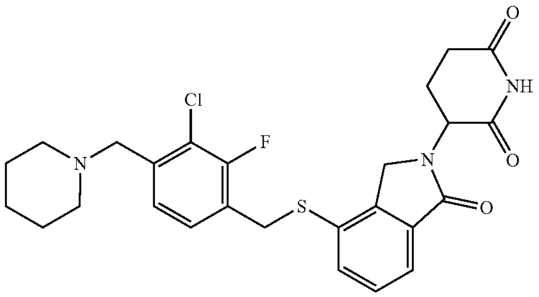 [SMILES: O=C1CCC(N2Cc3c(SCc4ccc(CN5CCCCC5)c(Cl)c4F)cccc3C2=O)C(=O)N1] | 3-(4-((3-chloro-2-fluoro-4-(piperidin-1-ylmethyl)benzyl)thio)-1-oxoisoindolin-2-yl)piperidine-2,6-dione |
| | 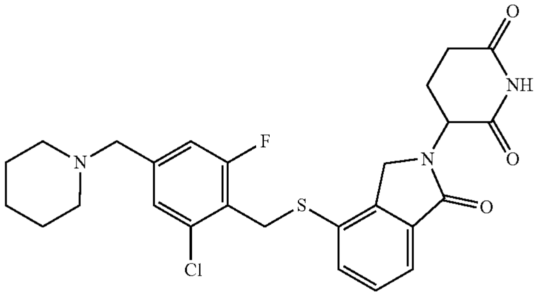 [SMILES: O=C1CCC(N2Cc3c(SCc4c(F)cc(CN5CCCCC5)cc4Cl)cccc3C2=O)C(=O)N1] | 3-(4-((2-chloro-6-fluoro-4-(piperidin-1-ylmethyl)benzyl)thio)-1-oxoisoindolin-2-yl)piperidine-2,6-dione |
| | 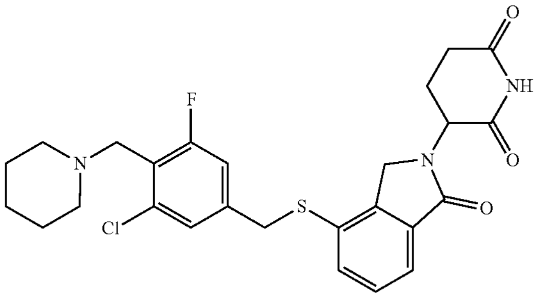 [SMILES: O=C1CCC(N2Cc3c(SCc4cc(F)c(CN5CCCCC5)c(Cl)c4)cccc3C2=O)C(=O)N1] | 3-(4-((3-chloro-5-fluoro-4-(piperidin-1-ylmethyl)benzyl)thio)-1-oxoisoindolin-2-yl)piperidine-2,6-dione |
| SIAIS12271-77 | 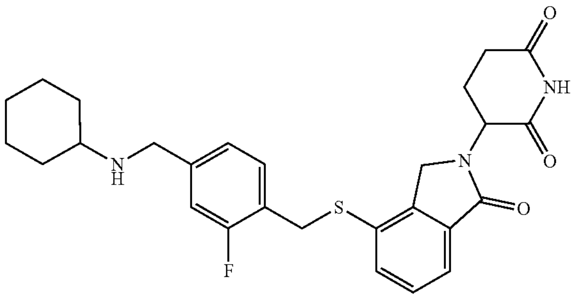 [SMILES: O=C1CCC(N2Cc3c(SCc4ccc(CNC5CCCCC5)cc4F)cccc3C2=O)C(=O)N1] | 3-(4-((4-((cyclohexylamino)methyl)-2-fluorobenzyl)thio)-1-oxoisoindolin-2-yl)piperidine-2,6-dione |
| SIAIS12271-79 | 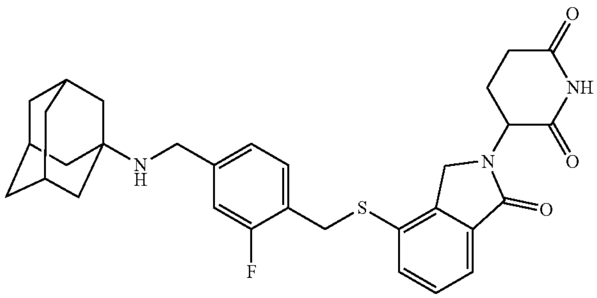 [SMILES: O=C1CCC(N2Cc3c(SCc4ccc(CNC56CC7CC(CC(C7)C5)C6)cc4F)cccc3C2=O)C(=O)N1] | 3-(4-((4-(((adamantan-1-yl)amino)methyl)-2-fluorobenzyl)thio)-1-oxoisoindolin-2-yl)piperidine-2,6-dione |

TABLE 1-continued

| The compounds of the present invention | | |
|---|---|---|
| Compound No. | Structure of the compounds | The compound's name |
| SIAIS12271-81 | 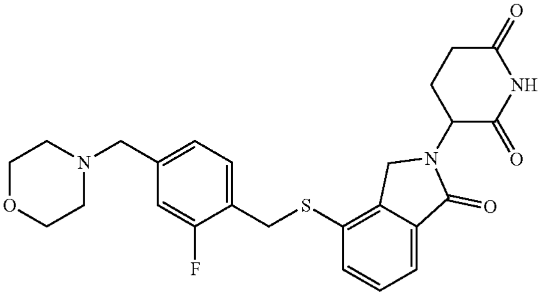 [SMILES: O=C1CCC(N2Cc3c(SCc4ccc(CN5CCOCC5)cc4F)cccc3C2=O)C(=O)N1] | 3-(4-((2-fluoro-4-(morpholinomethyl)benzyl)thio)-1-oxoisoindolin-2-yl)piperidine-2,6-dione |
| SIAIS12271-83 | 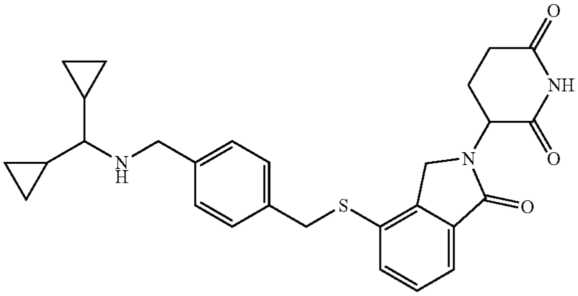 [SMILES: O=C1CCC(N2Cc3c(SCc4ccc(CNC(C5CC5)C5CC5)cc4)cccc3C2=O)C(=O)N1] | 3-(4-((4-(((dicyclopropylmethyl)amino)methyl)benzyl)thio)-1-oxoisoindolin-2-yl)piperidine-2,6-dione |
| | 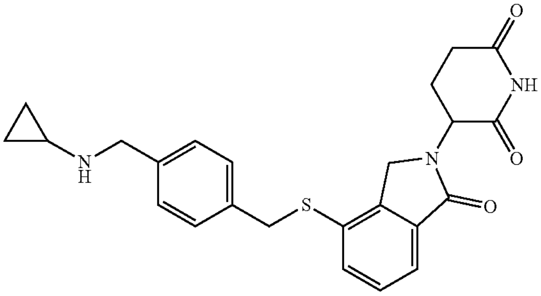 [SMILES: O=C1CCC(N2Cc3c(SCc4ccc(CNC5CC5)cc4)cccc3C2=O)C(=O)N1] | 3-(4-((4-((cyclopropylamino)methyl)benzyl)thio)-1-oxoisoindolin-2-yl)piperidine-2,6-dione |
| SIAIS12221-61 | 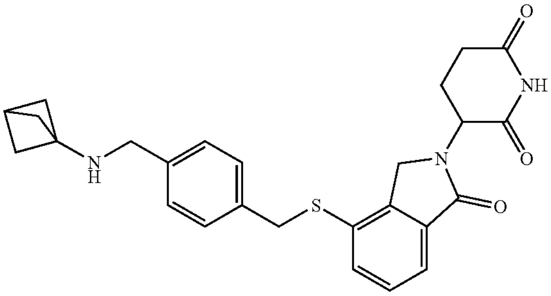 [SMILES: O=C1CCC(N2Cc3c(SCc4ccc(CNC56CC(C5)C6)cc4)cccc3C2=O)C(=O)N1] | 3-(4-((4-((bicyclo[1.1.1]pentan-1-ylamino)methyl)benzyl)thio)-1-oxoisoindolin-2-yl)piperidine-2,6-dione |
| SIAIS12221-59 | 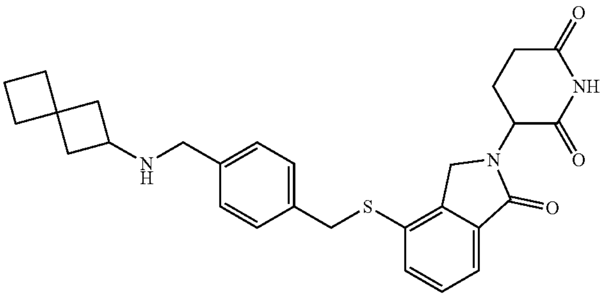 [SMILES: O=C1CCC(N2Cc3c(SCc4ccc(CNC5CC6(CCC6)C5)cc4)cccc3C2=O)C(=O)N1] | 3-(1-oxo-4-((4-((spiro[3.3]heptan-2-ylamino)methyl)benzyl)thio)isoindolin-2-yl)piperidine-2,6-dione |

TABLE 1-continued

| Compound No. | Structure of the compounds | The compound's name |
|---|---|---|
| SIAIS12210-71 | 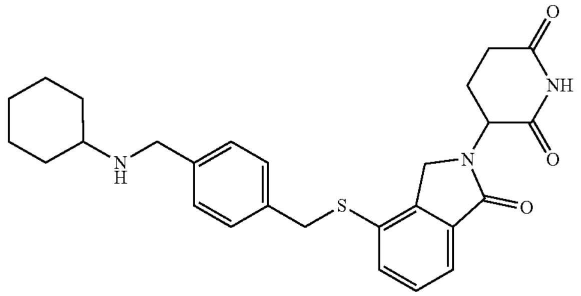 [SMILES: O=C1CCC(N2Cc3c(SCc4ccc(CNC5CCCCC5)cc4)cccc3C2=O)C(=O)N1] | 3-(4-((4-((cyclohexylamino)methyl)benzyl)thio)-1-oxoisoindolin-2-yl)piperidine-2,6-dione |
| SIAIS12221-87 | 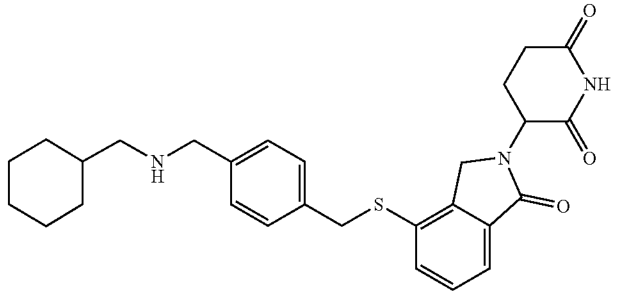 [SMILES: O=C1CCC(N2Cc3c(SCc4ccc(CNCC5CCCCC5)cc4)cccc3C2=O)C(=O)N1] | 3-(4-((4-(((cyclohexylmethyl)amino)methyl)benzyl)thio)-1-oxoisoindolin-2-yl)piperidine-2,6-dione |
| SIAIS12240-19 | 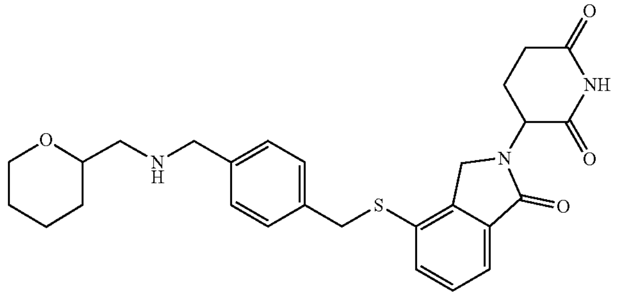 [SMILES: O=C1CCC(N2Cc3c(SCc4ccc(CNCC5CCCCO5)cc4)cccc3C2=O)C(=O)N1] | 3-(1-oxo-4-((4-((((tetrahydro-2H-pyran-2-yl)methyl)amino)methyl)benzyl)thio)isoindolin-2-yl)piperidine-2,6-dione |
| SIAIS12240-89 | 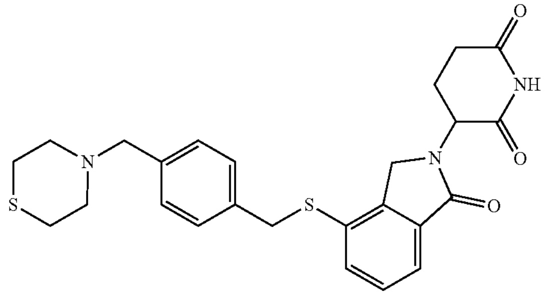 [SMILES: O=C1CCC(N2Cc3c(SCc4ccc(CN5CCSCC5)cc4)cccc3C2=O)C(=O)N1] | 3-(1-oxo-4-((4-(thiomorpholinomethyl)benzyl)thio)isoindolin-2-yl)piperidine-2,6-dione |
| SIAIS12270-55 | 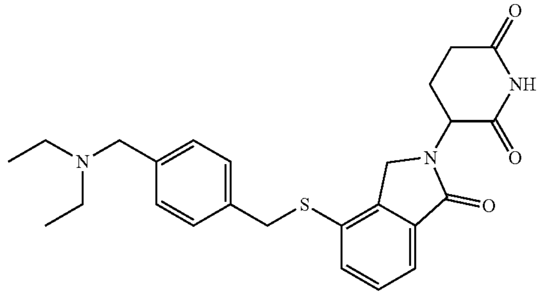 [SMILES: CCN(CC)Cc1ccc(CSc2cccc3c2CN(C2CCC(=O)NC2=O)C3=O)cc1] | 3-(4-((4-((diethylamino)methyl)benzyl)thio)-1-oxoisoindolin-2-yl)piperidine-2,6-dione |

TABLE 1-continued

The compounds of the present invention

| Compound No. | Structure of the compounds | The compound's name |
|---|---|---|
| SIAIS12270-57 | 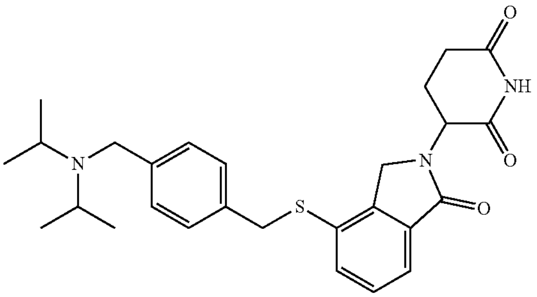 [SMILES: CC(C)N(Cc1ccc(CSc2cccc3c2CN(C2CCC(=O)NC2=O)C3=O)cc1)C(C)C] | 3-(4-((4-((diisopropylamino)methyl)benzyl)thio)-1-oxoisoindolin-2-yl)piperidine-2,6-dione |
| SIAIS12270-59 | 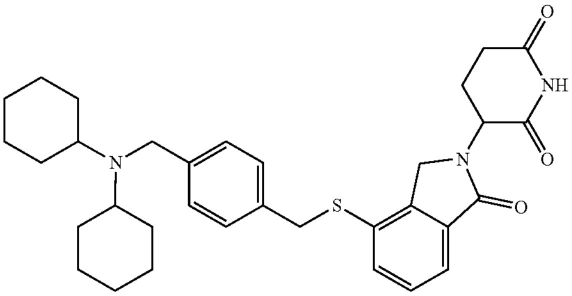 [SMILES: O=C1CCC(N2Cc3c(SCc4ccc(CN(C5CCCCC5)C5CCCCC5)cc4)cccc3C2=O)C(=O)N1] | 3-(4-((4-((dicyclohexylamino)methyl)benzyl)thio)-1-oxoisoindolin-2-yl)piperidine-2,6-dione |
| SIAIS12270-61 | 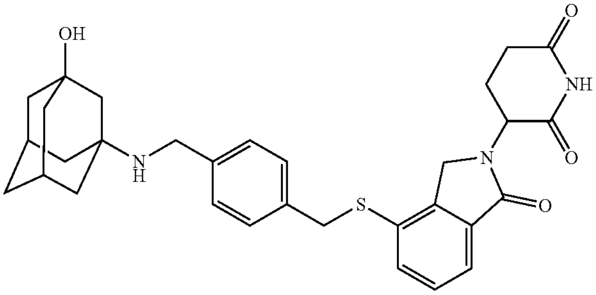 [SMILES: O=C1CCC(N2Cc3c(SCc4ccc(CNC56CC7CC(CC(O)(C7)C5)C6)cc4)cccc3C2=O)C(=O)N1] | 3-(4-((4-(((3-hydroxyadamantan-1-yl)amino)methyl)benzyl)thio)-1-oxoisoindolin-2-yl)piperidine-2,6-dione |
| SIAIS12271-03 | 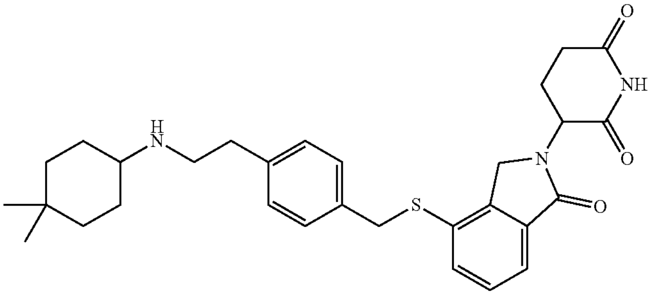 [SMILES: CC1(C)CCC(NCCc2ccc(CSc3cccc4c3CN(C3CCC(=O)NC3=O)C4=O)cc2)CC1] | 3-(4-((4-(2-((4,4-dimethylcyclohexyl)amino)ethyl)benzyl)thio)-1-oxoisoindolin-2-yl)piperidine-2,6-dione |
| SIAIS12271-05 | 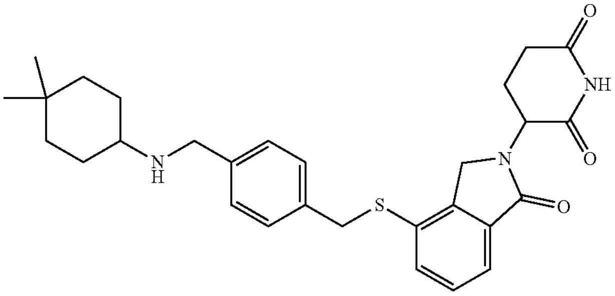 [SMILES: CC1(C)CCC(NCc2ccc(CSc3cccc4c3CN(C3CCC(=O)NC3=O)C4=O)cc2)CC1] | 3-(4-((4-(((4,4-dimethylcyclohexyl)amino)methyl)benzyl)thio)-1-oxoisoindolin-2-yl)piperidine-2,6-dione |

TABLE 1-continued

| The compounds of the present invention | | |
|---|---|---|
| Compound No. | Structure of the compounds | The compound's name |
| SIAIS12271-13 | 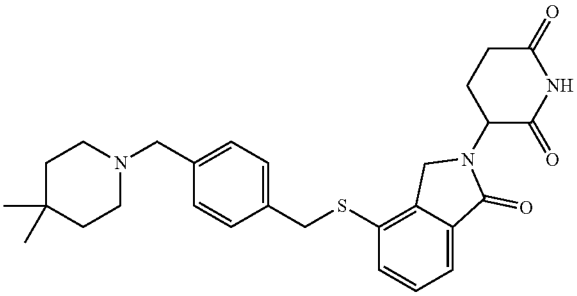 [SMILES: CC1(C)CCN(Cc2ccc(CSc3cccc4c3CN(C3CCC(=O)NC3=O)C4=O)cc2)CC1] | 3-(4-((4-((4,4-dimethylpiperidin-1-yl)methyl)benzyl)thio)-1-oxoisoindolin-2-yl)piperidine-2,6-dione |
| SIAIS12271-15 | 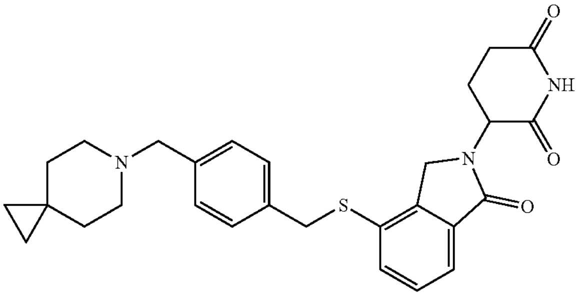 [SMILES: O=C1CCC(N2Cc3c(SCc4ccc(CN5CCC6(CC5)CC6)cc4)cccc3C2=O)C(=O)N1] | 3-(4-((4-((6-azaspiro[2.5]octan-6-yl)methyl)benzyl)thio)-1-oxoisoindolin-2-yl)piperidine-2,6-dione |
| SIAIS12271-17 | 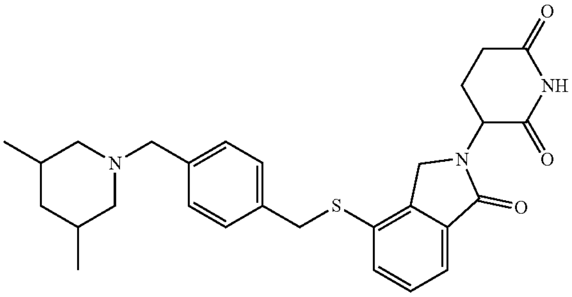 [SMILES: CC1CC(C)CN(Cc2ccc(CSc3cccc4c3CN(C3CCC(=O)NC3=O)C4=O)cc2)C1] | 3-(4-((4-((3,5-dimethylpiperidin-1-yl)methyl)benzyl)thio)-1-oxoisoindolin-2-yl)piperidine-2,6-dione |
| SIAIS12271-19 | 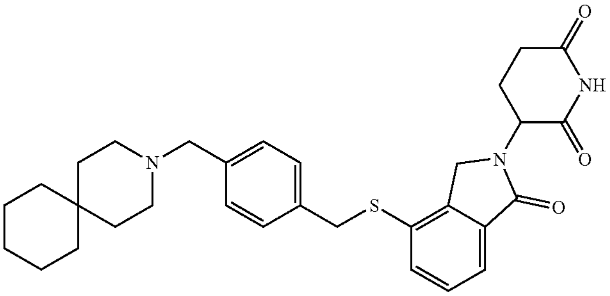 [SMILES: O=C1CCC(N2Cc3c(SCc4ccc(CN5CCC6(CCCCC6)CC5)cc4)cccc3C2=O)C(=O)N1] | 3-(4-((4-((3-azaspiro[5.5]undecan-3-yl)methyl)benzyl)thio)-1-oxoisoindolin-2-yl)piperidine-2,6-dione |
| SIAIS12271-07 | 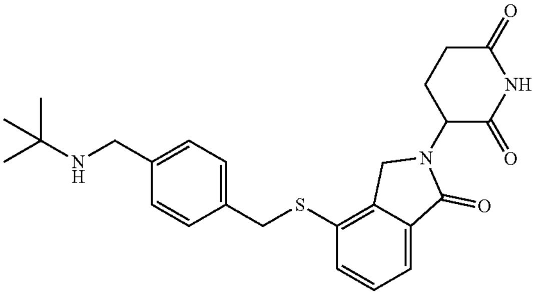 [SMILES: CC(C)(C)NCc1ccc(CSc2cccc3c2CN(C2CCC(=O)NC2=O)C3=O)cc1] | 3-(4-((4-((tert-butylamino)methyl)benzyl)thio)-1-oxoisoindolin-2-yl)piperidine-2,6-dione |

TABLE 1-continued

| The compounds of the present invention | | |
|---|---|---|
| Compound No. | Structure of the compounds | The compound's name |
| SIAIS12271-09 | 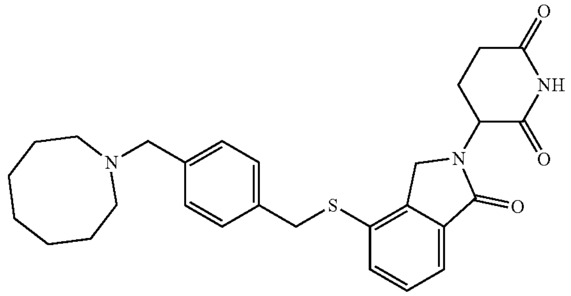 [SMILES: O=C1CCC(N2Cc3c(SCc4ccc(CN5CCCCCCC5)cc4)cccc3C2=O)C(=O)N1] | 3-(4-((4-(azocan-1-ylmethyl)benzyl)thio)-1-oxoisoindolin-2-yl)piperidine-2,6-dione |
| SIAIS12241-54 | 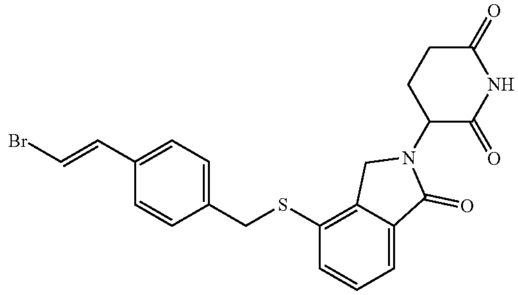 [SMILES: O=C1CCC(N2Cc3c(SCc4ccc(/C=C/Br)cc4)cccc3C2=O)C(=O)N1] | (E)-3-(4-((4-(2-bromovinyl)benzyl)thio)-1-oxoisoindolin-2-yl)piperidine-2,6-dione |
| SIAIS12241-53 | 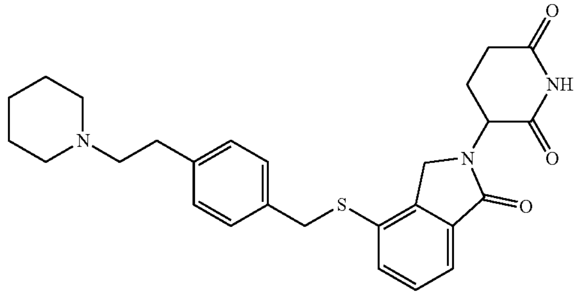 [SMILES: O=C1CCC(N2Cc3c(SCc4ccc(CCN5CCCCC5)cc4)cccc3C2=O)C(=O)N1] | 3-(1-oxo-4-((4-(2-(piperidin-1-yl)ethyl)benzyl)thio)isoindolin-2-yl)piperidine-2,6-dione |
| SIAIS12241-55 | 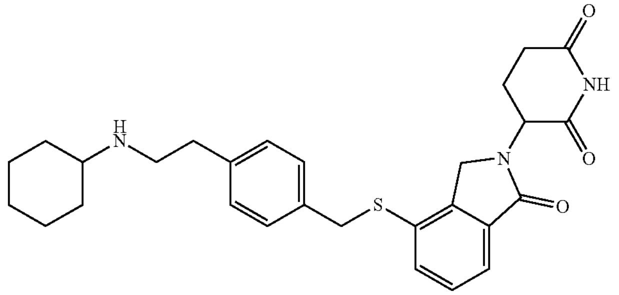 [SMILES: O=C1CCC(N2Cc3c(SCc4ccc(CCNC5CCCCC5)cc4)cccc3C2=O)C(=O)N1] | 3-(4-((4-(2-(cyclohexylamino)ethyl)benzyl)thio)-1-oxoisoindolin-2-yl)piperidine-2,6-dione |
| SIAIS12270-49 | 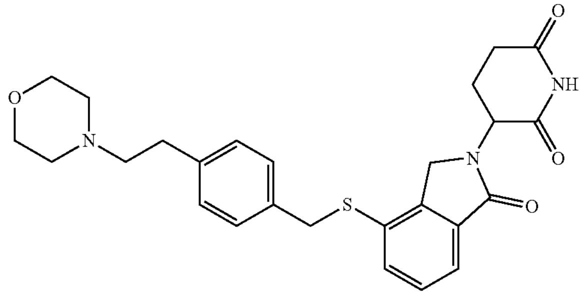 [SMILES: O=C1CCC(N2Cc3c(SCc4ccc(CCN5CCOCC5)cc4)cccc3C2=O)C(=O)N1] | 3-(4-((4-(2-morpholinoethyl)benzyl)thio)-1-oxoisoindolin-2-yl)piperidine-2,6-dione |

TABLE 1-continued

The compounds of the present invention

| Compound No. | Structure of the compounds | The compound's name |
|---|---|---|
| SIAIS12270-97 | 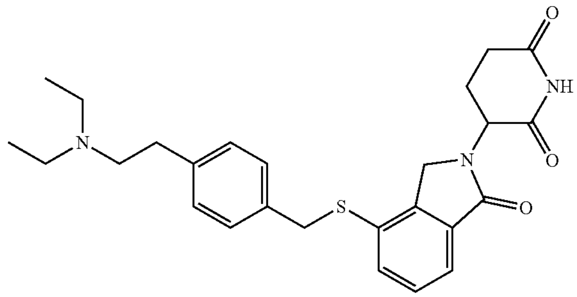 [SMILES: CCN(CC)CCc1ccc(CSc2cccc3c2CN(C2CCC(=O)NC2=O)C3=O)cc1] | 3-(4-((4-(2-(diethylamino)ethyl)benzyl)thio)-1-oxoisoindolin-2-yl)piperidine-2,6-dione |
| SIAIS12270-99 | 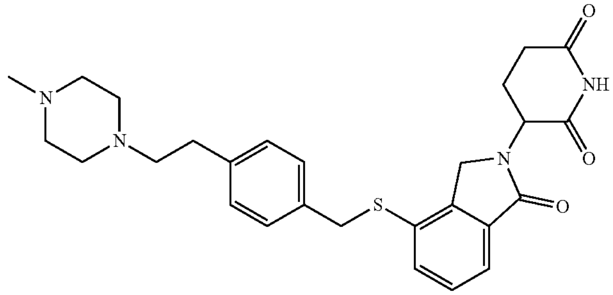 [SMILES: CN1CCN(CCc2ccc(CSc3cccc4c3CN(C3CCC(=O)NC3=O)C4=O)cc2)CC1] | 3-(4-((4-(2-(4-methylpiperazin-1-yl)ethyl)benzyl)thio)-1-oxoisoindolin-2-yl)piperidine-2,6-dione |
| SIAIS12270-51 | 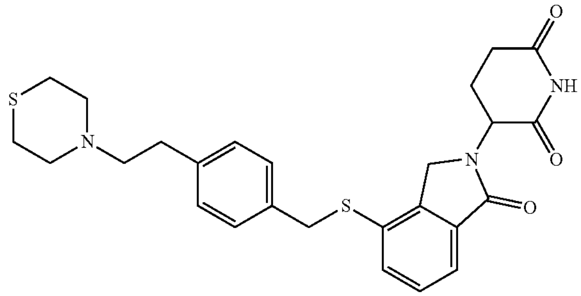 [SMILES: O=C1CCC(N2Cc3c(SCc4ccc(CCN5CCSCC5)cc4)cccc3C2=O)C(=O)N1] | 3-(1-oxo-4-((4-(2-thiomorpholinoethyl)benzyl)thio)isoindolin-2-yl)piperidine-2,6-dione |
| SIAIS12241-49 | 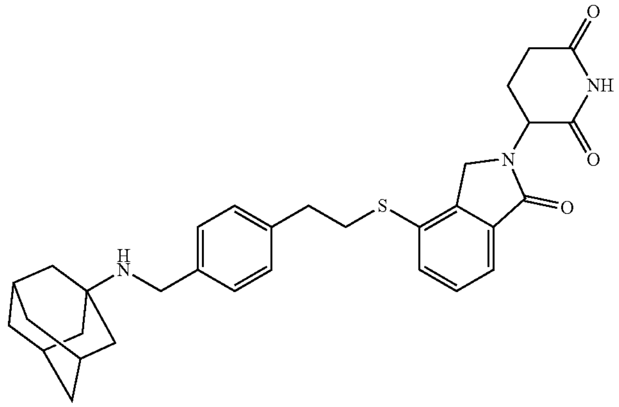 [SMILES: O=C1CCC(N2Cc3c(SCCc4ccc(CNC56CC7CC(CC(C7)C5)C6)cc4)cccc3C2=O)C(=O)N1] | 3-(4-((4-(((adamantan-1-yl)amino)methyl)phenethyl)thio)-1-oxoisoindolin-2-yl)piperidine-2,6-dione |

TABLE 1-continued

| The compounds of the present invention | | |
|---|---|---|
| Compound No. | Structure of the compounds | The compound's name |
| SIAIS12241-61 | 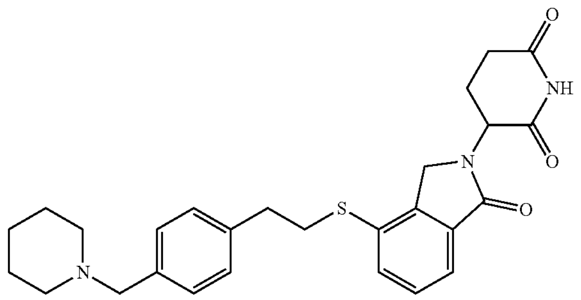 [SMILES: O=C1CCC(N2Cc3c(SCCc4ccc(CN5CCCCC5)cc4)cccc3C2=O)C(=O)N1] | 3-(1-oxo-4-((4-(piperidin-1-ylmethyl)phenethyl)thio)isoindolin-2-yl)piperidine-2,6-dione |
| SIAIS12270-07 | 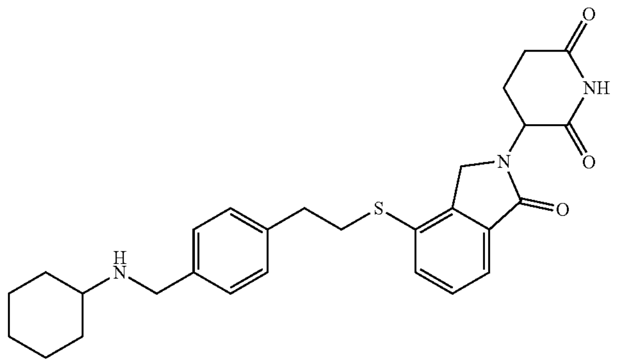 [SMILES: O=C1CCC(N2Cc3c(SCCc4ccc(CNC5CCCCC5)cc4)cccc3C2=O)C(=O)N1] | 3-(4-((4-((cyclohexylamino)methyl)phenethyl)thio)-1-oxoisoindolin-2-yl)piperidine-2,6-dione |
| SIAIS12270-43 | 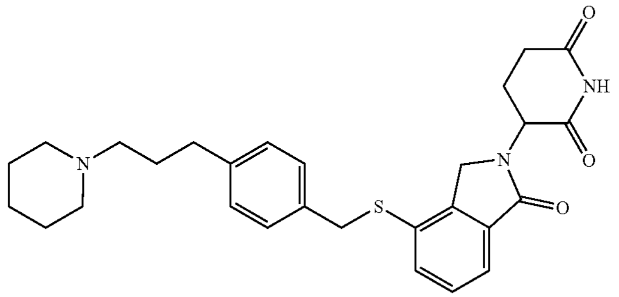 [SMILES: O=C1CCC(N2Cc3c(SCc4ccc(CCCN5CCCCC5)cc4)cccc3C2=O)C(=O)N1] | 3-(1-oxo-4-((4-(3-(piperidin-1-yl)propyl)benzyl)thio)isoindolin-2-yl)piperidine-2,6-dione |
| SIAIS12270-45 | 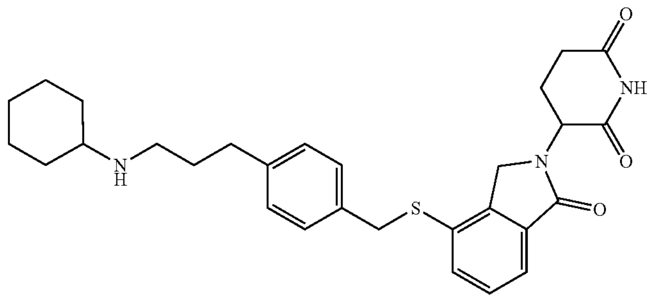 [SMILES: O=C1CCC(N2Cc3c(SCc4ccc(CCCNC5CCCCC5)cc4)cccc3C2=O)C(=O)N1] | 3-(4-((4-(3-(cyclohexylamino)propyl)benzyl)thio)-1-oxoisoindolin-2-yl)piperidine-2,6-dione |

TABLE 1-continued

| The compounds of the present invention | | |
|---|---|---|
| Compound No. | Structure of the compounds | The compound's name |
| SIAIS12270-47 | 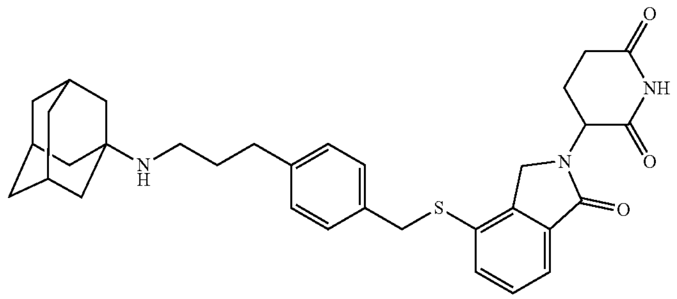 [SMILES: O=C1CCC(N2Cc3c(SCc4ccc(CCCNC56CC7CC(CC(C7)C5)C6)cc4)cccc3C2=O)C(=O)N1] | 3-(4-((4-(3-((adamantan-1-yl)amino)propyl)benzyl)thio)-1-oxoisoindolin-2-yl)piperidine-2,6-dione |
| SIAIS12270-53 | 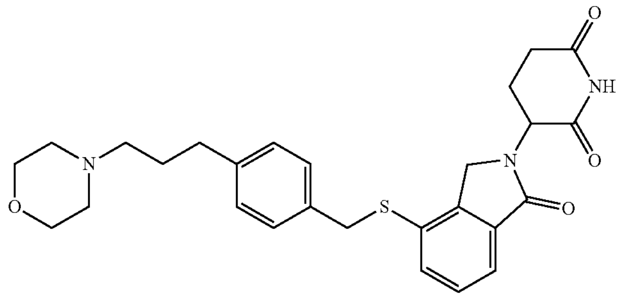 [SMILES: O=C1CCC(N2Cc3c(SCc4ccc(CCCN5CCOCC5)cc4)cccc3C2=O)C(=O)N1] | 3-(4-((4-(3-morpholinopropyl)benzyl)thio)-1-oxoisoindolin-2-yl)piperidine-2,6-dione |
| SIAIS12241-17 | 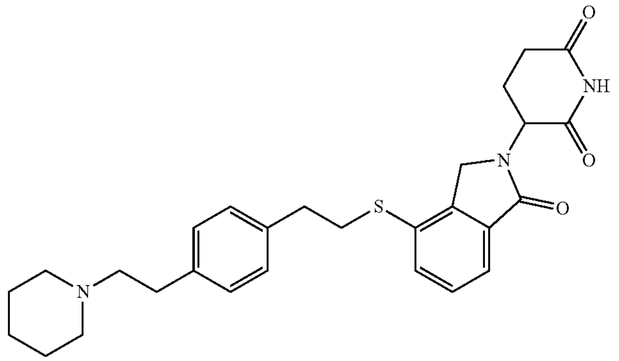 [SMILES: O=C1CCC(N2Cc3c(SCCc4ccc(CCN5CCCCC5)cc4)cccc3C2=O)C(=O)N1] | 3-(1-oxo-4-((4-(2-(piperidin-1-yl)ethyl)phenethyl)thio)isoindolin-2-yl)piperidine-2,6-dione |
| SIAIS12241-21 | 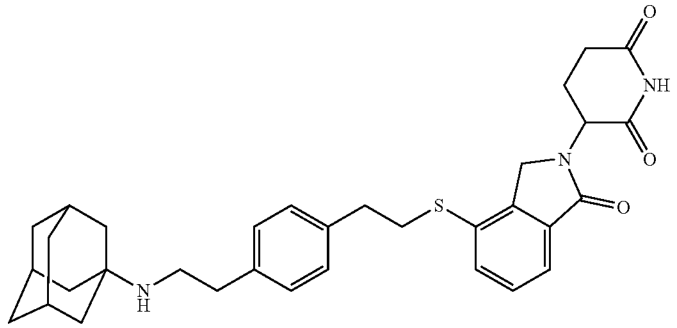 [SMILES: O=C1CCC(N2Cc3c(SCCc4ccc(CCNC56CC7CC(CC(C7)C5)C6)cc4)cccc3C2=O)C(=O)N1] | 3-(4-((4-(2-((adamantan-1-yl)amino)ethyl)phenethyl)thio)-1-oxoisoindolin-2-yl)piperidine-2,6-dione |

TABLE 1-continued

| The compounds of the present invention | | |
|---|---|---|
| Compound No. | Structure of the compounds | The compound's name |
| SIAIS12270-35 | 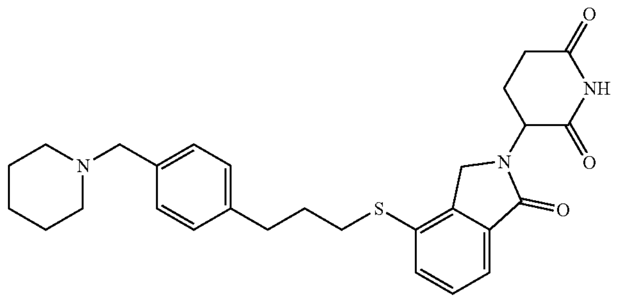 [SMILES: O=C1CCC(N2Cc3c(SCCCc4ccc(CN5CCCCC5)cc4)cccc3C2=O)C(=O)N1] | 3-(1-oxo-4-((3-(4-(piperidin-1-ylmethyl)phenyl)propyl)thio)isoindolin-2-yl)piperidine-2,6-dione |
| SIAIS12270-67 | 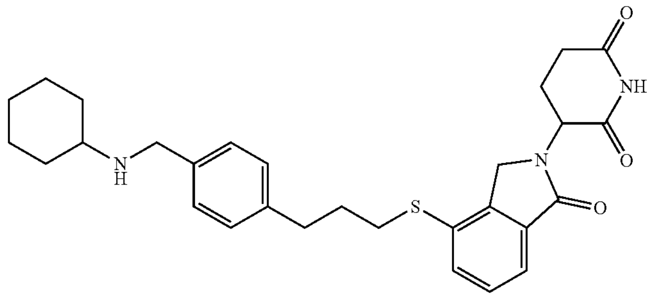 [SMILES: O=C1CCC(N2Cc3c(SCCCc4ccc(CNC5CCCCC5)cc4)cccc3C2=O)C(=O)N1] | 3-(4-((3-(4-((cyclohexylamino)methyl)phenyl)propyl)thio)-1-oxoisoindolin-2-yl)piperidine-2,6-dione |
| SIAIS12270-37 | 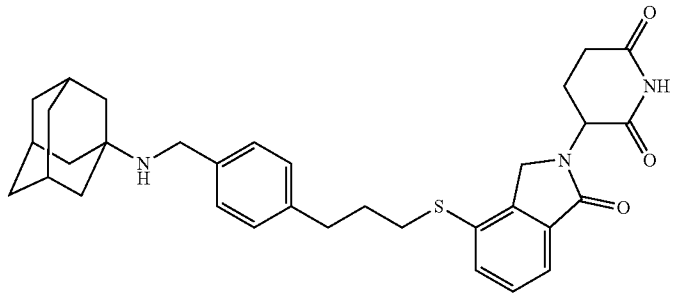 [SMILES: O=C1CCC(N2Cc3c(SCCCc4ccc(CNC56CC7CC(CC(C7)C5)C6)cc4)cccc3C2=O)C(=O)N1] | 3-(4-((3-(4-(((adamantan-1-yl)amino)methyl)phenyl)propyl)thio)-1-oxoisoindolin-2-yl)piperidine-2,6-dione |
| SIAIS12270-75 | 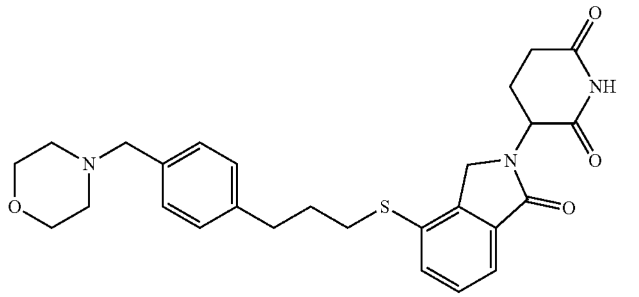 [SMILES: O=C1CCC(N2Cc3c(SCCCc4ccc(CN5CCOCC5)cc4)cccc3C2=O)C(=O)N1] | 3-(4-((3-(4-(morpholinomethyl)phenyl)propyl)thio)-1-oxoisoindolin-2-yl)piperidine-2,6-dione |
| | 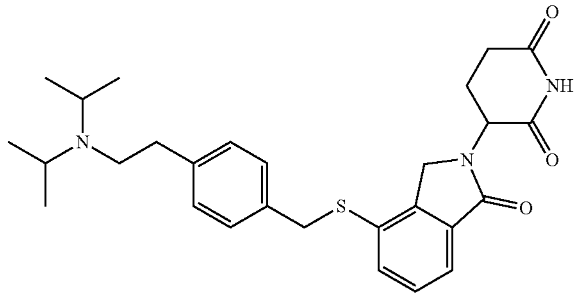 [SMILES: CC(C)N(CCc1ccc(CSc2cccc3c2CN(C2CCC(=O)NC2=O)C3=O)cc1)C(C)C] | 3-(4-((4-(2-(diisopropylamino)ethyl)benzyl)thio)-1-oxoisoindolin-2-yl)piperidine-2,6-dione |

TABLE 1-continued

The compounds of the present invention

| Compound No. | Structure of the compounds | The compound's name |
| --- | --- | --- |
| | 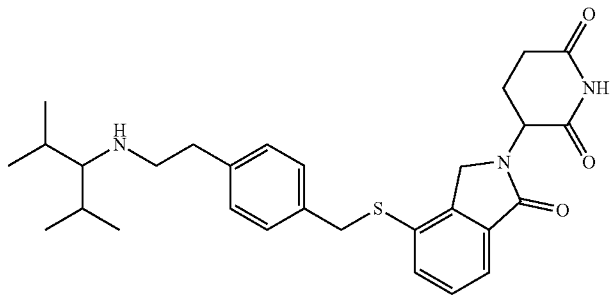 [SMILES: CC(C)C(NCCc1ccc(CSc2cccc3c2CN(C2CCC(=O)NC2=O)C3=O)cc1)C(C)C] | 3-(4-((4-(2-((2,4-dimethylpentan-3-yl)amino)ethyl)benzyl)thio)-1-oxoisoindolin-2-yl)piperidine-2,6-dione |
| | 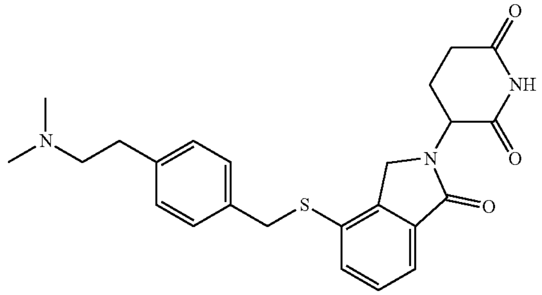 [SMILES: CN(C)CCc1ccc(CSc2cccc3c2CN(C2CCC(=O)NC2=O)C3=O)cc1] | 3-(4-((4-(2-(dimethylamino)ethyl)benzyl)thio)-1-oxoisoindolin-2-yl)piperidine-2,6-dione |
| | 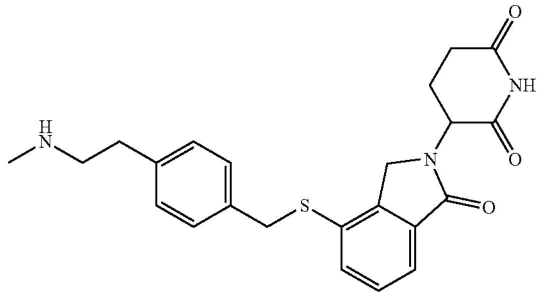 [SMILES: CNCCc1ccc(CSc2cccc3c2CN(C2CCC(=O)NC2=O)C3=O)cc1] | 3-(4-((4-(2-(methylamino)ethyl)benzyl)thio)-1-oxoisoindolin-2-yl)piperidine-2,6-dione |
| | 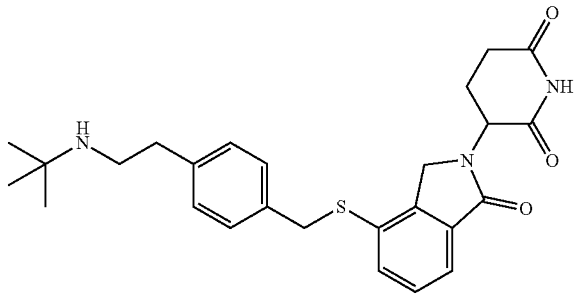 [SMILES: CC(C)(C)NCCc1ccc(CSc2cccc3c2CN(C2CCC(=O)NC2=O)C3=O)cc1] | 3-(4-((4-(2-(tert-butylamino)ethyl)benzyl)thio)-1-oxoisoindolin-2-yl)piperidine-2,6-dione |
| | 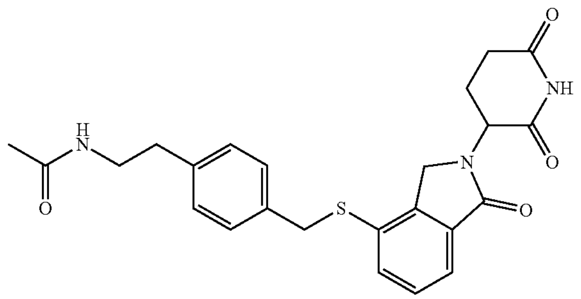 [SMILES: CC(=O)NCCc1ccc(CSc2cccc3c2CN(C2CCC(=O)NC2=O)C3=O)cc1] | N-(4-(((2-(2,6-dioxopiperidin-3-yl)-1-oxoisoindolin-4-yl)thio)methyl)phenethyl)acetamide |

TABLE 1-continued

| The compounds of the present invention | | |
|---|---|---|
| Compound No. | Structure of the compounds | The compound's name |
| | 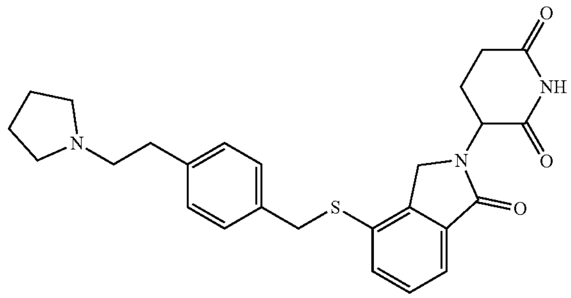 [SMILES: O=C1CCC(N2Cc3c(SCc4ccc(CCN5CCCC5)cc4)cccc3C2=O)C(=O)N1] | 3-(1-oxo-4-((4-(2-(pyrrolidin-1-yl)ethyl)benzyl)thio)isoindolin-2-yl)piperidine-2,6-dione |
| | 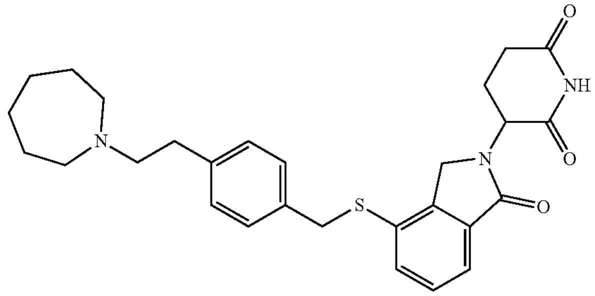 [SMILES: O=C1CCC(N2Cc3c(SCc4ccc(CCN5CCCCCC5)cc4)cccc3C2=O)C(=O)N1] | 3-(4-((4-(2-(azepan-1-yl)ethyl)benzyl)thio)-1-oxoisoindolin-2-yl)piperidine-2,6-dione |
| | 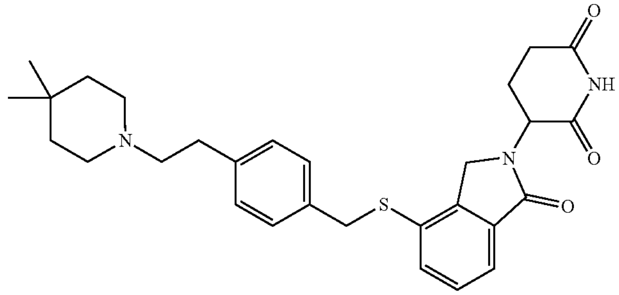 [SMILES: CC1(C)CCN(CCc2ccc(CSc3cccc4c3CN(C3CCC(=O)NC3=O)C4=O)cc2)CC1] | 3-(4-((4-(2-(4,4-dimethylpiperidin-1-yl)ethyl)benzyl)thio)-1-oxoisoindolin-2-yl)piperidine-2,6-dione |
| | 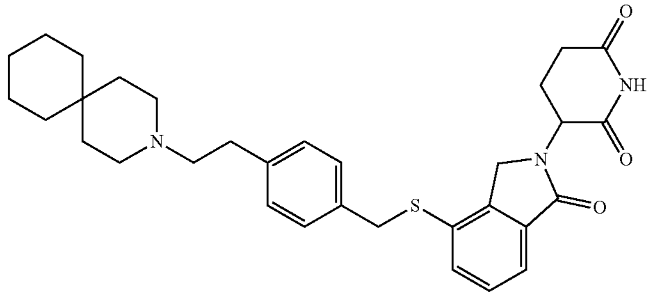 [SMILES: O=C1CCC(N2Cc3c(SCc4ccc(CCN5CCC6(CCCCC6)CC5)cc4)cccc3C2=O)C(=O)N1] | 3-(4-((4-(2-(3-azaspiro[5.5]undecan-3-yl)ethyl)benzyl)thio)-1-oxoisoindolin-2-yl)piperidine-2,6-dione |
| | 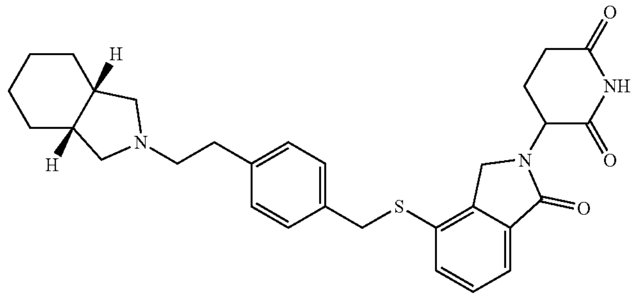 [SMILES: O=C1CCC(N2Cc3c(SCc4ccc(CCN5C[C@H]6CCCC[C@H]6C5)cc4)cccc3C2=O)C(=O)N1] | 3-(4-((4-(2-((3aR,7aS)-octahydro-2H-isoindol-2-yl)ethyl)benzyl)thio)-1-oxoisoindolin-2-yl)piperidine-2,6-dione |

TABLE 1-continued

| Compound No. | Structure of the compounds | The compound's name |
|---|---|---|
| | 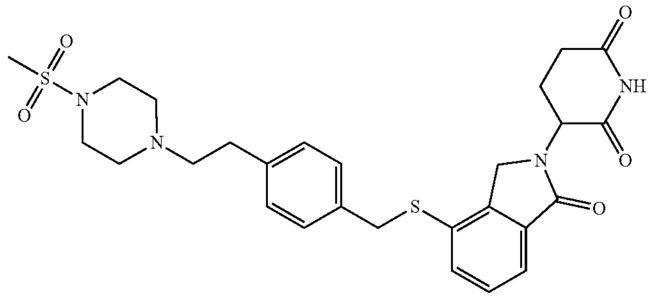 [SMILES: CS(=O)(=O)N1CCN(CCc2ccc(CSc3cccc4c3CN(C3CCC(=O)NC3=O)C4=O)cc2)CC1] | 3-(4-((4-(2-(4-(methylsulfonyl)piperazin-1-yl)ethyl)benzyl)thio)-1-oxoisoindolin-2-yl)piperidine-2,6-dione |
| | 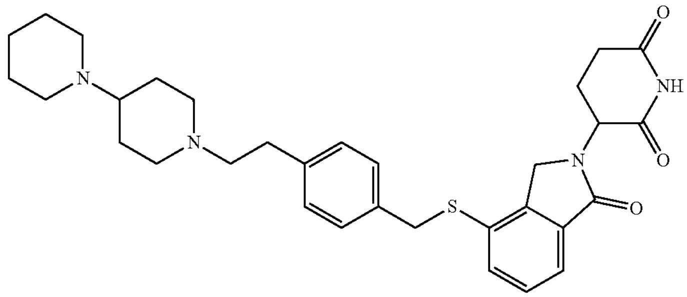 [SMILES: O=C1CCC(N2Cc3c(SCc4ccc(CCN5CCC(N6CCCCC6)CC5)cc4)cccc3C2=O)C(=O)N1] | 3-(4-((4-(2-([1,4'-bipiperidin]-1'-yl)ethyl)benzyl)thio)-1-oxoisoindolin-2-yl)piperidine-2,6-dione |
| | 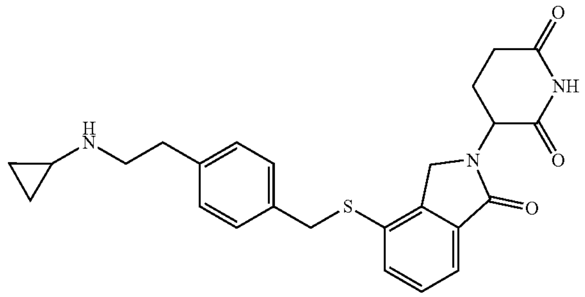 [SMILES: O=C1CCC(N2Cc3c(SCc4ccc(CCNC5CC5)cc4)cccc3C2=O)C(=O)N1] | 3-(4-((4-(2-(cyclopropylamino)ethyl)benzyl)thio)-1-oxoisoindolin-2-yl)piperidine-2,6-dione |
| | 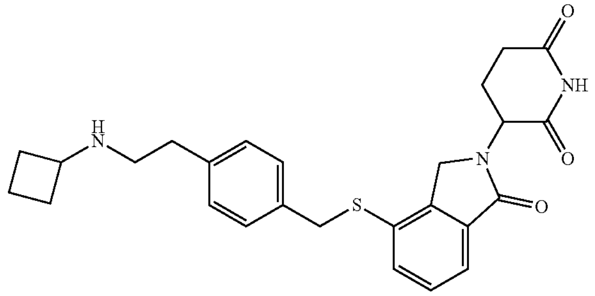 [SMILES: O=C1CCC(N2Cc3c(SCc4ccc(CCNC5CCC5)cc4)cccc3C2=O)C(=O)N1] | 3-(4-((4-(2-(cyclobutylamino)ethyl)benzyl)thio)-1-oxoisoindolin-2-yl)piperidine-2,6-dione |
| | 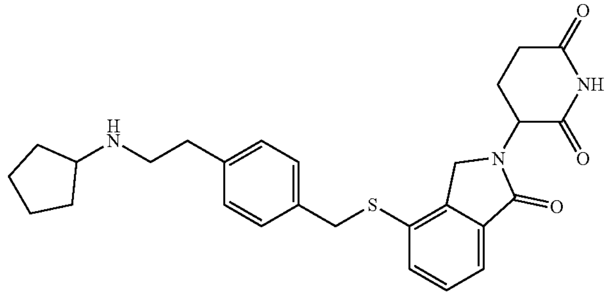 [SMILES: O=C1CCC(N2Cc3c(SCc4ccc(CCNC5CCCC5)cc4)cccc3C2=O)C(=O)N1] | 3-(4-((4-(2-(cyclopentylamino)ethyl)benzyl)thio)-1-oxoisoindolin-2-yl)piperidine-2,6-dione |

TABLE 1-continued

| The compounds of the present invention | | |
|---|---|---|
| Compound No. | Structure of the compounds | The compound's name |
| | 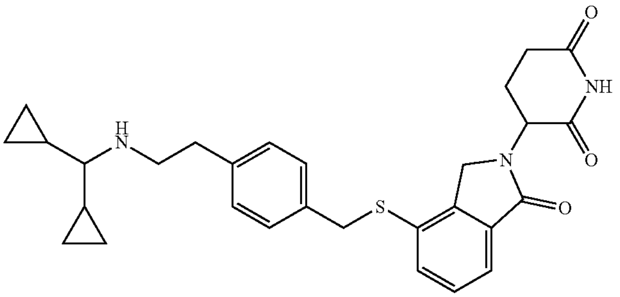 [SMILES: O=C1CCC(N2Cc3c(SCc4ccc(CCNC(C5CC5)C5CC5)cc4)cccc3C2=O)C(=O)N1] | 3-(4-((4-(2-((dicyclopropylmethyl)amino)ethyl)benzyl)thio)-1-oxoisoindolin-2-yl)piperidine-2,6-dione |
| | 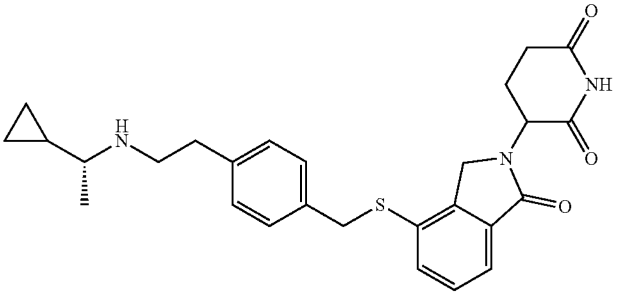 [SMILES: C[C@@H](NCCc1ccc(CSc2cccc3c2CN(C2CCC(=O)NC2=O)C3=O)cc1)C1CC1] | 3-(4-((4-(2-(((R)-1-cyclopropylethyl)amino)ethyl)benzyl)thio)-1-oxoisoindolin-2-yl)piperidine-2,6-dione |
| | 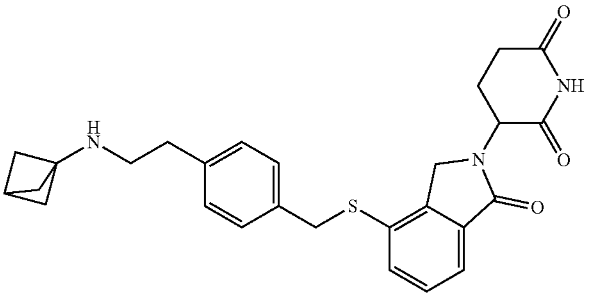 [SMILES: O=C1CCC(N2Cc3c(SCc4ccc(CCNC56CC(C5)C6)cc4)cccc3C2=O)C(=O)N1] | 3-(4-((4-(2-(bicyclo[1.1.1]pentan-1-ylamino)ethyl)benzyl)thio)-1-oxoisoindolin-2-yl)piperidine-2,6-dione |
| | 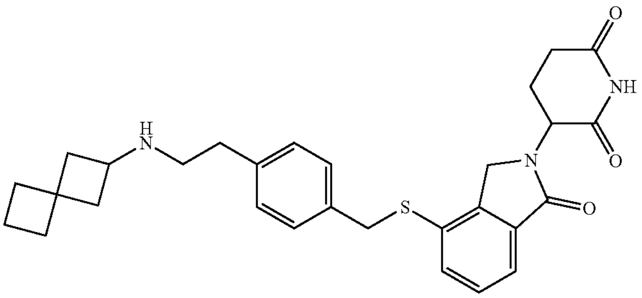 [SMILES: O=C1CCC(N2Cc3c(SCc4ccc(CCNC5CC6(CCC6)C5)cc4)cccc3C2=O)C(=O)N1] | 3-(1-oxo-4-((4-(2-(spiro[3.3]heptan-2-ylamino)ethyl)benzyl)thio)isoindolin-2-yl)piperidine-2,6-dione |
| | 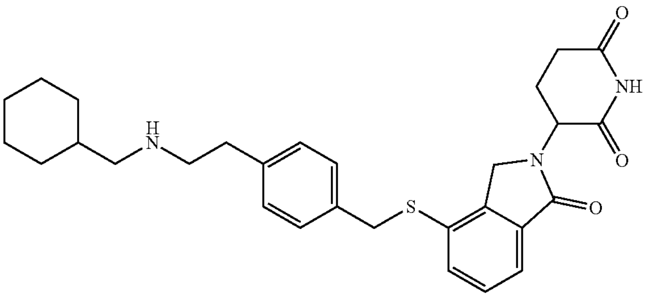 [SMILES: O=C1CCC(N2Cc3c(SCc4ccc(CCNCC5CCCCC5)cc4)cccc3C2=O)C(=O)N1] | 3-(4-((4-(2-((cyclohexylmethyl)amino)ethyl)benzyl)thio)-1-oxoisoindolin-2-yl)piperidine-2,6-dione |

TABLE 1-continued

| The compounds of the present invention | | |
|---|---|---|
| Compound No. | Structure of the compounds | The compound's name |
| | 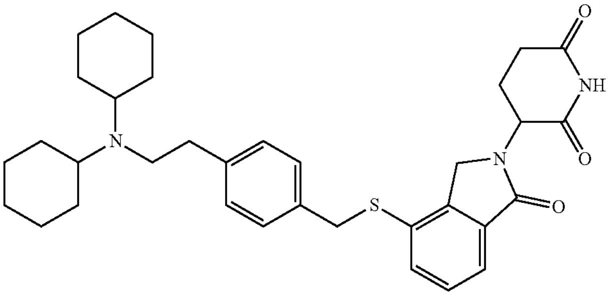 [SMILES: O=C1CCC(N2Cc3c(SCc4ccc(CCN(C5CCCCC5)C5CCCCC5)cc4)cccc3C2=O)C(=O)N1] | 3-(4-((4-(2-(dicyclohexylamino)ethyl)benzyl)thio)-1-oxoisoindolin-2-yl)piperidine-2,6-dione |
| | 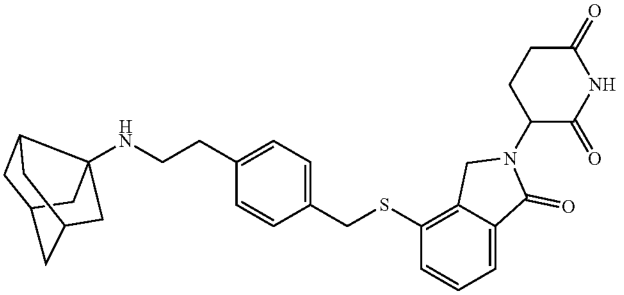 [SMILES: O=C1CCC(N2Cc3c(SCc4ccc(CCNC56CC7CC(CC5C7)C6)cc4)cccc3C2=O)C(=O)N1] | 3-(4-((4-(2-((hexahydro-2,5-methanopentalen-3a(1H)-yl)amino)ethyl)benzyl)thio)-1-oxoisoindolin-2-yl)piperidine-2,6-dione |
| | 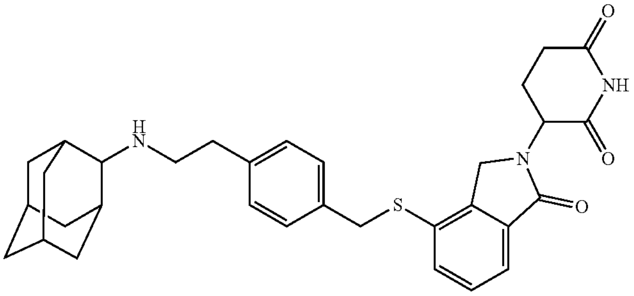 [SMILES: O=C1CCC(N2Cc3c(SCc4ccc(CCNC5C6CC7CC(C6)CC5C7)cc4)cccc3C2=O)C(=O)N1] | 3-(4-((4-(2-((adamantan-2-yl)amino)ethyl)benzyl)thio)-1-oxoisoindolin-2-yl)piperidine-2,6-dione |
| | 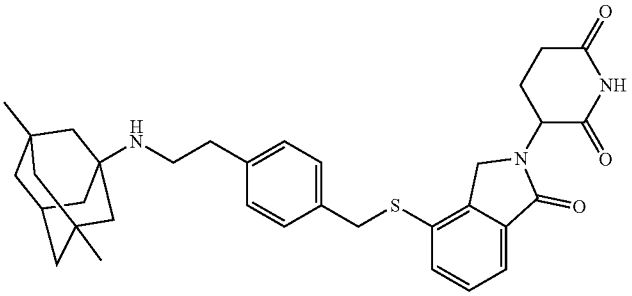 [SMILES: CC12CC3CC(C)(C1)CC(NCCc1ccc(CSc4cccc5c4CN(C4CCC(=O)NC4=O)C5=O)cc1)(C3)C2] | 3-(4-((4-(2-((3,5-dimethyladamantan-1-yl)amino)ethyl)benzyl)thio)-1-oxoisoindolin-2-yl)piperidine-2,6-dione |
| | 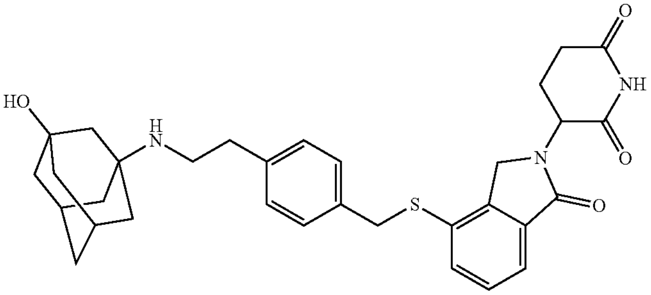 [SMILES: O=C1CCC(N2Cc3c(SCc4ccc(CCNC56CC7CC(CC(O)(C7)C5)C6)cc4)cccc3C2=O)C(=O)N1] | 3-(4-((4-(2-((3-hydroxyadamantan-1-yl)amino)ethyl)benzyl)thio)-1-oxoisoindolin-2-yl)piperidine-2,6-dione |

TABLE 1-continued

| The compounds of the present invention | | |
|---|---|---|
| Compound No. | Structure of the compounds | The compound's name |
| | 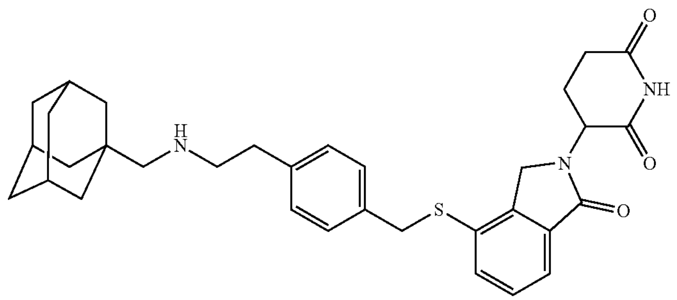 [SMILES: O=C1CCC(N2Cc3c(SCc4ccc(CCNCC56CC7CC(CC(C7)C5)C6)cc4)cccc3C2=O)C(=O)N1] | 3-(4-((4-(2-(((adamantan-1-yl)methyl)amino)ethyl)benzyl)thio)-1-oxoisoindolin-2-yl)piperidine-2,6-dione |
| | 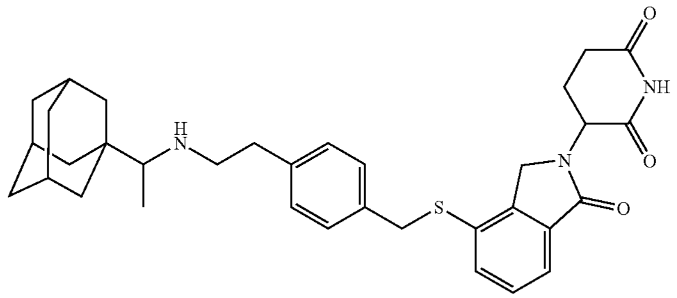 [SMILES: CC(NCCc1ccc(CSc2cccc3c2CN(C2CCC(=O)NC2=O)C3=O)cc1)C12CC3CC(CC(C3)C1)C2] | 3-(4-((4-(2-((1-(adamantan-1-yl)ethyl)amino)ethyl)benzyl)thio)-1-oxoisoindolin-2-yl)piperidine-2,6-dione |
| | 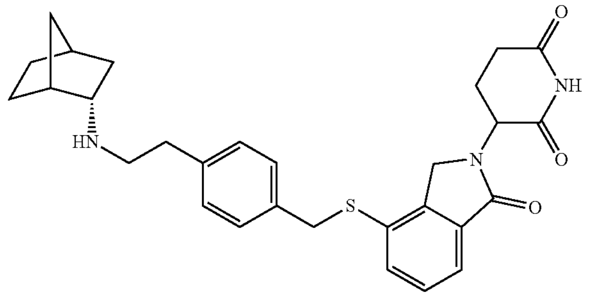 [SMILES: O=C1CCC(N2Cc3c(SCc4ccc(CCN[C@H]5CC6CCC5C6)cc4)cccc3C2=O)C(=O)N1] | 3-(4-((4-(2-(((1R,2S,4S)-bicyclo[2.2.1]heptan-2-yl)amino)ethyl)benzyl)thio)-1-oxoisoindolin-2-yl)piperidine-2,6-dione |
| | 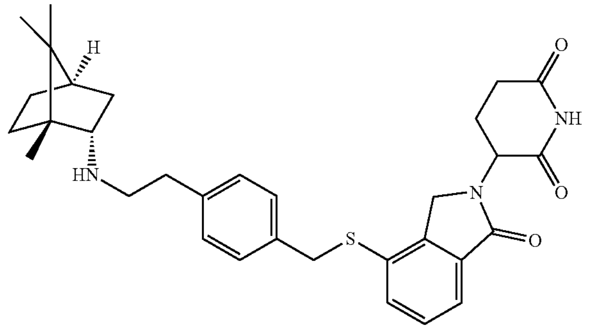 [SMILES: CC1(C)[C@@H]2CC[C@@]1(C)[C@@H](NCCc1ccc(CSc3cccc4c3CN(C3CCC(=O)NC3=O)C4=O)cc1)C2] | 3-(1-oxo-4-((4-(2-(((1R,2S,4R)-1,7,7-trimethylbicyclo[2.2.1]heptan-2-yl)amino)ethyl)benzyl)thio)isoindolin-2-yl)piperidine-2,6-dione |
| | 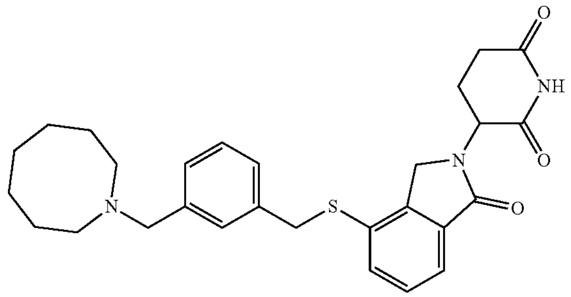 [SMILES: O=C1CCC(N2Cc3c(SCc4cccc(CN5CCCCCCC5)c4)cccc3C2=O)C(=O)N1] | 3-(4-((3-(azocan-1-ylmethyl)benzyl)thio)-1-oxoisoindolin-2-yl)piperidine-2,6-dione |

TABLE 1-continued

| The compounds of the present invention | | |
|---|---|---|
| Compound No. | Structure of the compounds | The compound's name |
| | 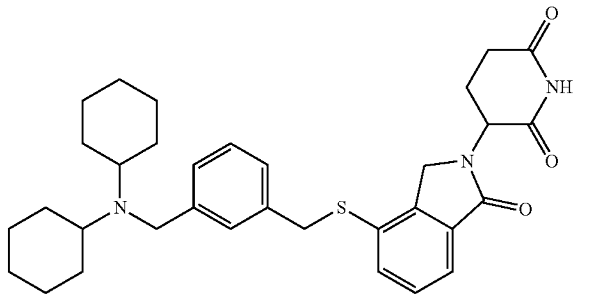 [SMILES: O=C1CCC(N2Cc3c(SCc4cccc(CN(C5CCCCC5)C5CCCCC5)c4)cccc3C2=O)C(=O)N1] | 3-(4-((3-((dicyclohexylamino)methyl)benzyl)thio)-1-oxoisoindolin-2-yl)piperidine-2,6-dione |
| | 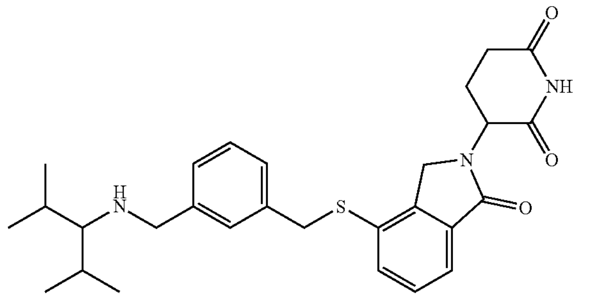 [SMILES: CC(C)C(NCc1cccc(CSc2cccc3c2CN(C2CCC(=O)NC2=O)C3=O)c1)C(C)C] | 3-(4-((3-(((2,4-dimethylpentan-3-yl)amino)methyl)benzyl)thio)-1-oxoisoindolin-2-yl)piperidine-2,6-dione |
| | 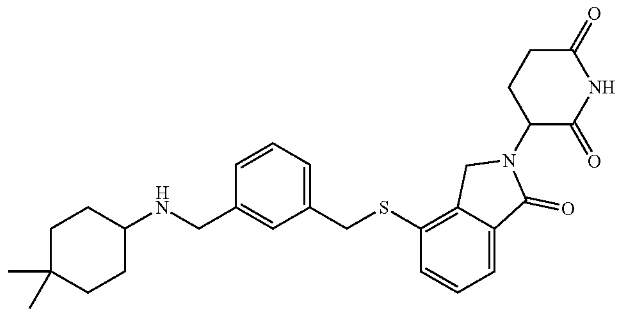 [SMILES: CC1(C)CCC(NCc2cccc(CSc3cccc4c3CN(C3CCC(=O)NC3=O)C4=O)c2)CC1] | 3-(4-((3-(((4,4-dimethylcyclohexyl)amino)methyl)benzyl)thio)-1-oxoisoindolin-2-yl)piperidine-2,6-dione |
| | 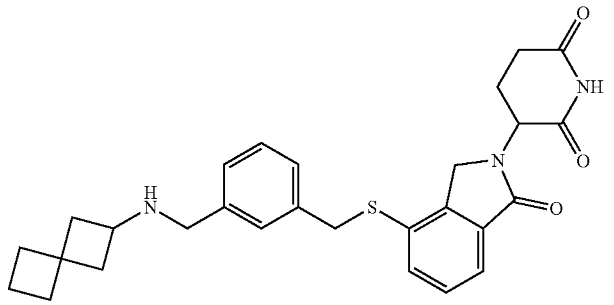 [SMILES: O=C1CCC(N2Cc3c(SCc4cccc(CNC5CC6(CCC6)C5)c4)cccc3C2=O)C(=O)N1] | 3-(1-oxo-4-((3-((spiro[3.3]heptan-2-ylamino)methyl)benzyl)thio)isoindolin-2-yl)piperidine-2,6-dione |

TABLE 1-continued

The compounds of the present invention

| Compound No. | Structure of the compounds | The compound's name |
| --- | --- | --- |
| | 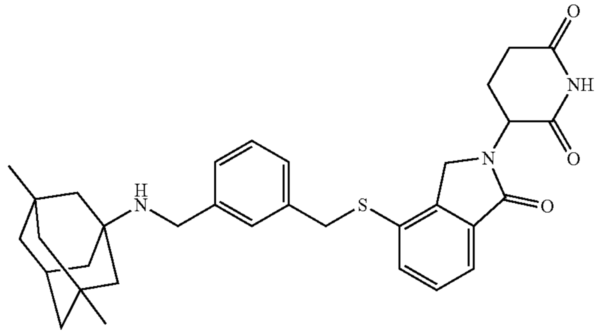 [SMILES: CC12CC3CC(C)(C1)CC(NCc1cccc(CSc4cccc5c4CN(C4CCC(=O)NC4=O)C5=O)c1)(C3)C2] | 3-(4-((3-(((3,5-dimethyladamantan-1-yl)amino)methyl)benzyl)thio)-1-oxoisoindolin-2-yl)piperidine-2,6-dione |
| | 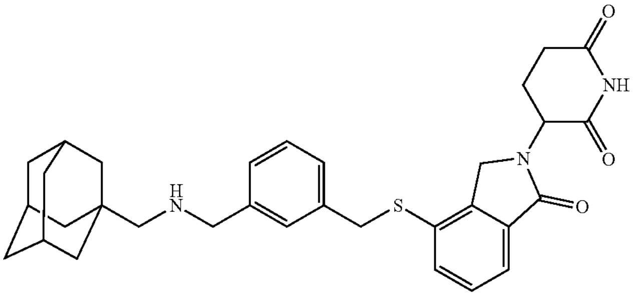 [SMILES: O=C1CCC(N2Cc3c(SCc4cccc(CNCC56CC7CC(CC(C7)C5)C6)c4)cccc3C2=O)C(=O)N1] | 3-(4-((3-((((adamantan-1-yl)methyl)amino)methyl)benzyl)thio)-1-oxoisoindolin-2-yl)piperidine-2,6-dione |
| | 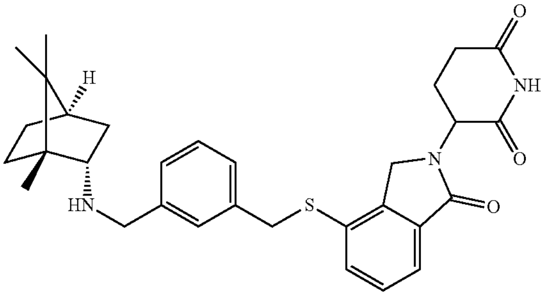 [SMILES: CC1(C)[C@@H]2CC[C@@]1(C)[C@@H](NCc1cccc(CSc3cccc4c3CN(C3CCC(=O)NC3=O)C4=O)c1)C2] | 3-(1-oxo-4-((3-((((1R,2S,4R)-1,7,7-trimethylbicyclo[2.2.1]heptan-2-yl)amino)methyl)benzyl)thio) isoindolin-2-yl)piperidine-2,6-dione |
| | 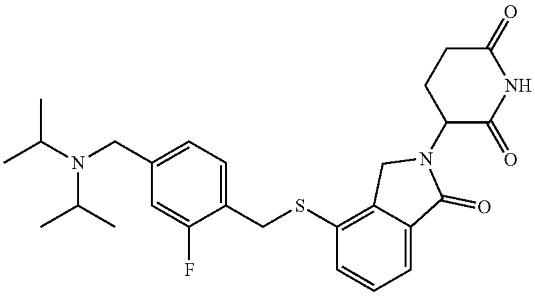 [SMILES: CC(C)N(Cc1ccc(CSc2cccc3c2CN(C2CCC(=O)NC2=O)C3=O)c(F)c1)C(C)C] | 3-(4-((4-((diisopropylamino)methyl)-2-fluorobenzyl)thio)-1-oxoisoindolin-2-yl)piperidine-2,6-dione |
| | 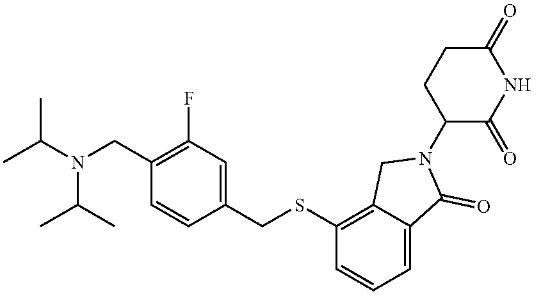 [SMILES: CC(C)N(Cc1ccc(CSc2cccc3c2CN(C2CCC(=O)NC2=O)C3=O)cc1F)C(C)C] | 3-(4-((4-((diisopropylamino)methyl)-3-fluorobenzyl)thio)-1-oxoisoindolin-2-yl)piperidine-2,6-dione |

TABLE 1-continued

| The compounds of the present invention | | |
|---|---|---|
| Compound No. | Structure of the compounds | The compound's name |
| | 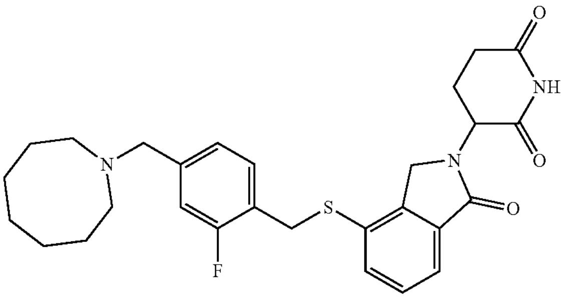 [SMILES: O=C1CCC(N2Cc3c(SCc4ccc(CN5CCCCCCC5)cc4F)cccc3C2=O)C(=O)N1] | 3-(4-((4-(azocan-1-ylmethyl)-2-fluorobenzyl)thio)-1-oxoisoindolin-2-yl)piperidine-2,6-dione |
| | 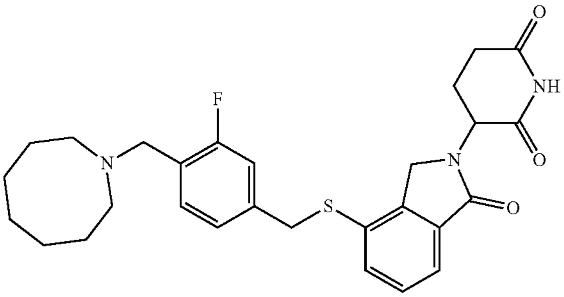 [SMILES: O=C1CCC(N2Cc3c(SCc4ccc(CN5CCCCCCC5)c(F)c4)cccc3C2=O)C(=O)N1] | 3-(4-((4-(azocan-1-ylmethyl)-3-fluorobenzyl)thio)-1-oxoisoindolin-2-yl)piperidine-2,6-dione |
| | 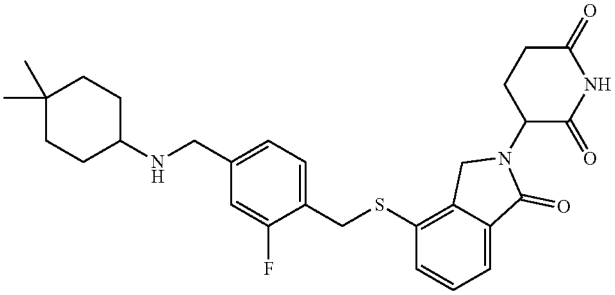 [SMILES: CC1(C)CCC(NCc2ccc(CSc3cccc4c3CN(C3CCC(=O)NC3=O)C4=O)c(F)c2)CC1] | 3-(4-((4-(((4,4-dimethylcyclohexyl)amino)methyl)-2-fluorobenzyl)thio)-1-oxoisoindolin-2-yl)piperidine-2,6-dione |
| | 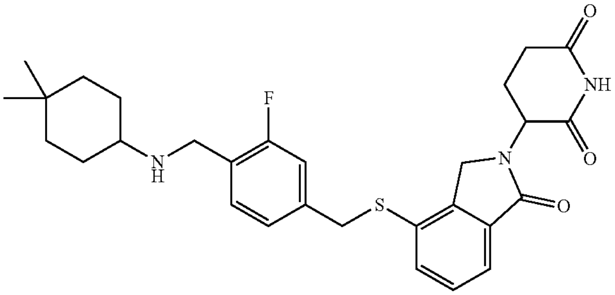 [SMILES: CC1(C)CCC(NCc2ccc(CSc3cccc4c3CN(C3CCC(=O)NC3=O)C4=O)cc2F)CC1] | 3-(4-((4-(((4,4-dimethylcyclohexyl)amino)methyl)-3-fluorobenzyl)thio)-1-oxoisoindolin-2-yl)piperidine-2,6-dione |
| | 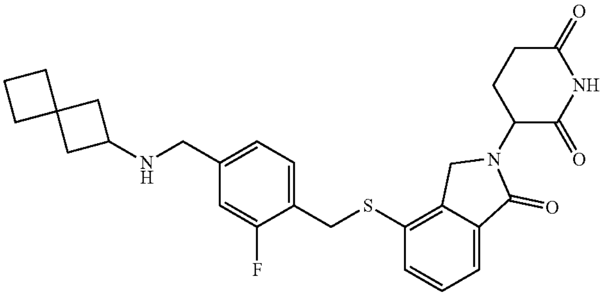 [SMILES: O=C1CCC(N2Cc3c(SCc4ccc(CNC5CC6(CCC6)C5)cc4F)cccc3C2=O)C(=O)N1] | 3-(4-((2-fluoro-4-((spiro[3.3]heptan-2-ylamino)methyl)benzyl)thio)-1-oxoisoindolin-2-yl)piperidine-2,6-dione |

TABLE 1-continued

| Compound No. | Structure of the compounds | The compound's name |
| --- | --- | --- |
| | The compounds of the present invention | |
| | 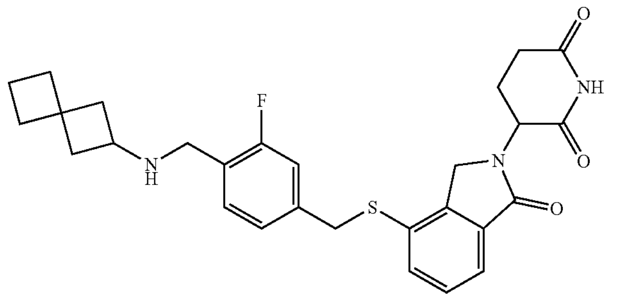 [SMILES: O=C1CCC(N2Cc3c(SCc4ccc(CNC5CC6(CCC6)C5)c(F)c4)cccc3C2=O)C(=O)N1] | 3-(4-((3-fluoro-4-((spiro[3.3]heptan-2-ylamino)methyl)benzyl)thio)-1-oxoisoindolin-2-yl)piperidine-2,6-dione |
| | 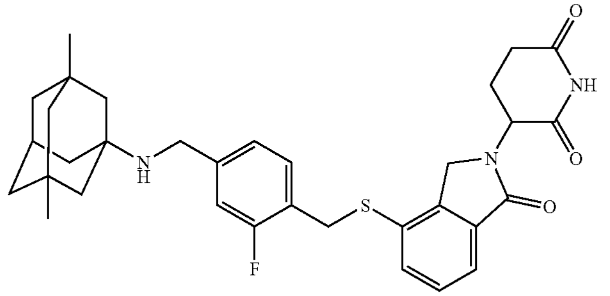 [SMILES: CC12CC3CC(C)(C1)CC(NCc1ccc(CSc4cccc5c4CN(C4CCC(=O)NC4=O)C5=O)c(F)c1)(C3)C2] | 3-(4-((4-(((3,5-dimethyladamantan-1-yl)amino)methyl)-2-fluorobenzyl)thio)-1-oxoisoindolin-2-yl)piperidine-2,6-dione |
| | 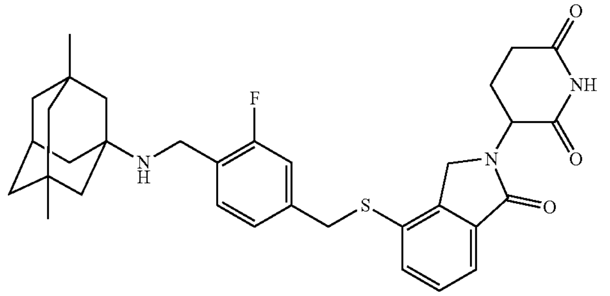 [SMILES: CC12CC3CC(C)(C1)CC(NCc1ccc(CSc4cccc5c4CN(C4CCC(=O)NC4=O)C5=O)cc1F)(C3)C2] | 3-(4-((4-(((3,5-dimethyladamantan-1-yl)amino)methyl)-3-fluorobenzyl)thio)-1-oxoisoindolin-2-yl)piperidine-2,6-dione |
| | 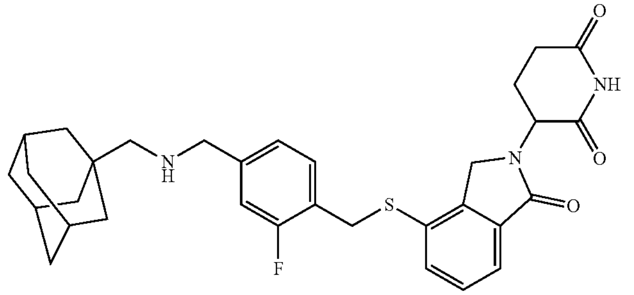 [SMILES: O=C1CCC(N2Cc3c(SCc4ccc(CNCC56CC7CC(CC(C7)C5)C6)cc4F)cccc3C2=O)C(=O)N1] | 3-(4-((4-((((adamantan-1-yl)methyl)amino)methyl)-2-fluorobenzyl)thio)-1-oxoisoindolin-2-yl)piperidine-2,6-dione |
| | 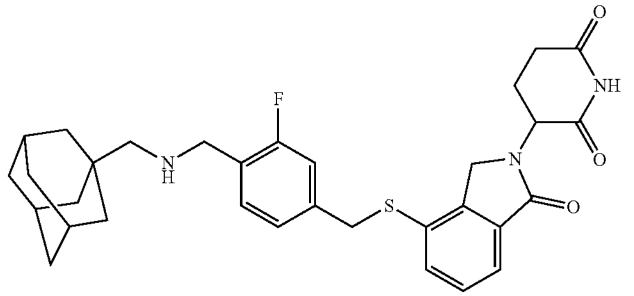 [SMILES: O=C1CCC(N2Cc3c(SCc4ccc(CNCC56CC7CC(CC(C7)C5)C6)c(F)c4)cccc3C2=O)C(=O)N1] | 3-(4-((4-((((adamantan-1-yl)methyl)amino)methyl)-3-fluorobenzyl)thio)-1-oxoisoindolin-2-yl)piperidine-2,6-dione |

TABLE 1-continued

| Compound No. | Structure of the compounds | The compound's name |
| --- | --- | --- |
| | The compounds of the present invention | |
| | 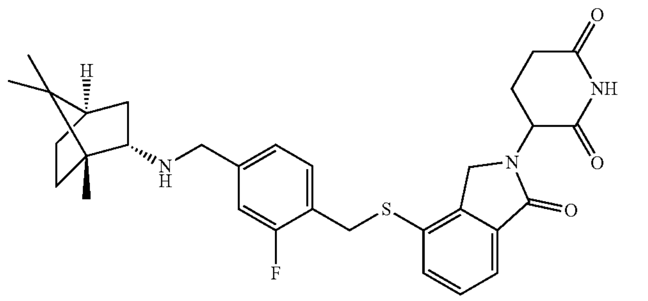 [SMILES: CC1(C)[C@@H]2CC[C@@]1(C)[C@@H](NCc1ccc(CSc3cccc4c3CN(C3CCC(=O)NC3=O)C4=O)c(F)c1)C2] | 3-(4-((2-fluoro-4-((((1R,2S,4R)-1,7,7-trimethylbicyclo[2.2.1]heptan-2-yl)amino)methyl)benzyl)thio)-1-oxoisoindolin-2-yl)piperidine-2,6-dione |
| | 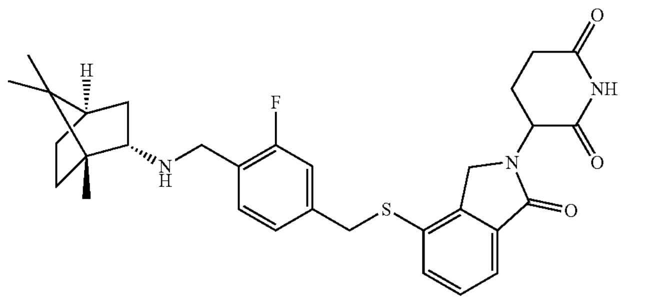 [SMILES: CC1(C)[C@@H]2CC[C@@]1(C)[C@@H](NCc1ccc(CSc3cccc4c3CN(C3CCC(=O)NC3=O)C4=O)cc1F)C2] | 3-(4-((3-fluoro-4-((((1R,2S,4R)-1,7,7-trimethylbicyclo[2.2.1]heptan-2-yl)amino)methyl)benzyl)thio)-1-oxoisoindolin-2-yl)piperidine-2,6-dione |
| | 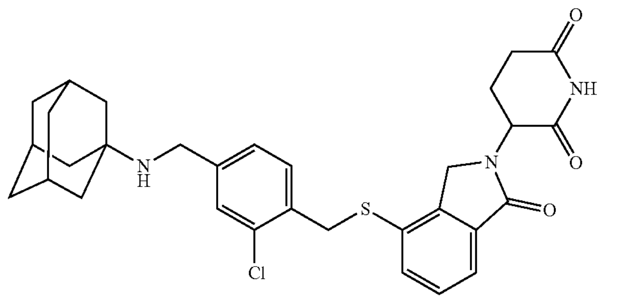 | 3-(4-((4-(((adamantan-1-yl)amino)methyl)-2-chlorobenzyl)thio)-1-oxoisoindolin-2-yl)piperidine-2,6-dione |
| | 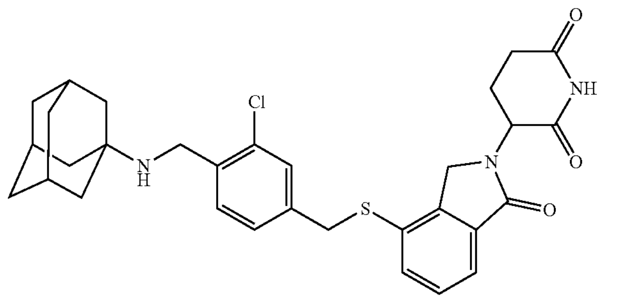 [SMILES: O=C1CCC(N2Cc3c(SCc4ccc(CNC56CC7CC(CC(C7)C5)C6)c(Cl)c4)cccc3C2=O)C(=O)N1] | 3-(4-((4-(((adamantan-1-yl)amino)methyl)-3-chlorobenzyl)thio)-1-oxoisoindolin-2-yl)piperidine-2,6-dione |
| | 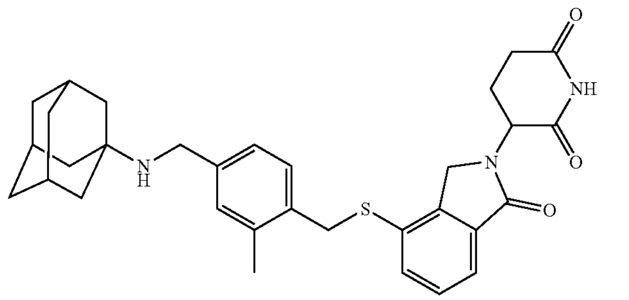 | 3-(4-((4-(((adamantan-1-yl)amino)methyl)-2-methylbenzyl)thio)-1-oxoisoindolin-2-yl)piperidine-2,6-dione |

TABLE 1-continued

| Compound No. | Structure of the compounds | The compound's name |
|---|---|---|
| | 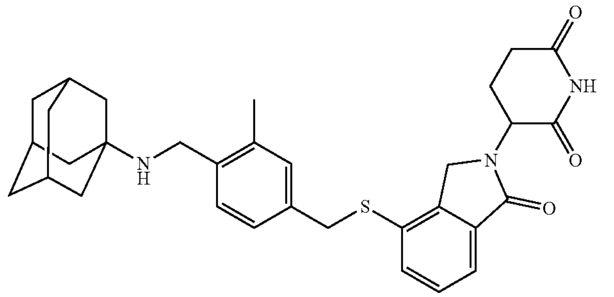 [SMILES: Cc1cc(CSc2cccc3c2CN(C2CCC(=O)NC2=O)C3=O)ccc1CNC12CC3CC(CC(C3)C1)C2] | 3-(4-((4-(((adamantan-1-yl)amino)methyl)-3-methylbenzyl)thio)-1-oxoisoindolin-2-yl)piperidine-2,6-dione |
| SIAIS12220-89 | 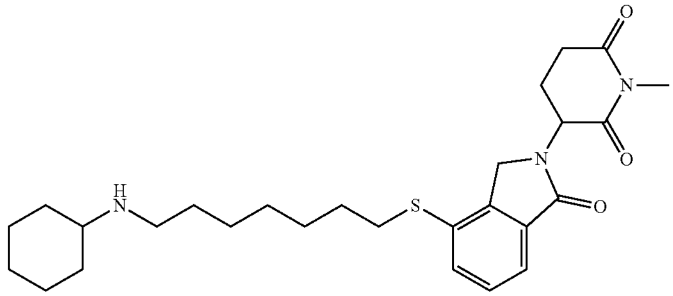 [SMILES: CN1C(=O)CCC(N2Cc3c(SCCCCCCCNC4CCCCC4)cccc3C2=O)C1=O] | 3-(4-((7-(cyclohexylamino)heptyl)thio)-1-oxoisoindolin-2-yl)-1-methylpiperidine-2,6-dione |
| SIAIS12220-91 | 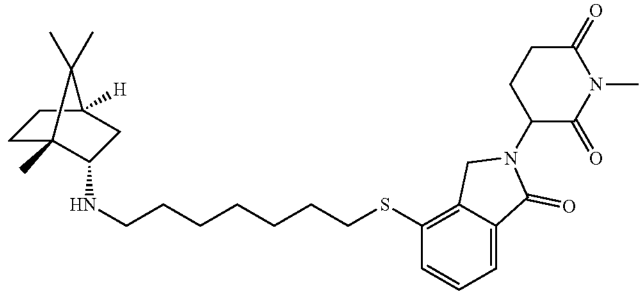 [SMILES: CN1C(=O)CCC(N2Cc3c(SCCCCCCCN[C@H]4C[C@H]5CC[C@]4(C)C5(C)C)cccc3C2=O)C1=O] | 1-methyl-3-(1-oxo-4-((7-(((1R,2S,4R)-1,7,7-trimethylbicyclo[2.2.1]heptan-2-yl)amino)heptyl)thio)isoindolin-2-yl)piperidine-2,6-dione |
| SIAIS12241-01 | 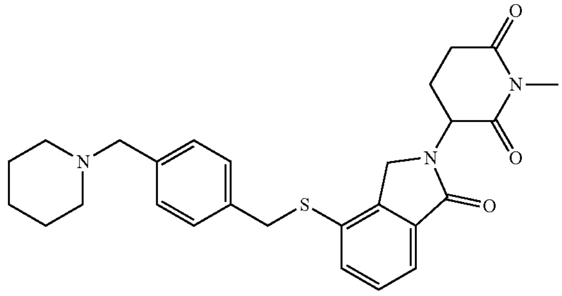 [SMILES: CN1C(=O)CCC(N2Cc3c(SCc4ccc(CN5CCCCC5)cc4)cccc3C2=O)C1=O] | 1-methyl-3-(1-oxo-4-((4-(piperidin-1-ylmethyl)benzyl)thio)isoindolin-2-yl)piperidine-2,6-dione |
| SIAIS12241-03 | 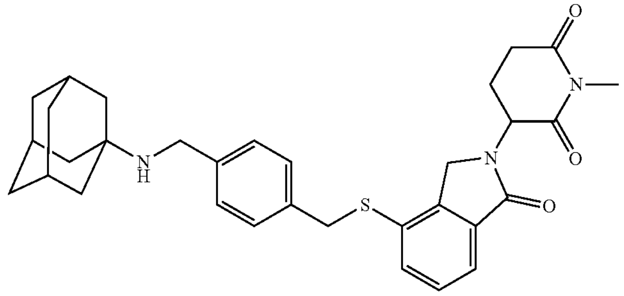 [SMILES: CN1C(=O)CCC(N2Cc3c(SCc4ccc(CNC56CC7CC(CC(C7)C5)C6)cc4)cccc3C2=O)C1=O] | 3-(4-((4-(((adamantan-1-yl)amino)methyl)benzyl)thio)-1-oxoisoindolin-2-yl)-1-methylpiperidine-2,6-dione |

TABLE 1-continued

| The compounds of the present invention | | |
|---|---|---|
| Compound No. | Structure of the compounds | The compound's name |
| SIAIS12221-19 | 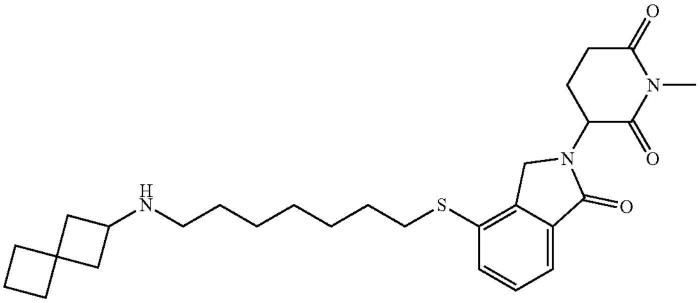 [SMILES: CN1C(=O)CCC(N2Cc3c(SCCCCCCCNC4CC5(CCC5)C4)cccc3C2=O)C1=O] | 1-methyl-3-(1-oxo-4-((7-(spiro[3.3]heptan-2-ylamino)heptyl)thio)isoindolin-2-yl)piperidine-2,6-dione |
| | 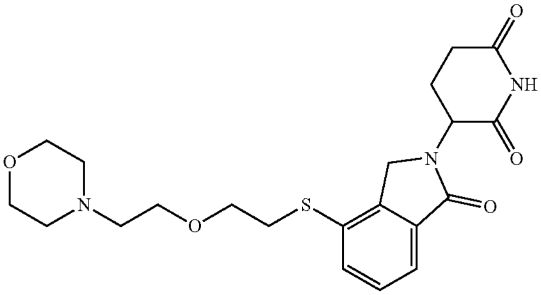 [SMILES: O=C1CCC(N2Cc3c(SCCOCCN4CCOCC4)cccc3C2=O)C(=O)N1] | 3-(4-((2-(2-morpholinoethoxy)ethyl)thio)-1-oxoisoindolin-2-yl)piperidine-2,6-dione |
| | 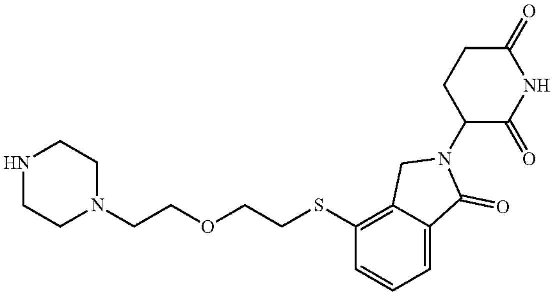 [SMILES: O=C1CCC(N2Cc3c(SCCOCCN4CCNCC4)cccc3C2=O)C(=O)N1] | 3-(1-oxo-4-((2-(2-(piperazin-1-yl)ethoxy)ethyl)thio)isoindolin-2-yl)piperidine-2,6-dione |
| | 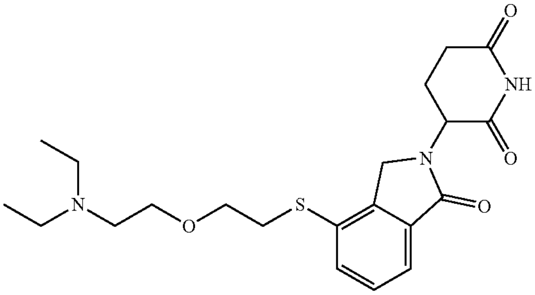 [SMILES: CCN(CC)CCOCCSc1cccc2c1CN(C1CCC(=O)NC1=O)C2=O] | 3-(4-((2-(2-(diethylamino)ethoxy)ethyl)thio)-1-oxoisoindolin-2-yl)piperidine-2,6-dione |
| SIAIS12161-99 | 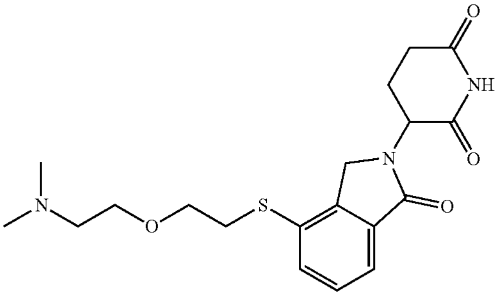 [SMILES: CN(C)CCOCCSc1cccc2c1CN(C1CCC(=O)NC1=O)C2=O] | 3-(4-((2-(2-(dimethylamino)ethoxy)ethyl)thio)-1-oxoisoindolin-2-yl)piperidine-2,6-dione |

TABLE 1-continued

| Compound No. | Structure of the compounds | The compound's name |
| --- | --- | --- |
| | The compounds of the present invention | |
| | 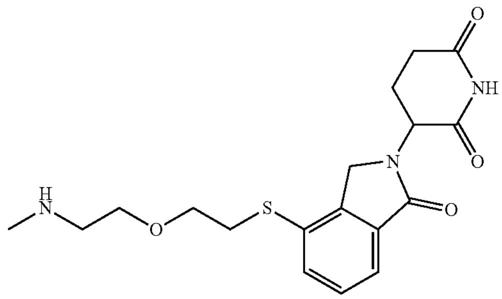 [SMILES: CNCCOCCSc1cccc2c1CN(C1CCC(=O)NC1=O)C2=O] | 3-(4-((2-(2-(methylamino)ethoxy)ethyl)thio)-1-oxoisoindolin-2-yl)piperidine-2,6-dione |
| | 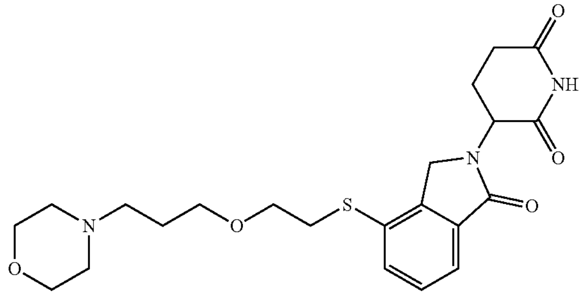 [SMILES: O=C1CCC(N2Cc3c(SCCOCCCN4CCOCC4)cccc3C2=O)C(=O)N1] | 3-(4-((2-(3-morpholinopropoxy)ethyl)thio)-1-oxoisoindolin-2-yl)piperidine-2,6-dione |
| | 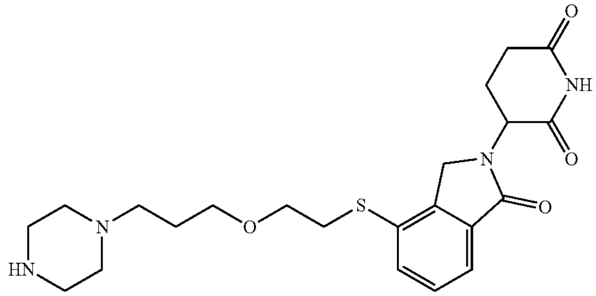 [SMILES: O=C1CCC(N2Cc3c(SCCOCCCN4CCNCC4)cccc3C2=O)C(=O)N1] | 3-(1-oxo-4-((2-(3-(piperazin-1-yl)propoxy)ethyl)thio)isoindolin-2-yl)piperidine-2,6-dione |
| | 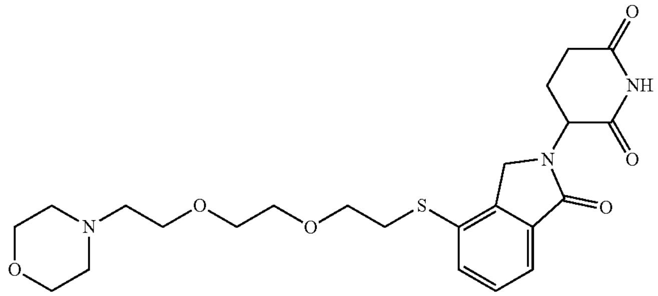 [SMILES: O=C1CCC(N2Cc3c(SCCOCCOCCN4CCOCC4)cccc3C2=O)C(=O)N1] | 3-(4-((2-(2-(2-morpholinoethoxy)ethoxy)ethyl)thio)-1-oxoisoindolin-2-yl)piperidine-2,6-dione |
| | 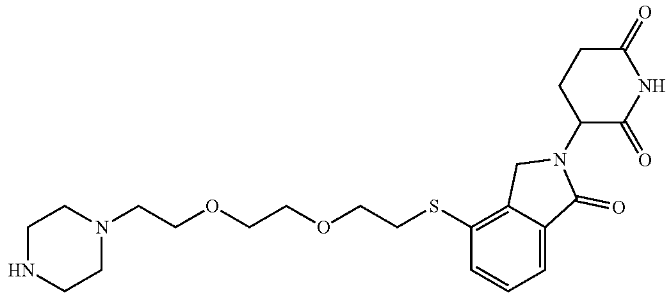 [SMILES: O=C1CCC(N2Cc3c(SCCOCCOCCN4CCNCC4)cccc3C2=O)C(=O)N1] | 3-(1-oxo-4-((2-(2-(2-(piperazin-1-yl)ethoxy)ethoxy)ethyl)thio)isoindolin-2-yl)piperidine-2,6-dione |

TABLE 1-continued

The compounds of the present invention

| Compound No. | Structure of the compounds | The compound's name |
| --- | --- | --- |
| | 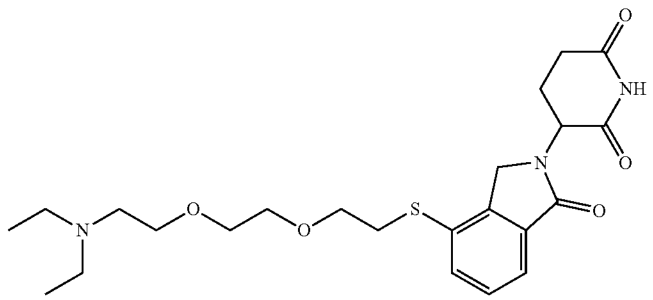 [SMILES: CCN(CC)CCOCCOCCSc1cccc2c1CN(C1CCC(=O)NC1=O)C2=O] | 3-(4-((2-(2-(2-(diethylamino)ethoxy)ethoxy)ethyl)thio)-1-oxoisoindolin-2-yl)piperidine-2,6-dione |
| SIAIS12161-95 | 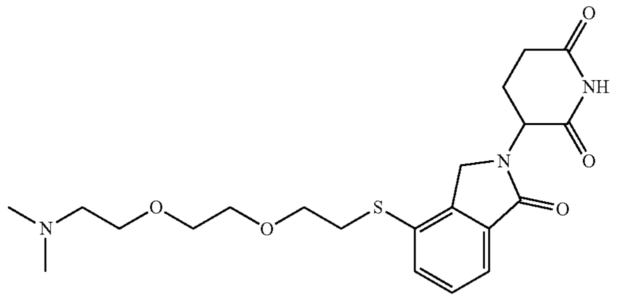 [SMILES: CN(C)CCOCCOCCSc1cccc2c1CN(C1CCC(=O)NC1=O)C2=O] | 3-(4-((2-(2-(2-(dimethylamino)ethoxy)ethoxy)ethyl)thio)-1-oxoisoindolin-2-yl)piperidine-2,6-dione |
| | 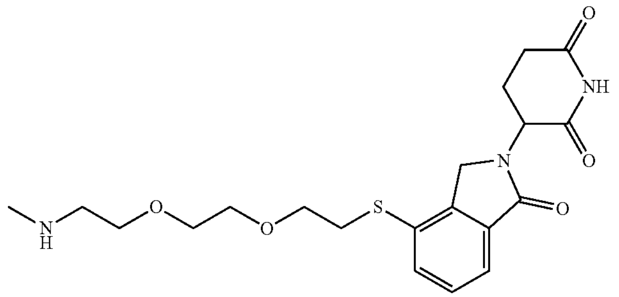 [SMILES: CNCCOCCOCCSc1cccc2c1CN(C1CCC(=O)NC1=O)C2=O] | 3-(4-((2-(2-(2-(methylamino)ethoxy)ethoxy)ethyl)thio)-1-oxoisoindolin-2-yl)piperidine-2,6-dione |
| | 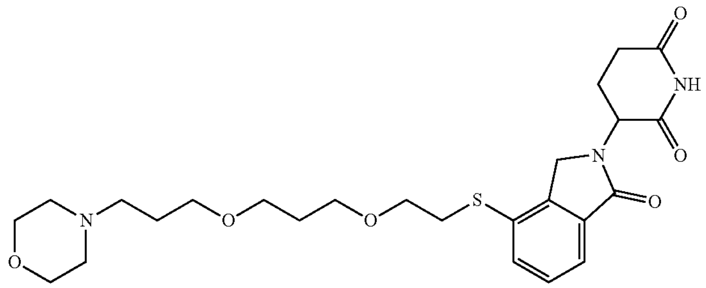 | 3-(4-((2-(3-(3-morpholinopropoxy)propoxy)ethyl)thio)-1-oxoisoindolin-2-yl)piperidine-2,6-dione |
| | 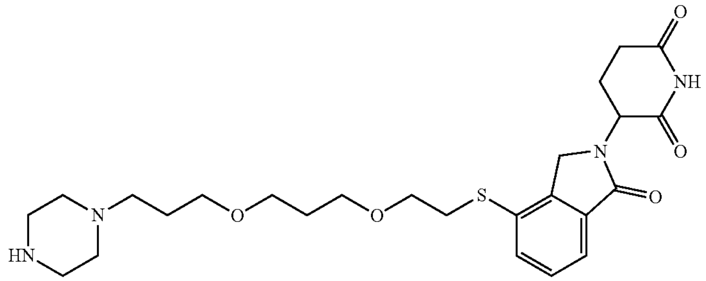 [SMILES: O=C1CCC(N2Cc3c(SCCOCCCOCCCN4CCNCC4)cccc3C2=O)C(=O)N1] | 3-(1-oxo-4-((2-(3-(3-(piperazin-1-yl)propoxy)propoxy)ethyl)thio)isoindolin-2-yl)piperidine-2,6-dione |

TABLE 1-continued

The compounds of the present invention

| Compound No. | Structure of the compounds | The compound's name |
|---|---|---|
| | 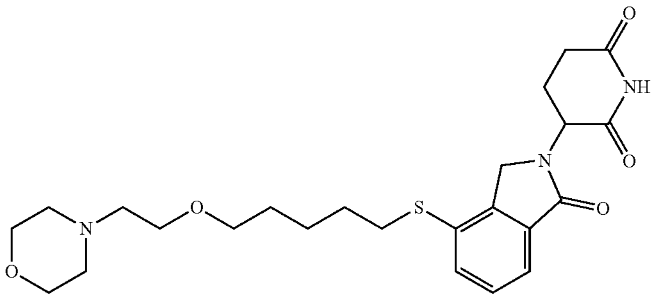 [SMILES: O=C1CCC(N2Cc3c(SCCCCCOCCN4CCOCC4)cccc3C2=O)C(=O)N1] | 3-(4-((5-(2-morpholinoethoxy)pentyl)thio)-1-oxoisoindolin-2-yl)piperidine-2,6-dione |
| | 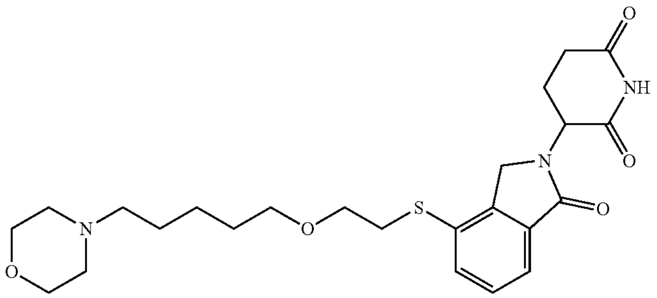 [SMILES: O=C1CCC(N2Cc3c(SCCOCCCCCN4CCOCC4)cccc3C2=O)C(=O)N1] | 3-(4-((2-((5-morpholinopentyl)oxy)ethyl)thio)-1-oxoisoindolin-2-yl)piperidine-2,6-dione |
| SIAIS26901-2 | 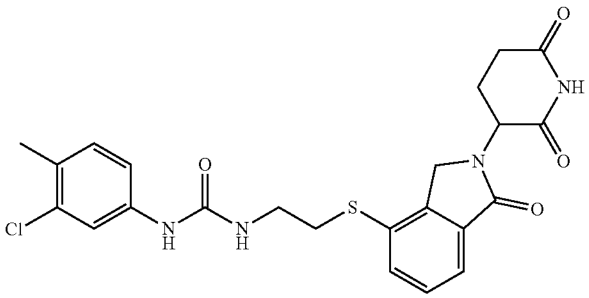 [SMILES: Cc1ccc(NC(=O)NCCSc2cccc3c2CN(C2CCC(=O)NC2=O)C3=O)cc1Cl] | 1-(3-chloro-4-methylphenyl)-3-(2-((2-(2,6-dioxopiperidin-3-yl)-1-oxoisoindolin-4-yl)thio)ethyl)urea |
| | 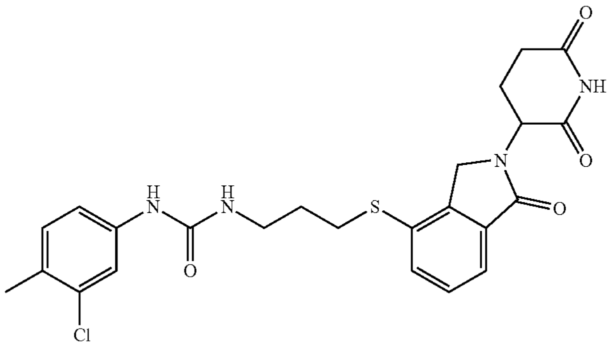 [SMILES: Cc1ccc(NC(=O)NCCCSc2cccc3c2CN(C2CCC(=O)NC2=O)C3=O)cc1Cl] | 1-(3-chloro-4-methylphenyl)-3-(3-((2-(2,6-dioxopiperidin-3-yl)-1-oxoisoindolin-4-yl)thio)propyl)urea |
| SIAIS26909-5 | 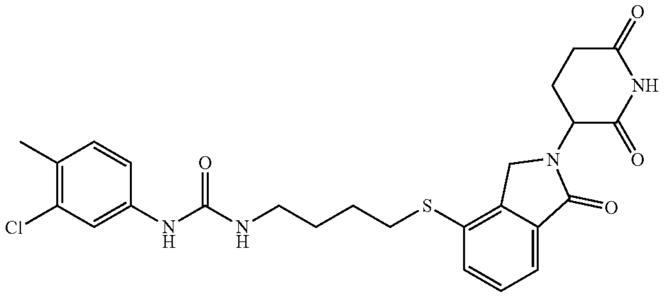 [SMILES: Cc1ccc(NC(=O)NCCCCSc2cccc3c2CN(C2CCC(=O)NC2=O)C3=O)cc1Cl] | 1-(3-chloro-4-methylphenyl)-3-(4-((2-(2,6-dioxopiperidin-3-yl)-1-oxoisoindolin-4-yl)thio)butyl)urea |

TABLE 1-continued

The compounds of the present invention

| Compound No. | Structure of the compounds | The compound's name |
|---|---|---|
| | 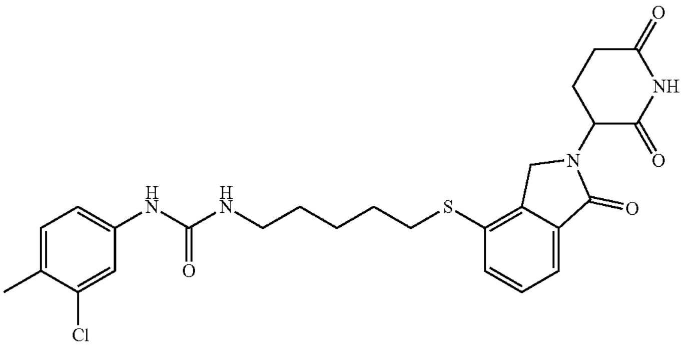 [SMILES: Cc1ccc(NC(=O)NCCCCCSc2cccc3c2CN(C2CCC(=O)NC2=O)C3=O)cc1Cl] | 1-(3-chloro-4-methylphenyl)-3-(5-((2-(2,6-dioxopiperidin-3-yl)-1-oxoisoindolin-4-yl)thio)pentyl)urea |
| | 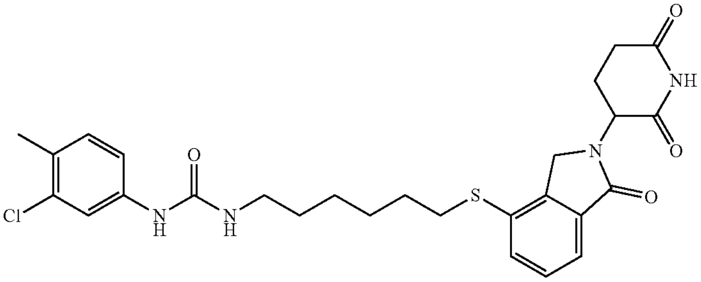 [SMILES: Cc1ccc(NC(=O)NCCCCCCSc2cccc3c2CN(C2CCC(=O)NC2=O)C3=O)cc1Cl] | 1-(3-chloro-4-methylphenyl)-3-(6-((2-(2,6-dioxopiperidin-3-yl)-1-oxoisoindolin-4-yl)thio)hexyl)urea |
| SIAIS26906-8 | 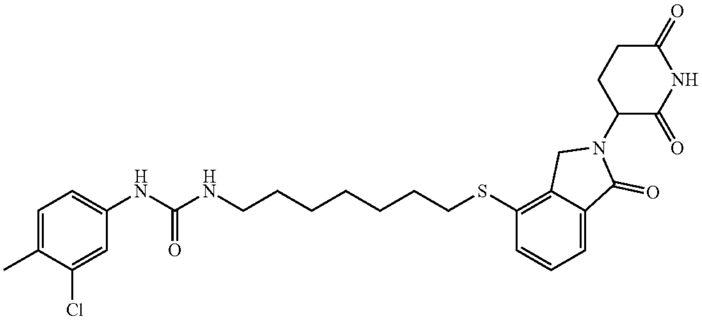 [SMILES: Cc1ccc(NC(=O)NCCCCCCCSc2cccc3c2CN(C2CCC(=O)NC2=O)C3=O)cc1Cl] | 1-(3-chloro-4-methylphenyl)-3-(7-((2-(2,6-dioxopiperidin-3-yl)-1-oxoisoindolin-4-yl)thio)heptyl)urea |
| SIAIS26907-2 | 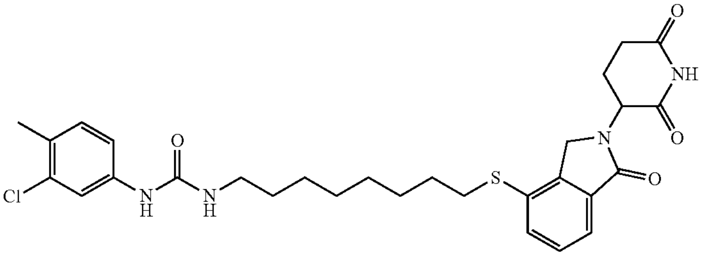 [SMILES: Cc1ccc(NC(=O)NCCCCCCCCSc2cccc3c2CN(C2CCC(=O)NC2=O)C3=O)cc1Cl] | 1-(3-chloro-4-methylphenyl)-3-(8-((2-(2,6-dioxopiperidin-3-yl)-1-oxoisoindolin-4-yl)thio)octyl)urea |
| | 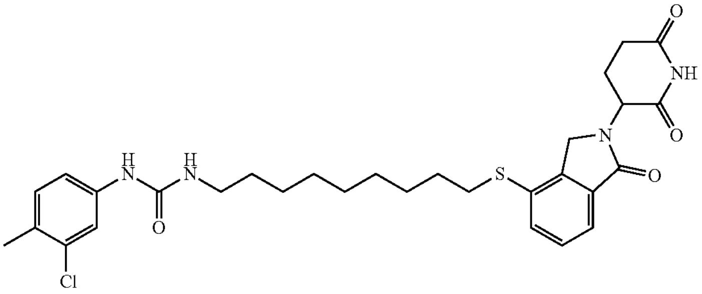 [SMILES: Cc1ccc(NC(=O)NCCCCCCCCCSc2cccc3c2CN(C2CCC(=O)NC2=O)C3=O)cc1Cl] | 1-(3-chloro-4-methylphenyl)-3-(9-((2-(2,6-dioxopiperidin-3-yl)-1-oxoisoindolin-4-yl)thio)nonyl)urea |

TABLE 1-continued

The compounds of the present invention

| Compound No. | Structure of the compounds | The compound's name |
| --- | --- | --- |
| | 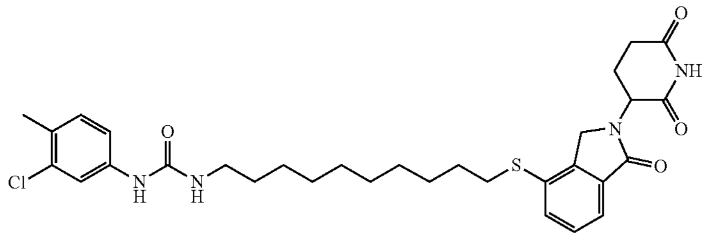 [SMILES: Cc1ccc(NC(=O)NCCCCCCCCCCSc2cccc3c2CN(C2CCC(=O)NC2=O)C3=O)cc1Cl] | 1-(3-chloro-4-methylphenyl)-3-(10-((2-(2,6-dioxopiperidin-3-yl)-1-oxoisoindolin-4-yl)thio)decyl)urea |
| | 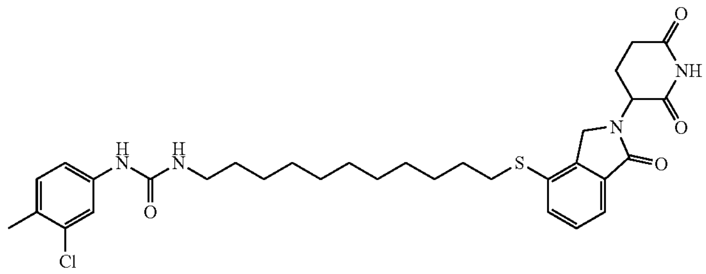 [SMILES: Cc1ccc(NC(=O)NCCCCCCCCCCCSc2cccc3c2CN(C2CCC(=O)NC2=O)C3=O)cc1Cl] | 1-(3-chloro-4-methylphenyl)-3-(11-((2-(2,6-dioxopiperidin-3-yl)-1-oxoisoindolin-4-yl)thio)undecyl)urea |
| SIAIS12161-37B | 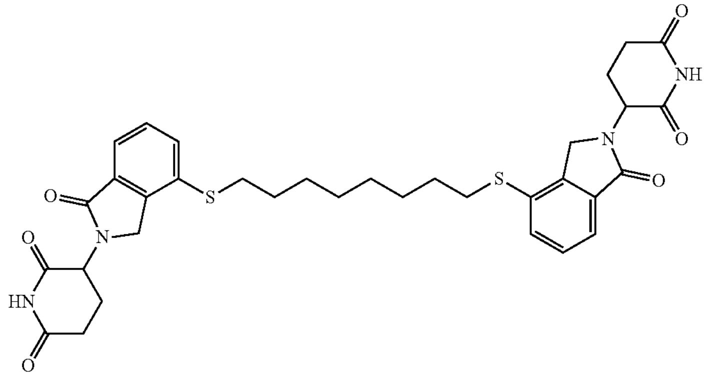 [SMILES: O=C1CCC(N2Cc3c(SCCCCCCCCSc4cccc5c4CN(C4CCC(=O)NC4=O)C5=O)cccc3C2=O)C(=O)N1] | 3,3'-((octane-1,8-diylbis(sulfanediyl))bis(1-oxoisoindoline-4,2-diyl))bis(piperidine-2,6-dione) |
| SIAIS12200-59B | 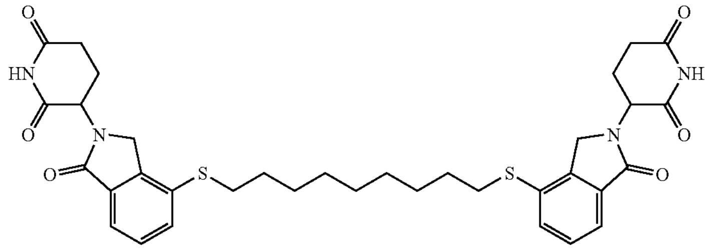 [SMILES: O=C1CCC(N2Cc3c(SCCCCCCCCCSc4cccc5c4CN(C4CCC(=O)NC4=O)C5=O)cccc3C2=O)C(=O)N1] | 3,3'-((nonane-1,9-diylbis(sulfanediyl))bis(1-oxoisoindoline-4,2-diyl))bis(piperidine-2,6-dione) |
| SIAIS12200-61 | 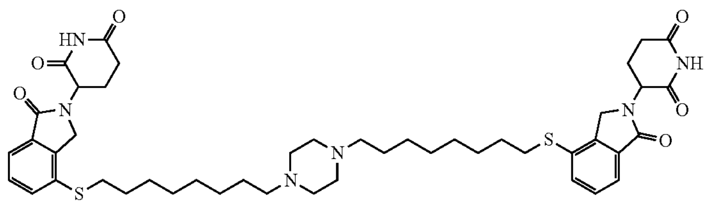 [SMILES: O=C1CCC(N2Cc3c(SCCCCCCCCN4CCN(CCCCCCCCSc5cccc6c5CN(C5CCC(=O)NC5=O)C6=O)CC4)cccc3C2=O)C(=O)N1] | 3,3'-(((piperazine-1,4-diylbis(octane-8,1-diyl))bis(sulfanediyl))bis(1-oxoisoindoline-4,2-diyl))bis(piperidine-2,6-dione) |

TABLE 1-continued

The compounds of the present invention

| Compound No. | Structure of the compounds | The compound's name |
|---|---|---|
| SIAIS12161-31 | 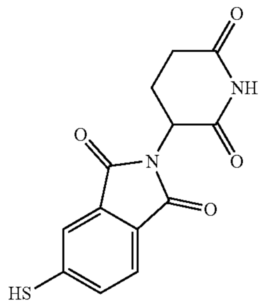 [SMILES: O=C1CCC(N2C(=O)c3ccc(S)cc3C2=O)C(=O)N1] | 2-(2,6-dioxopiperidin-3-yl)-5-mercaptoisoindoline-1,3-dione |
| | 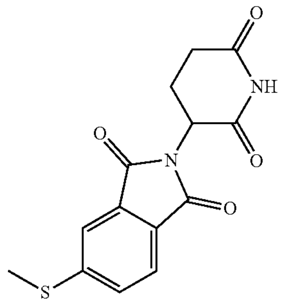 [SMILES: CSc1ccc2c(c1)C(=O)N(C1CCC(=O)NC1=O)C2=O] | 2-(2,6-dioxopiperidin-3-yl)-5-(methylthio)isoindoline-1,3-dione |
| SIAIS12131-75 | 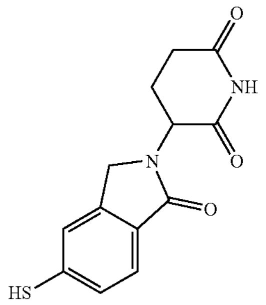 [SMILES: O=C1CCC(N2Cc3cc(S)ccc3C2=O)C(=O)N1] | 3-(5-mercapto-1-oxoisoindolin-2-yl)piperidine-2,6-dione |
| SIAIS12131-11 | 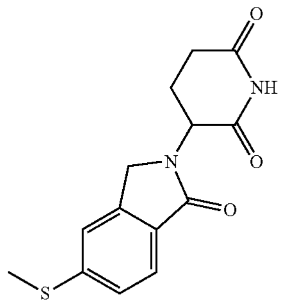 [SMILES: CSc1ccc2c(c1)CN(C1CCC(=O)NC1=O)C2=O] | 3-(5-(methylthio)-1-oxoisoindolin-2-yl)piperidine-2,6-dione |
| SIAIS12131-63 | 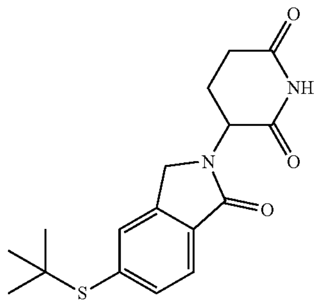 [SMILES: CC(C)(C)Sc1ccc2c(c1)CN(C1CCC(=O)NC1=O)C2=O] | 3-(5-(tert-butylthio)-1-oxoisoindolin-2-yl)piperidine-2,6-dione |

TABLE 1-continued
| The compounds of the present invention | | |
|---|---|---|
| Compound No. | Structure of the compounds | The compound's name |
| SIAIS12131-73 | 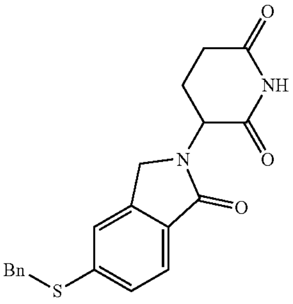 [SMILES: O=C1CCC(N2Cc3cc(SCc4ccccc4)ccc3C2=O)C(=O)N1] | 3-(5-(benzylthio)-1-oxoisoindolin-2-yl)piperidine-2,6-dione |
| | 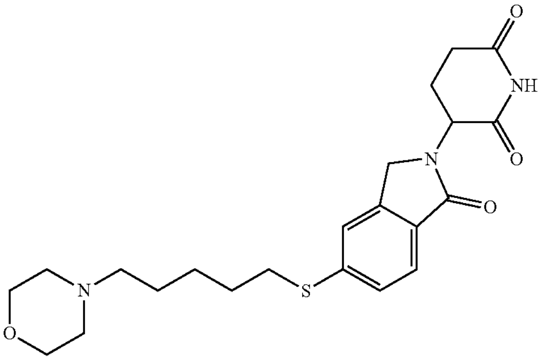 [SMILES: O=C1CCC(N2Cc3cc(SCCCCCN4CCOCC4)ccc3C2=O)C(=O)N1] | 3-(5-((5-morpholinopentyl)thio)-1-oxoisoindolin-2-yl)piperidine-2,6-dione |
| | 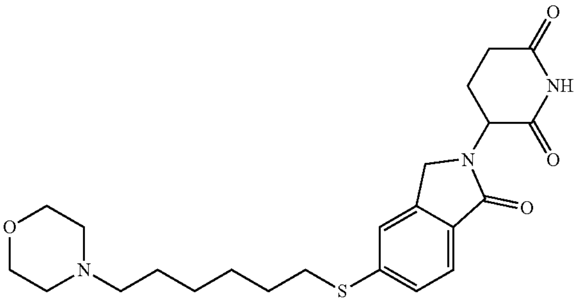 [SMILES: O=C1CCC(N2Cc3cc(SCCCCCCN4CCOCC4)ccc3C2=O)C(=O)N1] | 3-(5-((6-morpholinohexyl)thio)-1-oxoisoindolin-2-yl)piperidine-2,6-dione |
| | 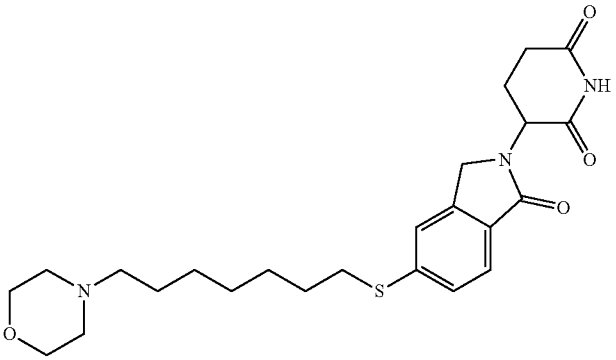 [SMILES: O=C1CCC(N2Cc3cc(SCCCCCCCN4CCOCC4)ccc3C2=O)C(=O)N1] | 3-(5-((7-morpholinoheptyl)thio)-1-oxoisoindolin-2-yl)piperidine-2,6-dione |

TABLE 1-continued

| The compounds of the present invention | | |
|---|---|---|
| Compound No. | Structure of the compounds | The compound's name |
| | 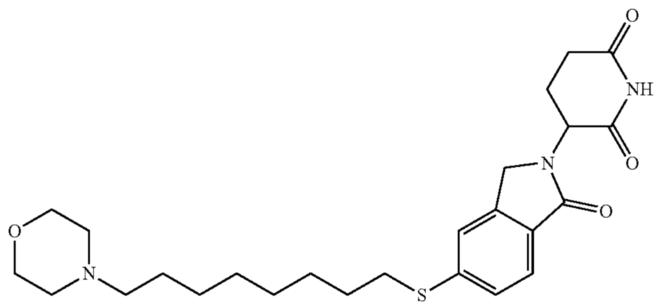 [SMILES: O=C1CCC(N2Cc3cc(SCCCCCCCCN4CCOCC4)ccc3C2=O)C(=O)N1] | 3-(5-((8-morpholinooctyl)thio)-1-oxoisoindolin-2-yl)piperidine-2,6-dione |
| | 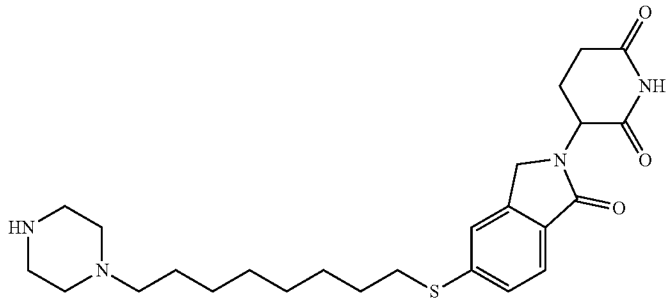 [SMILES: O=C1CCC(N2Cc3cc(SCCCCCCCCN4CCNCC4)ccc3C2=O)C(=O)N1] | 3-(1-oxo-5-((8-(piperazin-1-yl)octyl)thio)isoindolin-2-yl)piperidine-2,6-dione |
| | 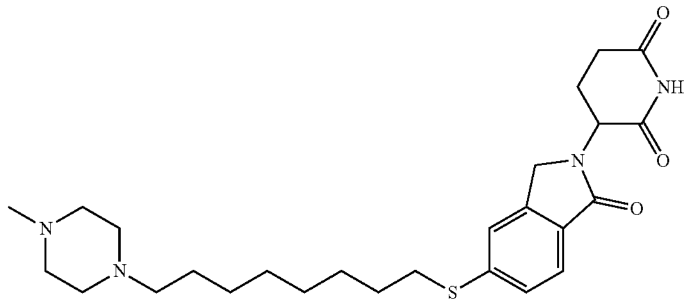 [SMILES: CN1CCN(CCCCCCCCSc2ccc3c(c2)CN(C2CCC(=O)NC2=O)C3=O)CC1] | 3-(5-((8-(4-methylpiperazin-1-yl)octyl)thio)-1-oxoisoindolin-2-yl)piperidine-2,6-dione |
| | 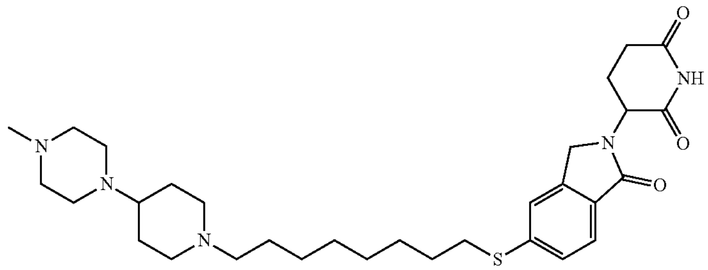 [SMILES: CN1CCN(C2CCN(CCCCCCCCSc3ccc4c(c3)CN(C3CCC(=O)NC3=O)C4=O)CC2)CC1] | 3-(5-((8-(4-(4-methylpiperazin-1-yl)piperidin-1-yl)octyl)thio)-1-oxoisoindolin-2-yl)piperidine-2,6-dione |
| | 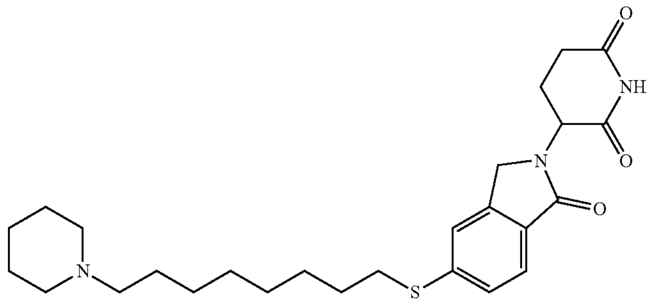 [SMILES: O=C1CCC(N2Cc3cc(SCCCCCCCCN4CCCCC4)ccc3C2=O)C(=O)N1] | 3-(1-oxo-5-((8-(piperidin-1-yl)octyl)thio)isoindolin-2-yl)piperidine-2,6-dione |

TABLE 1-continued

| The compounds of the present invention | | |
|---|---|---|
| Compound No. | Structure of the compounds | The compound's name |
| | 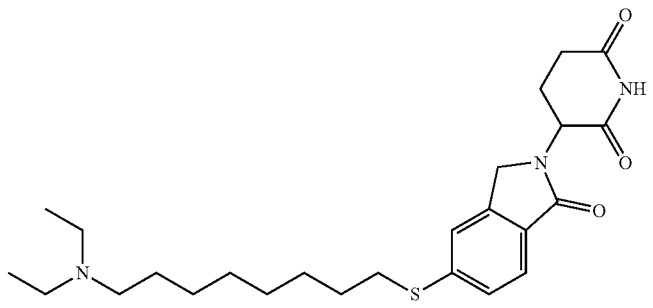 [SMILES: CCN(CC)CCCCCCCCSc1ccc2c(c1)CN(C1CCC(=O)NC1=O)C2=O] | 3-(5-((8-(diethylamino)octyl)thio)-1-oxoisoindolin-2-yl)piperidine-2,6-dione |
| | 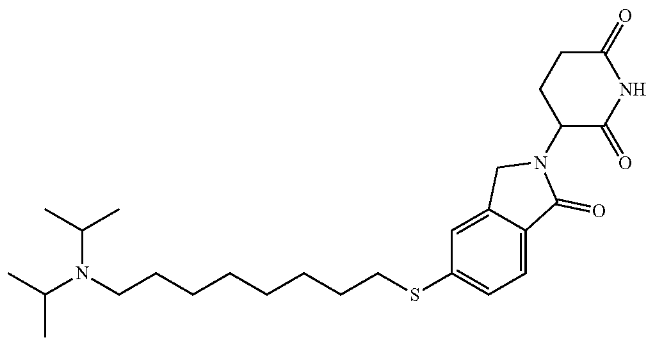 [SMILES: CC(C)N(CCCCCCCCSc1ccc2c(c1)CN(C1CCC(=O)NC1=O)C2=O)C(C)C] | 3-(5-((8-(diisopropylamino)octyl)thio)-1-oxoisoindolin-2-yl)piperidine-2,6-dione |
| | 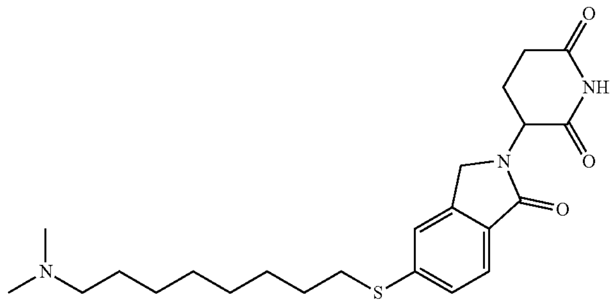 [SMILES: CN(C)CCCCCCCCSc1ccc2c(c1)CN(C1CCC(=O)NC1=O)C2=O] | 3-(5-((8-(dimethylamino)octyl)thio)-1-oxoisoindolin-2-yl)piperidine-2,6-dione |
| | 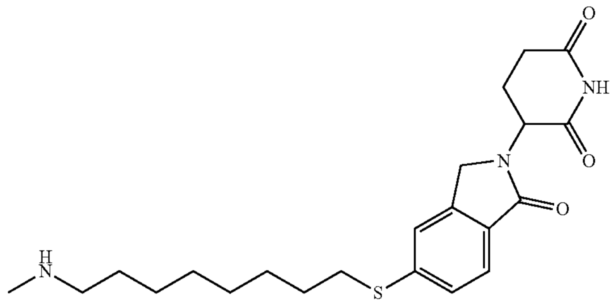 [SMILES: CNCCCCCCCCSc1ccc2c(c1)CN(C1CCC(=O)NC1=O)C2=O] | 3-(5-((8-(methylamino)octyl)thio)-1-oxoisoindolin-2-yl)piperidine-2,6-dione |

TABLE 1-continued

| The compounds of the present invention | | |
|---|---|---|
| Compound No. | Structure of the compounds | The compound's name |
| | 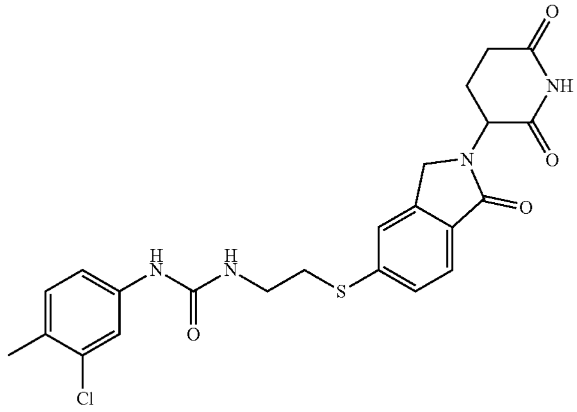 [SMILES: Cc1ccc(NC(=O)NCCSc2ccc3c(c2)CN(C2CCC(=O)NC2=O)C3=O)cc1Cl] | 1-(3-chloro-4-methylphenyl)-3-(2-((2-(2,6-dioxopiperidin-3-yl)-1-oxoisoindolin-5-yl)thio)ethyl)urea |
| | 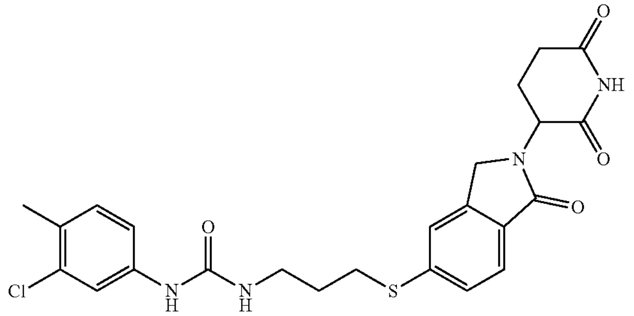 [SMILES: Cc1ccc(NC(=O)NCCCSc2ccc3c(c2)CN(C2CCC(=O)NC2=O)C3=O)cc1Cl] | 1-(3-chloro-4-methylphenyl)-3-(3-((2-(2,6-dioxopiperidin-3-yl)-1-oxoisoindolin-5-yl)thio)propyl)urea |
| | 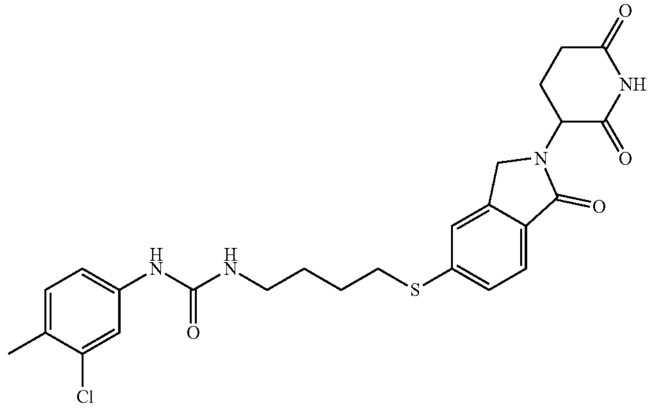 [SMILES: Cc1ccc(NC(=O)NCCCCSc2ccc3c(c2)CN(C2CCC(=O)NC2=O)C3=O)cc1Cl] | 1-(3-chloro-4-methylphenyl)-3-(4-((2-(2,6-dioxopiperidin-3-yl)-1-oxoisoindolin-5-yl)thio)butyl)urea |
| | 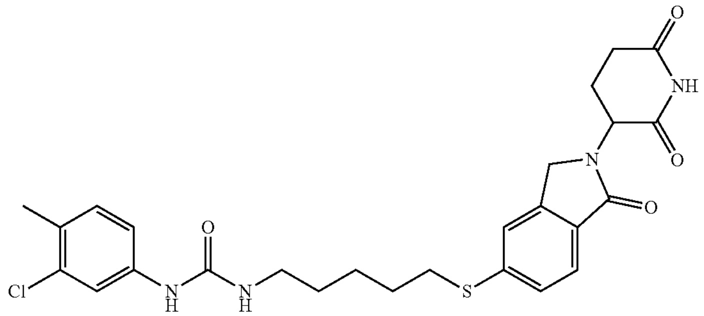 [SMILES: Cc1ccc(NC(=O)NCCCCCSc2ccc3c(c2)CN(C2CCC(=O)NC2=O)C3=O)cc1Cl] | 1-(3-chloro-4-methylphenyl)-3-(5-((2-(2,6-dioxopiperidin-3-yl)-1-oxoisoindolin-5-yl)thio)pentyl)urea |

TABLE 1-continued

| The compounds of the present invention | | |
|---|---|---|
| Compound No. | Structure of the compounds | The compound's name |
| | 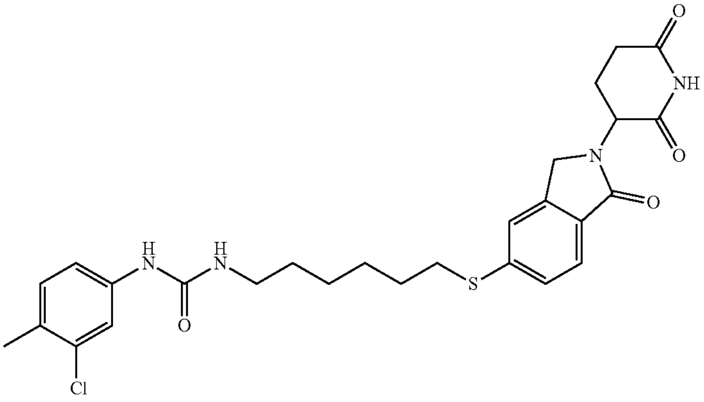 [SMILES: Cc1ccc(NC(=O)NCCCCCCSc2ccc3c(c2)CN(C2CCC(=O)NC2=O)C3=O)cc1Cl] | 1-(3-chloro-4-methylphenyl)-3-(6-((2-(2,6-dioxopiperidin-3-yl)-1-oxoisoindolin-5-yl)thio)hexyl)urea |
| | 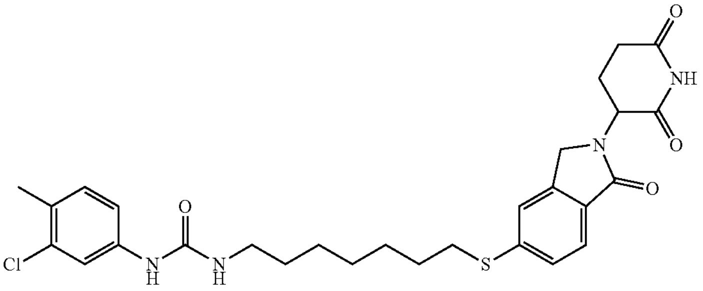 [SMILES: Cc1ccc(NC(=O)NCCCCCCCSc2ccc3c(c2)CN(C2CCC(=O)NC2=O)C3=O)cc1Cl] | 1-(3-chloro-4-methylphenyl)-3-(7-((2-(2,6-dioxopiperidin-3-yl)-1-oxoisoindolin-5-yl)thio)heptyl)urea |
| | 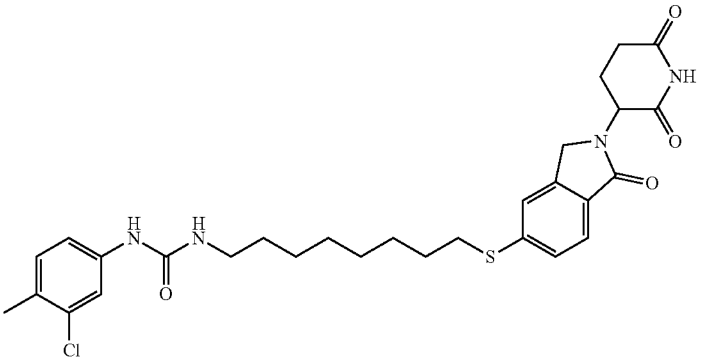 [SMILES: Cc1ccc(NC(=O)NCCCCCCCCSc2ccc3c(c2)CN(C2CCC(=O)NC2=O)C3=O)cc1Cl] | 1-(3-chloro-4-methylphenyl)-3-(8-((2-(2,6-dioxopiperidin-3-yl)-1-oxoisoindolin-5-yl)thio)octyl)urea |
| | 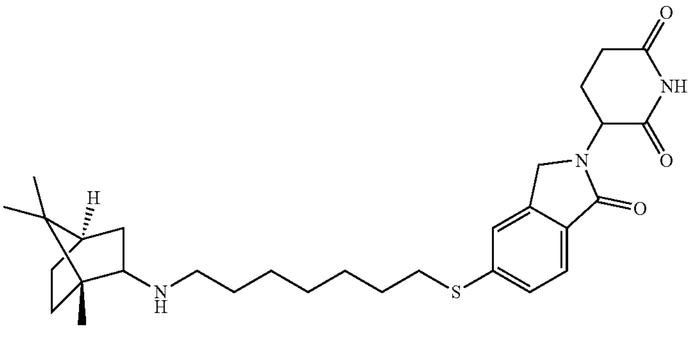 [SMILES: CC1(C)[C@@H]2CC[C@@]1(C)C(NCCCCCCCSc1ccc3c(c1)CN(C1CCC(=O)NC1=O)C3=O)C2] | 3-(1-oxo-5-((7-(((1R,2S,4R)-1,7,7-trimethylbicyclo[2.2.1]heptan-2-yl)amino)heptyl)thio)isoindolin-2-yl)piperidine-2,6-dione |

TABLE 1-continued

| The compounds of the present invention | | |
|---|---|---|
| Compound No. | Structure of the compounds | The compound's name |
| | 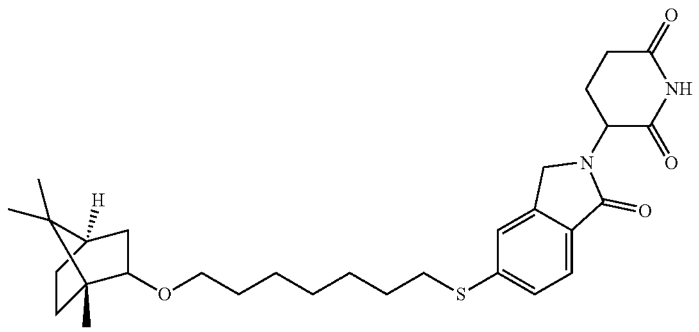 [SMILES: CC1(C)[C@@H]2CC[C@@]1(C)C(OCCCCCCCSc1ccc3c(c1)CN(C1CCC(=O)NC1=O)C3=O)C2] | 3-(1-oxo-5-((7-(((1R,2S,4R)-1,7,7-trimethylbicyclo[2.2.1]heptan-2-yl)oxy)heptyl)thio)isoindolin-2-yl)piperidine-2,6-dione |
| | 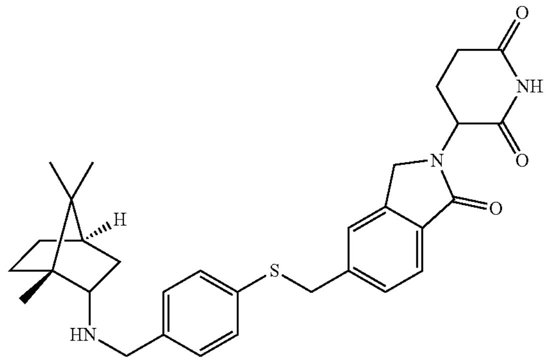 [SMILES: CC1(C)[C@@H]2CC[C@@]1(C)C(NCc1ccc(SCc3ccc4c(c3)CN(C3CCC(=O)NC3=O)C4=O)cc1)C2] | 3-(1-oxo-5-((4-((((1R,2S,4R)-1,7,7-trimethylbicyclo[2.2.1]heptan-2-yl)amino)methyl)benzyl)thio)iso-indolin-2-yl)piperidine-2,6-dione |
| | 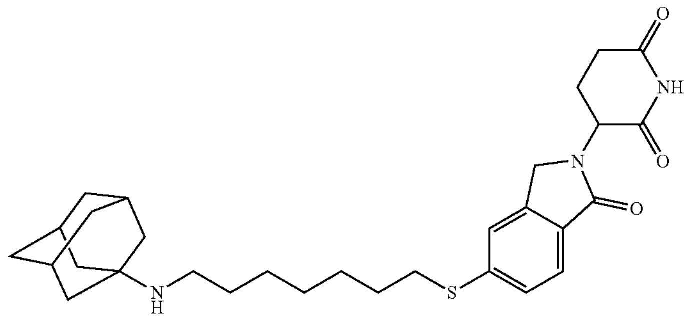 [SMILES: O=C1CCC(N2Cc3cc(SCCCCCCCNC45CC6CC(CC(C6)C4)C5)ccc3C2=O)C(=O)N1] | 3-(5-((7-((adamantan-1-yl)amino)heptyl)thio)-1-oxoisoindolin-2-yl)piperidine-2,6-dione |
| | 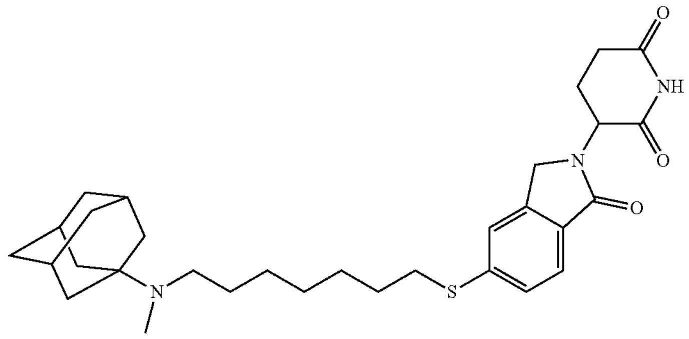 [SMILES: CN(CCCCCCCSc1ccc2c(c1)CN(C1CCC(=O)NC1=O)C2=O)C12CC3CC(CC(C3)C1)C2] | 3-(5-((7-((adamantan-1-yl)(methyl)amino)heptyl)thio)-1-oxoisoindolin-2-yl)piperidine-2,6-dione |

TABLE 1-continued

| The compounds of the present invention | | |
|---|---|---|
| Compound No. | Structure of the compounds | The compound's name |
| | 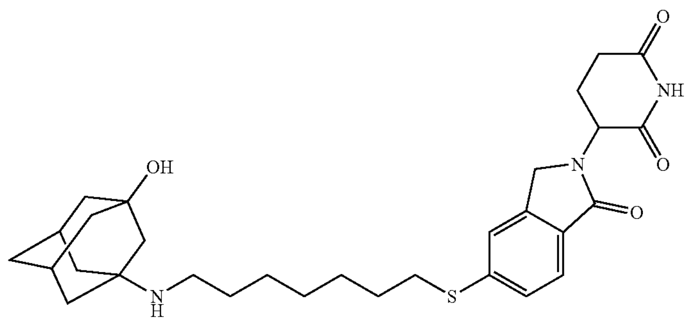 [SMILES: O=C1CCC(N2Cc3cc(SCCCCCCCNC45CC6CC(CC(O)(C6)C4)C5)ccc3C2=O)C(=O)N1] | 3-(5-((7-((3-hydroxyadamantan-1-yl)amino)heptyl)thio)-1-oxoisoindolin-2-yl)piperidine-2,6-dione |
| | 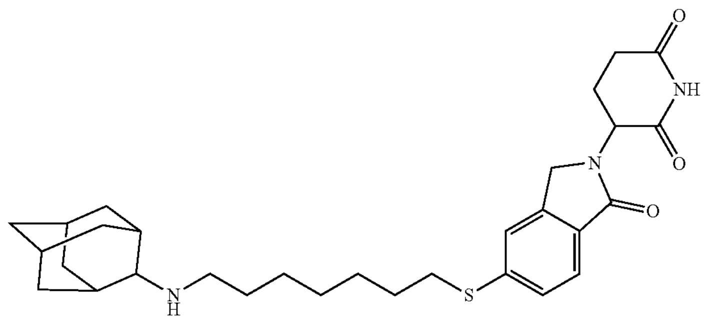 [SMILES: O=C1CCC(N2Cc3cc(SCCCCCCCNC4C5CC6CC(C5)CC4C6)ccc3C2=O)C(=O)N1] | 3-(5-((7-((adamantan-2-yl)amino)heptyl)thio)-1-oxoisoindolin-2-yl)piperidine-2,6-dione |
| | 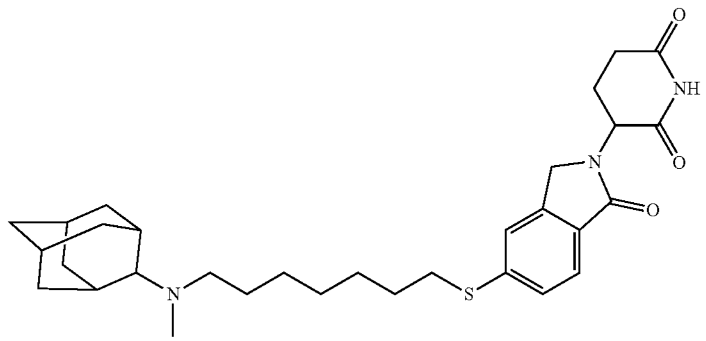 [SMILES: CN(CCCCCCCSc1ccc2c(c1)CN(C1CCC(=O)NC1=O)C2=O)C1C2CC3CC(C2)CC1C3] | 3-(5-((7-((adamantan-2-yl)(methyl)amino)heptyl)thio)-1-oxoisoindolin-2-yl)piperidine-2,6-dione |
| | 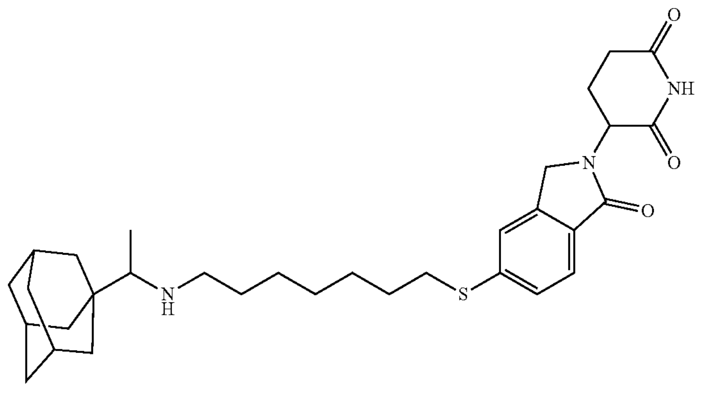 [SMILES: CC(NCCCCCCCSc1ccc2c(c1)CN(C1CCC(=O)NC1=O)C2=O)C12CC3CC(CC(C3)C1)C2] | 3-(5-((7-((1-(adamantan-1-yl)ethyl)amino)heptyl)thio)-1-oxoisoindolin-2-yl)piperidine-2,6-dione |

TABLE 1-continued
| The compounds of the present invention | | |
|---|---|---|
| Compound No. | Structure of the compounds | The compound's name |
| | 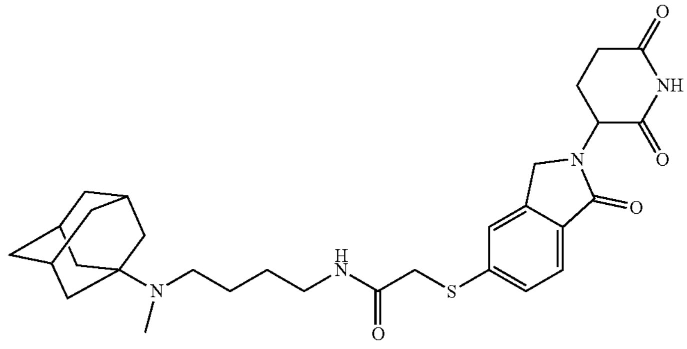 [SMILES: CN(CCCCNC(=O)CSc1ccc2c(c1)CN(C1CCC(=O)NC1=O)C2=O)C12CC3CC(CC(C3)C1)C2] | N-(4-((adamantan-1-yl)(methyl)amino)butyl)-2-((2-(2,6-dioxopiperidin-3-yl)-1-oxoisoindolin-5-yl)thio)acetamide |
| | 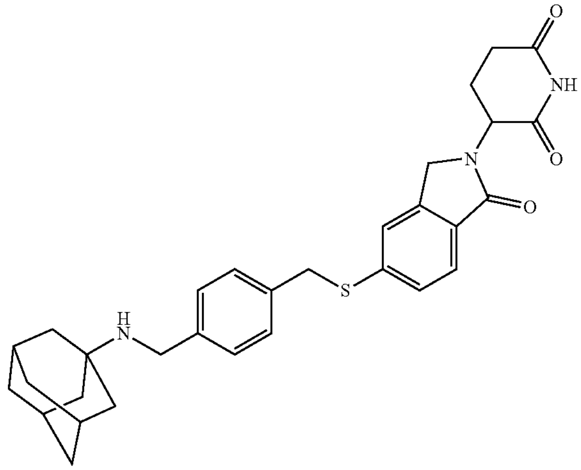 [SMILES: O=C1CCC(N2Cc3cc(SCc4ccc(CNC56CC7CC(CC(C7)C5)C6)cc4)ccc3C2=O)C(=O)N1] | 3-(5-((4-(((adamantan-1-yl)amino)methyl)benzyl)thio)-1-oxoisoindolin-2-yl)piperidine-2,6-dione |
| | 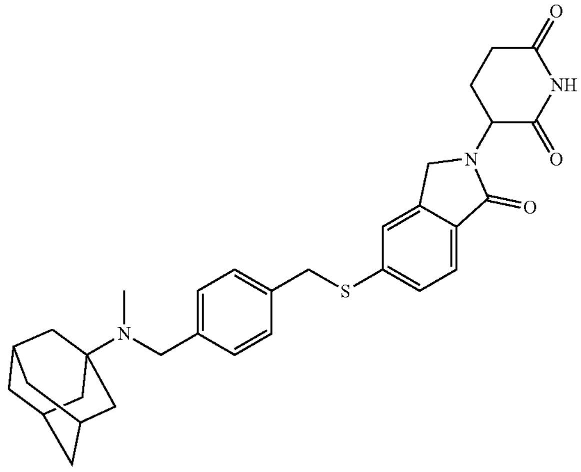 [SMILES: CN(Cc1ccc(CSc2ccc3c(c2)CN(C2CCC(=O)NC2=O)C3=O)cc1)C12CC3CC(CC(C3)C1)C2] | 3-(5-((4-(((adamantan-1-yl)(methyl)amino)methyl)benzyl)thio)-1-oxoisoindolin-2-yl)piperidine-2,6-dione |

TABLE 1-continued

| The compounds of the present invention | | |
|---|---|---|
| Compound No. | Structure of the compounds | The compound's name |
| | 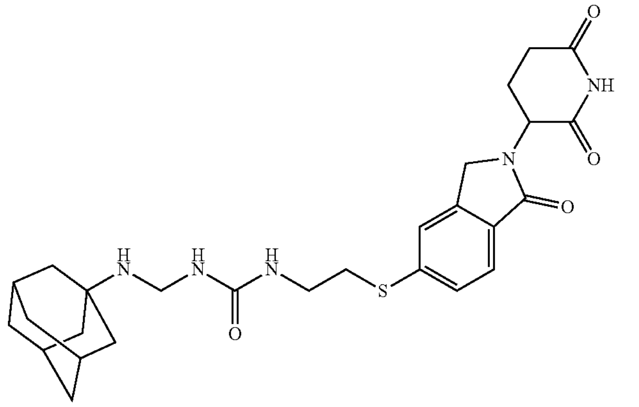 [SMILES: O=C1CCC(N2Cc3cc(SCCNC(=O)NCNC45CC6CC(CC(C6)C4)C5)ccc3C2=O)C(=O)N1] | 1-(((adamantan-1-yl)amino)methyl)-3-(2-((2-(2,6-dioxopiperidin-3-yl)-1-oxoisoindolin-5-yl)thio)ethyl)urea |
| | 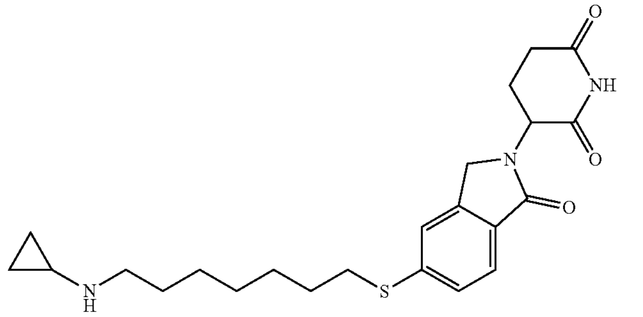 [SMILES: O=C1CCC(N2Cc3cc(SCCCCCCCNC4CC4)ccc3C2=O)C(=O)N1] | 3-(5-((7-(cyclopropylamino)heptyl)thio)-1-oxoisoindolin-2-yl)piperidine-2,6-dione |
| | 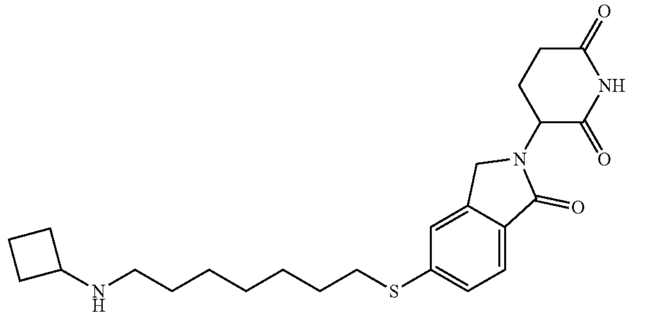 [SMILES: O=C1CCC(N2Cc3cc(SCCCCCCCNC4CCC4)ccc3C2=O)C(=O)N1] | 3-(5-((7-(cyclobutylamino)heptyl)thio)-1-oxoisoindolin-2-yl)piperidine-2,6-dione |
| | 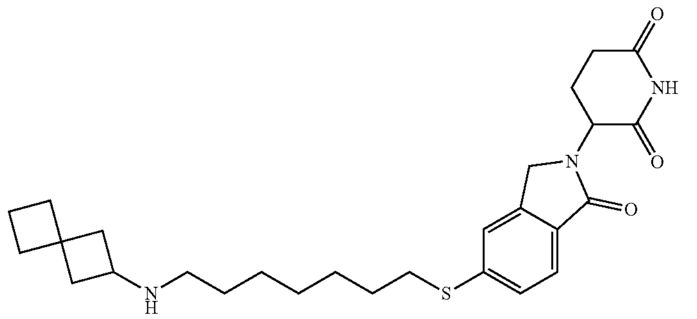 [SMILES: O=C1CCC(N2Cc3cc(SCCCCCCCNC4CC5(CCC5)C4)ccc3C2=O)C(=O)N1] | 3-(1-oxo-5-((7-(spiro[3.3]heptan-2-ylamino)heptyl)thio)isoindolin-2-yl)piperidine-2,6-dione |

TABLE 1-continued

| The compounds of the present invention | | |
|---|---|---|
| Compound No. | Structure of the compounds | The compound's name |
| | 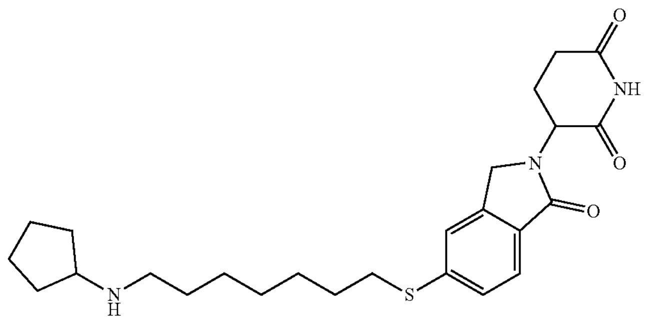 [SMILES: O=C1CCC(N2Cc3cc(SCCCCCCCNC4CCCC4)ccc3C2=O)C(=O)N1] | 3-(5-((7-(cyclopentylamino)heptyl)thio)-1-oxoisoindolin-2-yl)piperidine-2,6-dione |
| | 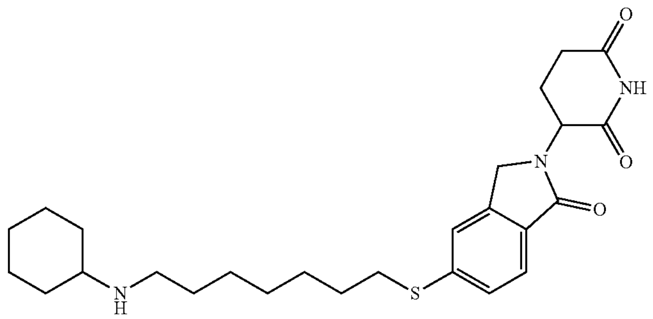 [SMILES: O=C1CCC(N2Cc3cc(SCCCCCCCNC4CCCCC4)ccc3C2=O)C(=O)N1] | 3-(5-((7-(cyclohexylamino)heptyl)thio)-1-oxoisoindolin-2-yl)piperidine-2,6-dione |
| | 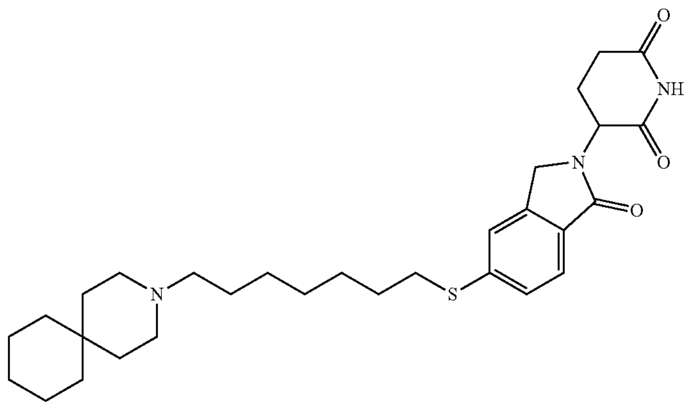 [SMILES: O=C1CCC(N2Cc3cc(SCCCCCCCN4CCC5(CCCCC5)CC4)ccc3C2=O)C(=O)N1] | 3-(5-((7-(3-azaspiro[5.5]undecan-3-yl)heptyl)thio)-1-oxoisoindolin-2-yl)piperidine-2,6-dione |
| | 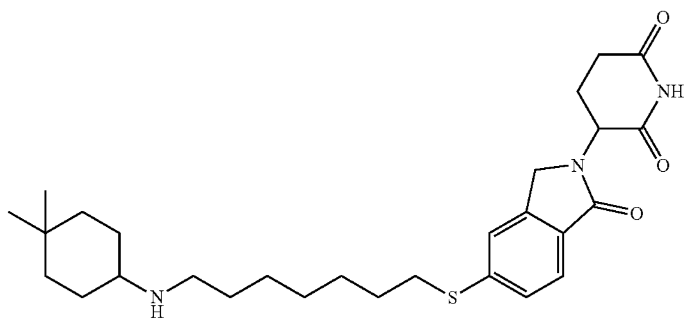 [SMILES: CC1(C)CCC(NCCCCCCCSc2ccc3c(c2)CN(C2CCC(=O)NC2=O)C3=O)CC1] | 3-(5-((7-((4,4-dimethylcyclohexyl)amino)heptyl)thio)-1-oxoisoindolin-2-yl)piperidine-2,6-dione |

TABLE 1-continued

| The compounds of the present invention | | |
|---|---|---|
| Compound No. | Structure of the compounds | The compound's name |
| | 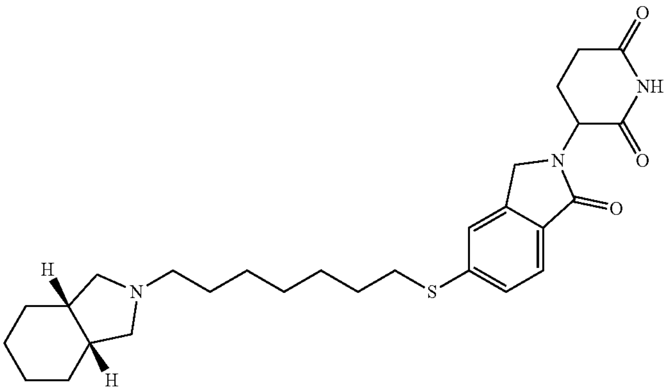 [SMILES: O=C1CCC(N2Cc3cc(SCCCCCCCN4C[C@H]5CCCC[C@H]5C4)ccc3C2=O)C(=O)N1] | 3-(5-((7-((3aR,7aS)-octahydro-2H-isoindol-2-yl)heptyl)thio)-1-oxoisoindolin-2-yl)piperidine-2,6-dione |
| SIAIS12210-75 | 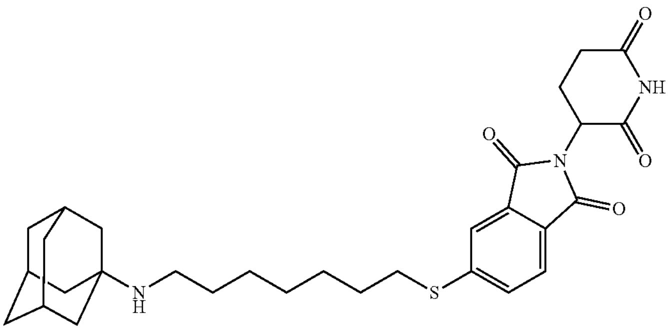 [SMILES: O=C1CCC(N2C(=O)c3ccc(SCCCCCCCNC45CC6CC(CC(C6)C4)C5)cc3C2=O)C(=O)N1] | 5-((7-((adamantan-1-yl)amino)heptyl)thio)-2-(2,6-dioxopiperidin-3-yl)isoindoline-1,3-dione |
| SIAIS27116-7 | 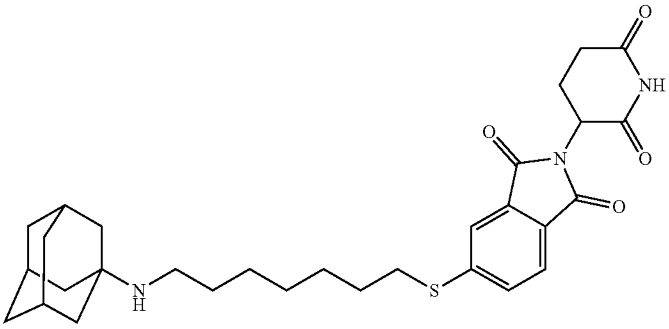 [SMILES: O=C1CCC(N2C(=O)c3ccc(SCCCCCCCNC45CC6CC(CC(C6)C4)C5)cc3C2=O)C(=O)N1] | 3-(5-((7-((adamantan-1-yl)amino)heptyl)thio)-1-oxoisoindolin-2-yl)piperidine-2,6-dione |
| SIAIS31312-3 | 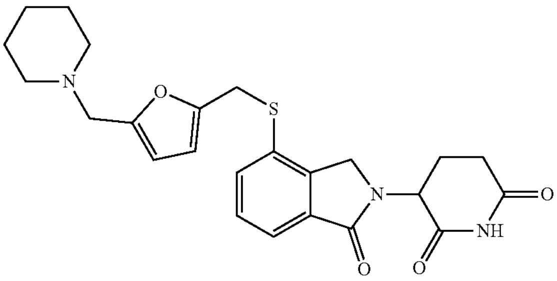 [SMILES: O=C1CCC(N2Cc3c(SCc4ccc(CN5CCCCC5)o4)cccc3C2=O)C(=O)N1] | 3-(1-oxo-4-(((5-(piperidin-1-ylmethyl)furan-2-yl)methyl)thio)isoindolin-2-yl)piperidine-2,6-dione |

TABLE 1-continued

| The compounds of the present invention | | |
|---|---|---|
| Compound No. | Structure of the compounds | The compound's name |
| SIAIS31312-6 | 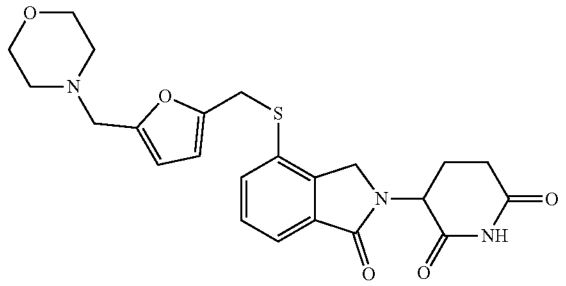 [SMILES: O=C1CCC(N2Cc3c(SCc4ccc(CN5CCOCC5)o4)cccc3C2=O)C(=O)N1] | 3-(4-(((5-(morpholinomethyl)furan-2-yl)methyl)thio)-1-oxoisoindolin-2-yl)piperidine-2,6-dione |
| SIAIS31312-9 | 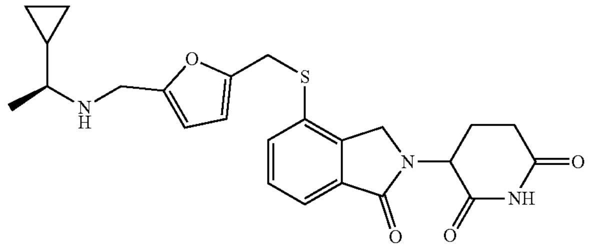 [SMILES: C[C@H](NCc1ccc(CSc2cccc3c2CN(C2CCC(=O)NC2=O)C3=O)o1)C1CC1] | 3-(4-(((5-((((S)-1-cyclopropylethyl)amino)methyl) furan-2-yl)methyl)thio)-1-oxoisoindolin-2-yl)piperidine-2,6-dione |
| SIAIS31313-5 | 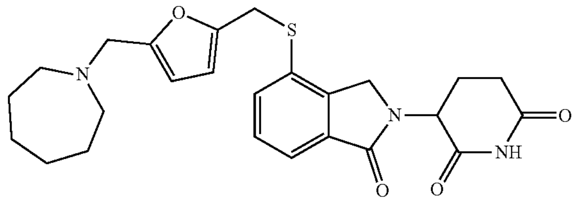 [SMILES: O=C1CCC(N2Cc3c(SCc4ccc(CN5CCCCCC5)o4)cccc3C2=O)C(=O)N1] | 3-(4-(((5-(azepan-1-ylmethyl)furan-2-yl)methyl)thio)-1-oxoisoindolin-2-yl)piperidine-2,6-dione |
| SIAIS31314-8 | 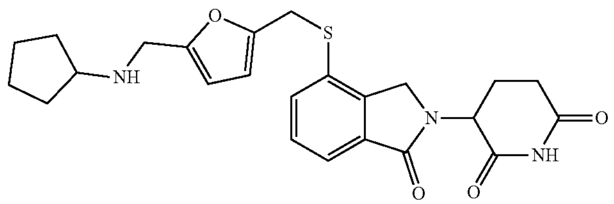 [SMILES: O=C1CCC(N2Cc3c(SCc4ccc(CNC5CCCC5)o4)cccc3C2=O)C(=O)N1] | 3-(4-(((5-((cyclopentylamino)methyl)furan-2-yl)methyl)thio)-1-oxoisoindolin-2-yl)piperidine-2,6-dione |
| SIAIS31314-9 | 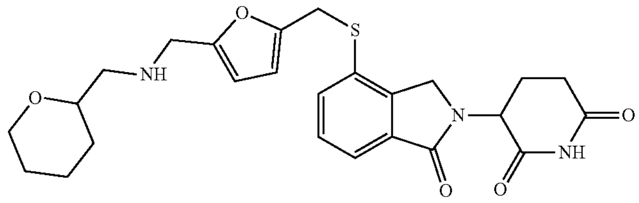 [SMILES: O=C1CCC(N2Cc3c(SCc4ccc(CNCC5CCCCO5)o4)cccc3C2=O)C(=O)N1] | 3-(1-oxo-4-(((5-((((tetrahydro-2H-pyran-2-yl)methyl)amino)methyl)furan-2-yl)methyl)thio)isoindolin-2-yl)piperidine-2,6-dione |
| SIAIS31315-0 | 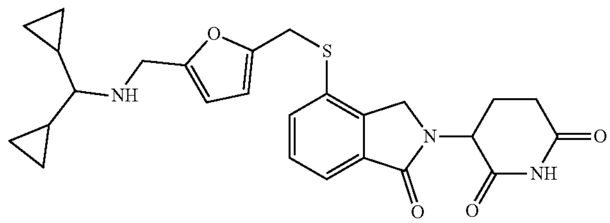 [SMILES: O=C1CCC(N2Cc3c(SCc4ccc(CNC(C5CC5)C5CC5)o4)cccc3C2=O)C(=O)N1] | 3-(4-(((5-(((dicyclopropylmethyl)amino) methyl)furan-2-yl)methyl)thio)-1-oxoisoindolin-2-yl)piperidine-2,6-dione |

TABLE 1-continued

The compounds of the present invention

| Compound No. | Structure of the compounds | The compound's name |
|---|---|---|
| SIAIS31316-3 | 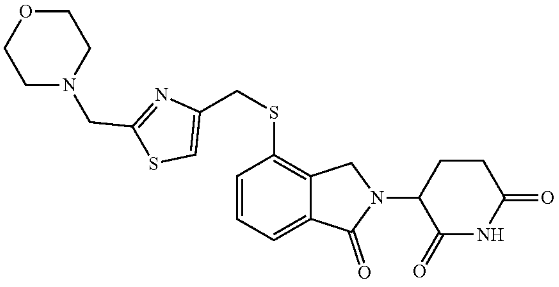 [SMILES: O=C1CCC(N2Cc3c(SCc4csc(CN5CCOCC5)n4)cccc3C2=O)C(=O)N1] | 3-(4-(((2-(morpholinomethyl)thiazol-4-yl)methyl)thio)-1-oxoisoindolin-2-yl)piperidine-2,6-dione |
| SIAIS31316-4 | 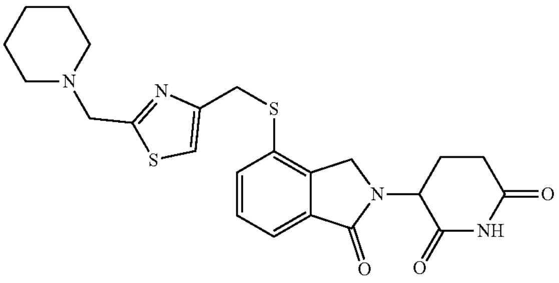 [SMILES: O=C1CCC(N2Cc3c(SCc4csc(CN5CCCCC5)n4)cccc3C2=O)C(=O)N1] | 3-(1-oxo-4-(((2-(piperidin-1-ylmethyl)thiazol-4-yl)methyl)thio)isoindolin-2-yl)piperidine-2,6-dione |
| SIAIS31316-5 | 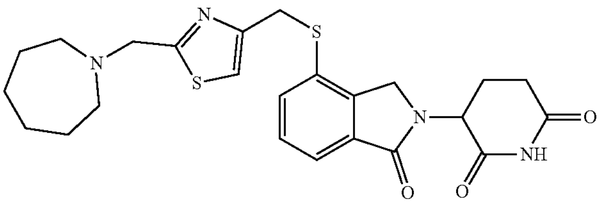 [SMILES: O=C1CCC(N2Cc3c(SCc4csc(CN5CCCCCC5)n4)cccc3C2=O)C(=O)N1] | 3-(4-(((2-(azepan-1-ylmethyl)thiazol-4-yl)methypthio)-1-oxoisoindolin-2-yl)piperidine-2,6-dione |
| SIAIS31316-6 | 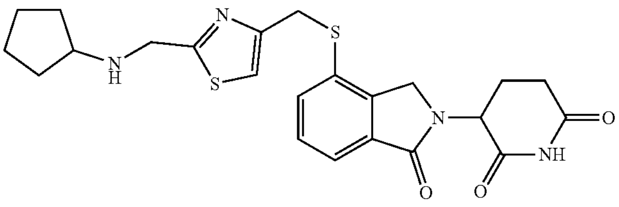 [SMILES: O=C1CCC(N2Cc3c(SCc4csc(CNC5CCCC5)n4)cccc3C2=O)C(=O)N1] | 3-(4-(((2-((cyclopentylamino)methyl)thiazol-4-yl)methyl)thio)-1-oxoisoindolin-2-yl)piperidine-2,6-dione |
| SIAIS31316-9 | 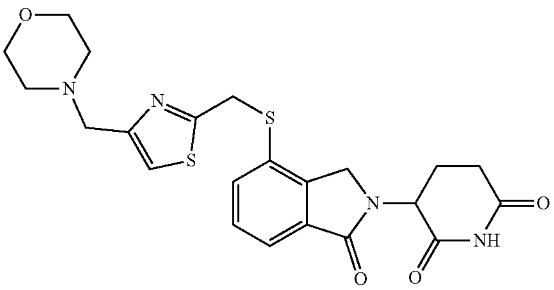 [SMILES: O=C1CCC(N2Cc3c(SCc4nc(CN5CCOCC5)cs4)cccc3C2=O)C(=O)N1] | 3-(4-(((4-(morpholinomethyl)thiazol-2-yl)methyl)thio)-1-oxoisoindolin-2-yl)piperidine-2,6-dione |

TABLE 1-continued

| The compounds of the present invention | | |
|---|---|---|
| Compound No. | Structure of the compounds | The compound's name |
| SIAIS31317-0 | 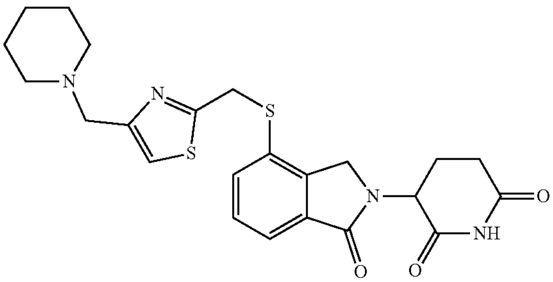 [SMILES: O=C1CCC(N2Cc3c(SCc4nc(CN5CCCCC5)cs4)cccc3C2=O)C(=O)N1] | 3-(1-oxo-4-(((4-(piperidin-1-ylmethyl)thiazol-2-yl)methyl)thio)isoindolin-2-yl)piperidine-2,6-dione |
| SIAIS31317-1 | 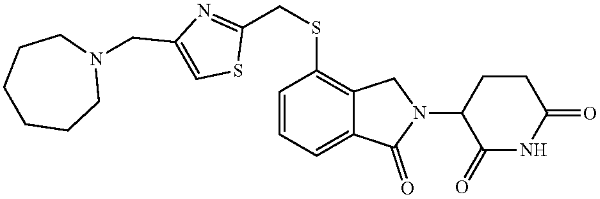 [SMILES: O=C1CCC(N2Cc3c(SCc4nc(CN5CCCCCC5)cs4)cccc3C2=O)C(=O)N1] | 3-(4-(((4-(azepan-1-ylmethyl)thiazol-2-yl)methyl)thio)-1-oxoisoindolin-2-yl)piperidine-2,6-dione |
| SIAIS31318-6 | 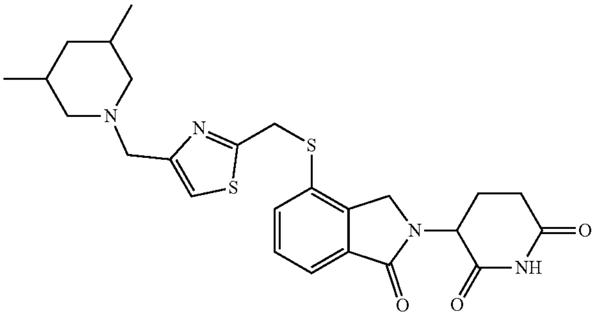 [SMILES: CC1CC(C)CN(Cc2csc(CSc3cccc4c3CN(C3CCC(=O)NC3=O)C4=O)n2)C1] | 3-(4-(((4-((3,5-dimethylpiperidin-1-yl)methyl)thiazol-2-yl)methyl)thio)-1-oxoisoindolin-2-yl)piperidine-2,6-dione |
| SIAIS31318-8 | 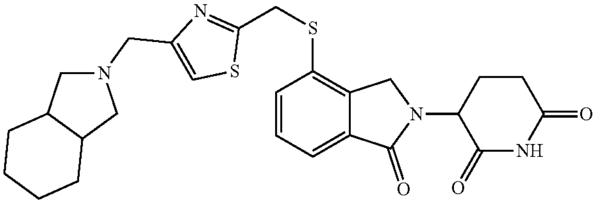 [SMILES: O=C1CCC(N2Cc3c(SCc4nc(CN5CC6CCCCC6C5)cs4)cccc3C2=O)C(=O)N1] | 3-(4-(((4-((hexahydro-1H-isoindol-2(3H)-yl)methyl)thiazol-2-yl)methyl)thio)-1-oxoisoindolin-2-yl)piperidine-2,6-dione |
| SIAIS35500-1 | 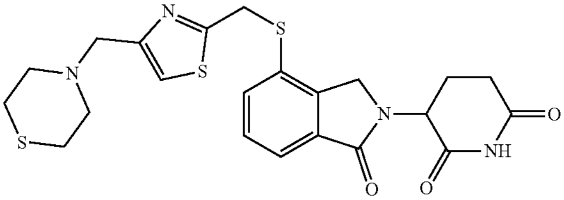 [SMILES: O=C1CCC(N2Cc3c(SCc4nc(CN5CCSCC5)cs4)cccc3C2=O)C(=O)N1] | 3-(1-oxo-4-(((4-(thiomorpholinomethyl)thiazol-2-yl)methyl)thio)isoindolin-2-yl)piperidine-2,6-dione |
| SIAIS35500-2 | 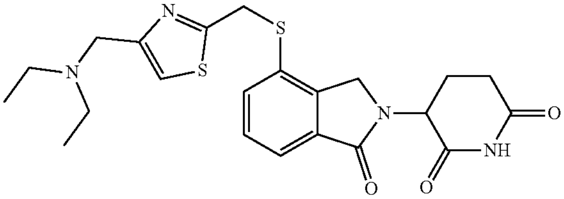 [SMILES: CCN(CC)Cc1csc(CSc2cccc3c2CN(C2CCC(=O)NC2=O)C3=O)n1] | 3-(4-(((4-((diethylamino)methypthiazol-2-yl)methyl)thio)-1-oxoisoindolin-2-yl)piperidine-2,6-dione |

TABLE 1-continued

| The compounds of the present invention | | |
|---|---|---|
| Compound No. | Structure of the compounds | The compound's name |
| SIAIS35500-3 | 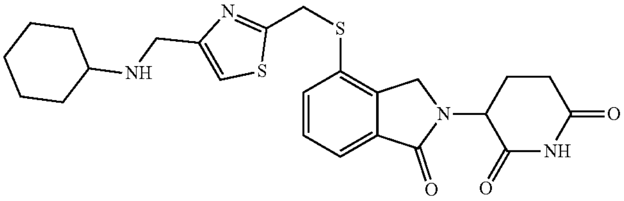 [SMILES: O=C1CCC(N2Cc3c(SCc4nc(CNC5CCCCC5)cs4)cccc3C2=O)C(=O)N1] | 3-(4-(((4-((cyclohexylamino)methyl)thiazol-2-yl)methyl)thio)-1-oxoisoindolin-2-yl)piperidine-2,6-dione |
| SIAIS35500-4 | 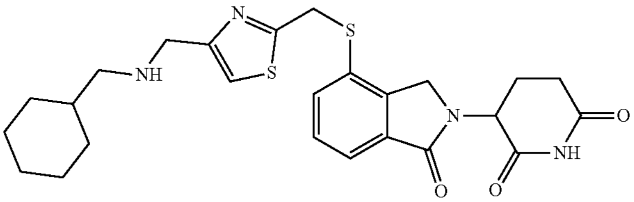 [SMILES: O=C1CCC(N2Cc3c(SCc4nc(CNCC5CCCCC5)cs4)cccc3C2=O)C(=O)N1] | 3-(4-(((4-(((cyclohexylmethyl)amino)methyl)thiazol-2-yl)methyl)thio)-1-oxoisoindolin-2-yl)piperidine-2,6-dione |
| SIAIS35507-4 | 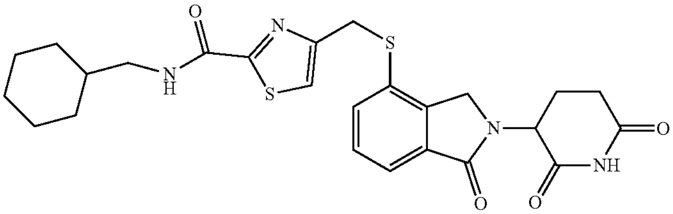 [SMILES: O=C1CCC(N2Cc3c(SCc4csc(C(=O)NCC5CCCCC5)n4)cccc3C2=O)C(=O)N1] | N-(cyclohexylmethyl)-4-(((2-(2,6-dioxopiperidin-3-yl)-1-oxoisoindolin-4-yl)thio)methyl)thiazole-2-carboxamide |
| SIAIS12281-37 | 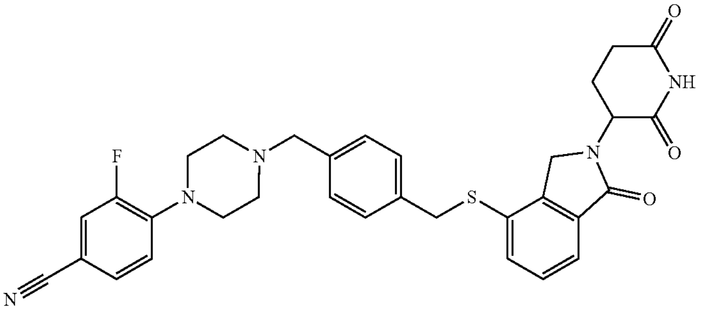 [SMILES: N#Cc1ccc(N2CCN(Cc3ccc(CSc4cccc5c4CN(C4CCC(=O)NC4=O)C5=O)cc3)CC2)c(F)c1] | 4-(4-(4-(((2-(2,6-dioxopiperidin-3-yl)-1-oxoisoindolin-4-yl)thio)methyl)benzyl)piperazin-1-yl)-3-fluorobenzonitrile |
| SIAIS12281-41 | 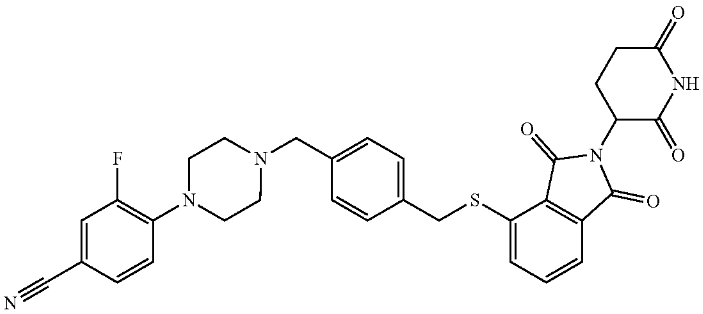 [SMILES: N#Cc1ccc(N2CCN(Cc3ccc(CSc4cccc5c4C(=O)N(C4CCC(=O)NC4=O)C5=O)cc3)CC2)c(F)c1] | 4-(4-(4-(((2-(2,6-dioxopiperidin-3-yl)-1,3-dioxoisoindolin-4-yl)thio)methyl)benzyl)piperazin-1-yl)-3-fluorobenzonitrile |
| SIAIS12281-43 | 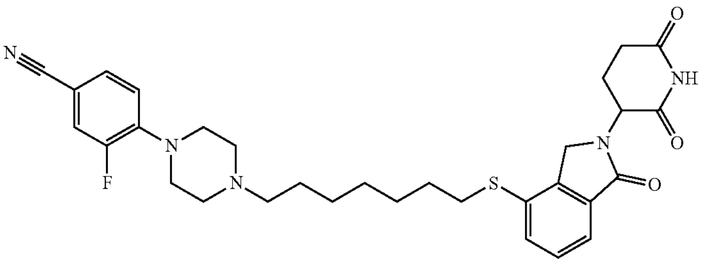 [SMILES: N#Cc1ccc(N2CCN(CCCCCCCSc3cccc4c3CN(C3CCC(=O)NC3=O)C4=O)CC2)c(F)c1] | 4-(4-(7-((2-(2,6-dioxopiperidin-3-yl)-1-oxoisoindolin-4-yl)thio)heptyl)piperazin-1-yl)-3-fluorobenzonitrile |

TABLE 1-continued

| Compound No. | Structure of the compounds | The compound's name |
|---|---|---|
| The compounds of the present invention | | |
| SIAIS12281-45 | 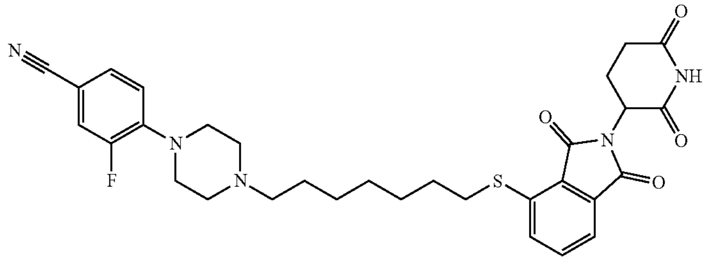 [SMILES: N#Cc1ccc(N2CCN(CCCCCCCSc3cccc4c3C(=O)N(C3CCC(=O)NC3=O)C4=O)CC2)c(F)c1] | 4-(4-(7-((2-(2,6-dioxopiperidin-3-yl)-1,3-dioxoisoindolin-4-yl)thio)heptyl)piperazin-1-yl)-3-fluorobenzonitrile |
| SIAIS12281-51 | 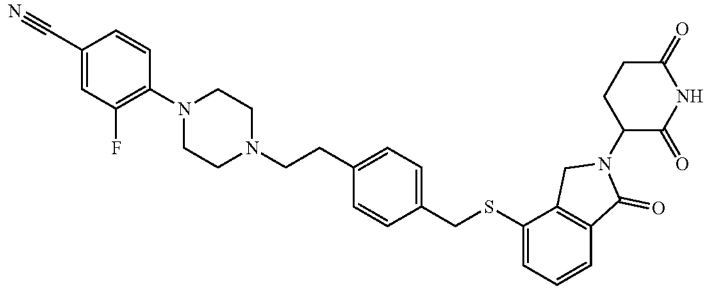 [SMILES: N#Cc1ccc(N2CCN(CCc3ccc(CSc4cccc5c4CN(C4CCC(=O)NC4=O)C5=O)cc3)CC2)c(F)c1] | 4-(4-(4-(((2-(2,6-dioxopiperidin-3-yl)-1-oxoisoindolin-4-yl)thio)methyl)phenethyl)piperazin-1-yl)-3-fluorobenzonitrile |
| SIAIS12280-55 | 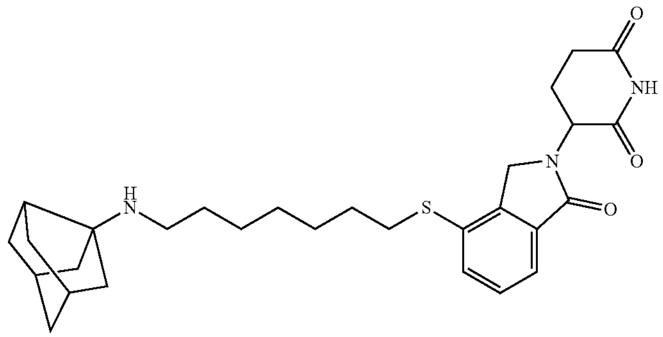 [SMILES: O=C1CCC(N2Cc3c(SCCCCCCCNC45CC6CC(CC4C6)C5)cccc3C2=O)C(=O)N1] | 3-(4-((7-((hexahydro-2,5-methanopentalen-3a(1H)-yl)amino)heptyl)thio)-1-oxoisoindolin-2-yl)piperidine-2,6-dione |
| SIAIS12280-19 | 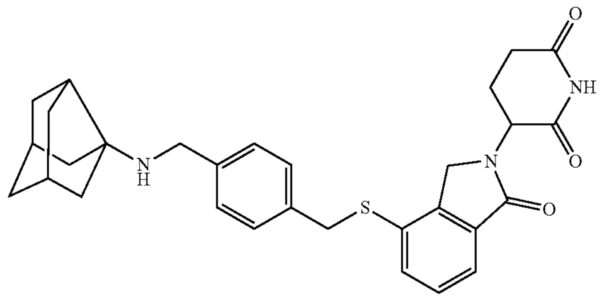 [SMILES: O=C1CCC(N2Cc3c(SCc4ccc(CNC56CC7CC(CC5C7)C6)cc4)cccc3C2=O)C(=O)N1] | 3-(4-((4-(((hexahydro-2,5-methanopentalen-3a(1H)-yl)amino)methyl)benzyl)thio)-1-oxoisoindolin-2-yl)piperidine-2,6-dione |
| SIAIS12280-59 | 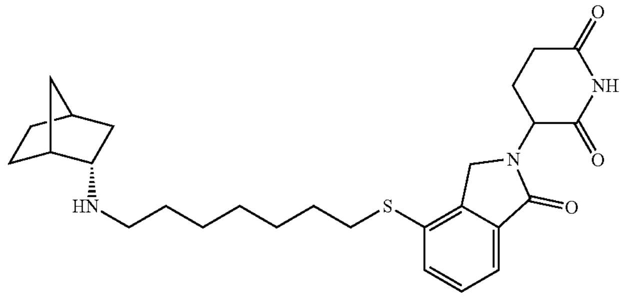 [SMILES: O=C1CCC(N2Cc3c(SCCCCCCCN[C@H]4CC5CCC4C5)cccc3C2=O)C(=O)N1] | 3-(4-((7-(((1R,2S,4S)-bicyclo[2.2.1]heptan-2-yl)amino)heptyl)thio)-1-oxoisoindolin-2-yl)piperidine-2,6-dione |

It is to be understood that the compounds of Formula (I), (Ia), (Ib), (Ic), (Id) or (I') of the present disclosure may have a stereo configuration and can therefore exist in more than one stereoisomer form. The present disclosure also relates to compounds of Formula (I) having a stereo configuration in pure or substantially pure isomeric form, e.g., greater than about 9000 enantiomeric/diastereomeric excess ("ee"), such as greater than about 9500 ee or 9700 ee, or greater than about 9900 ee, and mixtures thereof, including racemic mixtures. The purification of said isomers and the separation of said isomeric mixtures may be achieved by standard techniques known in the art, for example, asymmetric synthesis (e.g., by using chiral intermediates) and/or chiral resolution and the like.

In another aspect, the present disclosure also provides a pharmaceutical composition comprising:

as an active ingredient, the compound of Formula (I) according to the present disclosure or a pharmaceutically acceptable salt, a racemate, an enantiomer, a diastereomer, a solvate or a polymorph thereof, or the compound of Formula (P') according to the present disclosure or a pharmaceutically acceptable salt, a racemate, an enantiomer, a diastereomer, a solvate or a polymorph thereof; and a pharmaceutically acceptable carrier.

The pharmaceutical composition of the present disclosure further includes at least one additional therapeutic agent for treating or preventing a cancer or tumor.

In an embodiment of the present disclosure, the cancer or tumor includes, but is not limited to, multiple myeloma, myelodysplastic syndrome (MDS), previously treated myelodysplastic syndrome, plasma cell myeloma, transplantation-related cancer, myelofibrosis, plasma cell myeloma, bone marrow disease, neutropenia, leukemia, acute myeloid leukemia, anemia, chronic myelogenous leukemia, B-cell chronic lymphocytic leukemia, acute myeloid leukemia (AML), CD20 positive, primary lymphoma, B-cell lymphoma, recurrent B-cell non-Hodgkin's lymphoma, recurrent diffuse large B-cell lymphoma, recurrent primary mediastinal (thymus) large B-cell lymphoma, relapsed transformed non-Hodgkin's lymphoma, refractory B-cell non-Hodgkin's lymphoma, refractory diffuse large B-cell lymphoma, refractory primary mediastinal (thymus) large B-cell lymphoma, refractory transformed non-Hodgkin's lymphoma, smoldering myeloma, smoldering multiple myeloma, and Unverricht syndrome.

The pharmaceutical composition containing the active ingredient according to the present disclosure can be Formulated into any suitable Formulations such as sprays, patches, tablets, capsules, dragees, troches, powders, granules, powder injections, or liquid Formulations (such as suspensions, solutions, emulsions, or syrups) and the like, depending upon a suitable route of administration (including, but not limited to, nasal administration, inhalation administration, topical administration, oral administration, oral mucosal administration, rectal administration, intrapleural administration, intraperitoneal administration, vaginal administration, intramuscular administration, subcutaneous administration, transdermal administration, epidural administration, intrathecal administration, and intravenous administration).

In another aspect of the present disclosure, the compound of Formula (I) according to the present disclosure, or a pharmaceutically acceptable salt, racemate, enantiomer, diastereomer, solvate or polymorph thereof, is for use as a medicament.

In another aspect of the present disclosure, the compound of Formula (I) of the present disclosure, or a pharmaceutically acceptable salt, a racemate, a enantiomer, a diastereomer, a solvate, or a polymorph thereof, is useful for preventing and/or treating a cancer or tumor. In an embodiment of the present disclosure, the cancer or tumor includes, but is not limited to, multiple myeloma, myelodysplastic syndrome (MDS), previously treated myelodysplastic syndrome, plasma cell myeloma, transplantation-related cancer, myelofibrosis, plasma cell myeloma, bone marrow disease, neutropenia, leukemia, acute myeloid leukemia, anemia, chronic myelogenous leukemia, B-cell chronic lymphocytic leukemia, acute myeloid leukemia (AML), CD20 positive, primary lymphoma, B-cell lymphoma, recurrent B-cell non-Hodgkin's lymphoma, recurrent diffuse large B-cell lymphoma, recurrent primary mediastinal (thymus) large B-cell lymphoma, relapsed transformed non-Hodgkin's lymphoma, refractory B-cell non-Hodgkin's lymphoma, refractory diffuse large B-cell lymphoma, refractory primary mediastinal (thymus) large B-cell lymphoma, refractory transformed non-Hodgkin's lymphoma, smoldering myeloma, smoldering multiple myeloma, and Unverricht syndrome.

Another aspect of the present disclosure provides the use of the compound of Formula (I) or the compound of Formula (I') of the present disclosure, or a pharmaceutically acceptable salt, a racemate, an enantiomer, a diastereomer, a solvate, or a polymorph thereof, for the manufacture of a medicament for the prevention and/or treatment of a cancer or a tumor. In an embodiment of the present disclosure, the cancer or tumor includes, but is not limited to, multiple myeloma, myelodysplastic syndrome (MDS), previously treated myelodysplastic syndrome, plasma cell myeloma, transplantation-related cancer, myelofibrosis, plasma cell myeloma, bone marrow disease, neutropenia, leukemia, acute myeloid leukemia, anemia, chronic myelogenous leukemia, B-cell chronic lymphocytic leukemia, acute myeloid leukemia (AML), CD20 positive, primary lymphoma, B-cell lymphoma, recurrent B-cell non-Hodgkin's lymphoma, recurrent diffuse large B-cell lymphoma, recurrent primary mediastinal (thymus) large B-cell lymphoma, relapsed transformed non-Hodgkin's lymphoma, refractory B-cell non-Hodgkin's lymphoma, refractory diffuse large B-cell lymphoma, refractory primary mediastinal (thymus) large B-cell lymphoma, refractory transformed non-Hodgkin's lymphoma, smoldering myeloma; smoldering multiple myeloma, and Unverricht syndrome.

A further aspect of the present disclosure also provides a method for treating or preventing a cancer or a tumor comprising administering to a subject a therapeutically effective amount of the compound of Formula (I) or the compound of Formula (I') of the present disclosure, or a pharmaceutically acceptable salt, a racemate, an enantiomer, a diastereomer, a solvate, or a polymorph thereof, or the pharmaceutical composition of the present disclosure.

In an embodiment of the present disclosure, in the method for treating or preventing a cancer or a tumor of the present disclosure, the cancer or tumor includes, but is not limited to, multiple myeloma, myelodysplastic syndrome (MDS), previously treated myelodysplastic syndrome, plasma cell myeloma, transplantation-related cancer, myelofibrosis, plasma cell myeloma, bone marrow disease, neutropenia, leukemia, acute myeloid leukemia, anemia, chronic myelogenous leukemia, B-cell chronic lymphocytic leukemia, acute myeloid leukemia (AML), CD20 positive, primary lymphoma, B-cell lymphoma, recurrent B-cell non-Hodgkin's lymphoma, recurrent diffuse large B-cell lymphoma, recurrent primary mediastinal (thymus) large B-cell lymphoma, relapsed transformed non-Hodgkin's lymphoma, refractory B-cell non-Hodgkin's lymphoma, refractory diffuse large B-cell lymphoma, refractory primary mediastinal (thymus) large B-cell lymphoma, refractory transformed non-Hodgkin's lymphoma, smoldering myeloma, smoldering multiple myeloma, and Unverricht syndrome.

In the method for treating or preventing a cancer or a tumor of the present disclosure, the compound of Formula (I) or the compound of Formula (I') of the present disclosure, or a pharmaceutically acceptable salt, a racemate, an enantiomer, a diastereomer, a solvate, or a polymorph thereof, or the pharmaceutical composition of the present disclosure is administered to the subject by at least one mode of administration selected from: nasal, inhalation, topical, oral, oral mucosal, rectal, pleural, peritoneal, vaginal, intramuscular, subcutaneous, transdermal, epidural, intrathecal, and intravenous administration.

Definition

Unless otherwise specified, the following terms, phrases, and symbols used herein generally have the meanings as described below.

Herein, the general Formula (I) and the following general Formula (I-1) can be used interchangeably, Formula (I-1)

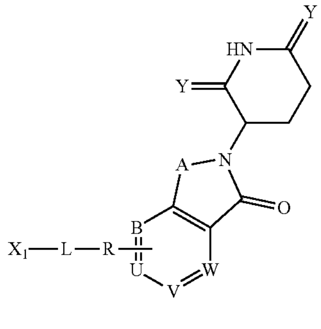

where A, B, U, V, W, R, L, $X_1$, and Y and all substituents are as defined in Formula (I). In the same way, Formula (Ia), Formula (Ib), Formula (Ic), Formula (Id), and Formula (Ie) can be used interchangeably with their respective general Formulas obtained by flipping 180 degrees respectively.

Herein, the general Formula (I') and the following general Formula (I'-1) can be used interchangeably, Formula (I'-1)

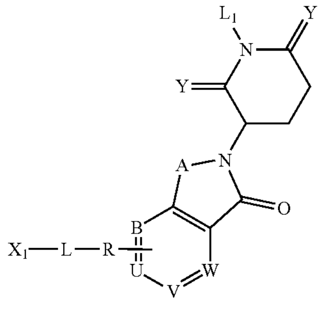

where A, B, U, V, W, R, L, $X_1$, $L_1$, and Y and all substituents are as defined in Formula (I').

As used herein, the singular forms "a", "an", and "the" include plural forms unless the context clearly dictates otherwise.

Herein, a bond interrupted by the wavy line shows the point of attachment of the depicted group to the rest of the molecule. For example, the group of Formula ($G_1$) depicted below

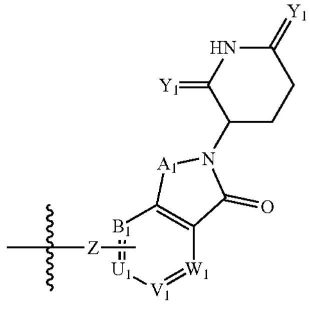

means that group Z of the chemical moiety represented by Formula ($G_1$) is covalently bonded to the group L of the compound of Formula (I).

Although the symbol "*" in the group L herein indicates the point of attachment of the group L to the group R, the present disclosure also covers embodiments where the symbol "*" in the group L represents indicates the point of attachment of the group L to the group $X_1$.

As used herein, the term "halogen atom" or "halogen" used alone or in combination refers to fluorine, chlorine, bromine, or iodine, and preferably F, Cl, or Br.

As used herein, the term "alkyl" used alone or in combination refers to a linear or branched alkyl group. The term "($C_x$-$C_y$) alkyl" or "$C_{x-y}$ alkyl" (x and y are each an integer) refers to a linear or branched chain alkyl group containing from x to y carbon atoms. The term "$C_{1-10}$ alkyl" used alone or in combination in the present disclosure refers to a linear or branched chain alkyl group containing from 1 to 10 carbon atoms. The $C_{1-10}$ alkyl group of the present disclosure is preferably a $C_{1-9}$ alkyl group, more preferably a $C_{1-8}$ alkyl group, still more preferably a $C_{2-8}$ alkyl group, more preferably a $C_{1-7}$ alkyl group, even more preferably a $C_{1-6}$ alkyl, $C_{1-5}$ alkyl, or $C_{1-4}$ alkyl. Representative examples include, but are not limited to, methyl, ethyl, n-propyl, isopropyl, n-butyl, isobutyl, sec-butyl, tert-butyl, pentyl, isopentyl, neopentyl, tert-pentyl, hexyl, heptyl, octyl, nonyl, and decyl. The term "$C_{1-3}$ alkyl group" in the present disclosure refers to an alkyl group containing from 1 to 3 carbon atoms, and its representative examples include methyl, ethyl, n-propyl, and isopropyl. As used herein, the "alkyl" is optionally substituted, and the substituent can be one or more selected from halogen, cyano, $C_{1-3}$ alkyl, $C_{1-3}$ alkoxy, trifluoromethyl, heterocyclyl, or any combination thereof.

As used herein, the term "alkylene" (which is used interchangeably with "alkylene chain") used alone or in combination refers to a linear or branched divalent saturated hydrocarbon group composed of carbon and hydrogen atoms. The term "$C_x$-$C_y$ alkylene" or "$C_{x-y}$ alkylene" (x and y are each an integer) refers to a linear or branched alkylene group containing from x to y carbon atoms. The $C_1$-$C_{30}$ alkylene group in the present disclosure is preferably $C_1$-$C_{29}$ alkylene, $C_1$-$C_{28}$ alkylene, $C_1$-$C_{27}$ alkylene, $C_1$-$C_{26}$ alkylene, $C_1$-$C_{25}$ alkylene, $C_1$-$C_{24}$ alkylene, $C_1$-$C_{23}$ alkylene, $C_1$-$C_{22}$ alkylene, $C_1$-$C_{21}$ alkylene, $C_1$-$C_{20}$ alkylene, $C_1$-$C_{19}$ alkylene, $C_1$-$C_{18}$ alkylene, $C_1$-$C_{17}$ alkylene, $C_1$-$C_{16}$ alkylene, $C_1$-$C_{15}$ alkylene, $C_1$-$C_{14}$ alkylene, $C_1$-$C_{13}$ alkylene, $C_1$-$C_{12}$ alkylene, $C_1$-$C_{11}$ alkylene, $C_1$-$C_{10}$ alkylene, $C_1$-$C_9$ alkylene, $C_1$-$C_8$ alkylene, $C_1$-$C_7$ alkylene, $C_1$-$C_6$ alkylene, $C_1$-$C_5$ alkylene, $C_1$-$C_4$ alkylene, $C_1$-$C_3$ alkylene, or $C_1$-$C_2$ alkylene. Representative examples include, but are not limited to, methylene, ethylene, propylene, isopropylidene, butylene, isobutylene, sec-butylene, tert-butylene, n-pentylene, isopentylene, neopentylene, tert-pentylene, hexylene, heptylene, octylene, nonylene, decylene, undecylene, dodecylene, tridecylene, tetradecylene, pentadecylene, hexadecylene, heptadecylene, octadecylene, nonadecylene, eicosylene, heneicosylene, docosylene, tricosylene, tetracosylene, pentacosylene, hexacosylene, peptacosylene, octacosylene, nonacosylene, and triacontylene. As used herein, the "alkylene" is optionally substituted, and the substituent can be one or more selected from halogen, cyano, $C_{1-3}$ alkyl, $C_{1-3}$ alkoxy, trifluoromethyl, heterocyclyl, or any combination thereof.

As used herein, the term "aryl" used alone or in combination refers to a aromatic hydrocarbon group containing from 5 to 14 carbon atoms and optionally one or more fused rings, such as phenyl group, naphthyl group, or fluorenyl group. As used herein, the "aryl" is optionally substituted. A substituted aryl group refers to an aryl group optionally substituted from 1 to 3 times with a substituent(s), wherein the substituent(s) is preferably selected from $C_{1-6}$ alkyl (e.g., $C_{1-3}$ alkyl), haloalkenyl, halogenated $C_{1-3}$ alkoxy, cyano, $C_{1-3}$ alkoxy, halogenated $C_{1-3}$ alkyl (e.g., trifluoromethyl), heterocyclyl, halogen, amino, or hydroxyl.

As used herein, the term "arylene" used alone or in combination refers to a divalent aromatic hydrocarbon group containing from 5 to 14 carbon atoms and optionally one or more fused rings, such as phenylene group, naphthylene group or fluorenylene group. As used herein, the "arylene" is an optionally substituted arylene. A substituted arylene group refers to an arylene group optionally substituted 1-3 times with a substituent(s), wherein the substituent(s) is selected from $C_{1-3}$ alkyl, haloalkenyl, halogenated $C_{1-3}$ alkoxy, cyano, $C_{1-3}$ alkoxy, halogenated $C_{1-3}$ alkyl (e.g., trifluoromethyl), heterocyclyl, halogen, amino, and hydroxyl.

As used herein, the term "alkoxy" used alone or in combination refers to a linear or branched alkoxy group having the Formula of —O-alkyl. Preferably, the alkyl of the alkoxy may contain 1-10 carbon atoms. Representative examples of "alkoxy" include, but are not limited to, methoxy, ethoxy, propoxy, isopropoxy, n-butoxy, isobutoxy, tert-butoxy, pentoxy, 2-pentyloxy, isopentyloxy, neopentyloxy, hexyloxy, 2-hexyloxy, 3-hexyloxy, 3-methylpentyloxy, etc. The term "$C_1$-$C_3$ alkoxy" or "$C_{1-3}$ alkoxy" used alone or in combination refers to a linear or branched alkoxy group containing from 1 to 3 carbon atoms. Representative examples of $C_{1-3}$ alkoxy include, but are not limited to, methoxy, ethoxy, n-propoxy, and isopropoxy. Preferred are methoxy and ethoxy.

As used herein, the term "cycloalkyl" used alone or in combination refers to a saturated or partially unsaturated (i.e., containing one or more double bonds, but not having a fully conjugated 71-electron system) monocyclic or bicyclic or polycyclic cyclic hydrocarbon radical having from 3 to 12 carbon atoms (e.g., from 3 to 12, from 3 to 11, from 3 to 10, from 3 to 8, from 3 to 7, from 3 to 6). The term "$C_3$-$C_{10}$ cycloalkyl" used alone or in combination refers to a saturated or partially unsaturated (i.e., containing one or more double bonds, but not having a fully conjugated π-electron system) monocyclic or bicyclic or polycyclic cyclic hydrocarbon radical having from 3 to 10 carbon atoms. The term "cycloalkyl" comprises monocyclic or bicyclic or tricyclic cyclic hydrocarbon radical having from 3 to 12 carbon atoms. Representative examples of monocyclic cycloalkyl include, but are not limited to, cyclopropyl, cyclobutyl, cyclopentyl, cyclopentenyl, cyclohexyl, cyclohexenyl, cycloheptyl, and cyclooctyl. The bicyclic and tricyclic cycloalkyl may include fused cyclic hydrocarbon group, bridged cyclic hydrocarbon group, or spiro cyclic hydrocarbon group, for example, but are not limited to, decalinyl, octahydropentalenyl, octahydro-1H-indenyl, 2,3-dihydro-1H-indenyl, spiro-cycloalkyl, adamantanyl, nordamantanyl, norcamphanyl (also named as bicyclo[2.2.1]heptanyl by IUPAC system). In the present disclosure, the "cycloalkyl" is optionally mono- or multi-substituted, and includes, but is not limited to, 2,2-, 2,3-, 2,4-, 2,5-, or 2,6-disubstituted cyclohexyl. The substituent(s) of the substituted "cycloalkyl" is/are preferably one or more selected from halogen, cyano, $C_{1-3}$ alkyl, $C_{1-3}$ alkoxy, halogenated $C_{1-3}$ alkyl (e.g. trifluoromethyl), amino, hydroxyl, heterocyclyl, or any combination thereof.

As used herein, the term "cycloalkylene" used alone or in combination refers to a saturated or partially unsaturated (i.e., containing one or more double bonds, but not having a fully conjugated 71-electron system) divalent monocyclic or bicyclic or polycyclic cyclic hydrocarbon radical having from 3 to 12 carbon atoms (e.g., from 3 to 12, from 3 to 11, from 3 to 10, from 3 to 8, from 3 to 7, from 3 to 6). The term "$C_3$-$C_{10}$ cycloalkylene" used alone or in combination refers to a saturated or partially unsaturated (i.e., containing one or more double bonds, but not having a fully conjugated 71-electron system) divalent monocyclic or bicyclic or polycyclic cyclic hydrocarbon radical having from 3 to 10 carbon atoms. The term "cycloalkylene" comprises divalent monocyclic or bicyclic or tricyclic cyclic hydrocarbon radical having from 3 to 12 carbon atoms. Representative examples of monocyclic cycloalkylene include, but are not limited to, cyclopropylene, cyclobutylene, cyclopentylene, cyclopentenylene, cyclohexylene, cyclohexenylene, cycloheptylene, and cyclooctylene. The bicyclic and tricyclic cycloalkylene may include divalent bridged cyclic hydrocarbon group, divalent fused cyclic hydrocarbon group, or divalent spiro cyclic hydrocarbon group, for example, but are not limited to, decalinylene, octahydropentalenylene, octahydro-1H-indenylene, 2,3-dihydro-1H-indenylene, spiro-cycloalkylene, adamantanylene, nordamantanylene, norcamphanylene (also named as bicyclo[2.2.1]heptanylene by IUPAC system). In the present disclosure, the "cycloalkylene" is optionally mono- or multi-substituted, and includes, but is not limited to, 2,2-, 2,3-, 2,4-, 2,5-, or 2,6-disubstituted cyclohexylene. The substituent(s) of the substituted "cycloalkylene" is/are preferably one or more selected from halogen, cyano, $C_{1-3}$ alkyl, $C_{1-3}$ alkoxy, halogenated $C_{1-3}$ alkyl (e.g. trifluoromethyl), amino, hydroxyl, heterocyclyl, or any combination thereof.

As used herein, the term "$C_{x-y}$ spirocycloalkyl" or "$C_{x-y}$ spirocyclic hydrocarbon group" (x and y are each integers) used alone or in combination refers to a spirocycloalkyl containing from x to y carbon atoms. The term "$C_{7-12}$ spirocycloalkyl" used alone or in combination in the present disclosure refers to a spirocycloalkyl group containing from 7 to 12 carbon atoms. Representative examples of the term "$C_{7-11}$ spirocycloalkyl" include, but are not limited to, spiro[3.3]heptyl, spiro[2.5]octyl, spiro[3.5]nonyl, spiro[4.4]nonyl, spiro[4.5]decyl, or spiro[5.5]undecyl. The "$C_{7-12}$ spirocycloalkyl" is optionally further substituted with one or more substituents selected from halogen, cyano, $C_{1-3}$ alkyl, $C_{1-3}$ alkoxy, halogenated $C_{1-3}$ alkyl (e.g. trifluoromethyl), amino, oxo, hydroxyl, heterocyclyl, or any combination thereof.

As used herein, the term "heteroaryl" used alone or in combination refers to a 5- to 10-membered monocyclic or bicyclic aromatic ring group containing one or more (eg, from 1 to 6, or from 1 to 5, or from 1 to 4, or from 1 to 3) heteroatoms independently selected from oxygen, nitrogen and sulfur. Representative examples of such heteroaryl groups include, but are not limited to, furanyl, oxazolyl, isoxazolyl, oxadiazolyl, thienyl, thiazolyl, isothiazolyl, thiadiazolyl, pyrrolyl, imidazolyl, pyrazolyl, triazolyl, pyridyl, pyrimidinyl, pyridazinyl, pyrazinyl, indolyl, isoindolyl, benzofuranyl, isobenzofuranyl, benzothienyl, indazolyl, benzimidazolyl, benzoxazolyl, benzoisoxazolyl, benzothiazolyl, benzoisothiazolyl, benzotriazolyl, benzo[2,1,3]oxadiazolyl, benzo[2,1,3]thiadiazolyl, benzo[1,2,3]thiadiazolyl, quinolyl, isoquinolyl, naphthyridinyl, cinnolinyl, quinazolinyl, quinoxalinyl, phthalazinyl, pyrazolo[1,5-a]pyridyl, pyrazolo [1,5-a]pyrimidyl, imidazo[1,2-a]pyridyl, 1H-pyrrolo[3,2-b] pyridyl, 1H-pyrrolo[2,3-b]pyridyl, 4H-fluoro[3,2-b]pyrrolyl, pyrrolo[2,1-b]thiazolyl, and imidazo[2,1-b]thiazolyl. The heteroaryl groups may be unsubstituted or substituted as explicitly defined. The substituted heteroaryl group refers to a heteroaryl group optionally substituted from 1 to 3 times with a substituent(s) preferably selected from $C_{1-3}$ alkyl, $C_{1-3}$ alkoxy, cyano, trifluoromethyl, heterocyclyl, halogen, amino, or hydroxyl.

As used herein, the term "heteroarylene" used alone or in combination refers to a 5- to 10-membered monocyclic or bicyclic divalent aromatic ring group containing one or more (e.g., from 1 to 6, or from 1 to 5, or from 1 to 4, or from 1 to 3) heteroatoms independently selected from oxygen, nitrogen, and sulfur. Representative examples of such heteroarylene groups include, but are not limited to, furanylene, oxazolylene, isoxazolylene, oxadiazolylene, thienylene, thiazolylene, isothiazolylene, thiadiazolylene, pyrrolylene, imidazolylene, pyrazolylene, triazolylene, pyridylene, pyrimidinylene, pyridazinylene, pyrazinylene, indolylene, isoindolylene, benzofuranylene, isobenzofuranylene, benzothienylene, indazolylene, benzimidazolylene, benzoxazolylene, benzoisoxazolylene, benzothiazolylene, benzoisothiazolylene, benzotriazolylene, benzo[2,1,3] oxadiazolylene, benzo[2,1,3]thiadiazolylene, benzo[1,2,3] thiadiazolylene, quinolylene, isoquinolylene, naphthyridinylene, cinnolinylene, quinazolinylene, quinoxalinylene, phthalazinylene, pyrazolo[1,5-a]pyridinylene, pyrazolo[1,5-a]pyrimidinylene, imidazo[1,2-a]pyridinylene, 1H-pyrrolo[3,2-b]pyridinylene, 1H-pyrrolo[2,3-b]pyridinylene, 4H-fluoro[3,2-b]pyrrolylene, pyrrolo[2,1-b]thiazolylene, and imidazo[2,1-b]thiazolylene. The heteroarylene group may be unsubstituted or substituted as explicitly defined. The substituted heteroarylene group refers to a heteroarylene group optionally substituted from 1 to 3 times with a substituent(s) preferably selected from $C_{1-3}$ alkyl, $C_{1-3}$ alkoxy, cyano, trifluoromethyl, heterocyclyl, halogen, amino, or hydroxyl.

As used herein, the term "heterocyclyl" or "heterocyclic group" used alone or in combination refers to a 3- to 12-membered saturated or partially unsaturated (i.e., containing one or more double bonds, but not having a fully conjugated π-electron system) monocyclic, bicyclic, or tricyclic cyclic hydrocarbon group containing one or more (e.g., from 1 to 5, or from 1 to 4) heteroatoms independently selected from sulfur, oxygen, and nitrogen. In some embodiments, "heterocyclyl" may preferably refer to a 3- to 6-membered saturated or partially unsaturated (i.e., containing one or more double bonds, but not having a fully conjugated π-electron system) monocyclic cyclic hydrocarbon group containing one or more heteroatoms independently selected from sulfur, oxygen, and nitrogen.

Representative examples of the heterocyclyl include, but are not limited to, azetidinyl, oxetanyl, pyrrolidinyl, imidazolidinyl, pyrazolidyl, triazolyl, tetrahydrofuranyl, tetrahydropyranyl, tetrahydrothienyl, tetrahydrothiopyranyl, oxazolidinyl, thiazolidinyl, piperidinyl, piperazinyl, morpholinyl, thiomorpholinyl, dioxacyclohexyl, 1,4-diazacycloheptan-1-yl, 3,8-diazabicyclo[3.2.1]octan-3-yl, 2,5-diazabicyclo[2.2.2]octan-2-yl, and azaspirocycloalkyl (especially 3-azaspiro[5.5]undecane-3-yl). The heterocyclyl may be unsubstituted or substituted as explicitly defined, and the substituent(s) of the heterocyclyl can be preferably selected from C1-6 alkyl (e.g. $C_{1-3}$ alkyl), $C_{1-3}$ alkoxy, cyano, trifluoromethyl, heterocyclyl, halogen, amino, or hydroxy.

As used herein, the term "heterocyclylene" used alone or in combination refers to a 3- to 12-membered monocyclic, bicyclic or tricyclic saturated or partially unsaturated (i.e., having one or more double bonds, but not having a fully conjugated π-electron system) divalent cyclic hydrocarbon group containing one or more (e.g., from 1 to 5, or from 1 to 4) heteroatoms independently selected from sulfur, oxygen, and nitrogen. In some embodiments, "heterocyclylene" may preferably refer to a 3 to 6-membered saturated or partially unsaturated (i.e., having one or more double bonds, but not having a fully conjugated π-electron system) divalent monocyclic cyclic hydrocarbon group containing one or more heteroatoms independently selected from sulfur, oxygen, and nitrogen. Representative examples of the heterocyclylene include, but are not limited to, azetidinylene, oxetanylene, pyrrolidinylene, imidazolidylene, pyrazolidylene, triazolylene, tetrahydrofuranylene, tetrahydropyranylene, tetrahydrothienylene, tetrahydrothiopyranylene, oxazolidinylene, thiazolidinylene, piperidinylene, piperazinylene, morpholinylene, thiomorpholinylene, and dioxanylene. The heterocyclylene group may be unsubstituted or substituted as explicitly defined, and the substituent(s) is preferably selected from $C_{1-3}$ alkyl, $C_{1-3}$ alkoxy, cyano, trifluoromethyl, heterocyclyl, halogen, amino, or hydroxyl.

As used herein, the term "quaternary ammonium salt group" used alone or in combination refers to a quaternary ammonium salt group having the Formula $N^+R_aR_bR_cX^-$, where $R_a$, $R_b$, and $R_c$ each independently represent $C_{1-20}$ alkyl group, and $X^-$ represents $F^-$, $Cl^-$, $Br^-$, or $I^-$; or where $R_a$ and $R_b$ together with the N atom to which they are attached form a 4- to 8-membered heterocyclyl (especially a 5- to 8-membered heterocyclyl, or a 5- to 6-membered heterocyclyl), and the ring atoms of the 5- to 8-membered heterocyclyl optionally further include a heteroatom selected from oxygen, nitrogen, and sulfur, and $R_c$ represents a $C_{1-20}$ alkyl group, and $X^-$ represents $F^-$, $Cl^-$, $Br^-$, or $I^-$. The heterocyclyl in the 5- to 8-membered heterocyclyl may be as defined above, and the heteroatom(s) of the heterocyclyl optionally further includes an oxygen atom, a nitrogen atom, and/or a sulfur atom. Exemplary heterocyclyl includes, but is not limited to, piperidinyl, morpholinyl, imidazolyl, triazolyl, piperazinyl. Exemplary heterocyclyl quaternary ammonium salt groups include, but are not limited to

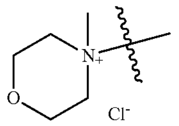

or

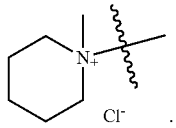

.

As used herein, "bornane" (also known as 1,7,7-trimethylbicyclo[2.2.1]heptane; camphane; bornylane) has a definition known to those skilled in the art, and its structural Formula is as follows:

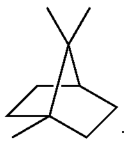

As used herein, "adamantane" (also known as tricyclo [3.3.1.1$^{3,7}$]decane) has a definition known to those skilled in the art, and its structural Formula is as follows:

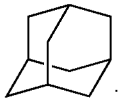

As used herein, "noradamantane" has a definition known to those skilled in the art, and its structural Formula is as follows:

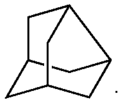

As used herein, "adamantanamine" has a definition known to those skilled in the art. An example of "adamantanamine" may be adamantan-1-amine (also named as tricyclo[3.3.1.1$^{3,7}$]decan-1-amine; CAS: 768-94-5), and its structural Formula is as follows:

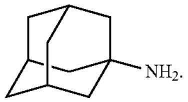 [SMILES: NC12CC3CC(CC(C3)C1)C2]

The term "about" used herein refers to approximately, roughly, or around. When the term "about" is used in combination with a numerical range, it modifies that range by extending the boundaries above and below the stated numerical value. In general, the term "about" may modify values above and below the stated value by variance of, for example, ±10%, ±5%, ±2%, or ±1%.

Salts or pharmaceutically acceptable salts, solvates, isotopically enriched analogs, tautomers, polymorphs, stereoisomers, or mixtures of stereoisomers of the compounds of Formula (I) or (I') according to the present disclosure are also encompassed within the scope of the present invention.

In all embodiments of the disclosure, the salt or pharmaceutically acceptable salt of the compound of Formula (I) or (I') refers to a non-toxic inorganic or organic acid and/or base addition salt. Examples include, but are not limited to, sulfate, hydrochloride, citrate, maleate, sulfonate, lactate, tartrate, fumarate, phosphate, dihydrophosphate, pyrophosphate, metaphosphate, oxalate, malonate, benzoate, mandelate, succinate, glycolate, or p-toluenesulfonate etc.

"Pharmaceutically acceptable carrier" refers to a pharmaceutically acceptable material, such as a filler, stabilizer, dispersant, suspending agent, diluent, excipient, thickener, solvent, or encapsulating material, with which the useful compounds according to the present disclosure are carried or transported into or administered to a patient so that they can perform their intended function. Generally, such constructs are carried or transported from one organ or part of the body to another organ or part of the body. The carrier is compatible with the other ingredients of the Formulation, including the compounds useful in the present disclosure, and is not harmful to the patient, and the carrier must be "acceptable". Some examples of materials that can be used as pharmaceutically acceptable carriers include, but are not limited to, sugars such as lactose, glucose, and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository wax; oils such as peanut oil, cottonseed oil, safflower oil, sesame oil, olive oil, corn oil and soybean oil; glycols such as propylene glycol; polyols such as glycerol, sorbitol, mannitol, and polyethylene glycol; esters such as ethyl oleate and ethyl laurate; agar; buffers such as magnesium hydroxide and aluminum hydroxide; surfactant phosphate buffer solution; and other common non-toxic compatible substances used in pharmaceutical Formulations.

The term "treatment" or "treating" refers to the administration of the compound of Formula (I) or (I') or a pharmaceutically acceptable salt thereof according to the present disclosure, or the pharmaceutical composition containing, as an active ingredient, the compound of Formula (I) or (I') or a pharmaceutically acceptable salt thereof according to the present disclosure, to a subject to mitigate (alleviate) undesirable diseases or conditions, such as the development of a cancer or tumor. The beneficial or desired clinical results of the present disclosure include, but are not limited to: alleviating symptoms, reducing the severity of the disease, stabilizing the state of the disease, slowing down or delaying the progression of the disease, improving or alleviating the condition, and alleviating the disease.

A "therapeutically effective amount" of a compound of the disclosure depends on the age, sex, and weight of the patient, the patient's current medical condition, and the cancer progression of the patient being treated. Those skilled in the art will be able to determine a suitable dosage based on these and other factors.

It should be understood that the choice of using one or more active compounds and/or compositions and their dosage depends on the basic situations of the individual (which should generally render the individual situation to achieve the best effect). Dosing and dosing regimens should be within the ability of those skilled in the art, and the appropriate dosage depends on many factors including the knowledge and ability of the physicians, veterinarians or researchers (Wells et al. eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000)).

The term "room temperature" used herein refers to the ambient temperature, such as a temperature of 20-30° C.

EXAMPLES

In the following description, numerous specific details are set forth in order to provide a thorough understanding of the present disclosure. The present disclosure may be practiced without some or all of these specific details. In other cases, well-known process operations have not been described in detail in order not to unnecessarily obscure the present disclosure. Although the present disclosure will be described in conjunction with specific embodiments, it should be understood that this is not intended to limit the present disclosure to these embodiments.

The following abbreviations are used throughout the description and examples:

BnCl benzyl chloride
Bipy bipyridine
BPO benzoyl peroxide
DCM dichloromethane
DIPEA N, N-diisopropylethylamine
DMF N,N-dimethylformamide
DMAP N,N-dimethylpyridin-4-amine
DMSO dimethyl sulfoxide
dppf 1,1'-bis(diphenylphosphino)ferrocene
equiv equivalent
EDCI 1-(3-dimethylaminopropyl)-3-ethylcarbodiimide
ESI electrospray ionization
EtOH ethanol
EtONa sodium ethoxide
HOAc or AcOH acetic acid
HOBT 1-hydroxybenzotriazole
HPLC high performance liquid chromatography
HRMS high resolution mass spectrometry
LC-MS liquid chromatography-mass spectrometry
LRMS low resolution mass spectrometry
LC liquid chromatography
mCPBA m-chloroperoxybenzoic acid
NBS N-bromosuccinimide
NMP N-methylpyrrolidone
$^1$H NMR Proton nuclear magnetic resonance
rt room temperature
TBHP tert-butyl hydroperoxide
TEA triethylamine
TFA trifluoroacetic acid
THF tetrahydrofuran
TLC thin layer chromatography
TMS trimethylsilyl
TsOH p-toluenesulfonic acid
TsO— p-toluenesulfonyloxy
Umemoto reagent 2,8-difluoro-5-(trifluoromethyl)-5H-dibenzo[B,D]thiophen-5-ium trifluoromethanesulfonate In the present disclosure, the $^1$H NMR spectra were recorded on a Bruker-500 MHz nuclear magnetic resonance instrument, by using, as a solvent and an internal standard, $CD_3OD$ containing 0.1% TMS ($^1$H NMR in $CD_3OD$; δ=3.31 ppm); or using, as a solvent and an internal standard, $CDCl_3$ containing 0.1% TMS ($^1$H NMR in $CDCl_3$; δ=7.26 ppm); or using, as a solvent and an internal standard, DMSO-$d_6$ containing 0.03% TMS ($^1$H NMR in DMSO-$d_6$; δ=2.50 ppm). HRMS spectrum was recorded on an AB Triple 4600 mass spectrometer, HPLC preparation was measured on a SHIMADZU LC-20AP type instrument, and HPLC purity was measured on a SHIMADZU LC-30AP or Waters 1525 type instrument. Unless otherwise specified, all reactions were performed in the air atmosphere. The reactions were followed by TLC or LC-MS, intermediates were isolated and purified. The reactions were tracked by TLC or LC-MS, the intermediates were separated and purified by column chromatography using an ISCO or Biotage, and the designed and synthesized target products were separated and purified by the Waters 2767 preparation liquid phase.

Solvents and reagents are processed as follows:

The solvents used in the reaction such as DCM, DMF, anhydrous EtOH, and anhydrous MeOH were purchased from Chinese Sinopharm Group; Preparative grade $CH_3CN$ and deionized water were used in HPLC preparation; Other reagents and medicines were purchased from the manufacturer and used directly without special instructions. In addition, the preparation methods of the starting materials SIAIS171092, SIAIS171134, SIAIS171123, SIAIS213132, and SIAIS213134 used in some of the following examples can be referred to the preparation methods of intermediate preparation examples 29, 35, 31, 42, and 43 of Chinese Patent Application No. 201910279248.9, respectively.

"Bornylamine" (also known as (1R,2S,4R)-born-2-ylamine; (1R,2S,4R)-1,7,7-trimethylbicyclo[2.2.1]heptane-2-amine; CAS No. 32511-34-5) used in examples of the present disclosure has a definition known to those skilled in the art, and its structural Formula is as follows:

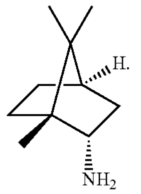

General Synthesis Methods

General synthesis method for thio-pomalidomide with alkylene chain linker-carboxylic acids group Scheme 1

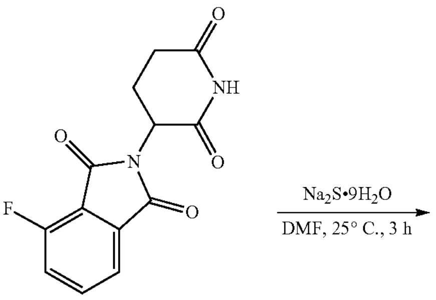

Fluoro-pomalidomide

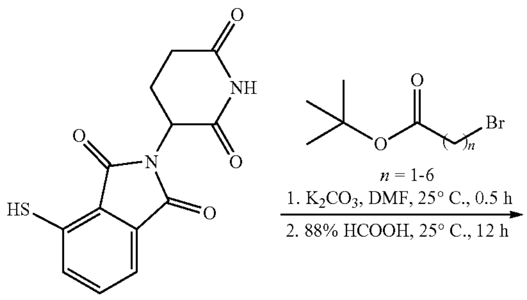

SIAIS151014

-continued

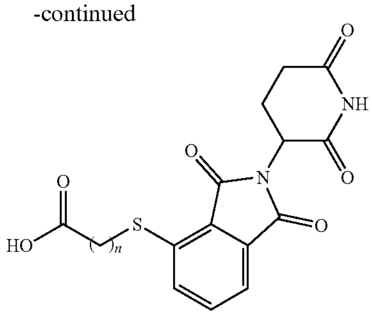

Synthesis of 2-(2,6-dioxopiperidin-3-yl)-4-mercaptoisoindoline-1,3-dione (SIAIS151014)

A 250 mL egg-shaped flask was charged with 2-(2,6-dioxopiperidin-3-yl)-4-fluoroisoindoline-1,3-dione (20 g, 72.4 mmol) and anhydrous N,N-dimethylformamide (60 mL), followed by addition of sodium sulfide nonahydrate (28 g, 108.6 mmol) in portions under stirring at room temperature, and the mixture was stirred at room temperature for 6 h. Then the reaction solution was slowly poured into 400 mL ice-water mixture. With stirring, the pH of the reaction solution was adjusted slowly to pH 2-3 with 6N aqueous hydrochloric acid solution. The color of the solution changed from blood red to light yellow, and a large amount of off-white solids were precipitated out. After stirring at room temperature for 0.5 h, the solids were filtrated, and the filter cake was washed 3 times with water; then the filter cake was slurried with 100 mL of anhydrous acetone, filtered, and washed 3 times with acetone, and dried under reduced pressure to afford SIAIS151014 (off-white solid, 14 g, yield 67%).

Synthesis of the Target Compound (Thio-Pomalidomide with Alkylene Chain Linker-Carboxylic Acids Group):

A 100 mL egg-shaped flask was charged with the intermediate SIAIS151014 (3.4 mmol, 1 equiv), anhydrous N,N-dimethylformamide (10 mL), and anhydrous potassium carbonate (6.8 mmol, 2 equiv), followed by slow addition of the corresponding brominated substrate (4.1 mmol, 1.2 equiv) under stirring at room temperature. After the completion of addition, the mixture was stirred at room temperature for 0.5 h. After the reaction was complete, 50 mL of water was poured into the reaction mixture, and the resulting mixture was extracted with ethyl acetate (2×50 mL). The organic phases were combined, washed with water (3×20 mL) and saturated brine (50 mL), dried over anhydrous sodium sulfate and concentrated under reduced pressure to remove the solvents. The crude product was purified by column chromatography (eluent (v/v):dichloromethane/ethyl acetate=20:1) to give the corresponding tert-butyl ester intermediate compound. The corresponding tert-butyl ester intermediate compound and 88% formic acid (10 mL) were sequentially added to a 25 mL egg-shaped flask, and stirred at room temperature for 12 h, and then concentrated under reduced pressure to remove the solvent. The resulting residue was treated by addition of water and lyophilized to afford the corresponding target compound (thio-pomalidomide with alkylene chain linker-carboxylic acids group).

General Synthesis Method for Thio-Pomalidomide with PEG Chain Linker-COOH Group

Scheme 2

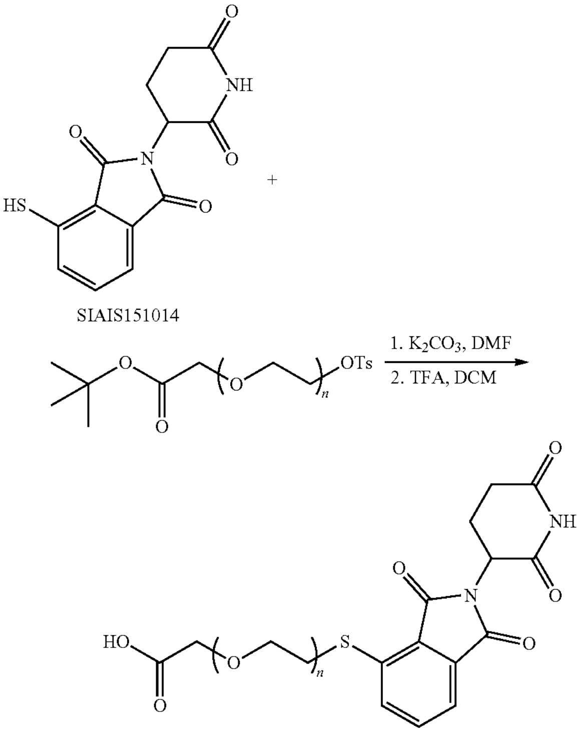

SIAIS151014

A 50 mL egg-shaped flask was charged with the intermediate SIAIS151014 (0.724 mmol, 1 equiv), anhydrous N,N-dimethylformamide (10 mL), and anhydrous potassium carbonate (1.448 mmol, 2 equiv), followed by slow addition of the corresponding p-toluenesulfonate substrate (0.869 mmol, 1.2 equiv), and the mixture was stirred at room temperature for 0.5 h. After reaction, the reaction mixture was filtered to remove the insoluble substance, and the filtrate was then subjected to a reverse phase C18 column chromatography (eluent (v/v):acetonitrile/water=10%-100%) for separation and purification, to give the corresponding tert-butyl ester intermediate compound. The tert-butyl ester intermediate compound, Dichloromethane (1 mL) and trifluoroacetic acid (3 mL) were sequentially added to a 25 mL egg-shaped flask, and stirred at room temperature for 1 h, and then concentrated under reduced pressure to remove the solvent. The resulting residue was treated by addition of water and lyophilized to afford the corresponding target compound.

General Synthesis Method for Thio-Pomalidomide with Alkylene Chain Linker-$NH_2$ Group Scheme 3

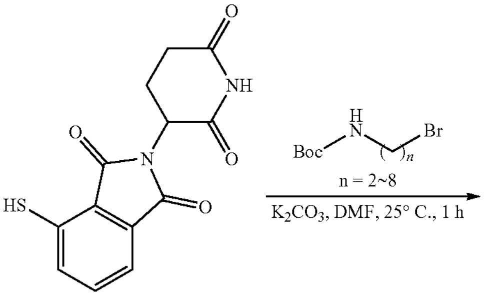

SIAIS151014

-continued

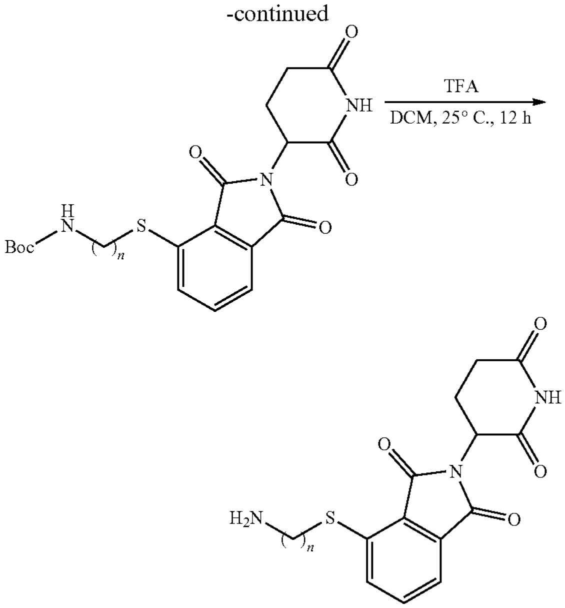

A 100 mL egg-shaped flask was charged with the intermediate SIAIS151014 (2.8 mmol, 1 equiv), anhydrous N,N-dimethylformamide (20 mL), and anhydrous potassium carbonate (5.6 mmol, 2 equiv), followed by slow addition of the corresponding brominated substrate (0.869 mmol, 1.2 equiv), and the mixture was stirred at room temperature for 0.5 h. After reaction, 50 mL of water was poured into the reaction mixture, and the resulting mixture was extracted with ethyl acetate (3×50 mL). The organic phases were combined, washed with water (3×20 mL) and saturated brine (50 mL), dried over anhydrous sodium sulfate and concentrated under reduced pressure to remove the solvent. The crude product was purified by a reverse phase C18 column chromatography (eluent (v/v):acetonitrile/(water+0.05% TFA)=10%-100%), and the collected fractions were concentrated under reduced pressure to remove the solvent, and then lyophilized to obtain the corresponding Boc protected alkylated intermediate. The Boc protected alkylated intermediate compound, Dichloromethane (5 mL), and trifluoroacetic acid (0.5 mL) were sequentially added to a 25 mL egg-shaped flask, and stirred at room temperature for 12 h, and then concentrated under reduced pressure to remove the solvent. The crude product was purified by a reverse phase C18 column chromatography (eluent (v/v):acetonitrile/(water+0.05% TFA)=10%-100%), and the collected fractions were concentrated under reduced pressure to remove the solvent, and then lyophilized to obtain the corresponding target compound (thio-pomalidomide with alkylene chain linker-$NH_2$ group).

General Synthesis Method for Thio-Lenalidomide with Alkylene Chain Linker-COOH Group Scheme 4

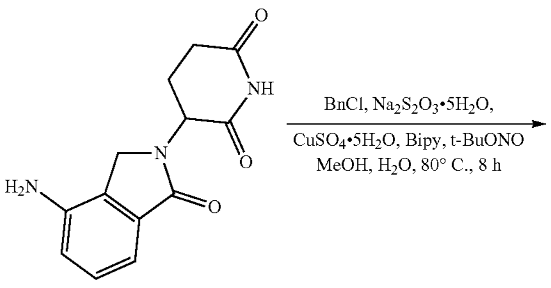

Lenalidomide

-continued

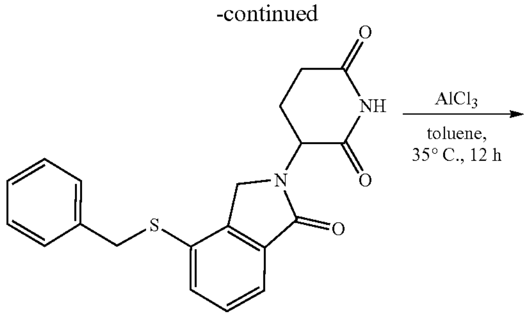

SIAIS171088

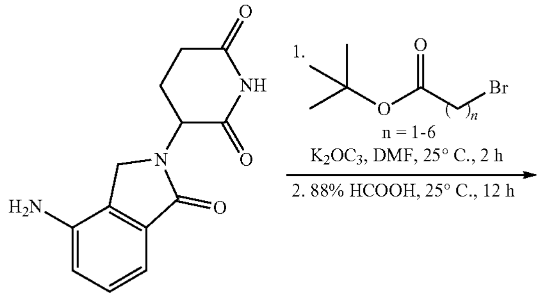

SIAIS151014

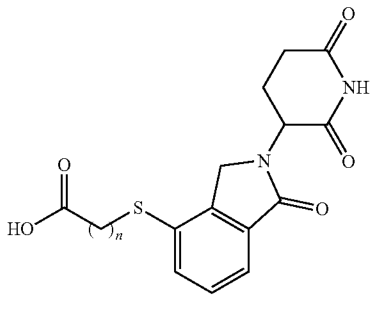

Synthesis of 3-(4-(benzylthio)-1-oxoisoindolin-2-yl) piperidine-2,6-dione (SIAIS171088)

A 500 mL egg-shaped flask containing methanol (120 mL) and water (120 mL) was charged with sodium thiosulfate pentahydrate (53.7 g, 216.3 mmol), benzyl chloride (27.4 g, 216.3 mmol), copper sulfate pentahydrate (77.4 mg, 0.31 mmol), and bipyridine (0.72 g, 4.6 mmol). The mixture was slowly warmed up to 80° C. and stirred for 2 h. After cooling to room temperature, to the reaction solution was added 3-(4-amino-1-oxoisoindolin-2-yl)piperidine-2,6-dione (lenalidomide) (8.0 g, 30.9 mmol), followed by slow addition dropwise of tert-butyl nitrite (4.78 g, 46.4 mmol). After the completion of addition, the reaction solution was warmed up to 80° C. again and stirred for 8 h. After reaction, the reaction solution was cooled to room temperature, followed by addition of water (200 mL), and extraction with ethyl acetate (2×200 mL). The organic phases were combined, washed with water (2×50 mL), and saturated brine (50 mL), dryed over anhydrous sodium sulfate and concentrated under reduced pressure to remove the solvent. The crude product was purified by column chromatography (eluent (v/v):petroleum ether/ethyl acetate=1:2) to give the product (SIAIS171088, white solid, 6.8 g, yield 60%).

Synthesis of 3-(4-mercapto-1-oxoisoindolin-2-yl) piperidine-2,6-dione (SIAIS171095)

A 250 mL egg-shaped flask was charged with anhydrous aluminum trichloride (2.61 g, 19.6 mmol) and anhydrous toluene (70 mL), followed by slow addition of the compound SIAIS171088 (1.8 g, 4.9 mmol) with stirring. The mixture was stirred overnight at 35° C. After the reaction was completed, 20% citric acid aqueous solution was slowly added to the reaction mixture with stirring, and a large amount of solids were precipitated out. After filtration, the filter cake was washed with water and ethyl acetate, respectively, and dried to give the product (SIAIS171095, white solid, 1.15 g, yield 85%).

Synthesis of the Target Product (Thio-Lenalidomide with Alkylene Chain Linker-COOH Group) from the Compound SIAIS171095

A 10 mL egg-shaped flask was charged with the compound SIAIS171095 (0.36 mmol, 1 equiv), the corresponding brominated substrate (0.43 mmol, 1.2 equiv), and anhydrous potassium carbonate (0.72 mmol, 2 equiv), followed by addition of anhydrous N,N-dimethylformamide (2 mL), and the mixture was stirred at room temperature for 0.5 h. After the reaction was complete, 50 mL of water was poured into the reaction mixture, and the resulting mixture was extracted with ethyl acetate (2×50 mL). The organic phases were combined, washed with water (2×30 mL) and saturated brine (50 mL), dried over anhydrous sodium sulfate and concentrated under reduced pressure to remove the solvent. The crude product was purified by a reverse phase C18 column chromatography (eluent (v/v):acetonitrile/(water+0.05% TFA)=10%-100%) to give the corresponding tert-butyl ester intermediate compound. The corresponding tert-butyl ester intermediate compound and 88% formic acid (3 mL) were sequentially added to a 10 mL egg-shaped flask, and stirred at room temperature for 12 h, and then concentrated under reduced pressure to remove the solvent. The resulting residue was treated by addition of water and lyophilized to afford the corresponding target compound.

General Synthesis Method for Thio-Lenalidomide with PEG Chain Linker-COOH Group

Scheme 5

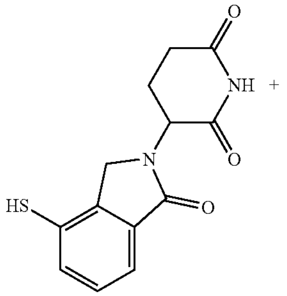

SIAIS171095

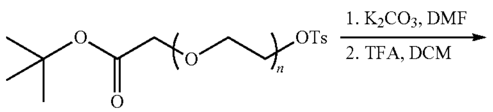

-continued

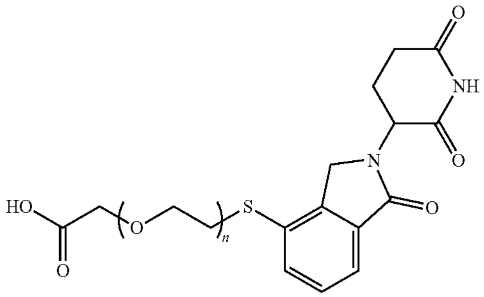

A 50 mL egg-shaped flask was charged with the intermediate SIAIS171095 (0.724 mmol, 1 equiv), anhydrous N,N-dimethylformamide (10 mL), and anhydrous potassium carbonate (1.448 mmol, 2 equiv), followed by slow addition of the corresponding p-toluenesulfonate substrate (0.869 mmol, 1.2 equiv) with stirring at room temperature. After the completion of addition, the mixture was stirred at room temperature for 0.5 h. After reaction, the reaction mixture was filtered to remove the insoluble substance, and the filtrate was then subjected to a reverse phase C18 column chromatography (eluent (v/v):acetonitrile/water=10%-100%) for separation and purification, to give the corresponding tert-butyl ester intermediate compound. The tert-butyl ester intermediate compound, Dichloromethane (1 mL) and trifluoroacetic acid (3 mL) were sequentially added to a 25 mL egg-shaped flask, and stirred at room temperature for 1 h, and then concentrated under reduced pressure to remove the solvent. The resulting residue was treated by addition of water and lyophilized to afford the corresponding target compound.

General Synthesis Method for Thio-Lenalidomide with Alkylene Chain Linker-$NH_2$ Group Scheme 6

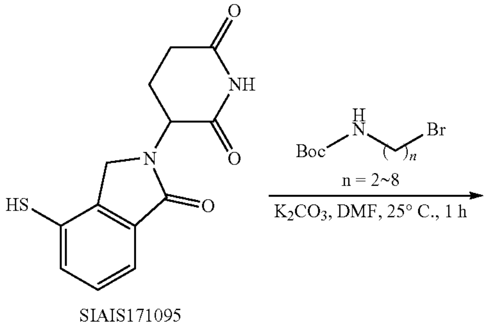

SIAIS171095

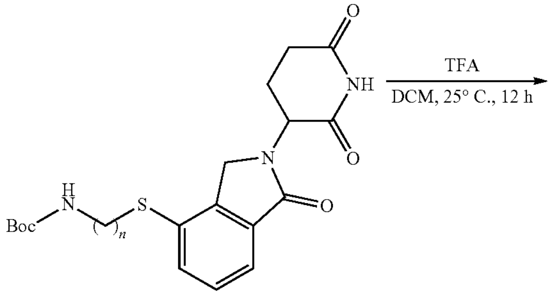

-continued

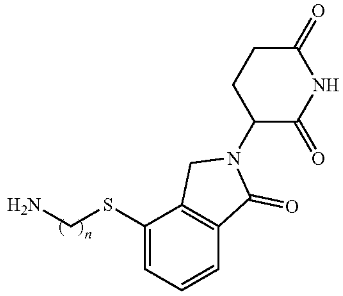

Step 1: A 10 mL egg-shaped flask was charged with the compound SIAIS171095 (0.36 mmol, 1 equiv), anhydrous N,N-dimethylformamide (2 mL), and anhydrous potassium carbonate (0.72 mmol, 2 equiv), followed by slow addition of the corresponding brominated substrate (0.43 mmol, 1.2 equiv) with stirring at room temperature. After the completion of addition, the mixture was stirred at room temperature for 1 h. After reaction, the crude product was purified by a reverse phase C18 column chromatography (eluent (v/v): acetonitrile/(water+0.05% TFA)=10%-100%), and the collected fractions were concentrated under reduced pressure to remove the solvent, and then lyophilized to give the corresponding Boc protected alkylated intermediate.

Step 2: The Boc protected alkylated intermediate compound obtained from step 1, anhydrous dichloromethane (2 mL) and trifluoroacetic acid (2 mL) were sequentially added in a 10 mL egg-shaped flask, and stirred at room temperature for 12 h, and then concentrated under reduced pressure to remove the solvent. The crude product was purified by a reverse phase C18 column chromatography (eluent (v/v): acetonitrile/(water+0.05% TFA)=10%-100%), and the collected fractions were concentrated under reduced pressure to remove the solvent, and then lyophilized to obtain the corresponding target compound.

General Synthesis Method for Thio-Lenalidomide with PEG Chain Linker-$NH_2$ Group Scheme 7

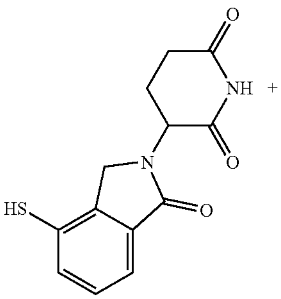

SIAIS171095

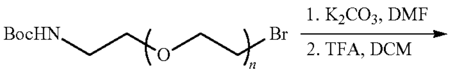

n = 1-5

-continued

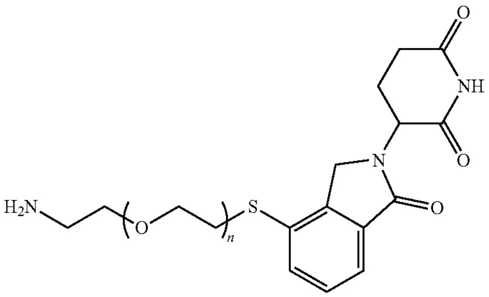

Step 1: A 10 mL egg-shaped flask was charged with the compound SIAIS171095 (0.36 mmol, 1 equiv), anhydrous N,N-dimethylformamide (2 mL), and anhydrous potassium carbonate (0.72 mmol, 2 equiv), followed by slow addition of the corresponding brominated substrate (0.43 mmol, 1.2 equiv) with stirring at room temperature. After the completion of addition, the mixture was stirred at room temperature for 1 h. After reaction, the crude product was purified by a reverse phase C18 column chromatography (eluent (v/v): acetonitrile/(water+0.05% TFA)=10%-100%), and the collected fractions were concentrated under reduced pressure to remove the solvent, and then lyophilized to give the corresponding Boc protected alkylated intermediate.

Step 2: The Boc protected alkylated intermediate compound obtained from step 1, anhydrous dichloromethane (2 mL) and trifluoroacetic acid (2 mL) were sequentially added in a 10 mL egg-shaped flask, and stirred at room temperature for 12 h, and then concentrated under reduced pressure to remove the solvent. The crude product was purified by a reverse phase C18 column chromatography (eluent (v/v): acetonitrile/(water+0.05% TFA)=10%-100%), and the collected fractions were concentrated under reduced pressure to remove the solvent, and then lyophilized to obtain the corresponding target compound.

General Synthesis Method for Thio-Pomalidomide with Alkyl Chain Group

Scheme 8

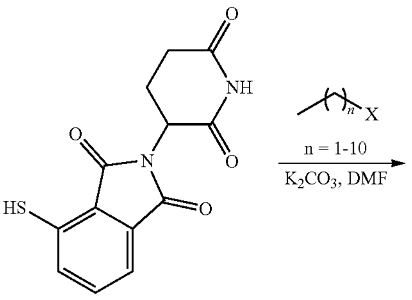

SIAIS151014

-continued

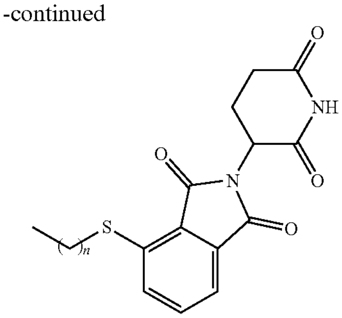

A 50 mL two-necked flask was charged with the compound SIAIS151014 (0.344 mmol, 1 equiv) prepared according to Scheme 1, potassium carbonate (0.688 mmol, 2 equiv), and DMF (5 mL), followed by evacuation and refilling with argon gas, and then addition of the corresponding brominated substrate (0.413 mmol, 1.2 equiv). The mixture was stirred at room temperature for 1 h. After reaction, the reaction mixture was filtered to remove the insoluble substance, and the filtrate was then subjected to a reverse phase C18 column chromatography (eluent (v/v): acetonitrile/water=10%-100%) for separation and purification. The collected fractions were concentrated under reduced pressure to remove the solvent to give the corresponding target compound.

General Synthesis Method for Thio-Lenalidomide with Alkyl Chain Group

Scheme 9

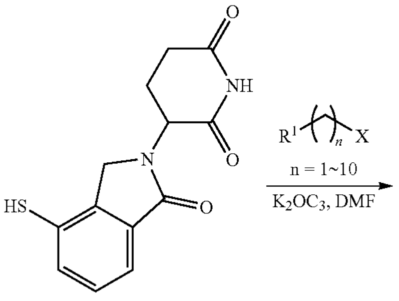

SIAIS171095

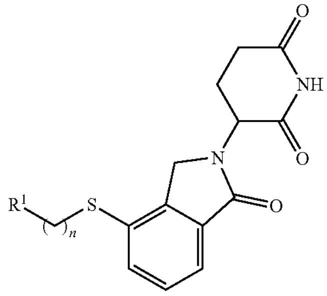

In Scheme 9, the group X represents halogen, and $R^1$ has the same definition as the group $X_1$ of the compound of Formula (I) according to the present disclosure.

According to Scheme 9, a 50 mL two-necked flask was charged with the compound SIAIS171095 (0.344 mmol, 1 equiv) prepared according to Scheme 4, potassium carbonate (0.688 mmol, 2 equiv), and DMF (5 mL), followed by evacuation and refilling with argon gas, and then addition of the corresponding halogenated substrate (0.413 mmol, 1.2 equiv). The mixture was stirred at room temperature for 1 h. After reaction, the reaction mixture was filtered to remove the insoluble substance, and the filtrate was then subjected to a reverse phase C18 column chromatography (eluent (v/v):acetonitrile/water=10%-100%) for separation and purification. The collected fractions were concentrated under reduced pressure to remove the solvent to give the corresponding target compound.

General Synthesis Method for Sulfinyl or Sulfonyl Substituted Pomalidomide or Lenalidomide Scheme 10

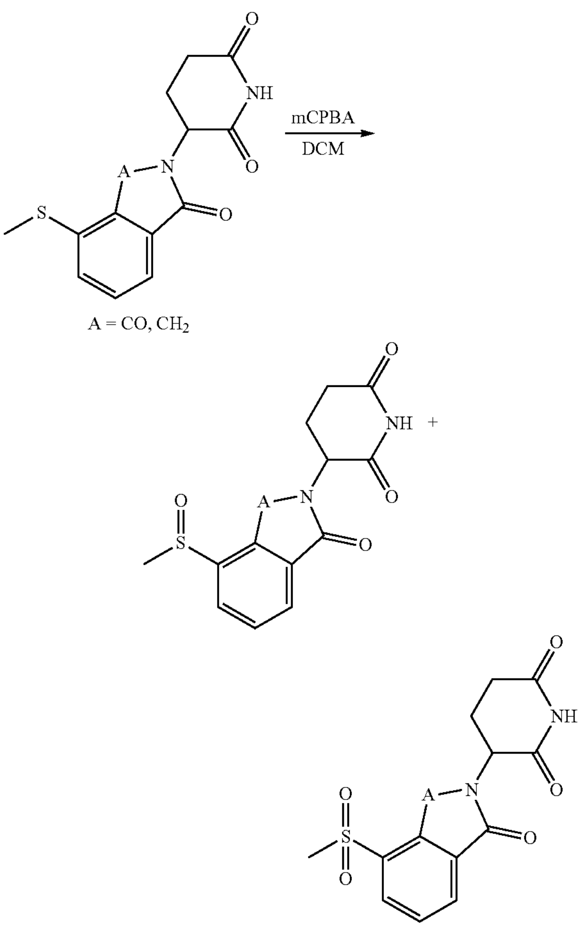

A 50 mL two-necked flask was sequentially charged with the compound SIAIS151014 or SIAIS171095 (0.164 mmol, 1 equiv), DCM (10 mL), and mCPBA (0.328 mmol, 2 equiv) with stirring, followed by evacuation and refilling with argon gas for three times, and then the mixture was stirred at room temperature for 2 h. The reaction was quenched with saturated sodium bicarbonate. The resulting mixture was extracted with DCM, dried over anhydrous sodium sulfate, and concentrated to obtain a colorless oily substance. To the oily substance was added 2 mL of acetonitrile. The resulting mixture was subjected to a C18 reverse phase column chromatography (eluent (v/v):acetonitrile/water=10%-100%) for separation and purification, and the collected fractions were concentrated under reduced pressure to remove the solvents, to give both of the target compounds of sulfoxide and sulfone.

General Synthesis Method for Thio-Pomalidomide Having Alkylene Chain Linker Substituted with Tertiary or Secondary Amine Group Scheme 11

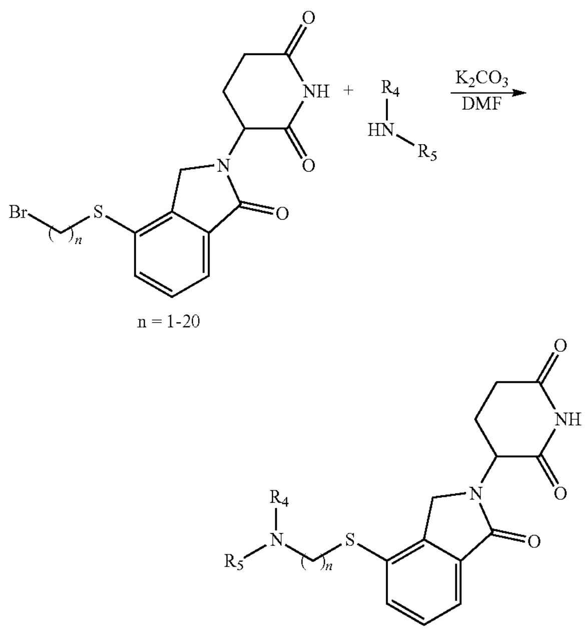

In Scheme 11, $NHR_4R_5$ represents a linear or branched alkyl secondary or primary amine or a nitrogen-containing heterocyclic substrate.

According to Scheme 11, to a 15 mL sample vial were sequentially added the corresponding brominated thio-lenalidomide compound (0.05 mmol, 1 equiv), potassium carbonate (0.10 mmol, 2 equiv), and DMF (2 mL), followed by addition of the corresponding secondary or primary amine or nitrogen-containing heterocyclic substrate (0.10 mmol, 2 equiv) with stirring. The mixture was reacted at 40° C. overnight. After filtration to remove insoluble materials, the filtrate was subjected to a preparative HPLC (eluent (v/v):acetonitrile/(water+0.05% HCl)=10%-100%) for separation. The collected fractions were concentrated under reduced pressure to remove acetonitrile, and then lyophilized to obtain the corresponding target compound.

General Synthesis Method for Thio-Lenalidomide Having Alkylene Chain Linker Substituted with Diethylamino Scheme 12

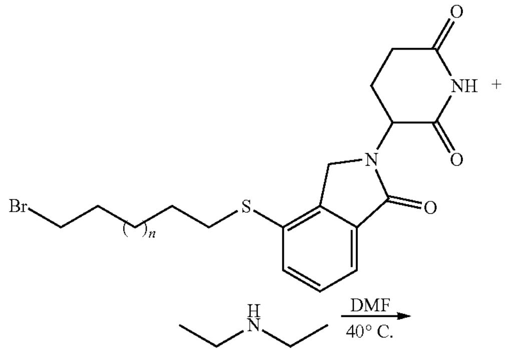

-continued

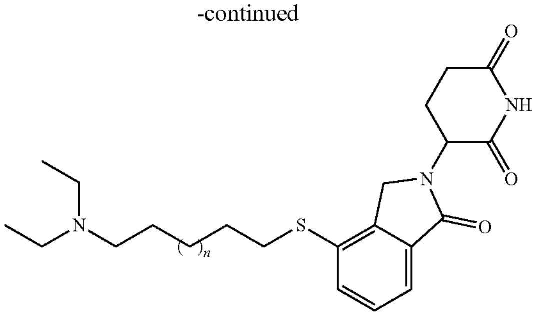

In Scheme 12, n may be an integer of 1-20.

According to Scheme 12, to a 15 mL sample vial were sequentially added the corresponding brominated thio-lenalidomide compound (0.05 mmol, 1 equiv), and DMF (2 mL), followed by addition of diethylamine (0.10 mmol, 2 equiv) with stirring. The mixture was reacted at 40° C. overnight. After filtration to remove insoluble materials, the filtrate was subjected to a preparative HPLC (eluent (v/v): acetonitrile/(water+0.05% HCl)=10%-100%) for separation. The collected fractions were concentrated under reduced pressure to remove the acetonitrile, and then lyophilized to obtain the corresponding target compound.

General Synthesis Method for Thio-Lenalidomide Having Alkylene Chain Linker Substituted with Terminal N-Methyl Amino Scheme 13

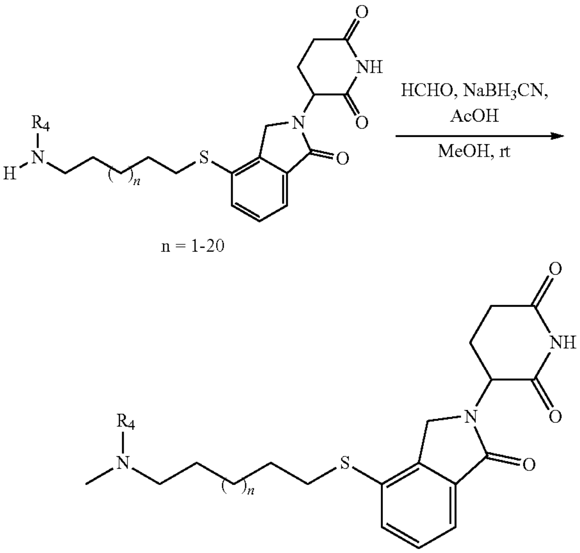

To a 15 mL sample vial were sequentially added the corresponding terminal NH-substituted thio-lenalidomide compound (0.033 mmol, 1 equiv), sodium cyanoborohydride (1.0 mmol, 3 equiv), and methanol (2 mL), followed by addition of formaldehyde (0.066 mmol, 2 equiv) with stirring. The mixture was stirred and reacted at room temperature overnight. After filtration, the filtrate was subjected to a preparative HPLC (eluent (v/v):acetonitrile/(water+0.05% HCl)=10%-100%) for separation. The collected fractions were concentrated under reduced pressure to remove the acetonitrile, and then lyophilized to obtain the corresponding target compound.

Example 1: Preparation of 3-(4-(benzylthio)-1-oxoisoindolin-2-yl)piperidine-2,6-dione (SIAIS171088)

Referring to the method of Scheme 4, the compound SIAIS171088 was prepared under appropriate conditions that will be recognized by one skilled in the art. The target compound was obtained as a white solid (6.8 g, yield 60%). $^{1}$H NMR (500 MHz, $CDCl_3$) δ 8.07 (s, 1H), 7.75 (t, J=7.3 Hz, 1H), 7.55 (dd, J=7.4, 6.8 Hz, 1H), 7.49-7.41 (m, 1H), 7.27-7.17 (m, 5H), 5.20-5.17 (m, 1H), 4.22 (d, J=16.5 Hz, 1H), 4.15-4.04 (m, 2H), 3.92 (d, J=16.5 Hz, 1H), 2.95-2.74 (m, 2H), 2.32-2.22 (m, 1H), 2.17-2.11 (m, 1H). HRMS (ESI) m/z: calcd for $C_{20}H_{19}N_2O_3S^+$ [M+H]$^+$, 367.1111; found, 367.1402.

Intermediate Example 1: 3-(4-mercapto-1-oxoisoindolin-2-yl)piperidine-2,6-dione (SIAIS171095)

Referring to the method of Scheme 4, the compound SIAIS171095 was prepared under appropriate conditions that will be recognized by one skilled in the art. The target compound was obtained as a white solid (1.15 g, yield 85%). $^{1}$H NMR (500 MHz, DMSO) δ 11.01 (s, 1H), 7.82-7.39 (m, 3H), 5.73 (s, 1H), 5.21-5.04 (m, 1H), 4.40-4.20 (m, 2H), 2.99-2.85 (m, 1H), 2.67-2.56 (m, 1H), 2.47-2.30 (m, 1H), 2.05-1.95 (m, 1H). HRMS (ESI) m/z: calcd for $C_{13}H_{13}N_2O_3S^+$ [M+H]$^+$, 277.0641; found, 276.8348.

Intermediate Example 2: Preparation of 3-(4-((5-aminopentyl)thio)-1-oxoisoindolin-2-yl)piperidine-2,6-dione (SIAIS171132)

Referring to the method of Scheme 6, the compound SIAIS171132 was prepared under appropriate conditions that will be recognized by one skilled in the art, except that the brominated substrate was tert-butyl (5-bromopentyl) carbamate. The target product SIAIS171132 was obtained as a light yellow solid (95 mg, total yield of two steps 73%). $^{1}$H NMR (500 MHz, DMSO) δ 11.00 (s, 1H), 7.85-7.45 (m, 6H), 5.21-5.07 (m, 1H), 4.42-4.16 (m, 2H), 3.16-3.05 (m, 2H), 2.92-2.85 (m, 1H), 2.84-2.71 (m, 2H), 2.64-2.60 (m, 1H), 2.45-2.40 (m, 1H), 2.07-1.93 (m, 1H), 1.66-1.58 (m, 2H), 1.54-1.50 (m, 2H), 1.49-1.44 (m, 2H). HRMS (ESI) m/z: calcd for $C_{18}H_{24}N_3O_3S^+$ [M+H]$^+$, 362.1533; found, 362.1537.

Intermediate Example 3: Preparation of 3-(4-((8-aminooctyl)thio)-1-oxoisoindolin-2-yl)piperidine-2,6-dione (SIAIS171136)

Referring to the method of Scheme 6, the compound SIAIS171136 was prepared under appropriate conditions that will be recognized by one skilled in the art, except that the brominated substrate was tert-butyl (8-bromooctyl)carbamate. The target product SIAIS171136 was obtained as a white solid (100 mg, total yield of two steps 68%). $^{1}$H NMR (500 MHz, DMSO) δ 10.99 (s, 1H), 7.75-7.47 (m, 6H), 5.13 (dd, J=13.3, 5.1 Hz, 1H), 4.28 (dd, J=70.1, 17.4 Hz, 2H), 3.13-3.00 (m, 2H), 2.98-2.84 (m, 1H), 2.78-2.74 (m, 2H), 2.64-2.59 (m, 1H), 2.47-2.38 (m, 1H), 2.06-1.93 (m, 1H), 1.68-1.54 (m, 2H), 1.52-1.48 (m, 2H), 1.45-1.34 (m, 2H), 1.30-1.20 (m, 6H). HRMS (ESI) m/z: calcd for $C_{21}H_{30}N_3O_3S^+$ [M+H]$^+$, 404.2002; found, 404.1996.

Example 2: Preparation of 2-(2,6-dioxopiperidin-3-yl)-4-(methylthio)isoindoline-1,3-dione (SIAIS1210073)

Referring to the method of Scheme 8, the compound SIAIS1210073 was prepared under appropriate conditions that will be recognized by one skilled in the art, except that the halogenated substrate was methyl iodide. The target compound SIAIS1210073 was obtained as a yellow solid (58 mg, yield 55%). $^{1}$H NMR (500 MHz, DMSO) δ 11.14 (s, 1H), 7.81 (dd, J=7.9, 7.5 Hz, 1H), 7.70 (d, J=8.1 Hz, 1H), 7.63 (d, J=7.2 Hz, 1H), 5.12 (dd, J=12.9, 5.4 Hz, 1H), 2.95-2.82 (m, 1H), 2.64-2.56 (m, 4H), 2.55-2.51 (m, 1H), 2.10-2.02 (m, 1H). HRMS (ESI) m/z: calcd for $C_{14}H_{13}N_2O_4S^+$ [M+H]$^+$, 305.0591; found, 305.0617.

Example 3: Preparation of 3-(4-(methylthio)-1-oxoisoindolin-2-yl)piperidine-2,6-dione (SIAIS1210071)

Referring to the method of Scheme 9, the compound SIAIS1210071 was prepared under appropriate conditions that will be recognized by one skilled in the art, except that the halogenated substrate was methyl iodide. The target compound SIAIS1210071 was obtained as a white solid (134 mg, yield 64%). $^{1}$H NMR (500 MHz, DMSO) δ 11.01 (s, 1H), 7.58-7.50 (m, 3H), 5.13 (dd, J=13.3, 5.1 Hz, 1H), 4.34 (d, J=17.4 Hz, 1H), 4.20 (d, J=17.3 Hz, 1H), 2.97-2.86 (m, 1H), 2.60 (d, J=9.8 Hz, 4H), 2.49-2.40 (m, 1H), 2.04-1.95 (m, 1H). HRMS (ESI) m/z: calcd for $C_{14}H_{15}N_2O_3S^+$ [M+H]$^+$, 291.0798; found, 291.0752.

Example 4: Preparation of 3-(4-(ethylthio)-1-oxoisoindolin-2-yl)piperidine-2,6-dione (SIAIS1213073)

Referring to the method of Scheme 9, the compound SIAIS1213073 was prepared under appropriate conditions that will be recognized by one skilled in the art, except that the halogenated substrate was bromoethane. The target compound SIAIS1213073 was obtained as orange solid (15 mg, yield 45%). $^{1}$H NMR (500 MHz, DMSO) δ 10.99 (s, 1H), 7.63 (dd, J=7.5, 1.0 Hz, 1H), 7.59-7.50 (m, 2H), 5.12 (dd, J=13.3, 5.1 Hz, 1H), 4.36 (d, J=17.3 Hz, 1H), 4.22 (d, J=17.4 Hz, 1H), 3.10 (q, J=7.3 Hz, 2H), 2.95-2.86 (m, 1H), 2.63-2.56 (m, 1H), 2.49-2.40 (m, 1H), 2.05-1.96 (m, 1H), 1.26 (t, J=7.3 Hz, 3H). HRMS (ESI) m/z: calcd for $C_{15}H_{17}N_2O_3S^+$ [M+H]$^+$, 305.0954; found, 305.0904.

Example 5: Preparation of 3-(1-oxo-4-(propylthio)isoindolin-2-yl)piperidine-2,6-dione (SIAIS1213071)

Referring to the method of Scheme 9, the compound SIAIS1213071 was prepared under appropriate conditions that will be recognized by one skilled in the art, except that the halogenated substrate was 1-bromopropane. The target compound SIAIS1213071 was obtained as a light yellow solid (15 mg, yield 43%). $^{1}$H NMR (500 MHz, DMSO) δ 10.99 (s, 1H), 7.63 (dd, J=7.5, 1.2 Hz, 1H), 7.57 (dd, J=7.5, 1.2 Hz, 1H), 7.54 (d, J=7.5 Hz, 1H), 5.12 (dd, J=13.3, 5.1 Hz, 1H), 4.36 (d, J=17.4 Hz, 1H), 4.22 (d, J=17.4 Hz, 1H), 3.06 (t, J=7.0 Hz, 2H), 2.96-2.85 (m, 1H), 2.63-2.56 (m, 1H), 2.48-2.40 (m, 1H), 2.04-1.97 (m, 1H), 1.66-1.58 (m, 2H), 0.99 (t, J=7.3 Hz, 3H). HRMS (ESI) m/z: calcd for $C_{16}H_{19}N_2O_3S^+$ [M+H]$^+$, 319.1111; found, 319.1164.

Example 6: Preparation of 3-(4-(isopropylthio)-1-oxoisoindolin-2-yl)piperidine-2,6-dione (SIAIS1213075)

Referring to the method of Scheme 9, the compound SIAIS1213075 was prepared under appropriate conditions that will be recognized by one skilled in the art, except that the halogenated substrate was 2-bromopropane. The target compound SIAIS1213075 was obtained as a light yellow solid (12 mg, yield 34%). $^1$H NMR (500 MHz, DMSO) δ 10.99 (s, 1H), 7.69 (dd, J=7.7, 0.9 Hz, 1H), 7.63 (dd, J=7.5, 0.9 Hz, 1H), 7.55 (t, J=7.6 Hz, 1H), 5.13 (dd, J=13.3, 5.1 Hz, 1H), 4.38 (d, J=17.5 Hz, 1H), 4.24 (d, J=17.5 Hz, 1H), 3.69-3.60 (m, 1H), 2.96-2.85 (m, 1H), 2.63-2.56 (m, 1H), 2.48-2.40 (m, 1H), 2.04-1.98 (m, 1H), 1.27 (dd, J=6.6, 2.8 Hz, 6H). HRMS (ESI) m/z: calcd for $C_{16}H_{19}N_2O_3S^+$ $[M+H]^+$, 319.1111; found, 318.1144.

Example 7: Preparation of 3-(1-oxo-4-(pentylthio) isoindolin-2-yl)piperidine-2,6-dione (SIAIS1213195)

Referring to the method of Scheme 9, the compound SIAIS1213195 was prepared under appropriate conditions that will be recognized by one skilled in the art, except that the halogenated substrate was 1-bromopentane. The target compound SIAIS1213195 was obtained as a light yellow solid (29 mg, yield 76%). $^1$H NMR (500 MHz, DMSO) δ 11.01 (s, 1H), 7.63 (dd, J=7.5, 1.2 Hz, 1H), 7.59-7.49 (m, 2H), 5.13 (dd, J=13.3, 5.1 Hz, 1H), 4.35 (d, J=17.4 Hz, 1H), 4.21 (d, J=17.4 Hz, 1H), 3.08 (t, J=7.3 Hz, 2H), 2.96-2.86 (m, 1H), 2.62-2.55 (m, 1H), 2.49-2.42 (m, 1H), 2.04-1.97 (m, 1H), 1.64-1.55 (m, 2H), 1.42-1.34 (m, 2H), 1.33-1.25 (m, 2H), 0.85 (t, J=7.3 Hz, 3H). HRMS (ESI) m/z: calcd for $C_{18}H_{23}N_2O_3S^+$ $[M+H]^+$, 347.1424; found, 347.1455.

Example 8: Preparation of 3-(4-(octylthio)-1-oxoisoindolin-2-yl)piperidine-2,6-dione (SIAIS1216025)

Referring to the method of Scheme 9, the compound SIAIS1216025 was prepared under appropriate conditions that will be recognized by one skilled in the art, except that the halogenated substrate was 1-bromooctane. The target compound SIAIS1216025 was obtained as a white solid (22.4 mg, yield 58%). $^1$H NMR (500 MHz, DMSO) δ 11.01 (s, 1H), 7.62 (dd, J=7.5, 1.1 Hz, 1H), 7.58-7.50 (m, 2H), 5.13 (dd, J=13.3, 5.1 Hz, 1H), 4.35 (d, J=17.4 Hz, 1H), 4.21 (d, J=17.4 Hz, 1H), 3.08 (t, J=7.3 Hz, 2H), 2.96-2.87 (m, 1H), 2.62-2.56 (m, 1H), 2.49-2.40 (m, 1H), 2.04-1.97 (m, 1H), 1.62-1.55 (m, 2H), 1.44-1.35 (m, 2H), 1.28-1.20 (m, 8H), 0.84 (t, J=6.9 Hz, 3H). HRMS (ESI) m/z: calcd for $C_{21}H_{29}N_2O_3S^+$ $[M+H]^+$, 389.1893; found, 389.1901.

Example 9: Preparation of 3-(4-((3-hydroxypropyl) thio)-1-oxoisoindolin-2-yl)piperidine-2,6-dione (SIAIS1216189)

Referring to the method of Scheme 9, the compound SIAIS1216189 was prepared under appropriate conditions that will be recognized by one skilled in the art, except that the halogenated substrate was 3-bromo-1-propanol. The target compound SIAIS1216189 was obtained as a light yellow solid (20 mg, yield 60%). $^1$H NMR (500 MHz, DMSO) δ 11.01 (s, 1H), 7.64 (dd, J=7.4, 1.2 Hz, 1H), 7.58-7.51 (m, 2H), 5.13 (dd, J=13.3, 5.1 Hz, 1H), 4.62 (t, J=5.2 Hz, 1H), 4.36 (d, J=17.4 Hz, 1H), 4.21 (d, J=17.4 Hz, 1H), 3.50 (dd, J=11.4, 6.0 Hz, 2H), 3.12 (t, J=7.3 Hz, 2H), 2.96-2.88 (m, 1H), 2.63-2.55 (m, 1H), 2.49-2.41 (m, 1H), 2.04-1.96 (m, 1H), 1.77-1.70 (m, 2H). HRMS (ESI) m/z: calcd for $C_{16}H_{19}N_2O_4S^+$ $[M+H]^+$, 335.1060; found, 335.1015.

Example 10: Preparation of 3-(4-((5-hydroxypentyl) thio)-1-oxoisoindolin-2-yl)piperidine-2,6-dione (SIAIS1220069)

Referring to the method of Scheme 9, the compound SIAIS1220069 was prepared under appropriate conditions that will be recognized by one skilled in the art, except that the halogenated substrate was 5-bromo-1-pentanol. The target compound SIAIS1220069 was obtained as a white solid (16 mg, yield 44%). $^1$H NMR (500 MHz, DMSO) δ 10.99 (s, 1H), 7.63 (dd, J=7.5, 1.2 Hz, 1H), 7.56 (dd, J=7.5, 1.2 Hz, 1H), 7.53 (t, J=7.5 Hz, 1H), 5.12 (dd, J=13.3, 5.2 Hz, 1H), 4.35 (d, J=17.4 Hz, 1H), 4.21 (d, J=17.4 Hz, 1H), 3.37 (t, J=5.8 Hz, 2H), 3.08 (t, J=7.3 Hz, 2H), 2.95-2.87 (m, 1H), 2.62-2.56 (m, 1H), 2.49-2.41 (m, 1H), 2.04-2.98 (m, 1H), 1.64-1.56 (m, 2H), 1.44-1.40 (m, 4H). HRMS (ESI) m/z: calcd for $C_{18}H_{23}N_2O_4S^+$ $[M+H]^+$, 363.1373; found, 363.1376.

Example 11: Preparation of 3-(4-((8-hydroxyoctyl) thio)-1-oxoisoindolin-2-yl)piperidine-2,6-dione (SIAIS264006)

Referring to the method of Scheme 9, the compound SIAIS264006 was prepared under appropriate conditions that will be recognized by one skilled in the art, except that the halogenated substrate was 8-bromo-1-octanol. The target compound SIAIS264006 was obtained as a white solid (40 mg, yield 55%). $^1$H NMR (500 MHz, DMSO) δ 10.99 (s, 1H), 7.62 (dd, J=7.5, 1.1 Hz, 1H), 7.56 (dd, J=7.5, 1.1 Hz, 1H), 7.53 (t, J=7.5 Hz, 1H), 5.13 (dd, J=13.3, 5.1 Hz, 1H), 4.35 (d, J=17.4 Hz, 1H), 4.31 (t, J=5.2 Hz, 1H), 4.21 (d, J=17.4 Hz, 1H), 3.39-3.35 (m, 2H), 3.07 (t, J=7.3 Hz, 2H), 2.95-2.87 (m, 1H), 2.59 (d, J=17.4 Hz, 1H), 2.49-2.41 (m, 1H), 2.04-1.97 (m, 1H), 1.63-1.56 (m, 2H), 1.42-1.35 (m, 4H), 1.29-1.22 (m, 6H). HRMS (ESI) m/z: calcd for $C_{21}H_{29}N_{204}S^+$ $[M+H]^+$, 405.1843; found, 405.1849.

Example 12: Preparation of 2-((2-(2,6-dioxopiperidin-3-yl)-1-oxoisoindolin-4-yl)thio)acetamide (SIAIS1213145)

Referring to the method of Scheme 9, the compound SIAIS1213145 was prepared under appropriate conditions that will be recognized by one skilled in the art, except that the halogenated substrate was 2-iodoacetamide. The target compound SIAIS1213145 was obtained as a white solid (14 mg, yield 39%). $^1$H NMR (500 MHz, DMSO) δ 11.00 (s, 1H), 7.64 (dd, J=7.7, 0.9 Hz, 1H), 7.58 (dd, J=7.5, 0.9 Hz, 1H), 7.53 (t, J=7.6 Hz, 1H), 5.13 (dd, J=13.3, 5.1 Hz, 1H), 4.40 (d, J=17.4 Hz, 1H), 4.26 (d, J=17.4 Hz, 1H), 3.74 (s, 2H), 2.96-2.87 (m, 1H), 2.64-2.57 (m, 1H), 2.49-2.41 (m, 1H), 2.04-1.97 (m, 1H). HRMS (ESI) m/z: calcd for $C_{15}H_{16}N_3O_4S^+$ $[M+H]^+$, 334.0856; found, 334.0820.

Intermediate Example 4: Preparation of 3-(4-((5-bromopentyl)thio)-1-oxoisoindolin-2-yl)piperidine-2,6-dione (SIAIS1216049)

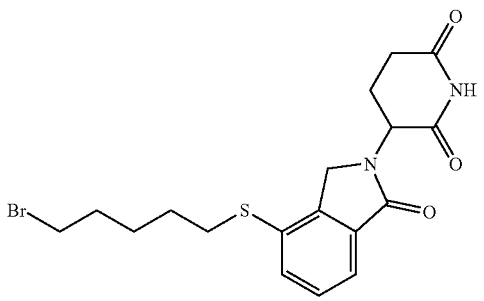 [SMILES: O=C1CCC(N2Cc3c(SCCCCCBr)cccc3C2=O)C(=O)N1]

Referring to the method of Scheme 9, the compound SIAIS1216049 was prepared under appropriate conditions that will be recognized by one skilled in the art, except that the halogenated substrate was 1,5-dibromopentane. The target compound SIAIS1216049 was obtained as a white solid (298 mg, yield 35%). $^1$H NMR (500 MHz, DMSO) δ 11.01 (s, 1H), 7.64 (dd, J=7.5, 0.9 Hz, 1H), 7.59-7.51 (m, 2H), 5.13 (dd, J=13.3, 5.1 Hz, 1H), 4.36 (d, J=17.4 Hz, 1H), 4.21 (d, J=17.4 Hz, 1H), 3.52 (t, J=6.6 Hz, 2H), 3.10 (t, J=7.1 Hz, 2H), 2.95-2.87 (m, 1H), 2.63-2.55 (m, 1H), 2.48-2.41 (m, 1H), 2.03-1.97 (m, 1H), 1.86-1.76 (m, 2H), 1.66-1.58 (m, 2H), 1.57-1.48 (m, 2H). HRMS (ESI) m/z: calcd for $C_{18}H_{22}BrN_2O_3S^+$ [M+H]$^+$, 425.0529; found, 425.0535.

Intermediate Example 5: Preparation of 3-(4-((6-bromohexyl)thio)-1-oxoisoindolin-2-yl)piperidine-2,6-dione (SIAIS1216133)

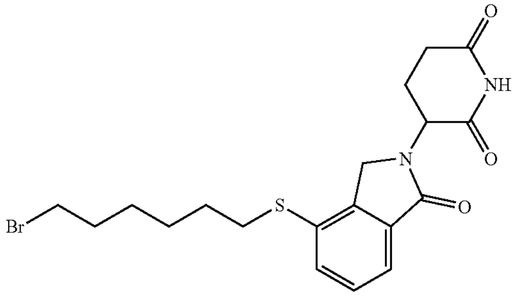 [SMILES: O=C1CCC(N2Cc3c(SCCCCCCBr)cccc3C2=O)C(=O)N1]

Referring to the method of Scheme 9, the compound SIAIS1216133 was prepared under appropriate conditions that will be recognized by one skilled in the art, except that the halogenated substrate was 1,6-dibromohexane. The target compound SIAIS1216133 was obtained as a white solid (339 mg, yield 38%). $^1$H NMR (500 MHz, DMSO) δ 11.01 (s, 1H), 7.63 (dd, J=7.5, 1.2 Hz, 1H), 7.58-7.51 (m, 2H), 5.13 (dd, J=13.3, 5.1 Hz, 1H), 4.35 (d, J=17.4 Hz, 1H), 4.21 (d, J=17.4 Hz, 1H), 3.52 (t, J=6.7 Hz, 2H), 3.08 (t, J=7.2 Hz, 2H), 2.96-2.87 (m, 1H), 2.59 (d, J=17.4 Hz, 1H), 2.49-2.41 (m, 1H), 2.04-1.97 (m, 1H), 1.82-1.74 (m, 2H), 1.63-1.56 (m, 2H), 1.46-1.36 (m, 4H). HRMS (ESI) m/z: calcd for $C_{19}H_{24}BrN_2O_3S^+$ [M+H]$^+$, 439.0686; found, 439.0680.

Intermediate Example 6: Preparation of 3-(4-((7-bromoheptyl)thio)-1-oxoisoindolin-2-yl)piperidine-2,6-dione (SIAIS1216135)

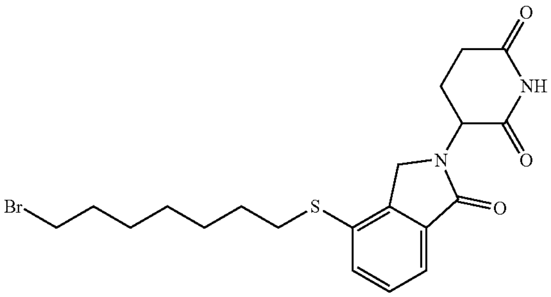 [SMILES: O=C1CCC(N2Cc3c(SCCCCCCCBr)cccc3C2=O)C(=O)N1]

Referring to the method of Scheme 9, the compound SIAIS1216135 was prepared under appropriate conditions that will be recognized by one skilled in the art, except that the halogenated substrate was 1,7-dibromoheptane. The target compound SIAIS1216135 was obtained as a white solid (212 mg, yield 23%). $^1$H NMR (500 MHz, DMSO) δ 11.02 (s, 1H), 7.63 (dd, J=7.5, 0.9 Hz, 1H), 7.58-7.51 (m, 2H), 5.13 (dd, J=13.3, 5.1 Hz, 1H), 4.35 (d, J=17.4 Hz, 1H), 4.21 (d, J=17.4 Hz, 1H), 3.52 (t, J=6.7 Hz, 2H), 3.08 (t, J=7.2 Hz, 2H), 2.96-2.87 (m, 1H), 2.63-2.56 (m, 1H), 2.49-2.40 (m, 1H), 2.04-1.97 (m, 1H), 1.82-1.73 (m, 2H), 1.63-1.56 (m, 2H), 1.44-1.27 (m, 6H). HRMS (ESI) m/z: calcd for $C_{20}H_{26}BrN_2O_3S^+$ [M+H]$^+$, 453.0842; found, 453.0840.

Intermediate Example 7: Preparation of 3-(4-((8-bromooctyl)thio)-1-oxoisoindolin-2-yl)piperidine-2,6-dione (SIAIS1216137)

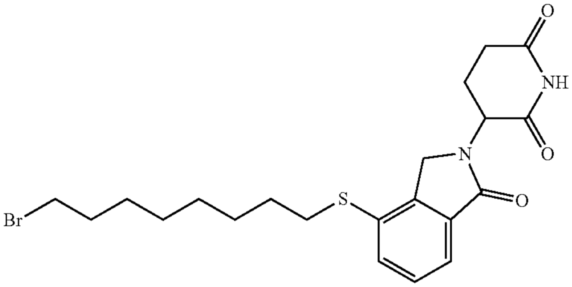 [SMILES: O=C1CCC(N2Cc3c(SCCCCCCCCBr)cccc3C2=O)C(=O)N1]

Referring to the method of Scheme 9, the compound SIAIS1216137 was prepared under appropriate conditions that will be recognized by one skilled in the art, except that the halogenated substrate was 1,8-dibromooctane. The target compound SIAIS1216137 was obtained as a white solid (351 mg, yield 38%). $^1$H NMR (500 MHz, DMSO) δ 11.01 (s, 1H), 7.63 (dd, J=7.5, 1.1 Hz, 1H), 7.57-7.51 (m, 2H), 5.13 (dd, J=13.3, 5.1 Hz, 1H), 4.35 (d, J=17.4 Hz, 1H), 4.20 (d, J=17.4 Hz, 1H), 3.51 (t, J=6.7 Hz, 2H), 3.08 (t, J=7.3 Hz, 2H), 2.95-2.87 (m, 1H), 2.63-2.55 (m, 1H), 2.49-2.41 (m, 1H), 2.03-1.97 (m, 1H), 1.81-1.73 (m, 2H), 1.64-1.55 (m, 2H), 1.44-1.32 (m, 4H), 1.31-1.23 (m, 4H). HRMS (ESI) m/z: calcd for $C_{21}H_{28}BrN_2O_3S^+$ [M+H]$^+$, 467.0999; found, 467.0996.

Intermediate Example 8: Preparation of 3-(4-((9-bromononyl)thio)-1-oxoisoindolin-2-yl)piperidine-2,6-dione (SIAIS1220059)

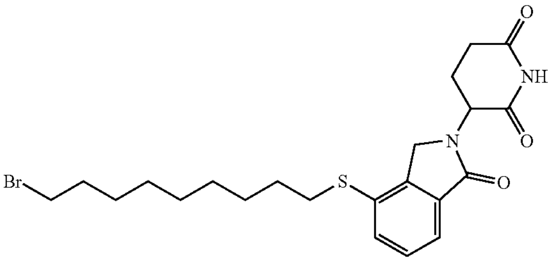 [SMILES: O=C1CCC(N2Cc3c(SCCCCCCCCCBr)cccc3C2=O)C(=O)N1]

Referring to the method of Scheme 9, the compound SIAIS1220059 was prepared under appropriate conditions that will be recognized by one skilled in the art, except that the halogenated substrate was 1,9-dibromononane. The target compound SIAIS1220059 was obtained as a white solid (400 mg, yield 42%). $^{1}H$ NMR (500 MHz, DMSO) δ 11.00 (s, 1H), 7.62 (dd, J=7.5, 0.9 Hz, 1H), 7.59-7.50 (m, 2H), 5.13 (dd, J=13.3, 5.1 Hz, 1H), 4.35 (d, J=17.4 Hz, 1H), 4.21 (d, J=17.4 Hz, 1H), 3.51 (t, J=6.7 Hz, 2H), 3.07 (t, J=7.2 Hz, 2H), 2.95-2.86 (m, 1H), 2.59 (d, J=17.4 Hz, 1H), 2.49-2.40 (m, 1H), 2.04-1.97 (m, 1H), 1.81-1.72 (m, 2H), 1.63-1.56 (m, 2H), 1.42-1.31 (m, 4H), 1.28-1.22 (m, 6H). HRMS (ESI) m/z: calcd for $C_{22}H_{30}BrN_2O_3S^+$ [M+H]$^+$, 481.1155; found, 481.1152.

Intermediate Example 9: Preparation of 3-(4-((10-bromodecyl)thio)-1-oxoisoindolin-2-yl)piperidine-2,6-dione (SIAIS1220013)

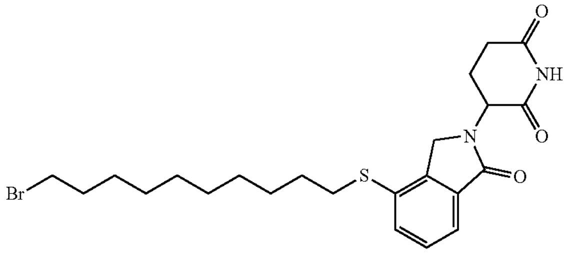 [SMILES: O=C1CCC(N2Cc3c(SCCCCCCCCCCBr)cccc3C2=O)C(=O)N1]

Referring to the method of Scheme 9, the compound SIAIS1220013 was prepared under appropriate conditions that will be recognized by one skilled in the art, except that the halogenated substrate was 1,10-dibromodecane. The target compound SIAIS1220013 was obtained as a light yellow solid (329 mg, yield 33%). $^{1}H$ NMR (500 MHz, DMSO) δ 11.01 (s, 1H), 7.62 (d, J=7.5 Hz, 1H), 7.58-7.51 (m, 2H), 5.13 (dd, J=13.3, 5.1 Hz, 1H), 4.35 (d, J=17.4 Hz, 1H), 4.20 (d, J=17.4 Hz, 1H), 3.52 (t, J=6.7 Hz, 2H), 3.08 (t, J=7.2 Hz, 2H), 2.95-2.87 (m, 1H), 2.62-2.56 (m, 1H), 2.49-2.42 (m, 1H), 2.03-1.97 (m, 1H), 1.81-1.73 (m, 2H), 1.62-1.55 (m, 2H), 1.43-1.32 (m, 4H), 1.24 (s, 8H). HRMS (ESI) m/z: calcd for $C_{23}H_{32}BrN_2O_3S^+$ [M+H]$^+$, 495.1312; found, 495.1310.

Intermediate Example 10: Preparation of 3-(4-((11-bromoundecyl)thio)-1-oxoisoindolin-2-yl)piperidine-2,6-dione (SIAIS1220015)

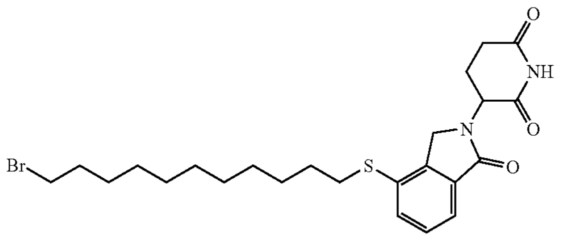 [SMILES: O=C1CCC(N2Cc3c(SCCCCCCCCCCCBr)cccc3C2=O)C(=O)N1]

Referring to the method of Scheme 9, the compound SIAIS1220015 was prepared under appropriate conditions that will be recognized by one skilled in the art, except that the halogenated substrate was 1,11-dibromoundecane. The target compound SIAIS1220015 was obtained as a white solid (276 mg, yield 27%). $^{1}H$ NMR (500 MHz, DMSO) δ 11.01 (s, 1H), 7.64-7.60 (m, 1H), 7.58-7.51 (m, 2H), 5.13 (dd, J=13.3, 5.1 Hz, 1H), 4.35 (d, J=17.4 Hz, 1H), 4.20 (d, J=17.4 Hz, 1H), 3.52 (t, J=6.7 Hz, 2H), 3.08 (t, J=7.2 Hz, 2H), 2.96-2.86 (m, 1H), 2.63-2.56 (m, 1H), 2.49-2.40 (m, 1H), 2.03-1.96 (m, 1H), 1.82-1.73 (m, 2H), 1.62-1.54 (m, 2H), 1.42-1.32 (m, 4H), 1.24 (s, 10H). HRMS (ESI) m1/z: calcd for $C_{24}H_{34}BrN_2O_3S^+$ [M+H]$^+$, 509.1468; found, 509.1466.

Example 13: Preparation of 3-(4-(methylsulfonyl)-1-oxoisoindolin-2-yl)piperidine-2,6-dione (SIAIS1210083)

Referring to the method of Scheme 10, the compound SIAIS1210083 was prepared under appropriate conditions that will be recognized by one skilled in the art, except that the substrate was thio-lenalidomide SIAIS171095. The target compound SIAIS1210083 was obtained as a white solid (16 mg, yield 72%). $^{1}H$ NMR (500 MHz, DMSO) δ 11.05 (s, 1H), 8.13 (dd, J=7.8, 0.8 Hz, 1H), 8.10 (dd, J=7.6, 0.7 Hz, 1H), 7.84 (t, J=7.7 Hz, 1H), 5.17 (dd, J=13.3, 5.1 Hz, 1H), 4.83 (d, J=18.6 Hz, 1H), 4.68 (d, J=18.5 Hz, 1H), 3.34 (s, 3H), 2.96-2.86 (m, 1H), 2.65-2.57 (m, 1H), 2.49-2.42 (m, 1H), 2.07-2.00 (m, 1H). HRMS (ESI) m/z: calcd for $C_{14}H_{15}N_2O_5S^+$ [M+H]$^+$, 323.0696; found, 323.0717.

Example 14: Preparation of 3-(4-((5-morpholinopentyl)thio)-1-oxoisoindolin-2-yl)piperidine-2,6-dione (SIAIS1216061)

Referring to the method of Scheme 11, the compound SIAIS1216061 was prepared under appropriate conditions that will be recognized by one skilled in the art, except that the substrates were 3-(4-((5-bromopentyl)thio)-1-oxoisoindolin-2-yl)piperidine-2,6-dione (SIAIS1216049) and morpholine. The target compound SIAIS1216061 was obtained as a light yellow solid (7.3 mg, yield 34%). $^{1}H$ NMR (500 MHz, DMSO) δ 11.02 (s, 1H), 10.44 (s, 1H), 7.65 (d, J=7.0 Hz, 1H), 7.60-7.52 (m, 2H), 5.14 (dd, J=13.3, 5.0 Hz, 1H), 4.36 (d, J=17.4 Hz, 1H), 4.21 (d, J=17.4 Hz, 1H), 4.05-3.65 (m, 4H), 3.41 (t, J=5.5 Hz, 2H), 3.15-2.97 (m, 6H), 2.96-2.88 (m, 1H), 2.63-2.57 (m, 1H), 2.49-2.40 (m, 1H), 2.04-1.97 (m, 1H), 1.75-1.57 (m, 4H), 1.44 (s, 2H). HRMS (ESI) m/z: calcd for $C_{22}H_{30}N_3O_4S^+$ [M+H]$^+$, 432.1952; found, 432.1963.

Example 15: Preparation of 3-(1-oxo-4-((5-(piperazin-1-yl)pentyl)thio)isoindolin-2-yl)piperidine-2,6-dione (SIAIS1216063)

Referring to the method of Scheme 11, the compound SIAIS1216063 was prepared under appropriate conditions that will be recognized by one skilled in the art, except that the substrates were 3-(4-((5-bromopentyl)thio)-1-oxoisoindolin-2-yl)piperidine-2,6-dione (SIAIS1216049) and piperazine. The hydrochloride salt of compound SIAIS1216063 was obtained (light yellow solid, 12 mg, yield 56%). $^{1}H$ NMR (500 MHz, DMSO) δ 11.02 (s, 1H), 9.02 (s, 2H), 7.64 (dd, J=7.6, 1.0 Hz, 1H), 7.59-7.52 (m, 2H), 5.14 (dd, J=13.3, 5.1 Hz, 1H), 4.35 (d, J=17.4 Hz, 1H), 4.21 (d, J=17.4 Hz, 1H), 3.50-3.48 (m, 4H), 3.43-3.39 (m, 2H), 3.341-3.20 (m, 4H), 3.11-3.08 (m, 2H), 2.95-2.90 (m, 1H), 2.60 (d, J=17.3 Hz, 1H), 2.48-2.40 (m, 1H), 2.05-1.98 (m, 1H), 1.67-1.55 (m, 4H), 1.44-1.39 (m, 2H). HRMS (ESI) m/z: calcd for $C_{22}H_{31}N_4O_3S^+$ [M+H]$^+$, 431.2111; found, 431.2114.

Example 16: Preparation of 3-(4-((5-(methylamino)pentyl)thio)-1-oxoisoindolin-2-yl)piperidine-2,6-dione (SIAIS1216141)

Referring to the method of Scheme 11, the compound SIAIS1216141 was prepared under appropriate conditions that will be recognized by one skilled in the art, except that the substrates were 3-(4-((5-bromopentyl)thio)-1-oxoisoindolin-2-yl)piperidine-2,6-dione (SIAIS1216049) and methylamine hydrochloride. The hydrochloride salt of compound SIAIS1216141 was obtained (white solid, 5 mg, yield 13%). $^1$H NMR (500 MHz, DMSO) δ 10.99 (s, 1H), 8.25 (s, 2H), 7.64 (dd, J=7.6, 1.1 Hz, 1H), 7.58 (dd, J=7.5, 1.0 Hz, 1H), 7.56-7.52 (m, 1H), 5.14 (dd, J=13.4, 5.1 Hz, 1H), 4.35 (d, J=17.4 Hz, 1H), 4.21 (d, J=17.4 Hz, 1H), 3.12-3.07 (m, 2H), 2.96-2.88 (m, 1H), 2.87-2.82 (m, 2H), 2.63-2.57 (m, 1H), 2.54 (dd, J=7.0, 4.6 Hz, 3H), 2.48-2.40 (m, 1H), 2.04-1.98 (m, 1H), 1.65-1.54 (m, 4H), 1.47-1.41 (m, 2H). HRMS (ESI) m/z: calcd for $C_{19}H_{26}N_3O_3S^+$ [M+H]$^+$, 376.1986; found, 376.1982.

Example 17: Preparation of 3-(4-((5-((2-(diethylamino)ethyl)amino)pentyl)thio)-1-oxoisoindolin-2-yl)piperidine-2,6-dione (SIAIS1220035)

Referring to the method of Scheme 11, the compound SIAIS1220035 was prepared under appropriate conditions that will be recognized by one skilled in the art, except that the substrates were 3-(4-((5-bromopentyl)thio)-1-oxoisoindolin-2-yl)piperidine-2,6-dione (SIAIS1216049) and N1,N1-diethylethane-1,2-diamine. The hydrochloride salt of compound SIAIS1220035 was obtained (white solid, 20 mg, yield 43%). $^1$H NMR (500 MHz, DMSO) δ 10.99 (s, 1H), 10.74 (s, 1H), 9.36 (s, 2H), 7.65 (d, J=7.4 Hz, 1H), 7.58 (d, J=7.0 Hz, 1H), 7.54 (t, J=7.5 Hz, 1H), 5.13 (dd, J=13.3, 5.1 Hz, 1H), 4.36 (d, J=17.3 Hz, 1H), 4.22 (d, J=17.4 Hz, 1H), 3.44-3.39 (m, 2H), 3.38-3.32 (m, 2H), 3.30 (t, J=7.1 Hz, 2H), 3.20-3.15 (m, 4H), 3.09-3.05 (m, 1H), 2.96-2.91 (m, 2H), 2.59 (d, J=16.4 Hz, 1H), 2.49-2.41 (m, 1H), 2.04-1.98 (m, 1H), 1.94-1.86 (m, 2H), 1.69-1.60 (m, 4H), 1.25 (t, J=7.2 Hz, 6H). HRMS (ESI) m/z: calcd for $C_{24}H_{37}N_4O_3S^+$ [M+H]$^+$, 461.2581; found 461.2517.

Example 18: Preparation of 3-(4-((6-morpholinohexyl)thio)-1-oxoisoindolin-2-yl)piperidine-2,6-dione (SIAIS1220027)

Referring to the method of Scheme 11, the compound SIAIS1220027 was prepared under appropriate conditions that will be recognized by one skilled in the art, except that the substrates were 3-(4-((6-bromohexyl)thio)-1-oxoisoindolin-2-yl)piperidine-2,6-dione (SIAIS1216133) and morpholine. The hydrochloride salt of compound SIAIS1220027 was obtained (white solid, 17 mg, yield 39%). $^1$H NMR (500 MHz, DMSO) δ 10.99 (s, 1H), 10.71 (s, 1H), 7.64 (dd, J=7.5, 1.0 Hz, 1H), 7.57 (d, J=6.4 Hz, 1H), 7.54 (t, J=7.5 Hz, 1H), 5.13 (dd, J=13.3, 5.1 Hz, 1H), 4.36 (d, J=17.3 Hz, 1H), 4.21 (d, J=17.4 Hz, 1H), 3.93 (d, J=11.9 Hz, 2H), 3.76 (t, J=12.0 Hz, 2H), 3.42-3.37 (m, 2H), 3.12-3.07 (m, 2H), 3.05-2.96 (m, 4H), 2.95-2.87 (m, 1H), 2.59 (d, J=17.7 Hz, 1H), 2.50-2.41 (m, 1H), 2.05-1.98 (m, 1H), 1.69-1.58 (m, 4H), 1.48-1.40 (m, 2H), 1.34-1.27 (m, 2H). HRMS (ESI) m/z: calcd for $C_{23}H_{32}N_3O_4S^+$ [M+H]$^+$, 446.2108; found, 446.2091.

Example 19: Preparation of 3-(4-((7-morpholinoheptyl)thio)-1-oxoisoindolin-2-yl)piperidine-2,6-dione (SIAIS1220031)

Referring to the method of Scheme 11, the compound SIAIS1220031 was prepared under appropriate conditions that will be recognized by one skilled in the art, except that the substrates were 3-(4-((7-bromoheptyl)thio)-1-oxoisoindolin-2-yl)piperidine-2,6-dione (SIAIS1216135) and morpholine. The hydrochloride salt of compound SIAIS1220031 was obtained (white solid, 30 mg, yield 65%). $^1$H NMR (500 MHz, DMSO) δ 10.99 (s, 2H), 7.63 (dd, J=7.5, 1.1 Hz, 1H), 7.57 (dd, J=7.4, 1.0 Hz, 1H), 7.53 (t, J=7.5 Hz, 1H), 5.13 (dd, J=13.3, 5.1 Hz, 1H), 4.36 (d, J=17.4 Hz, 1H), 4.22 (d, J=17.4 Hz, 1H), 3.98-3.88 (m, 2H), 3.79 (s, 2H), 3.35 (s, 2H), 3.11-3.06 (m, 2H), 3.00 (s, 4H), 2.95-2.87 (m, 1H), 2.59 (d, J=17.5 Hz, 1H), 2.49-2.42 (m, 1H), 2.04-1.97 (m, 1H), 1.67 (s, 2H), 1.63-1.57 (m, 2H), 1.45-1.37 (m, 2H), 1.33-1.24 (m, 4H). HRMS (ESI) m/z: calcd for $C_{24}H_{34}N_3O_4S^+$ [M+H]$^+$, 460.2265; found, 460.2253.

Example 20: Preparation of 3-(4-((8-morpholinooctyl)thio)-1-oxoisoindolin-2-yl)piperidine-2,6-dione (SIAIS1216143)

Referring to the method of Scheme 11, the compound SIAIS1216143 was prepared under appropriate conditions that will be recognized by one skilled in the art, except that the substrates were 3-(4-((8-bromooctyl)thio)-1-oxoisoindolin-2-yl)piperidine-2,6-dione (SIAIS1216137) and morpholine. The hydrochloride salt of compound SIAIS1216143 was obtained (light yellow solid, 16 mg, yield 68%). $^1$H NMR (500 MHz, DMSO) δ 11.02 (s, 1H), 10.59 (s, 1H), 7.63 (dd, J=7.5, 1.1 Hz, 1H), 7.58-7.51 (m, 2H), 5.14 (dd, J=13.3, 5.1 Hz, 1H), 4.35 (d, J=17.4 Hz, 1H), 4.21 (d, J=17.4 Hz, 1H), 3.94 (dd, J=12.6, 2.8 Hz, 2H), 3.75 (t, J=11.4 Hz, 2H), 3.38 (d, J=12.2 Hz, 2H), 3.11-3.06 (m, 2H), 3.05-2.97 (m, 4H), 2.96-2.88 (m, 1H), 2.63-2.56 (m, 1H), 2.49-2.41 (m, 1H), 2.04-1.97 (m, 1H), 1.69-1.63 (m, 2H), 1.63-1.57 (m, 2H), 1.45-1.35 (m, 2H), 1.30-1.22 (s, 6H). $^{13}$C NMR (126 MHz, DMSO) δ 173.35, 171.47, 168.28, 141.39, 132.58, 132.52, 130.69, 129.63, 120.65, 52.11, 47.16, 31.89, 31.69, 29.04, 28.84, 28.43, 22.82. HRMS (ESI) m/z: calcd for $C_{25}H_{36}N_3O_4S^+$ [M+H]$^+$, 474.2421; found, 474.2420.

Example 21: Preparation of 3-(1-oxo-4-((8-(piperazin-1-yl)octyl)thio)isoindolin-2-yl)piperidine-2,6-dione (SIAIS1216145)

Referring to the method of Scheme 11, the compound SIAIS1216145 was prepared under appropriate conditions that will be recognized by one skilled in the art, except that the substrates were 3-(4-((8-bromooctyl)thio)-1-oxoisoindolin-2-yl)piperidine-2,6-dione (SIAIS1216137) and piperazine. The hydrochloride salt of compound SIAIS1216145 was obtained (light yellow solid, 15 mg, yield 63%). $^1$H NMR (500 MHz, DMSO) δ 11.02 (s, 1H), 9.36 (s, 3H), 7.63 (dd, J=7.6, 0.9 Hz, 1H), 7.58 (dd, J=7.5, 0.9 Hz, 1H), 7.53 (t, J=7.5 Hz, 1H), 5.14 (dd, J=13.3, 5.3 Hz, 1H), 4.35 (d, J=17.4 Hz, 1H), 4.21 (d, J=17.4 Hz, 1H), 3.49 (t, J=6.6 Hz, 2H), 3.15-3.06 (m, 6H), 2.96-2.87 (m, 1H), 2.60 (d, J=16.5 Hz, 1H), 2.48-2.42 (m, 1H), 2.04-1.98 (m, 1H), 1.62-1.57 (m, 4H), 1.42-1.36 (m, 2H), 1.30-1.24 (m, 10H). HRMS (ESI) m/z: calcd for $C_{25}H_{37}N_4O_3S^+$ [M+H]$^+$, 473.2581; found, 473.2587.

Example 22: Preparation of 3-(4-((8-(3,5-dimethylpiperazin-1-yl)octyl)thio)-1-oxoisoindolin-2-yl)piperidine-2,6-dione (SIAIS1220057)

Referring to the method of Scheme 11, the compound SIAIS1220057 was prepared under appropriate conditions that will be recognized by one skilled in the art, except that the substrates were 3-(4-((8-bromooctyl)thio)-1-oxoisoindolin-2-yl)piperidine-2,6-dione (SIAIS1216137) and 2,6-dimethylpiperazine. The hydrochloride salt of compound SIAIS1220057 was obtained (white solid, 30 mg, yield 60%). $^{1}$H NMR (500 MHz, DMSO) δ 11.88 (s, 1H), 10.99 (s, 1H), 10.01 (s, 2H), 7.63 (dd, J=7.5, 1.1 Hz, 1H), 7.57 (dd, J=7.4, 1.1 Hz, 1H), 7.53 (t, J=7.5 Hz, 1H), 5.13 (dd, J=13.3, 5.1 Hz, 1H), 4.36 (d, J=17.4 Hz, 1H), 4.21 (d, J=17.4 Hz, 1H), 3.79-3.64 (m, 4H), 3.12-2.98 (m, 6H), 2.95-2.87 (m, 1H), 2.59 (d, J=17.5 Hz, 1H), 2.49-2.42 (m, 1H), 2.04-1.98 (m, 1H), 1.71 (s, 2H), 1.63-1.56 (m, 2H), 1.43-1.38 (m, 2H), 1.33-1.26 (m, 12H). HRMS (ESI) m/z: calcd for $C_{27}H_{41}N_4O_3S^+$ [M+H]$^+$, 501.2894; found, 501.2891.

Example 23: Preparation of 3-(1-oxo-4-((8-(piperidin-1-yl)octyl)thio)isoindolin-2-yl)piperidine-2,6-dione (SIAIS122009)

Referring to the method of Scheme 11, the compound SIAIS1220009 was prepared under appropriate conditions that will be recognized by one skilled in the art, except that the substrates were 3-(4-((8-bromooctyl)thio)-1-oxoisoindolin-2-yl)piperidine-2,6-dione (SIAIS1216137) and piperidine. The hydrochloride salt of compound SIAIS1220009 was obtained (white solid, 38 mg, yield 81%). $^{1}$H NMR (500 MHz, DMSO) δ 11.71 (s, 1H), 11.02 (s, 1H), 7.63 (d, J=7.4 Hz, 1H), 7.60-7.50 (m, 2H), 5.14 (dd, J=13.3, 5.0 Hz, 1H), 4.35 (d, J=17.4 Hz, 1H), 4.21 (d, J=17.4 Hz, 1H), 3.62-3.20 (m, 8H), 3.14-3.02 (m, 4H), 2.96-2.87 (m, 1H), 2.81 (s, 2H), 2.63-2.77 (m, 1H), 2.48-2.39 (m, 1H), 2.05-1.96 (m, 1H), 1.72-1.56 (m, 4H), 1.45-1.35 (m, 2H), 1.27 (s, 6H). HRMS (ESI) m/z: calcd for $C_{26}H_{38}N_3O_3S^+$ [M+H]$^+$, 472.2628; found, 472.2663.

Example 24: Preparation of 3-(4-((8-(4,4-difluoropiperidin-1-yl)octyl)thio)-1-oxoisoindolin-2-yl)piperidine-2,6-dione (SIAIS1220055)

Referring to the method of Scheme 11, the compound SIAIS1220055 was prepared under appropriate conditions that will be recognized by one skilled in the art, except that the substrates were 3-(4-((8-bromooctyl)thio)-1-oxoisoindolin-2-yl)piperidine-2,6-dione (SIAIS1216137) and 4,4-difluoropiperidine. The hydrochloride salt of compound SIAIS1220055 was obtained (white solid, 12 mg, yield 40%). $^{1}$H NMR (500 MHz, DMSO) δ 11.02 (s, 1H), 10.86 (s, 1H), 7.63 (dd, J=7.5, 1.2 Hz, 1H), 7.59-7.51 (m, 2H), 5.14 (dd, J=13.3, 5.1 Hz, 1H), 4.35 (d, J=17.4 Hz, 1H), 4.21 (d, J=17.4 Hz, 1H), 3.57 (d, J=12.4 Hz, 2H), 3.12-3.03 (m, 6H), 2.96-2.87 (m, 1H), 2.63-2.57 (m, 1H), 2.49-2.28 (m, 5H), 2.04-1.97 (m, 1H), 1.72-1.68 (m, 2H), 1.63-1.56 (m, 2H), 1.44-1.36 (m, 2H), 1.27 (s, 6H). HRMS (ESI) m/z: calcd for $C_{26}H_{36}F_2N_3O_3S^+$ [M+H]$^+$, 508.2440; found, 508.2415.

Example 25: Preparation of 3-(4-((8-(1,4-diazepan-1-yl)octyl)thio)-1-oxoisoindolin-2-yl)piperidine-2,6-dione (SIAIS1220017)

Referring to the method of Scheme 11, the compound SIAIS1220017 was prepared under appropriate conditions that will be recognized by one skilled in the art, except that the substrates were 3-(4-((8-bromooctyl)thio)-1-oxoisoindolin-2-yl)piperidine-2,6-dione (SIAIS1216137) and homopiperazine. The hydrochloride salt of compound SIAIS1220017 was obtained (white solid, 33 mg, yield 67%). $^{1}$H NMR (500 MHz, DMSO) δ 10.99 (s, 2H), 9.37 (s, 1H), 9.22 (s, 1H), 7.63 (dd, J=7.5, 1.1 Hz, 1H), 7.59-7.51 (m, 2H), 5.13 (dd, J=13.3, 5.1 Hz, 1H), 4.35 (d, J=17.4 Hz, 1H), 4.21 (d, J=17.4 Hz, 1H), 3.75-3.42 (m, 6H), 3.25-3.15 (m, 2H), 3.13-3.00 (m, 4H), 2.96-2.87 (m, 1H), 2.62-2.56 (m, 1H), 2.49-2.41 (m, 1H), 2.20-2.07 (m, 2H), 2.04-1.98 (m, 1H), 1.71-1.62 (m, 2H), 1.62-1.55 (m, 2H), 1.45-1.35 (m, 2H), 1.27 (s, 6H). HRMS (ESI) m/z: calcd for $C_{26}H_{39}N_4O_3S^+$ [M+H]$^+$, 487.2737; found, 487.2733.

Example 26: Preparation of 3-(1-oxo-4-((8-(4-(piperazin-1-yl)piperidin-1-yl)octyl)thio)isoindolin-2-yl)piperidine-2,6-dione (SIAIS1220019)

Referring to the method of Scheme 11, the compound SIAIS1220019 was prepared under appropriate conditions that will be recognized by one skilled in the art, except that the substrates were 3-(4-((8-bromooctyl)thio)-1-oxoisoindolin-2-yl)piperidine-2,6-dione (SIAIS1216137) and 1-(piperidin-4-yl)piperazine. The hydrochloride salt of compound SIAIS1220019 was obtained (white solid, 39 mg, yield 70%). $^{1}$H NMR (500 MHz, DMSO) δ 10.99 (s, 1H), 9.44 (s, 1H), 8.72 (s, 2H), 7.63 (dd, J=7.6, 1.0 Hz, 1H), 7.58 (dd, J=7.4, 1.0 Hz, 1H), 7.53 (t, J=7.5 Hz, 1H), 5.13 (dd, J=13.3, 5.1 Hz, 1H), 4.35 (d, J=17.4 Hz, 1H), 4.21 (d, J=17.4 Hz, 1H), 3.56-3.58 (m, 2H), 3.20-3.11 (m, 5H), 3.10-3.06 (m, 2H), 3.02-2.95 (m, 2H), 2.94-2.88 (m, 1H), 2.88-2.83 (m, 2H), 2.83-2.67 (m, 4H), 2.59 (d, J=17.5 Hz, 1H), 2.48-2.41 (m, 1H), 2.06-1.95 (m, 3H), 1.73-1.63 (m, 2H), 1.63-1.55 (m, 4H), 1.45-1.35 (m, 2H), 1.27 (s, 6H). HRMS (ESI) m/z: calcd for $C_{30}H_{46}N_5O_3S^+$ [M+H]$^+$, 556.3316; found, 556.3313.

Example 27: Preparation of 3-(4-((8-(methylamino)octyl)thio)-1-oxoisoindolin-2-yl)piperidine-2,6-dione (SIAIS1216151)

Referring to the method of Scheme 11, the compound SIAIS1216151 was prepared under appropriate conditions that will be recognized by one skilled in the art, except that the substrates were 3-(4-((8-bromooctyl)thio)-1-oxoisoindolin-2-yl)piperidine-2,6-dione (SIAIS1216137) and methylamine hydrochloride. The hydrochloride salt of compound SIAIS1216151 was obtained (white solid, 7 mg, yield 17%). $^{1}$H NMR (500 MHz, DMSO) δ 11.02 (s, 1H), 8.63 (s, 2H), 7.63 (d, J=7.5 Hz, 1H), 7.58-7.51 (m, 2H), 5.14 (dd, J=13.3, 5.1 Hz, 1H), 4.35 (d, J=17.4 Hz, 1H), 4.21 (d, J=17.4 Hz, 1H), 3.08 (t, J=6.8 Hz, 2H), 2.96-2.87 (m, 1H), 2.86-2.78 (m, 2H), 2.71 (d, J=4.9 Hz, 3H), 2.59 (d, J=16.1 Hz, 1H), 2.48-2.41 (m, 1H), 2.04-1.97 (m, 1H), 1.63-1.53 (m, 4H), 1.44-1.36 (m, 2H), 1.29-1.23 (m, 6H). HRMS (ESI) m/z: calcd for $C_{22}H_{32}N_3O_3S^+$ [M+H]$^+$, 418.2159; found. 418.2153.

Example 28: Preparation of 3-(4-((8-((2-(diethylamino)ethyl)amino)octyl)thio)-1-oxoisoindolin-2-yl)piperidine-2,6-dione (SIAIS1220037)

Referring to the method of Scheme 11, the compound SIAIS1220037 was prepared under appropriate conditions that will be recognized by one skilled in the art, except that the substrates were 3-(4-((8-bromooctyl)thio)-1-oxoisoindolin-2-yl)piperidine-2,6-dione (SIAIS1216137) and N1,N1-diethylethane-1,2-diamine. The hydrochloride salt of compound SIAIS1220037 was obtained (white solid, 16 mg, yield 36%). $^{1}$H NMR (500 MHz, DMSO) δ 10.99 (s, 1H), 10.56 (s, 1H), 9.14 (s, 2H), 7.63 (dd, J=7.5, 1.1 Hz, 1H), 7.57 (dd, J=7.5, 1.1 Hz, 1H), 7.53 (t, J=7.5 Hz, 1H), 5.13 (dd, J=13.3, 5.1 Hz, 1H), 4.35 (d, J=17.3 Hz, 1H), 4.21 (d, J=17.4 Hz, 1H), 3.41-3.35 (m, 4H), 3.22-3.15 (m, 4H), 3.08 (td, J=7.0, 1.2 Hz, 2H), 2.97-2.87 (m, 3H), 2.59 (d, J=17.5 Hz, 1H), 2.49-2.41 (m, 1H), 2.04-1.97 (m, 1H), 1.65-1.56 (m, 4H), 1.45-1.37 (m, 2H), 1.32-1.25 (m, 6H), 1.24 (t, J=7.1 Hz, 6H). HRMS (ESI) m/z: calcd for $C_{27}H_{43}N_4O_3S^+$ $[M+H]^+$, 503.3050; found. 503.3044.

Example 29: Preparation of 3-(4-((8-(4-methylpiperazin-1-yl)octyl)thio)-1-oxoisoindolin-2-yl)piperidine-2,6-dione (SIAIS1220011)

Referring to the method of Scheme 11, the compound SIAIS1220011 was prepared under appropriate conditions that will be recognized by one skilled in the art, except that the substrates were 3-(4-((8-bromooctyl)thio)-1-oxoisoindolin-2-yl)piperidine-2,6-dione (SIAIS1216137) and 1-methylpiperazine. The hydrochloride salt of compound SIAIS1220011 was obtained (white solid, 12 mg, yield 80%). $^1$H NMR (500 MHz, DMSO) δ 11.02 (s, 1H), 9.60 (s, 1H), 7.63 (dd, J=7.5, 1.1 Hz, 1H), 7.59-7.51 (m, 2H), 5.14 (dd, J=13.3, 5.1 Hz, 1H), 4.35 (d, J=17.4 Hz, 1H), 4.21 (d, J=17.4 Hz, 1H), 3.38 (d, J=12.1 Hz, 2H), 3.12-3.06 (m, 2H), 2.98-2.90 (m, 3H), 2.84-2.75 (m, 2H), 2.63-2.55 (m, 1H), 2.48-2.40 (m, 1H), 2.05-1.96 (m, 1H), 1.77 (d, J=11.1 Hz, 2H), 1.74-1.50 (m, 7H), 1.45-1.15 (m, 10H). HRMS (ESI) m/z: calcd for $C_{26}H_{39}N_4O_3S^+$ $[M+H]^+$, 487.2737; found, 487.2732.

Example 30: Preparation of 3-(4-((9-morpholinononyl)thio)-1-oxoisoindolin-2-yl)piperidine-2,6-dione (SIAIS1220065)

Referring to the method of Scheme 11, the compound SIAIS1220065 was prepared under appropriate conditions that will be recognized by one skilled in the art, except that the substrates were 3-(4-((9-bromononyl)thio)-1-oxoisoindolin-2-yl)piperidine-2,6-dione (SIAIS1220059) and morpholine. The hydrochloride salt of compound SIAIS1220065 was obtained (white solid, 7 mg, yield 17%). $^1$H NMR (500 MHz, DMSO) δ 10.99 (s, 2H), 7.63 (dd, J=7.5, 1.1 Hz, 1H), 7.57 (dd, J=7.4, 0.9 Hz, 1H), 7.53 (t, J=7.4 Hz, 1H), 5.13 (dd, J=13.3, 5.1 Hz, 1H), 4.35 (d, J=17.3 Hz, 1H), 4.21 (d, J=17.4 Hz, 1H), 3.93 (dd, J=12.5, 2.7 Hz, 2H), 3.80 (t, J=11.4 Hz, 2H), 3.35 (s, 2H), 3.08 (t, J=7.1 Hz, 2H), 3.02-2.88 (m, 4H), 2.96-2.87 (m, 1H), 2.59 (d, J=17.7 Hz, 1H), 2.49-2.42 (m, 1H), 2.04-1.97 (m, 1H), 1.67 (s, 2H), 1.63-1.57 (m, 2H), 1.43-1.37 (m, 2H), 1.26 (s, 8H). HRMS (ESI) m/z: calcd for $C_{26}H_{38}N_3O_4S^+$ $[M+H]^+$, 488.2578; found. 488.2576.

Example 31: 3-(4-((10-morpholinodecyl)thio)-1-oxoisoindolin-2-yl)piperidine-2,6-dione (SIAIS1220023)

Referring to the method of Scheme 11, the compound SIAIS1220023 was prepared under appropriate conditions that will be recognized by one skilled in the art, except that the substrates were 3-(4-((10-bromodecyl)thio)-1-oxoisoindolin-2-yl)piperidine-2,6-dione (SIAIS1220013) and morpholine. The hydrochloride salt of compound SIAIS1220023 was obtained (light yellow solid, 24 mg, yield 60%). $^1$H NMR (500 MHz, DMSO) δ 11.06 (s, 1H), 11.02 (s, 1H), 7.63 (dd, J=7.5, 1.0 Hz, 1H), 7.59-7.51 (m, 2H), 5.14 (dd, J=13.3, 5.1 Hz, 1H), 4.35 (d, J=17.4 Hz, 1H), 4.21 (d, J=17.4 Hz, 1H), 3.93 (dd, J=12.5, 2.9 Hz, 2H), 3.80 (t, J=11.4 Hz, 2H), 3.37 (d, J=12.2 Hz, 2H), 3.08 (t, J=7.2 Hz, 2H), 3.04-2.96 (m, 4H), 2.97-2.88 (m, 1H), 2.63-2.56 (m, 1H), 2.50-2.41 (m, 1H), 2.04-1.97 (m, 1H), 1.71-1.63 (m, 2H), 1.63-1.55 (m, 2H), 1.44-1.35 (m, 2H), 1.25 (s, 10H). HRMS (ESI) m/z: calcd for $C_{27}H_{40}N_3O_4S^+$ $[M+H]^+$, 502.2734; found. 502.2728.

Example 32: 3-(4-((11-morpholinoundecyl)thio)-1-oxoisoindolin-2-yl)piperidine-2,6-dione (SIAIS1220045)

Referring to the method of Scheme 11, the compound SIAIS1220045 was prepared under appropriate conditions that will be recognized by one skilled in the art, except that the substrates were 3-(4-((11-bromoundecyl)thio)-1-oxoisoindolin-2-yl)piperidine-2,6-dione (SIAIS1220015) and morpholine. The hydrochloride salt of compound SIAIS1220045 was obtained (white solid, 35 mg, yield 85%). $^1$H NMR (500 MHz, DMSO) δ 10.99 (s, 1H), 10.66 (s, 1H), 7.62 (dd, J=7.5, 0.9 Hz, 1H), 7.57 (d, J=6.6 Hz, 1H), 7.53 (t, J=7.4 Hz, 1H), 5.13 (dd, J=13.3, 5.1 Hz, 1H), 4.35 (d, J=17.4 Hz, 1H), 4.21 (d, J=17.4 Hz, 1H), 3.93 (d, J=12.2 Hz, 2H), 3.76 (t, J=11.3 Hz, 2H), 3.37 (s, 2H), 3.07 (t, J=7.2 Hz, 2H), 3.01 (s, 4H), 2.95-2.87 (m, 1H), 2.59 (d, J=17.9 Hz, 1H), 2.49-2.42 (m, 1H), 2.05-1.97 (m, 1H), 1.66 (s, 2H), 1.63-1.55 (m, 2H), 1.43-1.35 (m, 2H), 1.30-1.21 (m, 12H). HRMS (ESI) m/z: calcd for $C_{28}H_{42}N_3O_4S^+$ $[M+H]^+$, 516.2890; found 516.2899.

Example 33: 3-(4-((5-(diethylamino)pentyl)thio)-1-oxoisoindolin-2-yl)piperidine-2,6-dione (SIAIS1216139)

Referring to the method of Scheme 12, the compound SIAIS1216139 was prepared under appropriate conditions that will be recognized by one skilled in the art, except that the substrate was 3-(4-((5-bromopentyl)thio)-1-oxoisoindolin-2-yl)piperidine-2,6-dione (SIAIS1216049). The hydrochloride salt of compound SIAIS1216139 was obtained (light yellow solid, 21 mg, yield 71%). $^1$H NMR (500 MHz, DMSO) δ 11.02 (s, 1H), 9.13 (s, 1H), 7.64 (dd, J=7.6, 0.9 Hz, 1H), 7.59-7.52 (m, 2H), 5.14 (dd, J=13.3, 5.1 Hz, 1H), 4.37-4.33 (m, 1H), 4.21 (d, J=17.4 Hz, 1H), 3.71-3.30 (m, 10H), 3.14-3.05 (m, 4H), 2.92 (dd, J=11.2, 6.2 Hz, 1H), 2.60 (d, J=17.1 Hz, 1H), 2.48-2.41 (m, 1H), 2.03-1.99 (m, 1H), 1.62 (dd, J=14.7, 7.3 Hz, 4H), 1.44 (dd, J=14.4, 7.3 Hz, 2H). HRMS (ESI) m/z: calcd for $C_{22}H_{32}N_3O_3S^+$ $[M+H]^+$, 418.2159; found, 418.2155.

Example 34: 3-(4-((6-(diethylamino)hexyl)thio)-1-oxoisoindolin-2-yl)piperidine-2,6-dione (SIAIS1220029)

Referring to the method of Scheme 12, the compound SIAIS1220029 was prepared under appropriate conditions that will be recognized by one skilled in the art, except that the substrate was 3-(4-((6-bromohexyl)thio)-1-oxoisoindolin-2-yl)piperidine-2,6-dione (SIAIS1216133). The hydrochloride salt of compound SIAIS1220029 was obtained (white solid, 23 mg, yield 53%). $^1$H NMR (500 MHz, DMSO) δ 11.02 (s, 1H), 9.84 (s, 1H), 7.64 (dd, J=7.5, 1.1 Hz, 1H), 7.59-7.52 (m, 2H), 5.14 (dd, J=13.3, 5.1 Hz, 1H), 4.35 (d, J=17.4 Hz, 1H), 4.21 (d, J=17.4 Hz, 1H), 3.12-3.03 (m, 6H), 2.98-2.87 (m, 3H), 2.59 (d, J=16.5 Hz, 1H), 2.49-2.41 (m, 1H), 2.04-1.97 (m, 1H), 1.65-1.56 (m, 4H), 1.47-1.40 (m, 2H), 1.35-1.27 (m, 2H), 1.18 (t, J=7.2 Hz, 6H). HRMS (ESI) m/z: calcd for $C_{23}H_{34}N_3O_3S^+$ $[M+H]^+$, 432.2315; found, 432.2314.

Example 35: 3-(4-((7-(diethylamino)heptyl)thio)-1-oxoisoindolin-2-yl)piperidine-2,6-dione (SIAIS1220033)

Referring to the method of Scheme 12, the compound SIAIS1220033 was prepared under appropriate conditions that will be recognized by one skilled in the art, except that the substrate was 3-(4-((7-bromoheptyl)thio)-1-oxoisoindolin-2-yl)piperidine-2,6-dione (SIAIS1216135). The hydrochloride salt of compound SIAIS1220033 was obtained (white solid, 18 mg, yield 40%). $^1$H NMR (500 MHz, DMSO) δ 10.99 (s, 1H), 9.88 (s, 1H), 7.63 (dd, J=7.5, 1.1 Hz, 1H), 7.57 (dd, J=7.5, 1.1 Hz, 1H), 7.53 (t, J=7.5 Hz, 1H), 5.13 (dd, J=13.3, 5.1 Hz, 1H), 4.35 (d, J=17.4 Hz, 1H), 4.21 (d, J=17.4 Hz, 1H), 3.11-3.04 (m, 6H), 2.99-2.93 (m, 2H), 2.93-2.87 (m, 1H), 2.59 (d, J=17.5 Hz, 1H), 2.49-2.41 (m, 1H), 2.04-1.98 (m, 1H), 1.64-1.57 (m, 4H), 1.44-1.38 (m, 2H), 1.34-1.26 (m, 4H), 1.19 (t, J=7.3 Hz, 6H). HRMS (ESI) m/z: calcd for $C_{24}H_{36}N_3O_3S^+$ [M+H]$^+$, 446.2472; found, 446.2469.

Example 36: 3-(4-((8-(diethylamino)octyl)thio)-1-oxoisoindolin-2-yl)piperidine-2,6-dione (SIAIS1216147)

Referring to the method of Scheme 12, the compound SIAIS1216147 was prepared under appropriate conditions that will be recognized by one skilled in the art, except that the substrate was 3-(4-((8-bromooctyl)thio)-1-oxoisoindolin-2-yl)piperidine-2,6-dione (SIAIS1216137). The hydrochloride salt of compound SIAIS1216147 was obtained (white solid, 16 mg, yield 70%). $^1$H NMR (500 MHz, DMSO) δ 11.02 (s, 1H), 10.02 (s, 1H), 7.63 (dd, J=7.5, 1.2 Hz, 1H), 7.58-7.52 (m, 2H), 5.14 (dd, J=13.3, 5.1 Hz, 1H), 4.35 (d, J=17.4 Hz, 1H), 4.21 (d, J=17.4 Hz, 1H), 3.09-3.04 (m, 6H), 2.97-2.92 (m, 3H), 2.63-2.56 (m, 1H), 2.49-2.41 (m, 1H), 2.04-1.97 (m, 1H), 1.62-1.58 (m, 4H), 1.44-1.37 (m, 2H), 1.28 (s, 6H), 1.19 (t, J=3.6 Hz, 6H). HRMS (ESI) m/z: calcd for $C_{25}H_{38}N_3O_3S^+$ [M+H]$^+$, 460.2628; found. 460.2623.

Example 37: 3-(4-((9-(diethylamino)nonyl)thio)-1-oxoisoindolin-2-yl)piperidine-2,6-dione (SIAIS1220067)

Referring to the method of Scheme 12, the compound SIAIS1220067 was prepared under appropriate conditions that will be recognized by one skilled in the art, except that the substrate was 3-(4-((9-bromononyl)thio)-1-oxoisoindolin-2-yl)piperidine-2,6-dione (SIAIS1220059). The hydrochloride salt of compound SIAIS1220067 was obtained (white solid, 19 mg, yield 79%). $^1$H NMR (500 MHz, DMSO) δ 10.99 (s, 1H), 11.16 (s, 1H), 7.63 (dd, J=7.5, 1.0 Hz, 1H), 7.58-7.51 (m, 2H), 5.13 (dd, J=13.3, 5.1 Hz, 1H), 4.35 (d, J=17.4 Hz, 1H), 4.21 (d, J=17.4 Hz, 1H), 3.10-3.02 (m, 6H), 2.98-2.86 (m, 3H), 2.59 (d, J=17.5 Hz, 1H), 2.49-2.41 (m, 1H), 2.05-1.97 (m, 1H), 1.65-1.55 (m, 4H), 1.43-1.36 (m, 2H), 1.27 (s, 8H), 1.19 (t, J=7.3 Hz, 6H). HRMS (ESI) m/z: calcd for $C_{26}H_{40}N_3O_3S^+$ [M+H]$^+$, 474.2785; found. 474.2790.

Example 38: 3-(4-((10-(diethylamino)decyl)thio)-1-oxoisoindolin-2-yl)piperidine-2,6-dione (SIAIS1220025)

Referring to the method of Scheme 12, the compound SIAIS1220025 was prepared under appropriate conditions that will be recognized by one skilled in the art, except that the substrate was 3-(4-((10-bromodecyl)thio)-1-oxoisoindolin-2-yl)piperidine-2,6-dione (SIAIS1220013). The hydrochloride salt of compound SIAIS1220025 was obtained (light yellow solid, 23 mg, yield 59%). $^1$H NMR (500 MHz, DMSO) δ 11.02 (s, 1H), 10.00 (s, 1H), 7.63 (dd, J=7.5, 1.1 Hz, 1H), 7.58-7.51 (m, 2H), 5.14 (dd, J=13.3, 5.1 Hz, 1H), 4.35 (d, J=17.4 Hz, 1H), 4.21 (d, J=17.4 Hz, 1H), 3.10-3.03 (m, 6H), 2.98-2.86 (m, 3H), 2.63-2.55 (m, 1H), 2.49-2.40 (m, 1H), 2.04-1.97 (m, 1H), 1.64-1.55 (m, 4H), 1.44-1.36 (m, 2H), 1.26 (d, J=8.1 Hz, 10H), 1.19 (t, J=7.3 Hz, 6H). HRMS (ESI) m/z: calcd for $C_{27}H_{42}N_3O_3S^+$ [M+H]$^+$, 488.2941; found. 488.2929.

Example 39: 3-(4-((11-(diethylamino)undecyl)thio)-1-oxoisoindolin-2-yl)piperidine-2,6-dione (SIAIS1220047)

Referring to the method of Scheme 12, the compound SIAIS1220047 was prepared under appropriate conditions that will be recognized by one skilled in the art, except that the substrate was 3-(4-((11-bromoundecyl)thio)-1-oxoisoindolin-2-yl)piperidine-2,6-dione (SIAIS1220015). The hydrochloride salt of compound SIAIS1220047 was obtained (white solid, 19 mg, yield 48%). $^1$H NMR (500 MHz, DMSO) δ 10.99 (s, 1H), 9.66 (s, 1H), 7.62 (dd, J=7.5, 1.1 Hz, 1H), 7.57 (dd, J=7.5, 1.1 Hz, 1H), 7.53 (t, J=7.5 Hz, 1H), 5.13 (dd, J=13.3, 5.1 Hz, 1H), 4.35 (d, J=17.4 Hz, 1H), 4.21 (d, J=17.4 Hz, 1H), 3.07 (t, J=7.0 Hz, 6H), 2.99-2.87 (m, 3H), 2.59 (d, J=17.3 Hz, 1H), 2.49-2.41 (m, 1H), 2.04-1.97 (m, 1H), 1.62-1.56 (m, 4H), 1.43-1.55 (m, 2H), 1.28-1.23 (m, 12H), 1.18 (t, J=7.3 Hz, 6H). HRMS (ESI) m/z: calcd for $C_{28}H_{44}N_3O_3S^+$ [M+H]$^+$, 502.3098; found. 502.3097.

Example 40: 3-(4-((5-(dimethylamino)pentyl)thio)-1-oxoisoindolin-2-yl)piperidine-2,6-dione (SIAIS1216089)

Referring to the method of Scheme 13, the compound SIAIS1216089 was prepared under appropriate conditions that will be recognized by one skilled in the art, except that the substrate was 3-(4-((5-aminopentyl)thio)-1-oxoisoindolin-2-yl)piperidine-2,6-dione (SIAIS171132). The hydrochloride salt of compound SIAIS1216089 was obtained (light yellow solid, 7 mg, yield 54%). $^1$H NMR (500 MHz, DMSO) δ 11.00 (s, 1H), 9.82 (s, 1H), 7.65 (dd, J=7.5, 1.1 Hz, 1H), 7.58 (dd, J=7.5, 1.1 Hz, 1H), 7.54 (t, J=7.5 Hz, 1H), 5.14 (dd, J=13.3, 5.1 Hz, 1H), 4.36 (d, J=17.3 Hz, 1H), 4.22 (d, J=17.3 Hz, 1H), 3.13-3.07 (m, 2H), 3.02-2.96 (m, 2H), 2.95-2.87 (m, 1H), 2.72 (d, J=4.9 Hz, 6H), 2.63-2.57 (m, 1H), 2.47-2.41 (m, 1H), 2.04-1.97 (m, 1H), 1.67-1.59 (m, 4H), 1.46-1.39 (m, 2H). HRMS (ESI) m/z: calcd for $C_{20}H_{28}N_3O_3S^+$ [M+H]$^+$, 390.1846; found, 390.1849.

Example 41: 3-(4-((8-(dimethylamino)octyl)thio)-1-oxoisoindolin-2-yl)piperidine-2,6-dione (SIAIS1216149)

Referring to the method of Scheme 13, the compound SIAIS1216149 was prepared under appropriate conditions that will be recognized by one skilled in the art, except that the substrate was 3-(4-((8-aminooctyl)thio)-1-oxoisoindolin-2-yl)piperidine-2,6-dione (SIAIS171136). The hydrochloride salt of compound SIAIS1216149 was obtained (white solid, 14 mg, yield 63%). $^1$H NMR (500 MHz, DMSO) δ 11.02 (s, 1H), 9.98 (s, 1H), 7.63 (dd, J=7.5, 1.0

Hz, 1H), 7.59-7.51 (m, 2H), 5.14 (dd, J=13.3, 5.1 Hz, 1H), 4.35 (d, J=17.4 Hz, 1H), 4.21 (d, J=17.4 Hz, 1H), 3.12-3.06 (m, 2H), 3.00-2.93 (m, 2H), 2.93-2.87 (m, 1H), 2.71 (d, J=2.8 Hz, 6H), 2.62-2.56 (m, 1H), 2.49-2.41 (m, 1H), 2.04-1.97 (m, 1H), 1.64-1.55 (m, 4H), 1.44-1.36 (m, 2H), 1.30-1.20 (s, 6H). HRMS (ESI) m/z: calcd for $C_{23}H_{34}N_3O_3S^+$ $[M+H]^+$, 432.2315; found. 432.2324.

Example 42: 3-(4-((8-(4-methyl-1,4-diazepan-1-yl) octyl)thio)-1-oxoisoindolin-2-yl)piperidine-2,6-dione (SIAIS1220051)

Referring to the method of Scheme 13, the compound SIAIS1220051 was prepared under appropriate conditions that will be recognized by one skilled in the art, except that the substrate was 3-(4-((8-(1,4-diazepan-1-yl)octyl)thio)-1-oxoisoindolin-2-yl)piperidine-2,6-dione (SIAIS1220017). The hydrochloride salt of compound SIAIS1220051 was obtained (white solid, 12 mg, yield 62%). $^1$H NMR (500 MHz, DMSO) δ 11.40 (s, 1H), 11.15 (s, 1H), 10.99 (s, 1H), 7.63 (dd, J=7.5, 1.1 Hz, 1H), 7.57 (d, J=6.5 Hz, 1H), 7.53 (t, J=7.5 Hz, 1H), 5.13 (dd, J=13.3, 5.1 Hz, 1H), 4.35 (d, J=17.4 Hz, 1H), 4.21 (d, J=17.4 Hz, 1H), 3.85-3.42 (m, 8H), 3.11-3.02 (m, 4H), 2.95-2.88 (m, 1H), 2.77 (s, 3H), 2.59 (d, J=17.5 Hz, 1H), 2.49-2.41 (m, 1H), 2.18 (d, J=47.5 Hz, 2H), 2.05-1.98 (m, 1H), 1.72-1.63 (m, 2H), 1.63-1.56 (m, 2H), 1.44-1.36 (m, 2H), 1.27 (s, 6H). HRMS (ESI) m/z: calcd for $C_{27}H_{41}N_4O_3S^+$ $[M+H]^+$, 501.2894; found, 501.2891.

Example 43: 3-(4-((8-(4-(4-methylpiperazin-1-yl) piperidin-1-yl)octyl)thio)-1-oxoisoindolin-2-yl)piperidine-2,6-dione (SIAIS1220049)

Referring to the method of Scheme 13, the compound SIAIS1220049 was prepared under appropriate conditions that will be recognized by one skilled in the art, except that the substrate was 3-(1-oxo-4-((8-(4-(piperazin-1-yl)piperidin-1-yl)octyl)thio)isoindolin-2-yl)piperidine-2,6-dione (SIAIS1220019). The hydrochloride salt of compound SIAIS1220049 was obtained (white solid, 5 mg, yield 63%). $^1$H NMR (500 MHz, DMSO) δ 10.99 (s, 1H), 10.28 (s, 1H), 7.63 (dd, J=7.5, 1.0 Hz, 1H), 7.57 (dd, J=7.4, 1.0 Hz, 1H), 7.53 (t, J=7.5 Hz, 1H), 5.13 (dd, J=13.3, 5.1 Hz, 1H), 4.35 (d, J=17.4 Hz, 1H), 4.21 (d, J=17.4 Hz, 1H), 3.60-3.52 (m, 5H), 3.25-3.15 (m, 3H), 3.11-3.05 (m, 3H), 3.00-2.84 (m, 7H), 2.79 (s, 3H), 2.59 (d, J=18.0 Hz, 1H), 2.49-2.41 (m, 1H), 2.25-2.08 (m, 2H), 2.04-1.90 (m, 3H), 1.65 (s, 2H), 1.63-1.56 (m, 2H), 1.43-1.37 (m, 2H), 1.27 (s, 6H). HRMS (ESI) m/z: calcd for $C_{31}H_{48}N_5O_3S^+$ $[M+H]^+$, 570.3472; found, 570.3484.

Intermediate Example 11: 3-(4-((3-(bromomethyl) benzyl)thio)-1-oxoisoindolin-2-yl) piperidine-2,6-dione (SIAIS1227123)

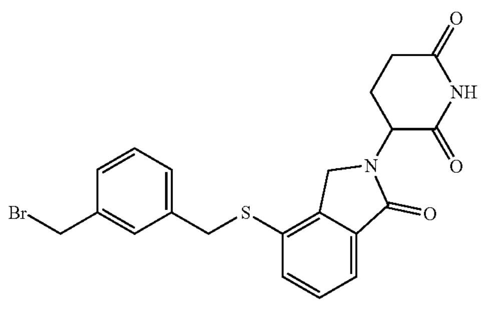 [SMILES: O=C1CCC(N2Cc3c(SCc4cccc(CBr)c4)cccc3C2=O)C(=O)N1]

Referring to the method of Scheme 9, the compound SIAIS1227123 was prepared under appropriate conditions that will be recognized by one skilled in the art, except that the halogenated substrate was 1,3-bis(bromomethyl)benzene. The target compound SIAIS1227123 was obtained as light yellow oily substance (357 mg, yield 39%). HRMS (ESI) m/z: calcd for $C_{21}H_{20}BrN_2O_3S^+$ $[M+H]^+$, 459.0373; found, 459.0379.

Example 44: Preparation of 3-(4-(tert-butylthio)-1-oxoisoindolin-2-yl)piperidine-2,6-dione (SIAIS1213167)

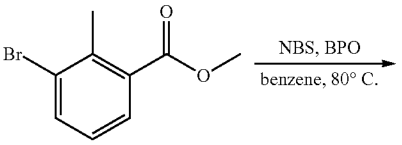

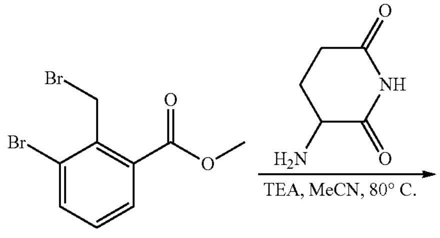

SIAIS1213017

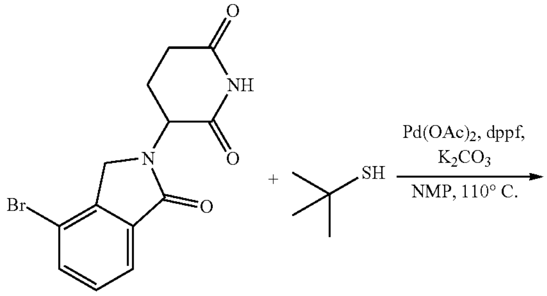

SIAIS1213029

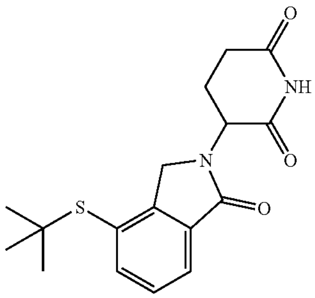

SIAIS1213167

Step 1: A 50 mL single-necked flask was charged with methyl 3-bromo-2-methylbenzoate (458 mg, 2.0 mmol), NBS (427 mg, 2.4 mmol) and BPO (24 mg, 0.1 mmol), followed by evacuation and refilling with argon gas for three times, and then the reaction mixture was heated at 80° C. in oil bath under argon atmosphere overnight. After filtration to remove the insoluble substance, a small amount of acetonitrile was added to the filtrate, which was then subjected to C18 reverse phase column chromatography (eluent (v/v): acetonitrile/water=10%-100%) for separation. The collected fractions were concentrated under reduced pressure to remove the solvent, to give the compound SIAIS1213017 as a light yellow solid (437 mg, yield 71%).

Step 2: A 100 mL single-necked flask was charged with methyl 3-bromo-2-bromomethylbenzoate (400 mg, 1.299 mmol), 3-aminopiperidine-2,6-dione hydrochloride (257 mg, 1.559 mmol), triethylamine (263 mg, 1.559 mmol), and acetonitrile (10 mL), and then the reaction mixture was reacted at 80° C. in oil bath overnight. After cooling to room temperature, the reaction mixture was allowed to stand, and filtered to obtain the crude product. 10 mL of DMSO was added to dissolve the crude product, which was then subjected to reverse phase C18 column chromatography (eluent (v/v):acetonitrile/water=10%-100%) for separation. The collected fractions were concentrated under reduced pressure to remove the solvent, to give 3-(4-bromo-1-oxoisoindolin-2-yl)piperidine-2,6-dione (SIAIS1213029) as a light purple solid (357 mg, yield 85%). $^1$H NMR (500 MHz, MeOD) δ 7.81 (dd, J=7.7, 3.7 Hz, 2H), 7.49 (t, J=7.8 Hz, 1H), 5.18 (dd, J=13.4, 5.2 Hz, 1H), 4.48 (d, J=17.4 Hz, 1H), 4.41 (d, J=17.4 Hz, 1H), 2.96-2.86 (m, 1H), 2.58-2.47 (m, 1H), 2.34-2.27 (m, 1H), 2.22-2.15 (m, 1H). HRMS (ESI) m/z: calcd for $C_{13}H_{12}BrN_2O_3^+$ [M+H]$^+$, 323.0026, 325.0005; found, 322.9970, 324.9954.

Step 3: A 25 mL two-necked flask was charged with 3-(4-bromo-1-oxoisoindolin-2-yl)piperidine-2,6-dione (32.3 mg, 0.100 mmol), potassium carbonate (27.6 mg, 0.200 mmol), and NMP (5 mL), sequentially followed by evacuation and refilling with argon gas, addition of palladium acetate (2.2 mg, 0.010 mmol) and dppf (11.1 mg, 0.020 mmol), another evacuation and refilling with argon gas, and addition of tert-butyl mercaptan (10.8 mg, 0.120 mmol). The reaction mixture was heated and reacted at 110° C. for 3 h. After removing insoluble materials by filtration using filtering membrane, the filtrate was subjected to a preparative HPLC (eluent (v/v):acetonitrile/(water+0.05% HCl)=10%-100%) for separation. The collected fractions were concentrated under reduced pressure to remove acetonitrile, and then lyophilized to obtain the compound SIAIS1213167 as a gray solid (10 mg, yield 30%). $^1$H NMR (500 MHz, $CDCl_3$) δ 8.00 (s, 1H), 7.83 (d, J=7.5 Hz, 1H), 7.64 (d, J=7.6 Hz, 1H), 7.43 (t, J=7.6 Hz, 1H), 5.17 (dd, J=13.4, 5.1 Hz, 1H), 4.46 (d, J=16.8 Hz, 1H), 4.33 (d, J=16.8 Hz, 1H), 2.90-2.83 (m, 1H), 2.82-2.73 (m, 1H), 2.40-2.29 (m, 1H), 2.20-2.13 (m, 1H), 1.27 (s, 9H). HRMS (ESI) m/z: calcd for $C_{17}H_{21}N_2O_3S^+$ [M+H]$^+$, 333.1267; found, 333.1264.

Example 45: Preparation of 2-(2,6-dioxopiperidin-3-yl)-1,3-dioxoisoindoline-4-sulfonamide (SIAIS164074)

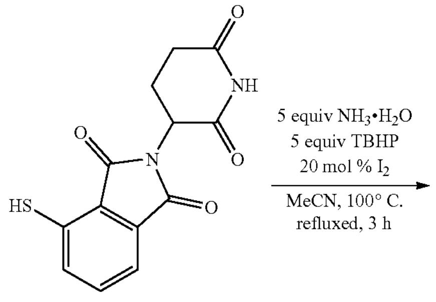

SIAIS15014

-continued

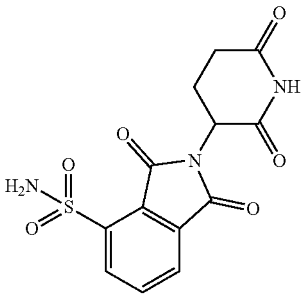

SIAIS164074

A 100 mL single-necked flask was charged with the compound SIAIS151014 (500 mg, 1.72 mmol) and 10 mL of MeCN, followed by sequential addition of aqueous ammonia (1.206 g, 8.6 mmol, 25% in water), iodine (87.3 mg, 0.344 mmol), and TBHP (1.107 g, 8.6 mmol) under stirring at room temperature. After the completion of addition, the reaction mixture was refluxed at 110° C. for 3 h. The reaction was quenched with water. The resulting mixture was extracted with ethyl acetate, dried over anhydrous sodium sulfate, and concentrated to remove the solvent to obtain the crude product. The crude product was subjected to column chromatography (eluent (v/v):DCM/MeOH=20:1) for purification, and the collected fractions were rotary evaporated to dryness to give the target product SIAIS164074 as a yellow solid (140 mg, yield 24%). $^1$H NMR (500 MHz, DMSO) δ 12.08 (s, 1H), 11.80 (s, 1H), 11.17 (s, 1H), 8.23 (d, J=7.1 Hz, 1H), 8.07-8.00 (m, 1H), 7.41 (d, J=7.1 Hz, 1H), 5.21 (dd, J=12.9, 5.4 Hz, 1H), 2.91-2.88 (m, 1H), 2.73-2.61 (m, 2H), 2.17-2.11 (m, 1H). HRMS (ESI) m/z: calcd for $C_{13}H_{12}N_3O_6S$ [M+H]$^+$, 338.0441; found, 338.0546.

Example 46: Preparation of N-(5-((2-(2,6-dioxopiperidin-3-yl)-1-oxoisoindolin-4-yl)thio)pentyl)acetamide (SIAIS1216095)

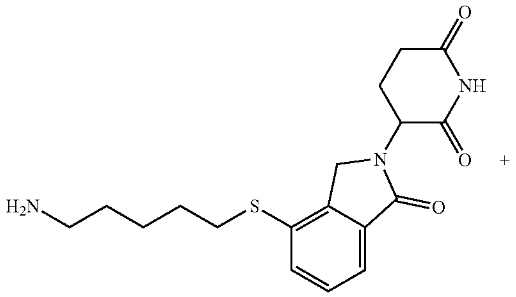

SIAIS171132

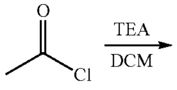

-continued

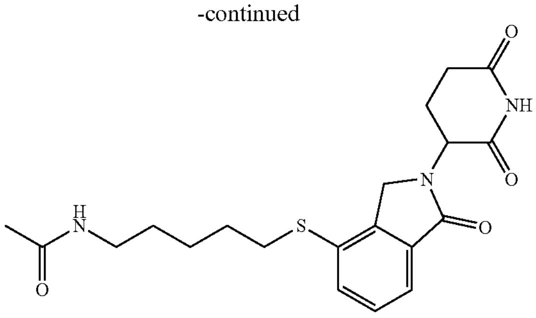

SIAIS126095

A 15 mL sample vial was charged with 3-(4-((5-amino)thio)-1-oxo-2-isoindolinyl)piperidine-2,6-dione SIAIS171132 (14.5 mg, 0.04 mmol), triethylamine (12.1 mg, 0.12 mmol), DCM (2 mL), followed by addition of acetyl chloride (3.8 mg, 0.048 mmol) with stirring. The reaction mixture was stirred and reacted at room temperature for 0.5 h. The reaction was quenched with 1 drop of water. After filtration by using filtering membrane, the filtrate was subjected to a preparative HPLC (eluent (v/v):acetonitrile/(water+0.05% HCl)=10%-100%) for separation. The collected fractions were concentrated under reduced pressure to remove acetonitrile, and then lyophilized to obtain the compound SIAIS1216095 as a light yellow solid (6 mg, yield 38%). $^{1}$H NMR (500 MHz, DMSO) δ 11.01 (s, 1H), 7.81 (s, 1H), 7.63 (dd, J=7.5, 1.2 Hz, 1H), 7.58-7.51 (m, 2H), 5.13 (dd, J=13.3, 5.1 Hz, 1H), 4.35 (d, J=17.4 Hz, 1H), 4.21 (d, J=17.4 Hz, 1H), 3.07 (t, J=7.3 Hz, 2H), 3.03-2.97 (m, 2H), 2.95-2.87 (m, 1H), 2.59 (d, J=18.0 Hz, 1H), 2.49-2.41 (m, 1H), 2.04-1.97 (m, 1H), 1.77 (s, 3H), 1.63-1.56 (m, 2H), 1.42-1.37 (m, 4H). HRMS (ESI) m/z: calcd for $C_{20}H_{26}N_3O_4S^+$ [M+H]$^+$, 404.1639; found, 404.1689.

Example 47: Preparation of 3-(4-((8-(diisopropylamino)octyl)thio)-1-oxoisoindolin-2-yl)piperidine-2,6-dione (SIAIS1220021)

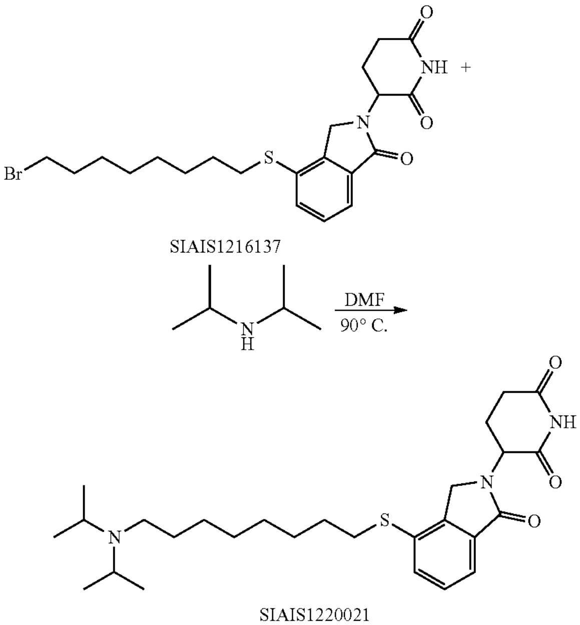

SIAIS1216137

SIAIS1220021

A 15 mL sample vial was charged with 3-(4-((8-bromooctyl)thio)-1-oxoisoindolin-2-yl)piperidine-2,6-dione SIAIS1216137 (23.4 mg, 0.05 mmol) and DMF (2 mL), followed by addition of diisopropylamine (10.1 mg, 0.10 mmol) with stirring. The reaction mixture was stirred and reacted at 90° C. for 3 h. The reaction mixture was filtered by using filtering membrane, and the filtrate was subjected to a preparative HPLC (eluent (v/v):acetonitrile/(water+0.05% HCl)=10%-100%) for separation. The collected fractions were rotary evaporated to remove acetonitrile, and then lyophilized to obtain the hydrochloride salt of compound SIAIS1220021 (white solid, 6 mg, yield 25%). $^{1}$H NMR (500 MHz, DMSO) δ 11.02 (s, 1H), 8.70 (s, 1H), 7.63 (dd, J=7.5, 1.1 Hz, 1H), 7.60-7.51 (m, 2H), 5.14 (dd, J=13.3, 5.1 Hz, 1H), 4.35 (d, J=17.4 Hz, 1H), 4.20 (d, J=17.4 Hz, 1H), 3.62-3.55 (m, 2H), 3.09 (t, J=7.2 Hz, 2H), 3.02-2.95 (m, 2H), 2.94-2.86 (m, 1H), 2.63-2.56 (m, 1H), 2.49-2.40 (m, 1H), 2.04-1.97 (m, 1H), 1.67-1.56 (m, 4H), 1.45-1.35 (m, 2H), 1.33-1.26 (m, 12H), 1.24 (d, J=6.4 Hz, 6H). HRMS (ESI) m/z: calcd for $C_{27}H_{42}N_3O_3S^+$ [M+H]$^+$, 488.2941; found, 488.2930.

Example 48: Preparation of 3,3'-((octane-1,8-diylbis(sulfanediyl))bis(1-oxoisoindoline-4,2-diyl))bis(piperidine-2,6-dione) (SIAIS1216137B)

Referring to the method of Scheme 9, the compound SIAIS1216137B was prepared under appropriate conditions that will be recognized by one skilled in the art, except that the halogenated substrate was 1,8-dibromooctane. The target compound SIAIS1216137B was obtained as a white solid (10 mg, yield 12%). $^{1}$H NMR (500 MHz, DMSO) δ 11.01 (s, 2H), 7.62 (dd, J=7.5, 0.9 Hz, 2H), 7.58-7.50 (m, 4H), 5.13 (dd, J=13.3, 5.1 Hz, 2H), 4.35 (d, J=17.4 Hz, 2H), 4.20 (d, J=17.4 Hz, 2H), 3.07 (t, J=7.2 Hz, 4H), 2.95-2.86 (m, 2H), 2.62-2.55 (m, 2H), 2.48-2.40 (m, 2H), 2.04-1.96 (m, 2H), 1.61-1.53 (m, 4H), 1.42-1.34 (m, 4H), 1.25 (s, 4H). HRMS (ESI) m/z: calcd for $C_{34}H_{39}N_4O_6S_2^+$ [M+H]$^+$, 663.2306; found, 663.2303.

Example 49: Preparation of 3,3'-((nonane-1,9-diylbis(sulfanediyl))bis(1-oxoisoindoline-4,2-diyl))bis(piperidine-2,6-dione) (SIAIS1220059B)

Referring to the method of Scheme 9, the compound SIAIS1220059B was prepared under appropriate conditions that will be recognized by one skilled in the art, except that the halogenated substrate was 1,9-dibromononane. The target compound SIAIS1220059B was obtained as a white solid (12 mg, yield 13%). $^{1}$H NMR (500 MHz, DMSO) δ 10.98 (s, 2H), 7.61 (dd, J=7.5, 1.1 Hz, 2H), 7.59-7.49 (m, 4H), 5.12 (dd, J=13.3, 5.1 Hz, 2H), 4.35 (d, J=17.4 Hz, 2H), 4.21 (d, J=17.4 Hz, 2H), 3.06 (t, J=7.2 Hz, 4H), 2.95-2.86 (m, 2H), 2.59 (d, J=17.0 Hz, 2H), 2.49-2.41 (m, 2H), 2.04-1.96 (m, 3.1 Hz, 2H), 1.61-1.53 (m, 4H), 1.42-1.34 (m, 4H), 1.29-1.20 (m, 6H). HRMS (ESI) m/z: calcd for $C_{35}H_{41}N_4O_6S_2^+$ [M+H]$^+$, 677.2462; found, 677.2468.

Example 50: Preparation of 3-(5-mercapto-1-oxoisoindolin-2-yl)piperidine-2,6-dione (SIAIS1213175)

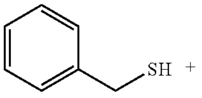

-continued

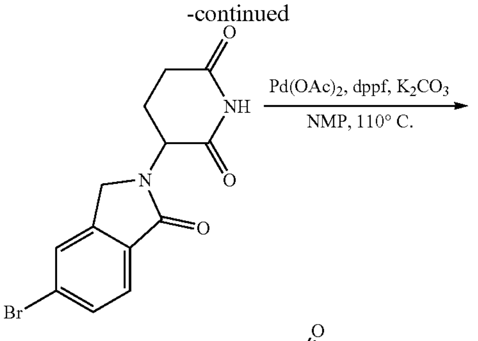

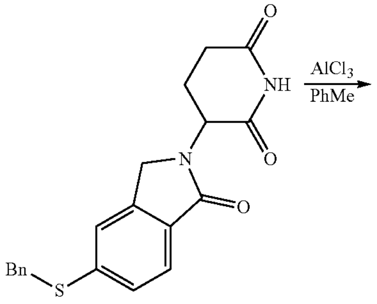

SIAIS1213173

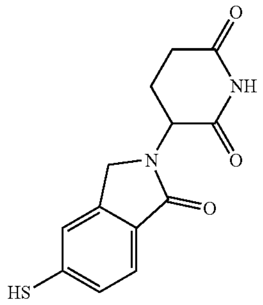

SIAIS1213175

Step 1: Preparation of 3-(5-(benzylthio)-1-oxoisoindolin-2-yl)piperidine-2,6-dione (SIAIS1213173)

A 25 mL two-necked flask was charged with 3-(5-bromo-1-oxoisoindolin-2-yl)piperidine-2,6-dione (64.6 mg, 0.200 mmol), potassium carbonate (55.2 mg, 0.400 mmol), and NMP (5 mL), sequentially followed by evacuation and refilling with argon gas, addition of palladium acetate (4.4 mg, 0.02 mmol) and dppf (22.2 mg, 0.04 mmol), another evacuation and refilling with argon gas, and addition of benzyl mercaptan (29 mg, 0.24 mmol). The reaction mixture was heated and reacted at 110° C. for 3 h. After removing insoluble materials by filtration using filtering membrane, the filtrate was subjected to a preparative HPLC (eluent (v/v):acetonitrile/(water+0.05% HCl)=10%-100%) for separation. The collected fractions were rotary evaporated to remove acetonitrile, and then lyophilized to obtain the compound SIAIS1213173 as a gray solid (50 mg, yield 68%). $^1$H NMR (500 MHz, $CDCl_3$) δ 7.95 (s, 1H), 7.78 (d, J=8.0 Hz, 1H), 7.41 (d, J=8.0 Hz, 1H), 7.39-7.31 (m, 5H), 7.31-7.29 (m, 1H), 5.22 (dd, J=13.2, 4.9 Hz, 1H), 4.46 (d, J=15.9 Hz, 1H), 4.30 (d, J=15.9 Hz, 1H), 4.24 (s, 2H), 2.95 (d, J=16.7 Hz, 1H), 2.89-2.81 (m, 1H), 2.40-2.31 (m, 1H), 2.27-2.20 (m, 1H). calcd for $C_{20}H_{19}N_2O_3S^+$ $[M+H]^+$, 367.1111; found, 367.1124.

Step 2: Preparation of 3-(5-mercapto-1-oxoisoindolin-2-yl)piperidine-2,6-dione (SIAIS1213175)

A 15 mL sample vial was charged with 3-(5-(benzylthio)-1-oxoisoindolin-2-yl)piperidine-2,6-dione (50 mg, 0.136 mmol) and toluene (3 mL). Another 15 mL sample vial was charged with aluminum trichloride (36.3 mg, 0.272 mmol) and toluene (2 mL), followed by the addition dropwise of the above suspension solution of 3-(5-(benzylthio)-1-oxoisoindolin-2-yl)piperidine-2,6-dione in toluene under ice bath. After the completion of addition, the reaction mixture was stirred at room temperature for 10 h and another 0.5 h after adding ice water. Then the pH was adjusted to acidic by adding dilute hydrochloric acid. The resulting mixture was allowed to stand, and filtered. The filter cake was dissolved in 3 mL of DMSO, and filtered by using filtering membrane. The filtrate was subjected to a preparative HPLC (eluent (v/v):acetonitrile/(water+0.05% HCl)=10%-100%) for separation. The collected fractions were rotary evaporated to remove acetonitrile, and then lyophilized to obtain the compound SIAIS1216175 as a light yellow solid (4 mg, yield 11%). $^1$H NMR (500 MHz, DMSO) δ 10.98 (s, 1H), 7.74 (d, J=8.1 Hz, 1H), 7.49 (d, J=0.8 Hz, 1H), 7.37 (dd, J=8.1, 1.6 Hz, 1H), 5.73 (s, 1H), 5.10 (dd, J=13.3, 5.1 Hz, 1H), 4.42 (d, J=17.3 Hz, 1H), 4.31 (d, J=17.3 Hz, 1H), 2.95-2.86 (m, 1H), 2.64-2.57 (m, 1H), 2.45-2.33 (m, 1H), 2.05-1.96 (m, 1H). calcd for $C_{13}H_{13}N_2O_3S^+$ $[M+H]^+$, 277.0641; found, 277.0633.

Example 51: Preparation of 3-(5-(methylthio)-1-oxoisoindolin-2-yl)piperidine-2,6-dione (SIAIS1213111)

Referring to the method of Scheme 9, the compound SIAIS1213111 was prepared under appropriate conditions that will be recognized by one skilled in the art, except that the substrates were 3-(5-mercapto-1-oxoisoindolin-2-yl)piperidine-2,6-dione (SIAIS1213175) and methyl iodide. The target compound SIAIS1213111 was obtained as a gray solid (7 mg, yield 12%). $^1$H NMR (500 MHz, DMSO) δ 10.98 (s, 1H), 7.63 (d, J=8.0 Hz, 1H), 7.49 (d, J=0.8 Hz, 1H), 7.37 (dd, J=8.1, 1.6 Hz, 1H), 5.09 (dd, J=13.3, 5.1 Hz, 1H), 4.42 (d, J=17.3 Hz, 1H), 4.30 (d, J=17.3 Hz, 1H), 2.95-2.86 (m, 1H), 2.64-2.57 (m, 1H), 2.55 (s, 3H), 2.44-2.33 (m, 1H), 2.04-1.96 (m, 1H). calcd for $C_{14}H_{15}N_2O_3S^+$ $[M+H]^+$, 291.0798; found, 291.0752.

Example 52: Preparation of 3-(5-(tert-butylthio)-1-oxoisoindolin-2-yl)piperidine-2,6-dione (SIAIS1213163)

The compound SIAIS1213163 was prepared according to the synthesis method of example 49, except that the substrates were 3-(5-bromo-1-oxoisoindolin-2-yl)piperidine-2,6-dione and tert-butyl mercaptan. The target compound SIAIS1213163 was obtained as a yellow solid (19 mg, yield 56%). $^1$H NMR (500 MHz, DMSO) δ 11.01 (s, 1H), 7.75 (d, J=0.6 Hz, 1H), 7.74 (d, J=7.9 Hz, 1H), 7.63 (dd, J=7.8, 1.4 Hz, 1H), 5.12 (dd, J=13.3, 5.1 Hz, 1H), 4.50 (d, J=17.5 Hz, 1H), 4.37 (d, J=17.5 Hz, 1H), 2.95-2.87 (m, 1H), 2.61 (d, J=16.7 Hz, 1H), 2.45-2.35 (m, 1H), 2.06-1.99 (m, 1H), 1.29 (s, 9H). calcd for $C_{17}H_{21}N_2O_3S^+$ $[M+H]^+$, 333.1267; found, 333.1263.

Example 53: Preparation of 2-(2,6-dioxopiperidin-3-yl)-5-mercaptoisoindoline-1,3-dione (SIAIS1216131)

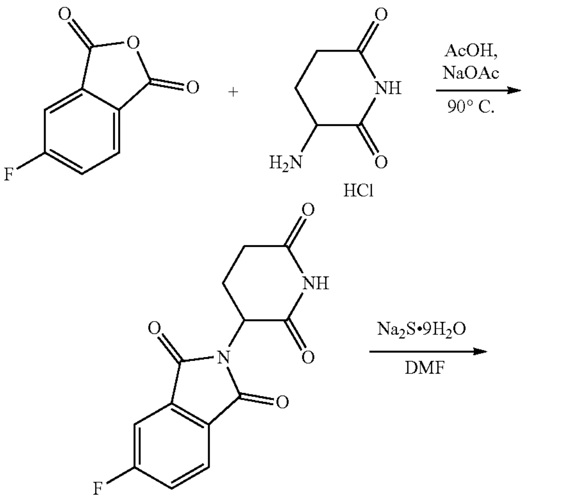

SIAIS1216157

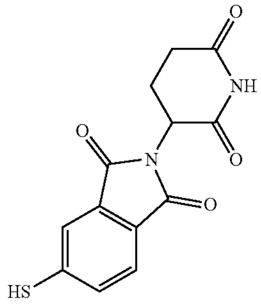

SIAIS1216131

Step 1: A 100 mL single-necked flask was charged with 4-fluorophthalic anhydride (996.7 mg, 6 mmol) and acetic acid (15 mL), followed by addition of 3-aminopiperidine-2,6-dione (1086.3 mg, 6.6 mmol) and sodium acetate (1476.5 mg, 18.0 mmol), and then the reaction mixture was reacted at 90° C. overnight. The mixture was diluted by adding water, and then stirred under ice bath, filtered to obtain a black solid. The solid was dissolved in 10 mL DMSO by heating, and was then subjected to C18 reverse phase column chromatography (eluent (v/v):acetonitrile/water=10%-100%) for separation. The collected fractions were concentrated under reduced pressure to remove the solvent, to give the compound 2-(2,6-dioxopiperidin-3-yl)-5-fluoroisoindoline-1,3-dione (SIAIS1216157) as a light purple solid (950 mg, yield 57%). $^1H$ NMR (500 MHz, DMSO) δ 11.14 (s, 1H), 8.01 (dd, J=8.3, 4.5 Hz, 1H), 7.85 (dd, J=7.4, 2.3 Hz, 1H), 7.75-7.70 (m, 1H), 5.17 (dd, J=12.9, 5.4 Hz, 1H), 2.94-2.85 (m, 1H), 2.64-2.58 (m, 1H), 2.58-2.52 (m, 1H), 2.10-2.04 (m, 1H). HRMS (ESI) m/z: calcd for $C_{13}H_{10}FN_2O_4^+$ [M+H]$^+$, 277.0619; found, 277.0621.

Step 2: A 15 mL sample vial was charged with 3-(5-fluoro-1,3-dioxo-2-isoindolinyl)piperidine-2,6-dione (165.7 mg, 0.6 mmol) and DMF (5 mL), followed by addition of sodium sulfide nonahydrate (216.2 mg, 0.9 mmol) with stirring, and then the mixture was stirred at room temperature for 2 h. After the reaction was complete, the mixture was extracted with EA for three times. The aqueous phase was acidified by addition dropwise of dilute Hydrochloric Acid in an ice bath, and a solid was precipitated out. The resulting mixture was allowed to stand, and filtered to give an off-white solid SIAIS1216131 (110 mg, yield 63%). $^1H$ NMR (500 MHz, DMSO) δ 11.12 (s, 1H), 8.00-7.70 (m, 3H), 6.47 (s, 1H), 5.12 (dd, J=12.9, 5.3 Hz, 1H), 2.93-2.83 (m, 1H), 2.59 (d, J=17.7 Hz, 1H), 2.56-2.51 (m, 1H), 2.08-2.01 (m, 1H). HRMS (ESI) m/z: calcd for $C_{13}H_{11}N_2O_4S^+$ [M+H]$^+$, 291.0434; found, 291.0410.

Intermediate Example 12: Preparation of 3-(4-((4-(bromomethyl)benzyl)thio)-1-oxoisoindolin-2-yl)piperidine-2,6-dione (SIAIS1220141)

Referring to the method of Scheme 9, the compound SIAIS1220141 was prepared under appropriate conditions that will be recognized by one skilled in the art, except that the halogenated substrate was 1,4-bis(bromomethyl)benzene. The target compound SIAIS1220141 was obtained as a light yellow solid (247 mg, yield 27%). $^1H$ NMR (500 MHz, DMSO) δ 11.00 (s, 1H), 7.67 (dd, J=7.7, 0.7 Hz, 1H), 7.58 (d, J=6.9 Hz, 1H), 7.50 (t, J=7.6 Hz, 1H), 7.43-7.31 (m, 4H), 5.10 (dd, J=13.3, 5.1 Hz, 1H), 4.67 (s, 2H), 4.34 (s, 2H), 4.24 (d, J=17.4 Hz, 1H), 4.13 (d, J=17.4 Hz, 1H), 2.95-2.86 (m, 1H), 2.58 (d, J=16.6 Hz, 1H), 2.45-2.35 (m, 1H), 2.00-1.94 (m, 1H). HRMS (ESI) m/z: calcd for $C_{21}H_{20}BrN_2O_3S^+$ [M+H]$^+$, 459.0373; found, 459.0370.

Example 54: Preparation of 3-(4-((4-(morpholinomethyl)benzyl)thio)-1-oxoisoindolin-2-yl)piperidine-2,6-dione (SIAIS1220167)

Referring to the method of Scheme 11, the compound SIAIS1220167 was prepared under appropriate conditions that will be recognized by one skilled in the art, except that the substrates were 3-(4-((4-(bromomethyl)benzyl)thio)-1-oxoisoindolin-2-yl)piperidine-2,6-dione (SIAIS1220141) and morpholine. The hydrochloride salt of compound SIAIS1220167 was obtained (white solid, 10 mg, yield 45%). $^1H$ NMR (500 MHz, DMSO) δ 11.01 (s, 1H), 10.71 (s, 1H), 7.69 (dd, J=7.7, 0.7 Hz, 1H), 7.59 (d, J=6.9 Hz, 1H), 7.51 (t, J=6.7 Hz, 1H), 7.48 (d, J=8.4 Hz, 2H), 7.42 (d, J=8.1 Hz, 2H), 5.11 (dd, J=13.3, 5.1 Hz, 1H), 4.37 (s, 2H), 4.30-4.24 (m, 3H), 4.12 (d, J=17.4 Hz, 1H), 3.93 (d, J=12.3 Hz, 2H), 3.71 (t, J=13.0 Hz, 2H), 3.20-3.13 (m, 2H), 3.10-3.00 (m, 2H), 2.95-2.86 (m, 1H), 2.59 (d, J=17.3 Hz, 1H), 2.46-2.36 (m, 1H), 2.01-1.94 (m, 1H). HRMS (ESI) m/z: calcd for $C_{25}H_{28}N_3O_4S^+$ [M+H]$^+$, 466.1795; found, 466.1802.

Example 55: Preparation of 3-(1-oxo-4-((4-(piperidin-1-ylmethyl)benzyl)thio)isoindolin-2-yl)piperidine-2,6-dione (SIAIS1220165)

Referring to the method of Scheme 11, the compound SIAIS1220165 was prepared under appropriate conditions that will be recognized by one skilled in the art, except that the substrates were 3-(4-((4-(bromomethyl)benzyl)thio)-1-oxoisoindolin-2-yl)piperidine-2,6-dione (SIAIS1220141) and piperidine. The hydrochloride salt of compound SIAIS1220165 was obtained (white solid, 12 mg, yield 52%). $^1H$ NMR (500 MHz, DMSO) δ 11.01 (s, 1H), 9.78 (s, 1H), 7.68 (dd, J=7.7, 0.7 Hz, 1H), 7.59 (d, J=6.9 Hz, 1H), 7.50 (t, J=7.6 Hz, 1H), 7.45 (d, J=8.3 Hz, 2H), 7.42 (d, J=8.3 Hz, 2H), 5.11 (dd, J=13.3, 5.1 Hz, 1H), 4.37 (s, 2H), 4.27 (d, J=17.4 Hz, 1H), 4.20 (d, J=5.3 Hz, 2H), 4.13 (d, J=17.4 Hz, 1H), 3.23 (d, J=11.8 Hz, 2H), 2.96-2.86 (m, 1H), 2.85-2.75

(m, 2H), 2.59 (d, J=16.8 Hz, 1H), 2.43-2.35 (m, 1H), 2.00-1.94 (m, 1H), 1.78 (d, J=13.6 Hz, 2H), 1.65-1.60 (m, 3H), 1.38-1.29 (m, 1H). HRMS (ESI) m/z: calcd for $C_{26}H_{30}N_3O_3S^+$ [M+H]$^+$, 464.2002; found, 464.2004.

Example 56: Preparation of 3-(1-oxo-4-((7-(pyrrolidin-1-yl)heptyl)thio)isoindolin-2-yl)piperidine-2,6-dione (SIAIS1220161)

Referring to the method of Scheme 11, the compound SIAIS1220161 was prepared under appropriate conditions that will be recognized by one skilled in the art, except that the substrates were 3-(4-((7-bromoheptyl)thio)-1-oxoisoindolin-2-yl)piperidine-2,6-dione (SIAIS1216135) and tetrahydropyrrole. The hydrochloride salt of compound SIAIS1220161 was obtained (light yellow solid, 14 mg, yield 45%). $^1$H NMR (500 MHz, DMSO) δ 11.02 (s, 1H), 10.38 (s, 1H), 7.63 (dd, J=7.5, 1.1 Hz, 1H), 7.57 (dd, J=7.5, 1.1 Hz, 1H), 7.56-7.52 (m, 1H), 5.14 (dd, J=13.3, 5.1 Hz, 1H), 4.35 (d, J=17.4 Hz, 1H), 4.21 (d, J=17.4 Hz, 1H), 3.48-3.44 (m, 2H), 3.11-3.01 (m, 5H), 2.95-2.90 (m, 2H), 2.59 (d, J=17.9 Hz, 1H), 2.49-2.41 (m, 1H), 2.00-1.95 (m, 3H), 1.88-1.82 (m, 2H), 1.64-1.58 (m, 4H), 1.43-1.38 (m, 2H), 1.33-1.24 (m, 4H). HRMS (ESI) m/z: calcd for $C_{24}H_{34}N_3O_3S^+$ [M+H]$^+$, 444.2315; found, 444.2321.

Example 57: Preparation of 3-(1-oxo-4-((7-(piperidin-1-yl)heptyl)thio)isoindolin-2-yl)piperidine-2,6-dione (SIAIS1220105)

Referring to the method of Scheme 11, the compound SIAIS1220105 was prepared under appropriate conditions that will be recognized by one skilled in the art, except that the substrates were 3-(4-((7-bromoheptyl)thio)-1-oxoisoindolin-2-yl)piperidine-2,6-dione (SIAIS1216135) and piperidine. The hydrochloride salt of compound SIAIS1220105 was obtained (light yellow solid, 14 mg, yield 63%). $^1$H NMR (500 MHz, DMSO) δ 10.99 (s, 1H), 8.93 (s, 1H), 7.63 (dd, J=7.6, 1.1 Hz, 1H), 7.58 (dd, J=7.4, 0.9 Hz, 1H), 7.53 (t, J=7.5 Hz, 1H), 5.14 (dd, J=13.3, 5.1 Hz, 1H), 4.35 (d, J=17.4 Hz, 1H), 4.21 (d, J=17.4 Hz, 1H), 3.40 (d, J=11.2 Hz, 2H), 3.09 (td, J=7.1, 2.6 Hz, 2H), 3.01-2.90 (m, 3H), 2.86-2.78 (m, 2H), 2.59 (d, J=17.5 Hz, 1H), 2.48-2.41 (m, 1H), 2.04-1.98 (m, 1H), 1.80 (d, J=14.0 Hz, 2H), 1.68-1.54 (m, 8H), 1.44-1.39 (m, 2H), 1.33-1.23 (m, 4H). HRMS (ESI) m/z: calcd for $C_{25}H_{36}N_3O_3S^+$ [M+H]$^+$, 458.2472; found, 458.2473.

Example 58: Preparation of 3-(4-((7-(azepan-1-yl)heptyl)thio)-1-oxoisoindolin-2-yl)piperidine-2,6-dione (SIAIS1220163)

Referring to the method of Scheme 11, the compound SIAIS1220163 was prepared under appropriate conditions that will be recognized by one skilled in the art, except that the substrates were 3-(4-((7-bromoheptyl)thio)-1-oxoisoindolin-2-yl)piperidine-2,6-dione (SIAIS1216135) and azepane. The hydrochloride salt of compound SIAIS1220163 was obtained (light yellow solid, 14 mg, yield 67%). $^1$H NMR (500 MHz, DMSO) δ 11.02 (s, 1H), 10.22 (s, 1H), 7.63 (dd, J=7.5, 1.2 Hz, 1H), 7.57 (dd, J=7.5, 1.1 Hz, 1H), 7.54 (t, J=7.5 Hz, 1H), 5.14 (dd, J=13.3, 5.1 Hz, 1H), 4.35 (d, J=17.4 Hz, 1H), 4.21 (d, J=17.4 Hz, 1H), 3.34-3.27 (m, 2H), 3.09 (td, J=7.0, 1.3 Hz, 2H), 3.06-2.96 (m, 4H), 2.96-2.87 (m, 1H), 2.59 (d, J=17.5 Hz, 1H), 2.49-2.41 (m, 1H), 2.04-1.98 (m, 1H), 1.83-1.75 (m, 4H), 1.69-1.54 (m, 8H), 1.44-1.38 (m, 2H), 1.33-1.22 (m, 4H). HRMS (ESI) m/z: calcd for $C_{26}H_{38}N_3O_3S^+$ [M+H]$^+$, 472.2628; found, 472.2632.

Example 59: Preparation of 3-(4-((7-(diisopropylamino)heptyl)thio)-1-oxoisoindolin-2-yl)piperidine-2,6-dione (SIAIS1220107)

Referring to the method of Scheme 11, the compound SIAIS1220107 was prepared under appropriate conditions that will be recognized by one skilled in the art, except that the substrates were 3-(4-((7-bromoheptyl)thio)-1-oxoisoindolin-2-yl)piperidine-2,6-dione (SIAIS1216135) and diisopropylamine. The hydrochloride salt of compound SIAIS1220107 was obtained (white solid, 2 mg, yield 8%). $^1$H NMR (500 MHz, DMSO) δ 11.02 (s, 1H), 8.59 (s, 1H), 7.63 (dd, J=7.5, 1.1 Hz, 1H), 7.57 (dd, J=7.5, 1.0 Hz, 1H), 7.53 (t, J=7.5 Hz, 1H), 5.14 (dd, J=13.3, 5.1 Hz, 1H), 4.35 (d, J=17.4 Hz, 1H), 4.20 (d, J=17.4 Hz, 1H), 3.62-3.54 (m, 2H), 3.12-3.07 (m, 2H), 3.03-2.96 (m, 2H), 2.96-2.88 (m, 1H), 2.59 (d, J=16.7 Hz, 1H), 2.48-2.41 (m, 1H), 2.04-1.98 (m, 1H), 1.65-1.58 (m, 4H), 1.45-1.38 (m, 2H), 1.35-1.28 (m, 4H), 1.25 (dd, J=13.1, 6.5 Hz, 12H). HRMS (ESI) m/z: calcd for $C_{26}H_{40}N_3O_3S^+$ [M+H]$^+$, 474.2785; found, 474.2783.

Example 60: Preparation of 3-(4-((7-((adamantan-1-yl)amino)heptyl)thio)-1-oxoisoindolin-2-yl)piperidine-2,6-dione (SIAIS1220155)

Referring to the method of Scheme 11, the compound SIAIS1220155 was prepared under appropriate conditions that will be recognized by one skilled in the art, except that the substrates were 3-(4-((7-bromoheptyl)thio)-1-oxoisoindolin-2-yl)piperidine-2,6-dione (SIAIS1216135) and adamantan-1-amine. The hydrochloride salt of compound SIAIS1220155 was obtained (white solid, 6 mg, yield 22%). $^1$H NMR (500 MHz, DMSO) δ 11.01 (s, 1H), 8.42 (s, 2H), 7.63 (d, J=7.3 Hz, 1H), 7.57 (d, J=7.3 Hz, 1H), 7.56-7.51 (m, 1H), 5.14 (dd, J=13.1, 4.9 Hz, 1H), 4.35 (d, J=17.3 Hz, 1H), 4.21 (d, J=17.3 Hz, 1H), 3.09 (t, J=6.8 Hz, 2H), 2.96-2.87 (m, 1H), 2.81 (s, 2H), 2.59 (d, J=17.5 Hz, 1H), 2.48-2.40 (m, 1H), 2.11 (s, 3H), 2.04-1.97 (m, 1H), 1.83 (s, 6H), 1.70-1.52 (m, 10H), 1.41 (s, 2H), 1.31 (s, 4H). HRMS (ESI) m/z: calcd for $C_{30}H_{42}N_3O_3S^+$ [M+H]$^+$, 524.2941; found, 524.2946.

Example 61: Preparation of 3-(4-((7-((3,5-dimethyladamantan-1-yl)amino)heptyl)thio)-1-oxoisoindolin-2-yl)piperidine-2,6-dione (SIAIS1220157)

Referring to the method of Scheme 11, the compound SIAIS1220157 was prepared under appropriate conditions that will be recognized by one skilled in the art, except that the substrates were 3-(4-((7-bromoheptyl)thio)-1-oxoisoindolin-2-yl)piperidine-2,6-dione (SIAIS1216135) and 3,5-dimethyladamantan-1-amine. The hydrochloride salt of compound SIAIS1220157 was obtained (white solid, 10 mg, yield 34%). $^1$H NMR (500 MHz, DMSO) δ 11.01 (s, 1H), 8.49 (s, 2H), 7.63 (d, J=7.1 Hz, 1H), 7.59-7.51 (m, 2H), 5.14 (dd, J=13.1, 4.8 Hz, 1H), 4.35 (d, J=17.3 Hz, 1H), 4.21 (d, J=17.5 Hz, 1H), 3.09 (d, J=6.3 Hz, 2H), 2.96-2.88 (m, 1H), 2.81 (s, 2H), 2.59 (d, J=17.0 Hz, 1H), 2.47-2.40 (m, 1H), 2.18 (s, 1H), 2.04-2.1.97 (m, 1H), 1.68 (s, 2H), 1.64-1.54 (m, 4H), 1.54-1.44 (m, 4H), 1.41 (s, 2H), 1.30 (s, 8H), 1.13 (dd, J=30.6, 12.4 Hz, 2H), 0.86 (s, 6H). HRMS (ESI) m/z: calcd for $C_{32}H_{46}N_3O_3S^+$ [M+H]$^+$, 552.3254; found, 552.3239.

Example 62: Preparation of 3-(4-((7-((adamantan-2-yl)amino)heptyl)thio)-1-oxoisoindolin-2-yl)piperidine-2,6-dione (SIAIS1220159)

Referring to the method of Scheme 11, the compound SIAIS1220159 was prepared under appropriate conditions that will be recognized by one skilled in the art, except that the substrates were 3-(4-((7-bromoheptyl)thio)-1-oxoisoindolin-2-yl)piperidine-2,6-dione (SIAIS1216135) and adamantan-2-amine. The hydrochloride salt of compound SIAIS1220159 was obtained (white solid, 7 mg, yield 25%). $^1$H NMR (500 MHz, DMSO) δ 11.02 (s, 1H), 8.36 (s, 2H), 7.63 (dd, J=7.5, 1.1 Hz, 1H), 7.57 (dd, J=7.4, 1.0 Hz, 1H), 7.54 (t, J=7.5 Hz, 1H), 5.14 (dd, J=13.3, 5.1 Hz, 1H), 4.35 (d, J=17.4 Hz, 1H), 4.20 (d, J=17.4 Hz, 1H), 3.26 (s, 1H), 3.12-3.07 (m, 2H), 2.96-2.85 (m, 3H), 2.59 (d, J=17.2 Hz, 1H), 2.48-2.41 (m, 1H), 2.12 (s, 2H), 2.04-1.97 (m, 3H), 1.84 (d, J=12.5 Hz, 4H), 1.72 (d, J=17.0 Hz, 4H), 1.68-1.52 (m, 6H), 1.45-1.38 (m, 2H), 1.33-1.26 (m, 4H). HRMS (ESI) m/z: calcd for $C_{30}H_{42}N_3O_3S^+$ [M+H]$^+$, 524.2941; found, 524.2957.

Example 63: Preparation of 3-(4-((8-((adamantan-1-yl)amino)octyl)thio)-1-oxoisoindolin-2-yl)piperidine-2,6-dione (SIAIS1220087)

Referring to the method of Scheme 11, the compound SIAIS1220087 was prepared under appropriate conditions that will be recognized by one skilled in the art, except that the substrates were 3-(4-((8-bromooctyl)thio)-1-oxoisoindolin-2-yl)piperidine-2,6-dione (SIAIS1216137) and adamantan-1-amine. The hydrochloride salt of compound SIAIS1220087 was obtained (white solid, 9 mg, yield 33%). $^1$H NMR (500 MHz, DMSO) δ 10.99 (s, 1H), 8.35 (s, 2H), 7.63 (dd, J=7.5, 1.0 Hz, 1H), 7.57 (d, J=6.5 Hz, 1H), 7.53 (t, J=7.5 Hz, 1H), 5.13 (dd, J=13.3, 5.1 Hz, 1H), 4.35 (d, J=17.4 Hz, 1H), 4.21 (d, J=17.4 Hz, 1H), 3.33-3.28 (m, 1H), 3.08 (t, J=7.0 Hz, 2H), 2.96-2.88 (m, 1H), 2.84-2.78 (m, 2H), 2.59 (d, J=17.4 Hz, 1H), 2.48-2.41 (m, 1H), 2.18 (t, J=8.1 Hz, 1H), 2.11 (s, 2H), 2.04-1.97 (m, 1H), 1.93-1.86 (m, 1H), 1.82 (s, 4H), 1.70-1.54 (m, 10H), 1.45-1.37 (m, 2H), 1.28 (s, 6H). HRMS (ESI) m/z: calcd for $C_{30}H_{44}N_3O_3S^+$ [M+H]$^+$, 538.3098; found, 538.3091.

Example 64: Preparation of 3-(4-((8-((adamantan-2-yl)amino)octyl)thio)-1-oxoisoindolin-2-yl)piperidine-2,6-dione (SIAIS1220089)

Referring to the method of Scheme 11, the compound SIAIS1220089 was prepared under appropriate conditions that will be recognized by one skilled in the art, except that the substrates were 3-(4-((8-bromooctyl)thio)-1-oxoisoindolin-2-yl)piperidine-2,6-dione (SIAIS1216137) and adamantan-2-amine. The hydrochloride salt of compound SIAIS1220089 was obtained (white solid, 14 mg, yield 50%). $^1$H NMR (500 MHz, DMSO) δ 11.02 (s, 1H), 8.49 (s, 2H), 7.63 (dd, J=7.5, 1.1 Hz, 1H), 7.57 (dd, J=7.4, 1.0 Hz, 1H), 7.53 (t, J=7.5 Hz, 1H), 5.14 (dd, J=13.3, 5.1 Hz, 1H), 4.35 (d, J=17.4 Hz, 1H), 4.21 (d, J=17.4 Hz, 1H), 3.26 (s, 1H), 3.09 (t, J=6.9 Hz, 2H), 2.96-2.84 (m, 3H), 2.59 (d, J=17.2 Hz, 1H), 2.49-2.41 (m, 1H), 2.13 (s, 2H), 2.07-1.97 (m, 3H), 1.83 (d, J=12.9 Hz, 4H), 1.75-1.65 (m, 6H), 1.62-1.58 (m, 2H), 1.54 (d, J=13.1 Hz, 2H), 1.45-1.37 (m, 2H), 1.28 (s, 6H). HRMS (ESI) m/z: calcd for $C_{30}H_{44}N_3O_3S^+$ [M+H]$^+$, 538.3098; found, 538.3088.

Example 65: Preparation of 3,3'-(((piperazine-1,4-diylbis(octane-8,1-diyl))bis(sulfanediyl))bis(1-oxoisoindoline-4,2-diyl))bis(piperidine-2,6-dione) (SIAIS1220061)

Referring to the method of Scheme 11, the compound SIAIS1220061 was prepared under appropriate conditions that will be recognized by one skilled in the art, except that the substrates were 3-(4-((8-bromooctyl)thio)-1-oxoisoindolin-2-yl)piperidine-2,6-dione (SIAIS1216137) and piperazine (0.5 equiv). The target compound SIAIS1220061 was obtained as a white solid (30 mg, yield 70%). $^1$H NMR (500 MHz, DMSO) δ 10.99 (s, 2H), 7.63 (dd, J=7.5, 1.0 Hz, 2H), 7.57 (d, J=6.7 Hz, 2H), 7.53 (t, J=7.5 Hz, 2H), 5.13 (dd, J=13.3, 5.1 Hz, 2H), 4.35 (d, J=17.4 Hz, 2H), 4.21 (d, J=17.4 Hz, 2H), 3.60-3.30 (m, 12H), 3.10-3.06 (m, 4H), 2.96-2.87 (m, 2H), 2.59 (d, J=17.2 Hz, 2H), 2.49-2.41 (m, 2H), 2.04-1.98 (m, 2H), 1.72-1.55 (m, 8H), 1.44-1.37 (m, 4H), 1.27 (s, 12H). HRMS (ESI) m/z: calcd for $C_{46}H_{63}N_6O_6S_2^+$ [M+H]$^+$, 859.4245; found, 859.4260.

Example 66: Preparation of 3-(1-oxo-4-((4,4,5,5,5-pentafluoropentyl)thio)isoindolin-2-yl)piperidine-2,6-dione (SIAIS1220133)

The compound SIAIS1220133 was prepared according to the procedure of step 3 of example 44, except that 4,4,5,5,5-pentafluoropentane-1-thiol was used instead of tert-butyl mercaptan. The target compound SIAIS1220133 was obtained as a brown solid (4 mg, yield 8%). $^1$H NMR (500 MHz, DMSO) δ 11.01 (s, 1H), 7.68 (s, 1H), 7.62-7.52 (m, 2H), 5.14 (s, 1H), 4.38 (d, J=17.3 Hz, 1H), 4.23 (d, J=17.3 Hz, 1H), 3.20 (s, 2H), 2.91 (s, 1H), 2.60-2.57 (m, 1H), 2.42-2.30 (m, 3H), 2.00 (s, 1H), 1.82 (s, 2H). HRMS (ESI) m/z: calcd for $C_{18}H_{18}F_5N_2O_3S^+$ [M+H]$^+$, 437.0953; found, 437.0951.

Example 67: Preparation of 3-(1-oxo-4-((9-((4,4,5,5,5-pentafluoropentyl)thio)nonyl)thio)isoindolin-2-yl)piperidine-2,6-dione (SIAIS1220131)

Referring to the method of Scheme 11, the compound SIAIS1220131 was prepared under appropriate conditions that will be recognized by one skilled in the art, except that 3-(4-((8-bromooctyl)thio)-1-oxoisoindolin-2-yl)piperidine-2,6-dione (SIAIS1216137) and 4,4,5,5,5-pentafluoropentane-1-thiol were used as the starting materials. The target compound SIAIS1220131 was obtained as a white solid (8 mg, yield 27%). $^1$H NMR (500 MHz, DMSO) δ 11.00 (s, 1H), 7.62 (d, J=7.2 Hz, 1H), 7.58-7.50 (m, 2H), 5.13 (d, J=13.0, 4.5 Hz, 1H), 4.35 (d, J=17.3 Hz, 1H), 4.21 (d, J=17.2 Hz, 1H), 3.10-3.04 (m, 2H), 2.96-2.85 (m, 1H), 2.63-2.54 (m, 3H), 2.48-2.42 (m, 3H), 2.37-2.23 (m, 2H), 2.04-1.97 (m, 1H), 1.80-1.70 (m, 2H), 1.63-1.55 (m, 2H), 1.53-1.45 (m, 2H), 1.43-1.26 (m, 2H), 1.35-1.26 (m, 2H), 1.24 (s, 6H). HRMS (ESI) m/z: calcd for $C_{27}H_{36}F_5N_2O_3S_2^+$ [M+H]$^+$, 595.2082; found, 595.2082.

Example 68: Preparation of 3-(1-oxo-4-((9-((4,4,5,5,5-pentafluoropentyl)sulfinyl)nonyl)thio)isoindolin-2-yl)piperidine-2,6-dione (SIAIS1220145)

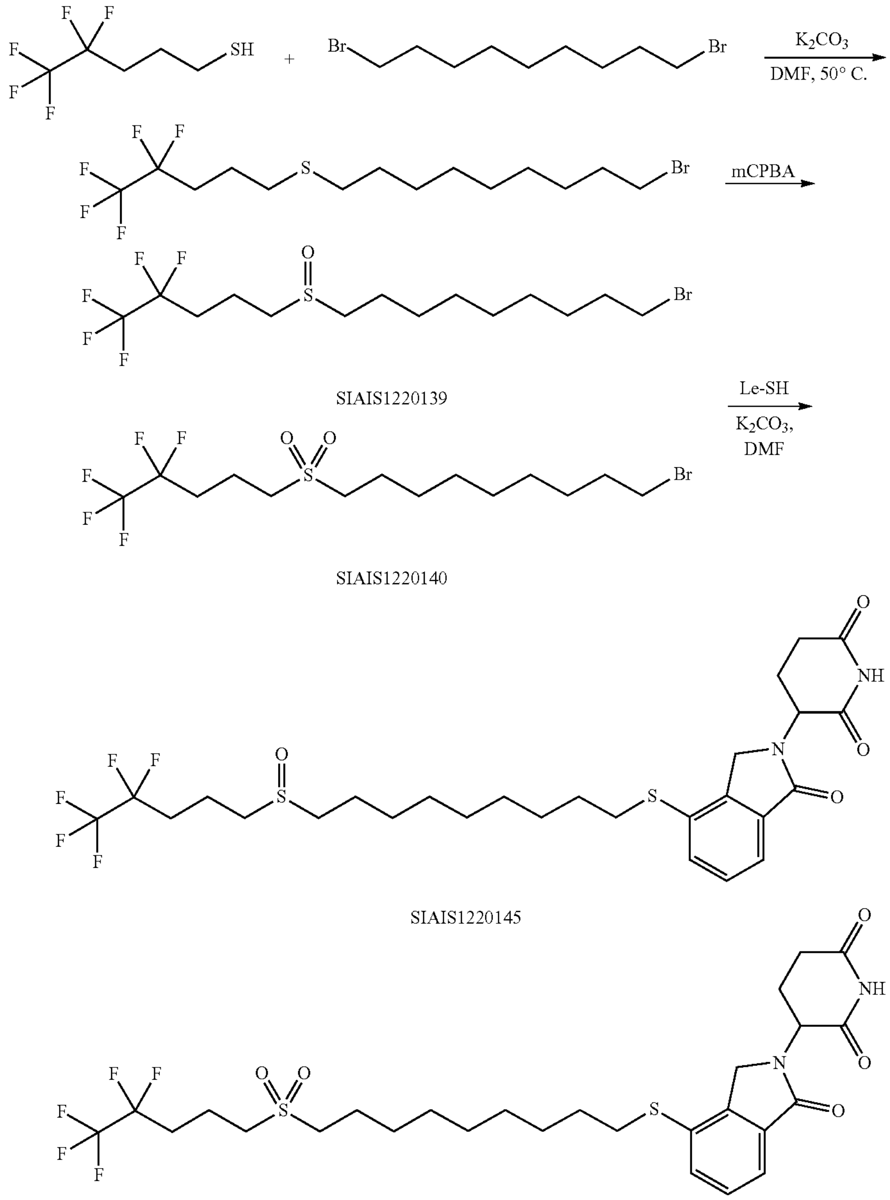

SIAIS1220139

SIAIS1220140

SIAIS1220145

SIAIS1220147

Steps 1 and 2: A 100 mL single-necked flask was charged with 4,4,5,5,5-pentafluoropentane-1-thiol (194.2 mg, 1 mmol), potassium carbonate (414.6 mg, 3 mmol), and DMF (5 mL), followed by addition of 1,9-dibromononane (582.5 mg, 3 mmol), and then the reaction mixture was reacted at 50° C. for 3 h. m-chloroperoxybenzoic acid was added thereto, and the mixture was reacted at room temperature for 1 h. The resulting mixture was subjected to a C18 reverse phase column chromatography (eluent (v/v):acetonitrile/water=10%-100%) for separation, and the collected fractions were concentrated under reduced pressure to remove the solvents, to give 9-((4,4,5,5,5-pentafluoropentyl)sulfinyl)-1-bromo-nonane (SIAIS1220139) (white solid, 120 mg, yield 29%) and 9-((4,4,5,5,5-pentafluoropentyl)sulfonyl)-1-bromo-nonane (SIAIS1220140) (white solid, 84 mg, yield 19%).

Step 3: Referring to the method of Scheme 9, the compound SIAIS1220145 was prepared under appropriate conditions that will be recognized by one skilled in the art, except that the halogenated substrate was 9-((4,4,5,5,5-pentafluoropentyl)sulfinyl)-1-bromo-nonane (SIAIS1220139). The target product SIAIS1220145 was obtained as a white solid (17 mg, yield 50%). $^{1}$H NMR (500 MHz, DMSO) δ 11.01 (s, 1H), 7.63 (dd, J=7.5, 1.2 Hz, 1H), 7.56 (dd, J=7.5, 1.1 Hz, 1H), 7.53 (t, J=7.5 Hz, 1H), 5.13 (dd, J=13.3, 5.1 Hz, 1H), 4.35 (d, J=17.4 Hz, 1H), 4.21 (d, J=17.4 Hz, 1H), 3.08 (t, J=7.2 Hz, 2H), 2.96-2.87 (m, 1H), 2.88-2.80 (m, 1H), 2.77-2.69 (m, 2H), 2.68-2.62 (m, 1H), 2.59 (d, J=17.3 Hz, 1H), 2.49-2.43 (m, 1H), 2.43-2.31 (m, 2H), 2.03-1.97 (m, 1H), 1.94-1.87 (m, 2H), 1.65-1.55 (m, 4H), 1.43-1.33 (m, 4H), 1.30-1.22 (m, 6H). HRMS (ESI) m/z: calcd for $C_{27}H_{36}F_5N_2O_4S_2^+$ [M+H]$^+$, 611.2031; found, 611.2032.

Example 69: Preparation of 3-(1-oxo-4-((9-((4,4,5,5,5-pentafluoropentyl)sulfonyl)nonyl)thio)isoindolin-2-yl)piperidine-2,6-dione (SIAIS1220147)

The target compound SIAIS1220147 was prepared according to the method of example 68, except that the halogenated substrate used in step 3 was 9-((4,4,5,5,5-pentafluoropentyl)sulfonyl)-1-bromo-nonane (SIAIS1220140). The target product SIAIS1220145 was obtained as a white solid (8 mg, yield 20%). $^1$H NMR (500 MHz, DMSO) δ 11.01 (s, 1H), 7.62 (dd, J=7.5, 1.1 Hz, 1H), 7.56 (dd, J=7.4, 1.1 Hz, 1H), 7.53 (t, J=7.5 Hz, 1H), 5.13 (dd, J=13.3, 5.1 Hz, 1H), 4.35 (d, J=17.4 Hz, 1H), 4.21 (d, J=17.4 Hz, 1H), 3.24-3.19 (m, 2H), 3.14-3.04 (m, 4H), 2.95-2.87 (m, 1H), 2.59 (d, J=16.8 Hz, 1H), 2.48-2.34 (m, 3H), 2.04-1.97 (m, 1H), 1.97-1.89 (m, 2H), 1.68-1.55 (m, 4H), 1.43-1.32 (m, 4H), 1.30-1.22 (s, 6H). HRMS (ESI) m/z: calcd for $C_{27}H_{36}F_5N_2O_5S_2^+$ [M+H]$^+$, 627.1980; found, 627.1979.

Example 70: Preparation of 3-(4-((8-mercaptooctyl)thio)-1-oxoisoindolin-2-yl)piperidine-2,6-dione (SIAIS1220143)

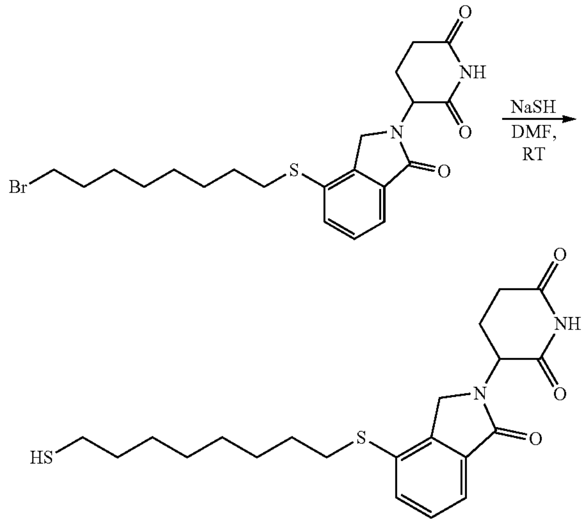

SIAIS1220143

A 15 mL sample vial was charged with 3-(4-((8-bromooctyl)thio)-1-oxoisoindolin-2-yl)piperidine-2,6-dione (SIAIS1216137) (28 mg, 0.06 mmol), followed by addition of DMF (2 mL) to dissolve, and then sodium sulfide (6.7 mg, 0.12 mmol) with stirring. The reaction mixture was reacted at room temperature for 10 min and then filtered using filtering membrane. The filtrate was subjected to a preparative HPLC (eluent (v/v):acetonitrile/(water+0.05% HCl)=10%-100%) for separation. The collected fractions were rotary evaporated to remove acetonitrile, and then lyophilized to obtain the compound SIAIS1220143 as a white solid (10 mg, yield 39%). $^1$H NMR (500 MHz, DMSO) δ 11.01 (s, 1H), 7.63 (dd, J=7.5, 1.1 Hz, 1H), 7.56 (dd, J=7.5, 1.1 Hz, 1H), 7.53 (t, J=7.5 Hz, 1H), 5.13 (dd, J=13.3, 5.1 Hz, 1H), 4.35 (d, J=17.4 Hz, 1H), 4.21 (d, J=17.4 Hz, 1H), 3.08 (t, J=7.2 Hz, 2H), 2.95-2.87 (m, 1H), 2.59 (d, J=17.4 Hz, 1H), 2.45 (dd, J=14.6, 7.4 Hz, 3H), 2.22 (t, J=7.7 Hz, 1H), 2.03-1.96 (m, 1H), 1.62-1.55 (m, 2H), 1.55-1.48 (m, 2H), 1.43-1.36 (m, 2H), 1.33-1.22 (m, 6H). HRMS (ESI) m/z: calcd for $C_{21}H_{29}N_{203}S_2^+$ [M+H]$^+$, 421.1614; found, 421.1611.

Example 71: Preparation of 3-(1-oxo-4-((7-oxo-7-(piperidin-1-yl)heptyl)thio)isoindolin-2-yl)piperidine-2,6-dione (SIAIS1220115)

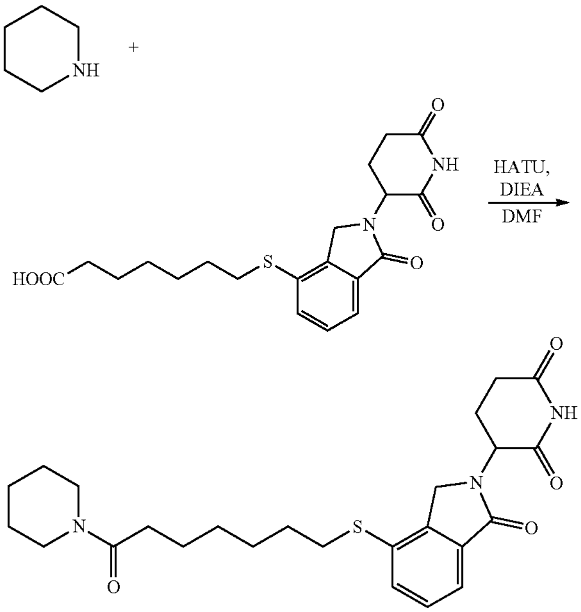

SIAIS1220115

A 15 mL sample vial was sequentially charged with 7-((2-(2,6-dioxopiperidin-3-yl)-1-oxoisoindolin-4-yl)thio)heptanoic acid (SIAIS171092) (20.2 mg, 0.05 mmol), piperidine (4.3 mg, 0.05 mmol), and HATU (38.0 mg, 0.1 mmol), followed by addition of DMF (2 mL) to dissolve, and then N, N-diisopropylethylamine (12.9 mg, 0.1 mmol) with stirring. The reaction mixture was reacted at room temperature for 12 h and then filtered using filtering membrane. The filtrate was subjected to a preparative HPLC (eluent (v/v):acetonitrile/(water+0.05% HCl)=10%-100%) for separation. The collected fractions were rotary evaporated to remove acetonitrile, and then lyophilized to obtain the compound SIAIS1220115 as a white solid (23 mg, yield 97%). $^1$H NMR (500 MHz, DMSO) δ 10.99 (s, 1H), 7.63 (dd, J=7.5, 1.1 Hz, 1H), 7.56 (dd, J=7.5, 1.1 Hz, 1H), 7.53 (t, J=7.5 Hz, 1H), 5.13 (dd, J=13.3, 5.1 Hz, 1H), 4.35 (d, J=17.4 Hz, 1H), 4.21 (d, J=17.4 Hz, 1H), 3.40-3.37 (m, 2H), 3.37-3.33 (m, 2H), 3.07 (t, J=7.2 Hz, 2H), 2.95-2.86 (m, 1H), 2.59 (d, J=16.7 Hz, 1H), 2.49-2.41 (m, 1H), 2.25 (t, J=7.4 Hz, 2H), 2.04-1.97 (m, 1H), 1.61-1.53 (m, 4H), 1.47-1.37 (m, 8H), 1.31-1.25 (m, 2H). HRMS (ESI) m/z: $C_{25}H_{34}N_3O_4S^+$ [M+H]$^+$, 472.2265; found, 472.2262.

Example 72: Preparation of 7-((2-(2,6-dioxopiperidin-3-yl)-1-oxoisoindolin-4-yl)thio)-N,N-diisopropylheptanamide (SIAIS1220117)

The target compound SIAIS1220117 was prepared according to the method of example 71, except that diisopropylamine was used instead of piperidine. The target product SIAIS1220117 was obtained as a white solid (13 mg, yield 8%). $^1H$ NMR (500 MHz, DMSO) δ 10.99 (s, 1H), 7.63 (dd, J=7.5, 1.0 Hz, 1H), 7.56 (d, J=7.4, 1.0 Hz, 1H), 7.52 (t, J=7.5 Hz, 1H), 5.13 (dd, J=13.3, 5.1 Hz, 1H), 4.35 (d, J=17.4 Hz, 1H), 4.21 (d, J=17.4 Hz, 1H), 3.99-3.91 (m, 1H), 3.44 (s, 1H), 3.08 (t, J=7.3 Hz, 2H), 2.96-2.86 (m, 1H), 2.59 (d, J=17.2 Hz, 1H), 2.48-2.41 (m, 1H), 2.21 (t, J=7.4 Hz, 2H), 2.04-1.97 (m, 1H), 1.63-1.56 (m, 2H), 1.47-1.38 (m, 4H), 1.32-1.27 (m, 2H), 1.26 (d, J=6.7 Hz, 6H), 1.11 (d, J=6.5 Hz, 6H). HRMS (ESI) m/z: $C_{26}H_{38}N_3O_4S^+$ $[M+H]^+$, 488.2578; found, 488.2573.

Example 73: Preparation of 8-((2-(2,6-dioxopiperidin-3-yl)-1-oxoisoindolin-4-yl)thio)-N,N,N-triethyloctan-1-aminium chloride (SIAIS1220093)

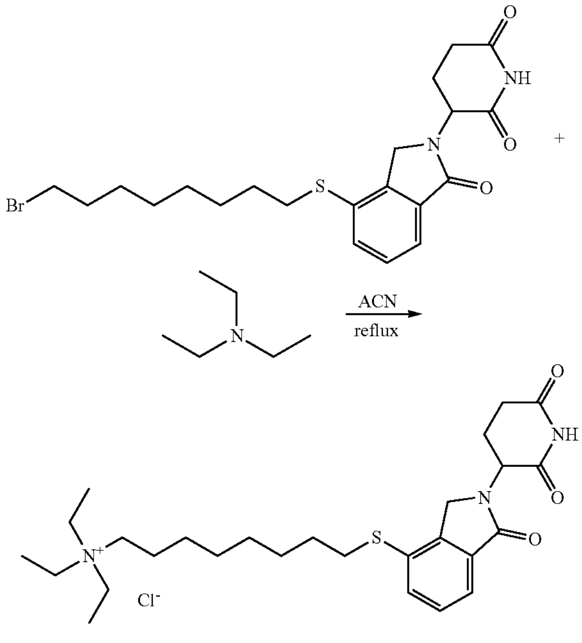

SIAIS1220093

A 15 mL sample vial was charged with 3-(4-((8-bromooctyl)thio)-1-oxoisoindolin-2-yl)piperidine-2,6-dione (SIAIS1216137) (23.4 mg, 0.05 mmol), followed by addition of acetonitrile (2 mL) to dissolve, and then triethylamine (6.1 mg, 0.06 mmol) with stirring. The reaction mixture was refluxed for 12 h and then filtered using filtering membrane. The filtrate was subjected to a preparative HPLC (eluent (v/v):acetonitrile/(water+0.05% HCl)=10%-100%) for separation. The collected fractions were rotary evaporated to remove acetonitrile, and then lyophilized to obtain the compound SIAIS1220093 as a white solid (8 mg, yield 31%). $^1H$ NMR (500 MHz, DMSO) δ 10.99 (s, 1H), 7.63 (dd, J=7.6, 1.1 Hz, 1H), 7.57 (d, J=7.2 Hz, 1H), 7.53 (t, J=7.5 Hz, 1H), 5.13 (dd, J=13.3, 5.2 Hz, 1H), 4.35 (d, J=17.4 Hz, 1H), 4.21 (d, J=17.4 Hz, 1H), 3.21 (q, J=7.2 Hz, 6H), 3.10-3.05 (m, 4H), 2.96-2.87 (m, 1H), 2.59 (d, J=17.7 Hz, 1H), 2.48-2.41 (m, 1H), 2.04-1.97 (m, 1H), 1.63-1.58 (m, 2H), 1.57-1.50 (m, 2H), 1.44-1.32 (m, 2H), 1.28 (s, 6H), 1.15 (t, J=7.2 Hz, 9H). HRMS (ESI) m/z: calcd for $C_{27}H_{42}N_3O_3S^+$ $[M+H]^+$, 488.2941; found, 488.2944.

Example 74: Preparation of 3-(1-oxo-4-((8-(quinazolin-4-ylamino)octyl)thio)isoindolin-2-yl)piperidine-2,6-dione (SIAIS264011)

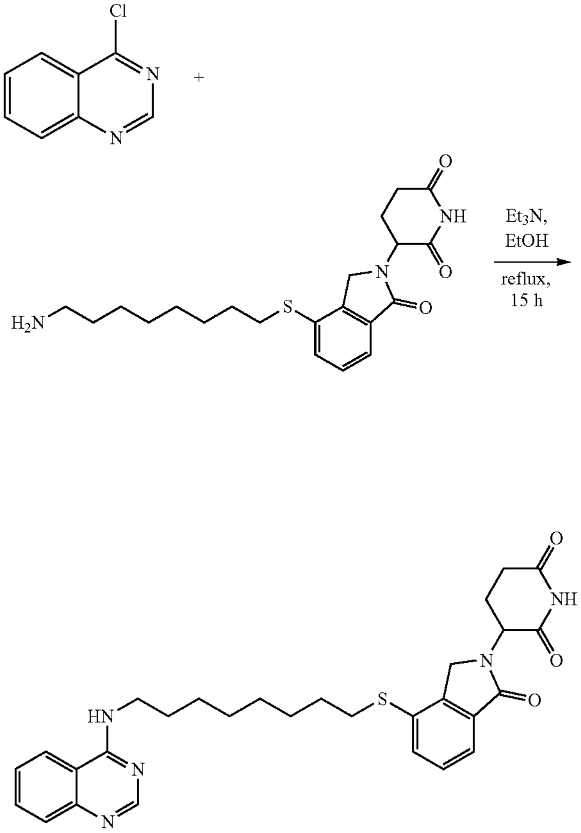

To a solution of 4-chloroquinazoline (25 mg, 0.15 mmol) and 3-(4-((8-aminooctyl)thio)-1 oxoisoindoline-2-yl)piperidine-2,6-dione (61 mg, 0.15 mmol) in absolute ethanol (2 mL) was added 41 μL of triethylamine. The reaction mixture was refluxed overnight. After the reaction was complete as monitored by TLC, the mixture was concentrated under reduced pressure to remove the solvents. The resulting residue was dissolved in DMF and subjected to a preparative chromatographic column for separation to give the compound SIAIS264011 as a white solid (31 mg, yield 39%). $^1H$ NMR (500 MHz, DMSO) δ 10.99 (s, 1H), 8.44 (s, 1H), 8.26 (s, 1H), 8.23 (d, J=7.6 Hz, 1H), 7.77-7.72 (m, 1H), 7.67-7.64 (m, 1H), 7.61 (dd, J=7.5, 1.1 Hz, 1H), 7.56 (dd, J=7.5, 1.1 Hz, 1H), 7.52 (d, J=7.5 Hz, 1H), 7.50-7.47 (m, 1H), 5.12 (dd, J=13.3, 5.1 Hz, 1H), 4.35 (d, J=17.4 Hz, 1H), 4.21 (d, J=17.4 Hz, 1H), 3.52 (dd, J=13.0, 6.9 Hz, 2H), 3.06 (t, J=7.3 Hz, 2H), 2.95-2.86 (m, 1H), 2.59 (d, J=17.6 Hz, 1H), 2.49-2.40 (m, 1H), 2.03-1.96 (m, 1H), 1.65-1.55 (m, 4H), 1.42-1.27 (m, 8H). HRMS (ESI) m/z: calcd for $C_{29}H_{34}N_5O_3S^+$ $[M+H]^+$, 532.2377; found, 532.2374.

Example 75: Preparation of 1-(3-chloro-4-methylphenyl)-3-(2-((2-(2,6-dioxopiperidin-3-yl)-1-oxoisoindolin-4-yl)thio)ethyl)urea (SIAIS269012)

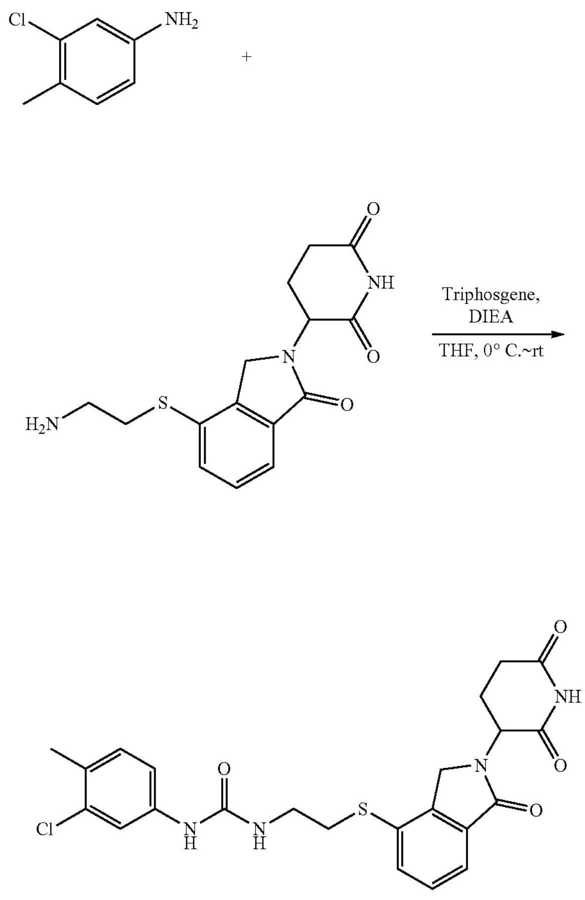

SIAIS269012

A 10 mL two-necked flask was sequentially charged with 3-chloro-4-methylaniline (10 mg, 1 equiv), THF (2 mL), and DIEA (36.5 mg, 4.0 equiv), followed by addition dropwise of a solution of triphosgene (25.1 mg, 1.2 equiv) in THF (1 mL). After the completion of addition, the flask was evacuated and refilled with argon gas for three times. The reaction mixture was reacted at 0° C. under argon atmosphere for 30 min and another 30 min at room temperature. To the mixture was added 3-(4-((2-aminoethyl)thio)-1-oxoisoindolin-2-yl)piperidine-2,6-dione (SIAIS171123) at room temperature, and the mixture was stirred overnight. The mixture was subjected to preparative HPLC (Eluent: water/acetonitrile) to give the product SIAIS269012 as a white solid (11.2 mg, yield 33%). $^{1}$H NMR (500 MHz, DMSO) δ 10.99 (s, 1H), 8.71 (s, 1H), 7.74 (dd, J=7.6, 1.0 Hz, 1H), 7.63 (d, J=2.1 Hz, 1H), 7.58 (dd, J=7.5, 1.0 Hz, 1H), 7.54 (t, J=7.5 Hz, 1H), 7.17 (d, J=8.5 Hz, 1H), 7.11 (dd, J=8.3, 2.2 Hz, 1H), 6.43 (t, J=5.1 Hz, 1H), 5.13 (dd, J=13.3, 5.1 Hz, 1H), 4.39 (d, J=17.4 Hz, 1H), 4.24 (d, J=17.3 Hz, 1H), 3.30 (d, J=7.2 Hz, 2H), 3.18 (t, J=6.9 Hz, 2H), 2.95-2.86 (m, 1H), 2.58 (d, J=17.5 Hz, 1H), 2.48-2.38 (m, 1H), 2.23 (s, 3H), 2.03-1.96 (m, 1H). HRMS (ESI) m/z: calcd for $C_{23}H_{24}ClN_4O_4S^+$ $[M+H]^+$, 487.1201; found, 487.1198.

Example 76: Preparation of 3-(1-oxo-4-((8-(2-oxopiperidin-1-yl)octyl)thio)isoindolin-2-yl)piperidine-2,6-dione (SIAIS264019)

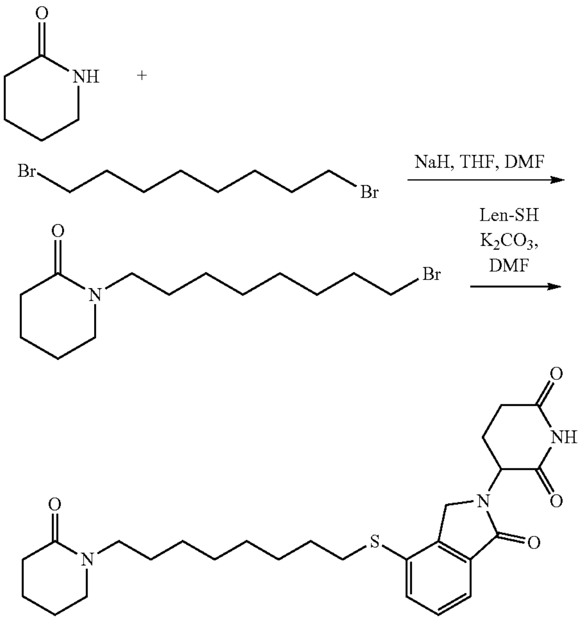

SIAIS264019

To a solution of sodium hydride (0.27 mg, 4 mmol) in DMF (1.5 mL) was added a solution of piperidone (2 mmol) dissolved in THF under ice bath. The mixture was stirred for 0.5 h, and then 1,8-dibromooctane was added thereto. The reaction mixture was stirred at room temperature for 4 h, and subjected to a column chromatography to obtain the crude which was used directly in the next step. To a mixture of the above intermediate crude product (0.17 mmol) and thio-lenalidomide SIAIS171095 (47 mg, 0.17 mmol) in DMF (2 mL) was added potassium carbonate (28 mg). The reaction mixture was stirred at room temperature overnight. After the reaction was complete as monitored by TLC, the mixture was subjected to a preparative chromatographic column for separation to give the compound SIAIS264019 as a white solid (31 mg, total yield of two steps 39%). $^{1}$H NMR (500 MHz, DMSO) δ 10.99 (s, 1H), 7.62 (dd, J=7.5, 1.1 Hz, 1H), 7.56 (dd, J=7.4, 1.0 Hz, 1H), 7.53 (t, J=7.5 Hz, 1H), 5.13 (dd, J=13.3, 5.1 Hz, 1H), 4.35 (d, J=17.4 Hz, 1H), 4.21 (d, J=17.4 Hz, 1H), 3.23-3.18 (m, 4H), 3.07 (t, J=7.2 Hz, 2H), 2.96-2.87 (m, 1H), 2.59 (d, J=17.4 Hz, 1H), 2.49-2.41 (m, 1H), 2.17 (t, J=6.3 Hz, 2H), 2.04-1.97 (m, 1H), 1.73-1.63 (m, 4H), 1.63-1.55 (m, 2H), 1.45-1.36 (m, 4H), 1.28-1.16 (m, 6H). HRMS (ESI) m/z: $C_{26}H_{36}N_3O_4S^+$ $[M+H]^+$, calcd for 486.2421; found, 486.2425.

Example 77: Preparation of 3-(4-((6-((adamantan-1-yl)amino)hexyl)thio)-1-oxoisoindolin-2-yl)piperidine-2,6-dione (SIAIS1220177)

Referring to the method of Scheme 11, the compound SIAIS1220177 was prepared under appropriate conditions that will be recognized by one skilled in the art, except that the substrates were 3-(4-((6-bromohexyl)thio)-1-oxoisoindolin-2-yl)piperidine-2,6-dione (SIAIS1216133) and adamantan-1-amine. The hydrochloride salt of compound SIAIS1220177 was obtained (light yellow solid, 7 mg, yield 28%). $^1$H NMR (500 MHz, DMSO) δ 10.99 (s, 1H), 8.55 (s, 2H), 7.64 (dd, J=7.5, 1.1 Hz, 1H), 7.57 (d, J=7.2 Hz, 1H), 7.54 (t, J=7.5 Hz, 1H), 5.13 (dd, J=13.3, 5.1 Hz, 1H), 4.36 (d, J=17.4 Hz, 1H), 4.21 (d, J=17.4 Hz, 1H), 3.10 (t, J=6.9 Hz, 2H), 2.96-2.87 (m, 1H), 2.80 (s, 2H), 2.59 (d, J=17.1 Hz, 1H), 2.49-2.40 (m, 1H), 2.11 (s, 3H), 2.04-1.98 (m, 1H), 1.83 (s, 6H), 1.70-155 (m, 10H), 1.47-1.40 (m, 2H), 1.38-1.31 (m, 2H). HRMS (ESI) m/z: calcd for $C_{29}H_{40}N3O_3S^+$ [M+H]$^+$, 510.2785; found, 510.2780.

Example 78: 3-(4-((6-((adamantan-2-yl)amino) hexyl)thio)-1-oxoisoindolin-2-yl)piperidine-2,6-dione (SIAIS1220179)

Referring to the method of Scheme 11, the compound SIAIS1220179 was prepared under appropriate conditions that will be recognized by one skilled in the art, except that the substrates used were 3-(4-((6-bromohexyl)thio)-1-oxoisoindolin-2-yl)piperidine-2,6-dione (SIAIS1216133) and adamantan-2-amine. The hydrochloride salt of compound SIAIS1220179 was obtained (light yellow solid, 22 mg, yield 87%). $^1$H NMR (500 MHz, DMSO) δ 10.99 (s, 1H), 8.42 (s, 2H), 7.63 (dd, J=7.5, 1.0 Hz, 1H), 7.57 (dd, J=7.4, 0.9 Hz, 1H), 7.54 (t, J=7.5 Hz, 1H), 5.13 (dd, J=13.3, 5.1 Hz, 1H), 4.35 (d, J=17.4 Hz, 1H), 4.21 (d, J=17.4 Hz, 1H), 3.26 (s, 1H), 3.12-3.07 (m, 2H), 2.96-2.84 (m, 3H), 2.59 (d, J=16.6 Hz, 1H), 2.48-2.40 (m, 1H), 2.12 (s, 2H), 2.05-1.99 (m, 3H), 1.84 (d, J=12.6 Hz, 4H), 1.76-1.57 (m, 9H), 1.55 (d, J=13.0 Hz, 2H), 1.47-1.40 (m, 2H), 1.36-1.30 (m, 2H). HRMS (ESI) m/z: calcd for $C_{29}H_{40}N_3O_3S^+$ [M+H]$^+$, 510.2785; found, 510.2783.

Example 79: 3-(4-((4-(((adamantan-1-yl)amino) methyl)benzyl)thio)-1-oxoisoindolin-2-yl)piperidine-2,6-dione (SIAIS1221003)

Referring to the method of Scheme 11, the compound SIAIS1221003 was prepared under appropriate conditions that will be recognized by one skilled in the art, except that the substrates used were 3-(4-((4-(bromomethyl)benzyl) thio)-1-oxoisoindolin-2-yl)piperidine-2,6-dione (SIAIS1220141) and adamantan-1-amine. The hydrochloride salt of compound SIAIS1221003 was obtained (white solid, 14 mg, yield 54%). $^1$H NMR (500 MHz, DMSO) δ 10.99 (s, 1H), 8.86 (s, 2H), 7.70 (d, J=7.7 Hz, 1H), 7.57 (d, J=7.5 Hz, 1H), 7.49 (dd, J=15.6, 7.9 Hz, 3H), 7.43 (d, J=8.1 Hz, 2H), 5.11 (dd, J=13.3, 5.1 Hz, 1H), 4.42-4.35 (m, 2H), 4.29 (d, J=17.4 Hz, 1H), 4.16 (d, J=17.4 Hz, 1H), 4.05 (s, 2H), 2.95-2.86 (m, 1H), 2.59 (d, J=16.8 Hz, 1H), 2.48-2.37 (m, 1H), 2.14 (s, 3H), 2.02-1.96 (m, 1H), 1.94 (s, 6H), 1.68 (d, J=12.3 Hz, 3H), 1.60 (d, J=12.0 Hz, 3H). HRMS (ESI) m/z: calcd for $C_{31}H_{36}N_3O_3S^+$ [M+H]$^+$, 530.2472; found, 530.2460.

Example 80: 3-(4-((4-((adamantan-2-ylamino) methyl)benzyl)thio)-1-oxoisoindolin-2-yl)piperidine-2,6-dione (SIAIS1221005)

Referring to the method of Scheme 11, the compound SIAIS1221005 was prepared under appropriate conditions that will be recognized by one skilled in the art, except that the substrates used were 3-(4-((4-(bromomethyl)benzyl) thio)-1-oxoisoindolin-2-yl)piperidine-2,6-dione (SIAIS1220141) and adamantan-2-amine. The hydrochloride salt of compound SIAIS1221005 was obtained (white solid, 20 mg, yield 77%). $^1$H NMR (500 MHz, DMSO) δ 10.99 (s, 1H), 9.07 (s, 2H), 7.67 (d, J=7.7 Hz, 1H), 7.58-7.52 (m, 3H), 7.49 (t, J=7.6 Hz, 1H), 7.43-7.39 (m, 2H), 5.11 (dd, J=13.3, 5.1 Hz, 1H), 4.41-4.34 (m, 2H), 4.29 (d, J=17.4 Hz, 1H), 4.17 (d, J=17.7 Hz, 1H), 4.13 (s, 2H), 3.12 (s, 1H), 2.96-2.86 (m, 1H), 2.59 (d, J=17.4 Hz, 1H), 2.48-2.38 (m, 1H), 2.17-2.07 (m, 4H), 2.02-1.94 (m, 1H), 1.81 (s, 4H), 1.68 (s, 2H), 1.61-1.49 (m, 4H). HRMS (ESI) m/z: calcd for $C_{31}H_{36}N_3O_3S^+$ [M+H]$^+$, 530.2472; found, 530.2465.

Example 81: 3-(4-((6-((adamantan-1-ylmethyl) amino)hexyl)thio)-1-oxoisoindolin-2-yl)piperidine-2,6-dione (SIAIS1221013)

Referring to the method of Scheme 11, the compound SIAIS1221013 was prepared under appropriate conditions that will be recognized by one skilled in the art, except that the substrates used were 3-(4-((6-bromohexyl)thio)-1-oxoisoindolin-2-yl)piperidine-2,6-dione (SIAIS1216133) and 1-adamantane methylamine. The hydrochloride salt of compound SIAIS1221013 was obtained (white solid, 23 mg, yield 88%). $^1$H NMR (500 MHz, DMSO) δ 10.99 (s, 1H), 8.06 (s, 2H), 7.63 (dd, J=7.5, 1.0 Hz, 1H), 7.58 (d, J=6.6 Hz, 1H), 7.54 (t, J=7.5 Hz, 1H), 5.14 (dd, J=13.3, 5.1 Hz, 1H), 4.35 (d, J=17.4 Hz, 1H), 4.21 (d, J=17.4 Hz, 1H), 3.09 (t, J=7.6, 2H), 2.96-2.88 (m, 1H), 2.87-2.80 (m, 2H), 2.63-2.57 (m, 3H), 2.48-2.40 (m, 1H), 2.05-1.98 (m, 1H), 1.97 (s, 3H), 1.70-1.57 (m, 10H), 1.54 (d, J=2.0 Hz, 6H), 1.46-1.39 (m, 2H), 1.34-1.27 (m, 2H). HRMS (ESI) m/z: calcd for $C_{30}H_{42}N_3O_3S^+$ [M+H]$^+$, 524.2941; found, 524.2945.

Example 82: 3-(4-((7-(adamantan-1-ylthio)heptyl) thio)-1-oxoisoindolin-2-yl)piperidine-2,6-dione (SIAIS1221025)

Referring to the method of Scheme 11, the compound SIAIS1221025 was prepared under appropriate conditions that will be recognized by one skilled in the art, except that the substrates used were 3-(4-((7-bromoheptyl)thio)-1-oxoisoindolin-2-yl)piperidine-2,6-dione (SIAIS1216135) and adamantane-1-thiol. The hydrochloride salt of compound SIAIS1221025 was obtained (white solid, 10 mg, yield 37%). $^1$H NMR (500 MHz, DMSO) δ 10.99 (s, 1H), 7.62 (dd, J=7.5, 1.1 Hz, 1H), 7.56 (dd, J=7.4, 1.0 Hz, 1H), 7.52 (t, J=7.5 Hz, 1H), 5.13 (dd, J=13.3, 5.1 Hz, 1H), 4.35 (d, J=17.4 Hz, 1H), 4.21 (d, J=17.4 Hz, 1H), 3.08 (t, J=7.2 Hz, 2H), 2.95-2.87 (m, 1H), 2.59 (d, J=17.0 Hz, 1H), 2.48-2.41 (m, 3H), 2.04-1.99 (m, 1H), 1.97 (s, 3H), 1.77 (d, J=2.8 Hz, 6H), 1.64 (d, J=13.4 Hz, 6H), 1.62-1.55 (m, 2H), 1.48-1.36 (m, 4H), 1.35-1.25 (m, 4H). HRMS (ESI) m/z: calcd for $C_{30}H_{41}N_2O_3S_2^+$ [M+H]$^+$, 541.2553; found, 541.2553.

Example 83: 3-(4-((7-(((adamantan-1-yl)methyl) amino)heptyl)thio)-1-oxoisoindolin-2-yl)piperidine-2,6-dione (SIAIS1220171)

Referring to the method of Scheme 11, the compound SIAIS1220171 was prepared under appropriate conditions that will be recognized by one skilled in the art, except that the substrates used were 3-(4-((7-bromoheptyl)thio)-1-oxoisoindolin-2-yl)piperidine-2,6-dione (SIAIS1216135) and 1-adamantane methylamine. The hydrochloride salt of compound SIAIS1220171 was obtained (white solid, 16 mg, yield 59%). $^1$H NMR (500 MHz, DMSO) δ 10.99 (s, 1H), 8.21 (s, 2H), 7.63 (dd, J=7.5, 1.0 Hz, 1H), 7.57 (d, J=6.5 Hz, 1H), 7.53 (t, J=7.5 Hz, 1H), 5.13 (dd, J=13.3, 5.1 Hz, 1H), 4.35 (d, J=17.4 Hz, 1H), 4.21 (d, J=17.4 Hz, 1H), 3.09 (t, J=6.8 Hz, 2H), 2.96-2.87 (m, 1H), 2.87-2.79 (m, 2H), 2.63-2.56 (m, 3H), 2.49-2.40 (m, 1H), 2.05-1.99 (m, 1H), 1.97 (s, 3H), 1.70-1.55 (m, 16H), 1.45-1.37 (m, 2H), 1.32-1.24 (m, 4H). HRMS (ESI) m/z: calcd for $C_{31}H_{44}N_3O_3S^+$ $[M+H]^+$, 538.3098; found, 538.3094.

Example 84: N-(adamantan-1-yl)-7-((2-(2,6-dioxopiperidin-3-yl)-1-oxoisoindolin-4-yl)thio)heptanamide (SIAIS1220195)

The compound SIAIS1220195 was prepared according to the method of example 71, except that adamantan-1-amine was used instead of piperidine. The target compound SIAIS1220195 was obtained as a white solid (18 mg, yield 67%). $^1$H NMR (500 MHz, DMSO) δ 10.99 (s, 1H), 7.62 (dd, J=7.5, 1.0 Hz, 1H), 7.56 (dd, J=7.4, 1.0 Hz, 1H), 7.52 (t, J=7.5 Hz, 1H), 7.18 (s, 1H), 5.13 (dd, J=13.3, 5.1 Hz, 1H), 4.35 (d, J=17.4 Hz, 1H), 4.21 (d, J=17.4 Hz, 1H), 3.07 (t, J=7.2 Hz, 2H), 2.96-2.86 (m, 1H), 2.59 (d, J=17.2 Hz, 1H), 2.49-2.41 (m, 1H), 2.04-1.95 (m, 6H), 1.89 (d, J=2.6 Hz, 6H), 1.63-1.55 (m, 8H), 1.47-1.35 (m, 4H), 1.27-1.20 (m, 2H). HRMS (ESI) m/z: calcd for $C_{30}H_{40}N_3O_4S^+$ $[M+H]^+$, 538.2734; found, 538.2736.

Example 85: N-(3,5-dimethyladamantan-1-yl)-7-((2-(2,6-dioxopiperidin-3-yl)-1-oxoisoindolin-4-yl)thio)heptanamide (SIAIS1220197)

The compound SIAIS1220197 was prepared according to the method of example 71, except that 3,5-dimethyladamantan-1-amine was used instead of piperidine. The target compound SIAIS1220197 was obtained as a white solid (21 mg, yield 75%). $^1$H NMR (500 MHz, DMSO) δ 10.99 (s, 1H), 7.62 (dd, J=7.5, 1.2 Hz, 1H), 7.56 (dd, J=7.5, 1.1 Hz, 1H), 7.52 (t, J=7.5 Hz, 1H), 7.21 (s, 1H), 5.13 (dd, J=13.3, 5.1 Hz, 1H), 4.35 (d, J=17.4 Hz, 1H), 4.21 (d, J=17.4 Hz, 1H), 3.07 (t, J=7.2 Hz, 2H), 2.96-2.87 (m, 1H), 2.59 (d, J=17.6 Hz, 1H), 2.49-2.41 (m, 1H), 2.06-1.94 (m, 4H), 1.72 (d, J=2.5 Hz, 2H), 1.62-1.50 (m, 6H), 1.46-1.35 (m, 4H), 1.31-1.20 (m, 6H), 1.07 (s, 2H), 0.79 (s, 6H). HRMS (ESI) m/z: calcd for $C_{32}H_{44}N_3O_4S^+$ $[M+H]^+$, 566.3047; found, 566.3040.

Example 86: N-(adamantan-2-yl)-7-((2-(2,6-dioxopiperidin-3-yl)-1-oxoisoindolin-4-yl)thio)heptanamide (SIAIS1220199)

The compound SIAIS1220199 was prepared according to the method of example 71, except that adamantan-2-amine was used instead of piperidine. The target compound SIAIS1220199 was obtained as a white solid (21 mg, yield 78%). $^1$H NMR (500 MHz, DMSO) δ 10.99 (s, 1H), 7.61 (dd, J=7.4, 0.8 Hz, 1H), 7.59 (s, 1H), 7.56 (d, J=6.5 Hz, 1H), 7.52 (t, J=7.5 Hz, 1H), 5.13 (dd, J=13.3, 5.1 Hz, 1H), 4.35 (d, J=17.4 Hz, 1H), 4.21 (d, J=17.4 Hz, 1H), 3.81 (d, J=7.3 Hz, 1H), 3.06 (t, J=7.2 Hz, 2H), 2.95-2.87 (m, 1H), 2.59 (d, J=18.0 Hz, 1H), 2.49-2.39 (m, 1H), 2.12 (t, J=7.3 Hz, 2H), 2.03-1.98 (m, 1H), 1.95 (d, J=12.6 Hz, 2H), 1.80-1.66 (m, 10H), 1.62-1.55 (m, 2H), 1.51-1.37 (m, 6H), 1.28-1.22 (m, 2H). HRMS (ESI) m/z: calcd for $C_{30}H_{40}N_3O_4S^+$ $[M+H]^+$, 538.2734; found, 538.2718.

Example 87: 3-(4-((6-(cyclohexylamino)hexyl)thio)-1-oxoisoindolin-2-yl)piperidine-2,6-dione (SIAIS1220183)

Referring to the method of Scheme 11, the compound SIAIS1220183 was prepared under appropriate conditions that will be recognized by one skilled in the art, except that the substrates used were 3-(4-((6-bromohexyl)thio)-1-oxoisoindolin-2-yl)piperidine-2,6-dione (SIAIS1216133) and cyclohexylamine. The hydrochloride salt of compound SIAIS1220183 was obtained (white solid, 18 mg, yield 78%). $^1$H NMR (500 MHz, DMSO) δ 10.99 (s, 1H), 8.40 (s, 2H), 7.63 (dd, J=7.5, 0.9 Hz, 1H), 7.58 (d, J=6.6 Hz, 1H), 7.54 (t, J=7.5 Hz, 1H), 5.13 (dd, J=13.3, 5.1 Hz, 1H), 4.35 (d, J=17.4 Hz, 1H), 4.21 (d, J=17.4 Hz, 1H), 3.12-3.06 (m, 2H), 2.96-2.83 (m, 4H), 2.60 (d, J=17.2 Hz, 1H), 2.48-2.40 (m, 1H), 2.04-1.96 (m, 3H), 1.78-1.96 (m, 2H), 1.64-1.53 (m, 5H), 1.46-1.39 (m, 2H), 1.37-1.30 (m, 2H), 1.27-1.18 (m, 4H), 1.14-1.05 (m, 1H). HRMS (ESI) m/z: calcd for $C_{25}H_{36}N_3O_3S^+$ $[M+H]^+$, 458.2472; found, 458.2580.

Example 88: 3-(4-((7-(cyclohexylamino)heptyl)thio)-1-oxoisoindolin-2-yl)piperidine-2,6-dione (SIAIS1220185)

Referring to the method of Scheme 11, the compound SIAIS1220185 was prepared under appropriate conditions that will be recognized by one skilled in the art, except that the substrates used were 3-(4-((7-bromoheptyl)thio)-1-oxoisoindolin-2-yl)piperidine-2,6-dione (SIAIS1216135) and cyclohexylamine. The hydrochloride salt of compound SIAIS1220185 was obtained (white solid, 7 mg, yield 29%). $^1$H NMR (500 MHz, DMSO) δ 10.99 (s, 1H), 8.29 (s, 2H), 7.63 (d, J=7.5 Hz, 1H), 7.57 (d, J=7.2 Hz, 1H), 7.53 (t, J=7.5 Hz, 1H), 5.14 (dd, J=13.0, 4.8 Hz, 1H), 4.35 (d, J=17.2 Hz, 1H), 4.21 (d, J=17.4 Hz, 1H), 3.09 (t, J=7.0 Hz, 2H), 2.99-2.82 (m, 4H), 2.60 (d, J=18.2 Hz, 1H), 2.48-2.40 (m, 1H), 1.99 (s, 3H), 1.76 (s, 2H), 1.64-1.52 (m, 5H), 1.41 (s, 2H), 1.30 (s, 4H), 1.23 (t, J=9.6 Hz, 4H), 1.10 (s, 1H). HRMS (ESI) m/z: calcd for $C_{26}H_{38}N_3O_3S^+$ $[M+H]^+$, 472.2628; found, 472.2625.

Example 89: 3-(1-oxo-4-((7-(phenylamino)heptyl)thio)isoindolin-2-yl)piperidine-2,6-dione (SIAIS1220187)

Referring to the method of Scheme 11, the compound SIAIS1220187 was prepared under appropriate conditions that will be recognized by one skilled in the art, except that the substrates used were 3-(4-((7-bromoheptyl)thio)-1-oxoisoindolin-2-yl)piperidine-2,6-dione (SIAIS1216135) and aniline. The target compound SIAIS1220187 was obtained as a white solid (8 mg, yield 35%). $^1$H NMR (500 MHz, $CDCl_3$) δ 8.69 (s, 1H), 7.75 (d, J=6.7 Hz, 1H), 7.59 (d, J=6.9 Hz, 2H), 7.53 (d, J=6.9 Hz, 1H), 7.49 (t, J=7.5 Hz, 1H), 7.44-7.36 (m, 3H), 5.26 (dd, J=13.3, 5.0 Hz, 1H), 4.43 (d, J=16.5 Hz, 1H), 4.32 (d, J=16.5 Hz, 1H), 3.30-3.22 (m, 2H), 2.97-2.92 (m, 2H), 2.90-2.81 (m, 1H), 2.48-2.38 (m, 1H), 2.28-2.21 (m, 1H), 1.88-1.80 (m, 2H), 1.65-1.56 (m, 6H), 1.38-1.25 (m, 4H). HRMS (ESI) m/z: calcd for $C_{26}H_{32}N_3O_3S^+$ $[M+H]^+$, 466.2159; found, 466.2159.

Example 90: 3-(4-((7-(methyl(phenyl)amino)heptyl)thio)-1-oxoisoindolin-2-yl)piperidine-2,6-dione (SIAIS1220189)

Referring to the method of Scheme 11, the compound SIAIS1220189 was prepared under appropriate conditions that will be recognized by one skilled in the art, except that the substrates used were 3-(4-((7-bromoheptyl)thio)-1-oxoisoindolin-2-yl)piperidine-2,6-dione (SIAIS1216135) and N-methylaniline. The target compound SIAIS1220189 was obtained as a white solid (13 mg, yield 54%). $^1$H NMR (500

MHz, $CDCl_3$) δ 8.70 (s, 1H), 7.85-7.68 (m, 3H), 7.62-7.43 (m, 5H), 5.25 (dd, J=13.3, 4.9 Hz, 1H), 4.43 (d, J=16.5 Hz, 1H), 4.32 (d, J=16.5 Hz, 1H), 3.61-3.38 (m, 1H), 3.27 (s, 1H), 3.00-2.90 (m, 3H), 2.90-2.81 (m, 1H), 2.50-2.38 (m, 1H), 2.29-2.22 (m, 1H), 1.95 (s, 1H), 1.69 (s, 3H), 1.65-1.53 (m, 2H), 1.50-1.34 (m, 3H), 1.27 (s, 4H). HRMS (ESI) m/z: calcd for $C_{27}H_{34}N_3O_3S^+$ [M+H]$^+$, 480.2315; found, 480.2313.

Example 91: 3-(4-((7-(azocan-1-yl)heptyl)thio)-1-oxoisoindolin-2-yl)piperidine-2,6-dione (SIAIS1220193)

Referring to the method of Scheme 11, the compound SIAIS1220193 was prepared under appropriate conditions that will be recognized by one skilled in the art, except that the substrates used were 3-(4-((7-bromoheptyl)thio)-1-oxoisoindolin-2-yl)piperidine-2,6-dione (SIAIS1216135) and azacyclooctane. The hydrochloride salt of compound SIAIS1220193 was obtained (light yellow solid, 22 mg, yield 92%). $^1$H NMR (500 MHz, DMSO) δ 10.99 (s, 1H), 9.39 (s, 1H), 7.63 (dd, J=7.5, 1.0 Hz, 1H), 7.57 (dd, J=7.4, 0.9 Hz, 1H), 7.53 (t, J=7.5 Hz, 1H), 5.13 (dd, J=13.3, 5.1 Hz, 1H), 4.35 (d, J=17.4 Hz, 1H), 4.21 (d, J=17.4 Hz, 1H), 3.36-3.29 (m, 2H), 3.12-3.05 (m, 4H), 3.04-2.99 (m, 2H), 2.97-2.87 (m, 1H), 2.59 (d, J=17.6 Hz, 1H), 2.49-2.41 (m, 1H), 2.05-1.98 (m, 1H), 1.92-1.82 (m, 2H), 1.74-1.58 (m, 9H), 1.55-1.47 (m, 3H), 1.45-1.38 (m, 2H), 1.33-1.23 (m, 4H). HRMS (ESI) m/z: calcd for $C_{27}H_{40}N_3O_3S^+$ [M+H]$^+$, 486.2785; found, 486.2784.

Example 92: 3-(1-oxo-4-((7-(((1R,2S,4R)-1,7,7-trimethylbicyclo[2.2.1]heptan-2-yl)amino)heptyl)thio)isoindolin-2-yl)piperidine-2,6-dione (SIAIS1221019)

Referring to the method of Scheme 11, the compound SIAIS1221019 was prepared under appropriate conditions that will be recognized by one skilled in the art, except that the substrates used were 3-(4-((7-bromoheptyl)thio)-1-oxoisoindolin-2-yl)piperidine-2,6-dione (SIAIS1216135) and bornylamine. The hydrochloride salt of compound SIAIS1221019 was obtained (white solid, 14 mg, yield 54%). $^1$H NMR (500 MHz, DMSO) δ 10.99 (s, 1H), 8.64 (s, 1H), 8.22 (s, 1H), 7.63 (d, J=7.5 Hz, 1H), 7.57 (d, J=7.3 Hz, 1H), 7.53 (t, J=7.5 Hz, 1H), 5.13 (dd, J=13.2, 4.9 Hz, 1H), 4.35 (d, J=17.3 Hz, 1H), 4.21 (d, J=17.3 Hz, 1H), 3.20 (s, 1H), 3.09 (t, J=7.1 Hz, 2H), 2.96-2.83 (m, 3H), 2.59 (d, J=17.7 Hz, 1H), 2.49-2.41 (m, 1H), 2.15 (t, J=11.9 Hz, 1H), 2.04-1.98 (m, 1H), 1.71-1.65 (m, 4H), 1.63-1.58 (m, 2H), 1.47-1.35 (m, 4H), 1.35-1.17 (m, 6H), 0.96 (s, 3H), 0.83 (s, 6H). HRMS (ESI) m/z: calcd for $C_{30}H_{44}N_3O_3S^+$ [M+H]$^+$, 526.3098; found, 526.3094.

Example 93: 3-(4-((7-(3-azaspiro[5.5]undecan-3-yl)heptyl)thio)-1-oxoisoindolin-2-yl)piperidine-2,6-dione (SIAIS1221015)

Referring to the method of Scheme 11, the compound SIAIS1221015 was prepared under appropriate conditions that will be recognized by one skilled in the art, except that the substrates used were 3-(4-((7-bromoheptyl)thio)-1-oxoisoindolin-2-yl)piperidine-2,6-dione (SIAIS1216135) and 3-azaspiro[5.5]undecane. The hydrochloride salt of compound SIAIS1221015 was obtained (white solid, 24 mg, yield 92%). $^1$H NMR (500 MHz, DMSO) δ 11.00 (d, J=11.1 Hz, 1H), 9.47 (s, 1H), 7.63 (d, J=7.5 Hz, 1H), 7.57 (d, J=7.4 Hz, 1H), 7.53 (t, J=7.4 Hz, 1H), 5.13 (dd, J=13.2, 5.0 Hz, 1H), 4.35 (d, J=17.4 Hz, 1H), 4.21 (d, J=17.4 Hz, 1H), 3.25 (d, J=11.9 Hz, 2H), 3.08 (t, J=7.1 Hz, 2H), 3.02-2.97 (m, 2H), 2.95-2.88 (m, 3H), 2.59 (d, J=17.1 Hz, 1H), 2.48-2.41 (m, 1H), 2.04-1.98 (m, 1H), 1.73 (d, J=14.1 Hz, 2H), 1.65-156 (m, 4H), 1.53-1.45 (m, 4H), 1.42-1.35 (m, 8H), 1.31-1.22 (m, 6H). HRMS (ESI) m/z: calcd for $C_{30}H_{44}N_3O_3S^+$ [M+H]$^+$, 526.3098; found, 526.3094.

Example 94: 3-(4-((7-(3,5-dimethylpiperidin-1-yl)heptyl)thio)-1-oxoisoindolin-2-yl)piperidine-2,6-dione (SIAIS1221021)

Referring to the method of Scheme 11, the compound SIAIS1221021 was prepared under appropriate conditions that will be recognized by one skilled in the art, except that the substrates used were 3-(4-((7-bromoheptyl)thio)-1-oxoisoindolin-2-yl)piperidine-2,6-dione (SIAIS1216135) and 3,5-dimethylpiperidine. The hydrochloride salt of compound SIAIS1221021 was obtained (white solid, 16 mg, yield 67%). $^1$H NMR (500 MHz, DMSO) δ 11.00 (s, 1H), 10.55 (s, 1H), 7.63 (d, J=7.4 Hz, 1H), 7.57 (d, J=7.3 Hz, 1H), 7.56-7.52 (m, 1H), 5.13 (dd, J=13.2, 4.9 Hz, 1H), 4.36 (d, J=17.4 Hz, 1H), 4.22 (d, J=17.4 Hz, 1H), 3.29 (d, J=11.1 Hz, 2H), 3.08 (t, J=7.1 Hz, 2H), 2.97-2.87 (m, 3H), 2.60 (d, J=17.1 Hz, 1H), 2.49-2.42 (m, 1H), 2.37 (dd, J=21.0, 11.2 Hz, 2H), 2.07-1.97 (m, 3H), 1.75-1.66 (m, 3H), 1.64-1.56 (m, 2H), 1.45-1.38 (m, 2H), 1.33-1.23 (m, 4H), 0.87 (d, J=6.5 Hz, 6H), 0.76 (q, J=12.3 Hz, 1H). HRMS (ESI) m/z: calcd for $C_{27}H_{40}N_3O_3S^+$ [M+H]$^+$, 486.2785; found, 486.2784.

Example 95: 3-(4-((7-(4,4-dimethylpiperidin-1-yl)heptyl)thio)-1-oxoisoindolin-2-yl)piperidine-2,6-dione (SIAIS1221027)

Referring to the method of Scheme 11, the compound SIAIS1221027 was prepared under appropriate conditions that will be recognized by one skilled in the art, except that the substrates used were 3-(4-((7-bromoheptyl)thio)-1-oxoisoindolin-2-yl)piperidine-2,6-dione (SIAIS1216135) and 4,4-dimethylpiperidine. The hydrochloride salt of compound SIAIS1221027 was obtained (white solid, 12 mg, yield 50%). $^1$H NMR (500 MHz, DMSO) δ 10.99 (s, 1H), 9.78 (s, 1H), 7.63 (d, J=7.4 Hz, 1H), 7.57 (d, J=7.4 Hz, 1H), 7.53 (t, J=7.4 Hz, 1H), 5.13 (dd, J=13.2, 5.1 Hz, 1H), 4.35 (d, J=17.3 Hz, 1H), 4.21 (d, J=17.3 Hz, 1H), 3.26 (d, J=12.1 Hz, 2H), 3.08 (t, J=7.0 Hz, 2H), 3.00-2.87 (m, 5H), 2.59 (d, J=17.5 Hz, 1H), 2.48-2.41 (m, 1H), 2.04-1.98 (m, 1H), 1.72-1.57 (m, 6H), 1.49-1.38 (m, 4H), 1.33-1.23 (m, 4H), 0.99 (s, 3H), 0.95 (s, 3H). HRMS (ESI) m/z: calcd for $C_{27}H_{40}N_3O_3S^+$ [M+H]$^+$, 486.2785; found, 486.2784.

Example 96: 3-(4-((7-((4,4-dimethylcyclohexyl)amino)heptyl)thio)-1-oxoisoindolin-2-yl)piperidine-2,6-dione (SIAIS1221029)

Referring to the method of Scheme 11, the compound SIAIS1221029 was prepared under appropriate conditions that will be recognized by one skilled in the art, except that the substrates used were 3-(4-((7-bromoheptyl)thio)-1-oxoisoindolin-2-yl)piperidine-2,6-dione (SIAIS1216135) and 4,4-dimethylcyclohexylamine. The hydrochloride salt of compound SIAIS1221029 was obtained (white solid, 12 mg, yield 50%). $^1$H NMR (500 MHz, DMSO) δ 10.99 (s, 1H), 8.33 (s, 2H), 7.63 (d, J=7.5 Hz, 1H), 7.57 (d, J=7.3 Hz, 1H), 7.53 (t, J=7.5 Hz, 1H), 5.13 (dd, J=13.3, 4.9 Hz, 1H), 4.35

(d, J=17.5 Hz, 1H), 4.21 (d, J=17.5 Hz, 1H), 3.09 (t, J=7.1 Hz, 2H), 2.96-2.84 (m, 4H), 2.59 (d, J=19.2 Hz, 1H), 2.48-2.40 (m, 1H), 2.05-1.97 (m, 1H), 1.81 (d, J=10.9 Hz, 2H), 1.64-1.38 (m, 10H), 1.30 (s, 4H), 1.25-1.14 (m, 2H), 0.89 (d, J=5.5 Hz, 6H). HRMS (ESI) m/z: calcd for $C_{28}H_{42}N_3O_3S^+$ [M+H]$^+$, 500.2941; found, 500.2945.

Example 97: 3-(4-((7-((adamantan-1-yl)(methyl)amino)heptyl)thio)-1-oxoisoindolin-2-yl)piperidine-2,6-dione (SIAIS1221031)

Referring to the method of Scheme 13, the compound SIAIS1221031 was prepared under appropriate conditions that will be recognized by one skilled in the art, except that the substrate used was compound SIAIS1220155. The hydrochloride salt of compound SIAIS1221031 was obtained (white solid, 16 mg, yield 100%). $^1$H NMR (500 MHz, DMSO) δ 10.99 (s, 1H), 9.47 (s, 1H), 7.63 (d, J=7.4 Hz, 1H), 7.57 (d, J=7.3 Hz, 1H), 7.53 (t, J=7.4 Hz, 1H), 5.13 (dd, J=13.3, 5.0 Hz, 1H), 4.35 (d, J=17.4 Hz, 1H), 4.21 (d, J=17.4 Hz, 1H), 3.32-3.24 (m, 1H), 3.09 (t, J=7.0 Hz, 2H), 2.96-2.87 (m, 1H), 2.68-2.57 (m, 5H), 2.49-2.41 (m, 1H), 2.15 (s, 3H), 2.04-1.97 (m, 1H), 1.96 (d, J=11.4 Hz, 3H), 1.89 (d, J=11.3 Hz, 3H), 1.68-1.58 (m, 10H), 1.45-1.38 (m, 2H), 1.36-1.23 (m, 4H). HRMS (ESI) m/z: calcd for $C_{31}H_{44}N_3O_3S^+$ [M+H]$^+$, 538.3098; found, 538.3095.

Example 98: 3-(4-((4-((cyclohexylamino)methyl)benzyl)thio)-1-oxoisoindolin-2-yl)piperidine-2,6-dione (SIAIS1221071)

Referring to the method of Scheme 11, the compound SIAIS1221071 was prepared under appropriate conditions that will be recognized by one skilled in the art, except that the substrates used were 3-(4-((4-(bromomethyl)benzyl)thio)-1-oxoisoindolin-2-yl)piperidine-2,6-dione (SIAIS1220141) and cyclohexylamine. The hydrochloride salt of compound SIAIS1221071 was obtained (white solid, 15 mg, yield 63%). $^1$H NMR (500 MHz, DMSO) δ 10.99 (s, 1H), 9.07 (s, 2H), 7.68 (d, J=7.7 Hz, 1H), 7.57 (d, J=7.5 Hz, 1H), 7.52-7.47 (m, 3H), 7.41 (d, J=7.6 Hz, 2H), 5.11 (dd, J=13.2, 5.0 Hz, 1H), 4.37 (s, 2H), 4.29 (d, J=17.4 Hz, 1H), 4.15 (d, J=17.4 Hz, 1H), 4.11-4.06 (m, 2H), 2.96-2.86 (m, 2H), 2.59 (d, J=17.3 Hz, 1H), 2.47-2.37 (m, 1H), 2.08 (d, J=10.9 Hz, 2H), 2.02-1.94 (m, 1H), 1.76 (d, J=13.0 Hz, 2H), 1.60 (d, J=12.3 Hz, 1H), 1.41-1.31 (m, 2H), 1.19 (dd, J=25.7, 12.8 Hz, 2H), 1.09 (dd, J=25.0, 12.4 Hz, 1H). HRMS (ESI) m/z: calcd for $C_{27}H_{32}N_3O_3S^+$ [M+H]$^+$, 478.2159; found, 478.2154.

Example 99: 3-(1-oxo-4-((4-((((1R,2S,4R)-1,7,7-trimethylbicyclo[2.2.1]heptan-2-yl)amino)methyl)benzyl)thio)isoindolin-2-yl)piperidine-2,6-dione (SIAIS1221073)

Referring to the method of Scheme 11, the compound SIAIS1221073 was prepared under appropriate conditions that will be recognized by one skilled in the art, except that the substrates used were 3-(4-((4-(bromomethyl)benzyl)thio)-1-oxoisoindolin-2-yl)piperidine-2,6-dione (SIAIS1220141) and bornylamine. The hydrochloride salt of compound SIAIS1221073 was obtained (white solid, 17 mg, yield 63%). $^1$H NMR (500 MHz, DMSO) δ 10.99 (s, 1H), 9.12 (s, 1H), 8.64 (s, 1H), 7.64 (d, J=7.7 Hz, 1H), 7.56 (d, J=7.5 Hz, 1H), 7.53-7.44 (m, 3H), 7.41 (d, J=7.6 Hz, 2H), 5.11 (dd, J=13.2, 5.0 Hz, 1H), 4.38 (s, 2H), 4.29 (d, J=17.8 Hz, 1H), 4.20-4.03 (m, 3H), 3.07 (s, 1H), 2.95-2.87 (m, 1H), 2.59 (d, J=17.0 Hz, 1H), 2.47-2.38 (m, 1H), 2.01-1.95 (m, 1H), 1.87 (s, 1H), 1.62 (s, 3H), 1.42-1.30 (m, 2H), 1.14-1.05 (m, 1H), 0.85 (s, 3H), 0.80 (s, 3H), 0.69 (d, J=7.1 Hz, 3H). HRMS (ESI) m/z: calcd for $C_{31}H_{38}N_3O_3S^+$ [M+H]$^+$, 532.2628; found, 532.2625.

Example 100: 3-(1-oxo-4-((7-(2-oxopiperidin-1-yl)heptyl)thio)isoindolin-2-yl)piperidine-2,6-dione (SIAIS264042)

The target compound SIAIS264042 was prepared according to the method of example 76, except that the substrate used in step 1 was 1,7-dibromoheptane. The target product SIAIS264042 was obtained as a white solid (10.1 mg, yield 38%). $^1$H NMR (500 MHz, DMSO) δ 10.99 (s, 1H), 7.63 (d, J=7.5 Hz, 1H), 7.56 (d, J=6.6 Hz, 1H), 7.53 (t, J=7.5 Hz, 1H), 5.13 (dd, J=13.3, 5.1 Hz, 1H), 4.35 (d, J=17.4 Hz, 1H), 4.21 (d, J=17.4 Hz, 1H), 3.20 (dd, J=13.4, 6.8 Hz, 4H), 3.07 (t, J=7.2 Hz, 2H), 2.95-2.87 (m, 1H), 2.59 (d, J=17.7 Hz, 1H), 2.49-2.41 (m, 1H), 2.17 (t, J=6.3 Hz, 2H), 2.04-1.97 (m, 1H), 1.71-1.63 (m, 4H), 1.62-1.55 (m, 2H), 1.46-1.36 (m, 4H), 1.32-1.25 (m, 2H), 1.22-1.16 (m, 2H). HRMS (ESI) m/z: calcd for $C_{25}H_{34}N_3O_4S^+$ [M+H]$^+$, 472.2265; found, 472.2261.

Example 101: N-(2-((2-(2,6-dioxopiperidin-3-yl)-1-oxoisoindolin-4-yl)thio)ethyl)-5-(piperidin-1-yl)pentanamide (SIAIS1220169)

The target compound SIAIS1220169 was prepared according to the method of example 71, except that the substrates used were 5-(piperidin-1-yl)pentanoic acid and 3-(4-((2-aminoethyl)thio)-1-oxoisoindolin-2-yl)piperidine-2,6-dione (SIAIS171123). The hydrochloride salt of compound SIAIS1220169 was obtained (yellow solid, 4 mg, yield 27%). $^1$H NMR (500 MHz, DMSO) δ 11.00 (s, 1H), 9.78 (s, 1H), 8.17 (t, J=5.5 Hz, 1H), 7.73 (d, J=7.5 Hz, 1H), 7.59 (d, J=7.3 Hz, 1H), 7.54 (t, J=7.5 Hz, 1H), 5.14 (dd, J=13.3, 5.0 Hz, 1H), 4.38 (d, J=17.3 Hz, 1H), 4.23 (d, J=17.3 Hz, 1H), 3.28 (dd, J=12.6, 6.4 Hz, 2H), 3.14 (t, J=6.7 Hz, 2H), 2.99-2.88 (m, 3H), 2.79 (d, J=11.2 Hz, 2H), 2.60 (d, J=17.0 Hz, 1H), 2.48-2.40 (m, 1H), 2.09 (t, J=7.2 Hz, 2H), 2.04-1.99 (m, 1H), 1.79-1.60 (m, 8H), 1.53-1.46 (m, 2H), 1.43-1.30 (m, 2H). HRMS (ESI) m/z: calcd for $C_{25}H_{35}N_4O_4S^+$ [M+H]$^+$, 487.2374; found, 487.2384.

Example 102: 3-(1-oxo-4-((5-(((1R,2S,4R)-1,7,7-trimethylbicyclo[2.2.1]heptan-2-yl)amino)pentyl)thio)isoindolin-2-yl)piperidine-2,6-dione (SIAIS1221113)

Referring to the method of Scheme 11, the compound SIAIS1221113 was prepared under appropriate conditions that will be recognized by one skilled in the art, except that the substrates used were 3-(4-((5-bromopentyl)thio)-1-oxoisoindolin-2-yl)piperidine-2,6-dione (SIAIS1216049) and bornylamine (CAS No. 32511-34-5). The hydrochloride salt of compound SIAIS1221113 was obtained (white solid, 11 mg, yield 44%). $^1$H NMR (500 MHz, DMSO) δ 11.00 (s, 1H), 8.36 (s, 1H), 8.05 (s, 1H), 7.64 (d, J=7.4 Hz, 1H), 7.58 (d, J=7.4 Hz, 1H), 7.54 (t, J=7.5 Hz, 1H), 5.14 (dd, J=13.2, 4.9 Hz, 1H), 4.36 (d, J=17.4 Hz, 1H), 4.22 (d, J=17.3 Hz, 1H), 3.22 (s, 1H), 3.11 (t, J=7.0 Hz, 2H), 2.96-2.84 (m, 3H), 2.60 (d, J=16.5 Hz, 1H), 2.48-2.40 (m, 1H), 2.16 (s, 1H), 2.05-1.98 (m, 1H), 1.74-1.55 (m, 7H), 1.49-1.34 (m, 4H), 1.17 (d, J=11.1 Hz, 1H), 0.94 (s, 3H), 0.84 (s, 6H). HRMS (ESI) m/z: calcd for $C_{28}H_{40}N_3O_3S^+$ [M+H]$^+$, 498.2785; found, 498.2784.

Example 103: 3-(1-oxo-4-((6-(((1R,2S,4R)-1,7,7-trimethylbicyclo[2.2.1]heptan-2-yl)amino)hexyl)thio)isoindolin-2-yl)piperidine-2,6-dione (SIAIS1221115)

Referring to the method of Scheme 11, the compound SIAIS1221115 was prepared under appropriate conditions that will be recognized by one skilled in the art, except that the substrates used were 3-(4-((6-bromohexyl)thio)-1-oxoisoindolin-2-yl)piperidine-2,6-dione (SIAIS1216133) and bornylamine. The hydrochloride salt of compound SIAIS1221115 was obtained (white solid, 16 mg, yield 62%). $^1$H NMR (500 MHz, DMSO) δ 10.99 (s, 1H), 8.41 (s, 1H), 8.08 (s, 1H), 7.63 (d, J=7.5 Hz, 1H), 7.57 (d, J=7.2 Hz, 1H), 7.54 (t, J=7.5 Hz, 1H), 5.13 (dd, J=13.2, 5.0 Hz, 1H), 4.35 (d, J=17.3 Hz, 1H), 4.21 (d, J=17.3 Hz, 1H), 3.21 (s, 1H), 3.10 (t, J=7.0 Hz, 2H), 2.96-2.83 (m, 3H), 2.60 (d, J=16.6 Hz, 1H), 2.45 (dd, J=15.6, 11.4 Hz, 1H), 2.15 (t, J=12.0 Hz, 1H), 2.05-1.98 (m, 1H), 1.71-1.56 (m, 7H), 1.48-1.29 (m, 6H), 1.18 (d, J=13.6 Hz, 1H), 0.95 (s, 3H), 0.83 (d, J=2.0 Hz, 6H). HRMS (ESI) m/z: calcd for $C_{29}H_{42}N_3O_3S^+$ [M+H]$^+$, 512.2941; found, 512.2944.

Example 104: 3-(4-((5-((adamantan-1-yl)amino)pentyl)thio)-1-oxoisoindolin-2-yl)piperidine-2,6-dione (SIAIS1221117)

Referring to the method of Scheme 11, the compound SIAIS1221117 was prepared under appropriate conditions that will be recognized by one skilled in the art, except that the substrates used were 3-(4-((5-bromopentyl)thio)-1-oxoisoindolin-2-yl)piperidine-2,6-dione (SIAIS1216049) and 1-adamantanamine. The hydrochloride salt of compound SIAIS1221117 was obtained (white solid, 10 mg, yield 40%). $^1$H NMR (500 MHz, DMSO) δ 11.00 (s, 1H), 8.50 (s, 2H), 7.65 (d, J=7.5 Hz, 1H), 7.58 (d, J=7.4 Hz, 1H), 7.56-7.52 (m, 1H), 5.13 (dd, J=13.3, 5.0 Hz, 1H), 4.36 (d, J=17.3 Hz, 1H), 4.22 (d, J=17.3 Hz, 1H), 3.10 (t, J=7.0 Hz, 2H), 2.96-2.88 (m, 1H), 2.81 (s, 2H), 2.59 (d, J=17.5 Hz, 1H), 2.48-2.41 (m, 1H), 2.11 (s, 3H), 2.04-1.98 (m, 1H), 1.83 (s, 6H), 1.68-1.55 (m, 10H), 1.52-1.45 (m, 2H). HRMS (ESI) m/z: calcd for $C_{28}H_{38}N_3O_3S^+$ [M+H]$^+$, 496.2628; found, 496.2623.

Example 105: 3-(4-((6-(3-azaspiro[5.5]undecan-3-yl)hexyl)thio)-1-oxoisoindolin-2-yl)piperidine-2,6-dione (SIAIS1221121)

Referring to the method of Scheme 11, the compound SIAIS1221121 was prepared under appropriate conditions that will be recognized by one skilled in the art, except that the substrates used were 3-(4-((6-bromohexyl)thio)-1-oxoisoindolin-2-yl)piperidine-2,6-dione (SIAIS1216133) and 3-azaspiro[5.5]undecane. The hydrochloride salt of compound SIAIS1221121 was obtained (white solid, 25 mg, yield 98%). $^1$H NMR (500 MHz, DMSO) δ 11.00 (s, 1H), 9.98 (s, 1H), 7.64 (d, J=7.4 Hz, 1H), 7.57 (d, J=7.3 Hz, 1H), 7.54 (t, J=7.4 Hz, 1H), 5.13 (dd, J=13.2, 4.8 Hz, 1H), 4.36 (d, J=17.3 Hz, 1H), 4.22 (d, J=17.4 Hz, 1H), 3.22 (d, J=11.1 Hz, 2H), 3.09 (t, J=7.0 Hz, 2H), 3.00-2.87 (m, 5H), 2.60 (d, J=17.3 Hz, 1H), 2.49-2.41 (m, 1H), 2.05-1.98 (m, 1H), 1.73-1.53 (m, 8H), 1.48-1.36 (m, 10H), 1.33-1.27 (m, 2H), 1.23 (s, 2H). HRMS (ESI) m/z: calcd for $C_{29}H_{42}N_{303}S^+$ [M+H]$^+$, 512.2941; found, 512.2944.

Example 106: 3-(4-((5-(3-azaspiro[5.5]undecan-3-yl)pentyl)thio)-1-oxoisoindolin-2-yl)piperidine-2,6-dione (SIAIS1221123)

Referring to the method of Scheme 11, the compound SIAIS1221123 was prepared under appropriate conditions that will be recognized by one skilled in the art, except that the substrates used were 3-(4-((5-bromopentyl)thio)-1-oxoisoindolin-2-yl)piperidine-2,6-dione (SIAIS1216049) and 3-azaspiro[5.5]undecane. The hydrochloride salt of compound SIAIS1221123 was obtained (white solid, 22 mg, yield 87%). $^1$H NMR (500 MHz, DMSO) δ 11.00 (s, 1H), 9.99 (s, 1H), 7.65 (d, J=7.5 Hz, 1H), 7.58 (d, J=7.3 Hz, 1H), 7.54 (t, J=7.4 Hz, 1H), 5.13 (dd, J=13.3, 5.0 Hz, 1H), 4.36 (d, J=17.3 Hz, 1H), 4.22 (d, J=17.4 Hz, 1H), 3.23 (d, J=11.9 Hz, 2H), 3.11 (t, J=7.1 Hz, 2H), 3.00-2.87 (m, 5H), 2.60 (d, J=17.1 Hz, 1H), 2.49-2.41 (m, 1H), 2.04-1.99 (m, 1H), 1.72-1.53 (m, 8H), 1.46-1.35 (m, 10H), 1.23 (s, 2H). HRMS (ESI) m/z: calcd for $C_{28}H_{40}N_3O_3S^+$ [M+H]$^+$, 498.2785; found, 498.2784.

Example 107: 3-(4-((7-((4,4-dimethylcyclohexyl)(methyl)amino)heptyl)thio)-1-oxoisoindolin-2-yl)piperidine-2,6-dione (SIAIS1221125)

Referring to the method of Scheme 13, the compound SIAIS1221125 was prepared under appropriate conditions that will be recognized by one skilled in the art, except that the substrate used was 3-(4-((7-((4,4-dimethylcyclohexyl)amino)heptyl)thio)-1-oxoisoindolin-2-yl)piperidine-2,6-dione (SIAIS1221029). The hydrochloride salt of compound SIAIS1221125 was obtained (light yellow solid, 6 mg, yield 76%). $^1$H NMR (500 MHz, DMSO) δ 10.99 (s, 1H), 10.05 (s, 1H), 7.63 (d, J=7.4 Hz, 1H), 7.57 (d, J=7.2 Hz, 1H), 7.53 (t, J=7.4 Hz, 1H), 5.13 (dd, J=13.3, 4.9 Hz, 1H), 4.35 (d, J=17.3 Hz, 1H), 4.21 (d, J=17.4 Hz, 1H), 3.11-3.03 (m, 4H), 2.96-2.87 (m, 2H), 2.65 (d, J=4.7 Hz, 3H), 2.59 (d, J=17.1 Hz, 1H), 2.49-2.42 (m, 1H), 2.04-1.98 (m, 1H), 1.81 (dd, J=26.8, 12.0 Hz, 2H), 1.67-1.55 (m, 6H), 1.47-1.39 (m, 4H), 1.33-1.20 (m, 6H), 0.90 (d, J=3.1 Hz, 6H). HRMS (ESI) m/z: calcd for $C_{29}H_{44}N_3O_3S^+$ [M+H]$^+$, 514.3098; found, 514.3094.

Example 108: 3-(4-((6-((adamantan-1-ylmethyl)(methyl)amino)hexyl)thio)-1-oxoisoindolin-2-yl)piperidine-2,6-dione (SIAIS1221127)

Referring to the method of Scheme 13, the compound SIAIS1221127 was prepared under appropriate conditions that will be recognized by one skilled in the art, except that the substrate used was 3-(4-((6-((adamantan-1-ylmethyl)amino)hexyl)thio)-1-oxoisoindolin-2-yl)piperidine-2,6-dione (SIAIS1221013). The hydrochloride salt of compound SIAIS1221127 was obtained (white solid, 8 mg, yield 70%). $^1$H NMR (500 MHz, DMSO) δ 10.99 (s, 1H), 9.20 (s, 1H), 7.64 (d, J=7.4 Hz, 1H), 7.57 (d, J=7.2 Hz, 1H), 7.53 (t, J=7.4 Hz, 1H), 5.13 (dd, J=13.3, 5.0 Hz, 1H), 4.35 (d, J=17.4 Hz, 1H), 4.21 (d, J=17.4 Hz, 1H), 3.09 (t, J=7.0 Hz, 2H), 3.02-2.87 (m, 4H), 2.78-2.70 (m, 4H), 2.59 (d, J=17.6 Hz, 1H), 2.49-2.41 (m, 1H), 2.05-1.99 (m, 1H), 1.96 (s, 3H), 1.72-1.57 (m, 16H), 1.47-1.40 (m, 2H), 1.32-1.25 (m, 2H). HRMS (ESI) m/z: calcd for $C_{31}H_{44}N_3O_3S^+$ [M+H]$^+$, 538.3098; found, 538.3094.

Example 109: 3-(1-oxo-4-((7-(spiro[3.3]heptan-2-ylamino)heptyl)thio)isoindolin-2-yl)piperidine-2,6-dione (SIAIS1222077)

Referring to the method of Scheme 11, the compound SIAIS1222077 was prepared under appropriate conditions that will be recognized by one skilled in the art, except that the substrates used were 3-(4-((7-bromoheptyl)thio)-1-oxoisoindolin-2-yl)piperidine-2,6-dione (SIAIS1216135) and spiro[3.3]heptan-2-amine hydrochloride. The hydrochloride salt of compound SIAIS1222077 was obtained (white solid, 10.9 mg, yield 23%). $^1$H NMR (500 MHz, DMSO) δ 10.99 (s, 1H), 8.62 (s, 2H), 7.63 (d, J=7.4 Hz, 1H), 7.58 (d, J=7.3 Hz, 1H), 7.54 (t, J=7.5 Hz, 1H), 5.13 (dd, J=12.9, 4.5 Hz, 1H), 4.35 (d, J=17.3 Hz, 1H), 4.21 (d, J=17.3 Hz, 1H), 3.54-3.45 (m, 1H), 3.08 (t, J=7.0 Hz, 2H), 2.96-2.87 (m, 1H), 2.71 (s, 2H), 2.60 (d, J=17.1 Hz, 1H), 2.48-2.40 (m, 1H), 2.27 (t, J=9.0 Hz, 2H), 2.07 (t, J=9.5 Hz, 2H), 2.01 (t, J=7.3 Hz, 3H), 1.92 (t, J=7.3 Hz, 2H), 1.82-1.74 (m, 2H), 1.63-1.56 (m, 2H), 1.51 (s, 2H), 1.40 (s, 2H), 1.27 (s, 4H). HRMS (ESI) m/z: calcd for $C_{27}H_{38}N_3O_3S^+$ [M+H]$^+$, 484.2628; found, 484.2682.

Example 110: 3-(4-((7-(tert-butylamino)heptyl)thio)-1-oxoisoindolin-2-yl)piperidine-2,6-dione (SIAIS1222079)

Referring to the method of Scheme 11, the compound SIAIS1222079 was prepared under appropriate conditions that will be recognized by one skilled in the art, except that the substrates used were 3-(4-((7-bromoheptyl)thio)-1-oxoisoindolin-2-yl)piperidine-2,6-dione (SIAIS1216135) and tert-butylamine. The hydrochloride salt of compound SIAIS1222079 was obtained (white solid, 7.4 mg, yield 17%). $^1$H NMR (500 MHz, DMSO) δ 11.00 (s, 1H), 8.39 (s, 2H), 7.63 (d, J=7.3 Hz, 1H), 7.58 (d, J=7.2 Hz, 1H), 7.54 (t, J=7.3 Hz, 1H), 5.13 (dt, J=13.3, 4.7 Hz, 1H), 4.35 (d, 1H), 4.21 (d, J=17.4 Hz, 1H), 3.09 (t, J=7.1 Hz, 2H), 2.96-2.86 (m, 1H), 2.81 (s, 2H), 2.60 (d, J=16.9 Hz, 1H), 2.44 (dd, J=25.7, 13.1 Hz, 1H), 2.00 (dd, J=15.5, 9.7 Hz, 1H), 1.64-1.54 (m, 4H), 1.41 (s, 2H), 1.31 (s, 4H), 1.26 (s, 9H). HRMS (ESI) m/z: calcd for $C_{24}H_{36}N_3O_3S^+$ [M+H]$^+$, 446.2472; found, 446.2514.

Example 111: 3-(4-((4-(((adamantan-1-ylmethyl)amino)methyl)benzyl)thio)-1-oxoisoindolin-2-yl)piperidine-2,6-dione (SIAIS1222085)

Referring to the method of Scheme 11, the compound SIAIS1222085 was prepared under appropriate conditions that will be recognized by one skilled in the art, except that the substrates used were 3-(4-((4-(bromomethyl)benzyl)thio)-1-oxoisoindolin-2-yl)piperidine-2,6-dione (SIAIS1220141) and 1-adamantanemethylamine. The hydrochloride salt of compound SIAIS1222085 was obtained (white solid, 23 mg, yield 17%). $^1$H NMR (500 MHz, DMSO) δ 10.99 (s, 1H), 8.68 (s, 2H), 7.66 (d, J=7.7 Hz, 1H), 7.58 (d, J=7.5 Hz, 1H), 7.48 (dd, J=13.0, 7.5 Hz, 3H), 7.42 (d, J=7.4 Hz, 2H), 5.11 (dd, J=13.3, 4.5 Hz, 1H), 4.37 (s, 2H), 4.29 (d, J=17.3 Hz, 1H), 4.16 (d, J=17.5 Hz, 1H), 4.08 (s, 2H), 2.95-2.86 (m, 1H), 2.60 (d, J=17.0 Hz, 1H), 2.45-2.35 (m, 1H), 2.02-1.96 (m, 1H), 1.93 (s, 3H), 1.65 (d, J=12.0 Hz, 3H), 1.57 (d, J=12.0 Hz, 3H), 1.48 (s, 6H), 1.27 (dd, J=11.4, 6.1 Hz, 2H). HRMS (ESI) m/z: calcd for $C_{32}H_{38}N_3O_3S^+$ [M+H]$^+$, 544.2628; found, 544.2622.

Example 112: 3-(4-((7-(cyclopropyl(methyl)amino)heptyl)thio)-1-oxoisoindolin-2-yl)piperidine-2,6-dione (SIAIS1222103)

Referring to the method of Scheme 11, the compound SIAIS1222103 was prepared under appropriate conditions that will be recognized by one skilled in the art, except that the substrates used were 3-(4-((7-bromoheptyl)thio)-1-oxoisoindolin-2-yl)piperidine-2,6-dione (SIAIS1216135) and N-methylcyclopropylamine. The hydrochloride salt of compound SIAIS1222103 was obtained (light yellow solid, 10.5 mg, yield 47%). $^1$H NMR (500 MHz, DMSO) δ 10.99 (s, 1H), 10.09 (s, 1H), 7.63 (d, J=7.1 Hz, 1H), 7.57 (d, J=7.4 Hz, 1H), 7.53 (t, J=7.2 Hz, 1H), 5.13 (dd, J=12.9, 4.3 Hz, 1H), 4.36 (d, J=17.1 Hz, 1H), 4.21 (d, J=17.2 Hz, 1H), 3.13-3.06 (m, 4H), 2.91 (dd, J=22.1, 9.2 Hz, 1H), 2.77 (s, 4H), 2.59 (d, J=17.1 Hz, 1H), 2.44 (d, J=12.1 Hz, 1H), 2.04-1.97 (m, 1H), 1.70 (s, 2H), 1.63-1.57 (m, 2H), 1.42 (s, 2H), 1.30 (s, 4H), 1.05 (s, 1H), 0.97 (s, 1H), 0.83 (d, J=6.3 Hz, 1H), 0.77 (d, J=6.5 Hz, 1H). HRMS (ESI) m/z: calcd for $C_{24}H_{34}N_3O_3S^+$ [M+H]$^+$, 444.2315; found, 444.2314.

Example 113: 3-(4-((7-(cyclopropylamino)heptyl)thio)-1-oxoisoindolin-2-yl)piperidine-2,6-dione (SIAIS1222105)

Referring to the method of Scheme 11, the compound SIAIS1222105 was prepared under appropriate conditions that will be recognized by one skilled in the art, except that the substrates used were 3-(4-((7-bromoheptyl)thio)-1-oxoisoindolin-2-yl)piperidine-2,6-dione (SIAIS1216135) and cyclopropylamine. The hydrochloride salt of compound SIAIS1222105 was obtained (white solid, 10 mg, yield 47%). $^1$H NMR (500 MHz, DMSO) δ 10.99 (s, 1H), 8.78 (s, 2H), 7.63 (d, J=7.2 Hz, 1H), 7.57 (d, J=7.2 Hz, 1H), 7.53 (t, J=7.2 Hz, 1H), 5.13 (dd, J=13.1, 4.2 Hz, 1H), 4.35 (d, J=17.3 Hz, 1H), 4.21 (d, J=17.3 Hz, 1H), 3.09 (t, J=7.0 Hz, 2H), 2.97-2.86 (m, 3H), 2.66 (s, 1H), 2.59 (d, J=17.0 Hz, 1H), 2.44 (d, J=13.0 Hz, 1H), 2.05-1.97 (m, 1H), 1.64-1.55 (m, 4H), 1.41 (s, 2H), 1.30 (s, 4H), 0.82 (s, 2H), 0.73 (d, J=6.8 Hz, 2H). HRMS (ESI) m/z: calcd for $C_{23}H_{32}N_{303}S^+$ [M+H]$^+$, 430.2159; found, 430.2153.

Example 114: 3-(4-((7-((3aR,7aS)-hexahydro-1H-isoindol-2(3H)-yl)heptyl)thio)-1-oxoisoindolin-2-yl)piperidine-2,6-dione (SIAIS1222107)

Referring to the method of Scheme 11, the compound SIAIS1222107 was prepared under appropriate conditions that will be recognized by one skilled in the art, except that the substrates used were 3-(4-((7-bromoheptyl)thio)-1-oxoisoindolin-2-yl)piperidine-2,6-dione (SIAIS1216135) and cis-Octahydroisoindole. The hydrochloride salt of compound SIAIS1222107 was obtained (white solid, 14.1 mg, yield 57%). $^1$H NMR (500 MHz, DMSO) δ 11.11 (s, 1H), 11.00 (s, 1H), 7.64 (d, J=7.2 Hz, 1H), 7.59-7.52 (m, 2H), 5.14 (dd, J=13.0, 4.0 Hz, 1H), 4.36 (d, J=17.3 Hz, 1H), 4.22 (d, J=17.3 Hz, 1H), 3.11-3.02 (m, 5H), 2.97-2.85 (m, 2H), 2.60 (d, J=16.7 Hz, 1H), 2.45 (d, J=13.1 Hz, 1H), 2.35 (s, 1H), 2.24 (s, 1H), 2.05-1.98 (m, 1H), 1.70-1.38 (m, 14H), 1.28 (s, 6H). HRMS (ESI) m/z: calcd for $C_{28}H_{40}N_3O_3S^+$ [M+H]$^+$, 498.2785; found, 498.2788.

Example 115: 3-(4-((7-(cyclobutylamino)heptyl)thio)-1-oxoisoindolin-2-yl)piperidine-2,6-dione (SIAIS1222115)

Referring to the method of Scheme 11, the compound SIAIS1222115 was prepared under appropriate conditions that will be recognized by one skilled in the art, except that the substrates used were 3-(4-((7-bromoheptyl)thio)-1-oxoisoindolin-2-yl)piperidine-2,6-dione (SIAIS1216135) and cyclobutylamine. The hydrochloride salt of compound SIAIS1222115 was obtained (white solid, 14.1 mg, yield 66%). $^{1}$H NMR (500 MHz, DMSO) δ 11.00 (s, 1H), 9.04 (s, 2H), 7.64 (d, J=5.6 Hz, 1H), 7.60-7.51 (m, 2H), 5.14 (d, J=13.0 Hz, 1H), 4.36 (d, J=17.0 Hz, 1H), 4.22 (d, J=17.2 Hz, 1H), 3.62 (s, 1H), 3.09 (s, 2H), 2.91 (d, J=14.4 Hz, 1H), 2.71 (s, 2H), 2.60 (d, J=16.9 Hz, 1H), 2.46 (s, 1H), 2.16 (s, 4H), 2.03 (s, 1H), 1.82-1.71 (m, 2H), 1.64-1.54 (m, 4H), 1.41 (s, 2H), 1.29 (s, 4H). HRMS (ESI) m/z: calcd for $C_{24}H_{34}N_{3}O_{3}S^{+}$ [M+H]$^{+}$, 444.2315; found, 444.2314.

Example 116: 3-(4-((7-(cyclopentylamino)heptyl)thio)-1-oxoisoindolin-2-yl)piperidine-2,6-dione (SIAIS1222117)

Referring to the method of Scheme 11, the compound SIAIS1222117 was prepared under appropriate conditions that will be recognized by one skilled in the art, except that the substrates used were 3-(4-((7-bromoheptyl)thio)-1-oxoisoindolin-2-yl)piperidine-2,6-dione (SIAIS1216135) and cyclopentamine. The hydrochloride salt of compound SIAIS1222117 was obtained (white solid, 20.4 mg, yield 89%). $^{1}$H NMR (500 MHz, DMSO) δ 10.99 (s, 1H), 8.88 (s, 2H), 7.63 (d, J=7.3 Hz, 1H), 7.57 (d, J=7.2 Hz, 1H), 7.55-7.51 (m, 1H), 5.13 (dd, J=13.1, 4.2 Hz, 1H), 4.35 (d, J=17.3 Hz, 1H), 4.21 (d, J=17.3 Hz, 1H), 3.42-3.36 (m, 1H), 3.09 (t, J=6.8 Hz, 2H), 2.95-2.87 (m, 1H), 2.81 (s, 2H), 2.59 (d, J=17.2 Hz, 1H), 2.44 (d, J=12.7 Hz, 1H), 2.04-1.98 (m, 1H), 1.93 (d, J=5.4 Hz, 2H), 1.70 (s, 2H), 1.61 (d, J=6.4 Hz, 6H), 1.51 (s, 2H), 1.41 (s, 2H), 1.30 (s, 4H). HRMS (ESI) m/z: calcd for $C_{25}H_{36}N_{3}O_{3}S^{+}$ [M+H]$^{+}$, 458.2472; found, 458.2474.

Example 117: 3-(4-((7-(bicyclo[1.1.1]pentan-1-ylamino)heptyl)thio)-1-oxoisoindolin-2-yl)piperidine-2,6-dione (SIAIS1222123)

Referring to the method of Scheme 11, the compound SIAIS1222123 was prepared under appropriate conditions that will be recognized by one skilled in the art, except that the substrates used were 3-(4-((7-bromoheptyl)thio)-1-oxoisoindolin-2-yl)piperidine-2,6-dione (SIAIS1216135) and bicyclo[1.1.1]pentane-1-amine hydrochloride. The hydrochloride salt of compound SIAIS1222123 was obtained (light yellow solid, 10 mg, yield 44%). $^{1}$H NMR (500 MHz, DMSO) δ 10.99 (s, 1H), 9.48 (s, 2H), 7.63 (d, J=7.4 Hz, 1H), 7.57 (d, J=7.1 Hz, 1H), 7.53 (t, J=7.2 Hz, 1H), 5.13 (dd, J=13.1, 4.0 Hz, 1H), 4.35 (d, J=17.3 Hz, 1H), 4.21 (d, J=17.1 Hz, 1H), 3.09 (t, J=6.8 Hz, 2H), 2.96-2.87 (m, 1H), 2.78 (s, 2H), 2.65 (s, 1H), 2.59 (d, J=16.8 Hz, 1H), 2.44 (d, J=12.4 Hz, 1H), 2.01 (s, 1H), 1.99 (s, 6H), 1.60 (dd, J=15.2, 7.6 Hz, 4H), 1.40 (s, 2H), 1.30 (s, 4H). HRMS (ESI) m/z: calcd for $C_{25}H_{34}N_{3}O_{3}S^{+}$ [M+H]$^{+}$, 456.2315; found, 456.2314.

Example 118: 3-(4-((6-((1-(adamantan-1-yl)ethyl)amino)hexyl)thio)-1-oxoisoindolin-2-yl)piperidine-2,6-dione (SIAIS1222139)

Referring to the method of Scheme 11, the compound SIAIS1222139 was prepared under appropriate conditions that will be recognized by one skilled in the art, except that the substrates used were 3-(4-((6-bromohexyl)thio)-1-oxoisoindolin-2-yl)piperidine-2,6-dione (SIAIS1216133) and 1-(1-adamantyl)ethylamine hydrochloride. The hydrochloride salt of compound SIAIS1222139 was obtained (light yellow solid, 15.5 mg, yield 58%). $^{1}$H NMR (500 MHz, DMSO) δ 10.99 (s, 1H), 8.55 (s, 1H), 7.64 (d, J=7.1 Hz, 1H), 7.57 (d, J=6.8 Hz, 1H), 7.54 (d, J=7.6 Hz, 1H), 5.13 (dd, J=13.0, 4.6 Hz, 1H), 4.35 (d, J=17.2 Hz, 1H), 4.21 (d, J=17.3 Hz, 1H), 3.10 (t, J=6.4 Hz, 2H), 2.95-2.82 (m, 3H), 2.72 (d, J=11.8 Hz, 1H), 2.59 (d, J=16.9 Hz, 1H), 2.45 (s, 1H), 2.00 (s, 1H), 1.98 (s, 3H), 1.64 (d, J=12.7 Hz, 14H), 1.49 (d, J=11.4 Hz, 3H), 1.46-1.41 (m, 2H), 1.32 (d, J=5.8 Hz, 2H), 1.12 (d, J=6.2 Hz, 3H). HRMS (ESI) m/z: calcd for $C_{31}H_{44}N_{3}O_{3}S^{+}$ [M+H]$^{+}$, 538.3098; found, 538.3096.

Example 119: 3-(4-((7-(3-hydroxyadamantan-1-yl)amino)heptyl)thio)-1-oxoisoindolin-2-yl)piperidine-2,6-dione (SIAIS1222141)

Referring to the method of Scheme 11, the compound SIAIS1222141 was prepared under appropriate conditions that will be recognized by one skilled in the art, except that the substrates used were 3-(4-((7-bromoheptyl)thio)-1-oxoisoindolin-2-yl)piperidine-2,6-dione (SIAIS1216135) and 3-hydroxy-1-adamantanamine. The hydrochloride salt of compound SIAIS1222141 was obtained (white solid, 19.1 mg, yield 71%). $^{1}$H NMR (500 MHz, DMSO) δ 10.99 (s, 1H), 8.79 (s, 2H), 7.63 (d, J=7.2 Hz, 1H), 7.58-7.51 (m, 2H), 5.13 (dd, J=12.7, 3.8 Hz, 1H), 4.80 (s, 1H), 4.35 (d, J=17.2 Hz, 1H), 4.21 (d, J=17.1 Hz, 1H), 3.09 (s, 2H), 2.96-2.87 (m, 1H), 2.79 (s, 2H), 2.60 (d, J=16.3 Hz, 1H), 2.46-2.43 (m, 1H), 2.22 (s, 2H), 2.01 (s, 1H), 1.75 (s, 6H), 1.61 (s, 4H), 1.54 (s, 4H), 1.43 (d, J=19.8 Hz, 4H), 1.30 (s, 4H). HRMS (ESI) m/z: calcd for $C_{30}H_{42}N_{3}O_{4}S^{+}$ [M+H]$^{+}$, 540.2891; found, 540.2896.

Example 120: N-(6-((2-(2,6-dioxopiperidin-3-yl)-1-oxoisoindolin-4-yl)thio)hexyl)adamantane-1-carboxamide (SIAIS1222143)

Referring to the method of example 71, the compound SIAIS1222143 was prepared under appropriate conditions that will be recognized by one skilled in the art, except that the precursors for condensation were 3-(4-((6-aminohexyl)thio)-1-oxoisoindolin-2-yl)piperidine-2,6-dione (SIAIS171134) and 1-adamantanecarboxylic acid. The hydrochloride salt of compound SIAIS1222143 was obtained (white solid, 16.5 mg, yield 51%). $^{1}$H NMR (500 MHz, DMSO) δ 10.99 (s, 1H), 7.62 (d, J=7.3 Hz, 1H), 7.56 (d, J=7.3 Hz, 1H), 7.55-7.50 (m, 1H), 7.29 (s, 1H), 5.13 (dd, J=12.8, 4.1 Hz, 1H), 4.35 (d, J=17.2 Hz, 1H), 4.21 (d, J=17.4 Hz, 1H), 3.07 (t, J=6.8 Hz, 2H), 3.03-2.98 (m, 2H), 2.91 (t, J=13.0 Hz, 1H), 2.59 (d, J=17.0 Hz, 1H), 2.44 (d, J=12.7 Hz, 1H), 2.04-1.98 (m, 1H), 1.93 (s, 3H), 1.73 (s, 6H), 1.70-1.55 (m, 8H), 1.42-1.35 (m, 4H), 1.24 (d, J=6.5 Hz, 2H). HRMS (ESI) m/z: calcd for $C_{30}H_{40}N_{3}O_{4}S^{+}$ [M+H]$^{+}$, 538.2734; found, 538.2735.

Example 121: 3-chloro-N-(6-((2-(2,6-dioxopiperidin-3-yl)-1-oxoisoindolin-4-yl)thio)hexyl)adamantane-1-carboxamide (SIAIS1222145)

Referring to the method of example 71, the compound SIAIS1222145 was prepared under appropriate conditions that will be recognized by one skilled in the art, except that the precursors for condensation were 3-(4-((6-aminohexyl)thio)-1-oxoisoindolin-2-yl)piperidine-2,6-dione (SIAIS171134) and 3-chloroadamantane-1-carboxylic acid. The hydrochloride salt of compound SIAIS1222145 was obtained (light yellow solid, 14.8 mg, yield 51%). $^{1}$H NMR (500 MHz, DMSO) δ 10.98 (s, 1H), 7.62 (d, J=7.4 Hz, 1H), 7.56 (d, J=7.3 Hz, 1H), 7.52 (t, J=7.5 Hz, 1H), 7.44 (d, J=5.0 Hz, 1H), 5.13 (dd, J=13.2, 5.0 Hz, 1H), 4.35 (d, J=17.4 Hz, 1H), 4.21 (d, J=17.4 Hz, 1H), 3.07 (t, J=7.1 Hz, 2H), 3.01 (dd, J=12.7, 6.5 Hz, 2H), 2.95-2.87 (m, 1H), 2.59 (d, J=17.5 Hz, 1H), 2.45 (dd, J=13.3, 9.3 Hz, 1H), 2.16 (s, 2H), 2.11 (s, 2H), 2.07-1.97 (m, 5H), 1.69 (s, 4H), 1.62-1.51 (m, 4H), 1.44 (dt, J=20.7, 7.0 Hz, 4H), 1.24 (dd, J=14.6, 7.6 Hz, 2H). HRMS (ESI) m/z: calcd for $C_{30}H_{39}ClN_3O_4S^+$ $[M+H]^+$, 572.2344; found, 572.2345.

Example 122: 3-(4-((6-((cyclohexylmethyl)amino)hexyl)thio)-1-oxoisoindolin-2-yl)piperidine-2,6-dione (SIAIS1222147)

Referring to the method of Scheme 11, the compound SIAIS1222147 was prepared under appropriate conditions that will be recognized by one skilled in the art, except that the substrates used were 3-(4-((6-bromohexyl)thio)-1-oxoisoindolin-2-yl)piperidine-2,6-dione (SIAIS1216133) and cyclohexylmethanamine. The hydrochloride salt of compound SIAIS1222147 was obtained (light yellow solid, 19.2 mg, yield 81%). $^1$H NMR (500 MHz, DMSO) δ 10.99 (s, 1H), 8.53 (s, 2H), 7.63 (d, J=7.4 Hz, 1H), 7.57 (d, J=7.4 Hz, 1H), 7.53 (t, J=7.4 Hz, 1H), 5.13 (dd, J=13.2, 5.0 Hz, 1H), 4.35 (d, J=17.3 Hz, 1H), 4.21 (d, J=17.3 Hz, 1H), 3.09 (t, J=7.1 Hz, 2H), 2.96-2.87 (m, 1H), 2.82 (s, 2H), 2.71 (s, 2H), 2.59 (d, J=16.8 Hz, 1H), 2.48-2.41 (m, 1H), 2.04-1.97 (m, 1H), 1.75 (d, J=12.7 Hz, 2H), 1.68 (d, J=12.7 Hz, 2H), 1.66-1.55 (m, 6H), 1.42 (dt, J=14.7, 7.4 Hz, 2H), 1.32 (dd, J=14.7, 7.5 Hz, 2H), 1.25-1.10 (m, 3H), 0.92 (q, J=11.6 Hz, 2H). HRMS (ESI) m/z: calcd for $C_{26}H_{38}N_3O_3S^+$ $[M+H]^+$, 472.2628; found, 472.2625.

Example 123: 3-(4-((4-(((1-(adamantan-1-yl)ethyl)amino)methyl)benzyl)thio)-1-oxoisoindolin-2-yl)piperidine-2,6-dione (SIAIS1222157)

Referring to the method of Scheme 11, the compound SIAIS1222157 was prepared under appropriate conditions that will be recognized by one skilled in the art, except that the substrates used were 3-(4-((4-(bromomethyl)benzyl)thio)-1-oxoisoindolin-2-yl)piperidine-2,6-dione (SIAIS1220141) and 1-(1-adamantyl)ethylamine hydrochloride. The hydrochloride salt of compound SIAIS1222157 was obtained (light yellow solid, 15.4 mg, yield 29%). $^1$H NMR (500 MHz, DMSO) δ 10.99 (s, 1H), 9.14 (s, 1H), 7.95 (s, 1H), 7.62 (d, J=7.7 Hz, 1H), 7.56 (d, J=7.2 Hz, 1H), 7.51 (d, J=7.5 Hz, 2H), 7.46 (t, J=7.6 Hz, 1H), 7.42 (d, J=7.5 Hz, 2H), 5.11 (dd, J=13.2, 4.6 Hz, 1H), 4.37 (s, 2H), 4.34-4.14 (m, 3H), 4.09 (s, 1H), 2.90 (dd, J=21.7, 9.3 Hz, 1H), 2.59 (d, J=16.5 Hz, 1H), 2.47-2.38 (m, 1H), 2.37-2.30 (m, 1H), 1.99 (s, 1H), 1.92 (s, 3H), 1.62 (d, J=12.0 Hz, 3H), 1.56 (d, J=11.9 Hz, 6H), 1.29 (d, J=11.3 Hz, 3H), 1.13 (d, J=6.4 Hz, 3H). HRMS (ESI) m/z: calcd for $C_{33}H_{40}N_3O_3S^+$ $[M+H]^+$, 558.2785; found, 558.2791.

Example 124: 3-(1-oxo-4-((4-((spiro[3.3]heptan-2-ylamino)methyl)benzyl)thio)isoindolin-2-yl)piperidine-2,6-dione (SIAIS1222159)

Referring to the method of Scheme 11, the compound SIAIS1222159 was prepared under appropriate conditions that will be recognized by one skilled in the art, except that the substrates used were 3-(4-((4-(bromomethyl)benzyl)thio)-1-oxoisoindolin-2-yl)piperidine-2,6-dione (SIAIS1220141) and spiro[3.3]heptan-2-amine hydrochloride. The hydrochloride salt of compound SIAIS1222159 was obtained (light yellow solid, 16.1 mg, yield 66%). $^1$H NMR (500 MHz, DMSO) δ 10.99 (s, 1H), 9.46 (s, 2H), 7.67 (d, J=7.7 Hz, 1H), 7.57 (d, J=7.4 Hz, 1H), 7.49 (t, J=7.6 Hz, 1H), 7.44 (d, J=7.7 Hz, 2H), 7.39 (d, J=7.7 Hz, 2H), 5.10 (dd, J=13.1, 4.9 Hz, 1H), 4.40-4.33 (m, 2H), 4.28 (d, J=17.5 Hz, 1H), 4.15 (d, J=17.5 Hz, 1H), 3.92 (s, 2H), 3.44 (d, J=8.2 Hz, 1H), 2.95-2.86 (m, 1H), 2.59 (d, J=16.8 Hz, 1H), 2.47-2.37 (m, 1H), 2.21-2.12 (m, 4H), 1.97 (t, J=7.1 Hz, 3H), 1.89 (t, J=7.4 Hz, 2H), 1.80-1.73 (m, 2H). HRMS (ESI) m/z: calcd for $C_{28}H_{32}N_3O_3S^+$ $[M+H]^+$, 490.2159; found, 490.2171.

Example 125: 3-(4-((4-((bicyclo[1.1.1]pentan-1-ylamino)methyl)benzyl)thio)-1-oxoisoindolin-2-yl)piperidine-2,6-dione (SIAIS1222161)

Referring to the method of Scheme 11, the compound SIAIS1222161 was prepared under appropriate conditions that will be recognized by one skilled in the art, except that the substrates used were 3-(4-((4-(bromomethyl)benzyl)thio)-1-oxoisoindolin-2-yl)piperidine-2,6-dione (SIAIS1220141) and bicyclo[1.1.1]pentane-1-amine hydrochloride. The hydrochloride salt of compound SIAIS1222161 was obtained (light yellow solid, 12.6 mg, yield 55%). $^1$H NMR (500 MHz, DMSO) δ 10.99 (s, 1H), 10.01 (s, 2H), 7.67 (d, J=7.6 Hz, 1H), 7.57 (d, J=7.4 Hz, 1H), 7.48 (dd, J=13.4, 5.8 Hz, 3H), 7.39 (d, J=7.7 Hz, 2H), 5.10 (dd, J=13.2, 4.9 Hz, 1H), 4.40-4.33 (m, 2H), 4.28 (d, J=17.4 Hz, 1H), 4.16 (d, J=17.4 Hz, 1H), 4.02 (s, 2H), 2.95-2.86 (m, 1H), 2.63 (s, 1H), 2.59 (d, J=17.4 Hz, 1H), 2.47-2.38 (m, 1H), 2.02-1.97 (m, 1H), 1.96 (s, 6H). HRMS (ESI) m/z: calcd for $C_{26}H_{28}N_3O_3S^+$ $[M+H]^+$, 462.1846; found, 462.1844.

Example 126: 3-(4-((2-(adamantan-1-yl)ethyl)thio)-1-oxoisoindolin-2-yl)piperidine-2,6-dione (SIAIS1222173)

Referring to the method of Scheme 9, the compound SIAIS1222173 was prepared under appropriate conditions that will be recognized by one skilled in the art, except that 2-(adamantan-1-yl)ethyl 4-methylbenzenesulfonate was used instead of the halogenated substrate used in the synthesis method of Scheme 9. The target compound SIAIS1222173 was obtained as a white solid (17.2 mg, yield 39%). $^1$H NMR (500 MHz, DMSO) δ 10.99 (s, 1H), 7.61 (d, J=6.7 Hz, 1H), 7.57-7.51 (m, 2H), 5.12 (dd, J=13.1, 4.4 Hz, 1H), 4.34 (d, J=17.4 Hz, 1H), 4.20 (d, J=17.3 Hz, 1H), 3.08-3.02 (m, 2H), 2.95-2.86 (m, 1H), 2.59 (d, J=16.4 Hz, 1H), 2.48-2.41 (m, 1H), 2.04-1.97 (m, 1H), 1.93 (s, 3H), 1.67 (d, J=11.9 Hz, 3H), 1.60 (d, J=11.9 Hz, 3H), 1.50 (s, 6H), 1.40-1.35 (m, 2H). HRMS (ESI) m/z: calcd for $C_{25}H_{31}N_2O_3S^+$ $[M+H]^+$, 439.2050; found, 439.2053.

Example 127: 3-(4-((3-(adamantan-1-ylamino)propyl)thio)-1-oxoisoindolin-2-yl)piperidine-2,6-dione (SIAIS1222177)

Referring to the method of Scheme 11, the compound SIAIS1222177 was prepared under appropriate conditions that will be recognized by one skilled in the art, except that the substrates used were 3-(4-((3-bromopropyl)thio)-1-oxoisoindolin-2-yl)piperidine-2,6-dione (SIAIS213132) and 1-adamantanamine. The hydrochloride salt of compound SIAIS1222177 was obtained (light pink solid, 4 mg, yield 39%). $^1$H NMR (500 MHz, DMSO) δ 11.00 (s, 1H), 8.61 (s, 2H), 7.71 (d, J=7.4 Hz, 1H), 7.61 (d, J=7.6 Hz, 1H), 7.57 (t, J=7.8 Hz, 1H), 5.14 (dd, J=13.2, 4.6 Hz, 1H), 4.39 (d, J=17.7 Hz, 1H), 4.25 (d, J=17.2 Hz, 1H), 3.20 (t, J=7.1 Hz, 2H), 2.98 (s, 2H), 2.91 (d, J=12.4 Hz, 1H), 2.60 (d, J=16.7 Hz, 1H), 2.46 (s, 1H), 2.11 (s, 3H), 2.02 (d, J=6.0 Hz, 1H), 1.96-1.88 (m, 2H), 1.82 (s, 6H), 1.66 (d, J=12.3 Hz, 3H), 1.58 (d, J=12.4 Hz, 3H). HRMS (ESI) m/z: calcd for $C_{26}H_{34}N_3O_3S^+$ $[M+H]^+$, 468.2315; found, 468.2314.

Example 128: 3-(4-((4-((adamantan-1-yl)amino)butyl)thio)-1-oxoisoindolin-2-yl)piperidine-2,6-dione (SIAIS1222179)

Referring to the method of Scheme 11, the compound SIAIS1222179 was prepared under appropriate conditions that will be recognized by one skilled in the art, except that the substrates used were 3-(4-((4-bromobutyl)thio)-1-oxoisoindolin-2-yl)piperidine-2,6-dione (SIAIS213134) and 1-adamantanamine. The hydrochloride salt of compound SIAIS1222179 was obtained (light yellow solid, 22.2 mg, yield 55%). $^1$H NMR (500 MHz, DMSO) δ 11.00 (s, 1H), 8.72 (s, 2H), 7.68 (d, J=7.4 Hz, 1H), 7.59 (d, J=7.1 Hz, 1H), 7.54 (t, J=7.3 Hz, 1H), 5.13 (dd, J=13.1, 4.5 Hz, 1H), 4.38 (d, J=16.5 Hz, 1H), 4.23 (d, J=17.3 Hz, 1H), 3.14 (t, J=6.5 Hz, 2H), 2.96-2.88 (m, 1H), 2.85 (s, 2H), 2.59 (d, J=16.8 Hz, 1H), 2.45 (d, J=12.3 Hz, 1H), 2.10 (s, 3H), 2.05-1.99 (m, 1H), 1.85 (s, 6H), 1.77 (s, 2H), 1.70-1.63 (m, 5H), 1.58 (d, J=12.0 Hz, 3H). HRMS (ESI) m/z: calcd for $C_{27}H_{36}N_3O_3S^+$ $[M+H]^+$, 482.2472; found, 482.2475.

Example 129: 3-(4-((4-(((cyclohexylmethyl)amino)methyl)benzyl)thio)-1-oxoisoindolin-2-yl)piperidine-2,6-dione (SIAIS1222187)

Referring to the method of Scheme 11, the compound SIAIS1222187 was prepared under appropriate conditions that will be recognized by one skilled in the art, except that the substrates used were 3-(4-((4-(bromomethyl)benzyl)thio)-1-oxoisoindolin-2-yl)piperidine-2,6-dione (SIAIS1220141) and cyclohexylmethanamine. The hydrochloride salt of compound SIAIS1222187 was obtained (white solid, 14 mg, yield 57%). $^1$H NMR (500 MHz, DMSO) δ 10.99 (s, 1H), 8.96 (s, 2H), 7.68 (d, J=7.6 Hz, 1H), 7.57 (d, J=7.4 Hz, 1H), 7.52-7.48 (m, 1H), 7.46 (d, J=7.6 Hz, 2H), 7.41 (d, J=7.4 Hz, 2H), 5.11 (dd, J=13.1, 4.5 Hz, 1H), 4.41-4.33 (m, 2H), 4.28 (d, J=17.4 Hz, 1H), 4.15 (d, J=17.5 Hz, 1H), 4.07 (s, 2H), 2.95-2.86 (m, 1H), 2.68 (d, J=4.0 Hz, 2H), 2.59 (d, J=16.9 Hz, 1H), 2.42 (dd, J=26.2, 13.1 Hz, 1H), 2.02-1.94 (m, 1H), 1.72 (d, J=13.2 Hz, 2H), 1.66 (d, J=11.3 Hz, 3H), 1.60 (d, J=10.4 Hz, 1H), 1.23-1.09 (m, 3H), 0.94-0.85 (m, 2H). HRMS (ESI) m/z: calcd for $C_{28}H_{34}N_3O_3S^+$ $[M+H]^+$, 492.2315; found, 492.2315.

Example 130: 3-(4-((7-(6-azaspiro[2.5]octan-6-yl)heptyl)thio)-1-oxoisoindolin-2-yl)piperidine-2,6-dione (SIAIS1222195)

Referring to the method of Scheme 11, the compound SIAIS1222195 was prepared under appropriate conditions that will be recognized by one skilled in the art, except that the substrates used were 3-(4-((7-bromoheptyl)thio)-1-oxoisoindolin-2-yl)piperidine-2,6-dione (SIAIS1216135) and 6-azaspiro[2.5]octane. The hydrochloride salt of compound SIAIS1222195 was obtained (light yellow solid, 22.3 mg, yield 92%). $^1$H NMR (500 MHz, DMSO) δ 10.99 (s, 1H), 10.37 (s, 1H), 7.63 (d, J=7.3 Hz, 1H), 7.57 (d, J=7.2 Hz, 1H), 7.54 (t, J=7.2 Hz, 1H), 5.13 (dd, J=13.1, 4.4 Hz, 1H), 4.36 (d, J=17.5 Hz, 1H), 4.22 (d, J=17.4 Hz, 1H), 3.40 (d, J=11.5 Hz, 2H), 3.09 (t, J=6.9 Hz, 2H), 3.00 (s, 2H), 2.97-2.84 (m, 3H), 2.59 (d, J=16.8 Hz, 1H), 2.44 (d, J=13.0 Hz, 1H), 2.19 (t, J=12.7 Hz, 2H), 2.05-1.97 (m, 1H), 1.69 (s, 2H), 1.60 (dd, J=14.0, 6.9 Hz, 2H), 1.45-1.38 (m, 2H), 1.34-1.24 (m, 4H), 1.07 (d, J=13.9 Hz, 2H), 0.46-0.40 (m, 2H), 0.38-0.32 (m, 2H). HRMS (ESI) m/z: calcd for $C_{27}H_{38}N_3O_3S^+$ $[M+H]^+$, 484.2628; found, 484.2625.

Example 131: 3-(1-oxo-4-((7-(piperazin-1-yl)heptyl)thio)isoindolin-2-yl)piperidine-2,6-dione (SIAIS1222197)

Referring to the method of Scheme 11, the compound SIAIS1222197 was prepared under appropriate conditions that will be recognized by one skilled in the art, except that the substrates used were 3-(4-((7-bromoheptyl)thio)-1-oxoisoindolin-2-yl)piperidine-2,6-dione (SIAIS1216135) and piperazine. The hydrochloride salt of compound SIAIS1222197 was obtained (light yellow solid, 60 mg, yield 68%). $^1$H NMR (500 MHz, DMSO) δ 11.00 (s, 1H), 9.31 (s, 2H), 7.63 (d, J=7.3 Hz, 1H), 7.58 (d, J=7.2 Hz, 1H), 7.54 (t, J=7.2 Hz, 1H), 5.13 (dd, J=13.1, 4.4 Hz, 1H), 4.35 (d, J=17.4 Hz, 1H), 4.22 (d, J=17.3 Hz, 1H), 3.55-3.25 (m, 8H), 3.14-3.06 (m, 4H), 2.96-2.87 (m, 1H), 2.60 (d, J=16.9 Hz, 1H), 2.49-2.41 (m, 1H), 2.05-1.98 (m, 1H), 1.65-1.57 (m, 4H), 1.41 (s, 2H), 1.29 (s, 4H). HRMS (ESI) m/z: calcd for $C_{24}H_{35}N_4O_3S^+$ $[M+H]^+$, 459.2424; found, 459.2437.

Example 132: 3-(4-((7-((cyclohexylmethyl)amino)heptyl)thio)-1-oxoisoindolin-2-yl)piperidine-2,6-dione (SIAIS1222199)

Referring to the method of Scheme 11, the compound SIAIS1222199 was prepared under appropriate conditions that will be recognized by one skilled in the art, except that the substrates used were 3-(4-((7-bromoheptyl)thio)-1-oxoisoindolin-2-yl)piperidine-2,6-dione (SIAIS1216135) and cyclohexylmethylamine. The hydrochloride salt of compound SIAIS1222199 was obtained (light yellow solid, 9.2 mg, yield 38%). $^1$H NMR (500 MHz, DMSO) δ 10.99 (s, 1H), 8.51 (s, 2H), 7.63 (d, J=7.3 Hz, 1H), 7.57 (d, J=7.0 Hz, 1H), 7.53 (t, J=7.5 Hz, 1H), 5.13 (dd, J=13.0, 4.3 Hz, 1H), 4.35 (d, J=17.4 Hz, 1H), 4.21 (d, J=17.5 Hz, 1H), 3.09 (t, J=6.9 Hz, 2H), 2.96-2.87 (m, 1H), 2.83 (s, 2H), 2.71 (d, J=4.5 Hz, 2H), 2.59 (d, J=17.4 Hz, 1H), 2.48-2.41 (m, 1H), 2.05-1.97 (m, 1H), 1.75 (d, J=12.5 Hz, 2H), 1.71-1.58 (m, 8H), 1.41 (s, 2H), 1.29 (s, 4H), 1.24-1.11 (m, 3H), 0.93 (q, J=11.6 Hz, 2H). HRMS (ESI) m/z: calcd for $C_{27}H_{40}N_3O_3S^+$ $[M+H]^+$, 486.2785; found, 486.2785.

Example 133: 3-(1-oxo-4-((4-((((tetrahydro-2H-pyran-2-yl)methyl)amino)methyl)benzyl)thio)isoindolin-2-yl)piperidine-2,6-dione (SIAIS1224019)

Referring to the method of Scheme 11, the compound SIAIS1224019 was prepared under appropriate conditions that will be recognized by one skilled in the art, except that the substrates used were 3-(4-((4-(bromomethyl)benzyl)thio)-1-oxoisoindolin-2-yl)piperidine-2,6-dione (SIAIS1220141) and (tetrahydro-2H-pyran-2-yl)methylamine. The hydrochloride salt of compound SIAIS1224019 was obtained (light yellow solid, 9.2 mg, yield 38%). $^1$H NMR (500 MHz, DMSO) δ 10.98 (s, 1H), 9.19 (s, 1H), 8.97 (s, 1H), 7.67 (d, J=7.5 Hz, 1H), 7.58 (d, J=7.4 Hz, 1H), 7.50 (t, J=7.5 Hz, 1H), 7.44 (d, J=7.6 Hz, 2H), 7.40 (d, J=7.5 Hz, 2H), 5.11 (dd, J=13.0, 4.6 Hz, 1H), 4.40-4.33 (m, 2H), 4.28

(d, J=17.5 Hz, 1H), 4.15 (d, J=17.3 Hz, 1H), 4.07 (s, 2H), 3.91 (d, J=11.1 Hz, 1H), 3.60 (t, J=10.1 Hz, 1H), 3.35 (s, 1H), 2.96-2.86 (m, 2H), 2.78 (s, 1H), 2.59 (d, J=17.1 Hz, 1H), 2.41 (dd, J=27.8, 14.8 Hz, 1H), 2.02-1.94 (m, 1H), 1.76 (s, 1H), 1.57-1.40 (m, 4H), 1.20-1.10 (m, 1H). HRMS (ESI) m/z: calcd for $C_{27}H_{32}N_3O_4S^+$ [M+H]$^+$, 494.2108; found, 494.2105.

Example 134: 3-(4-((7-((dicyclopropylmethyl)amino)heptyl)thio)-1-oxoisoindolin-2-yl)piperidine-2,6-dione (SIAIS1224031)

Referring to the method of Scheme 11, the compound SIAIS1224031 was prepared under appropriate conditions that will be recognized by one skilled in the art, except that the substrates used were 3-(4-((7-bromoheptyl)thio)-1-oxoisoindolin-2-yl)piperidine-2,6-dione (SIAIS1216135) and dicyclopropylmethylamine. The hydrochloride salt of compound SIAIS1224031 was obtained (light yellow solid, 3 mg, yield 12%). $^1$H NMR (500 MHz, DMSO) δ 10.99 (s, 1H), 8.62 (s, 2H), 7.63 (d, J=7.2 Hz, 1H), 7.57 (d, J=7.2 Hz, 1H), 7.56-7.51 (m, 1H), 5.13 (dd, J=13.3, 4.4 Hz, 1H), 4.35 (d, J=17.4 Hz, 1H), 4.21 (d, J=17.5 Hz, 1H), 3.09 (t, J=6.9 Hz, 2H), 3.02-2.87 (m, 3H), 2.59 (d, J=17.3 Hz, 1H), 2.44 (d, J=13.9 Hz, 1H), 2.00 (s, 2H), 1.67-1.58 (m, 4H), 1.42 (s, 2H), 1.31 (s, 4H), 1.04 (s, 2H), 0.57 (d, J=7.2 Hz, 4H), 0.46 (s, 2H), 0.39 (s, 2H). HRMS (ESI) m/z: calcd for $C_{27}H_{38}N_3O_3S^+$ [M+H]$^+$, 484.2628; found, 484.2650.

Example 135: 3-(4-((7-(isoindolin-2-yl)heptyl)thio)-1-oxoisoindolin-2-yl)piperidine-2,6-dione (SIAIS1224033)

Referring to the method of Scheme 11, the compound SIAIS1224033 was prepared under appropriate conditions that will be recognized by one skilled in the art, except that the substrates used were 3-(4-((7-bromoheptyl)thio)-1-oxoisoindolin-2-yl)piperidine-2,6-dione (SIAIS1216135) and isoindoline. The hydrochloride salt of compound SIAIS1224033 was obtained (white solid, 4.6 mg, yield 12%). $^1$H NMR (500 MHz, DMSO) δ 11.28 (s, 1H), 10.99 (s, 1H), 7.64 (d, J=7.4 Hz, 1H), 7.57 (d, J=7.3 Hz, 1H), 7.54 (t, J=7.4 Hz, 1H), 7.38 (d, J=2.5 Hz, 4H), 5.13 (dd, J=13.1, 4.5 Hz, 1H), 4.75 (s, 2H), 4.47 (s, 2H), 4.36 (d, J=17.3 Hz, 1H), 4.22 (d, J=17.4 Hz, 1H), 3.32-3.26 (m, 2H), 3.09 (t, J=7.0 Hz, 2H), 2.96-2.86 (m, 1H), 2.59 (d, J=16.7 Hz, 1H), 2.44 (d, J=12.8 Hz, 1H), 2.05-1.98 (m, 1H), 1.71 (s, 2H), 1.65-1.58 (m, 2H), 1.43 (s, 2H), 1.33 (s, 4H). HRMS (ESI) m/z: calcd for $C_{28}H_{34}N_3O_3S^+$ [M+H]$^+$, 492.2315; found, 492.2313.

Example 136: 3-(1-oxo-4-((7-(((S)-quinuclidin-3-yl)amino)heptyl)thio)isoindolin-2-yl)piperidine-2,6-dione (SIAIS1224035)

Referring to the method of Scheme 11, the compound SIAIS1224035 was prepared under appropriate conditions that will be recognized by one skilled in the art, except that the substrates used were 3-(4-((7-bromoheptyl)thio)-1-oxoisoindolin-2-yl)piperidine-2,6-dione (SIAIS1216135) and (S)-quinuclidin-3-amine. The hydrochloride salt of compound SIAIS1224035 was obtained (light yellow solid, 20.5 mg, yield 82%). $^1$H NMR (500 MHz, DMSO) δ 11.00 (s, 1H), 8.95 (s, 3H), 7.64 (d, J=7.4 Hz, 1H), 7.58 (d, J=7.2 Hz, 1H), 7.54 (t, J=7.3 Hz, 1H), 5.14 (dd, J=13.2, 4.8 Hz, 1H), 4.36 (d, J=17.3 Hz, 1H), 4.22 (d, J=17.4 Hz, 1H), 3.81-3.72 (m, 2H), 3.64 (s, 1H), 3.43 (dd, J=34.8, 9.9 Hz, 4H), 3.22-3.17 (m, 2H), 3.09 (t, J=6.7 Hz, 2H), 2.96-2.87 (m, 1H), 2.60 (d, J=17.1 Hz, 1H), 2.49-2.42 (m, 1H), 2.37 (s, 1H), 2.28 (s, 1H), 2.04-1.92 (m, 3H), 1.87 (s, 1H), 1.65-1.57 (m, 4H), 1.45-1.39 (m, 2H), 1.32 (s, 2H), 1.25 (d, J=6.8 Hz, 2H). HRMS (ESI) m/z: calcd for $C_{27}H_{39}N_4O_3S^+$ [M+H]$^+$, 499.2737; found, 499.2736.

Example 137: 3-(1-oxo-4-((7-(((R)-quinuclidin-3-yl)amino)heptyl)thio)isoindolin-2-yl)piperidine-2,6-dione (SIAIS1224037)

Referring to the method of Scheme 11, the compound SIAIS1224037 was prepared under appropriate conditions that will be recognized by one skilled in the art, except that the substrates used were 3-(4-((7-bromoheptyl)thio)-1-oxoisoindolin-2-yl)piperidine-2,6-dione (SIAIS1216135) and (R)-quinuclidin-3-amine. The hydrochloride salt of compound SIAIS1224037 was obtained (white solid, 20 mg, yield 80%). $^1$H NMR (500 MHz, DMSO) δ 11.00 (s, 1H), 8.87 (s, 3H), 7.63 (d, J=7.3 Hz, 1H), 7.58 (d, J=7.3 Hz, 1H), 7.54 (t, J=7.3 Hz, 1H), 5.14 (dd, J=13.1, 4.5 Hz, 1H), 4.36 (d, J=17.3 Hz, 1H), 4.22 (d, J=17.4 Hz, 1H), 3.75 (s, 2H), 3.61 (s, 1H), 3.47-3.35 (m, 4H), 3.21-3.16 (m, 2H), 3.08 (d, J=6.7 Hz, 2H), 2.96-2.87 (m, 1H), 2.60 (d, J=17.2 Hz, 1H), 2.44 (d, J=13.1 Hz, 1H), 2.35 (s, 1H), 2.27 (s, 1H), 2.05-1.92 (m, 3H), 1.88 (d, J=12.6 Hz, 1H), 1.64-1.58 (m, 4H), 1.45-1.38 (m, 2H), 1.37-1.28 (m, 2H), 1.25 (d, J=6.6 Hz, 2H). HRMS (ESI) m/z: calcd for $C_{27}H_{39}N_4O_3S^+$ [M+H]$^+$, 499.2737; found, 499.2730.

Example 138: 3-(4-((7-(4-(methylsulfonyl)piperazin-1-yl)heptyl)thio)-1-oxoisoindolin-2-yl)piperidine-2,6-dione (SIAIS1224039)

Referring to the method of Scheme 11, the compound SIAIS1224039 was prepared under appropriate conditions that will be recognized by one skilled in the art, except that the substrates used were 3-(4-((7-bromoheptyl)thio)-1-oxoisoindolin-2-yl)piperidine-2,6-dione (SIAIS1216135) and 1-(methylsulfonyl)piperazine. The hydrochloride salt of compound SIAIS1224039 was obtained (light yellow solid, 12 mg, yield 80%). $^1$H NMR (500 MHz, DMSO) δ 11.33 (s, 1H), 10.99 (s, 1H), 7.63 (d, J=7.3 Hz, 1H), 7.57 (d, J=7.2 Hz, 1H), 7.56-7.51 (m, 1H), 5.13 (dd, J=13.1, 4.2 Hz, 1H), 4.36 (d, J=17.4 Hz, 1H), 4.22 (d, J=17.4 Hz, 1H), 3.67 (d, J=11.9 Hz, 2H), 3.52 (d, J=10.4 Hz, 2H), 3.33-3.26 (m, 2H), 3.11-3.02 (m, 6H), 3.00 (s, 3H), 2.96-2.87 (m, 1H), 2.60 (d, J=16.9 Hz, 1H), 2.45 (d, J=13.0 Hz, 1H), 2.05-1.98 (m, 1H), 1.69 (s, 2H), 1.63-1.56 (m, 2H), 1.41 (s, 2H), 1.29 (s, 4H). HRMS (ESI) m/z: calcd for $C_{25}H_{37}N_4O_5S_2^+$ [M+H]$^+$, 537.2200; found, 537.2195.

Example 139: 3-(1-oxo-4-((4-(thiomorpholinomethyl)benzyl)thio)isoindolin-2-yl)piperidine-2,6-dione (SIAIS1224089)

Referring to the method of Scheme 11, the compound SIAIS1224089 was prepared under appropriate conditions that will be recognized by one skilled in the art, except that the substrates used were 3-(4-((4-(bromomethyl)benzyl)thio)-1-oxoisoindolin-2-yl)piperidine-2,6-dione (SIAIS1220141) and thiomorpholine. The hydrochloride salt of compound SIAIS1224089 was obtained (white solid, 21 mg, yield 88%). $^1$H NMR (500 MHz, DMSO) δ 11.21 (s, 1H), 10.99 (s, 1H), 7.68 (d, J=7.6 Hz, 1H), 7.59 (d, J=7.5 Hz, 1H), 7.55-7.7 (m, 3H), 7.40 (d, J=7.5 Hz, 2H), 5.11 (dd, J=13.2, 4.7 Hz, 1H), 4.36 (s, 2H), 4.30-4.24 (m, 3H), 4.13

(d, J=17.4 Hz, 1H), 3.50 (s, 2H), 3.20 (t, J=11.1 Hz, 2H), 3.03 (d, J=9.7 Hz, 2H), 2.95-2.86 (m, 1H), 2.78 (d, J=14.1 Hz, 2H), 2.59 (d, J=17.3 Hz, 1H), 2.41 (dd, J=25.0, 15.0 Hz, 1H), 2.01-1.94 (m, 1H). HRMS (ESI) m/z: calcd for $C_{25}H_{28}N_3O_3S_2^+$ $[M+H]^+$, 482.1567; found, 482.1564.

Example 140: 1-methyl-3-(1-oxo-4-((4-(piperidin-1-ylmethyl)benzyl)thio)isoindolin-2-yl)piperidine-2,6-dione (SIAIS1224101)

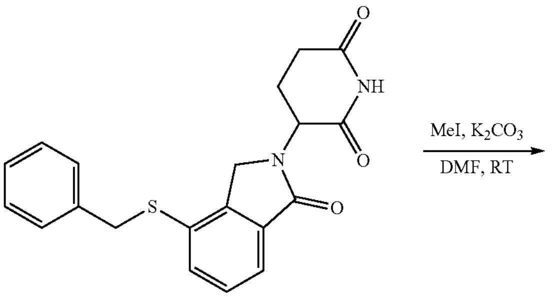

1
(SIAIS171088)

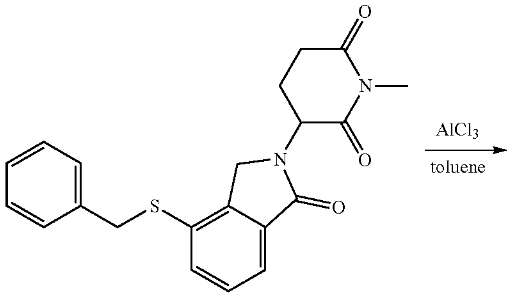

2

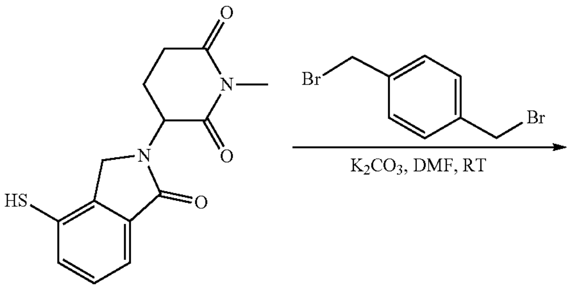

3

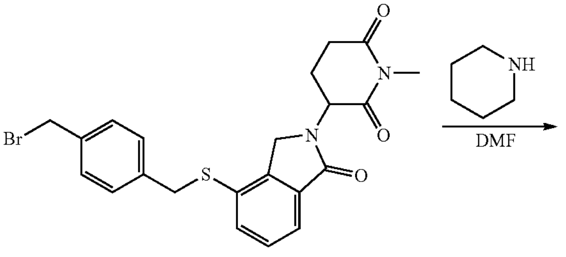

4

-continued

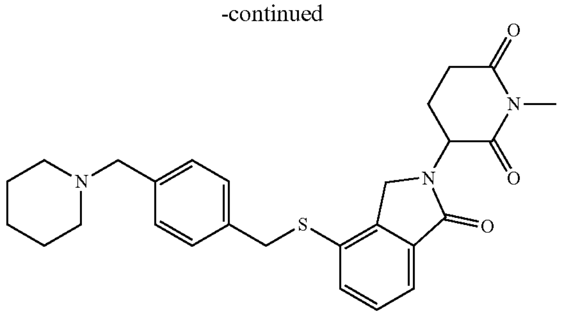

SIAIS1224101

Step 1: A 50 mL single-necked flask was charged with SIAIS171088 (3.0 mmol, 1 equiv), DMF, and potassium carbonate (6 mmol, 2 equiv), followed by addition dropwise of methyl iodide (4.5 mmol, 1.5 equiv), and then the mixture was reacted at room temperature overnight. After the reaction mixture was filtered to remove the insoluble substance, the filtrate was subjected to ISCO reverse phase column chromatography (eluent (v/v):acetonitrile/(water+0.05% HCl)=10%-100%) for separation. The collected fractions were concentrated under reduced pressure to remove the solvent, to give the intermediate 2 (light yellow solid, 428 mg, yield 38%).

Step 2: A 250 mL egg-shaped flask was charged with anhydrous aluminum trichloride (4 mmol, 4 equiv) and anhydrous toluene (25 mL), followed by slow addition of the intermediate 2 (1 mmol, 1 equiv). After the completion of addition, the flask was evacuated and refilled with argon gas for three times. The reaction mixture was then reacted at 35° C. under argon atomosphere overnight.

After the reaction was complete, 20% citric acid aqueous solution was added slowly into the reaction mixture with stirring, and a large amount of solids were precipitated out. After filtration, the filter cake was washed with water and ethyl acetate, respectively, and dried to give the intermediate 3 as a yellow solid (130 mg, yield 45%).

Step 3: A 25 mL egg-shaped flask was charged with the intermediate 3 (0.3 mmol, 1 equiv), potassium carbonate (0.6 mmol, 2 equiv), and DMF (5 mL), followed by addition of 1,4-bis(bromomethyl)benzene (0.6 mmol, 2 equiv), and then the reaction mixture was stirred and reacted at room temperature for 1 h. After the reaction was complete, the reaction mixture was filtered to remove the insoluble substance, and the filtrate was then subjected to ISCO reverse phase column chromatography (eluent (v/v):acetonitrile/water=10%-100%) for separation. The collected fractions were concentrated under reduced pressure to remove the solvents to give the intermediate 4 as a light yellow solid (52 mg, yield 37%).

Step 4: A 25 mL single-necked flask was charged with the intermediate 4 (0.05 mmol, 1 equiv), and DMF (2 mL), followed by addition of piperidine (0.1 mmol, 2 equiv), and then the reaction mixture was stirred and reacted at 40° C. overnight. After the reaction was complete, the reaction mixture was filtered to remove the insoluble substance, and the filtrate was then subjected to Waters 2767 HPLC system (eluent (v/v):acetonitrile/(water+0.05% HCl)=10%-100%) for separation.

The collected fractions were concentrated under reduced pressure to remove the solvents, and then lyophilized to give the hydrochloride salt of compound SIAIS1224101 (white solid, 11 mg, yield 77%). $^1H$ NMR (500 MHz, DMSO) δ 10.36 (s, 1H), 7.68 (d, J=7.6 Hz, 1H), 7.59 (d, J=7.4 Hz, 1H), 7.50 (t, J=6.5 Hz, 3H), 7.40 (d, J=7.4 Hz, 2H), 5.18 (dd, J=13.1, 4.3 Hz, 1H), 4.40-4.33 (m, 2H), 4.26 (d, J=17.5 Hz, 1H), 4.21-4.13 (m, 3H), 3.21 (d, J=10.8 Hz, 2H), 3.03-2.93 (m, 4H), 2.75 (d, J=15.9 Hz, 3H), 2.41 (dd, J=25.2, 14.8 Hz, 1H), 2.02-1.95 (m, 1H), 1.79-1.64 (m, 5H), 1.32 (s, 1H). HRMS (ESI) m/z: calcd for $C_{27}H_{32}N_3O_3S^+$ $[M+H]^+$, 478.2159; found, 478.2155.

Example 141: 3-(4-((4-(((adamantan-1-yl)amino) methyl)benzyl)thio)-1-oxoisoindolin-2-yl)-1-methylpiperidine-2,6-dione (SIAIS1224103)

Referring to the method of example 140, the compound SIAIS1224103 was prepared under appropriate conditions that will be recognized by one skilled in the art, except that the amine used in the last step was 1-adamantanamine. The hydrochloride salt of compound SIAIS1224103 was obtained (light yellow solid, 15 mg, yield 55%). $^1H$ NMR (500 MHz, DMSO) δ 8.97 (s, 2H), 7.70 (d, J=7.7 Hz, 1H), 7.57 (d, J=7.4 Hz, 1H), 7.51 (d, J=7.5 Hz, 3H), 7.43 (d, J=7.7 Hz, 2H), 5.18 (dd, J=13.3, 4.6 Hz, 1H), 4.43-4.34 (m, 2H), 4.28 (d, J=17.4 Hz, 1H), 4.17 (d, J=17.4 Hz, 1H), 4.04 (s, 2H), 3.03-2.94 (m, 4H), 2.75 (d, J=17.4 Hz, 1H), 2.48-2.38 (m, 1H), 2.13 (s, 3H), 1.99 (dd, J=12.4, 6.6 Hz, 1H), 1.95 (s, 6H), 1.68 (d, J=12.1 Hz, 3H), 1.60 (d, J=12.0 Hz, 3H). HRMS (ESI) m/z: calcd for $C_{32}H_{38}N_3O_3S^+$ $[M+H]^+$, 544.2628; found, 544.2626.

Example 142: 3-(4-((7-(adamantan-1-ylamino)heptyl)thio)-1-oxoisoindolin-2-yl)-1-methylpiperidine-2,6-dione (SIAIS1221149)

Referring to the method of example 140, the compound SIAIS1221149 was prepared under appropriate conditions that will be recognized by one skilled in the art, except that the bromide used was 1,7-dibromoheptane and the amine used in the last step was 1-adamantanamine. The hydrochloride salt of compound SIAIS1221149 was obtained (light yellow solid, 13 mg, yield 59%). $^1H$ NMR (500 MHz, DMSO) δ 8.51 (s, 2H), 7.64 (d, J=7.5 Hz, 1H), 7.58 (d, J=7.3 Hz, 1H), 7.56-7.52 (m, 1H), 5.20 (dd, J=13.4, 5.0 Hz, 1H), 4.34 (d, J=17.3 Hz, 1H), 4.21 (d, J=17.3 Hz, 1H), 3.09 (t, J=6.8 Hz, 2H), 3.04-2.95 (m, 4H), 2.84-2.72 (m, 3H), 2.48-2.40 (m, 1H), 2.11 (s, 3H), 2.05-1.99 (m, 1H), 1.84 (s, 6H), 1.68-1.57 (m, 10H), 1.41 (s, 2H), 1.31 (s, 4H). HRMS (ESI) m/z: calcd for $C_{31}H_{44}N_3O_3S^+$ $[M+H]^+$, 538.3098; found, 538.3095.

Example 143: 3-(4-((7-(cyclohexylamino)heptyl) thio)-1-oxoisoindolin-2-yl)-1-methylpiperidine-2,6-dione (SIAIS1222089)

Referring to the method of example 140, the compound SIAIS1222089 was prepared under appropriate conditions that will be recognized by one skilled in the art, except that the bromide used was 1,7-dibromoheptane and the amine used in the last step was cyclohexylamine. The hydrochloride salt of compound SIAIS1222089 was obtained (white solid, 16.5 mg, yield 68%). $^1H$ NMR (500 MHz, DMSO) δ 8.35 (s, 2H), 7.63 (d, J=7.3 Hz, 1H), 7.58 (d, J=7.2 Hz, 1H), 7.54 (t, J=7.4 Hz, 1H), 5.19 (dd, J=13.4, 4.3 Hz, 1H), 4.34 (d, J=17.5 Hz, 1H), 4.21 (d, J=17.4 Hz, 1H), 3.09 (t, J=7.0 Hz, 2H), 3.01 (s, 4H), 2.94 (d, J=10.9 Hz, 1H), 2.86 (t, J=7.5 Hz, 2H), 2.76 (d, J=17.3 Hz, 1H), 2.43 (dd, J=26.5, 13.4 Hz, 1H), 2.01 (d, J=24.0 Hz, 3H), 1.76 (s, 2H), 1.63-1.54 (m, 5H), 1.41 (s, 2H), 1.30 (s, 4H), 1.24 (s, 4H), 1.11 (s, 1H). HRMS (ESI) m/z: calcd for $C_{27}H_{40}N_3O_3S^+$ $[M+H]^+$, 486.2785; found, 486.2784.

Example 144: 1-methyl-3-(1-oxo-4-((7-(((1R,2S,4R)-1,7,7-trimethylbicyclo[2.2.1]heptan-2-yl)amino) heptyl)thio)isoindolin-2-yl)piperidine-2,6-dione (SIAIS1222091)

Referring to the method of example 140, the compound SIAIS1222091 was prepared under appropriate conditions that will be recognized by one skilled in the art, except that the bromide used was 1,7-dibromoheptane and the amine used in the last step was bornylamine. The hydrochloride salt of compound SIAIS1222091 was obtained (white solid, 17.6 mg, yield 65%). $^1H$ NMR (500 MHz, DMSO) δ 8.48 (s, 1H), 8.13 (s, 1H), 7.64 (d, J=7.2 Hz, 1H), 7.58 (d, J=7.3 Hz, 1H), 7.54 (t, J=7.4 Hz, 1H), 5.20 (dd, J=13.3, 4.4 Hz, 1H), 4.35 (d, J=17.3 Hz, 1H), 4.21 (d, J=17.4 Hz, 1H), 3.21 (s, 1H), 3.09 (t, J=7.0 Hz, 2H), 3.04-2.94 (m, 4H), 2.87 (s, 2H), 2.76 (d, J=17.2 Hz, 1H), 2.48-2.40 (m, 1H), 2.16 (t, J=11.3 Hz, 1H), 2.06-1.98 (m, 1H), 1.68 (s, 4H), 1.63-1.57 (m, 3H), 1.40 (d, J=13.3 Hz, 4H), 1.29 (s, 4H), 1.20 (d, J=13.2 Hz, 1H), 0.95 (s, 3H), 0.84 (s, 6H). HRMS (ESI) m/z: calcd for $C_{31}H_{46}N_3O_3S^+$ $[M+H]^+$, 540.3245; found, 540.3245.

Example 145: 3-(1-oxo-4-((7-thiomorpholinoheptyl) thio)isoindolin-2-yl)piperidine-2,6-dione (SIAIS1224125)

Referring to the method of Scheme 11, the compound SIAIS1224125 was prepared under appropriate conditions that will be recognized by one skilled in the art, except that the substrates used were 3-(4-((7-bromoheptyl)thio)-1-oxoisoindolin-2-yl)piperidine-2,6-dione (SIAIS1216135) and thiomorpholine. The hydrochloride salt of compound SIAIS1224125 was obtained (light yellow solid, 5 mg, yield 19%). $^1H$ NMR (500 MHz, DMSO) δ 10.99 (s, 1H), 10.46 (s, 1H), 7.63 (d, J=7.4 Hz, 1H), 7.57 (d, J=7.3 Hz, 1H), 7.53 (t, J=7.4 Hz, 1H), 5.13 (dd, J=13.2, 4.8 Hz, 1H), 4.36 (d, J=17.4 Hz, 1H), 4.21 (d, J=17.4 Hz, 1H), 3.66 (d, J=11.9 Hz, 2H), 3.22-3.11 (m, 2H), 3.10-2.97 (m, 6H), 2.96-2.87 (m, 1H), 2.80 (d, J=11.8 Hz, 2H), 2.59 (d, J=17.4 Hz, 1H), 2.49-2.41 (m, 1H), 2.04-1.97 (m, 1H), 1.65 (d, J=18.9 Hz, 2H), 1.64-1.56 (m, 2H), 1.45-1.37 (m, 2H), 1.33-1.22 (m, 4H). HRMS (ESI) m/z: calcd for $C_{24}H_{34}N_3O_3S_2^+$ $[M+H]^+$, 476.2036; found, 476.2035.

Example 146: 3-(4-((7-(((R)-1-cyclopropylethyl) amino)heptyl)thio)-1-oxoisoindolin-2-yl)piperidine-2,6-dione (SIAIS1224127)

Referring to the method of Scheme 11, the compound SIAIS1224127 was prepared under appropriate conditions that will be recognized by one skilled in the art, except that the substrates used were 3-(4-((7-bromoheptyl)thio)-1-oxoisoindolin-2-yl)piperidine-2,6-dione (SIAIS1216135) and (R)-1-cyclopropylethane-1-amine. The hydrochloride salt of compound SIAIS1224127 was obtained (light yellow solid, 5 mg, yield 19%). $^1H$ NMR (500 MHz, DMSO) δ 10.99 (s, 1H), 8.70 (d, J=40.0 Hz, 2H), 7.63 (d, J=7.4 Hz, 1H), 7.57 (d, J=7.3 Hz, 1H), 7.53 (t, J=7.4 Hz, 1H), 5.13 (dd, J=13.2, 4.1 Hz, 1H), 4.35 (d, J=17.4 Hz, 1H), 4.21 (d, J=17.4 Hz, 1H), 3.09 (t, J=6.8 Hz, 2H), 2.98-2.84 (m, 3H), 2.59 (d, J=17.0 Hz, 1H), 2.43 (d, J=13.5 Hz, 2H), 2.05-1.97 (m, 1H), 1.60 (d, J=5.7 Hz, 4H), 1.41 (s, 2H), 1.34-1.25 (m, 7H), 0.96

(s, 1H), 0.58 (d, J=7.8 Hz, 1H), 0.56-0.45 (m, 2H), 0.23 (d, J=4.6 Hz, 1H). HRMS (ESI) m/z: calcd for $C_{25}H_{36}N_3O_3S^+$ [M+H]$^+$, 458.2472; found, 458.2475.

Example 147: 1-methyl-3-(1-oxo-4-((7-(spiro[3.3]heptan-2-ylamino)heptyl)thio)isoindolin-2-yl)piperidine-2,6-dione (SIAIS1222119)

Referring to the method of example 142, the compound SIAIS1222119 was prepared under appropriate conditions that will be recognized by one skilled in the art, except that the bromide used was 1,7-dibromoheptane and the amine used in the last step was spiro[3.3]heptan-2-amine hydrochloride. The hydrochloride salt of compound SIAIS1222119 was obtained (white solid, 11.2 mg, yield 45%). $^1$H NMR (500 MHz, DMSO) δ 9.13 (s, 2H), 7.66-7.50 (m, 3H), 5.21 (dd, J=13.5, 4.7 Hz, 1H), 4.48 (d, J=17.6 Hz, 1H), 4.22 (d, J=17.3 Hz, 1H), 3.36 (t, J=15.7 Hz, 3H), 3.08 (s, 2H), 3.01 (s, 4H), 2.68 (s, 2H), 2.58 (d, J=3.2 Hz, 1H), 2.48-2.44 (m, 1H), 2.25 (t, J=9.8 Hz, 2H), 2.06-1.97 (m, 3H), 1.91 (t, J=7.5 Hz, 2H), 1.82-1.74 (m, 2H), 1.64-1.52 (m, 4H), 1.41 (s, 2H), 1.28 (s, 4H). HRMS (ESI) m/z: calcd for $C_{28}H_{40}N_3O_3S^+$ [M+H]$^+$, 498.2785; found, 498.2785.

Example 148: 3-(4-((4-((diethylamino)methyl)benzyl)thio)-1-oxoisoindolin-2-yl)piperidine-2,6-dione (SIAIS1227055)

Referring to the method of Scheme 12, the compound SIAIS1227055 was prepared under appropriate conditions that will be recognized by one skilled in the art, except that the substrate used was 3-(4-((4-(bromomethyl)benzyl)thio)-1-oxoisoindolin-2-yl)piperidine-2,6-dione (SIAIS1220141). The hydrochloride salt of compound SIAIS1227055 was obtained (white solid, 12.2 mg, yield 54%). $^1$H NMR (500 MHz, DMSO) δ 10.99 (s, 1H), 10.03 (s, 1H), 7.66 (d, J=7.6 Hz, 1H), 7.58 (d, J=7.3 Hz, 1H), 7.50 (d, J=5.9 Hz, 3H), 7.41 (d, J=7.3 Hz, 2H), 5.11 (dd, J=13.3, 4.5 Hz, 1H), 4.37 (s, 2H), 4.28 (d, J=17.6 Hz, 1H), 4.23 (d, J=4.8 Hz, 2H), 4.14 (d, J=17.4 Hz, 1H), 3.08-2.86 (m, 5H), 2.59 (d, J=16.6 Hz, 1H), 2.41 (dd, J=28.5, 15.4 Hz, 1H), 2.01-1.94 (m, 1H), 1.21 (t, J=7.1 Hz, 6H). HRMS (ESI) m/z: calcd for $C_{25}H_{30}N_3O_3S^+$ [M+H]$^+$, 452.2002; found, 452.1999.

Example 149: 3-(4-((4-((diisopropylamino)methyl)benzyl)thio)-1-oxoisoindolin-2-yl)piperidine-2,6-dione (SIAIS1227057)

Referring to the method of Scheme 11, the compound SIAIS1227057 was prepared under appropriate conditions that will be recognized by one skilled in the art, except that the substrates used were 3-(4-((4-(bromomethyl)benzyl)thio)-1-oxoisoindolin-2-yl)piperidine-2,6-dione (SIAIS1220141) and diisopropylamine. The hydrochloride salt of compound SIAIS1227057 was obtained (white solid, 5.8 mg, yield 24%). $^1$H NMR (500 MHz, DMSO) δ 10.99 (s, 1H), 9.11 (s, 1H), 7.65 (d, J=7.5 Hz, 1H), 7.58 (d, J=7.4 Hz, 1H), 7.55 (d, J=7.5 Hz, 2H), 7.48 (t, J=7.4 Hz, 1H), 7.41 (d, J=7.4 Hz, 2H), 5.11 (dd, J=13.2, 4.3 Hz, 1H), 4.37 (s, 2H), 4.32 (s, 2H), 4.28 (d, J=12.5 Hz, 1H), 4.16 (d, J=17.4 Hz, 1H), 3.61 (s, 2H), 2.96-2.86 (m, 1H), 2.59 (d, J=16.7 Hz, 1H), 2.47-2.36 (m, 1H), 2.03-1.94 (m, 1H), 1.31 (dd, J=21.2, 6.2 Hz, 12H). HRMS (ESI) m/z: calcd for $C_{27}H_{34}N_3O_3S^+$ [M+H]$^+$, 480.2315; found, 480.2326.

Example 150: 3-(4-((4-((dicyclohexylamino)methyl)benzyl)thio)-1-oxoisoindolin-2-yl)piperidine-2,6-dione (SIAIS1227059)

Referring to the method of Scheme 11, the compound SIAIS1227059 was prepared under appropriate conditions that will be recognized by one skilled in the art, except that the substrates used were 3-(4-((4-(bromomethyl)benzyl)thio)-1-oxoisoindolin-2-yl)piperidine-2,6-dione (SIAIS1220141) and dicyclohexylamine. The hydrochloride salt of compound SIAIS1227059 was obtained (white solid, 8.5 mg, yield 30%). $^1$H NMR (500 MHz, DMSO) δ 10.99 (s, 1H), 8.79 (s, 1H), 7.64 (d, J=7.4 Hz, 1H), 7.57 (d, J=7.1 Hz, 1H), 7.53-7.45 (m, 3H), 7.42 (d, J=7.4 Hz, 2H), 5.11 (dd, J=12.7, 4.6 Hz, 1H), 4.38 (s, 4H), 4.30 (d, J=17.0 Hz, 1H), 4.17 (d, J=17.4 Hz, 1H), 3.28 (t, J=11.3 Hz, 2H), 2.90 (dd, J=21.2, 9.7 Hz, 1H), 2.59 (d, J=16.0 Hz, 1H), 2.46-2.37 (m, 1H), 2.10 (d, J=9.8 Hz, 2H), 2.00 (t, J=14.6 Hz, 3H), 1.77 (s, 4H), 1.54 (dd, J=25.2, 12.3 Hz, 6H), 1.31-1.17 (m, 4H), 1.10 (t, J=11.8 Hz, 2H). HRMS (ESI) m/z: calcd for $C_{33}H_{42}N_3O_3S^+$ [M+H]$^+$, 560.2941; found, 560.2967.

Example 151: 3-(4-(((4-(((3-hydroxyadamantan-1-yl)amino)methyl)benzyl)thio)-1-oxoisoindolin-2-yl)piperidine-2,6-dione (SIAIS1227061)

Referring to the method of Scheme 11, the compound SIAIS1227061 was prepared under appropriate conditions that will be recognized by one skilled in the art, except that the substrates used were 3-(4-((4-(bromomethyl)benzyl)thio)-1-oxoisoindolin-2-yl)piperidine-2,6-dione (SIAIS1220141) and 3-hydroxy-1-adamantanamine. The hydrochloride salt of compound SIAIS1227061 was obtained (white solid, 15.3 mg, yield 56%). $^1$H NMR (500 MHz, DMSO) δ 10.99 (s, 1H), 9.01 (s, 2H), 7.70 (d, J=7.6 Hz, 1H), 7.57 (d, J=7.3 Hz, 1H), 7.53-7.46 (m, 3H), 7.43 (d, J=7.4 Hz, 2H), 5.11 (dd, J=13.2, 4.5 Hz, 1H), 4.43-4.35 (m, 2H), 4.29 (d, J=17.5 Hz, 1H), 4.16 (d, J=17.4 Hz, 1H), 4.04 (s, 2H), 2.95-2.86 (m, 1H), 2.59 (d, J=16.7 Hz, 1H), 2.43 (dd, J=26.5, 13.1 Hz, 1H), 2.25 (s, 2H), 2.03-1.95 (m, 1H), 1.84 (s, 6H), 1.61-1.52 (m, 4H), 1.52-1.43 (m, 2H). HRMS (ESI) m/z: calcd for $C_{31}H_{36}N_3O_4S^+$ [M+H]$^+$, 546.2421; found, 560.2967.

Example 152: 3-(4-((4-((tert-butylamino)methyl)benzyl)thio)-1-oxoisoindolin-2-yl)piperidine-2,6-dione (SIAIS1227107)

Referring to the method of Scheme 11, the compound SIAIS1227107 was prepared under appropriate conditions that will be recognized by one skilled in the art, except that the substrates used were 3-(4-((4-(bromomethyl)benzyl)thio)-1-oxoisoindolin-2-yl)piperidine-2,6-dione (SIAIS1220141) and tert-butylamine. The hydrochloride salt of compound SIAIS1227107 was obtained (yellow solid, 7.5 mg, yield 56%). $^1$H NMR (500 MHz, DMSO) δ 10.99 (s, 1H), 8.95 (s, 2H), 7.70 (d, J=5.7 Hz, 1H), 7.56 (s, 1H), 7.50 (s, 3H), 7.44 (s, 2H), 5.11 (d, J=11.4 Hz, 1H), 4.39 (s, 2H), 4.29 (d, J=17.1 Hz, 1H), 4.15 (d, J=17.1 Hz, 1H), 4.03 (s, 2H), 2.95-2.86 (m, 1H), 2.59 (d, J=17.6 Hz, 1H), 2.41 (s, 1H), 2.00 (s, 1H), 1.35 (s, 9H). HRMS (ESI) m/z: calcd for $C_{25}H_{30}N_3O_3S^+$ [M+H]$^+$, 452.2002; found, 452.2006.

Example 153: 3-(4-((4-(azocan-1-ylmethyl)benzyl)thio)-1-oxoisoindolin-2-yl)piperidine-2,6-dione (SIAIS1227109)

Referring to the method of Scheme 11, the compound SIAIS1227109 was prepared under appropriate conditions that will be recognized by one skilled in the art, except that the substrates used were 3-(4-((4-(bromomethyl)benzyl)thio)-1-oxoisoindolin-2-yl)piperidine-2,6-dione (SIAIS1220141) and azacyclooctane. The hydrochloride salt of compound SIAIS1227109 was obtained (light yellow solid, 11.3 mg, yield 77%). $^1$H NMR (500 MHz, DMSO) δ 10.99 (s, 1H), 10.36 (s, 1H), 7.66 (d, J=7.4 Hz, 1H), 7.58 (d, J=7.3 Hz, 1H), 7.55 (d, J=7.3 Hz, 2H), 7.51 (d, J=7.5 Hz, 1H), 7.40 (d, J=7.2 Hz, 2H), 5.11 (d, J=9.6 Hz, 1H), 4.36 (s, 2H), 4.27 (d, J=18.5 Hz, 3H), 4.14 (d, J=17.5 Hz, 1H), 3.24 (s, 2H), 3.00 (s, 2H), 2.92 (d, J=14.7 Hz, 1H), 2.59 (d, J=17.4 Hz, 1H), 2.46-2.36 (m, 1H), 1.99 (s, 1H), 1.87 (s, 2H), 1.77-1.47 (m, 8H). HRMS (ESI) m/z: calcd for $C_{28}H_{34}N_3O_3S^+$ [M+H]$^+$, 492.2315; found, 492.2316.

Example 154: (E)-3-(4-((4-(2-bromovinyl)benzyl)thio)-1-oxoisoindolin-2-yl)piperidine-2,6-dione (SIAIS1224154)

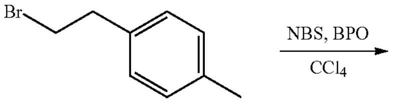

1

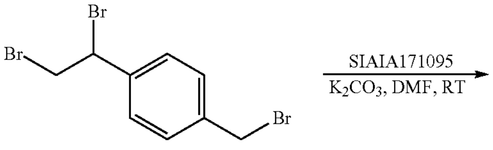

2

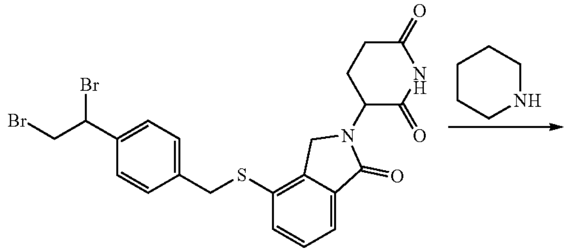

3

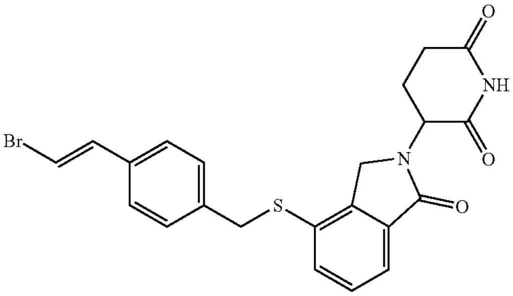

SIAIS1224154

Step 1: A 50 mL single-necked flask was charged with 1-(2-bromo-ethyl)-4-methyl-benzene (5 mmol, 1 equiv), NBS (10 mmol, 2 equiv), and BPO (0.25 mmol, 0.05 equiv), followed by addition of carbon tetrachloride (20 mL), and evacuation and refilling with argon gas. The reaction mixture was reacted at 80° C. in oil bath under argon atmosphere overnight. After the reaction was complete, the mixture was subjected to a positive phase column chromatography (eluent: PE) for separation. The collected fractions were concentrated under reduced pressure to remove the solvent, to obtain a pale yellow oily substance, which was used directly in the next step.

Step 2: A 50 mL single-necked flask was charged with SIAIS171095 (1 mmol, 1 equiv), potassium carbonate (2 mmol, 2 equiv), and DMF (10 mL), followed by addition of the oily substance obtained above (1 mmol, 1 equiv). The mixture was stirred and reacted at room temperature for 1 h. After the reaction was complete, the reaction mixture was filtered to remove the insoluble substance. The filtrate was subjected to ISCO reverse phase column chromatography (eluent (v/v): acetonitrile/water=10%-100%) for separation. The collected fractions were concentrated under reduced pressure to remove the solvents, to give the compound 3 (light yellow solid, 174 mg, yield 32%).

Step 3: A 25 mL single-necked flask was charged with the compound 3 (0.05 mmol, 1 equiv) and DMF (2 mL), followed by addition of piperidine (0.10 mmol, 2 equiv). The mixture was stirred and reacted at 40° C. overnight. After the reaction was complete, the reaction mixture was filtered to remove the insoluble substance. The filtrate was subjected to Waters 2767 HPLC system (eluent (v/v): acetonitrile/(water+0.05% HCl)=10%-100%) for separation. The collected fractions were concentrated under reduced pressure to remove the solvents, and then lyophilized to give the target compound SIAIS1224154 as a white solid (20 mg, yield 19%). $^1$H NMR (500 MHz, DMSO) δ 10.98 (s, 1H), 7.68 (d, J=7.7 Hz, 1H), 7.59 (d, J=7.3 Hz, 1H), 7.56 (d, J=7.6 Hz, 2H), 7.51 (t, J=7.6 Hz, 1H), 7.37 (d, J=7.5 Hz, 2H), 6.37 (s, 1H), 5.84 (s, 1H), 5.10 (dd, J=12.8, 4.6 Hz, 1H), 4.40-4.32 (m, 2H), 4.24-4.14 (m, 2H), 2.90 (t, J=13.1 Hz, 1H), 2.58 (d, J=16.9 Hz, 1H), 2.40 (d, J=13.0 Hz, 1H), 1.97 (s, 1H). HRMS (ESI) m/z: calcd for $C_{22}H_{20}BrN_2O_3S^+$ [M+H]$^+$, 471.0373; found, 471.0372.

Example 155: 3-(1-oxo-4-((4-(2-(piperidin-1-yl)ethyl)benzyl)thio)isoindolin-2-yl)piperidine-2,6-dione (SIAIS1224153)

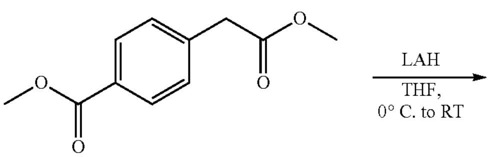

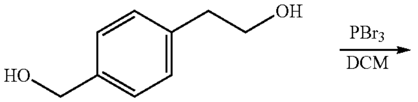

SIAIS1227001

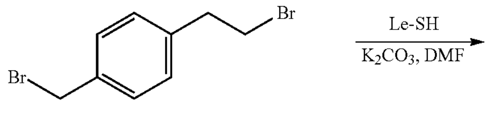

SIAIS1227003

-continued

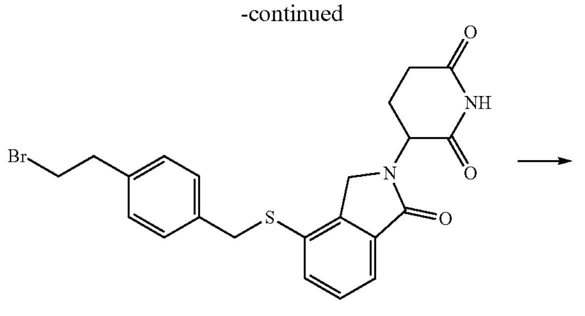

SIAIS1227095

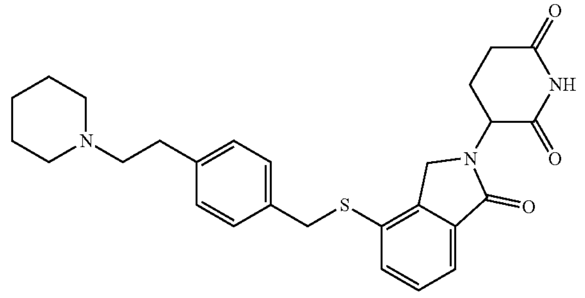

SIAIS1224153

Step 1: A 100 mL egg-shaped flask was charged with methyl 4-methoxycarbonylphenylacetate (10 mmol, 1 equiv) and anhydrous tetrahydrofuran (20 mL), followed by slow addition of lithium aluminum hydride (25 mmol, 2.5 equiv) under ice bath. Then the reaction mixture was stirred and reacted at room temperature overnight. After the reaction was complete as monitored by TLC, to the mixture was added water (1 mL), 10% NaOH (2 mL), and water (3 mL) in sequence. After filtration to remove the insoluble substance, the filtrate was directly rotary evaporated to give the compound 4-hydroxymethylphenethyl alcohol SIAIS1227001 (light yellow oil, 1.4 g, yield 90%).

Step 2: A 100 mL egg-shaped flask was charged with the compound SIAIS1227001 (8 mmol, 1 equiv) and dichloromethane (10 mL), followed by slow addition of phosphorus tribromide (8 mmol, 1 equiv) under ice bath. Then the reaction mixture was stirred and reacted at room temperature overnight. After the reaction was complete as monitored by TLC, the reaction was quenched with a small amount of water. After mixing the reaction mixture with silica gel powder, the obtained sample was subjected to positive column chromatography (eluent: petroleum ether:ethyl acetate=9:1) for separation. The collected fractions were concentrated under reduced pressure to remove the solvents, to give the target compound SIAIS1227003 as a pale yellow solid (277 mg, yield 12%).

Steps 3-4: A 50 mL single necked flask was charged with the compound SIAIS171095 (0.3 mmol, 1 equiv), potassium carbonate (0.6 mmol, 2 equiv), and DMF (5 mL), followed by addition of SIAIS1227003 (0.3 mmol, 1.0 equiv). Then the reaction mixture was stirred and reacted at room temperature for 0.5 h. After the reaction was completed, the mixture was filtered to remove the insoluble materials. The filtrate was subjected to a C18 reverse phase column chromatography for separation to give the intermediate product which was directly used in the next step. To the obtained the intermediate product was added potassium carbonate (0.6 mmol, 2 equiv) and DMF (5 mL), followed by addition of piperidine (0.6 mmol, 2 equiv). The reaction mixture was reacted at room temperature for 2 h, and then subjected to a C18 column chromatography (eluent (v/v): acetonitrile/(water+0.05% HCl)=10%-100%) for separation. The collected fractions were concentrated under reduced pressure to remove acetonitrile to give the hydrochloride salt of the corresponding target compound SIAIS1224153 (pale yellow solid, 68 mg, total yield of two steps 48%). $^1$H NMR (500 MHz, DMSO) δ 10.98 (s, 1H), 9.12 (s, 1H), 7.67 (d, J=7.6 Hz, 1H), 7.58 (d, J=7.6 Hz, 1H), 7.50 (t, J=7.5 Hz, 1H), 7.32 (d, J=7.3 Hz, 2H), 7.19 (d, J=7.4 Hz, 2H), 5.11 (dd, J=13.2, 4.8 Hz, 1H), 4.36-4.28 (m, 2H), 4.25 (d, J=17.3 Hz, 1H), 4.14 (d, J=17.5 Hz, 1H), 3.48 (s, 2H), 3.23 (d, J=5.0 Hz, 2H), 2.97-2.85 (m, 5H), 2.59 (d, J=16.4 Hz, 1H), 2.45-2.37 (m, 1H), 2.00-1.94 (m, 1H), 1.83 (d, J=13.9 Hz, 2H), 1.74-1.57 (m, 3H), 1.38 (d, J=11.6 Hz, 1H). HRMS (ESI) m/z: calcd for $C_{27}H_{32}N_3O_3S^+$ [M+H]$^+$, 478.2159; found, 478.2155.

Example 156: 3-(4-((4-(2-(cyclohexylamino)ethyl)benzyl)thio)-1-oxoisoindolin-2-yl)piperidine-2,6-dione (SIAIS1224155)

Referring to the method of example 155, the compound SIAIS1224155 was prepared under appropriate conditions that will be recognized by one skilled in the art, except that the amine employed in the step 4 was cyclohexylamine. The hydrochloride salt of compound SIAIS1224155 was obtained (light yellow solid, 5 mg, yield 19%). $^1$H NMR (500 MHz, DMSO) δ 10.98 (s, 1H), 8.49 (s, 2H), 7.69 (d, J=7.7 Hz, 1H), 7.58 (d, J=7.4 Hz, 1H), 7.50 (t, J=7.8 Hz, 1H), 7.32 (d, J=7.6 Hz, 2H), 7.20 (d, J=7.2 Hz, 2H), 5.11 (dd, J=12.8, 4.5 Hz, 1H), 4.38-4.29 (m, 2H), 4.25 (d, J=17.5 Hz, 1H), 4.15 (d, J=17.2 Hz, 1H), 3.13 (s, 2H), 3.00 (s, 1H), 2.96-2.85 (m, 3H), 2.59 (d, J=17.5 Hz, 1H), 2.46-2.37 (m, 1H), 2.05-1.94 (m, 3H), 1.75 (d, J=8.9 Hz, 2H), 1.60 (d, J=11.6 Hz, 1H), 1.31-1.16 (m, 4H), 1.15-1.04 (m, 1H). HRMS (ESI) m/z: calcd for $C_{28}H_{34}N_3O_3S^+$ [M+H]$^+$, 492.2315; found, 492.2312.

Example 157: 3-(4-((4-(2-morpholinoethyl)benzyl)thio)-1-oxoisoindolin-2-yl)piperidine-2,6-dione (SIAIS1227049)

Referring to the method of example 155, the compound SIAIS1227049 was prepared under appropriate conditions that will be recognized by one skilled in the art, except that the amine employed in the step 4 was morpholine. The hydrochloride salt of compound SIAIS1227049 was obtained (light yellow solid, 14 mg, yield 49%). $^1$H NMR (500 MHz, DMSO) δ 10.99 (s, 2H), 7.68 (d, J=7.7 Hz, 1H), 7.58 (d, J=7.2 Hz, 1H), 7.54-7.50 (m, 1H), 7.31 (d, J=7.2 Hz, 2H), 7.19 (d, J=7.4 Hz, 2H), 5.10 (dd, J=13.5, 4.3 Hz, 1H), 4.35-4.27 (m, 2H), 4.24 (d, J=17.2 Hz, 1H), 4.13 (d, J=17.7 Hz, 1H), 3.97 (d, J=10.6 Hz, 2H), 3.79 (d, J=11.1 Hz, 2H), 3.46 (d, J=12.8 Hz, 2H), 3.31-3.25 (m, 2H), 3.10-3.00 (m, 4H), 2.95-2.86 (m, 1H), 2.59 (d, J=16.1 Hz, 1H), 2.45-2.35 (m, 1H), 1.97 (d, J=12.3 Hz, 1H). HRMS (ESI) m/z: calcd for $C_{26}H_{30}N_3O_4S^+$ [M+H]$^+$, 480.1952; found, 480.1956.

Example 158: 3-(4-((4-(2-(diethylamino)ethyl)benzyl)thio)-1-oxoisoindolin-2-yl)piperidine-2,6-dione (SIAIS1227097)

Referring to the method of example 155, the compound SIAIS1227097 was prepared under appropriate conditions that will be recognized by one skilled in the art, except that the amine employed in the step 4 was diethylamine. The hydrochloride salt of compound SIAIS1227097 was obtained (light yellow solid, 7.3 mg, yield 52%). $^1$H NMR (500 MHz, DMSO) δ 10.98 (s, 1H), 9.61 (s, 1H), 7.68 (d, J=7.5 Hz, 1H), 7.58 (d, J=7.3 Hz, 1H), 7.50 (t, J=7.4 Hz, 1H), 7.32 (d, J=7.4 Hz, 2H), 7.23 (d, J=7.1 Hz, 2H), 5.10 (dd, J=13.1, 4.5 Hz, 1H), 4.36-4.28 (m, 2H), 4.25 (d, J=17.3 Hz, 1H), 4.14 (d, J=17.3 Hz, 1H), 3.25-3.11 (m, 6H), 2.96-2.86 (m, 3H), 2.59 (d, J=17.5 Hz, 1H), 2.45-2.37 (m, 1H), 2.01-1.93 (m, 1H), 1.21 (t, J=6.9 Hz, 6H). HRMS (ESI) m/z: calcd for $C_{26}H_{32}N_3O_3S^+$ [M+H]$^+$, 466.2159; found, 466.1956.

Example 159: 3-(4-((4-(2-(4-methylpiperazin-1-yl)ethyl)benzyl)thio)-1-oxoisoindolin-2-yl)piperidine-2,6-dione (SIAIS1227099)

Referring to the method of example 155, the compound SIAIS1227099 was prepared under appropriate conditions that will be recognized by one skilled in the art, except that the amine employed in the step 4 was N-methylpiperazine. The hydrochloride salt of compound SIAIS1227099 was obtained (light yellow solid, 1.6 mg, yield 11%). $^1$H NMR (500 MHz, DMSO) δ 11.55 (s, 1H), 10.98 (s, 1H), 7.68 (d, J=7.5 Hz, 1H), 7.58 (d, J=7.4 Hz, 1H), 7.50 (t, J=7.5 Hz, 1H), 7.32-7.27 (m, 2H), 7.21-7.17 (m, 2H), 5.10 (dd, J=13.2, 4.5 Hz, 1H), 4.36-4.27 (m, 2H), 4.24 (d, J=17.4 Hz, 1H), 4.14 (d, J=17.4 Hz, 1H), 3.70-2.41 (m, 12H), 2.94-2.86 (m, 1H), 2.80 (s, 3H), 2.59 (d, J=17.2 Hz, 1H), 2.46-2.36 (m, 1H), 2.01-1.93 (m, 1H). HRMS (ESI) m/z: calcd for $C_{27}H_{33}N_4O_3S^+$ [M+H]$^+$, 493.2268; found, 493.2263.

Example 160: 3-(1-oxo-4-((4-(2-thiomorpholinoethyl)benzyl)thio)isoindolin-2-yl)piperidine-2,6-dione (SIAIS1227051)

Referring to the method of example 155, the compound SIAIS1227051 was prepared under appropriate conditions that will be recognized by one skilled in the art, except that the amine employed in the step 4 was thiomorpholine. The hydrochloride salt of compound SIAIS1227051 was obtained (light yellow solid, 16 mg, yield 81%). $^1$H NMR (500 MHz, DMSO) δ 10.98 (s, 1H), 10.75 (s, 1H), 7.68 (d, J=7.6 Hz, 1H), 7.58 (d, J=7.4 Hz, 1H), 7.50 (t, J=7.3 Hz, 1H), 7.31 (d, J=7.3 Hz, 2H), 7.19 (d, J=7.4 Hz, 2H), 5.10 (dd, J=13.2, 4.2 Hz, 1H), 4.36-4.28 (m, 2H), 4.24 (d, J=17.4 Hz, 1H), 4.13 (d, J=17.4 Hz, 1H), 3.76 (d, J=10.0 Hz, 2H), 3.27 (s, 2H), 3.20-3.10 (m, 4H), 3.02 (d, J=5.8 Hz, 2H), 2.95-2.81 (m, 3H), 2.59 (d, J=16.3 Hz, 1H), 2.41 (dd, J=26.4, 13.5 Hz, 1H), 2.00-1.94 (m, 1H). HRMS (ESI) m/z: calcd for $C_{26}H_{30}N_3O_3S_2^+$ [M+H]$^+$, 496.1723; found, 496.1725.

Example 161: 3-(1-oxo-4-((4-(piperidin-1-ylmethyl)phenethyl)thio)isoindolin-2-yl)piperidine-2,6-dione (SIAIS1224161)

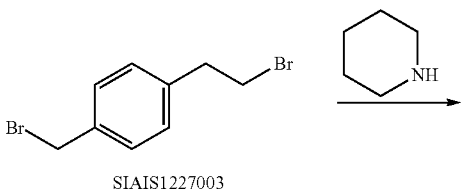

SIAIS1227003

-continued

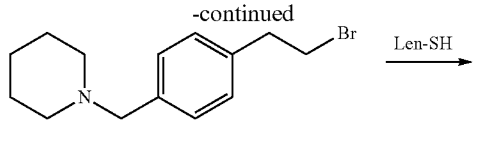

SIAIS1224157

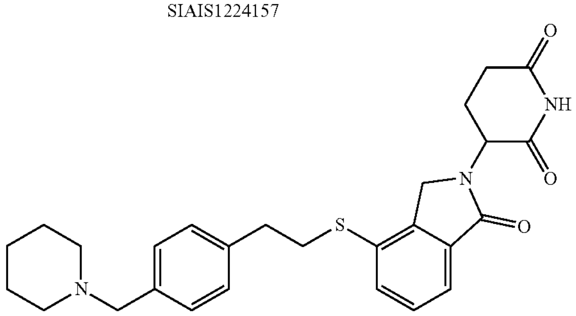

SIAIS1224161

Step 1: To a 15 mL sample vial were sequentially added 1-(2-bromoethyl)-4-(bromomethyl)benzene (SIAIS1227003) (0.125 mmol, 1 equiv), piperidine (0.25 mmol, 2 equiv), and DMF (2 mL). The mixture was stirred and reacted at room temperature for 1 h. After the reaction was complete, the mixture was filtered to remove the insoluble materials. The filtrate was subjected to a preparative HPLC (eluent (v/v):acetonitrile/(water+0.05% HCl)=10%-100%) for separation. The collected fractions were rotary evaporated to remove acetonitrile, and then lyophilized to give the corresponding target compound SIAIS1224157.

Step 2: To a 50 mL single-necked flask were sequentially added the compound SIAIS171095 (0.3 mmol, 1 equiv), potassium carbonate (0.6 mmol, 2 equiv), and DMF (5 mL), followed by addition of SIAIS1224157 (0.3 mmol, 1.0 equiv). Then the mixture was stirred and reacted at room temperature for 0.5 h. After the reaction was complete, the mixture was filtered to remove the insoluble materials. The filtrate was subjected to a reverse phase C18 column chromatography (eluent (v/v):acetonitrile/(water+0.05% HCl)=10%-100%) for separation. The collected fractions were concentrated under reduced pressure to remove the solvents to give the hydrochloride salt of the corresponding target compound SIAIS1224161 (light yellow solid, 10 mg, yield 51%). $^1$H NMR (500 MHz, DMSO) δ 11.00 (s, 1H), 10.34 (s, 1H), 7.68 (d, J=7.6 Hz, 1H), 7.58 (d, J=7.4 Hz, 1H), 7.54 (t, J=7.6 Hz, 1H), 7.50 (d, J=7.7 Hz, 2H), 7.34 (d, J=7.3 Hz, 2H), 5.13 (dd, J=13.1, 4.8 Hz, 1H), 4.33 (d, J=17.4 Hz, 1H), 4.22-4.16 (m, 3H), 3.48-3.43 (m, 2H), 3.24 (d, J=11.5 Hz, 2H), 2.97-2.87 (m, 3H), 2.80 (d, J=7.7 Hz, 2H), 2.59 (d, J=17.2 Hz, 1H), 2.48-2.40 (m, 1H), 2.05-1.97 (m, 1H), 1.80-1.65 (m, 5H), 1.34 (d, J=6.4 Hz, 1H). HRMS (ESI) m/z: calcd for $C_{27}H_{32}N_3O_3S^+$ [M+H]$^+$, 478.2159; found, 478.2169.

Example 162: 3-(4-((4-((cyclohexylamino)methyl)phenethyl)thio)-1-oxoisoindolin-2-yl)piperidine-2,6-dione (SIAIS1227007)

Referring to the method of example 161, the compound SIAIS1227007 was prepared under appropriate conditions that will be recognized by one skilled in the art, except that the amine used in the first step was cyclohexylamine. The hydrochloride salt of compound SIAIS1227007 was obtained (light yellow solid, 34 mg, yield 55%). $^1$H NMR (500 MHz, DMSO) δ 11.00 (s, 1H), 9.19 (s, 2H), 7.70 (d, J=6.8 Hz, 1H), 7.59 (d, J=7.3 Hz, 1H), 7.56 (t, J=7.1 Hz, 1H), 7.51 (d, J=7.5 Hz, 2H), 7.32 (d, J=6.7 Hz, 2H), 5.13 (dd, J=12.7, 4.8 Hz, 1H), 4.35-4.30 (m, 1H), 4.19 (d, J=17.4 Hz, 1H), 4.09 (s, 2H), 3.37 (t, J=6.8 Hz, 2H), 2.92 (t, J=11.8 Hz, 4H), 2.60 (d, J=14.1 Hz, 1H), 2.48-2.39 (m, 1H), 2.11 (d, J=11.4 Hz, 2H), 2.05-1.97 (m, 1H), 1.77 (d, J=11.8 Hz, 2H), 1.60 (d, J=11.0 Hz, 1H), 1.44-1.35 (m, 2H), 1.20 (dd, J=24.8, 12.2 Hz, 2H), 1.15-1.06 (m, 1H). HRMS (ESI) m/z: calcd for $C_{28}H_{34}N_3O_3S^+$ [M+H]$^+$, 492.2315; found, 492.2304.

Example 163: 3-(4-((4-(((adamantan-1-yl)amino) methyl)phenethyl)thio)-1-oxoisoindolin-2-yl)piperidine-2,6-dione (SIAIS1224149)

Referring to the method of example 161, the compound SIAIS1224149 was prepared under appropriate conditions that will be recognized by one skilled in the art, except that the amine used in the first step was 1-adamantanamine. The hydrochloride salt of compound SIAIS1224149 was obtained (light yellow solid, 7.7 mg, yield 35%). $^1$H NMR (500 MHz, DMSO) δ 11.00 (s, 1H), 8.80 (s, 2H), 7.70 (d, J=7.5 Hz, 1H), 7.60 (d, J=7.3 Hz, 1H), 7.58-7.53 (m, 1H), 7.48 (d, J=7.5 Hz, 2H), 7.34 (d, J=7.3 Hz, 2H), 5.14 (dd, J=13.2, 4.6 Hz, 1H), 4.33 (d, J=17.4 Hz, 1H), 4.19 (d, J=17.4 Hz, 1H), 4.07 (s, 2H), 3.40-3.35 (m, 2H), 2.92 (dd, J=16.2, 9.5 Hz, 3H), 2.60 (d, J=17.0 Hz, 1H), 2.48-2.40 (m, 1H), 2.15 (s, 3H), 2.05-1.99 (m, 1H), 1.96 (s, 6H), 1.69 (d, J=12.4 Hz, 3H), 1.62 (d, J=12.0 Hz, 3H). HRMS (ESI) m/z: calcd for $C_{32}H_{38}N_3O_3S^+$ [M+H]$^+$, 544.2628; found, 558.2632.

Example 164: 3-(1-oxo-4-((4-(3-(piperidin-1-yl) propyl)benzyl)thio)isoindolin-2-yl)piperidine-2,6-dione (SIAIS1227043)

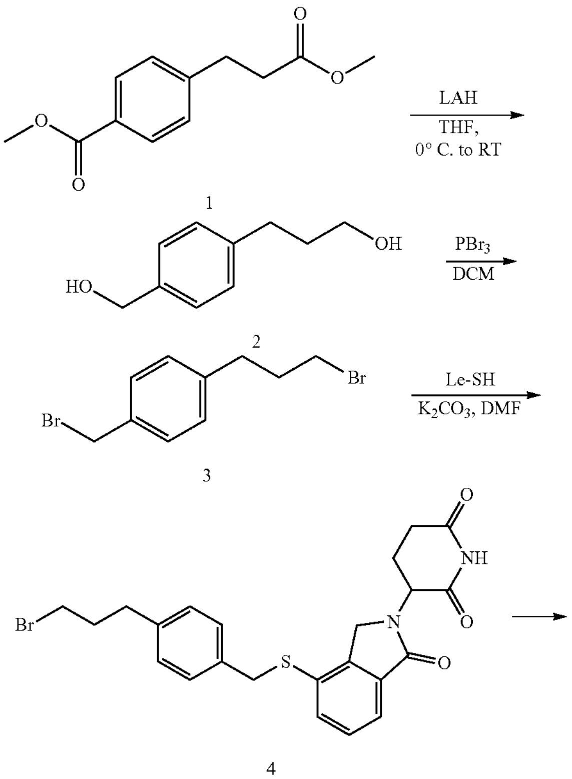

1
2
3
4
(SIAIS1227033)

-continued

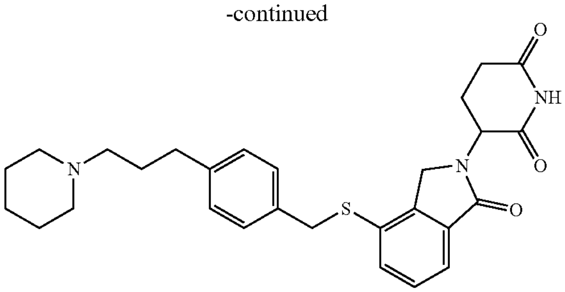

SIAIS1227043

Step 1: A 100 mL egg-shaped flask was charged with methyl 3-(4-methoxycarbonylphenyl)propionate (5 mmol, 1 equiv) and anhydrous tetrahydrofuran (20 mL), followed by slow addition of lithium aluminum hydride (12.5 mmol, 2.5 equiv) under ice bath. Then the reaction mixture was stirred and reacted at room temperature for 3 h. After the reaction was complete as monitored by TLC, to the mixture was added water (1 mL), 10% NaOH (2 mL), and water (3 mL) in sequence. After filtration to remove the insoluble substance, the filtrate was directly rotary evaporated to give the compound 2 (light yellow oil, 651 mg, yield 78%).

Step 2: A 100 mL egg-shaped flask was charged with the compound 2 (3 mmol, 1 equiv) and dichloromethane (10 mL), followed by slow addition of phosphorus tribromide (4 mmol, 1 equiv) under ice bath. Then the reaction mixture was stirred and reacted at room temperature for 3 h. After the reaction was complete as monitored by TLC, the reaction was quenched with a small amount of water. After mixing the reaction mixture with silica gel powder, the obtained sample was subjected to ISCO column chromatography (eluent: petroleum ether:ethyl acetate=9:1) for separation. The collected fractions were concentrated under reduced pressure to remove the solvents, to give the compound 3 (1-(bromomethyl)-4-(3-bromopropyl)benzene) as a pale yellow solid (117 mg, yield 13%).

Step 3: A 50 mL single necked flask was charged with the compound SIAIS171095 (0.3 mmol, 1 equiv), potassium carbonate (0.6 mmol, 2 equiv), and DMF (5 mL), followed by addition of the intermediate compound 3 (0.3 mmol, 1.0 equiv). Then the reaction mixture was stirred and reacted at room temperature for 1 h. After the reaction was completed, the mixture was filtered to remove the insoluble materials. The filtrate was subjected to a ISCO reverse phase column chromatography (eluent (v/v):acetonitrile/water=10%-100%) for separation. The collected fractions were concentrated under reduced pressure to remove the solvents to give the intermediate compound SIAIS1227033 as a pale yellow solid (68 mg, yield 47%).

Step 4: A 25 mL single necked flask was sequentially charged with the compound SIAIS1227033 (0.05 mmol, 1 equiv), DMF (2 mL), and piperidine (0.10 mmol, 2 equiv). The reaction mixture was reacted at 40° C. overnight. After the reaction was completed, the mixture was filtered to remove the insoluble materials. The filtrate was subjected to a Waters 2767 HPLC system (eluent (v/v):acetonitrile/(water+0.05% HCl)=10%-100%) for separation. The collected fractions were concentrated under reduced pressure to remove the solvents, and then lyophilized to give the hydrochloride salt of compound SIAIS1227043 (pale yellow solid, 22.6 mg, yield 61%). $^1$H NMR (500 MHz, DMSO) δ 10.98 (s, 1H), 9.91 (s, 1H), 7.68 (d, J=7.6 Hz, 1H), 7.58 (d, J=7.6 Hz, 1H), 7.50 (t, J=7.5 Hz, 1H), 7.28 (d, J=7.2 Hz, 2H), 7.16 (d, J=7.3 Hz, 2H), 5.11 (dd, J=13.1, 4.4 Hz, 1H), 4.36-4.28 (m, 2H), 4.25 (d, J=17.5 Hz, 1H), 4.15 (d, J=17.5 Hz, 1H), 3.44 (s, 2H), 2.90 (dd, J=28.3, 15.1 Hz, 3H), 2.81 (d, J=10.1 Hz, 2H), 2.58 (t, J=7.5 Hz, 3H), 2.41 (dd, J=28.3, 15.3 Hz, 1H), 1.96 (s, 3H), 1.78-1.66 (m, 5H), 1.35 (d, J=11.1 Hz, 1H). HRMS (ESI) m/z: calcd for $C_{28}H_{34}N_3O_3S^+$ $[M+H]^+$, 492.2315; found, 492.2312.

Example 165: 3-(4-((4-(3-(cyclohexylamino)propyl)benzyl)thio)-1-oxoisoindolin-2-yl)piperidine-2,6-dione (SIAIS1227045)

Referring to the method of example 164, the compound SIAIS1227045 was prepared under appropriate conditions that will be recognized by one skilled in the art, except that the amine used was cyclohexylamine. The hydrochloride salt of compound SIAIS1227045 was obtained (white solid, 15.6 mg, yield 51%). $^1$H NMR (500 MHz, DMSO) δ 10.98 (s, 1H), 8.58 (s, 2H), 7.66 (d, J=7.2 Hz, 1H), 7.58 (d, J=7.4 Hz, 1H), 7.50 (t, J=7.4 Hz, 1H), 7.29 (d, J=7.2 Hz, 2H), 7.15 (d, J=7.2 Hz, 2H), 5.11 (dd, J=13.1, 4.2 Hz, 1H), 4.35-4.28 (m, 2H), 4.26 (d, J=17.5 Hz, 1H), 4.16 (d, J=17.4 Hz, 1H), 2.98-2.83 (m, 4H), 2.61 (dd, J=17.3, 11.2 Hz, 3H), 2.46-2.36 (m, 1H), 1.98 (d, J=7.6 Hz, 3H), 1.87 (s, 2H), 1.74 (d, J=9.6 Hz, 2H), 1.59 (d, J=12.2 Hz, 1H), 1.30-1.17 (m, 4H), 1.09 (d, J=10.8 Hz, 1H). HRMS (ESI) m/z: calcd for $C_{29}H_{36}N_3O_3S^+$ $[M+H]^+$, 506.2472; found, 506.2497.

Example 166: 3-(4-((4-(3-((adamantan-1-yl)amino)propyl)benzyl)thio)-1-oxoisoindolin-2-yl)piperidine-2,6-dione (SIAIS1227047)

Referring to the method of example 164, the compound SIAIS1227047 was prepared under appropriate conditions that will be recognized by one skilled in the art, except that the amine used was 1-adamantanamine. The hydrochloride salt of compound SIAIS1227047 was obtained (white solid, 7.7 mg, yield 35%). $^1$H NMR (500 MHz, DMSO) δ 10.99 (s, 1H), 8.41 (s, 2H), 7.66 (d, J=7.5 Hz, 1H), 7.57 (d, J=7.1 Hz, 1H), 7.50 (t, J=7.5 Hz, 1H), 7.29 (d, J=7.2 Hz, 2H), 7.16 (d, J=7.4 Hz, 2H), 5.11 (dd, J=13.1, 4.1 Hz, 1H), 4.36-4.29 (m, 2H), 4.26 (d, J=17.2 Hz, 1H), 4.16 (d, J=17.7 Hz, 1H), 2.95-2.80 (m, 3H), 2.67-2.56 (m, 3H), 2.45-2.35 (m, 1H), 2.12 (s, 3H), 1.99 (s, 1H), 1.88-1.82 (m, 2H), 1.81 (s, 6H), 1.66 (d, J=12.0 Hz, 3H), 1.59 (d, J=12.3 Hz, 3H). HRMS (ESI) m/z: calcd for $C_{33}H_{40}N_3O_3S^+$ $[M+H]^+$, 558.2785; found, 558.2820.

Example 167: 3-(4-((4-(3-morpholinopropyl)benzyl)thio)-1-oxoisoindolin-2-yl)piperidine-2,6-dione (SIAIS1227053)

Referring to the method of example 164, the compound SIAIS1227053 was prepared under appropriate conditions that will be recognized by one skilled in the art, except that the amine used was morpholine. The hydrochloride salt of compound SIAIS1227053 was obtained (light yellow solid, 22.6 mg, yield 61%). $^1$H NMR (500 MHz, DMSO) δ 10.98 (s, 1H), 10.39 (s, 1H), 7.68 (d, J=7.6 Hz, 1H), 7.58 (d, J=7.4 Hz, 1H), 7.51 (t, J=7.5 Hz, 1H), 7.29 (d, J=7.3 Hz, 2H), 7.16 (d, J=7.5 Hz, 2H), 5.11 (dd, J=13.1, 4.5 Hz, 1H), 4.35-4.28 (m, 2H), 4.25 (d, J=17.4 Hz, 1H), 4.15 (d, J=17.4 Hz, 1H), 3.94 (d, J=12.8 Hz, 2H), 3.74 (d, J=11.8 Hz, 2H), 3.40 (d, J=7.6 Hz, 2H), 3.02 (dd, J=22.1, 10.5 Hz, 4H), 2.95-2.86 (m, 1H), 2.62-2.55 (m, 3H), 2.46-2.36 (m, 1H), 1.97 (d, J=6.0 Hz, 3H). HRMS (ESI) m/z: calcd for $C_{27}H_{32}N_3O_4S^+$ $[M+H]^+$, 494.2108; found, 494.2117.

Example 168: 3-(1-oxo-4-((4-(2-(piperidin-1-yl)ethyl)phenethyl)thio)isoindolin-2-yl)piperidine-2,6-dione (SIAIS1224117)

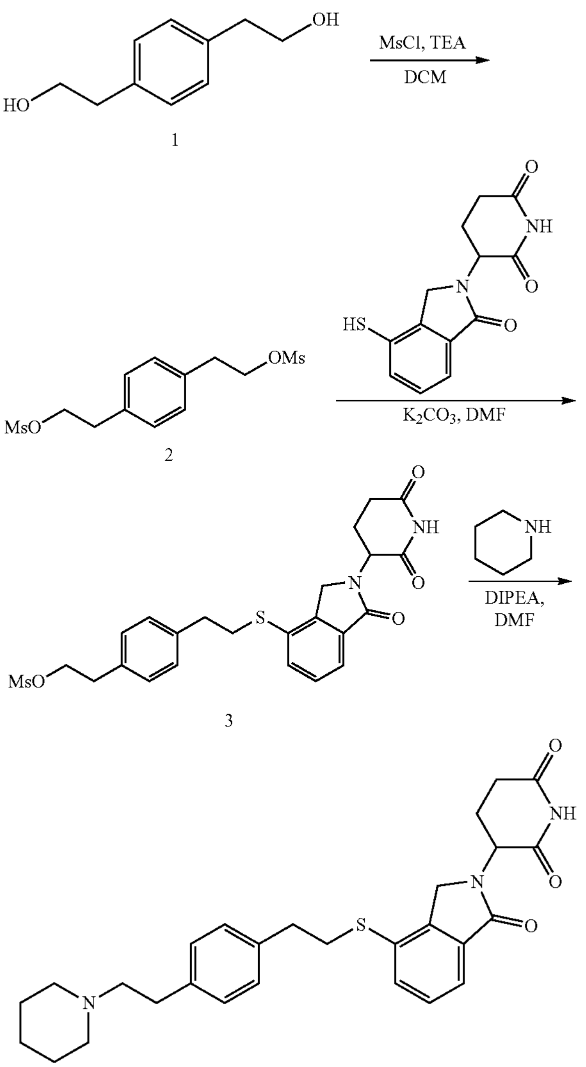

1

2

3

SIAIS1224117

Step 1: To a solution of 1,4-benzenediethanol (2 mmol, 1 equiv) in DCM (15 mL) were sequentially added triethylamine (8 mmol, 1 equiv) and methanesulfonyl chloride (4 mmol, 1 equiv), and the reaction system becomes clear. Then the reaction solution was stirred and reacted at room temperature overnight. The reaction solution was washed with saturated brine and then concentrated under reduced pressure to remove the solvents to give a solid which was used directly in the next step.

Step 2: A 25 mL egg-shaped flask was charged with the solid obtained from the previous step (2 mmol, 2 equiv), SIAIS171095 (1 mmol, 1 equiv), potassium carbonate (0.688 mmol, 2 equiv) and DMF (10 mL). Then the reaction mixture was stirred and reacted at 40° C. for 3 h. After the reaction was complete, the reaction mixture was filtered to remove the insoluble substance. The filtrate was subjected to ISCO reverse phase column chromatography (eluent (v/v): acetonitrile/water=10%-100%) for separation. The collected fractions were concentrated under reduced pressure to remove the solvents, to give the intermediate compound 3 (light yellow solid, 142 mg, yield 28%).

Step 3: A 25 mL single-necked flask was charged with the intermediate compound 3 (0.05 mmol, 1 equiv), DIPEA (0.10 mmol, 2 equiv), and DMF (2 mL), followed by addition of piperidine (0.10 mmol, 2 equiv). The mixture was stirred and reacted at 40° C. overnight. After the reaction was complete, the reaction mixture was filtered to remove the insoluble substance. The filtrate was subjected to Waters 2767 HPLC system (eluent (v/v):acetonitrile/(water+0.05% HCl)=10%-100%) for separation. The collected fractions were concentrated under reduced pressure to remove the solvents, and then lyophilized to give the hydrochloride salt of the target compound SIAIS1224117 (white solid, 5 mg, yield 25%). $^1$H NMR (500 MHz, DMSO) δ 11.00 (s, 1H), 9.92 (s, 1H), 7.67 (d, J=7.4 Hz, 1H), 7.58 (d, J=7.6 Hz, 1H), 7.53 (t, J=7.3 Hz, 1H), 7.22 (d, J=7.4 Hz, 2H), 7.18 (d, J=7.3 Hz, 2H), 5.13 (dd, J=13.5, 4.7 Hz, 1H), 4.31 (d, J=17.3 Hz, 1H), 4.18 (d, J=17.2 Hz, 1H), 3.49 (d, J=11.7 Hz, 2H), 3.37-3.34 (m, 2H), 3.18 (d, J=5.0 Hz, 2H), 2.99 (s, 2H), 2.92-2.85 (m, 5H), 2.60 (d, J=16.7 Hz, 1H), 2.42 (d, J=12.9 Hz, 1H), 2.04-1.97 (m, 1H), 1.82 (d, J=12.0 Hz, 2H), 1.73 (s, 4H). HRMS (ESI) m/z: calcd for $C_{28}H_{34}N_3O_3S^+$ [M+H]$^+$, 492.2315; found, 492.2317.

Example 169: 3-(4-((4-(2-((adamantan-1-yl)amino) ethyl)phenethyl)thio)-1-oxoisoindolin-2-yl)piperidine-2,6-dione (SIAIS1224121)

Referring to the method of example 168, the compound SIAIS1224121 was prepared under appropriate conditions that will be recognized by one skilled in the art, except that the amine employed in the last step was 1-adamantanamine. The hydrochloride salt of compound SIAIS1224121 was obtained (white solid, 7.7 mg, yield 35%). $^1$H NMR (500 MHz, DMSO) δ 10.99 (s, 1H), 8.83 (s, 2H), 7.68 (d, J=7.4 Hz, 1H), 7.59-7.54 (m, 2H), 7.25-7.17 (m, 4H), 5.13 (dd, J=13.1, 4.4 Hz, 1H), 4.32 (d, J=17.3 Hz, 1H), 4.19 (d, J=17.4 Hz, 1H), 3.35 (s, 2H), 3.03 (s, 2H), 2.95-2.84 (m, 5H), 2.59 (d, J=17.6 Hz, 1H), 2.43 (d, J=13.4 Hz, 1H), 2.12 (s, 3H), 2.01 (d, J=12.5 Hz, 1H), 1.89 (s, 6H), 1.63 (dd, J=31.0, 11.9 Hz, 6H). HRMS (ESI) m/z: calcd for $C_{33}H_{40}N_3O_3S^+$ [M+H]$^+$, 558.2785; found, 558.2782.

Example 170: 3-(1-oxo-4-((3-(4-(piperidin-1-ylmethyl)phenyl)propyl)thio)isoindolin-2-yl)piperidine-2,6-dione (SIAIS1227035)

Referring to the method of example 161, the compound SIAIS1227035 was prepared under appropriate conditions that will be recognized by one skilled in the art, except that the bromide used in the step 1 was 1-(bromomethyl)-4-(3-bromopropyl)benzene. The hydrochloride salt of compound SIAIS1227035 was obtained (white solid, 16.4 mg, yield 83%). $^1$H NMR (500 MHz, DMSO) δ 10.99 (s, 1H), 10.19 (s, 1H), 7.59 (t, J=7.7 Hz, 1H), 7.52-7.50 (m, 1H), 7.48 (d, J=8.0 Hz, 2H), 7.33-7.27 (m, 3H), 5.13 (dd, J=12.8, 4.9 Hz, 1H), 4.40-4.35 (m, 1H), 4.23 (d, J=18.4 Hz, 1H), 4.20 (d, J=4.6 Hz, 2H), 3.25 (d, J=10.6 Hz, 2H), 3.09 (t, J=6.6 Hz, 2H), 2.91 (dd, J=21.8, 9.0 Hz, 1H), 2.82-2.74 (m, 4H), 2.60 (d, J=15.5 Hz, 1H), 2.44 (d, J=12.9 Hz, 1H), 2.05-2.00 (m, 1H), 1.91 (dd, J=14.3, 7.2 Hz, 2H), 1.76 (s, 3H), 1.72-1.65 (m, 2H), 1.33 (d, J=6.5 Hz, 1H). HRMS (ESI) m/z: calcd for $C_{28}H_{34}N_3O_3S^+$ [M+H]$^+$, 492.2315; found, 492.2345.

Example 171: 3-(4-((3-(4-((cyclohexylamino) methyl)phenyl)propyl)thio)-1-oxoisoindolin-2-yl) piperidine-2,6-dione (SIAIS1227067)

Referring to the method of example 161, the compound SIAIS1227067 was prepared under appropriate conditions that will be recognized by one skilled in the art, except that the bromide used was 1-(bromomethyl)-4-(3-bromopropyl) benzene, and the amine used was cyclohexylamine. The hydrochloride salt of compound SIAIS1227067 was obtained (light yellow solid, 25.7 mg, yield 68%). $^1$H NMR (500 MHz, DMSO) δ 11.00 (s, 1H), 8.96 (s, 2H), 7.59 (t, J=7.5 Hz, 2H), 7.55-7.50 (m, 1H), 7.46 (d, J=7.9 Hz, 2H), 7.26 (d, J=7.3 Hz, 2H), 5.13 (dd, J=13.0, 4.8 Hz, 1H), 4.37 (d, J=17.3 Hz, 1H), 4.23 (d, J=17.3 Hz, 1H), 4.10 (s, 2H), 3.07 (t, J=6.9 Hz, 2H), 2.91 (dd, J=22.1, 8.8 Hz, 2H), 2.75 (t, J=7.6 Hz, 2H), 2.60 (d, J=15.3 Hz, 1H), 2.44 (d, J=12.2 Hz, 1H), 2.10 (d, J=10.4 Hz, 2H), 2.04-1.99 (m, 1H), 1.92-1.85 (m, 2H), 1.77 (d, J=11.2 Hz, 2H), 1.60 (d, J=12.3 Hz, 1H), 1.39-1.31 (m, 2H), 1.24-1.16 (m, 2H), 1.14-1.06 (m, 1H). HRMS (ESI) m/z: calcd for $C_{29}H_{36}N_{303}S^+$ [M+H]$^+$, 506.2472; found, 506.2497.

Example 172: 3-(4-((3-(4-(((adamantan-1-yl)amino) methyl)phenyl)propyl)thio)-1-oxoisoindolin-2-yl) piperidine-2,6-dione (SIAIS1227037)

Referring to the method of example 161, the compound SIAIS1227037 was prepared under appropriate conditions that will be recognized by one skilled in the art, except that the bromide used was 1-(bromomethyl)-4-(3-bromopropyl) benzene, and the amine used was 1-adamantanamine. The hydrochloride salt of compound SIAIS1227037 was obtained (white solid, 15 mg, yield 36%). $^1$H NMR (500 MHz, DMSO) δ 11.00 (s, 1H), 8.74 (s, 2H), 7.59 (t, J=8.4 Hz, 2H), 7.53 (t, J=7.3 Hz, 1H), 7.45 (d, J=8.1 Hz, 2H), 7.27 (d, J=7.3 Hz, 2H), 5.14 (dd, J=13.1, 4.6 Hz, 1H), 4.37 (d, J=17.5 Hz. 1H), 4.23 (d, J=17.3 Hz, 1H), 4.06 (s, 2H), 3.08 (t, J=7.1 Hz, 2H), 2.91 (dd, J=21.9, 8.7 Hz, 1H), 2.75 (t, J=7.4 Hz, 2H), 2.60 (d, J=17.2 Hz, 1H), 2.44 (d, J=13.4 Hz, 1H), 2.15 (s, 3H), 2.01 (d, J=7.7 Hz, 1H), 1.95 (s, 6H), 1.89 (dd, J=15.9, 7.8 Hz, 2H), 1.69 (d, J=12.1 Hz, 3H), 1.61 (d, J=11.9 Hz, 3H). HRMS (ESI) m/z: calcd for $C_{33}H_{40}N_3O_3S^+$ [M+H]$^+$, 558.2785; found, 558.2784.

Example 173: 3-(4-((3-(4-(morpholinomethyl)phenyl)propyl)thio)-1-oxoisoindolin-2-yl)piperidine-2,6-dione (SIAIS1227075)

Referring to the method of example 161, the compound SIAIS1227075 was prepared under appropriate conditions that will be recognized by one skilled in the art, except that the bromide used was 1-(bromomethyl)-4-(3-bromopropyl) benzene, and the amine used was morpholine. The hydrochloride salt of compound SIAIS1227075 was obtained (light yellow solid, 21.1 mg, yield 57%). $^1$H NMR (500 MHz, DMSO) δ 10.99 (s, 1H), 10.58 (s, 1H), 7.59 (t, J=8.6 Hz, 2H), 7.53 (d, J=7.3 Hz, 1H), 7.48 (s, 2H), 7.29 (d, J=7.1 Hz, 2H), 5.13 (dd, J=12.8, 4.6 Hz, 1H), 4.37 (d, J=17.5 Hz, 1H), 4.29 (s, 2H), 4.23 (d, J=17.4 Hz, 1H), 3.93 (d, J=12.6 Hz, 2H), 3.71 (s, 2H), 3.20 (d, J=11.1 Hz, 2H), 3.08 (d, J=7.2 Hz, 4H), 2.96-2.87 (m, 1H), 2.76 (t, J=7.3 Hz, 2H), 2.60 (d, J=16.8 Hz, 1H), 2.44 (d, J=13.8 Hz, 1H), 2.05-2.00 (m, 1H), 1.94-1.85 (m, 2H). HRMS (ESI) m/z: calcd for $C_{27}H_{32}N_3O_4S^+$ [M+H]+, 494.2108; found, 494.2136.

Example 174: N-(4-(adamantan-1-yl(methyl)amino) butyl)-2-((2-(2,6-dioxopiperidin-3-yl)-1-oxoisoindolin-4-yl)thio)acetamide (SIAIS287105)

Step 2: To a solution of the compound obtained from the step 1 (100 mg, 0.31 mmol) and aqueous formaldehyde solution (1 ml) in methanol (5 mL) was added acetic acid (2 drops) at room temperature. After the mixture was stirred at room temperature for 1 hour, sodium cyanoborohydride (39 mg, 0.62 mmol) was added thereto. Then the mixture was stirred at room temperature for 16 hours. The mixture was

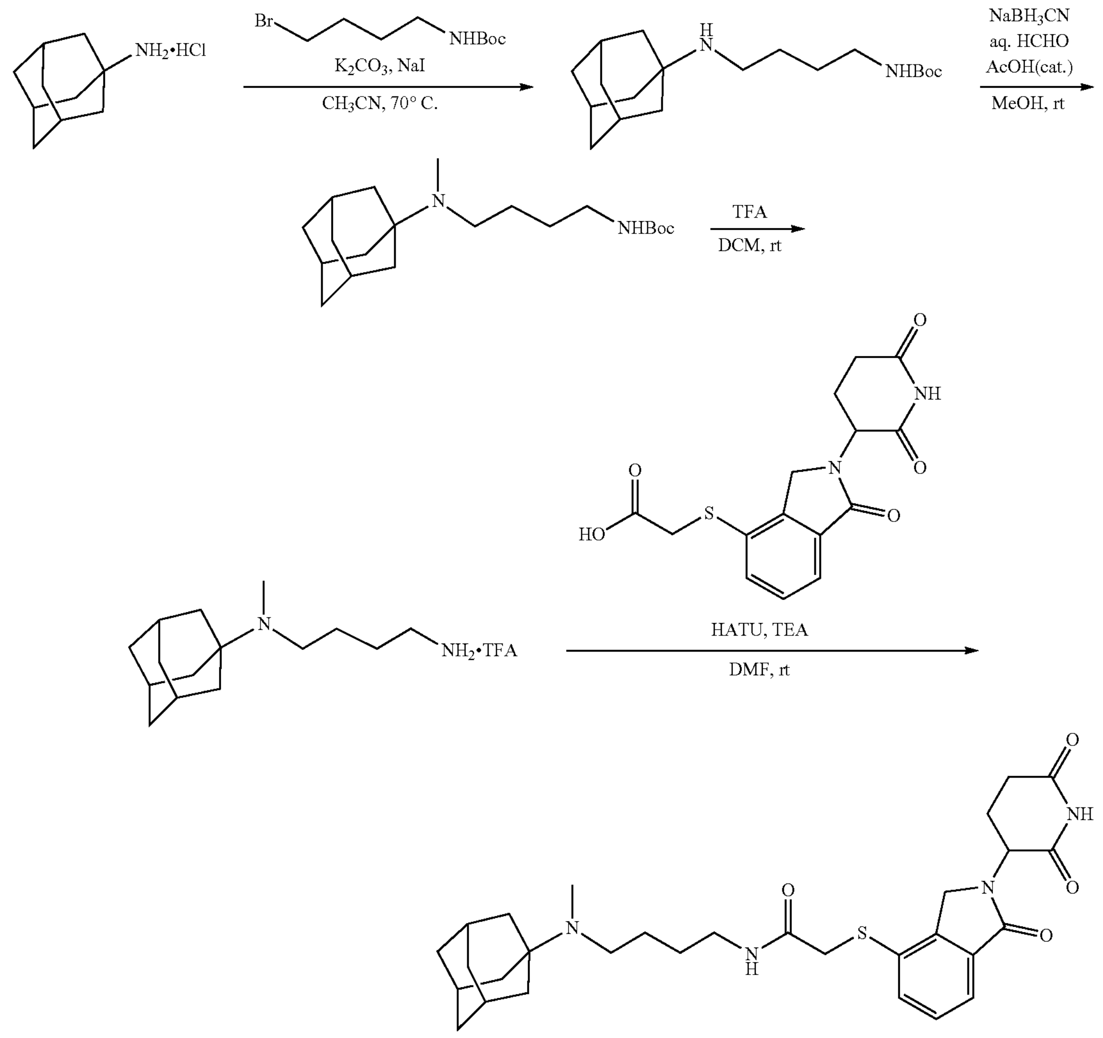

SIAIS287105

Step 1: To a solution of (1s,3s)-adamantane-1-amine hydrochloride (500 mg, 2.66 mmol) and tert-butyl (4-bromobutyl)carbamate (873 mg, 3.46 mmol) in acetonitrile (10 mL) were sequentially added potassium carbonate (1.1 g, 7.99 mmol) and sodium iodide (40 mg, 0.266 mmol) at room temperature. The mixture was then stirred at 70° C. for 16 hours. The mixture was filtered, and the filtrate was concentrated under reduced pressure. The resulting residue was subjected to a column chromatography (DCM:MeOH=10:1) for separation to give tert-butyl (4-((adamantan-1-yl)amino) butyl)carbamate as a pale yellow solid (208 mg, 24% yield). $^1$H NMR (500 MHz, CDCl3) δ 8.46 (s, 2H), 3.35-3.27 (m, 3H), 3.18-3.15 (m, 2H), 3.08-2.97 (m, 2H), 2.21 (s, 3H), 2.15 (s, 6H), 2.08-2.02 (m, 2H), 1.86-1.79 (m, 3H), 1.68-1.64 (m, 2H), 1.45 (s, 9H). MS m/z: 323.4 [M+H].

concentrated under reduced pressure, and the residue was dissolved in water (10 mL), extracted with dichloromethane (20 mL×3). The organic phase was combined, dried over anhydrous sodium sulfate, and filtered. The filtrate was concentrated under reduced pressure, and the residue was subjected to a column chromatography (DCM:MeOH=10:1) for separation to give tert-butyl (4-((adamantan-1-yl) (methyl)amino)butyl)carbamate (a colorless oil, 72 mg, yield 71% ). MS m/z: 337.5 [M+H].

Step 3: To a solution of the compound obtained from the step 2 (72 mg, 0.21 mmol) in dichloromethane (2 mL) was added trifluoroacetic acid (2 mL) at room temperature. After the mixture was stirred at room temperature for 1 hour, it was concentrated under reduced pressure to give N1-(adamantan-1-yl)-N1-methylbutane-1,4-diamine trifluoroacetate (light yellow oil, 80 mg). The crude product was used directly in the next step. MS m/z: 237.5 [M+H].

Step 4: To a solution of the compound obtained from the step 3 (20 mg, 0.06 mmol), 2-((2-(2,6-dioxopiperidin-3-yl)-1-oxoisoindoline-4-yl)thio)acetic acid (20 mg, 0.06 mmol), and HATU (34 mg, 0.09 mmol) in DMF (2 mL) was added triethylamine (18 mg, 0.18 mmol) at room temperature. The mixture was stirred at room temperature for 3 hours. The mixture was subjected to HPLC (HCl system) for separation to obtain SIAIS287105 as a white solid (4 mg, yield 12%). $^{1}$H NMR (500 MHz, MeOD) δ 7.75 (d, J=10.0 Hz, 1H), 7.72 (d, J=10.0 Hz, 1H), 7.56 (t, J=10.0 Hz, 1H), 5.19-5.15 (m, 1H), 4.57-4.46 (m, 2H), 3.76-3.65 (m, 2H), 3.39-3.32 (m, 1H), 3.22-3.07 (m, 2H), 2.96-2.89 (m, 1H), 2.82-2.77 (m, 1H), 2.72-2.64 (m, 4H), 2.59-2.49 (m, 1H), 2.24 (s, 3H), 2.21-2.18 (m, 1H), 1.99-1.90 (m, 6H), 1.78-1.70 (M, 6H), 1.49-1.28 (m, 4H). HRMS (ESI) m/z: calcd for $C_{30}H_{41}N_4O_4S$ $[M+H]^+$ 553.2843, found 553.2827.

Example 175: 3-(4-((4-(2-(adamantan-1-ylamino)ethyl)benzyl)thio)-1-oxoisoindolin-2-yl)piperidine-2,6-dione (SIAIS287128)

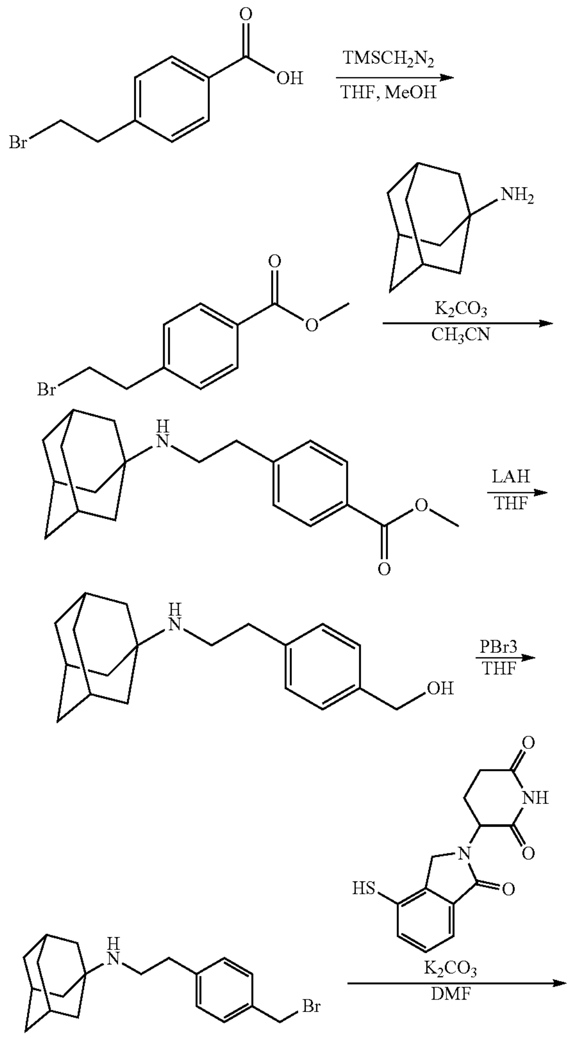

-continued

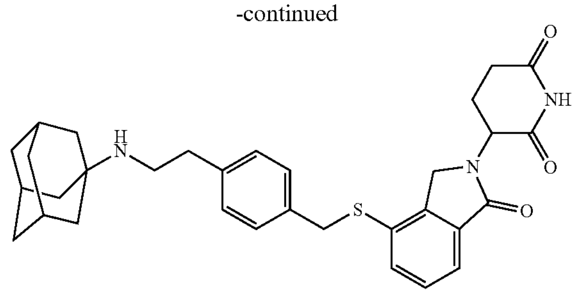

SIAIS287128

Step 1: To a solution of 4-(2-bromoethyl)benzoic acid (800 mg, 3.49 mmol) in dichloromethane (10 mL) and methanol (10 mL) was added dropwise a solution of 2M trimethylsilyl diazomethane (1.92 ml, 3.84 mmol) in cyclohexane at 0° C. The mixture was then stirred at room temperature for 2 hours. The reaction solution was quenched with water (10 mL), and extracted with dichloromethane (20 mL×3). The organic phases were combined, dried over anhydrous sodium sulfate, and filtered. The filtrate was concentrated under reduced pressure, and the residue was subjected to a column chromatography (petroleum ether: ethyl acetate=2:1) for separation to give methyl 4-(2-bromoethyl)benzoates a colorless oil (0.72 g, yield 85%). $^{1}$H NMR (500 MHz, $CDCl_3$) δ 7.99 (d, J=10.0 Hz, 2H), 7.29 (d, J=10.0 Hz, 2H), 3.91 (s, 3H), 3.59 (t, J=10.0 Hz, 2H), 3.22 (t, J=10.0 Hz, 2H).

Step 2: To a solution of the compound obtained from the step 1 (400 mg, 1.65 mmol) and 1-adamantanamine (309 mg, 1.65 mmol) in acetonitrile (10 mL) was added potassium carbonate (682 mg, 4.94 mmol) at room temperature. The mixture was then warmed up to 70° C. and stirred at 70° C. for 16 hours. The mixture was filtered, and the filtrate was concentrated under reduced pressure. The residue was washed with water (10 mL), extracted with dichloromethane (20 mL×3). The organic phases were combined, dried over anhydrous sodium sulfate, and filtered. The filtrate was concentrated under reduced pressure, and the residue was subjected to a column chromatography (DCM:MeOH=10:1) for separation to give methyl 4-(2-((adamantan-1-yl)amino)ethyl)benzoate as a light yellow solid (240 mg, yield 46%). MS m/z: 314.3 [M+H].

Step 3: To a solution of the compound obtained from the step 2 (100 mg, 0.32 mmol) in anhydrous tetrahydrofuran (4 mL) was added lithium aluminum hydride (24 mg, 0.64 mmol) at 0° C. The reaction solution was stirred at 0° C. for 1 hour. Then the reaction solution was quenched with water (0.1 mL), stirred for 10 minutes, dried over anhydrous sodium sulfate, and filtered. The filtrate was concentrated under reduced pressure to give (4-(2-((adamantan-1-yl)amino)ethyl)phenyl) methanol as a pale yellow solid (102 mg), and the crude product was used directly in the next step. MS m/z: 286.3 [M+H].

Step 4: To a solution of the compound obtained from the step 3 (110 mg, 0.39 mmol) in anhydrous tetrahydrofuran (4 mL) was added phosphorus tribromide (104 mg, 0.39 mmol) at 0° C. The reaction solution was stirred at 0° C. for 2 hours, and then quenched with water (10 mL), extracted with dichloromethane (20 mL×3). The organic phases were combined, dried over anhydrous sodium sulfate, and filtered. The filtrate was concentrated under reduced pressure to give N-(4-(bromomethyl)phenethyl)adamantan-1-amine as a white solid (150 mg). The crude product was used directly in the next step. MS m/z: 348.2, 350.2 [M+H].

Step 5: To a solution of the compound obtained from the step 4 (30 mg, 0.09 mmol) and 3-(4-mercapto-1-oxoisoindolin-2-yl)piperidine-2,6-dione (24 mg, 0.09 mmol) in DMF (2 mL) was added potassium carbonate (24 mg, 0.18 mmol) at room temperature. The mixture was then stirred at room temperature for 2 hours. The mixture was filtered, and the filtrate was subjected to HPLC (HCl system) for separation to give a white solid SIAIS287128 (14 mg, yield 31%). $^1H$ NMR (500 MHz, MeOD) δ 7.66 (d, J=10.0 Hz, 2H), 7.48 (t, J=10.0 Hz, 1H), 7.21 (d, J=5.0 Hz, 2H), 7.16 (d, J=5.0 Hz, 2H), 5.10 (dd, J=10.0, 5.0 Hz, 1H), 4.26-4.13 (m, 4H), 3.21-3.06 (m, 2H), 2.92-2.85 (m, 3H), 2.79-2.74 (m, 1H), 2.49-2.40 (m, 1H), 2.20 (s, 3H), 2.12-2.09 (m, 1H), 1.91 (s, 6H), 1.84-1.67 (m, 6H). HRMS (ESI) m/z: calcd for $C_{32}H_{38}N_3O_3S$ $[M+H]^+$ 544.2628, found 544.2535.

Example 176: 1-(3-chloro-4-methylphenyl)-3-(4-((2-(2,6-dioxopiperidin-3-yl)-1-oxoisoindolin-4-yl)thio)butyl)urea (SIAIS269095)

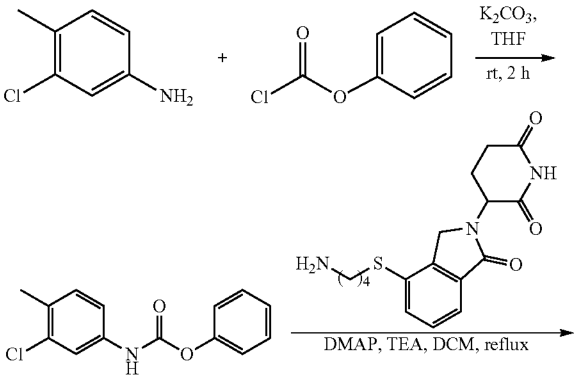

SIAIS269066

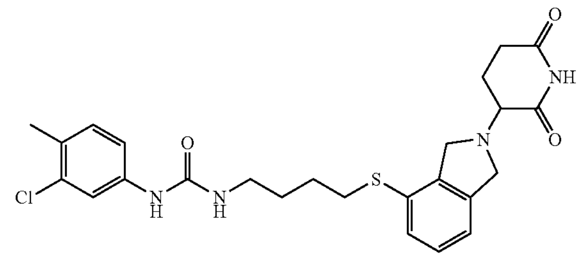

SIAIS269095

Step 1: A single-necked flask was sequentially charged with 3-chloro-4-methylaniline (7.06 mmol, 1.0 eq), anhydrous THF (25 mL), and potassium carbonate (9.18 mmol, 1.3 eq), followed by addition dropwise of phenyl chloroformate (7.42 mmol, 1.05 eq). After the mixture was reacted at room temperature for 2 h, it was filtered, and the filtrate was rotary evaporated until about 5 mL of solvent remained. To the residue were added water (20 mL) and ethanol to make it homogeneous. Then the resulting mixture was stirred at room temperature for 1 h, and a white solid was precipitated out. After filtration, the filter cake was dried to give 1.06 g of white solid SIAIS 269066 (yield 57%). LRMS (ESI) m/z: calcd for $C_{14}H_{13}ClNO_2^+$ $[M+H]^+$, 262.06; found, 262.1.

Step 2: A single-necked flask was sequentially charged with SIAIS 269066 (0.03821 mmol, 1.0 eq), DCM (3 mL), the corresponding intermediate containing terminal amine (0.042 mmol, 1.1 eq), DMAP (0.042 mmol, 1.1 eq), and triethylamine (0.042 mmol, 1.1 eq). The mixture was refluxed overnight. After cooling to room temperature, the resulting mixture was rotary evaporated to dryness. The residue was dissolved in a small amount of DMF and then subjected to HPLC (eluent (v/v): acetonitrile/(water+0.05% HCl)=10%-100%) for separation. The collected fractions were rotary evaporated to remove acetonitrile, and lyophilized to give the target compound SIAIS269095 as a white solid (11.8 mg, yield 60%). $^1H$ NMR (500 MHz, DMSO) δ 10.98 (s, 1H), 8.49 (s, 1H), 7.64 (dd, J=7.0, 1.5 Hz, 2H), 7.56 (d, J=6.6 Hz, 1H), 7.51 (t, J=7.6 Hz, 1H), 7.16 (d, J=8.4 Hz, 1H), 7.08 (dd, J=8.3, 2.2 Hz, 1H), 6.19 (t, J=5.4 Hz, 1H), 5.12 (dd, J=13.3, 5.1 Hz, 1H), 4.35 (d, J=17.4 Hz, 1H), 4.22 (d, J=17.4 Hz, 1H), 3.15-3.06 (m, 4H), 2.95-2.86 (m, 1H), 2.58 (d, J=18.3 Hz, 1H), 2.49-2.41 (m, 1H), 2.22 (s, 3H), 2.03-1.97 (m, 1H), 1.66-1.52 (m, 4H). HRMS (ESI) m/z: calcd for $C_{25}H_{28}ClN_4O_4S^+$ $[M+H]^+$, 515.1514; found, 515.1511.

Example 177: 1-(3-chloro-4-methylphenyl)-3-(7-((2-(2,6-dioxopiperidin-3-yl)-1-oxoisoindolin-4-yl)thio)heptyl)urea (SIAIS269068)

Referring to the method of example 176, under appropriate conditions that will be recognized by one skilled in the art, the compound SIAIS269068 was prepared from the compound SIAIS269066 and the intermediate SIAIS171135. The compound SIAIS269068 was obtained as a white solid (12.3 mg, yield 58%). $^1H$ NMR (500 MHz, DMSO) δ 10.98 (s, 1H), 8.47 (s, 1H), 7.63 (d, J=2.2 Hz, 1H), 7.62 (dd, J=7.5, 1.1 Hz, 1H), 7.56 (dd, J=7.4, 1.0 Hz, 1H), 7.52 (t, J=7.5 Hz, 1H), 7.15 (d, J=8.4 Hz, 1H), 7.08 (dd, J=8.3, 2.1 Hz, 1H), 6.13 (t, J=5.6 Hz, 1H), 5.12 (dd, J=13.3, 5.1 Hz, 1H), 4.35 (d, J=17.4 Hz, 1H), 4.21 (d, J=17.4 Hz, 1H), 3.10-3.01 (m, 4H), 2.95-2.86 (m, 1H), 2.59 (d, J=18.0 Hz, 1H), 2.49-2.41 (m, 1H), 2.22 (s, 3H), 2.03-1.96 (m, 1H), 1.64-1.57 (m, 2H), 1.45-1.37 (m, 4H), 1.34-1.20 (m, 4H). HRMS (ESI) m/z: calcd for $C_{28}H_{34}ClN_4O_4S^+$ $[M+H]^+$, 557.1984; found, 557.1989.

Example 178: 1-(3-chloro-4-methylphenyl)-3-(8-((2-(2,6-dioxopiperidin-3-yl)-1-oxoisoindolin-4-yl)thio)octyl)urea (SIAIS269072)

Referring to the method of example 176, under appropriate conditions that will be recognized by one skilled in the art, the compound SIAIS269072 was prepared from the compound SIAIS269066 and the intermediate SIAIS171136. The compound SIAIS269072 was obtained as a white solid (11.5 mg, yield 53%). $^1H$ NMR (500 MHz, DMSO) δ 10.98 (s, 1H), 8.46 (s, 1H), 7.63 (d, J=2.1 Hz, 1H), 7.62 (d, J=7.4 Hz, 1H), 7.56 (d, J=6.5 Hz, 1H), 7.52 (t, J=7.5 Hz, 1H), 7.15 (d, J=8.3 Hz, 1H), 7.08 (dd, J=8.3, 2.1 Hz, 1H), 6.12 (t, J=5.6 Hz, 1H), 5.12 (dd, J=13.4, 5.2 Hz, 1H), 4.35 (d, J=17.4 Hz, 1H), 4.21 (d, J=17.4 Hz, 1H), 3.10-3.01 (m, 4H), 2.95-2.86 (m, 1H), 2.59 (d, J=15.9 Hz, 1H), 2.49-2.41 (m, 1H), 2.22 (s, 3H), 2.04-1.97 (m, 1H), 1.64-1.55 (m, 2H), 1.44-1.35 (m, 4H), 1.26 (s, 6H). HRMS (ESI) m/z: calcd for $C_{29}H_{36}ClN_4O_4S^+$ $[M+H]^+$, 571.2140; found, 571.2135.

Example 179: 3-(4-((7-(adamantan-2-yloxy)heptyl)thio)-1-oxoisoindolin-2-yl)piperidine-2,6-dione (SIAIS269159)

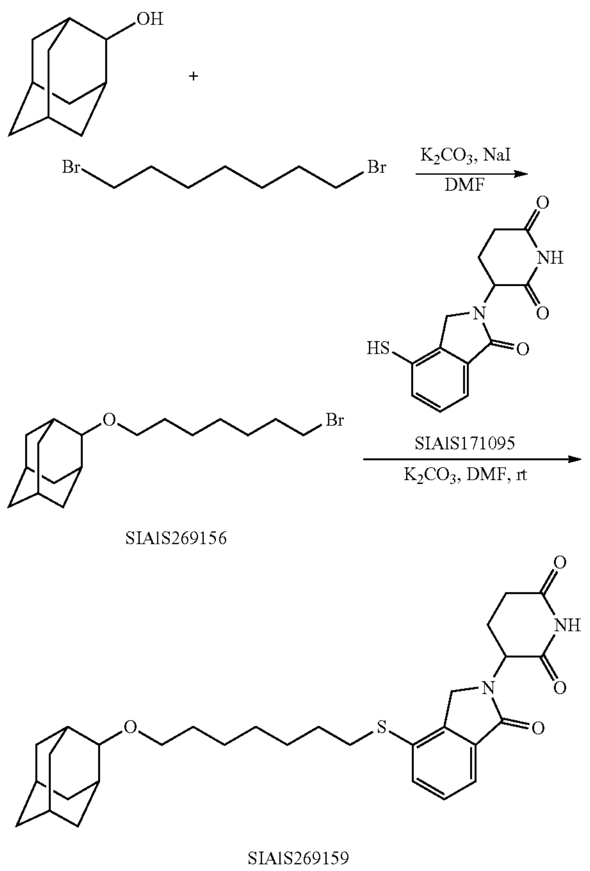

Step 1: A single-necked flask was sequentially charged with adamantane-2-ol (6.57 mmol, 1.0 eq), DMF (5 mL), 1,7-dibromoheptane (13.14 mmol, 2.0 eq), potassium carbonate (13.14 mmol, 2.0 eq), and sodium iodide (6.57 mmol, 1.0 eq). The mixture was reacted at 40° C. for 1 h and heated to 80° C. overnight. The reaction was quenched with water and extracted with ethyl acetate for three times. The organic phases were combined, washed with saturated brine, dried over anhydrous sodium sulfate, and subjected to silica gel column chromatography (eluent (v/v):pure petroleum ether to petroleum ether:ethyl acetate=10%) for separation to obtain 1.2 g of colorless oily liquid (yield 55%).

Step 2: A single-necked flask was sequentially charged with SIAIS269156 (0.061 mmol, 1.0 eq), DMF (2 mL), SIAIS171095 (0.067 mmol, 1.1 eq), and potassium carbonate (0.12 mmol, 2.0 eq). Then the mixture was reacted at room temperature for 1 h. The reaction mixture was subjected to preparative HPLC (eluent (v/v):acetonitrile/(water+0.05% HCl)=10%-100%) for separation. The collected fractions were rotary evaporated to remove acetonitrile, and lyophilized to give the target compound SIAIS 269159 as a white solid (12 mg, yield 30%). $^1$H NMR (500 MHz, DMSO) δ 10.98 (s, 1H), 7.62 (d, J=7.3 Hz, 1H), 7.56 (d, J=7.2 Hz, 1H), 7.52 (t, J=7.3 Hz, 1H), 5.12 (dd, J=13.4, 4.8 Hz, 1H), 4.35 (d, J=17.3 Hz, 1H), 4.21 (d, J=17.4 Hz, 1H), 3.37-3.33 (m, 3H), 3.07 (t, J=7.0 Hz, 2H), 2.96-2.86 (m, 1H), 2.58 (d, J=18.4 Hz, 1H), 2.48-2.41 (m, 1H), 2.04-1.97 (m, 1H), 1.91 (s, 4H), 1.76 (d, J=8.4 Hz, 3H), 1.70 (s, 1H), 1.65-1.55 (m, 5H), 1.48 (s, 2H), 1.39 (d, J=11.9 Hz, 4H), 1.31 (s, 4H), 1.23 (s, 1H). HRMS (ESI) m/z: calcd for $C_{30}H_{41}ClN_2O_4S^+$ [M+H]$^+$, 525.2782; found, 525.2781.

Example 180: 3-(4-((4-(((dicyclopropylmethyl)amino)methyl)benzyl)thio)-1-oxoisoindolin-2-yl)piperidine-2,6-dione (SIAIS1227183)

Referring to the method of Scheme 11, the compound SIAIS1227183 was prepared under appropriate conditions that will be recognized by one skilled in the art, except that the substrates used were 3-(4-((4-(bromomethyl)benzyl)thio)-1-oxoisoindolin-2-yl)piperidine-2,6-dione (SIAIS1220141) and dicyclopropylmethylamine. The hydrochloride salt of compound SIAIS1227183 was obtained (white solid, 7.7 mg, yield 31%). $^1$H NMR (500 MHz, DMSO) δ 10.99 (s, 1H), 9.06 (s, 2H), 7.69 (d, J=7.4 Hz, 1H), 7.57 (d, J=7.2 Hz, 1H), 7.52-7.46 (m, 3H), 7.43 (d, J=7.4 Hz, 2H), 5.11 (d, J=13.4, 3.9 Hz, 1H), 4.42-4.34 (m, 2H), 4.29 (d, J=17.5 Hz, 1H), 4.21 (s, 2H), 4.15 (d, J=17.8 Hz, 1H), 2.91 (t, J=12.4 Hz, 1H), 2.59 (d, J=17.2 Hz, 1H), 2.48-2.38 (m, 1H), 2.06-1.95 (m, 2H), 1.11 (s, 2H), 0.59 (d, J=6.9 Hz, 4H), 0.44 (d, J=21.7 Hz, 4H). HRMS (ESI) m/z: calcd for $C_{28}H_{32}N_3O_3S^+$ [M+H]$^+$, 490.2159; found, 490.2155.

Example 181: 3-(4-((4-(2-((4,4-dimethylcyclohexyl)amino)ethyl)benzyl)thio)-1-oxoisoindolin-2-yl)piperidine-2,6-dione (SIAIS1227103)

Referring to the method of example 155, the compound SIAIS1227103 was prepared under appropriate conditions that will be recognized by one skilled in the art, except that the amine used in the step 4 was 4,4-dimethylcyclohexylamine. The hydrochloride salt of compound SIAIS1227103 was obtained (white solid, 13 mg, yield 83%). $^1$H NMR (500 MHz, DMSO) δ 10.98 (s, 1H), 8.68 (s, 2H), 7.68 (d, J=7.2 Hz, 1H), 7.58 (d, J=7.3 Hz, 1H), 7.50 (t, J=7.2 Hz, 1H), 7.32 (d, J=7.4 Hz, 2H), 7.20 (d, J=7.4 Hz, 2H), 5.11 (dd, J=13.2, 4.6 Hz, 1H), 4.36-4.29 (m, 2H), 4.25 (d, J=17.3 Hz, 1H), 4.15 (d, J=17.3 Hz, 1H), 3.11 (s, 2H), 3.00-2.86 (m, 4H), 2.59 (d, J=17.8 Hz, 1H), 2.41 (d, J=14.2 Hz, 1H), 1.98 (s, 1H), 1.84 (d, J=11.5 Hz, 2H), 1.56-1.46 (m, 2H), 1.41 (d, J=13.2 Hz, 2H), 1.18 (t, J=13.7 Hz, 2H), 0.89 (s, 6H). HRMS (ESI) m/z: calcd for $C_{30}H_{38}N_3O_3S^+$ [M+H]$^+$, 520.2625; found, 520.2627.

Example 182: 3-(4-((4-(((4,4-dimethylcyclohexyl)amino)methyl)benzyl)thio)-1-oxoisoindolin-2-yl)piperidine-2,6-dione (SIAIS1227105)

Referring to the method of Scheme 11, the compound SIAIS1227105 was prepared under appropriate conditions that will be recognized by one skilled in the art, except that the substrates used were 3-(4-((4-(bromomethyl)benzyl)thio)-1-oxoisoindolin-2-yl)piperidine-2,6-dione (SIAIS1220141) and 4,4-dimethylcyclohexylamine. The hydrochloride salt of compound SIAIS1227105 was obtained (white solid, 9.3 mg, yield 62%). $^1$H NMR (500 MHz, DMSO) δ 10.99 (s, 1H), 9.06 (s, 2H), 7.68 (d, J=7.2 Hz, 1H), 7.57 (d, J=7.1 Hz, 1H), 7.52-7.45 (m, 3H), 7.42 (d, J=6.2 Hz, 2H), 5.11 (d, J=11.8 Hz, 1H), 4.38 (s, 2H), 4.29 (d, J=17.2 Hz, 1H), 4.15 (d, J=17.3 Hz, 1H), 4.09 (s, 2H), 2.96-2.83 (m, 2H), 2.59 (d, J=17.2 Hz, 1H), 2.42 (d, J=12.9 Hz, 1H), 1.99 (s, 1H), 1.89 (d, J=12.0 Hz, 2H), 1.61 (d, J=11.9 Hz, 2H), 1.41 (d, J=12.9 Hz, 2H), 1.16 (t, J=12.6 Hz, 2H), 0.89 (s, 6H). HRMS (ESI) m/z: calcd for $C_{29}H_{36}N_3O_3S^+$ [M+H]$^+$, 506.2472; found, 506.2477.

Example 183: 3-(4-((4-((4,4-dimethylpiperidin-1-yl) methyl)benzyl)thio)-1-oxoisoindolin-2-yl)piperidine-2,6-dione (SIAIS1227113)

Referring to the method of Scheme 11, the compound SIAIS1227113 was prepared under appropriate conditions that will be recognized by one skilled in the art, except that the substrates used were 3-(4-((4-(bromomethyl)benzyl) thio)-1-oxoisoindolin-2-yl)piperidine-2,6-dione (SIAIS1220141) and 4,4-dimethylpiperidine. The hydrochloride salt of compound SIAIS1227113 was obtained (yellow solid, 8.5 mg, yield 58%). $^1$H NMR (500 MHz, DMSO) δ 10.99 (s, 1H), 10.02 (s, 1H), 7.66 (d, J=7.7 Hz, 1H), 7.58 (d, J=7.3 Hz, 1H), 7.53-7.46 (m, 3H), 7.41 (d, J=7.5 Hz, 2H), 5.11 (d, J=9.0 Hz, 1H), 4.36 (s, 2H), 4.32-4.21 (m, 3H), 4.14 (d, J=17.2 Hz, 1H), 3.07 (s, 2H), 3.04-2.86 (m, 3H), 2.59 (d, J=17.3 Hz, 1H), 2.48-2.38 (m, 1H), 2.01-1.94 (m, 1H), 1.65 (s, 2H), 1.47 (d, J=13.7 Hz, 2H), 0.96 (d, J=21.3 Hz, 6H). HRMS (ESI) m/z: calcd for $C_{28}H_{34}N_3O_3S^+$ [M+H]$^+$, 492.2315; found, 492.2316.

Example 184: 3-(4-((4-((6-azaspiro[2.5]octan-6-yl) methyl)benzyl)thio)-1-oxoisoindolin-2-yl)piperidine-2,6-dione (SIAIS1227115)

Referring to the method of Scheme 11, the compound SIAIS1227115 was prepared under appropriate conditions that will be recognized by one skilled in the art, except that the substrates used were 3-(4-((4-(bromomethyl)benzyl) thio)-1-oxoisoindolin-2-yl)piperidine-2,6-dione (SIAIS1220141) and 6-azaspiro[2.5]octane. The hydrochloride salt of compound SIAIS1227115 was obtained (light yellow solid, 9 mg, yield 61%). $^1$H NMR (500 MHz, DMSO) δ 10.98 (s, 1H), 10.34 (s, 1H), 7.66 (s, 1H), 7.58 (s, 1H), 7.50 (s, 3H), 7.41 (s, 2H), 5.10 (d, J=13.0 Hz, 1H), 4.36 (s, 2H), 4.26 (s, 3H), 4.14 (d, J=16.6 Hz, 1H), 3.24 (s, 2H), 2.90 (s, 3H), 2.63-2.56 (m, 1H), 2.46-2.33 (m, 1H), 2.13 (s, 2H), 1.98 (s, 1H), 1.08 (d, J=13.0 Hz, 2H), 0.41 (s, 2H), 0.34 (s, 2H). HRMS (ESI) m/z: calcd for $C_{28}H_{32}N_3O_3S^+$ [M+H]$^+$, 490.2159; found, 490.2156.

Example 185: 3-(4-((4-((3,5-dimethylpiperidin-1-yl) methyl)benzyl)thio)-1-oxoisoindolin-2-yl)piperidine-2,6-dione (SIAIS1227117)

Referring to the method of Scheme 11, the compound SIAIS1227117 was prepared under appropriate conditions that will be recognized by one skilled in the art, except that the substrates used were 3-(4-((4-(bromomethyl)benzyl) thio)-1-oxoisoindolin-2-yl)piperidine-2,6-dione (SIAIS1220141) and 3,5-dimethylpiperidine. The hydrochloride salt of compound SIAIS1227117 was obtained (light yellow solid, 9.4 mg, yield 64%). $^1$H NMR (500 MHz, DMSO) δ 10.99 (s, 1H), 10.42 (s, 1H), 7.67 (d, J=7.4 Hz, 1H), 7.58 (d, J=7.3 Hz, 1H), 7.49 (d, J=6.6 Hz, 3H), 7.42 (d, J=7.2 Hz, 2H), 5.11 (dd, J=13.4, 4.0 Hz, 1H), 4.37 (s, 2H), 4.28 (d, J=17.6 Hz, 1H), 4.20 (s, 2H), 4.14 (d, J=17.5 Hz, 1H), 3.15 (d, J=11.0 Hz, 2H), 2.97-2.86 (m, 1H), 2.59 (d, J=16.9 Hz, 1H), 2.46-2.33 (m, 3H), 1.96 (s, 3H), 1.76-1.68 (m, 1H), 0.84 (d, J=6.1 Hz, 6H), 0.73 (q, J=12.2 Hz, 1H). HRMS (ESI) m/z: calcd for $C_{28}H_{34}N_3O_3S^+$ [M+H]$^+$, 492.2315; found, 492.2316.

Example 186: 3-(4-((4-((3-azaspiro[5.5]undecan-3-yl)methyl)benzyl)thio)-1-oxoisoindolin-2-yl)piperidine-2,6-dione (SIAIS1227119)

Referring to the method of Scheme 11, the compound SIAIS1227119 was prepared under appropriate conditions that will be recognized by one skilled in the art, except that the substrates used were 3-(4-((4-(bromomethyl)benzyl) thio)-1-oxoisoindolin-2-yl)piperidine-2,6-dione (SIAIS1220141) and 3-azaspiro[5.5]undecane. The hydrochloride salt of compound SIAIS1227119 was obtained (light yellow solid, 9.4 mg, yield 74%). $^1$H NMR (500 MHz, DMSO) δ 10.99 (s, 1H), 9.73 (s, 1H), 7.66 (d, J=7.4 Hz, 1H), 7.58 (d, J=7.3 Hz, 1H), 7.49 (t, J=7.6 Hz, 1H), 7.47-7.39 (m, 4H), 5.11 (d, J=9.9 Hz, 1H), 4.36 (s, 2H), 4.31-4.20 (m, 3H), 4.14 (d, J=17.3 Hz, 1H), 3.10-2.86 (m, 5H), 2.59 (d, J=17.8 Hz, 1H), 2.46-2.37 (m, 1H), 1.98 (s, 1H), 1.73 (d, J=13.3 Hz, 2H), 1.43 (d, J=25.6 Hz, 4H), 1.37 (s, 5H), 1.21 (s, 2H), 0.96 (d, J=21.4 Hz, 1H). HRMS (ESI) m/z: calcd for $C_{31}H_{38}N_3O_3S^+$ [M+H]$^+$, 532.2628; found, 532.2626.

Example 187: 3-(4-((4-chlorobenzyl)thio)-1-oxoisoindolin-2-yl)piperidine-2,6-dione (SIAIS1227127)

Referring to the method of Scheme 9, the compound SIAIS1227127 was prepared under appropriate conditions that will be recognized by one skilled in the art, except that the substrate used was 1-(bromomethyl)-4-chlorobenzene. The target compound SIAIS1227127 was obtained as a light yellow solid (12 mg, yield 30%). $^1$H NMR (500 MHz, DMSO) δ 10.98 (s, 1H), 7.64 (s, 1H), 7.58 (t, J=5.8 Hz, 1H), 7.50 (dd, J=12.8, 7.2 Hz, 1H), 7.34 (d, J=5.1 Hz, 4H), 5.10 (d, J=13.1 Hz, 1H), 4.33 (s, 2H), 4.23 (dd, J=17.2, 4.3 Hz, 1H), 4.17 (dd, J=17.4, 4.6 Hz, 1H), 2.90 (t, J=15.1 Hz, 1H), 2.58 (d, J=18.5 Hz, 1H), 2.47-2.35 (m, 1H), 1.97 (s, 1H). HRMS (ESI) m/z: calcd for $C_{20}H_{18}N_2O_3S^+$ [M+H]$^+$, 401.0721; found, 401.0724.

Example 188: 3-(1-oxo-4-((3-(piperidin-1-ylmethyl) benzyl)thio)isoindolin-2-yl)piperidine-2,6-dione (SIAIS1227131)

Referring to the method of Scheme 11, the compound SIAIS1227131 was prepared under appropriate conditions that will be recognized by one skilled in the art, except that the substrates used were the compound SIAIS1227123 and piperidine. The hydrochloride salt of compound SIAIS1227131 was obtained (yellow solid, 8.5 mg, yield 41%). $^1$H NMR (500 MHz, DMSO) δ 11.00 (s, 1H), 10.14 (s, 1H), 7.66 (d, J=7.5 Hz, 1H), 7.58 (d, J=7.3 Hz, 1H), 7.49 (d, J=7.1 Hz, 1H), 7.44 (s, 3H), 7.39 (d, J=7.3 Hz, 1H), 5.11 (d, J=9.1 Hz, 1H), 4.35 (s, 2H), 4.27 (d, J=17.5 Hz, 1H), 4.15 (d, J=17.7 Hz, 3H), 3.16 (d, J=12.0 Hz, 1H), 3.10 (d, J=11.2 Hz, 1H), 2.96-2.86 (m, 1H), 2.76-2.65 (m, 2H), 2.62-2.56 (m, 1H), 2.47-2.36 (m, 1H), 1.99 (s, 1H), 1.76-1.61 (m, 5H), 1.35-1.23 (m, 1H). HRMS (ESI) m/z: calcd for $C_{26}H_{30}N_3O_3S^+$ [M+H]$^+$, 464.2002; found, 464.2006.

Example 189: 3-(4-((3-((cyclohexylamino)methyl) benzyl)thio)-1-oxoisoindolin-2-yl)piperidine-2,6-dione (SIAIS1227133)

Referring to the method of Scheme 11, the compound SIAIS1227133 was prepared under appropriate conditions that will be recognized by one skilled in the art, except that the substrates used were the compound SIAIS1227123 and cyclohexylamine. The hydrochloride salt of compound SIAIS1227133 was obtained (light yellow solid, 11 mg, yield 46%). $^1$H NMR (500 MHz, DMSO) δ $^1$H NMR (500 MHz, DMSO) δ 10.99 (s, 1H), 8.99 (s, 2H), 7.68 (d, J=7.3 Hz, 1H), 7.61-7.54 (m, 2H), 7.51 (s, 1H), 7.42-7.34 (m, 1H), 7.38 (d, J=12.3 Hz, 2H), 5.12 (d, J=11.8 Hz, 1H), 4.36 (s, 2H), 4.29 (d, J=17.3 Hz, 1H), 4.17 (d, J=17.5 Hz, 1H), 4.11 (s, 2H), 3.07 (s, 1H), 2.97-2.86 (m, 3H), 2.73 (s, 1H), 2.60 (d, J=17.2 Hz, 1H), 2.46-2.36 (m, 1H), 2.07 (d, J=10.7 Hz, 2H), 1.99 (s, 1H), 1.76 (d, J=11.7 Hz, 2H), 1.60 (d, J=11.1 Hz, 1H), 1.40-1.29 (m, 2H). HR-MS (ESI) m/z: calcd for $C_{27}H_{32}N_3O_3S^+$ [M+H]$^+$, 478.2159; found, 478.2155.

Example 190: 3-(4-((3-(((adamantan-1-yl)amino)methyl)benzyl)thio)-1-oxoisoindolin-2-yl)piperidine-2,6-dione (SIAIS1227135)

Referring to the method of Scheme 11, the compound SIAIS1227135 was prepared under appropriate conditions that will be recognized by one skilled in the art, except that the substrates used were the compound SIAIS1227123 and 1-adamantanamine. The hydrochloride salt of compound SIAIS1227135 was obtained (light yellow solid, 11 mg, yield 43%). $^1$H NMR (500 MHz, DMSO) δ 11.00 (s, 1H), 8.90 (s, 2H), 7.70 (d, J=7.6 Hz, 1H), 7.58 (s, 2H), 7.52 (t, J=7.6 Hz, 1H), 7.47 (d, J=7.2 Hz, 1H), 7.42-7.34 (m, 2H), 5.12 (d, J=9.2 Hz, 1H), 4.37 (s, 2H), 4.31 (d, J=17.7 Hz, 1H), 4.18 (d, J=17.2 Hz, 1H), 4.07 (s, 2H), 2.96-2.87 (m, 1H), 2.59 (d, J=17.3 Hz, 1H), 2.48-2.37 (m, 1H), 2.14 (s, 3H), 2.02-1.97 (m, 1H), 1.95 (s, 6H), 1.68 (d, J=11.8 Hz, 3H), 1.61 (d, J=11.8 Hz, 3H). HRMS (ESI) m/z: calcd for $C_{31}H_{36}N_3O_3S^+$ [M+H]$^+$, 530.2472; found, 530.2476.

Example 191: 3-(4-((3-(morpholinomethyl)benzyl)thio)-1-oxoisoindolin-2-yl)piperidine-2,6-dione (SIAIS1227137)

Referring to the method of Scheme 11, the compound SIAIS1227137 was prepared under appropriate conditions that will be recognized by one skilled in the art, except that the substrates used were the compound SIAIS1227123 and morpholine. The hydrochloride salt of compound SIAIS1227137 was obtained (white solid, 11 mg, yield 39%). $^1$H NMR (500 MHz, DMSO) δ 11.00 (s, 1H), 10.85 (s, 1H), 7.66 (d, J=6.8 Hz, 1H), 7.58 (s, 1H), 7.53-7.42 (m, 4H), 7.42-7.36 (m, 1H), 5.11 (d, J=12.5 Hz, 1H), 4.35 (s, 2H), 4.26 (s, 3H), 4.15 (d, J=17.2 Hz, 1H), 3.91 (d, J=12.2 Hz, 2H), 3.80-3.67 (m, 2H), 3.09 (t, J=12.4 Hz, 2H), 3.05-2.85 (m, 3H), 2.59 (d, J=17.0 Hz, 1H), 2.46-2.35 (m, 1H), 1.99 (s, 1H). HRMS (ESI) m/z: calcd for $C_{25}H_{28}N_3O_4S^+$ [M+H]$^+$, 466.1795; found, 466.1795.

Example 192: 3-(4-((2,5-dibromo-4-(piperidin-1-ylmethyl)benzyl)thio)-1-oxoisoindolin-2-yl)piperidine-2,6-dione (SIAIS1227139)

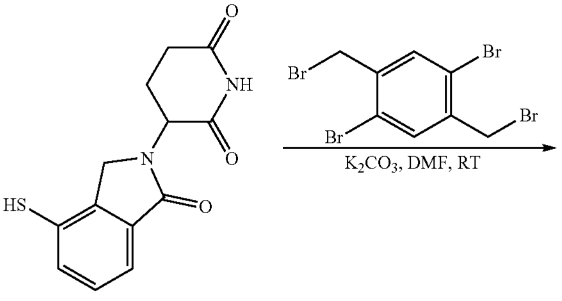

1
(SIAIS171075)

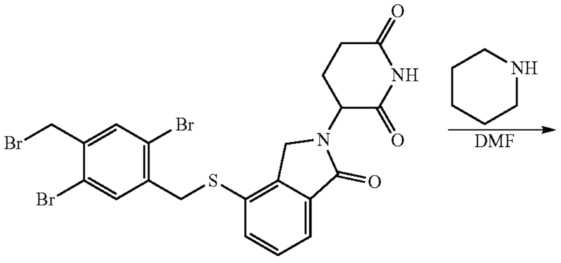

2

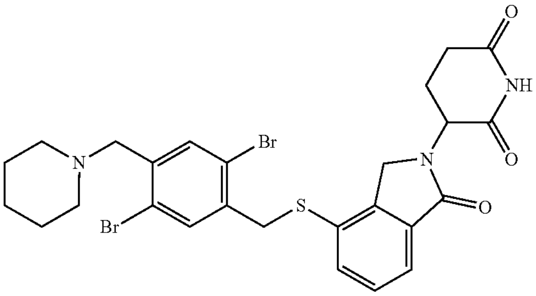

SIAIS1227139

Step 1: A 25 mL egg-shaped flask was charged with SIAIS171075 (1 mmol, 1 equiv), potassium carbonate (2 mmol, 2 equiv), and DMF (5 mL), followed by 1,4-dibromo-2,5-bis(bromomethyl)benzene (1.5 mmol, 1.5 equiv). The reaction mixture was stirred and reacted at room temperature for 1 h. After the reaction was complete, the mixture was filtered to remove the insoluble materials. The filtrate was subjected to ISCO reverse phase column chromatography (eluent (v/v):acetonitrile/water=10%-100%) for separation. The collected fractions were concentrated under reduced pressure to remove the solvents to give the intermediate 2 (white solid, 134 mg, yield 22%).

Step 2: A 25 mL single-necked flask was charged with the intermediate 2 (0.05 mmol, 1 equiv) and DMF (2 mL), followed by addition of piperidine (0.1 mmol, 2 equiv). The reaction mixture was then stirred at 40° C. overnight. After the reaction was complete, the reaction mixture was filtered to remove the insoluble substance, and the filtrate was then subjected to Waters 2767 HPLC system (eluent (v/v):acetonitrile/(water+0.05% HCl)=10%-100%) for separation. The collected fractions were concentrated under reduced pressure to remove the solvents, and then lyophilized to give the hydrochloride salt of compound SIAIS1227139 (light yellow solid, 13.3 mg, yield 72%). $^1$H NMR (500 MHz, DMSO) δ 10.99 (s, 1H), 10.18 (s, 1H), 8.19 (s, 1H), 7.72-7.65 (m, 2H), 7.60 (s, 1H), 7.54 (s, 1H), 5.11 (d, J=11.5 Hz, 1H), 4.35 (s, 4H), 4.28 (d, J=17.4 Hz, 1H), 4.11 (d, J=17.4 Hz, 1H), 3.30 (s, 2H), 3.00 (s, 2H), 2.89 (s, 1H), 2.59 (d, J=17.2 Hz, 1H), 2.45-2.36 (m, 1H), 1.98 (s, 1H), 1.74 (d, J=34.6 Hz, 4H), 1.68 (d, J=14.7 Hz, 1H), 1.40 (s, 1H). HRMS (ESI) m/z: calcd for $C_{26}H_{28}Br_2N_3O_3S^+$ [M+H]$^+$, 620.0213; found, 620.0213.

Example 193: 3-(4-((2,5-dibromo-4-((cyclohexylamino)methyl)benzyl)thio)-1-oxoisoindolin-2-yl)piperidine-2,6-dione (SIAIS1227141)

Referring to the method of example 192, the compound SIAIS1227141 was prepared under appropriate conditions that will be recognized by one skilled in the art, except that the amine used was cyclohexylamine. The hydrochloride salt of compound SIAIS1227141 was obtained (light yellow solid, 15.3 mg, yield 80%). $^1$H NMR (500 MHz, DMSO) δ 10.99 (s, 1H), 9.02 (s, 2H), 8.02 (s, 1H), 7.72 (d, J=7.6 Hz, 1H), 7.66 (s, 2H), 7.55 (t, J=7.4 Hz, 1H), 5.11 (d, J=9.0 Hz, 1H), 4.37 (q, J=12.9 Hz, 2H), 4.28 (d, J=17.4 Hz, 1H), 4.21 (s, 2H), 4.12 (d, J=17.4 Hz, 1H), 3.10 (s, 1H), 2.95-2.85 (m, 1H), 2.59 (d, J=17.0 Hz, 1H), 2.46-2.37 (m, 1H), 2.11 (d, J=10.4 Hz, 2H), 1.99 (s, 1H), 1.78 (d, J=12.1 Hz, 2H), 1.62 (d, J=12.1 Hz, 1H), 1.42-1.32 (m, 2H), 1.31-1.22 (m, 2H), 1.16-1.07 (m, 1H). HRMS (ESI) m/z: calcd for $C_{27}H_{30}Br_2N_3O_3S^+$ [M+H]$^+$, 634.0369; found, 434.3604.

Example 194: 3-(4-((4-(((adamantan-1-yl)amino)methyl)-2,5-dibromobenzyl)thio)-1-oxoisoindolin-2-yl)piperidine-2,6-dione (SIAIS1227143)

Referring to the method of example 192, the compound SIAIS1227143 was prepared under appropriate conditions that will be recognized by one skilled in the art, except that the amine used was 1-adamantanamine. The hydrochloride salt of compound SIAIS1227143 was obtained (white solid, 11.8 mg, yield 57%). $^1$H NMR (500 MHz, DMSO) δ 11.00 (s, 1H), 8.88 (s, 2H), 8.04 (s, 1H), 7.74 (d, J=8.0 Hz, 1H), 7.69 (s, 1H), 7.66 (d, J=7.4 Hz, 1H), 7.56 (t, J=7.4 Hz, 1H), 5.12 (d, J=8.8 Hz, 1H), 4.39 (dd, J=26.1, 13.1 Hz, 2H), 4.29 (d, J=17.5 Hz, 1H), 4.18 (s, 2H), 4.13 (d, J=17.8 Hz, 1H), 2.96-2.86 (m, 1H), 2.59 (d, J=17.1 Hz, 1H), 2.46-2.38 (m, 1H), 2.16 (s, 3H), 1.95 (s, 7H), 1.68 (d, J=12.6 Hz, 3H), 1.63 (d, J=12.7 Hz, 3H). HRMS (ESI) m/z: calcd for $C_{31}H_{34}Br_2N_3O_3S^+$ [M+H]$^+$, 686.0682; found, 686.0684.

Example 195: 3-(4-((4-(2-(azocan-1-yl)ethyl)benzyl)thio)-1-oxoisoindolin-2-yl)piperidine-2,6-dione (SIAIS1227159)

Referring to the method of example 155, the compound SIAIS1227159 was prepared under appropriate conditions that will be recognized by one skilled in the art, except that the amine used was azacyclooctane. The hydrochloride salt of compound SIAIS1227159 was obtained (light yellow solid, 8.9 mg, yield 59%). $^1$H NMR (500 MHz, DMSO) δ 10.98 (s, 1H), 9.66 (s, 1H), 7.67 (s, 1H), 7.57 (s, 1H), 7.50 (s, 1H), 7.31 (s, 2H), 7.21 (s, 2H), 5.10 (d, J=13.1 Hz, 1H), 4.32 (s, 2H), 4.25 (d, J=17.9 Hz, 1H), 4.14 (d, J=17.1 Hz, 1H), 3.39 (s, 2H), 3.24 (s, 2H), 3.16 (s, 2H), 3.03-2.85 (m, 3H), 2.59 (d, J=17.9 Hz, 1H), 2.47-2.37 (m, 1H), 1.98 (s, 1H), 1.89 (s, 2H), 1.79-1.60 (m, 5H), 1.53 (s, 3H). HRMS (ESI) m/z: calcd for $C_{29}H_{36}N_3O_3S^+$ [M+H]$^+$, 506.2472; found, 506.2476.

Example 196: 3-(4-((4-(2-(4,4-difluoropiperidin-1-yl)ethyl)benzyl)thio)-1-oxoisoindolin-2-yl)piperidine-2,6-dione (SIAIS1227161)

Referring to the method of example 154, the compound SIAIS1227161 was prepared under appropriate conditions that will be recognized by one skilled in the art, except that the amine used in the last step was 4,4-difluoropiperidine. The hydrochloride salt of compound SIAIS1227161 was obtained (white solid, 8 mg, yield 59%). $^1$H NMR (500 MHz, DMSO) δ 10.98 (s, 1H), 10.91 (s, 1H), 7.67 (s, 1H), 7.57 (s, 1H), 7.50 (s, 1H), 7.31 (s, 2H), 7.19 (s, 2H), 5.10 (d, J=12.9 Hz, 1H), 4.32 (s, 2H), 4.24 (d, J=17.0 Hz, 1H), 4.14 (d, J=17.7 Hz, 1H), 3.66 (s, 2H), 3.16 (s, 2H), 3.02 (s, 2H), 2.96-2.85 (s, 1H), 2.63-2.53 (m, 3H), 2.47-2.31 (m, 5H), 1.97 (s, 1H). HRMS (ESI) m/z: calcd for $C_{29}H_{30}F_2N_3O_3S^+$ [M+H]$^+$, 514.1920; found, 514.1925.

Example 197: 3-(4-((4-(2-(6-azaspiro[2.5]octan-6-yl)ethyl)benzyl)thio)-1-oxoisoindolin-2-yl)piperidine-2,6-dione (SIAIS1227163)

Referring to the method of example 155, the compound SIAIS1227163 was prepared under appropriate conditions that will be recognized by one skilled in the art, except that the amine used in the last step was 6-azaspiro[2.5]octane. The hydrochloride salt of compound SIAIS1227163 was obtained (light yellow solid, 9.5 mg, yield 63%). $^1$H NMR (500 MHz, DMSO) δ 10.98 (s, 1H), 10.31 (s, 1H), 7.67 (s, 1H), 7.57 (s, 1H), 7.50 (s, 1H), 7.31 (s, 2H), 7.20 (s, 2H), 5.10 (d, J=12.9 Hz, 1H), 4.32 (s, 2H), 4.25 (d, J=17.0 Hz, 1H), 4.14 (d, J=17.2 Hz, 1H), 3.50 (d, J=9.0 Hz, 2H), 3.26 (s, 2H), 3.03-2.83 (m, 5H), 2.59 (d, J=18.5 Hz, 1H), 2.48-2.36 (m, 1H), 2.16 (s, 2H), 1.97 (s, 1H), 1.11 (d, J=13.0 Hz, 2H), 0.44 (s, 2H), 0.37 (s, 2H). HRMS (ESI) m/z: calcd for $C_{29}H_{34}N_3O_3S^+$ [M+H]$^+$, 504.2315; found, 504.2315.

Example 198: 3-(4-((4-(2-(3,5-dimethylpiperidin-1-yl)ethyl)benzyl)thio)-1-oxoisoindolin-2-yl)piperidine-2,6-dione (SIAIS1227165)

Referring to the method of example 155, the compound SIAIS1227165 was prepared under appropriate conditions that will be recognized by one skilled in the art, except that the amine used in the last step was 3,5-dimethylpiperidine. The hydrochloride salt of compound SIAIS1227165 was obtained (light yellow solid, 5.4 mg, yield 36%). $^1$H NMR (500 MHz, DMSO) δ 10.98 (s, 1H), 10.49 (s, 1H), 7.67 (d, J=7.5 Hz, 1H), 7.58 (d, J=7.3 Hz, 1H), 7.50 (t, J=7.4 Hz, 1H), 7.31 (d, J=7.3 Hz, 2H), 7.19 (d, J=7.4 Hz, 2H), 5.10 (d, J=9.4 Hz, 1H), 4.35-4.28 (m, 2H), 4.25 (d, J=17.4 Hz, 1H), 4.14 (d, J=17.4 Hz, 1H), 3.40 (s, 4H), 3.17 (s, 2H), 3.04 (d, J=8.5 Hz, 2H), 2.91 (t, J=13.0 Hz, 1H), 2.59 (d, J=17.0 Hz, 1H), 2.48-2.38 (m, 2H), 1.98 (s, 3H), 1.75 (d, J=12.5 Hz, 1H), 0.89 (d, J=6.1 Hz, 6H). HRMS (ESI) m/z: calcd for $C_{29}H_{36}N_3O_3S^+$ [M+H]$^+$, 506.2472; found, 506.2476.

Example 199: 3-(4-((4-((4,4-difluoropiperidin-1-yl)methyl)benzyl)thio)-1-oxoisoindolin-2-yl)piperidine-2,6-dione (SIAIS1227167)

Referring to the method of Scheme 11, the compound SIAIS1227167 was prepared under appropriate conditions that will be recognized by one skilled in the art, except that the substrates used were 3-(4-((4-(bromomethyl)benzyl) thio)-1-oxoisoindolin-2-yl)piperidine-2,6-dione (SIAIS1220141) and 4,4-difluoropiperidine. The hydrochloride salt of compound SIAIS1227167 was obtained (light yellow solid, 11.8 mg, yield 47%). $^1$H NMR (500 MHz, DMSO) δ 11.25 (s, 1H), 10.99 (s, 1H), 7.68 (d, J=7.4 Hz, 1H), 7.59 (d, J=7.3 Hz, 1H), 7.51 (d, J=7.1 Hz, 3H), 7.41 (d, J=7.3 Hz, 2H), 5.11 (dd, J=12.8, 3.7 Hz, 1H), 4.36 (s, 2H), 4.32 (m, 2H), 4.28 (d, J=17.6 Hz, 1H), 4.13 (d, J=17.5 Hz, 1H), 3.39-3.31 (m, 2H), 3.10 (s, 2H), 2.95-2.86 (m, 1H), 2.59 (d, J=17.3 Hz, 1H), 2.47-2.26 (m, 5H), 1.98 (d, J=6.1 Hz, 1H). HRMS (ESI) m/z: calcd for $C_{26}H_{28}F_2N_3O_3S^+$ $[M+H]^+$, 500.1814; found, 500.1815.

Example 200: 3-(4-((4-(((4-methylpiperazin-1-yl) methyl)benzyl)thio)-1-oxoisoindolin-2-yl)piperidine-2,6-dione (SIAIS1227169)

Referring to the method of Scheme 11, the compound SIAIS1227169 was prepared under appropriate conditions that will be recognized by one skilled in the art, except that the substrates used were 3-(4-((4-(bromomethyl)benzyl) thio)-1-oxoisoindolin-2-yl)piperidine-2,6-dione (SIAIS1220141) and 4-methylpiperazine. The hydrochloride salt of compound SIAIS1227169 was obtained (light yellow solid, 8.4 mg, yield 35%). $^1$H NMR (500 MHz, DMSO) δ 10.98 (s, 1H), 7.69 (d, J=7.6 Hz, 1H), 7.59 (d, J=7.1 Hz, 1H), 7.55-7.43 (m, 3H), 7.40 (s, 2H), 5.11 (d, J=13.1 Hz, 1H), 4.36 (s, 2H), 4.27 (d, J=17.2 Hz, 1H), 4.13 (d, J=17.1 Hz, 1H), 3.59 (s, 2H), 3.51-3.19 (m, 8H), 2.95-2.86 (m, 1H), 2.79 (s, 3H), 2.59 (d, J=17.5 Hz, 1H), 2.46-2.35 (m, 1H), 1.99 (s, 1H). HRMS (ESI) m/z: calcd for $C_{26}H_{31}N_4O_3S^+$ $[M+H]^+$, 479.2111; found, 479.2115.

Example 201: 3-(4-((4-(((3aR,7aS)-octahydro-2H-isoindol-2-yl)methyl)benzyl)thio)-1-oxoisoindolin-2-yl)piperidine-2,6-dione (SIAIS1227171)

Referring to the method of Scheme 11, the compound SIAIS1227171 was prepared under appropriate conditions that will be recognized by one skilled in the art, except that the substrates used were 3-(4-((4-(bromomethyl)benzyl) thio)-1-oxoisoindolin-2-yl)piperidine-2,6-dione (SIAIS1220141) and cis-Octahydroisoindole. The hydrochloride salt of compound SIAIS1227171 was obtained (light yellow solid, 10.7 mg, yield 42%). $^1$H NMR (500 MHz, DMSO) δ 10.98 (s, 1H), 10.81 (s, 1H), 7.68 (d, J=7.4 Hz, 1H), 7.60-7.53 (m, 3H), 7.50 (t, J=7.5 Hz, 1H), 7.40 (d, J=7.5 Hz, 2H), 5.11 (d, J=8.9 Hz, 1H), 4.36 (s, 2H), 4.32 (d, J=5.5 Hz, 1H), 4.27 (d, J=17.2 Hz, 2H), 4.13 (d, J=17.5 Hz, 1H), 3.34 (s, 1H), 3.14 (s, 2H), 3.00-2.86 (m, 2H), 2.59 (d, J=16.9 Hz, 1H), 2.46-2.35 (m, 2H), 2.24 (s, 1H), 2.01-1.93 (m, 1H), 1.56 (s, 1H), 1.53-1.37 (m, 5H), 1.28 (s, 2H). HRMS (ESI) m/z: calcd for $C_{29}H_{34}N_3O_3S^+$ $[M+H]^+$, 504.2315; found, 504.2316.

Example 202: 3-(4-((4-((((R)-1-cyclopropylethyl) amino)methyl)benzyl)thio)-1-oxoisoindolin-2-yl) piperidine-2,6-dione (SIAIS1227173)

Referring to the method of Scheme 11, the compound SIAIS1227173 was prepared under appropriate conditions that will be recognized by one skilled in the art, except that the substrates used were 3-(4-((4-(bromomethyl)benzyl) thio)-1-oxoisoindolin-2-yl)piperidine-2,6-dione (SIAIS1220141) and (R)-1-(cyclopropylethyl)amine. The hydrochloride salt of compound SIAIS1227173 was obtained (white solid, 2.2 mg, yield 9%). $^1$H NMR (500 MHz, DMSO) δ 10.99 (s, 1H), 9.10 (s, 2H), 7.69 (d, J=7.5 Hz, 1H), 7.57 (d, J=7.5 Hz, 1H), 7.52-7.47 (m, 3H), 7.42 (d, J=7.7 Hz, 2H), 6.52 (s, 1H), 5.11 (dd, J=13.2, 4.8 Hz, 1H), 4.41-4.34 (m, 2H), 4.28 (d, J=17.3 Hz, 1H), 4.15 (d, J=17.9 Hz, 1H), 3.31 (s, 2H), 2.96-2.86 (m, 1H), 2.59 (d, J=17.3 Hz, 1H), 2.42 (dd, J=17.8, 8.7 Hz, 1H), 2.02-1.95 (m, 1H), 1.32 (d, J=6.4 Hz, 3H), 1.03 (s, 1H), 0.64 (s, 1H), 0.55 (s, 1H), 0.48 (s, 1H), 0.25 (s, 1H). HRMS (ESI) m/z: calcd for $C_{26}H_{30}N_3O_3S^+$ $[M+H]^+$, 464.2002; found, 464.2005.

Example 203: 3-(4-((4-(bromomethyl)-2-fluorobenzyl)thio)-1-oxoisoindolin-2-yl)piperidine-2,6-dione (SIAIS1227157)

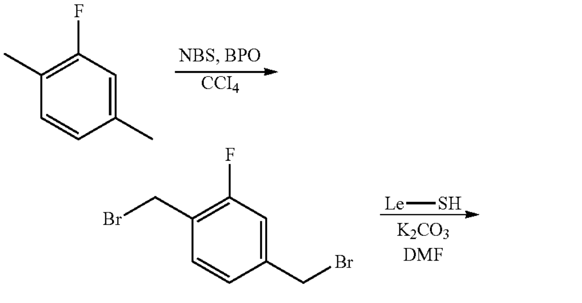

SIAIS1227151

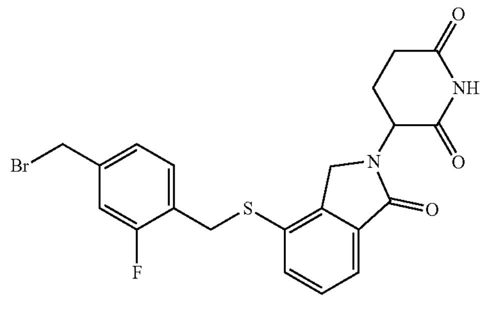

SIAIS1227157

Step 1: A 100 mL single-necked flask was charged with 1,4-dimethyl-2-fluorobenzene (10 mmol, 1 equiv), NBS (10 mmol, 2 equiv), and BPO (0.5 mmol, 0.05 equiv), followed by addition of carbon tetrachloride (20 mL). The reaction mixture was reacted at 80° C. in oil bath overnight. After the reaction was complete, the mixture was subjected to a positive phase column chromatography (eluent: PE) for separation. The collected fractions were concentrated under reduced pressure to remove the solvent, to give the compound SIAIS1227151 as a light yellow solid (1 g, yield 35%).

Step 2: A 50 mL single-necked flask was charged with SIAIS171095 (2 mmol, 1 equiv), potassium carbonate (4 mmol, 2 equiv) and DMF (10 mL), followed by the compound SIAIS1227151 (3 mmol, 1.5 equiv). Then the reaction mixture was stirred at room temperature for 0.5 h. After the reaction was complete, the reaction mixture was filtered to remove the insoluble materials. The filtrate was subjected to C18 reverse phase column chromatography (eluent (v/v): acetonitrile/water=10%-100%) for separation. The collected fractions were concentrated under reduced pressure to remove the solvents, to give the target compound SIAIS1227157 as a pale yellow solid (274 mg, yield 29%). HRMS (ESI) m/z: calcd for $C_{21}H_{19}BrFN_2O_3S^+$ [M+H]$^+$, 477.0278; found, 477.0277.

Example 204: 3-(4-((2-fluoro-4-(piperidin-1-ylmethyl)benzyl)thio)-1-oxoisoindolin-2-yl)piperidine-2,6-dione (SIAIS1227175)

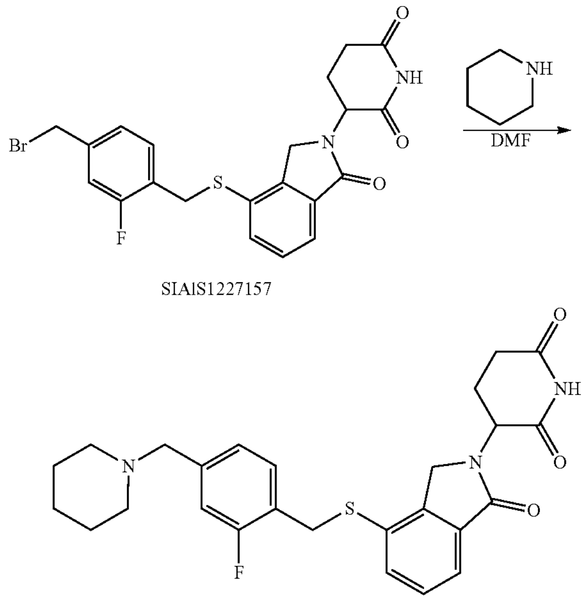

SIAIS1227157

SIAIS1227175

A 25 mL single-necked flask was charged with the compound SIAIS1227157 (0.05 mmol, 1 equiv) and DMF (2 mL), followed by addition of piperidine (0.1 mmol, 2 equiv). Then the reaction mixture was stirred at 40° C. for 2 h. After the reaction was complete, the reaction mixture was filtered to remove the insoluble materials. The filtrate was subjected to preparative HPLC (eluent (v/v):acetonitrile/(water+0.05% HCl)=10%-100%) for separation. The collected fractions were concentrated under reduced pressure to remove the solvents, to give the hydrochloride salt of target compound SIAIS1227175 (pale yellow solid, 11.8 mg, yield 49%). $^1$H NMR (500 MHz, DMSO) δ 10.98 (s, 1H), 10.60 (s, 1H), 7.70 (d, J=7.6 Hz, 1H), 7.62 (d, J=7.4 Hz, 1H), 7.51 (d, J=8.2 Hz, 2H), 7.37 (t, J=7.7 Hz, 1H), 7.30 (d, J=7.6 Hz, 1H), 5.10 (dd, J=13.1, 4.3 Hz, 1H), 4.34 (s, 2H), 4.30-4.18 (m, 3H), 4.12 (d, J=17.4 Hz, 1H), 3.30-3.17 (m, 2H), 2.95-2.72 (m, 3H), 2.59 (d, J=16.7 Hz, 1H), 2.45-2.34 (m, 1H), 2.01-1.93 (m, 1H), 1.76 (s, 4H), 1.68 (d, J=12.3 Hz, 1H), 1.33 (s, 1H). HRMS (ESI) m/z: calcd for $C_{26}H_{29}FN_3O_3S^+$ [M+H]$^+$, 482.1908; found, 482.1905.

Example 205: 3-(4-((4-((cyclohexylamino)methyl)-2-fluorobenzyl)thio)-1-oxoisoindolin-2-yl)piperidine-2,6-dione (SIAIS1227177)

Referring to the method of example 204, the compound SIAIS1227177 was prepared under appropriate conditions that will be recognized by one skilled in the art, except that the substrate used was cyclohexylamine. The hydrochloride salt of compound SIAIS1227177 was obtained (white solid, 16.6 mg, yield 67%). $^1$H NMR (500 MHz, DMSO) δ 10.99 (s, 1H), 9.19 (s, 2H), 7.70 (d, J=7.4 Hz, 1H), 7.61 (d, J=7.4 Hz, 1H), 7.55-7.46 (m, 2H), 7.40 (t, J=7.5 Hz, 1H), 7.30 (d, J=7.0 Hz, 1H), 5.11 (dd, J=12.9, 3.1 Hz, 1H), 4.35 (s, 2H), 4.28 (d, J=16.9 Hz, 1H), 4.17-4.09 (m, 3H), 3.04-2.85 (m, 2H), 2.59 (d, J=17.0 Hz, 1H), 2.48-2.35 (m, 1H), 2.08 (d, J=10.9 Hz, 2H), 2.02-1.94 (m, 1H), 1.76 (d, J=11.9 Hz, 2H), 1.36 (dd, J=23.8, 12.0 Hz, 2H), 1.26-1.16 (m, 3H), 0.85 (s, 1H). HRMS (ESI) m/z: calcd for $C_{27}H_{31}FN_3O_3S^+$ [M+H]$^+$, 496.2065; found, 496.2065.

Example 206: 3-(4-((4-(((adamantan-1-yl)amino)methyl)-2-fluorobenzyl)thio)-1-oxoisoindolin-2-yl)piperidine-2,6-dione (SIAIS1227179)

Referring to the method of example 204, the compound SIAIS1227179 was prepared under appropriate conditions that will be recognized by one skilled in the art, except that the substrate used was 1-adamantanamine. The hydrochloride salt of compound SIAIS1227179 was obtained (white solid, 13.1 mg, yield 48%). $^1$H NMR (500 MHz, DMSO) δ 10.99 (s, 1H), 8.98 (s, 2H), 7.72 (d, J=7.8 Hz, 1H), 7.61 (d, J=7.6 Hz, 1H), 7.53 (t, J=8.1 Hz, 1H), 7.48 (d, J=10.9 Hz, 1H), 7.43 (t, J=7.7 Hz, 1H), 7.31 (d, J=8.6 Hz, 1H), 5.11 (dd, J=12.9, 3.8 Hz, 1H), 4.42-4.35 (m, 2H), 4.32 (d, J=17.1 Hz, 1H), 4.14 (dd, J=17.3 Hz, 1H), 4.08 (s, 2H), 2.95-2.85 (m, 1H), 2.59 (d, J=17.6 Hz, 1H), 2.47-2.38 (m, 1H), 2.14 (s, 3H), 2.02-1.96 (m, 1H), 1.93 (s, 6H), 1.68 (d, J=12.1 Hz, 3H), 1.60 (d, J=11.9 Hz, 3H). HRMS (ESI) m/z: calcd for $C_{31}H_{35}FN_3O_3S^+$ [M+H]$^+$, 548.2378; found, 548.2376.

Example 207: 3-(4-((2-fluoro-4-(morpholinomethyl)benzyl)thio)-1-oxoisoindolin-2-yl)piperidine-2,6-dione (SIAIS1227181)

Referring to the method of example 204, the compound SIAIS1227181 was prepared under appropriate conditions that will be recognized by one skilled in the art, except that the substrate used was morpholine. The hydrochloride salt of compound SIAIS1227181 was obtained (white solid, 15.3 mg, yield 63%). $^1$H NMR (500 MHz, DMSO) δ 11.20 (s, 1H), 10.98 (s, 1H), 7.70 (d, J=7.9 Hz, 1H), 7.63 (d, J=7.2 Hz, 1H), 7.54-7.48 (m, 2H), 7.38 (t, J=7.4 Hz, 1H), 7.32-7.28 (m, 1H), 5.11 (d, J=12.6 Hz, 1H), 4.34 (s, 2H), 4.33-4.23 (m, 3H), 4.10 (d, J=17.4 Hz, 1H), 3.92 (d, J=12.2 Hz, 2H), 3.76 (s, 2H), 3.15 (dd, J=53.0, 41.1 Hz, 4H), 2.95-2.86 (m, 1H), 2.59 (d, J=16.8 Hz, 1H), 2.46-2.35 (m, 1H), 2.00-1.93 (m, 1H). HRMS (ESI) m/z: calcd for $C_{25}H_{27}FN_3O_4S^+$ [M+H]$^+$, 484.1701; found, 484.1705.

Intermediate Example 13: Preparation of 4-((7-bromoheptyl)thio)-2-(2,6-dioxopiperidin-3-yl)isoindoline-1,3-dione (SIAIS1221039)

Referring to the method of Scheme 9, the compound SIAIS1221039 was prepared under appropriate conditions that will be recognized by one skilled in the art, except that the halogenated substrate was 1,7-dibromoheptane, and 2-(2,6-dioxopiperidin-3-yl)-4-mercaptoisoindoline-1,3-dione (SIAIS151014) was used instead of the starting material SIAIS171095. The target compound SIAIS1221039 was obtained as a white solid (212 mg, yield 23%). $^1$H NMR (500 MHz, DMSO) δ 11.12 (s, 1H), 7.79 (t, J=7.5 Hz, 1H), 7.74 (d, J=8.1 Hz, 1H), 7.62 (d, J=7.0 Hz, 1H), 5.11 (dd, J=12.8, 5.3 Hz, 1H), 3.53 (t, J=6.6 Hz, 2H), 3.13 (t, J=7.2 Hz, 2H), 2.93-2.84 (m, 1H), 2.63-2.51 (m, 2H), 2.08-2.02 (m, 1H), 1.83-1.76 (m, 2H), 1.70-1.63 (m, 2H), 1.48-1.30

(m, 6H). HRMS (ESI) m/z: calcd for $C_{20}H_{24}BrN_2O_4S^+$ $[M+H]^+$, 467.0635; found, 467.0632.

Example 208: 2-(2,6-dioxopiperidin-3-yl)-4-((7-(piperidin-1-yl)heptyl)thio)isoindoline-1,3-dione (SIAIS1221033)

Referring to the method of Scheme 11, the compound SIAIS1221033 was prepared under appropriate conditions that will be recognized by one skilled in the art, except that the substrates were 4-((7-bromoheptyl)thio)-2-(2,6-dioxopiperidin-3-yl)isoindoline-1,3-dione (SIAIS1221039) and piperidine. The hydrochloride salt of compound SIAIS1221033 was obtained (light yellow solid, 7 mg, yield 31%). $^1$H NMR (500 MHz, DMSO) δ 11.13 (s, 1H), 10.17 (s, 1H), 7.80 (t, J=7.6 Hz, 1H), 7.75 (d, J=8.2 Hz, 1H), 7.63 (d, J=7.0 Hz, 1H), 5.11 (dd, J=12.8, 5.3 Hz, 1H), 3.14 (t, J=7.1 Hz, 2H), 2.98-2.85 (m, 3H), 2.84-2.75 (m, 2H), 2.60 (d, J=17.8 Hz, 1H), 2.56-2.52 (m, 1H), 2.09-2.02 (m, 1H), 1.76 (s, 5H), 1.72-1.65 (m, 5H), 1.50-1.43 (m, 2H), 1.38-1.26 (m, 6H). HRMS (ESI) m/z: calcd for $C_{25}H_{34}N_3O_4S^+$ $[M+H]^+$, 472.2256; found, 472.2253.

Example 209: 4-((7-((adamantan-1-yl)amino)heptyl)thio)-2-(2,6-dioxopiperidin-3-yl)isoindoline-1,3-dione (SIAIS1221069)

Referring to the method of Scheme 11, the compound SIAIS1221069 was prepared under appropriate conditions that will be recognized by one skilled in the art, except that the substrates were compound (SIAIS1221039) and 1-adamantanamine. The hydrochloride salt of compound SIAIS1221069 was obtained (light yellow solid, 12 mg, yield 44%). $^1$H NMR (500 MHz, DMSO) δ 11.12 (s, 1H), 8.39 (s, 2H), 7.79 (t, J=7.6 Hz, 1H), 7.75 (d, J=8.1 Hz, 1H), 7.63 (d, J=7.0 Hz, 1H), 5.11 (dd, J=12.8, 5.2 Hz, 1H), 3.15 (t, J=7.0 Hz, 2H), 2.94-2.80 (m, 3H), 2.64-2.52 (m, 2H), 2.11 (s, 3H), 2.08-2.02 (m, 1H), 1.83 (s, 6H), 1.71-1.55 (m, 10H), 1.46 (s, 2H), 1.35 (s, 4H). HRMS (ESI) m/z: calcd for $C_{30}H_{40}N_3O_4S^+$ $[M+H]^+$, 538.2734; found, 538.2737.

Example 210: 5-((7-((adamantan-1-yl)amino)heptyl)thio)-2-(2,6-dioxopiperidin-3-yl)isoindoline-1,3-dione (SIAIS1221075)

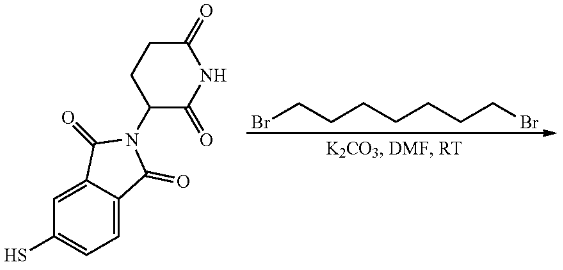

1
(SIAIS1216131)

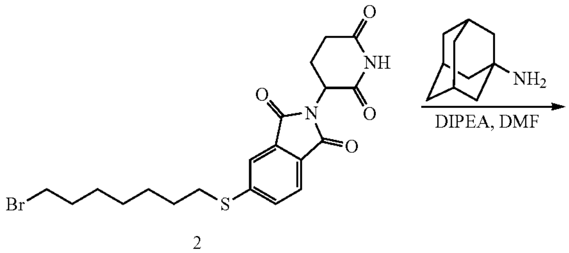

2

-continued

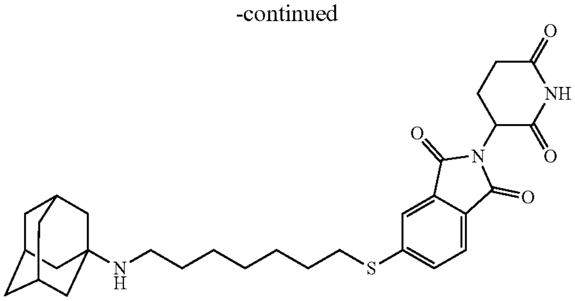

SIAIS1221075

Step 1: A 25 mL egg-shaped flask was charged with SIAIS1216131 (1 mmol, 1 equiv), potassium carbonate (2 mmol, 2 equiv), and DMF (5 mL), followed by addition of 1,7-dibromoheptane (1.5 mmol, 1.5 equiv). Then the reaction mixture was stirred at room temperature for 0.5 h. After the reaction was complete, the reaction mixture was filtered to remove the insoluble materials. The filtrate was subjected to ISCO reverse phase column chromatography (eluent (v/v): acetonitrile/water=10%-100%) for separation. The collected fractions were concentrated under reduced pressure to remove the solvents to give the intermediate 2 as a yellow solid (128 mg, yield 27%).

Step 2: A 25 mL egg-shaped flask was charged with the intermediate 2 (0.05 mmol, 1 equiv) and DMF (2 mL), followed by addition of 1-adamantanamine (0.1 mmol, 2 equiv) and DIPEA (0.1 mmol, 2 equiv). Then the reaction mixture was stirred at 40° C. overnight. After the reaction was complete, the reaction mixture was filtered to remove the insoluble substance, and the filtrate was subjected to Waters 2767 HPLC system (eluent (v/v):acetonitrile/(water+0.05% HCl)=10%-10$^{0\%}$) for separation. The collected fractions were concentrated under reduced pressure to remove the solvents, and then lyophilized to give the hydrochloride salt of compound SIAIS1221075 (pale yellow solid, 5 mg, yield 19%). $^1$H NMR (500 MHz, DMSO) δ 11.13 (s, 1H), 8.33 (s, 2H), 7.81 (d, J=7.9 Hz, 1H), 7.75 (s, 1H), 7.72 (d, J=7.9 Hz, 1H), 5.14 (dd, J=12.8, 5.5 Hz, 1H), 3.19 (t, J=7.1 Hz, 2H), 2.94-2.80 (m, 3H), 2.60 (d, J=18.2 Hz, 1H), 2.11 (s, 3H), 2.08-2.03 (m, 1H), 1.82 (s, 6H), 1.66 (d, J=9.0 Hz, 5H), 1.59 (d, J=12.3 Hz, 5H), 1.44 (s, 2H), 1.34 (s, 4H), 1.24 (s, 1H). HRMS (ESI) m/z: calcd for $C_{30}H_{40}N_3O_4S^+$ $[M+H]^+$, 538.2734; found, 538.2726.

Example 211: 2-(2,6-dioxopiperidin-3-yl)-4-((4-((((1R,2S,4R)-1,7,7-trimethylbicyclo[2.2.1]heptan-2-yl)amino)methyl)benzyl)thio)isoindoline-1,3-dione (SIAIS1221147)

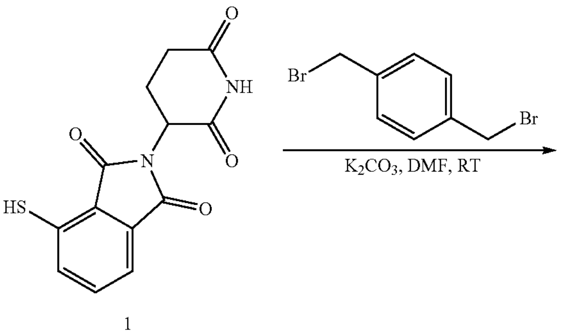

1
(SIAIS151014)

-continued

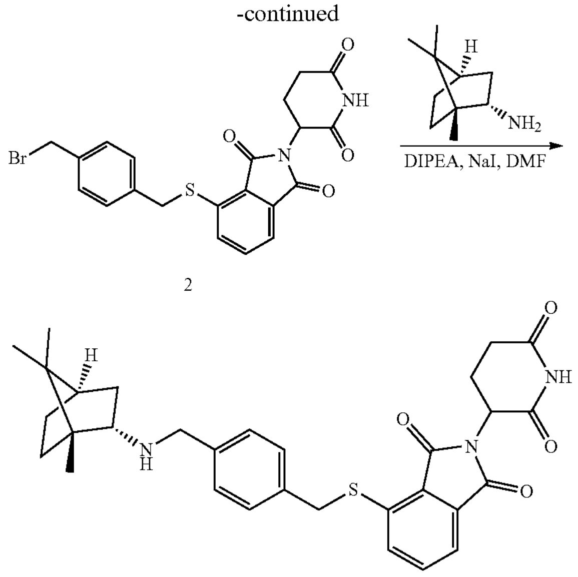

2

SIAIS1221147

Step 1: A 25 mL egg-shaped flask was charged with SIAIS151014 (1 mmol, 1 equiv), potassium carbonate (2 mmol, 2 equiv), and DMF (5 mL), followed by addition of 1,4-bis(bromomethyl)benzene (1.5 mmol, 1.5 equiv). Then the reaction mixture was stirred at room temperature for 0.5 h. After the reaction was complete, the reaction mixture was filtered to remove the insoluble substance, and the filtrate was subjected to ISCO reverse phase column chromatography (eluent (v/v):acetonitrile/water=10%-100%) for separation. The collected fractions were concentrated under reduced pressure to remove the solvents to give intermediate 2 as a yellow solid, (153 mg, yield 32%).

Step 2: A 25 mL single-necked flask was charged with the intermediate 2 (0.05 mmol, 1 equiv) and DMF (2 mL), followed by addition of bornylamine (0.1 mmol, 2 equiv), DIPEA (0.1 mmol, 2 equiv) and sodium iodide (0.1 mmol, 2 equiv). Then the reaction mixture was stirred at 50° C. overnight. After the reaction was complete, the reaction mixture was filtered to remove the insoluble substance. The filtrate was subjected to Waters 2767 HPLC system (eluent (v/v): acetonitrile/(water+0.05% HCl)=10%-100%) for separation. The collected fractions were concentrated under reduced pressure to remove the solvents, to give the hydrochloride salt of SIAIS1221147 (yellow solid, 13 mg, yield 48%). $^1$H NMR (500 MHz, DMSO) δ 11.12 (s, 1H), 9.11 (s, 1H), 8.66 (s, 1H), 7.81 (d, J=8.1 Hz, 1H), 7.74 (t, J=7.7 Hz, 1H), 7.63 (d, J=7.2 Hz, 1H), 7.56 (q, J=8.0 Hz, 4H), 5.11 (dd, J=12.9, 5.3 Hz, 1H), 4.49 (s, 2H), 4.21-4.06 (m, 2H), 3.10 (s, 1H), 2.93-2.83 (m, 1H), 2.63-2.46 (m, 2H), 2.07-2.01 (m, 1H), 1.92 (t, J=11.7 Hz, 1H), 1.69-1.60 (m, 3H), 1.38 (t, J=9.5 Hz, 2H), 1.14 (dd, J=13.2, 3.6 Hz, 1H), 0.87 (s, 3H), 0.81 (s, 3H), 0.70 (s, 3H). HRMS (ESI) m/z: calcd for $C_{31}H_{36}N_3O_6S$ [M+H]$^+$, 546.2421; found, 546.2424.

Example 212: 2-(2,6-dioxopiperidin-3-yl)-4-((7-(((1R,2S,4R)-1,7,7-trimethylbicyclo[2.2.1]heptan-2-yl)amino)heptyl)thio)isoindoline-1,3-dione (SIAIS1221177)

Referring to the method of Scheme 11, the compound SIAIS1221177 was prepared under appropriate conditions that will be recognized by one skilled in the art, except that the substrates used were the compound SIAIS1221039 and bornylamine. The hydrochloride salt of compound SIAIS1221177 was obtained (light yellow solid, 9 mg, yield 33%). $^1$H NMR (500 MHz, DMSO) δ 11.12 (s, 1H), 8.37 (s, 1H), 8.06 (s, 1H), 7.79 (t, J=7.6 Hz, 1H), 7.75 (d, J=8.0 Hz, 1H), 7.63 (d, J=7.0 Hz, 1H), 5.11 (dd, J=12.7, 5.3 Hz, 1H), 3.22 (s, 1H), 3.14 (t, J=7.0 Hz, 2H), 2.93-2.84 (m, 3H), 2.60 (d, J=17.5 Hz, 1H), 2.53 (s, 1H), 2.17 (t, J=11.5 Hz, 1H), 2.09-2.01 (m, 1H), 1.69 (s, 6H), 1.64-1.55 (m, 1H), 1.50-1.30 (m, 8H), 1.18 (d, J=13.0 Hz, 1H), 0.95 (s, 3H), 0.84 (s, 6H). HRMS (ESI) m/z: calcd for $C_{30}H_{42}N_3O_4S^+$ [M+H]$^+$, 540.2891; found, 540.2895.

Example 213: 4-((4-(((adamantan-1-yl)amino)methyl)benzyl)thio)-2-(2,6-dioxopiperidin-3-yl)isoindoline-1,3-dione (SIAIS1222013)

Referring to the method of example 211, the compound SIAIS1222013 was prepared under appropriate conditions that will be recognized by one skilled in the art, except that the amine used was 1-adamantanamine. The hydrochloride salt of compound SIAIS1222013 was obtained (yellow solid, 11 mg, yield 41%). $^1$H NMR (500 MHz, DMSO) δ 11.12 (s, 1H), 8.87 (s, 2H), 7.85 (d, J=8.1 Hz, 1H), 7.77 (t, J=7.5 Hz, 1H), 7.64 (d, J=7.3 Hz, 1H), 7.58-7.51 (m, 4H), 5.11 (dd, J=12.8, 5.0 Hz, 1H), 4.49 (s, 2H), 4.07 (s, 2H), 2.94-2.83 (m, 1H), 2.63-2.54 (m, 2H), 2.14 (s, 3H), 2.08-2.02 (m, 1H), 1.95 (s, 6H), 1.68 (d, J=12.0 Hz, 3H), 1.61 (d, J=11.8 Hz, 3H). HRMS (ESI) m/z: calcd for $C_{31}H_{34}N_3O_3S^+$ [M+H]$^+$, 544.2265; found, 544.2265.

Example 214: 4-((4-(((adamantan-1-yl)amino)methyl)phenethyl)thio)-2-(2,6-dioxopiperidin-3-yl)isoindoline-1,3-dione (SIAIS1224151)

Referring to the method of example 161, the compound SIAIS1224151 was prepared under appropriate conditions that will be recognized by one skilled in the art, except that the substrates used were 2-(2,6-dioxopiperidin-3-yl)-4-mercaptoisoindoline-1,3-dione (SIAIS151014) and 1-adamantanamine. The hydrochloride salt of compound SIAIS1224151 was obtained (yellow solid, 10 mg, yield 29%). $^1$H NMR (500 MHz, DMSO) δ 11.12 (s, 1H), 8.79 (s, 2H), 7.65 (s, 1H), 7.50 (d, J=7.5 Hz, 2H), 7.40 (d, J=7.2 Hz, 2H), 7.21 (d, J=7.4 Hz, 1H), 7.13 (d, J=7.1 Hz, 1H), 5.10 (d, J=13.2, 4.4 Hz, 1H), 4.07 (s, 2H), 3.44 (t, J=6.6 Hz, 2H), 3.03 (t, J=6.8 Hz, 2H), 2.93-2.83 (m, 1H), 2.63-2.55 (m, 2H), 2.08-2.00 (m, 3H), 2.05 (s, 1H), 1.95 (s, 6H), 1.69 (d, J=11.3 Hz, 3H), 1.62 (d, J=12.0 Hz, 3H). HRMS (ESI) m/z: calcd for $C_{32}H_{36}N_3O_4S^+$ [M+H]$^+$, 558.2421; found, 558.2428.

Example 215: 2-(2,6-dioxopiperidin-3-yl)-4-((4-(piperidin-1-ylmethyl)phenethyl)thio)isoindoline-1,3-dione (SIAIS1224163)

Referring to the method of example 161, the compound SIAIS1224163 was prepared under appropriate conditions that will be recognized by one skilled in the art, except that the substrates used were 2-(2,6-dioxopiperidin-3-yl)-4-mercaptoisoindoline-1,3-dione (SIAIS151014) and piperidine. The hydrochloride salt of compound SIAIS1224163 was obtained (yellow solid, 16.6 mg, yield 54%). $^1$H NMR (500 MHz, DMSO) δ 11.12 (s, 1H), 9.95 (s, 1H), 7.80 (s, 2H), 7.65 (s, 1H), 7.51 (s, 2H), 7.42 (d, J=7.5 Hz, 2H), 5.11 (dd, J=12.8, 4.7 Hz, 1H), 4.23 (s, 2H), 3.45 (t, J=7.0 Hz, 2H), 3.26 (d, J=11.9 Hz, 2H), 3.03 (t, J=7.1 Hz, 2H), 2.93-2.78

(m, 3H), 2.62-2.53 (m, 2H), 2.08-2.02 (m, 1H), 1.82-1.65 (m, 5H), 1.40-1.30 (m, 1H). HRMS (ESI) m/z: calcd for $C_{27}H_{30}N_3O_4S^+$ [M+H]$^+$, 492.1952; found, 492.1955.

Example 216: 4-((4-((cyclohexylamino)methyl) phenethyl)thio)-2-(2,6-dioxopiperidin-3-yl)isoindoline-1,3-dione (SIAIS1227019)

Referring to the method of example 161, the compound SIAIS1227019 was prepared under appropriate conditions that will be recognized by one skilled in the art, except that the substrates used were 2-(2,6-dioxopiperidin-3-yl)-4-mercaptoisoindoline-1,3-dione (SIAIS151014) and cyclohexylamine. The hydrochloride salt of compound SIAIS1227019 was obtained (yellow solid, 16 mg, yield 51%). $^1$H NMR (500 MHz, DMSO) δ 11.12 (s, 1H), 8.99 (s, 2H), 7.82 (s, 2H), 7.65 (s, 1H), 7.50 (s, 2H), 7.40 (d, J=7.5 Hz, 2H), 5.10 (dd, J=12.9, 4.9 Hz, 1H), 4.12 (s, 2H), 3.44 (t, J=7.0 Hz, 2H), 3.03 (t, J=7.0 Hz, 2H), 2.96 (s, 1H), 2.93-2.83 (m, 1H), 2.60 (d, J=17.6 Hz, 1H), 2.53-2.45 (m, 1H), 2.11 (d, J=11.0 Hz, 2H), 2.08-2.02 (m, 1H), 1.77 (d, J=12.7 Hz, 2H), 1.61 (d, J=11.9 Hz, 1H), 1.43-1.31 (m, 2H), 1.27-1.17 (m, 2H), 1.16-1.06 (m, 1H). HRMS (ESI) m/z: calcd for $C_{28}H_{32}N_3O_4S^+$ [M+H]$^+$, 506.2108; found, 506.2105.

Example 217: 2-(2,6-dioxopiperidin-3-yl)-4-((4-(3-(piperidin-1-yl)propyl)benzyl)thio)isoindoline-1,3-dione (SIAIS1227085)

Referring to the method of example 164, the compound SIAIS1227085 was prepared under appropriate conditions that will be recognized by one skilled in the art, except that the thiophenol substrate used was 2-(2,6-dioxopiperidin-3-yl)-4-mercaptoisoindoline-1,3-dione (SIAIS151014). The hydrochloride salt of compound SIAIS1227085 was obtained (light yellow solid, 7 mg, yield 46%). $^1$H NMR (500 MHz, DMSO) δ 11.12 (s, 1H), 9.66 (s, 1H), 7.86-7.80 (m, 1H), 7.80-7.73 (m, 1H), 7.63 (t, J=5.9 Hz, 1H), 7.42 (t, J=5.4 Hz, 2H), 7.25-7.19 (m, 2H), 5.10 (d, J=12.5 Hz, 1H), 4.43 (s, 2H), 3.38 (s, 2H), 2.98 (s, 2H), 2.92-2.77 (m, 3H), 2.61 (s, 4H), 2.05 (s, 1H), 1.98 (s, 2H), 1.80-1.62 (m, 5H), 1.40-1.30 (s, 1H). HRMS (ESI) m/z: calcd for $C_{28}H_{32}N_3O_4S^+$ [M+H]$^+$, 506.2108; found, 506.2102.

Example 218: 4-((4-(3-(cyclohexylamino)propyl) benzyl)thio)-2-(2,6-dioxopiperidin-3-yl)isoindoline-1,3-dione (SIAIS1227087)

Referring to the method of example 164, the compound SIAIS1227087 was prepared under appropriate conditions that will be recognized by one skilled in the art, except that the the thiophenol substrate used was 2-(2,6-dioxopiperidin-3-yl)-4-mercaptoisoindoline-1,3-dione (SIAIS151014), and the amine used was cyclohexylamine. The hydrochloride salt of compound SIAIS1227087 was obtained (yellow solid, 13 mg, yield 83%). $^1$H NMR (500 MHz, DMSO) δ 11.12 (s, 1H), 8.56 (s, 2H), 7.83 (d, J=7.9 Hz, 1H), 7.77 (t, J=7.5 Hz, 1H), 7.63 (d, J=6.8 Hz, 1H), 7.42 (d, J=7.2 Hz, 2H), 7.21 (d, J=7.2 Hz, 2H), 5.11 (dd, J=12.2, 4.4 Hz, 1H), 4.43 (s, 2H), 2.95 (s, 1H), 2.88 (s, 3H), 2.64 (t, J=7.0 Hz, 2H), 2.60-2.53 (m, 2H), 2.08-2.02 (m, 1H), 1.97 (s, 2H), 1.89 (s, 2H), 1.74 (d, J=9.6 Hz, 2H), 1.59 (d, J=12.3 Hz, 1H), 1.29-1.19 (m, 4H), 1.14-1.03 (m, 1H). HRMS (ESI) m/z: calcd for $C_{29}H_{34}N_{304}S^+$ [M+H]$^+$, 520.2265; found, 520.2266.

Example 219: 2-(2,6-dioxopiperidin-3-yl)-4-((4-(3-morpholinopropyl)benzyl)thio) isoindoline-1,3-dione (SIAIS1227091)

Referring to the method of example 164, the compound SIAIS1227091 was prepared under appropriate conditions that will be recognized by one skilled in the art, except that the thiophenol substrate used was 2-(2,6-dioxopiperidin-3-yl)-4-mercaptoisoindoline-1,3-dione (SIAIS151014), and the amine used was morpholine. The hydrochloride salt of compound SIAIS1227091 was obtained (yellow solid, 13 mg, yield 86%). $^1$H NMR (500 MHz, DMSO) δ 11.12 (s, 1H), 10.30 (s, 1H), 7.83 (d, J=8.1 Hz, 1H), 7.77 (t, J=7.3 Hz, 1H), 7.63 (d, J=7.0 Hz, 1H), 7.42 (d, J=7.3 Hz, 2H), 7.23 (d, J=7.4 Hz, 2H), 5.11 (dd, J=12.8, 4.6 Hz, 1H), 4.43 (s, 2H), 3.94 (d, J=11.7 Hz, 2H), 3.73 (s, 2H), 3.41 (d, J=12.2 Hz, 2H), 3.11-2.98 (m, 4H), 2.93-2.84 (m, 1H), 2.61 (d, J=6.1 Hz, 2H), 2.56 (d, J=17.5 Hz, 2H), 2.08-1.94 (m, 3H). HRMS (ESI) m/z: calcd for $C_{27}H_{30}N_3O_5S^+$ [M+H]$^+$, 508.1901; found, 508.1906.

Example 220: 2-(2,6-dioxopiperidin-3-yl)-4-((3-(4-(piperidin-1-ylmethyl)phenyl)propyl)thio)isoindoline-1,3-dione (SIAIS1227039)

Referring to the method of example 161, the compound SIAIS1227039 was prepared under appropriate conditions that will be recognized by one skilled in the art, except that the thiophenol substrate used was 2-(2,6-dioxopiperidin-3-yl)-4-mercaptoisoindoline-1,3-dione (SIAIS151014), and the bromide used was 1-(bromomethyl)-4-(3-bromopropyl) benzene. The hydrochloride salt of compound SIAIS1227039 was obtained (white solid, 30 mg, yield 79%). $^1$H NMR (500 MHz, DMSO) δ 11.12 (s, 1H), 9.87 (s, 1H), 7.77 (t, J=7.5 Hz, 1H), 7.69 (d, J=8.0 Hz, 1H), 7.63 (d, J=7.1 Hz, 1H), 7.48 (s, 2H), 7.33 (d, J=7.6 Hz, 2H), 5.11 (dd, J=12.9, 5.0 Hz, 1H), 4.21 (s, 2H), 3.25 (s, 2H), 3.14 (t, J=6.9 Hz, 2H), 2.93-2.85 (m, 1H), 2.85-2.77 (m, 4H), 2.60 (d, J=18.2 Hz, 2H), 2.08-1.96 (m, 3H), 1.81-1.64 (m, 5H), 1.40-1.28 (m, 1H). HRMS (ESI) m/z: calcd for $C_{28}H_{32}N_3O_4S^+$ [M+H]$^+$, 506.2108; found, 506.2109.

Example 221: 4-((3-(4-((cyclohexylamino)methyl) phenyl)propyl)thio)-2-(2,6-dioxopiperidin-3-yl) isoindoline-1,3-dione (SIAIS1227069)

Referring to the method of example 161, the compound SIAIS1227069 was prepared under appropriate conditions that will be recognized by one skilled in the art, except that the bromide used was 1-(bromomethyl)-4-(3-bromopropyl) benzene, the amine used was cyclohexylamine, and the thiophenol substrate used was SIAIS151014. The hydrochloride salt of compound SIAIS1227069 was obtained (yellow solid, 25.8 mg, yield 66%). $^1$H NMR (500 MHz, DMSO) δ 11.12 (s, 1H), 9.02 (s, 2H), 7.78 (t, J=7.5 Hz, 1H), 7.69 (d, J=8.0 Hz, 1H), 7.64 (d, J=6.9 Hz, 1H), 7.49 (d, J=7.4 Hz, 2H), 7.31 (d, J=7.6 Hz, 2H), 5.12 (dd, J=12.7, 4.6 Hz, 1H), 4.10 (s, 2H), 3.13 (t, J=6.7 Hz, 2H), 3.00-2.84 (m, 2H), 2.79 (t, J=7.2 Hz, 2H), 2.60 (d, J=17.5 Hz, 1H), 2.51 (s, 1H), 2.10 (d, J=11.5 Hz, 2H), 2.05 (d, J=6.6 Hz, 1H), 2.00-1.93 (m, 2H), 1.76 (d, J=12.0 Hz, 2H), 1.60 (d, J=12.0 Hz, 1H), 1.41-1.31 (m, 2H), 1.26-1.16 (m, 2H), 1.14-1.04 (m, 1H). HRMS (ESI) m/z: calcd for $C_{29}H_{34}N_{304}S^+$ [M+H]$^+$, 520.2265; found, 520.2268.

Example 222: 4-((3-(4-(((adamantan-1-yl)amino) methyl)phenyl)propyl)thio)-2-(2,6-dioxopiperidin-3-yl)isoindoline-1,3-dione (SIAIS1227041)

Referring to the method of example 161, the compound SIAIS1227041 was prepared under appropriate conditions that will be recognized by one skilled in the art, except that the bromide used was 1-(bromomethyl)-4-(3-bromopropyl) benzene, the amine used was 1-adamantanamine, and the thiophenol substrate used was SIAIS151014. The hydrochloride salt of compound SIAIS1227041 was obtained (yellow solid, 20.7 mg, yield 79%). $^1$H NMR (500 MHz, DMSO) δ 11.12 (s, 1H), 8.86 (s, 2H), 7.78 (t, J=7.5 Hz, 1H), 7.70 (d, J=8.0 Hz, 1H), 7.64 (d, J=7.1 Hz, 1H), 7.49 (d, J=7.3 Hz, 2H), 7.31 (d, J=7.4 Hz, 2H), 5.12 (dd, J=12.6, 4.5 Hz, 1H), 4.06 (d, J=4.3 Hz, 2H), 3.13 (t, J=6.7 Hz, 2H), 2.94-2.84 (m, 1H), 2.79 (t, J=7.1 Hz, 2H), 2.60 (d, J=17.4 Hz, 1H), 2.57-2.52 (m, 1H), 2.14 (s, 3H), 2.08-2.02 (m, 1H), 1.96 (s, 8H), 1.68 (d, J=12.2 Hz, 3H), 1.61 (d, J=12.0 Hz, 3H). HRMS (ESI) m/z: calcd for $C_{33}H_{38}N_3O_4S^+$ [M+H]$^+$, 572.2578; found, 572.2575.

Example 223: 4-((7-((adamantan-1-yl)(methyl) amino)heptyl)thio)-2-(2,6-dioxopiperidin-3-yl)isoindoline-1,3-dione (SIAIS1222029)

Referring to the method of Scheme 13, the compound SIAIS1222029 was prepared under appropriate conditions that will be recognized by one skilled in the art, except that the substrate was 4-((7-((adamantan-1-yl)amino)heptyl) thio)-2-(2,6-dioxopiperidin-3-yl)isoindoline-1,3-dione (SIAIS1221069). The hydrochloride salt of compound SIAIS1222029 was obtained (yellow solid, 19 mg, yield 93%). $^1$H NMR (500 MHz, DMSO) δ 11.09 (s, 1H), 10.16 (s, 1H), 7.72-7.66 (m, 2H), 7.47 (d, J=7.4 Hz, 1H), 5.12 (dd, J=13.3, 5.0 Hz, 1H), 4.12 (t, J=7.0 Hz, 2H), 3.32-3.23 (m, 1H), 2.98 (s, 1H), 2.92-2.85 (m, 1H), 2.65-2.57 (m, 5H), 2.15 (s, 3H), 2.00 (d, J=11.4 Hz, 4H), 1.90 (d, J=11.3 Hz, 3H), 1.62 (s, 10H), 1.45-1.33 (m, 6H). HRMS (ESI) m/z: calcd for $C_{31}H_{42}N_3O_4S^+$ [M+H]$^+$, 552.2891; found, 552.2895.

Example 224: 4-((6-(((adamantan-1-yl)methyl) amino)hexyl)thio)-2-(2,6-dioxopiperidin-3-yl)isoindoline-1,3-dione (SIAIS1222071)

Referring to the method of example 211, the compound SIAIS1222071 was prepared under appropriate conditions that will be recognized by one skilled in the art, except that the bromide used was 1,6-dibromohexane, and the amine used was 1-adamantanemethylamine. The hydrochloride salt of compound SIAIS1222071 was obtained (yellow solid, 5 mg, yield 9%). $^1$H NMR (500 MHz, DMSO-$d_6$) δ 11.13 (s, 1H), 8.06 (s, 2H), 7.80 (t, J=7.2 Hz, 1H), 7.75 (d, J=8.1 Hz, 1H), 7.64 (d, J=7.2 Hz, 1H), 5.11 (dd, J=13.1, 5.4 Hz, 1H), 3.49 (s, 2H), 3.15 (t, J=7.7 Hz, 2H), 2.86 (s, 3H), 2.62 (d, J=19.7 Hz, 3H), 2.09-2.02 (m, 1H), 1.97 (s, 3H), 1.68 (d, J=10.7 Hz, 5H), 1.60 (d, J=12.1 Hz, 4H), 1.55 (s, 6H), 1.46 (d, J=7.7 Hz, 2H), 1.35 (d, J=8.0 Hz, 2H). HRMS (ESI) m/z: calcd for $C_{30}H_{40}N_3O_4S^+$ [M+H]$^+$, 538.2734; found, 538.2731.

Example 225: 4-((5-((adamantan-1-yl)amino)pentyl) thio)-2-(2,6-dioxopiperidin-3-yl)isoindoline-1,3-dione (SIAIS1222097)

Referring to the method of example 211, the compound SIAIS1222097 was prepared under appropriate conditions that will be recognized by one skilled in the art, except that the bromide used was 1,5-dibromopentane, and the amine used was 1-adamantanamine. The hydrochloride salt of compound SIAIS1222097 was obtained (yellow solid, 5.8 mg, yield 23%). $^1$H NMR (500 MHz, DMSO) δ 11.10 (s, 1H), 8.58 (s, 2H), 7.60 (t, J=7.8 Hz, 1H), 7.12 (d, J=8.5 Hz, 1H), 7.04 (d, J=7.0 Hz, 1H), 5.05 (dd, J=13.2, 5.3 Hz, 1H), 3.67 (t, J=6.4 Hz, 2H), 2.85-2.78 (m, 3H), 2.59 (d, J=17.5 Hz, 2H), 2.10 (d, J=12.5 Hz, 3H), 2.07-2.00 (m, 1H), 1.78 (s, 6H), 1.70-1.63 (m, 6H), 1.62-1.55 (m, 4H), 1.45-1.39 (m, 2H). HRMS (ESI) m/z: calcd for $C_{28}H_{36}N_3O_4S^+$ [M+H]$^+$, 510.2421; found, 510.2420.

Example 226: 4-((6-((adamantan-1-yl)amino)hexyl) thio)-2-(2,6-dioxopiperidin-3-yl)isoindoline-1,3-dione (SIAIS1222109)

Referring to the method of example 210, the compound SIAIS1222109 was prepared under appropriate conditions that will be recognized by one skilled in the art, except that the bromide used was 1,6-dibromohexane, and the amine used was 1-adamantanamine. The hydrochloride salt of compound SIAIS1222109 was obtained (yellow solid, 7.6 mg, yield 29%). $^1$H NMR (500 MHz, DMSO) δ 11.10 (s, 1H), 8.56 (s, 2H), 7.59 (t, J=7.7 Hz, 1H), 7.13 (d, J=8.5 Hz, 1H), 7.06 (d, J=7.0 Hz, 1H), 5.11 (dd, J=12.7, 5.3 Hz, 1H), 3.34 (s, 2H), 2.92-2.80 (m, 3H), 2.60 (d, J=17.5 Hz, 2H), 2.12 (s, 3H), 2.06-2.00 (m, 1H), 1.84 (s, 6H), 1.76-1.55 (m, 10H), 1.44 (s, 4H). HRMS (ESI) m/z: calcd for $C_{29}H_{38}N_3O_4S^+$ [M+H]$^+$, 524.2578; found, 524.2579.

Example 227: 4-((8-((adamantan-1-yl)amino)octyl) thio)-2-(2,6-dioxopiperidin-3-yl)isoindoline-1,3-dione (SIAIS1224011)

Referring to the method of example 211, the compound SIAIS1224011 was prepared under appropriate conditions that will be recognized by one skilled in the art, except that the bromide used was 1,8-dibromooctane, and the amine used was 1-adamantanamine. The hydrochloride salt of compound SIAIS1224011 was obtained (white solid, 18.3 mg, yield 36%). $^1$H NMR (500 MHz, DMSO) δ 10.97 (s, 1H), 8.38 (s, 2H), 7.59 (t, J=7.5 Hz, 1H), 7.10 (d, J=8.7 Hz, 1H), 7.04 (d, J=7.0 Hz, 1H), 5.11 (dd, J=12.7, 5.2 Hz, 1H), 4.12 (s, 2H), 2.93-2.80 (m, 1H), 2.74-2.66 (m, 2H), 2.59 (d, J=18.5 Hz, 1H), 2.48-2.40 (m, 1H), 2.11 (s, 3H), 2.05-1.98 (m, 1H), 1.83 (s, 6H), 1.76 (d, J=12.0 Hz, 2H), 1.60 (d, J=10.5 Hz, 8H), 1.44 (s, 2H), 1.32 (s, 6H). HRMS (ESI) m/z: calcd for $C_{31}H_{42}N_3O_4S^+$ [M+H]$^+$, 552.2891; found, 552.2896.

Example 228: 2-(2,6-dioxopiperidin-3-yl)-4-((7-(spiro[3.3]heptan-2-ylamino)heptyl)thio)isoindoline-1,3-dione (SIAIS1224015)

Referring to the method of Scheme 11, the compound SIAIS1224015 was prepared under appropriate conditions that will be recognized by one skilled in the art, except that the substrates were 4-((7-bromoheptyl)thio)-2-(2,6-dioxopiperidin-3-yl)isoindoline-1,3-dione (SIAIS1221039) and spiro[3.3]heptan-2-amine hydrochloride. The hydrochloride salt of compound SIAIS1224015 was obtained (white solid, 18.3 mg, yield 36%). $^1$H NMR (500 MHz, DMSO) δ 11.12 (s, 1H), 8.90 (s, 2H), 7.79 (t, J=7.6 Hz, 1H), 7.75 (d, J=7.8 Hz, 1H), 7.63 (d, J=6.8 Hz, 1H), 5.11 (dd, J=12.8, 5.4 Hz, 1H), 3.54-3.45 (m, 1H), 3.14 (t, J=6.9 Hz, 2H), 2.93-2.84 (m, 1H), 2.70 (s, 2H), 2.60 (d, J=18.2 Hz, 2H), 2.26 (t, J=8.9 Hz, 2H), 2.13 (t, J=9.9 Hz, 2H), 2.08-2.03 (m, 1H), 2.00 (t, J=7.3 Hz, 2H), 1.92 (t, J=7.2 Hz, 2H), 1.82-1.75 (m, 2H), 1.71-1.64 (m, 2H), 1.56 (s, 2H), 1.44 (s, 2H), 1.31 (s, 4H). HRMS (ESI) m/z: calcd for $C_{27}H_{36}N_3O_4S^+$ [M+H]$^+$, 498.2421; found, 498.2425.

Example 229: 3-(5-((7-((adamantan-1-yl)amino)heptyl)thio)-1-oxoisoindolin-2-yl)piperidine-2,6-dione (SIAIS271167)

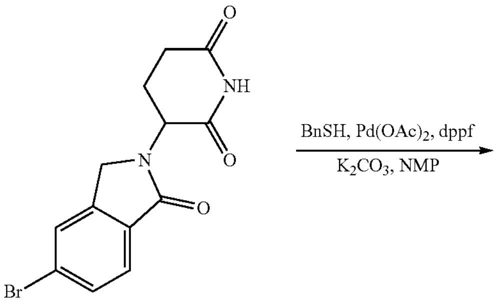

1

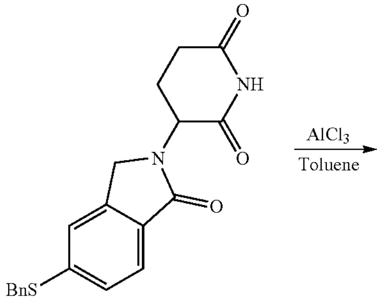

SIAIS271163

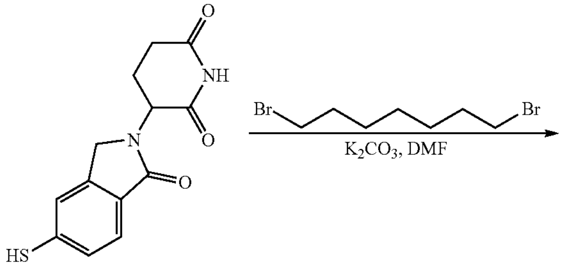

SIAIS271165

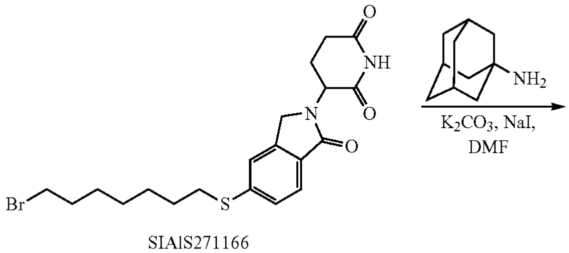

SIAIS271166

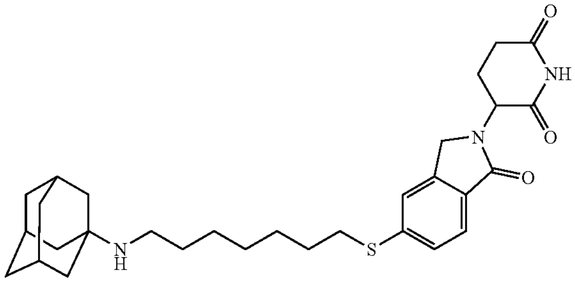

SIAIS271167

Step 1: A 25 mL reaction flask was charged with the compound 1 (500 mg, 1.55 mmol) and N-methylpyrrolidone (15 mL), followed by sequentially addition of palladium acetate (35 mg, 0.15 mmol), dppf (172 mg, 0.31 mmol), potassium carbonate (642 mg, 4.65 mmol), and benzyl mercaptan (384 mg, 3.1 mmol) under nitrogen gas protection. After the completion of addition, the reaction mixture was heated to 110° C. and stirred at 110° C. for 15 h, and then water was added thereto. The resulting mixture was stirred for 0.5 h, and filtered. The filter cake was slurried in petroleum ether:ethyl acetate=10:1, filtered, and dried to give the compound SIAIS SIAIS271163 as a yellow solid (400 mg, yield 70.6%). LCMS (ESI) m/z: calcd for $C_{20}H_{19}N_2O_3S^+$ [M+H]$^+$, 367.1111; found, 367.34.

Step 2: A 25 mL reaction flask was charged with the compound SIAIS271163 (200 mg, 0.55 mmol) and anhydrous toluene (10 mL), followed by addition of aluminum trichloride (363 mg, 2.73 mmol) under nitrogen gas atmosphere. After the completion of addition, the reaction mixture was stirred at 45° C. for 15 h. 20% citric acid aqueous solution was added to the reaction mixture and stirred for another 0.5 h. The resulting mixture was filtered, and the residue was dried to give the target compound SIAIS271165 as a yellow solid (90 mg, yield 59.7%). LCMS (ESI) m/z: calcd for $C_{13}H_{13}N_2O_3S^+$ [M+H]$^+$, 277.0641; found, 277.30.

Step 3: A 10 mL reaction flask was charged with the compound SIAIS271165 (85 mg, 0.31 mmol) and anhydrous DMF (3 mL), followed by sequential addition of potassium carbonate (85 mg, 0.62 mmol) and 1,7-dibromoheptane (119 mg, 0.46 mmol). After the completion of addition, the reaction mixture was stirred at room temperature for 0.5 h. The mixture was poured into water, extracted with ethyl acetate. The organic phase was sequentially washed with water and saturated brine, and concentrated under vacuum. The residue was subjected to column chromatography (petroleum ether:ethyl acetate=1:2) for purification to give the compound SIAIS271166 as a white solid (35 mg, yield 25.1%). $^1$H NMR (500 MHz, $CDCl_3$) δ 8.19 (d, J=48.5 Hz, 1H), 7.75 (t, J=13.3 Hz, 1H), 7.35 (dd, J=17.9, 10.1 Hz, 2H), 5.19 (dt, J=27.5, 13.8 Hz, 1H), 4.50-4.27 (m, 2H), 3.40 (q, J=6.6 Hz, 2H), 2.98 (dd, J=22.5, 15.2 Hz, 2H), 2.95-2.75 (m, 2H), 2.43-2.29 (m, 1H), 2.26-2.18 (m, 1H), 1.82 (s, 10H). LCMS (ESI) m/z: calcd for $C_{20}H_{26}BrN_2O_3S^+$ [M+H]$^+$, 453.0842; found, 453.33.

Step 4: A 10 mL reaction flask was charged with the compound SIAIS271166 (30 mg, 0.066 mmol) and anhydrous DMF (2 mL), followed by sequential addition of Potassium carbonate (24.7 mg, 0.18 mmol), sodium iodide (20 mg, 0.13 mmol) and 1-adamantanamine (15 mg, 0.099 mmol). After the completion of addition, the reaction mixture was stirred at 45° C. for 15 h. The mixture was subjected to preparative HPLC (eluent (v/v):acetonitrile/(water+0.05% HCl)=10%-90%) for separation and purification to give the hydrochloride salt of compound SIAIS271167 (white solid, 7 mg, yield 20.2%). $^1$H NMR (500 MHz, MeOD) δ 7.69 (d, J=8.1 Hz, 1H), 7.50 (s, 1H), 7.42 (d, J=8.1 Hz, 1H), 5.13 (dd, J=13.2, 5.1 Hz, 1H), 4.46 (q, J=17.1 Hz, 2H), 3.08 (t, J=7.1 Hz, 2H), 2.98-2.84 (m, 3H), 2.78 (d, J=17.6 Hz, 1H), 2.48 (qd, J=13.2, 4.3 Hz, 1H), 2.23-2.12 (m, 4H), 1.90 (s, 6H), 1.80 (d, J=12.6 Hz, 3H), 1.72 (d, J=9.3 Hz, 5H), 1.64 (s, 2H), 1.53 (d, J=6.6 Hz, 2H), 1.42 (s, 4H). HRMS (ESI) m/z: calcd for $C_{30}H_{42}N_3O_3S^+$ [M+H]$^+$, 524.2941; found, 524.2951.

Example 230: 3-(1-oxo-4-(((5-(piperidin-1-ylmethyl)furan-2-yl)methyl)thio)isoindolin-2-yl)piperidine-2,6-dione (SIAIS313123)

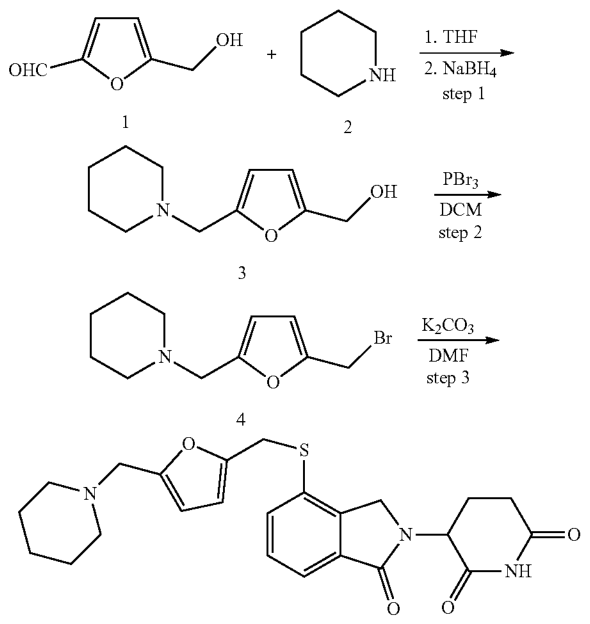

1 2 3 4

Step 1: To a solution of 5-hydroxymethylfurfural 1 (0.126 g, 1 mmol) in tetrahydrofuran (5 ml) was added piperidine 2 (1 eq). Then the reaction mixture was reacted at room temperature for 2 h. Once the reaction was complete as detected, to the mixture was added $NaBH_4$ (56.7 mg, 1.5 eq) in batches under ice bath, and then reacted at room temperature for 1 h. Once the starting materials were consumed as monitored by LC-MS, 2 ml of water was added to the mixture under ice bath. The resulting mixture was extracted with ethyl acetate, and the organic phase was washed with saturated brine, concentrated under vacuum. The residue was used directly in the next step.

Step 2: To a solution of the above concentrated residue in DCM (5 ml) was slowly added dropwise $PBr_3$ (112 μl, 1.2 eq) under ice bath. Then the mixture was reacted under ice bath for 2 h, concentrated under reduced pressure, and the residue was used directly in the next step.

Step 3: To a solution of the above concentrated residue in N,N-dimethylformamide (5 ml) was added 3-(4-mercapto-1-oxoisoindolin-2-yl)piperidine-2,6-dione (1 eq) and potassium carbonate (1.2 eq). The mixture was reacted at room temperature for 2 h, and filtered. The filtrate was subjected to preparative HPLC (eluent (v/v):acetonitrile/(water+0.05% HCl)=10%-100%) for separation. The collected fractions were rotary evaporated to remove acetonitrile, and lyophilized to give the hydrochloride salt of compound SIAIS313123 (white solid, 80 mg, yield 17%). $^1$H NMR (500 MHz, DMSO) δ 11.00 (d, J=6.4 Hz, 1H), 10.72 (s, 1H), 7.78-7.69 (m, 1H), 7.67-7.58 (m, 1H), 7.52 (t, J=7.6 Hz, 1H), 6.60 (d, J=2.9 Hz, 1H), 6.32 (d, J=2.8 Hz, 1H), 5.13 (dd, J=13.2, 4.8 Hz, 1H), 4.51-4.28 (m, 3H), 4.26-4.10 (m, 3H), 3.15 (dd, J=24.6, 11.9 Hz, 2H), 2.99-2.81 (m, 1H), 2.71-2.56 (m, 3H), 2.48-2.35 (m, 1H), 2.07-1.95 (m, 1H), 1.75-1.60 (m, 5H), 1.30-1.14 (m, 1H). HRMS (ESI) $C_{24}H_{28}N_3O_4S^+$ [M+H]$^+$, calcd for 454.1801; found, 454.1795.

Example 231: 3-(4-(((5-(morpholinomethyl)furan-2-yl)methyl)thio)-1-oxoisoindolin-2-yl)piperidine-2,6-dione (SIAIS313126)

Referring to the method of example 230, the compound SIAIS313126 was prepared under appropriate conditions that will be recognized by one skilled in the art, except that the substrate used was morpholine. The hydrochloride salt of compound SIAIS313126 was obtained (white solid, 60 mg, yield 13%). $^1$H NMR (500 MHz, DMSO) δ 11.60 (s, 1H), 11.01 (d, J=6.7 Hz, 1H), 7.73 (t, J=6.8 Hz, 1H), 7.64 (dd, J=13.5, 6.8 Hz, 1H), 7.54 (dd, J=12.6, 5.0 Hz, 1H), 6.62 (d, J=2.5 Hz, 1H), 6.31 (d, J=2.5 Hz, 1H), 5.13 (dd, J=13.2, 4.9 Hz, 1H), 4.52-4.30 (m, 5H), 4.23 (dd, J=29.3, 12.3 Hz, 4H), 3.88 (t, J=16.4 Hz, 1H), 3.74 (dd, J=29.8, 18.3 Hz, 1H), 3.15 (t, J=12.0 Hz, 1H), 3.00-2.84 (m, 2H), 2.58 (t, J=20.5 Hz, 1H), 2.47-2.33 (m, 2H), 2.01 (dd, J=11.7, 5.8 Hz, 1H). HRMS (ESI) $C23H_{26}N_3O_5S^+$ [M+H]$^+$, calcd for 456.1593; found, 456.1585.

Example 232: 3-(4-(((5-((((S)-1-cyclopropylethyl)amino)methyl)furan-2-yl)methyl)thio)-1-oxoisoindolin-2-yl)piperidine-2,6-dione (SIAIS313129)

Referring to the method of example 230, the compound SIAIS313129 was prepared under appropriate conditions that will be recognized by one skilled in the art, except that the substrate used was (S)-1-cyclopropylethane-1-amine. The hydrochloride salt of compound SIAIS313129 was obtained (white solid, 60 mg, yield 13%). $^1$H NMR (500 MHz, DMSO) δ 11.00 (s, 1H), 9.14 (s, 2H), 7.70 (d, J=7.7 Hz, 1H), 7.62 (d, J=7.4 Hz, 1H), 7.53 (t, J=7.5 Hz, 1H), 6.53 (s, 1H), 6.30 (s, 1H), 5.13 (dd, J=13.3, 4.9 Hz, 1H), 4.39 (s, 2H), 4.31 (d, J=17.6 Hz, 1H), 4.27-4.15 (m, 3H), 2.99-2.81 (m, 1H), 2.65-2.58 (m, 1H), 2.47-2.35 (m, 1H), 2.04-1.92 (m, 1H), 1.32-1.17 (m, 5H), 0.95 (s, 1H), 0.67-0.38 (m, 3H), 0.22 (s, 1H). HRMS (ESI) $C_{24}H_{28}N_3O_4S^+$ [M+H]$^+$, calcd for 454.1801; found, 454.1806.

Example 233: 3-(4-(((5-(azepan-1-ylmethyl)furan-2-yl)methyl)thio)-1-oxoisoindolin-2-yl)piperidine-2,6-dione (SIAIS313135)

Referring to the method of example 230, the compound SIAIS313135 was prepared under appropriate conditions that will be recognized by one skilled in the art, except that the substrate used was azepane. The hydrochloride salt of compound SIAIS313135 was obtained (white solid, 0.12 g, yield 26%). $^1$H NMR (500 MHz, DMSO) δ 11.00 (s, 1H), 10.23 (s, 1H), 7.72 (d, J=7.5 Hz, 1H), 7.62 (d, J=7.3 Hz, 1H), 7.52 (t, J=7.5 Hz, 1H), 6.60 (s, 1H), 6.32 (s, 1H), 5.22-5.04 (m, 1H), 4.41 (s, 2H), 4.32 (d, J=16.8 Hz, 3H), 4.19 (d, J=17.3 Hz, 1H), 3.30-3.15 (m, 2H), 3.01-2.85 (m, 3H), 2.65-2.55 (m, 1H), 2.45-2.35 (m, 1H), 2.00 (s, 1H), 1.72 (d, J=33.7 Hz, 4H), 1.59 (s, 2H), 1.47 (s, 2H). HRMS (ESI) $C_{25}H_{30}N_3O_4S^+$ [M+H]$^+$, calcd for 468.1957; found, 468.1959.

Example 234: 3-(4-(((5-((cyclopentylamino)methyl)furan-2-yl)methyl)thio)-1-oxoisoindolin-2-yl)piperidine-2,6-dione (SIAIS313148)

Referring to the method of example 229, the compound SIAIS313148 was prepared under appropriate conditions that will be recognized by one skilled in the art, except that the substrate used was cyclopentylamine. The hydrochloride salt of compound SIAIS313148 was obtained (white solid, 0.1 g, yield 22%). $^{1}$H NMR (500 MHz, DMSO) δ 11.00 (s, 1H), 9.12 (s, 2H), 7.71 (d, J=7.7 Hz, 1H), 7.62 (d, J=7.4 Hz, 1H), 7.53 (t, J=7.5 Hz, 1H), 6.52 (s, 1H), 6.30 (s, 1H), 5.13 (dd, J=13.0, 4.6 Hz, 1H), 4.40 (s, 2H), 4.25 (dd, J=60.4, 17.0 Hz, 2H), 4.15 (s, 1H), 3.45-3.30 (m, 2H), 3.01-2.82 (m, 1H), 2.61 (t, J=14.0 Hz, 1H), 2.41 (dd, J=27.6, 14.5 Hz, 1H), 2.08-1.96 (m, 1H), 1.88 (s, 2H), 1.67 (s, 2H), 1.61-1.53 (m, 2H), 1.48 (s, 2H). HRMS (ESI) $C_{24}H_{28}N_3O_4S^+$ $[M+H]^+$, calcd for 454.1801; found, 454.1793.

Example 235: 3-(1-oxo-4-(((5-((((tetrahydro-2H-pyran-2-yl)methyl)amino)methyl)furan-2-yl)methyl)thio)isoindolin-2-yl)piperidine-2,6-dione (SIAIS313149)

Referring to the method of example 230, the compound SIAIS313149 was prepared under appropriate conditions that will be recognized by one skilled in the art, except that the substrate used was (tetrahydro-2H-pyran-2-yl)methylamine. The hydrochloride salt of compound SIAIS313149 was obtained (white solid, 0.1 g, yield 16%). $^{1}$H NMR (500 MHz, DMSO) δ 11.00 (s, 1H), 9.50 (s, 1H), 9.16 (s, 1H), 7.70 (d, J=7.6 Hz, 1H), 7.62 (d, J=7.3 Hz, 1H), 7.53 (t, J=7.5 Hz, 1H), 6.53 (s, 1H), 6.27 (s, 1H), 5.13 (dd, J=13.3, 4.7 Hz, 1H), 4.38 (s, 2H), 4.31 (d, J=17.4 Hz, 1H), 4.25-4.15 (m, 1H), 4.12 (s, 2H), 3.90 (d, J=10.9 Hz, 1H), 3.66-3.50 (m, 1H), 3.35 (t, J=10.7 Hz, 1H), 3.00-2.83 (m, 2H), 2.82-2.68 (m, 1H), 2.60 (d, J=16.8 Hz, 1H), 2.49-2.33 (m, 1H), 1.96 (dd, J=35.1, 29.2 Hz, 1H), 1.76 (s, 1H), 1.47 (dd, J=31.2, 12.5 Hz, 4H), 1.12 (d, J=10.4 Hz, 1H). HRMS (ESI) $C_{25}H_{30}N_3O_5S$ $[M+H]^+$, calcd for 484.1906; found, 484.1899.

Example 236: 3-(4-(((5-(((dicyclopropylmethyl)amino)methyl)furan-2-yl)methyl)thio)-1-oxoisoindolin-2-yl)piperidine-2,6-dione (SIAIS313150)

Referring to the method of example 230, the compound SIAIS313150 was prepared under appropriate conditions that will be recognized by one skilled in the art, except that the substrate used was dicyclopropylmethylamine. The hydrochloride salt of compound SIAIS313150 was obtained (white solid, 0.1 g, yield 16%). $^{1}$H NMR (500 MHz, DMSO) δ 11.00 (s, 1H), 9.11 (s, 2H), 7.70 (d, J=7.7 Hz, 1H), 7.62 (t, J=9.3 Hz, 1H), 7.53 (t, J=7.7 Hz, 1H), 6.54 (s, 1H), 6.29 (d, J=20.6 Hz, 1H), 5.14 (dd, J=13.2, 4.6 Hz, 1H), 4.40 (s, 2H), 4.34-4.24 (m, 3H), 4.19 (d, J=17.4 Hz, 1H), 2.99-2.83 (m, 1H), 2.60 (dd, J=30.4, 13.3 Hz, 2H), 2.41 (dd, J=28.1, 14.4 Hz, 1H), 2.00 (d, J=13.1 Hz, 2H), 1.03 (s, 2H), 0.58 (d, J=7.3 Hz, 4H), 0.51-0.30 (m, 4H). HRMS (ESI) $C_{26}H_{30}N_3O_4S^+$ $[M+H]^+$, calcd for 480.1957; found, 480.1955.

Example 237: 3-(4-(((2-(morpholinomethyl)thiazol-4-yl)methyl)thio)-1-oxoisoindolin-2-yl)piperidine-2,6-dione (SIAIS313163)

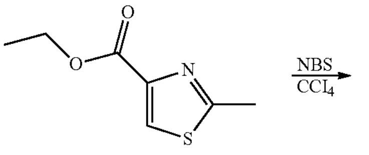

1

-continued

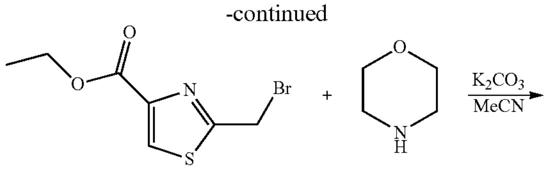

2

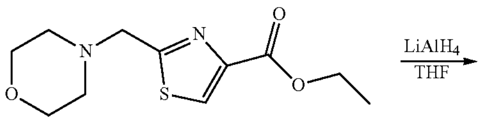

3

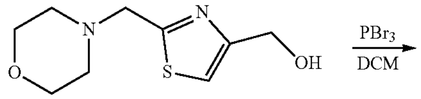

4

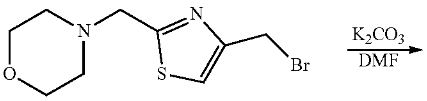

5

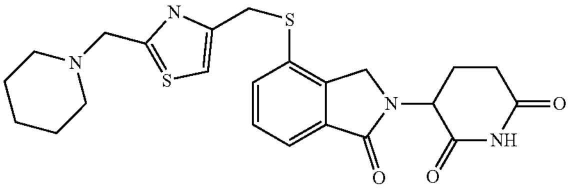

Step 1: To a suspension of ethyl 2-methylthiazole-4-carboxylate 1 (2 g, 11.68 mmol) in carbon tetrachloride (20 ml) were added N-bromosuccinimide (NBS) (2.28 g, 1.1 eq) and a catalytic amount of azobisisobutyronitrile. The reaction mixture was stirred under reflux for 4 h under $N_2$ gas atmosphere, and then concentrated. The residue was purified by silica gel column chromatography to give compound 2 (pale yellow solid, 0.8 g, yield 27.3%).

Step 2: To a solution of compound 2 (0.15 g, 0.6 mmol) in acetonitrile were added potassium carbonate (91 mg, 1.1 eq) and morpholine (99.6 mg, 1.1 eq). The reaction mixture was stirred at 35° C. for 2 h, then concentrated, and the residue was purified by column chromatography to give compound 3 (0.16 g, yield 81.6%).

Step 3: To a suspension of compound 3 (0.16 g, 0.5 mmol) in THF was slowly added $LiAlH_4$ (21 mg, 1.1 eq) under ice bath. Then the mixture was stirred at room temperature for 1 h. To the mixture were added 5 mL of ethyl acetate, and then quenched with 2M NaOH. The mixture was filtered, extracted with ethyl acetate, and concentrated under vacuum, and the resulting residue was used directly in the next step.

Step 4: To a solution of the concentrated residue containing the compound 4 from step 3 in dichloromethane was added dropwise $PBr_3$ (60 μl, 1.1 eq) under ice bath. The reaction mixture was stirred at room temperature for 1 h, and concentrated. The residue was used directly in the next step.

Step 5: To a solution of the above concentrate from step 4 in DMF (5 mL) were added 3-(4-mercapto-1-oxoisoindolin-2-yl)piperidine-2,6-dione (1 eq) and potassium carbonate (1.2 eq). Then the reaction mixture was stirred at room temperature for 2 h, filtered, and the filtrate was subjected to preparative HPLC (eluent (v/v):acetonitrile/(water+0.05% HCl)=10%-100%) for separation. The collected fractions were rotary evaporated to remove acetonitrile, and lyophilized to give the hydrochloride salt of compound SIAIS313163 (white solid, 20 mg, yield 16%). $^1$H NMR (500 MHz, DMSO) δ 11.52 (s, 1H), 11.01 (s, 1H), 7.72 (d, J=7.6 Hz, 1H), 7.66 (s, 1H), 7.60 (d, J=7.4 Hz, 1H), 7.51 (t, J=7.5 Hz, 1H), 5.13 (dd, J=13.1, 4.5 Hz, 1H), 4.67 (s, 2H), 4.52-4.42 (m, 2H), 4.32 (d, J=17.4 Hz, 1H), 4.17 (d, J=17.4 Hz, 1H), 3.98-3.72 (m, 4H), 3.32-3.05 (m, 4H), 2.98-2.81 (m, 1H), 2.60 (d, J=17.0 Hz, 1H), 2.41 (dd, J=27.8, 14.7 Hz, 1H), 2.05-1.93 (m, 1H). HRMS (ESI) $C_{22}H_{25}N_4O_4S_2^+$ [M+H]$^+$, calcd for 473.1317; found, 473.1310.

Example 238: 3-(1-oxo-4-(((2-(piperidin-1-ylmethyl)thiazol-4-yl)methyl)thio)isoindolin-2-yl)piperidine-2,6-dione (SIAIS313164)

Referring to the method of example 237, the compound SIAIS313164 was prepared under appropriate conditions that will be recognized by one skilled in the art, except that the substrate used was piperidine. The hydrochloride salt of compound SIAIS313164 was obtained (white solid, 42 mg, yield 19%). $^1$H NMR (500 MHz, DMSO) δ 11.01 (s, 1H), 10.26 (s, 1H), 7.72 (d, J=7.5 Hz, 1H), 7.67 (s, 1H), 7.60 (d, J=7.3 Hz, 1H), 7.50 (t, J=7.6 Hz, 1H), 5.13 (dd, J=13.2, 4.4 Hz, 1H), 4.62 (s, 2H), 4.48 (s, 2H), 4.32 (d, J=17.4 Hz, 1H), 4.17 (d, J=17.4 Hz, 1H), 3.76-3.75 (m, 1H), 2.91 (dd, J=21.0, 8.3 Hz, 3H), 2.60 (dd, J=28.6, 10.8 Hz, 1H), 2.41 (dd, J=27.2, 14.2 Hz, 1H), 2.05-1.93 (m, 1H), 1.76 (s, 2H), 1.65 (s, 3H), 1.38-1.17 (m, 2H). HRMS (ESI) $C_{23}H_{27}N_4O_3S_2^+$ [M+H]$^+$, calcd for 471.1525; found, 471.1523.

Example 239: 3-(4-(((2-(azepan-1-ylmethyl)thiazol-4-yl)methyl)thio)-1-oxoisoindolin-2-yl)piperidine-2,6-dione (SIAIS313165)

Referring to the method of example 237, the compound SIAIS313165 was prepared under appropriate conditions that will be recognized by one skilled in the art, except that the substrate used was azepane. The hydrochloride salt of compound SIAIS313165 was obtained (white solid, 21 mg, yield 16%). $^1$H NMR (500 MHz, DMSO) δ 11.00 (s, 1H), 10.57 (s, 1H), 7.73 (t, J=7.7 Hz, 1H), 7.66 (s, 1H), 7.62 (dd, J=17.8, 8.2 Hz, 1H), 7.51 (t, J=7.7 Hz, 1H), 5.13 (dd, J=13.0, 4.5 Hz, 1H), 4.67 (s, 2H), 4.52-4.42 (m, 2H), 4.37-4.26 (m, 1H), 4.17 (d, J=17.4 Hz, 1H), 3.37-3.25 (m, 2H), 3.11 (d, J=5.4 Hz, 2H), 2.99-2.82 (m, 1H), 2.60 (d, J=17.3 Hz, 1H), 2.41 (dd, J=27.0, 14.6 Hz, 1H), 2.06-1.92 (m, 1H), 1.75 (s, 4H), 1.61 (d, J=5.8 Hz, 2H), 1.53 (d, J=6.4 Hz, 2H). HRMS (ESI) $C_{24}H_{29}N_4O_3S_2^+$ [M+H]$^+$, calcd for 485.1681; found, 485.1683.

Example 240: 3-(4-(((2-((cyclopentylamino)methyl)thiazol-4-yl)methyl)thio)-1-oxoisoindolin-2-yl)piperidine-2,6-dione (SIAIS313166)

Referring to the method of example 237, the compound SIAIS313166 was prepared under appropriate conditions that will be recognized by one skilled in the art, except that the substrate used was cyclopentylamine. The hydrochloride salt of compound SIAIS313166 was obtained (white solid, 15 mg, yield 22%). $^1$H NMR (500 MHz, DMSO) δ 11.00 (s, 1H), 9.46 (s, 2H), 7.72 (d, J=7.7 Hz, 1H), 7.60 (d, J=6.5 Hz, 2H), 7.52 (t, J=7.5 Hz, 1H), 5.13 (dd, J=13.2, 4.6 Hz, 1H), 4.52 (s, 2H), 4.45 (d, J=14.0 Hz, 2H), 4.31 (d, J=17.4 Hz, 1H), 4.18 (d, J=17.2 Hz, 1H), 3.49 (s, 1H), 2.98-2.84 (m, 1H), 2.61 (t, J=13.8 Hz, 1H), 2.41 (dd, J=27.1, 13.8 Hz, 1H), 2.04-1.88 (m, 3H), 1.75-1.58 (m, 4H), 1.50 (s, 2H). HRMS (ESI) $C_{23}H_{27}N_4O_3S_2^+$ [M+H]$^+$, calcd for 471.1525; found, 471.1533.

Example 241: 3-(4-(((4-(morpholinomethyl)thiazol-2-yl)methyl)thio)-1-oxoisoindolin-2-yl)piperidine-2,6-dione (SIAIS313169)

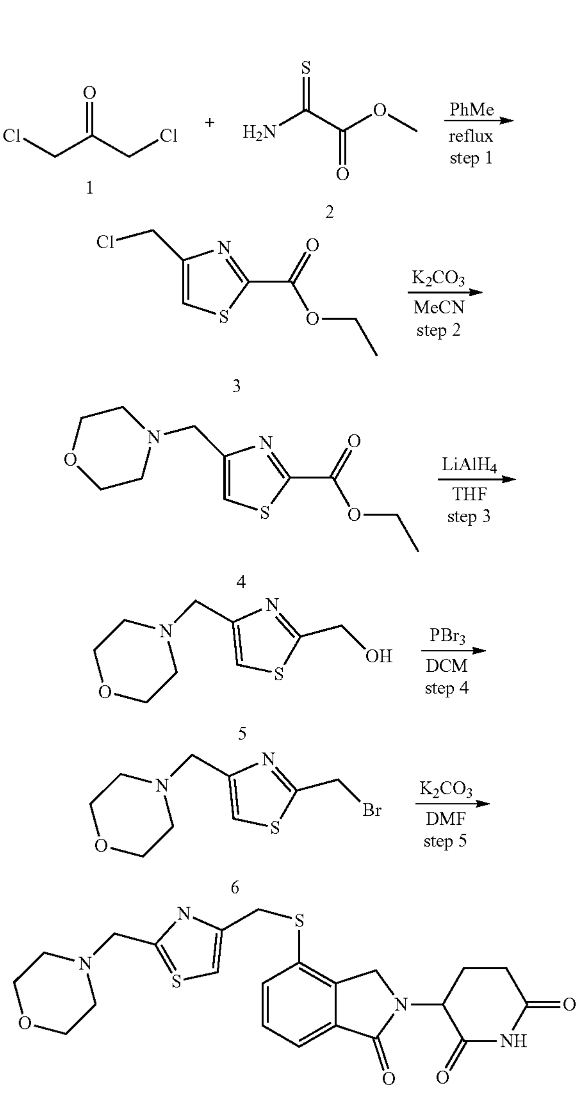

SIAIS313169

Step 1: A solution of the substrate 1 (2.84 g, 22 mmol, 1.1 eq) and substrate 2 (2.66 g, 20 mmol, 1 eq) in toluene (20 ml) was stirred and reflux under nitrogen atmosphere for 3 h, and then concentrated. The residue was subjected to silica gel column chromatography for separation to give compound 3 (light yellow liquid, 3 g, yield 73%). $^1$H NMR (500 MHz, $CDCl_3$) δ 7.66 (s, 1H), 4.80 (s, 2H), 4.51 (q, J=7.0 Hz, 2H), 1.46 (t, J=7.0 Hz, 3H).

Step 2: To a solution of compound 3 (0.2 g, 0.8 mmol) in acetonitrile were added potassium carbonate (91 mg, 1.1 eq) and morpholine (76.6 μl, 1.1 eq). The reaction mixture was stirred at 35° C. for 2 h, then concentrated, and the residue was used directly in the next step.

Step 3: To a suspension of compound 4 in THF was slowly added $LiAlH_4$ (33 mg, 1.1 eq) under ice bath. Then the mixture was stirred at room temperature for 1 h, and 5 mL of ethyl acetate was added thereto. The reaction was quenched with 2M NaOH. The resulting mixture was filtered, extracted with ethyl acetate, and concentrated under vacuum. The residue was subjected to column chromatography for separation to give compound 5 (30 mg, yield 17%).

Step 4: To a solution of the concentrate containing compound 5 in dichloromethane was added dropwise $PBr_3$ (14.4 μl, 1.1 eq) under ice bath. The reaction mixture was stirred at room temperature for 1 h. The mixture was concentrated, and the residue was used directly in the next step.

Step 5: To a solution of the above concentrate from step 4 in 5 mL of DMF were added 3-(4-mercapto-1-oxoisoindolin-2-yl)piperidine-2,6-dione (1 eq) and potassium carbonate (1.2 eq). The reaction mixture was stirred at room temperature for 2 h, filtered, and the filtrate was subjected to preparative HPLC (eluent (v/v):acetonitrile/(water+0.05% HCl)=10%-100%) for separation. The collected fractions were rotary evaporated to remove acetonitrile, and lyophilized to give the hydrochloride salt of SIAIS313169 (white solid, 8 mg, yield 12%). $^1$H NMR (500 MHz, DMSO) δ 11.01 (s, 1H), 10.89 (s, 1H), 7.84 (s, 1H), 7.70 (d, J=7.8 Hz, 1H), 7.63 (d, J=7.5 Hz, 2H), 7.50 (t, J=7.7 Hz, 1H), 5.13 (dd, J=13.3, 4.9 Hz, 1H), 4.74 (d, J=3.9 Hz, 2H), 4.37 (d, J=17.1 Hz, 3H), 4.24 (d, J=17.3 Hz, 1H), 3.94-3.87 (m, 3H), 3.72-3.60 (m, 2H), 3.21-3.11 (m, 1H), 3.04-2.96 (m, 1H), 2.96-2.86 (m, 1H), 2.65-2.56 (m, 1H), 2.47-2.35 (m, 1H), 2.04-1.95 (m, 1H). HRMS (ESI) $C_{22}H_{25}N_4O_4S_2^+$ [M+H]$^+$, calcd for 473.1317; found, 473.1313.

Example 242: 3-(1-oxo-4-(((4-(piperidin-1-ylmethyl)thiazol-2-yl)methyl)thio)isoindolin-2-yl)piperidine-2,6-dione (SIAIS313170)

Referring to the method of example 241, the compound SIAIS313170 was prepared under appropriate conditions that will be recognized by one skilled in the art, except that the substrate was piperidine. The hydrochloride salt of compound SIAIS313170 was obtained (white solid, 20 mg, yield 18%). $^1$H NMR (500 MHz, DMSO) δ 11.01 (s, 1H), 10.64 (s, 1H), 7.88 (s, 1H), 7.72 (d, J=7.8 Hz, 1H), 7.62 (d, J=7.3 Hz, 1H), 7.50 (t, J=7.6 Hz, 1H), 5.13 (dd, J=13.2, 4.9 Hz, 1H), 4.80-4.71 (m, 2H), 4.38 (d, J=17.5 Hz, 1H), 4.29-4.21 (m, 3H), 3.18 (dd, J=30.7, 11.8 Hz, 2H), 2.97-2.85 (m, 1H), 2.70 (t, J=14.1 Hz, 2H), 2.61 (t, J=13.0 Hz, 1H), 2.48-2.39 (m, 1H), 2.05-1.94 (m, 1H), 1.75-1.61 (m, 5H), 1.23 (s, 1H). HRMS (ESI) $C_{23}H_{27}N_4O_3S_2^+$ [M+H]$^+$, calcd for 471.1525; found, 471.1526.

Example 243: 3-(4-(((4-(azepan-1-ylmethyl)thiazol-2-yl)methyl)thio)-1-oxoisoindolin-2-yl)piperidine-2,6-dione (SIAIS313171)

Referring to the method of example 241, the compound SIAIS313171 was prepared under appropriate conditions that will be recognized by one skilled in the art, except that the substrate was azepane. The hydrochloride salt of compound SIAIS313171 was obtained (white solid, 22 mg, yield 17%). $^1$H NMR (500 MHz, DMSO) δ 11.00 (s, 1H), 10.92 (s, 1H), 7.93 (s, 1H), 7.72 (d, J=7.9 Hz, 1H), 7.63 (t, J=6.7 Hz, 1H), 7.50 (t, J=7.7 Hz, 1H), 5.13 (dd, J=13.2, 4.7 Hz, 1H), 4.75 (s, 2H), 4.38 (d, J=17.6 Hz, 1H), 4.29 (d, J=4.0 Hz, 2H), 4.25 (d, J=17.4 Hz, 1H), 3.30-3.13 (m, 2H), 2.90 (dt, J=19.3, 12.1 Hz, 3H), 2.60 (d, J=16.9 Hz, 1H), 2.49-2.36 (m, 1H), 2.04-1.95 (m, 1H), 1.75 (d, J=6.2 Hz, 2H), 1.64 (dd, J=16.3, 8.1 Hz, 4H), 1.46 (d, J=5.3 Hz, 2H). HRMS (ESI) $C_{24}H_{29}N_4O_3S_2^+$ [M+H]$^+$, calcd for 485.1681; found, 485.1681.

Example 244: 3-(4-(((4-((3,5-dimethylpiperidin-1-yl)methyl)thiazol-2-yl)methyl)thio)-1-oxoisoindolin-2-yl)piperidine-2,6-dione (SIAIS313186)

Referring to the method of example 241, the compound SIAIS313186 was prepared under appropriate conditions that will be recognized by one skilled in the art, except that the substrate was 3,5-dimethylpiperidine. The hydrochloride salt of compound SIAIS313186 was obtained (white solid, 15 mg, yield 17%). $^1$H NMR (500 MHz, DMSO) δ 11.01 (s, 1H), 10.81 (s, 1H), 7.90 (s, 1H), 7.71 (d, J=7.7 Hz, 1H), 7.62 (d, J=7.5 Hz, 1H), 7.50 (t, J=7.6 Hz, 1H), 5.13 (dd, J=13.3, 4.9 Hz, 1H), 4.76 (s, 2H), 4.38 (d, J=17.5 Hz, 1H), 4.28 (d, J=4.0 Hz, 2H), 4.24 (d, J=17.4 Hz, 1H), 3.16 (t, J=9.6 Hz, 2H), 2.96-2.87 (m, 1H), 2.60 (d, J=16.9 Hz, 1H), 2.47-2.39 (m, 1H), 2.38-2.31 (m, 2H), 1.99 (dd, J=11.6, 5.6 Hz, 3H), 1.70 (d, J=12.9 Hz, 1H), 1.07 (t, J=6.7 Hz, 1H), 0.83 (s, 3H), 0.81 (s, 3H). HRMS (ESI) $C_{25}H_{31}N_4O_3S_2^+$ [M+H]$^+$, calcd for 499.1838; found, 499.1831.

Example 245: 3-(4-(((4-((hexahydro-1H-isoindol-2(3H)-yl)methyl)thiazol-2-yl)methyl)thio)-1-oxoisoindolin-2-yl)piperidine-2,6-dione (SIAIS313188)

Referring to the method of example 241, the compound SIAIS313188 was prepared under appropriate conditions that will be recognized by one skilled in the art, except that the substrate was octahydro-1H-isoindole. The hydrochloride salt of compound SIAIS313188 was obtained (white solid, 5 mg, yield 4%). $^1$H NMR (500 MHz, DMSO) δ 11.01 (s, 1H), 10.90 (s, 1H), 7.87 (s, 1H), 7.72 (t, J=6.6 Hz, 1H), 7.63 (d, J=7.5 Hz, 1H), 7.51 (q, J=6.9 Hz, 1H), 5.13 (dd, J=13.3, 4.6 Hz, 1H), 4.75 (s, 2H), 4.39 (dd, J=19.0, 10.9 Hz, 2H), 4.24 (d, J=17.4 Hz, 1H), 3.22-3.04 (m, 2H), 3.03-2.84 (m, 2H), 2.68-2.55 (m, 1H), 2.46-2.34 (m, 1H), 2.21 (s, 2H), 2.00 (d, J=11.2 Hz, 2H), 1.59-1.19 (m, 9H). HRMS (ESI) $C_{26}H_{31}N_4O_3S_2^+$ [M+H]$^+$, calcd for 511.1838; found, 511.1831.

Example 246: 3-(1-oxo-4-(((4-(thiomorpholinomethyl)thiazol-2-yl)methyl)thio)isoindolin-2-yl)piperidine-2,6-dione (SIAIS355001)

Referring to the method of example 241, the compound SIAIS355001 was prepared under appropriate conditions that will be recognized by one skilled in the art, except that the substrate was thiomorpholine. The hydrochloride salt of compound SIAIS355001 was obtained (white solid, 80 mg, yield 20%). $^1$H NMR (500 MHz, DMSO) δ 11.01 (s, 1H), 10.97 (s, 1H), 7.86 (s, 1H), 7.70 (d, J=7.6 Hz, 1H), 7.63 (d, J=7.3 Hz, 1H), 7.51 (t, J=7.5 Hz, 1H), 5.13 (dd, J=13.1, 4.3 Hz, 1H), 4.79-4.69 (m, 2H), 4.38 (d, J=18.5 Hz, 3H), 4.24 (d, J=17.4 Hz, 1H), 3.54 (t, J=12.6 Hz, 2H), 3.08 (d, J=12.2 Hz, 2H), 3.04-2.85 (m, 3H), 2.77 (d, J=13.8 Hz, 2H), 2.60 (d, J=17.2 Hz, 1H), 2.47-2.34 (m, 1H), 2.05-1.89 (m, 1H). HRMS (ESI) $C_{22}H_{25}N_4O_3S_3^+$ [M+H]$^+$, calcd for 489.1089; found, 489.1085.

Example 247: 3-(4-(((4-((diethylamino)methyl)thiazol-2-yl)methyl)thio)-1-oxoisoindolin-2-yl)piperidine-2,6-dione (SIAIS355002)

Referring to the method of example 241, the compound SIAIS355002 was prepared under appropriate conditions that will be recognized by one skilled in the art, except that the substrate used in step 2 was diethylamine. The hydrochloride salt of compound SIAIS355002 was obtained (white solid, 58 mg, yield 24%). $^1$H NMR (500 MHz, DMSO) δ 11.00 (s, 1H), 10.41 (s, 1H), 7.91 (s, 1H), 7.73 (t, J=7.2 Hz, 1H), 7.63 (d, J=6.8 Hz, 1H), 7.51 (q, J=8.0 Hz, 1H), 5.12 (dd, J=13.2, 4.5 Hz, 1H), 4.81-4.66 (m, 2H), 4.37 (d, J=17.1 Hz, 1H), 4.29 (d, J=2.1 Hz, 2H), 4.22 (d, J=17.5 Hz, 1H), 2.97-2.82 (m, 5H), 2.60 (d, J=17.1 Hz, 1H), 2.42 (dd, J=30.6, 18.4 Hz, 1H), 2.06-1.94 (m, 1H), 1.19 (t, J=7.0 Hz, 6H). HRMS (ESI) $C_{22}H_{27}N_4O_4S_2^+$ [M+H]$^+$, calcd for 459.1525; found, 459.1524.

Example 248: 3-(4-(((4-((cyclohexylamino)methyl)thiazol-2-yl)methyl)thio)-1-oxoisoindolin-2-yl)piperidine-2,6-dione (SIAIS355003)

Referring to the method of example 241, the compound SIAIS355003 was prepared under appropriate conditions that will be recognized by one skilled in the art, except that the substrate was cyclohexylamine. The hydrochloride salt of compound SIAIS355003 was obtained (white solid, 10 mg, yield 23%). $^1$H NMR (500 MHz, DMSO) δ 11.01 (s, 1H), 9.02 (s, 2H), 7.76 (s, 1H), 7.74-7.68 (m, 1H), 7.63 (d, J=7.6 Hz, 1H), 7.52 (t, J=7.8 Hz, 1H), 5.13 (dd, J=13.0, 5.1 Hz, 1H), 4.79-4.71 (m, 2H), 4.38 (d, J=17.1 Hz, 1H), 4.23 (d, J=26.5 Hz, 2H), 2.97-2.85 (m, 2H), 2.65-2.56 (m, 1H), 2.47-2.38 (m, 1H), 2.04 (dd, J=29.3, 16.8 Hz, 4H), 1.74 (d, J=12.2 Hz, 2H), 1.35-1.14 (m, 6H). HRMS (ESI) $C24H_{29}N_{403}S_2^+$ [M+H]$^+$, calcd for 485.1681; found, 485.1684.

Example 249: 3-(4-(((4-(((cyclohexylmethyl)amino)methyl)thiazol-2-yl)methyl)thio)-1-oxoisoindolin-2-yl)piperidine-2,6-dione (SIAIS355004)

Referring to the method of example 241, under appropriate conditions that will be recognized by one skilled in the art, the hydrochloride salt of compound SIAIS355004 was obtained (white solid, 5 mg, yield 7%). $^1$H NMR (500 MHz, DMSO) δ 11.01 (s, 1H), 9.12 (s, 2H), 7.78 (s, 1H), 7.71 (d, J=7.7 Hz, 1H), 7.60 (dd, J=21.5, 7.3 Hz, 1H), 7.51 (t, J=7.6 Hz, 1H), 5.13 (dd, J=13.2, 5.0 Hz, 1H), 4.80-4.69 (m, 2H), 4.37 (d, J=17.4 Hz, 1H), 4.24 (d, J=17.5 Hz, 1H), 4.17 (t, J=4.8 Hz, 2H), 2.98-2.84 (m, 1H), 2.68 (d, J=5.0 Hz, 2H), 2.60 (d, J=16.0 Hz, 1H), 2.47-2.35 (m, 1H), 2.04-1.94 (m, 1H), 1.73-1.56 (m, 6H), 1.26-1.08 (m, 4H), 0.93-0.80 (m, 2H). HRMS (ESI) $C_{25}H_{31}N_4O_3S_2^+$ [M+H]$^+$, calcd for 499.1838; found, 499.1838.

Example 250: N-(cyclohexylmethyl)-4-(((2-(2,6-dioxopiperidin-3-yl)-1-oxoisoindolin-4-yl)thio)methyl)thiazole-2-carboxamide (SIAIS355074)

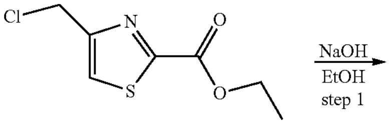

1

-continued

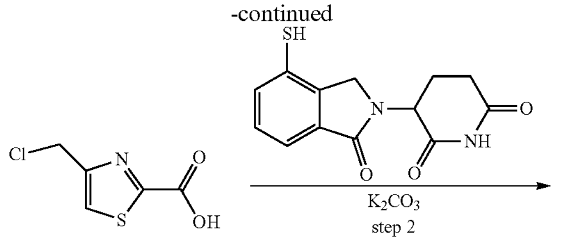

2

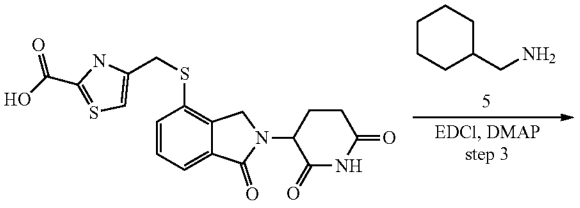

4

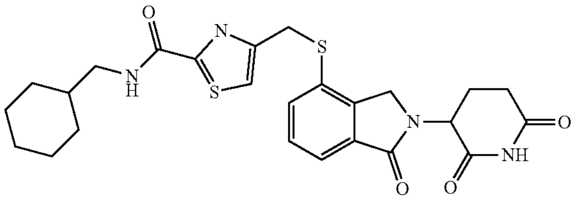

Step 1: To a solution of compound 1 (0.5 g, 2.4 mmol) in ethanol (4 ml) was added dropwise 1N NaOH (4 ml). Then the reaction mixture was stirred at room temperature for 2 h, and the pH was adjusted to 2 with 1N HCl. The mixture was extracted with ethyl acetate, and concentrated to give compound 2 which was used directly in the next step.

Step 2: To a mixture of compound 2 (0.35 g, 2 mmol) and compound 3 (0.55 g, 1 eq) in DMF (10 mL) was added potassium carbonate (0.41 g, 1.5 eq). The reaction mixture was stirred at room temperature for 2 h, and then the pH was adjusted to acidic with 1N HCl. The resulting mixture was subjected to reverse phase column chromatography for purification to give the target compound 4 (pink solid, 0.19 g, yield 23%).

Step 3: A 10 mL egg-shaped flask was charged with compound 4 (38 mg, 0.09 mmol) and cyclohexylmethylamine 5 (15 mg, 1.1 eq), followed by addition of EDCI (26 mg, 1.5 eq) and a catalytic amount of DMAP, and DMF. The mixture was stirred at room temperature overnight. The reaction solution was filtered, and the filtrate was subjected to preparative HPLC (eluent (v/v): acetonitrile/(water+0.05% HCl)=10%-100%) for separation. The collected fractions were rotary evaporated to remove acetonitrile, and lyophilized to give the target compound SIAIS355074 (white solid, 5 mg, yield 11%). $^1$H NMR (500 MHz, DMSO) δ 10.99 (s, 1H), 8.63 (s, 1H), 7.73 (s, 1H), 7.69 (d, J=7.5 Hz, 1H), 7.60 (d, J=7.8 Hz, 1H), 7.51 (t, J=7.5 Hz, 1H), 5.12 (d, J=8.9 Hz, 1H), 4.53-4.43 (m, 2H), 4.25 (q, J=17.3 Hz, 2H), 3.09 (t, J=6.3 Hz, 2H), 2.92 (t, J=13.0 Hz, 1H), 2.67-2.56 (m, 1H), 2.47-2.33 (m, 1H), 1.99 (s, 2H), 1.70-1.52 (m, 6H), 1.20-1.10 (m, 3H), 0.96-0.81 (m, 2H). HRMS: calcd for $C_{25}H_{29}N_4O_4S_2^+$ [M+H]$^+$ 513.1630, found 513.1628.

Example 251: 4-(4-(4-(((2-(2,6-dioxopiperidin-3-yl)-1-oxoisoindolin-4-yl)thio)methyl)benzyl)piperazin-1-yl)-3-fluorobenzonitrile (SIAIS1228137)

Referring to the method of Scheme 11, the compound SIAIS1228137 was prepared under appropriate conditions that will be recognized by one skilled in the art, except that the substrates were 3-(4-((4-(bromomethyl)benzyl)thio)-1-oxoisoindolin-2-yl)piperidine-2,6-dione (SIAIS1220141) and 3-fluoro-4-(piperazin-1-yl)benzonitrile. The hydrochloride salt of compound SIAIS1228137 was obtained (white solid, 21.2 mg, yield 73%). $^1$H NMR (500 MHz, DMSO) δ 10.99 (s, 1H), 10.50 (s, 1H), 7.78 (d, J=13.0 Hz, 1H), 7.68 (d, J=7.7 Hz, 1H), 7.63 (d, J=8.4 Hz, 1H), 7.59 (d, J=7.5 Hz, 1H), 7.54-7.47 (m, 3H), 7.43 (d, J=8.0 Hz, 2H), 7.21 (t, J=8.7 Hz, 1H), 5.11 (dd, J=13.8, 5.0 Hz, 1H), 4.37 (s, 2H), 4.35 (s, 2H), 4.28 (d, J=17.4 Hz, 1H), 4.14 (d, J=17.4 Hz, 1H), 3.69 (d, J=12.2 Hz, 2H), 3.30-3.13 (m, 6H), 2.96-2.86 (m, 1H), 2.59 (d, J=17.1 Hz, 1H), 2.48-2.36 (m, 1H), 2.02-1.93 (m, 1H). HRMS (ESI) m/z: calcd for $C_{32}H_{31}FN_5O_3S^+$ [M+H]$^+$, 584.2126; found, 584.2129.

Example 252: 4-(4-(4-(((2-(2,6-dioxopiperidin-3-yl)-1,3-dioxoisoindolin-4-yl)thio)methyl)benzyl)piperazin-1-yl)-3-fluorobenzonitrile (SIAIS1228141)

Referring to the method of example 211, the compound SIAIS1228141 was prepared under appropriate conditions that will be recognized by one skilled in the art, except that the amine used was 3-fluoro-4-(piperazin-1-yl)benzonitrile. The hydrochloride salt of compound SIAIS1228141 was obtained (pale yellow solid, 18.6 mg, yield 62%). $^1$H NMR (500 MHz, DMSO) δ 11.12 (s, 1H), 10.68 (s, 1H), 7.84 (d, J=8.2 Hz, 1H), 7.80-7.75 (m, 2H), 7.67-7.61 (m, 2H), 7.59 (s, 4H), 7.21 (t, J=8.9 Hz, 1H), 5.11 (dd, J=13.9, 5.3 Hz, 1H), 4.50 (s, 2H), 4.37 (s, 2H), 3.69 (d, J=12.6 Hz, 2H), 3.42-3.35 (m, 2H), 3.31-3.15 (m, 4H), 2.93-2.84 (m, 1H), 2.60 (d, J=17.0 Hz, 1H), 2.08-2.02 (m, 1H). HRMS (ESI) m/z: calcd for $C_{32}H_{29}FN_5O_4S^+$ [M+H]$^+$, 598.1919; found, 598.1922.

Example 253: 4-(4-(7-((2-(2,6-dioxopiperidin-3-yl)-1-oxoisoindolin-4-yl)thio)heptyl)piperazin-1-yl)-3-fluorobenzonitrile (SIAIS1228143)

Referring to the method of Scheme 11, the compound SIAIS1228143 was prepared under appropriate conditions that will be recognized by one skilled in the art, except that the substrates were 3-(4-((7-bromoheptyl)thio)-1-oxoisoindolin-2-yl)piperidine-2,6-dione (SIAIS1216135) and 3-fluoro-4-(piperazin-1-yl)benzonitrile. The hydrochloride salt of compound SIAIS1228143 was obtained (white solid, 20.2 mg, yield 70%). $^1$H NMR (500 MHz, DMSO-$d_6$) δ 10.99 (s, 1H), 10.85 (s, 1H), 7.79 (d, J=13.0 Hz, 1H), 7.63 (d, J=8.1 Hz, 2H), 7.58 (d, J=7.5 Hz, 1H), 7.54 (t, J=8.6 Hz, 1H), 7.23 (t, J=8.8 Hz, 1H), 5.13 (dd, J=14.0, 5.1 Hz, 1H), 4.36 (d, J=17.4 Hz, 1H), 4.22 (d, J=17.4 Hz, 1H), 3.69 (d, J=13.1 Hz, 2H), 3.54 (d, J=12.3 Hz, 2H), 3.35-3.24 (m, 2H), 3.14 (d, J=11.7 Hz, 2H), 3.09 (t, J=7.5 Hz, 4H), 2.97-2.87 (m, 1H), 2.60 (d, J=16.0 Hz, 1H), 2.50-2.41 (m, 1H), 2.05-1.97 (m, 1H), 1.74-1.66 (m, 2H), 1.64-1.57 (m, 2H), 1.46-1.39 (m, 2H), 1.35-1.25 (m, 4H). HRMS (ESI) m/z: calcd for $C_{31}H_{37}FN_5O_3S^+$ [M+H]$^+$, 578.2596; found, 578.2599.

Example 254: 4-(4-(7-((2-(2,6-dioxopiperidin-3-yl)-1,3-dioxoisoindolin-4-yl)thio)heptyl)piperazin-1-yl)-3-fluorobenzonitrile (SIAIS1228145)

Referring to the method of Scheme 11, the compound SIAIS1228145 was prepared under appropriate conditions that will be recognized by one skilled in the art, except that the substrates were 4-((7-bromoheptyl)thio)-2-(2,6-dioxopiperidin-3-yl)isoindoline-1,3-dione (SIAIS1221039) and 3-fluoro-4-(piperazin-1-yl)benzonitrile. The hydrochloride salt of compound SIAIS1228145 was obtained (yellow solid, 16.5 mg, yield 56%). $^1$H NMR (500 MHz, DMSO-$d_6$) δ 11.12 (s, 1H), 10.66 (s, 1H), 7.82-7.73 (m, 3H), 7.63 (d, J=7.8 Hz, 2H), 7.23 (t, J=8.2 Hz, 1H), 5.11 (dd, J=13.9, 5.3 Hz, 1H), 3.69 (d, J=13.2 Hz, 2H), 3.55 (d, J=12.2 Hz, 2H), 3.29 (d, J=12.5 Hz, 2H), 3.19-3.08 (m, 6H), 2.94-2.84 (m, 1H), 2.60 (d, J=17.3 Hz, 1H), 2.53 (s, 1H), 2.09-2.01 (m, 1H), 1.76-1.65 (m, 4H), 1.51-1.43 (m, 2H), 1.40-1.28 (m, 4H). HRMS (ESI) m/z: calcd for $C_{31}H_{35}FN_5O_4S^+$ [M+H]$^+$, 592.2388; found, 592.2389.

Example 255: 4-(4-(4-(((2-(2,6-dioxopiperidin-3-yl)-1-oxoisoindolin-4-yl)thio)methyl)phenethyl)piperazin-1-yl)-3-fluorobenzonitrile (SIAIS1228151)

Referring to the method of example 155, the compound SIAIS1228151 was prepared under appropriate conditions that will be recognized by one skilled in the art, except that the amine used in the last step was 3-fluoro-4-(piperazin-1-yl)benzonitrile. The hydrochloride salt of compound SIAIS1228151 was obtained (white solid, 14.6 mg, yield 49%). $^1$H NMR (500 MHz, DMSO-$d_6$) δ 10.98 (s, 1H), 10.09 (s, 1H), 7.80 (d, J=13.0 Hz, 1H), 7.68 (d, J=7.7 Hz, 1H), 7.64 (d, J=8.5 Hz, 1H), 7.58 (d, J=7.5 Hz, 1H), 7.50 (t, J=7.7 Hz, 1H), 7.33 (d, J=7.7 Hz, 2H), 7.25 (t, J=8.7 Hz, 1H), 7.21 (d, J=7.6 Hz, 2H), 5.11 (dd, J=14.3, 5.0 Hz, 1H), 4.32 (s, 2H), 4.25 (d, J=17.4 Hz, 1H), 4.14 (d, J=17.4 Hz, 1H), 3.74 (d, J=10.6 Hz, 2H), 3.65 (d, J=10.0 Hz, 2H), 3.37 (s, 2H), 3.23 (s, 4H), 3.00 (s, 2H), 2.93-2.86 (m, 1H), 2.59 (d, J=17.3 Hz, 1H), 2.47-2.37 (m, 1H), 2.01-1.94 (m, 1H). HRMS (ESI) m/z: calcd for $C_{33}H_{33}FN_5O_3S^+$ [M+H]$^+$, 598.2283; found, 598.2286.

Example 256: 3-(4-((7-((hexahydro-2,5-methanopentalen-3a(1H)-yl)amino)heptyl)thio)-1-oxoisoindolin-2-yl)piperidine-2,6-dione (SIAIS1228055)

Referring to the method of Scheme 11, the compound SIAIS1228055 was prepared under appropriate conditions that will be recognized by one skilled in the art, except that the substrates were 3-(4-((7-bromoheptyl)thio)-1-oxoisoindolin-2-yl)piperidine-2,6-dione (SIAIS1216135) and 3-noradamantanamine hydrochloride. The hydrochloride salt of compound SIAIS1228055 was obtained (white solid, 10.7 mg, yield 42%). $^1$H NMR (500 MHz, DMSO) δ 10.99 (s, 1H), 9.08 (s, 2H), 7.63 (d, J=7.4 Hz, 1H), 7.57 (d, J=7.4 Hz, 1H), 7.56-7.51 (m, 1H), 5.14 (dd, J=14.9, 4.1 Hz, 1H), 4.35 (d, J=17.2 Hz, 1H), 4.21 (d, J=17.3 Hz, 1H), 3.09 (t, J=7.5 Hz, 2H), 2.96-2.87 (m, 1H), 2.82 (s, 2H), 2.59 (d, J=18.3 Hz, 1H), 2.44-2.35 (m, 2H), 2.30 (s, 2H), 2.05-1.98 (m, 1H), 1.95-1.83 (m, 6H), 1.66-1.54 (m, 7H), 1.51-1.40 (m, 3H), 1.34-1.31 (m, 4H). HRMS (ESI) m/z: calcd for $C_{29}H_{40}N3O_3S^+$ [M+H]$^+$, 510.2785; found, 510.2788.

Example 257: 3-(4-((4-(((hexahydro-2,5-methanopentalen-3a(1H)-yl)amino)methyl)benzyl)thio)-1-oxoisoindolin-2-yl)piperidine-2,6-dione (SIAIS1228019)

Referring to the method of Scheme 11, the compound SIAIS1228019 was prepared under appropriate conditions that will be recognized by one skilled in the art, except that the substrates were 3-(4-((4-(bromomethyl)benzyl)thio)-1-oxoisoindolin-2-yl)piperidine-2,6-dione (SIAIS1220141) and 3-noradamantanamine hydrochloride. The hydrochloride salt of compound SIAIS1228019 was obtained (white solid, 15.5 mg, yield 60%). $^1$H NMR (500 MHz, DMSO) δ 10.99 (s, 1H), 9.33 (s, 2H), 7.68 (d, J=8.7 Hz, 1H), 7.57 (d, J=8.7 Hz, 1H), 7.48 (t, J=8.5 Hz, 3H), 7.44 (d, J=7.7 Hz, 2H), 5.11 (dd, J=13.9, 5.2 Hz, 1H), 4.38 (s, 2H), 4.29 (d, J=18.8 Hz, 1H), 4.15 (d, J=17.4 Hz, 1H), 4.07 (d, J=6.5 Hz, 2H), 2.96-2.85 (m, 1H), 2.63-2.56 (m, 2H), 2.44-2.40 (m, 2H), 2.33 (s, 2H), 2.02-1.86 (m, 6H), 1.65-1.58 (m, 3H), 1.49 (d, J=13.1 Hz, 1H). HRMS (ESI) m/z: calcd for $C_{30}H_{34}N_3O_3S^+$ [M+H]$^+$, 516.2315; found, 516.2319.

Example 258: 3-(4-((7-(((1R,2S,4S)-bicyclo[2.2.1]heptan-2-yl)amino)heptyl)thio)-1-oxoisoindolin-2-yl)piperidine-2,6-dione (SIAIS1228059)

Referring to the method of Scheme 11, the compound SIAIS1228059 was prepared under appropriate conditions that will be recognized by one skilled in the art, except that the substrates were 3-(4-((7-bromoheptyl)thio)-1-oxoisoindolin-2-yl)piperidine-2,6-dione (SIAIS1216135) and (2S)-bicyclo[2.2.1]heptane-2-amine. The hydrochloride salt of compound SIAIS1228059 was obtained (white solid, 14.9 mg, yield 62%). $^1$H NMR (500 MHz, DMSO) δ 10.99 (s, 1H), 8.55 (s, 1H), 8.36 (s, 1H), 7.63 (d, J=7.4 Hz, 1H), 7.57 (d, J=7.5 Hz, 1H), 7.57-7.50 (m, 1H), 5.13 (dd, J=14.2, 5.1 Hz, 1H), 4.35 (d, J=17.3 Hz, 1H), 4.21 (d, J=17.3 Hz, 1H), 3.09 (t, J=7.4 Hz, 2H), 2.99 (s, 1H), 2.96-2.87 (m, 1H), 2.81 (s, 2H), 2.59 (d, J=17.1 Hz, 1H), 2.47 (s, 3H), 2.28 (s, 1H), 2.00 (dd, J=12.3, 6.3 Hz, 1H), 1.74 (d, J=10.6 Hz, 1H), 1.65-1.57 (m, 5H), 1.49-1.37 (m, 5H), 1.31-1.27 (m, 4H), 1.14 (d, J=11.0 Hz, 2H). HRMS (ESI) m/z: calcd for $C_{27}H_{38}N_3O_3S^+$ [M+H]$^+$, 484.2628; found, 484.2622.

Example 259: 3-(4-((7-(methyl((1R,2S,4R)-1,7,7-trimethylbicyclo[2.2.1]heptan-2-yl)amino)heptyl)thio)-1-oxoisoindolin-2-yl)piperidine-2,6-dione (SIAIS1221129)

Referring to the method of Scheme 13, the compound SIAIS1221129 was prepared under appropriate conditions that will be recognized by one skilled in the art, except that the substrate was SIAIS1221019. The hydrochloride salt of compound SIAIS1221129 was obtained (white solid, 6 mg, yield 73%). HRMS (ESI) m/z: calcd for $C_{31}H_{46}N_3O_3S^+$ [M+H]$^+$, 540.3254; found, 540.3055.

Biological Activity Assay

Materials:

Cell Culture

Multiple myeloma cell line. MM.1S (B lymphoblast) was purchased from ATCC. Complete medium was RPMI1640 supplemented with 10% FBS and 1% Penicillin-Streptomycin. The cells used were identified as correct cells by STR cells, and were negative for mycoplasma through routine inspections.

Western Blotting Assay

Tumor cells were plated in a 24-well plate at a cell seeding density of $3\times10^5$ cells/mL, with 1 mL culture media per well. After 24 h, the cells were treated with different concentrations of the compounds of the present disclosure. After 16 hours, the cells were collected, and washed with PBS. The supernatant was discarded, and the cells were placed on ice, and treated with RIPA protein lysate containing Halt protease and phosphatase inhibitor. The lysate was centrifuged at 10000 RPM at 4° C. for 10 minutes, and the supernatant was collected. An equal amount of proteins were loaded in 4×SDS sample solution, denatured at 95° C. for 5 minutes, and then freezed to −20° C. or directly subjected to protein electrophoresis (4-15% gradient gel, Bio-rad). Electrophoresis apparatus and related components were purchased from Bio-rad company, and electrophoresis set at a constant pressure of 120V for 1 h. Then transferring membrane was conducted by using PVDF at 400 mA for 1 h on ice. Afterwards, the membranes were block for 30 minutes by using the TarKara Blocking Buffer at room temperature. Western blotting was conducted according to the antibody product manual of Cell Signaling Technology Company. Results were shown in FIG. 2.

Determination of Half Inhibitory Concentration ($IC_{50}$) of the Compounds of the Present Disclosure $IC_{50}$ values of the compounds of the present disclosure were measured using Cell Titer Blue, Cell Titer GLO, or WST reagent from Promega Company. Assay details are as follows: Cells were seeded in 100 μL RPMI1640 complete medium containing serum at a density of 15,000 cells/well. After 24 h, the inoculated cells were treated with diluted commercial inhibitor and the compounds of the present disclosure to be tested after serial dilution. After the cells were treated with the compounds of the present disclosure to be tested for 72 h, cell viability was determined after adding the cell viability detection kit listed above according to the reagent operating instructions. The negative control was DMSO, and the positive control was a commercial inhibitor, both of which were used to treat the cells through the same method as that of the compounds of the present disclosure.

| Reagents and biological materials | Manufacturers |
|---|---|
| Halt proteosome and phosphatase inhibitors | Thermo Fisher |
| Cell TITER BLUE detection kits | Promega |
| Cell TITER GLO detection kits | Promega |
| CCK8 (WST) reagent | DOJINDO LABORATORIES, Japan |
| RPMI1640 | GIBICO Company |
| Fetal bovine serum (FBS) | GIBICO Company |
| Penicillin-Streptomycin | GIBICO Company |
| SuperSignal West Pico Chemiluminescent Substrate | Thermo Fisher |
| SuperSignal West Femto Maximum Sensitivity Substrate | Thermo Fisher |
| Cycloheximide | Sigma |

Antibodies:

Most antibodies were purchased from Cell Signaling Technology, including IKZF1 (#9034S), IKZF3(#151035). CK1α(#ab108296) and GAPDH were purchased from Abcam Company.

The growth inhibition of the compounds of the present disclosure on cells was plotted by Prism Graphpad software, and the $IC_{50}$ values of the compounds of the present disclosure were calculated therefrom. Results were shown in Table 2.

Results

Compounds of the present invention in our research were based on the immunomodulatory drugs. We studied the cell inhibition and protein degradation activities of the compounds of the present invention designed on the basis of immunomodulatory drugs including pomalidomide and lenalidomide. It was found that the compounds of the present invention designed on the basis of heteroatom-substituted lenalidomide derivatives were more active against multiple myeloma cancer cell MM.1S than lenalidomide. The compounds of the present invention could not only inhibit cancer cell proliferation, but also promote the degradation of IKZF, and thus can be developed as a therapeutic drug for immune-related tumor patients. Detailed experiment results were shown below.

1.1 Proliferation Inhibition of the Compounds of the Present Invention Based on Pomalidomide and Lenalidomide in MM.1S We tested the activities of the compounds of the present invention in MM.1S cell (which overexpressed IKZF1/3 and is highly sensitive to immunomodulatory drugs) through a dose-dependent manner. The cells were treated with the compounds of the present invention at 10 different successively decreasing concentrations (starting at the highest concentration of 10 μM; 5-fold serial dilutions) for 72 h, and then the cell viability determination was performed in accordance with CCK-8 reagent operating instructions. The experiment was repeated more than three times. Results were shown in Table 2.

The compounds of the present invention designed on the basis of lenalidomide showed satisfying anti-proliferation of MM.1S (Table 2). Compared with the $IC_{50}$ of lenalidomide against MM.1S cells of 19.6 nM, the compounds of the present invention greatly increased the inhibitory effect. Many compounds of the present invention have $IC_{50}$ significantly lower than that of lenalidomide. For example, $IC_{50}$ of compound SIAIS1220009 was about 0.12 nM, which was 163 times lower than lenalidomide.

TABLE 2

The $IC_{50}$ values of the compounds of the present invention on the proliferation inhibitory activity of MM.1S cells (half inhibitory cencerntration)

| Cell line | Compounds | Reagent | $IC_{50}$ (nM) |
|---|---|---|---|
| MM.1S | Pomalidomide | WST | 9.4 ± 1.3 |
| MM.1S | Lenalidomide | WST | 19.6 ± 3.3 |
| MM.1S | SIAIS1210071 | WST | 3.37 ± 0.48 |
| MM.1S | SIAIS1213073 | WST | 1.71 ± 0.71 |
| MM.1S | SIAIS1213071 | WST | 2.83 ± 0.76 |
| MM.1S | SIAIS1213195 | WST | 1.48 ± 0.06 |
| MM.1S | SIAIS1216025 | WST | 2.10 ± 0.67 |
| MM.1S | SIAIS1216189 | WST | 2.25 |
| MM.1S | SIAIS1220069 | WST | 3.21 |
| MM.1S | SIAIS264006 | WST | 0.83 |
| MM.1S | SIAIS1220143 | WST | 2.73 |
| MM.1S | SIAIS1216061 | WST | 2.52 ± 0.22 |
| MM.1S | SIAIS1216063 | WST | 8.58 ± 2.58 |
| MM.1S | SIAIS1216139 | WST | 4.06 ± 0.64 |
| MM.1S | SIAIS1216089 | WST | 2.83 ± 0.76 |
| MM.1S | SIAIS1216141 | WST | 12.58 ± 3.47 |
| MM.1S | SIAIS1216095 | WST | 1.53 ± 0.40 |
| MM.1S | SIAIS1220027 | WST | 0.70 |
| MM.1S | SIAIS1220029 | WST | 1.13 |
| MM.1S | SIAIS1220031 | WST | 0.22 ± 0.04 |
| MM.1S | SIAIS1220033 | WST | 0.23 ± 0.08 |
| MM.1S | SIAIS1216143 | WST | 0.17 ± 0.04 |
| MM.1S | SIAIS1216145 | WST | 3.86 ± 0.87 |
| MM.1S | SIAIS1220011 | WST | 0.57 ± 0.21 |
| MM.1S | SIAIS1220057 | WST | 0.77 |
| MM.1S | SIAIS1220017 | WST | 2.77 |
| MM.1S | SIAIS1220019 | WST | 2.08 |
| MM.1S | SIAIS264011 | WST | 0.34 |
| MM.1S | SIAIS1220009 | WST | 0.12 ± 0.03 |
| MM.1S | SIAIS1220055 | WST | 0.26 |
| MM.1S | SIAIS264019 | WST | 0.13 |
| MM.1S | SIAIS1220115 | WST | 0.05 |
| MM.1S | SIAIS1220165 | WST | 0.09 |
| MM.1S | SIAIS1220051 | WST | 0.75 |
| MM.1S | SIAIS1220049 | WST | 0.26 |
| MM.1S | SIAIS1220107 | WST | 0.03 |
| MM.1S | SIAIS1220021 | WST | 0.16 ± 0.05 |
| MM.1S | SIAIS1220117 | WST | 0.07 |
| MM.1S | SIAIS1220093 | WST | 8.20 |
| MM.1S | SIAIS1220035 | WST | 4.13 ± 1.43 |
| MM.1S | SIAIS1216147 | WST | 0.19 ± 0.04 |
| MM.1S | SIAIS1216149 | WST | 0.32 ± 0.15 |
| MM.1S | SIAIS1216151 | WST | 0.33 ± 0.15 |
| MM.1S | SIAIS1220065 | WST | 0.49 |
| MM.15 | SIAIS1220067 | WST | 0.25 |
| MM.1S | SIAIS1220023 | WST | 0.46 ± 0.19 |
| MM.1S | SIAIS1220045 | WST | 0.36 ± 0.13 |
| MM.1S | SIAIS1220047 | WST | 0.11 ± 0.01 |
| MM.1S | SIAIS1220037 | WST | 0.83 ± 0.39 |
| MM.1S | SIAIS1220133 | WST | 4.73 |

TABLE 2-continued

The $IC_{50}$ values of the compounds of the present invention on the proliferation inhibitory activity of MM.1S cells (half inhibitory cencerntration)

| Cell line | Compounds | Reagent | $IC_{50}$ (nM) |
|---|---|---|---|
| MM.1S | SIAIS1220131 | WST | 9.71 |
| MM.1S | SIAIS1220145 | WST | 4.73 |
| MM.1S | SIAIS1220147 | WST | 1.59 |
| MM.1S | SIAIS269012 | WST | 3.79 |
| MM.1S | SIAIS1216195 | WST | 4.96 ± 0.54 |
| MM.1S | SIAIS1216137B | WST | 1.41 |
| MM.1S | SIAIS1220059B | WST | 1.70 |
| MM.1S | SIAIS1220061 | WST | 0.49 |
| MM.1S | SIAIS1220161 | WST | 0.12 |
| MM.1S | SIAIS1220105 | WST | 0.06 |
| MM.1S | SIAIS1220163 | WST | 0.03 |
| MM.1S | SIAIS1220087 | WST | 0.12 |
| MM.1S | SIAIS1220089 | WST | 0.07 |
| MM.1S | SIAIS1220155 | WST | 0.02 |
| MM.1S | SIAIS1220157 | WST | 0.02 |
| MM.1S | SIAIS1220159 | WST | 0.01 |
| MM.1S | SIAIS1221033 | WST | 1.623 |
| MM.1S | SIAIS1221069 | WST | 0.020 |
| MM.1S | SIAIS1222097 | WST | 0.409 |
| MM.1S | SIAIS1222071 | WST | 2.117 |
| MM.1S | SIAIS1222013 | WST | 0.621 |
| MM.1S | SIAIS1221177 | WST | 0.258 |
| MM.1S | SIAIS1221147 | WST | 0.458 |
| MM.1S | SIAIS1221175 | WST | 0.938 |
| MM.1S | SIAIS1220167 | WST | 0.25 ± 0.01 |
| MM.1S | SIAIS1227053 | WST | 0.079 |
| MM.1S | SIAIS1227075 | WST | 0.499 |
| MM.1S | SIAIS1227055 | WST | 0.285 |
| MM.1S | SIAIS1227097 | WST | 0.163 |
| MM.1S | SIAIS1227057 | WST | 0.252 |
| MM.1S | SIAIS1222079 | WST | 0.135 |
| MM.1S | SIAIS1220193 | WST | 0.03 ± 0.01 |
| MM.1S | SIAIS1220169 | WST | 42.97 |
| MM.1S | SIAIS264042 | WST | 0.051 |
| MM.1S | SIAIS1221027 | WST | 0.038 ± 0.006 |
| MM.1S | SIAIS1222195 | WST | 0.046 |
| MM.1S | SIAIS1221021 | WST | 0.047 ± 0.001 |
| MM.1S | SIAIS1221015 | WST | 0.04 ± 0.01 |
| MM.1S | SIAIS1221121 | WST | 0.057 |
| MM.1S | SIAIS1221123 | WST | 0.051 |
| MM.1S | SIAIS1224101 | WST | 287.4 |
| MM.1S | SIAIS1224153 | WST | 0.024 ± 0.002 |
| MM.1S | SIAIS1224161 | WST | 3.625 |
| MM.1S | SIAIS1227043 | WST | 0.024 ± 0.006 |
| MM.1S | SIAIS1224117 | WST | 0.19 ± 0.01 |
| MM.1S | SIAIS1227035 | WST | 0.14 ± 0.04 |
| MM.1S | SIAIS1224154 | WST | 0.809 |
| MM.1S | SIAIS1224039 | WST | 0.54 |
| MM.1S | SIAIS1227099 | WST | 0.311 |
| MM.1S | SIAIS1224125 | WST | 0.046 |
| MM.1S | SIAIS1224089 | WST | 0.144 |
| MM.1S | SIAIS1222107 | WST | 0.050 |
| MM.1S | SIAIS1224033 | WST | 0.082 |
| MM.1S | SIAIS1222105 | WST | 0.181 |
| MM.1S | SIAIS1222103 | WST | 0.250 |
| MM.1S | SIAIS1224031 | WST | 0.105 |
| MM.1S | SIAIS1222115 | WST | 0.182 |
| MM.1S | SIAIS1222123 | WST | 0.053 |
| MM.1S | SIAIS1222161 | WST | 0.035 |
| MM.1S | SIAIS1222077 | WST | 0.006 |
| MM.1S | SIAIS1222159 | WST | 0.050 |
| MM.1S | SIAIS1222117 | WST | 0.123 |
| MM.1S | SIAIS1220183 | WST | 0.197 |
| MM.1S | SIAIS1220185 | WST | 0.026 ± 0.007 |
| MM.1S | SIAIS1221029 | WST | 0.025 |
| MM.1S | SIAIS1221125 | WST | 0.035 |
| MM.1S | SIAIS1222199 | WST | 0.062 |
| MM.1S | SIAIS1222147 | WST | 0.083 |
| MM.1S | SIAIS1222187 | WST | 0.005 |
| MM.1S | SIAIS1221071 | WST | 0.072 ± 0.004 |
| MM.1S | SIAIS1224155 | WST | 0.021 ± 0.004 |
| MM.1S | SIAIS1227007 | WST | 0.67 ± 0.27 |
| MM.1S | SIAIS1227045 | WST | 0.06 ± 0.01 |
| MM.1S | SIAIS1227067 | WST | 0.11 ± 0.02 |
| MM.1S | SIAIS1224019 | WST | 0.048 |

TABLE 2-continued

The $IC_{50}$ values of the compounds of the present invention on the proliferation inhibitory activity of MM.1S cells (half inhibitory cencerntration)

| Cell line | Compounds | Reagent | $IC_{50}$ (nM) |
|---|---|---|---|
| MM.1S | SIAIS1227059 | WST | 0.022 |
| MM.1S | SIAIS1224035 | WST | 15.11 |
| MM.1S | SIAIS1224037 | WST | 14.03 |
| MM.1S | SIAIS1222173 | WST | 0.420 |
| MM.1S | SIAIS1222177 | WST | 0.693 |
| MM.1S | SIAIS1222179 | WST | 0.074 |
| MM.1S | SIAIS1221117 | WST | 0.060 |
| MM.1S | SIAIS1220177 | WST | 0.041 ± 0.018 |
| MM.1S | SIAIS1220179 | WST | 0.036 ± 0.010 |
| MM.1S | SIAIS1221149 | WST | 21.89 |
| MM.1S | SIAIS1221031 | WST | 0.0009 |
| MM.1S | SIAIS269175 | WST | 0.314 |
| MM.1S | SIAIS1222141 | WST | 0.342 |
| MM.1S | SIAIS1221013 | WST | 0.028 ± 0.012 |
| MM.1S | SIAIS1221127 | WST | 0.059 |
| MM.1S | SIAIS1222139 | WST | 0.131 |
| MM.1S | SIAIS1220171 | WST | 0.044 ± 0.003 |
| MM.1S | SIAIS1220195 | WST | 0.048 |
| MM.1S | SIAIS1220197 | WST | 0.578 |
| MM.1S | SIAIS1220199 | WST | 0.026 ± 0.001 |
| MM.1S | SIAIS1222143 | WST | 0.070 |
| MM.1S | SIAIS1222145 | WST | 0.043 |
| MM.1S | SIAIS269159 | WST | 0.068 |
| MM.1S | SIAIS1221025 | WST | 0.061 |
| MM.1S | SIAIS1221003 | WST | 0.024 ± 0.010 |
| MM.1S | SIAIS1221005 | WST | 0.035 ± 0.007 |
| MM.1S | SIAIS1222157 | WST | 0.040 |
| MM.1S | SIAIS1222085 | WST | 0.029 |
| MM.1S | SIAIS287128 | WST | 0.018 ± 0.005 |
| MM.1S | SIAIS1224149 | WST | 0.44 ± 0.10 |
| MM.1S | SIAIS1227047 | WST | 0.028 ± 0.003 |
| MM.1S | SIAIS1224121 | WST | 0.48 ± 0.05 |
| MM.1S | SIAIS1227037 | WST | 0.04 ± 0.02 |
| MM.1S | SIAIS287105 | WST | 5.008 |
| MM.1S | SIAIS1227061 | WST | 0.721 |
| MM.1S | SIAIS1221113 | WST | 0.027 |
| MM.1S | SIAIS1221115 | WST | 0.082 |
| MM.1S | SIAIS1221019 | WST | 0.007 |
| MM.1S | SIAIS1221129 | WST | 0.021 |
| MM.1S | SIAIS1221073 | WST | 0.0003 |
| MM.1S | SIAIS1220187 | WST | 0.598 |
| MM.1S | SIAIS1220189 | WST | 0.553 |
| MM.1S | SIAIS269095 | WST | 0.334 |
| MM.1S | SIAIS269068 | WST | 0.901 |
| MM.1S | SIAIS269072 | WST | 0.468 |
| MM.1S | SIAIS1222029 | WST | 0.21 |
| MM.1S | SIAIS1222109 | WST | 0.404 |
| MM.1S | SIAIS1224015 | WST | 0.691 |
| MM.1S | SIAIS1221075 | WST | 15.84 |
| MM.1S | SIAIS1227049 | WST | 0.10 ± 0.05 |
| MM.1S | SIAIS1227051 | WST | 0.004 ± 0.002 |
| MM.1S | SIAIS1227103 | WST | 0.02 ± 0.00 |
| MM.1S | SIAIS1227105 | WST | 0.05 ± 0.01 |
| MM.1S | SIAIS1227107 | WST | 0.27 ± 0.07 |
| MM.1S | SIAIS1227109 | WST | 0.03 ± 0.004 |
| MM.1S | SIAIS1227113 | WST | 0.03 ± 0.01 |
| MM.1S | SIAIS1227115 | WST | 0.04 ± 0.01 |
| MM.1S | SIAIS1227117 | WST | 0.20 ± 0.08 |
| MM.1S | SIAIS1227119 | WST | 0.20 ± 0.00 |
| MM.1S | SIAIS1227131 | WST | 0.89 ± 0.22 |
| MM.1S | SIAIS1227133 | WST | 0.13 ± 0.07 |
| MM.1S | SIAIS1227135 | WST | 0.03 ± 0.01 |
| MM.1S | SIAIS1227137 | WST | 1.04 ± 0.49 |
| MM.1S | SIAIS1227139 | WST | 1.04 ± 0.21 |
| MM.1S | SIAIS1227141 | WST | 4.98 ± 0.99 |
| MM.1S | SIAIS1227143 | WST | 0.11 ± 0.17 |
| MM.1S | SIAIS271167 | WST | 164.3 |
| MM.1S | SIAIS313123 | WST | 2.29 ± 0.95 |
| MM.1S | SIAIS313126 | WST | 2.97 ± 0.79 |
| MM.1S | SIAIS313129 | WST | 0.97 ± 0.55 |
| MM.1S | SIAIS313148 | WST | 0.95 ± 0.45 |
| MM.1S | SIAIS313149 | WST | 1.3 ± 0.96 |
| MM.1S | SIAIS313150 | WST | 0.7 ± 0.27 |
| MM.1S | SIAIS313135 | WST | 2.62 ± 0.94 |
| MM.1S | SIAIS313163 | WST | 9.38 ± 1.37 |

TABLE 2-continued

The $IC_{50}$ values of the compounds of the present invention on the proliferation inhibitory activity of MM.1S cells (half inhibitory cencerntration)

| Cell line | Compounds | Reagent | $IC_{50}$ (nM) |
|---|---|---|---|
| MM.1S | SIAIS313164 | WST | 2.78 ± 0.73 |
| MM.1S | SIAIS313165 | WST | 2.77 ± 1.12 |
| MM.1S | SIAIS313166 | WST | 7.55 ± 1.89 |
| MM.1S | SIAIS313169 | WST | 5.03 ± 2.13 |
| MM.1S | SIAIS313170 | WST | 2.56 ± 0.56 |
| MM.1S | SIAIS313171 | WST | 1.34 ± 0.32 |
| MM.1S | SIAIS313186 | WST | 1.63 ± 0.61 |
| MM.1S | SIAIS313188 | WST | 1.43 ± 0.3 |
| MM.1S | SIAIS355001 | WST | 2.51 ± 0.54 |
| MM.1S | SIAIS355002 | WST | 1.07 ± 0.39 |
| MM.1S | SIAIS355003 | WST | 0.75 ± 0.1 |
| MM.1S | SIAIS355004 | WST | 0.61 ± 0.42 |
| MM.1S | SIAIS1228019 | WST | 0.051 |
| MM.1S | SIAIS1228055 | WST | 0.028 |
| MM.1S | SIAIS1228059 | WST | 0.037 |
| MM.1S | SIAIS1220025 | WST | 0.49 ± 0.05 |
| MM.1S | SIAIS1224151 | WST | 3.412 |
| MM.1S | SIAIS1224163 | WST | 7.406 |
| MM.1S | SIAIS1227019 | WST | 34.33 |
| MM.1S | SIAIS1227085 | WST | 0.370 |
| MM.1S | SIAIS1227087 | WST | 0.283 |
| MM.1S | SIAIS1227091 | WST | 1.998 |
| MM.1S | SIAIS1227039 | WST | 2.491 |
| MM.1S | SIAIS1227069 | WST | 1.125 |
| MM.1S | SIAIS1227041 | WST | 0.095 |
| MM.1S | SIAIS1227159 | WST | 0.020 |
| MM.1S | SIAIS1227161 | WST | 0.025 |
| MM.1S | SIAIS1227163 | WST | 0.021 |
| MM.1S | SIAIS1227165 | WST | 0.023 |
| MM.1S | SIAIS1227167 | WST | 0.064 |
| MM.1S | SIAIS1227169 | WST | 0.120 |
| MM.1S | SIAIS1227171 | WST | 0.021 |
| MM.1S | SIAIS1227173 | WST | 0.095 |
| MM.1S | SIAIS1227175 | WST | 0.073 |
| MM.1S | SIAIS1227177 | WST | 0.097 |
| MM.1S | SIAIS1227179 | WST | 0.029 |
| MM.1S | SIAIS1227181 | WST | 0.113 |
| MM.1S | SIAIS1227183 | WST | 0.039 |

1.2 Proliferation Inhibition of the Compounds of the Present Invention Based on Pomalidomide and Lenalidomide in Lymphoma Cells We tested the anti-proliferation activities of the compounds of the present invention in ALCL cell line SR and Mantle cell lymphoma Mino (which overexpressed IKZF1/3, but were not sensitive to immunomodulatory drugs) through a dose-dependent manner. The cells were treated with the compounds of the present invention at 10 different successively decreasing concentrations (starting at the highest concentration of 10 μM; 5-fold serial dilutions) for 72 h, and then the cell viability determination was performed in accordance with CCK-8 reagent operating instructions. The experiment was repeated more than three times. Results were shown in Table 3.

The compounds of the present invention designed on the basis of lenalidomide showed satisfying anti-proliferation of SR and Mino cells (Table 3). The $IC_{50}$ of lenalidomide cannot be detected (i.e., the inhibitory effect of lenalidomide on SR cells was less than 50%), while the compounds of the present invention exhibited a stronger inhibitory effect. For example, the $IC_{50}$ of compound SIAIS287128 was about 0.3 nM. The $IC_{50}$ of pomalidomide in Mino cells was 48 nM, while many compounds of the present invention have $IC_{50}$ significantly lower than those of pomalidomide and lenalidomide. For example, $IC_{50}$ of SIAIS287128 was about 0.29 nM, which was 165 times lower than Pomalidomide.

TABLE 3

The $IC_{50}$ values of the compounds of the present invention on the proliferation inhibitory activity of lymphoma cells (half inhibitory cencerntration)

| Cell line | Compounds | Reagent | $IC_{50}$ (nM) |
|---|---|---|---|
| SR | Lenalidomide | WST | NA |
| SR | SIAIS1220155 | WST | 7.424 |
| SR | SIAIS1220165 | WST | 1.893 |
| SR | SIAIS287128 | WST | 0.297 |
| Mino | Pomalidomide | WST | 48.02 |
| Mino | SIAIS1220155 | WST | 0.776 |

TABLE 3-continued

The $IC_{50}$ values of the compounds of the present invention on the proliferation inhibitory activity of lymphoma cells (half inhibitory cencerntration)

Figure 2:
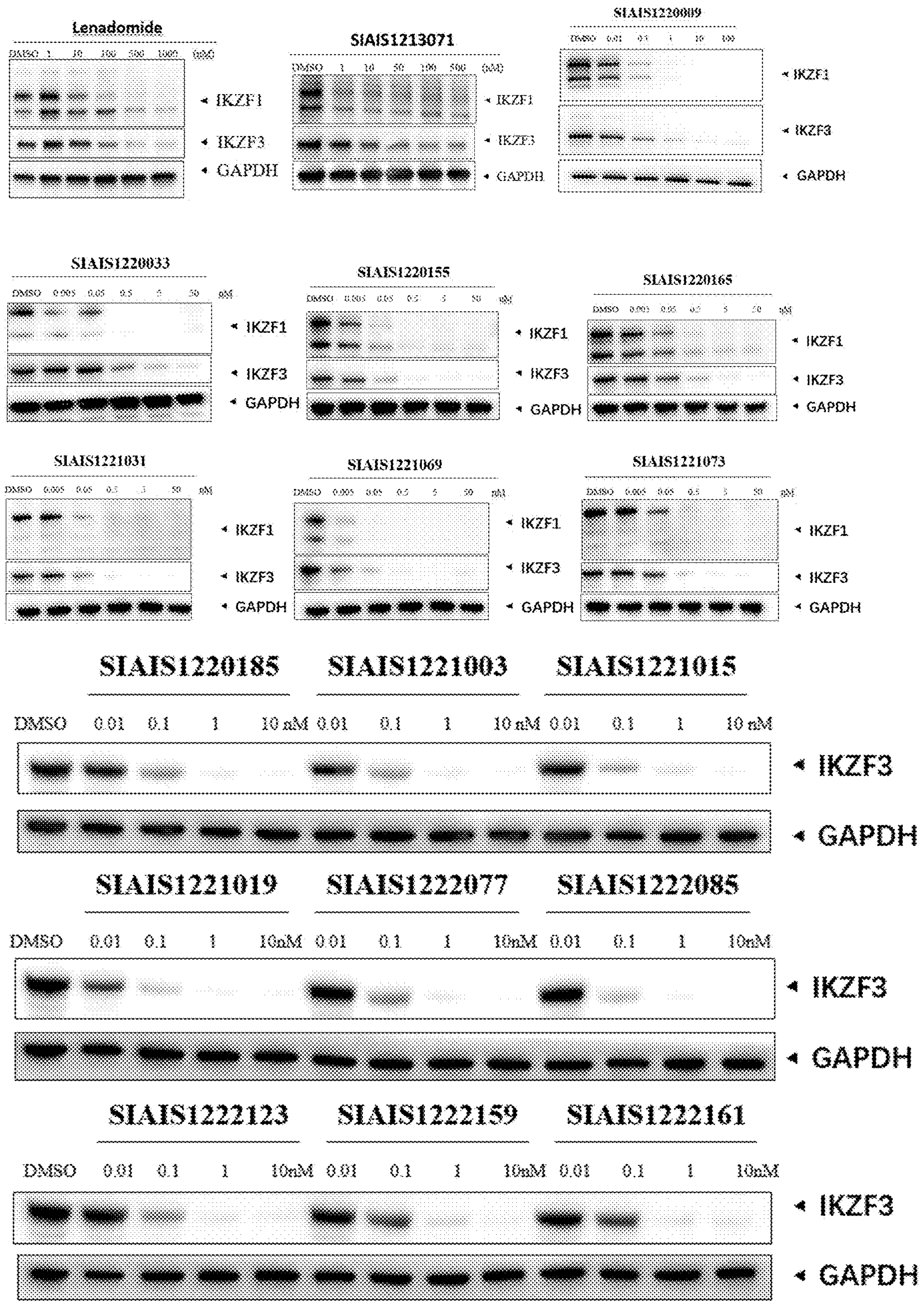
FIG. 2 shows the study of the degradation of IKZF1 and IKZF3 proteins in MM.1S cells by the compounds of the present invention.
Figure 2:
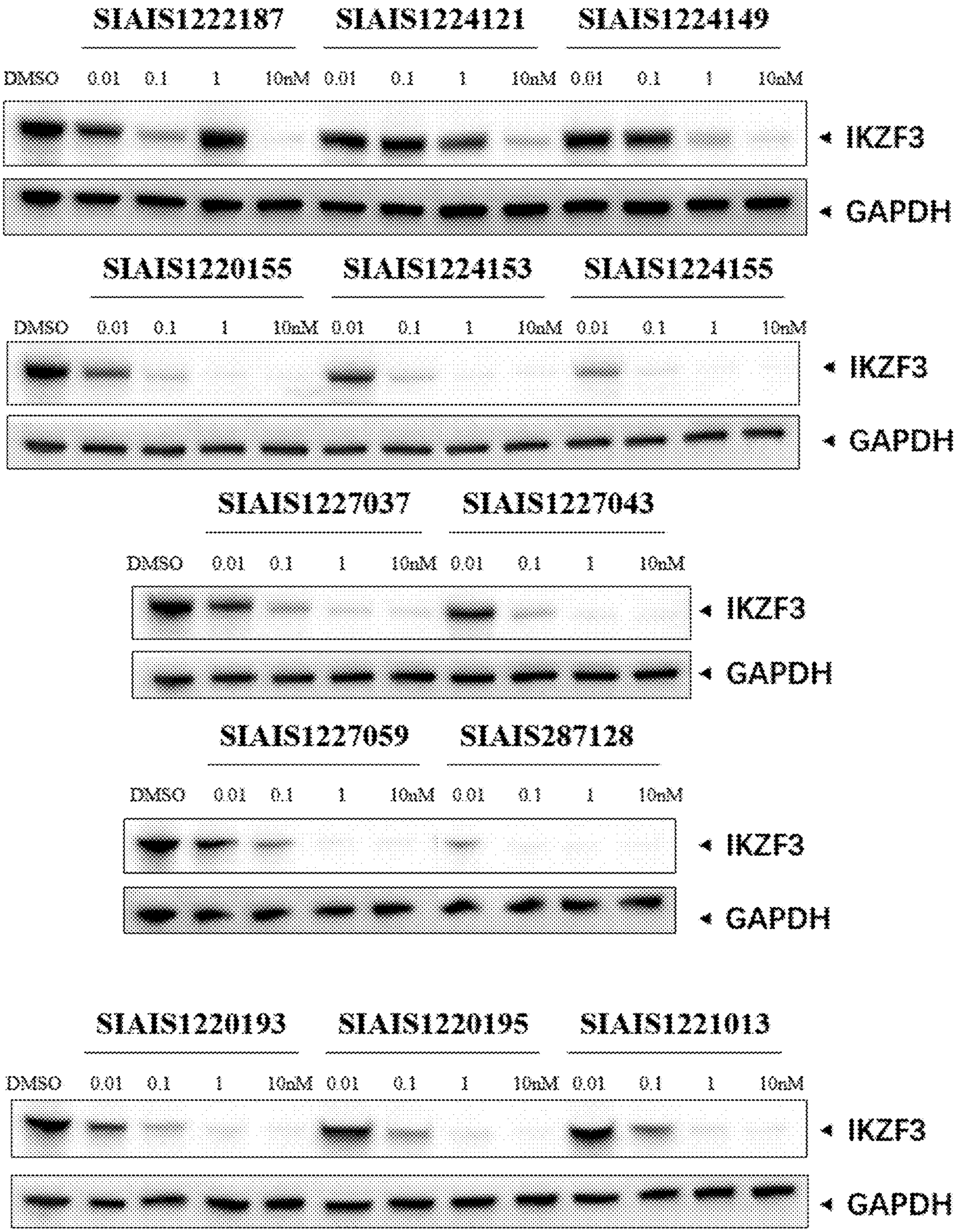

| Cell line | Compounds | Reagent | $IC_{50}$ (nM) |
|---|---|---|---|
| Mino | SIAIS1220165 | WST | 5.83 |
| Mino | SIAIS287128 | WST | 0.289 |

note:
NA stands for $IC_{50}$ values not detected 1.3 Study on the IKZF Degradation of the Compounds of the Present Invention Based on Pomalidomide and Lenalidomide We studied the abundance of IKZF1 and IKZF3 in MM.1S cells which overexpress IKZF1/3 after treatment by the compounds of the present invention. The results of western blotting were shown in FIG. 2. Firstly, we treated the MM.1S cells with lenalidomide at different concentrations (1, 10, 100, 500, and 1000 nM) for 16 h. After cell lysis, the effects of lenalidomide on IKZF1 and IKZF3 protein contents were detected by western blot (FIG. 2). The results showed that half IKZF1/3 degradation concentration of lenalidomide was around 10-100 nM.

$DC_{50}$ value (the drug concentration required for degrading proteins by 50%, abbreviated as $DC_{50}$) reads method: comparing the gray values of the Western blotting bands for the drug treatment with the gray values of the Western blotting band for the DMSO control, and reading the drug concentration range corresponding to the gray value of the Western blotting bands for the drug treatment which is equal to half of the gray value of the Western blotting band for the DMSO control.

$DC_{50}$ value could also be calculated as follows: using software ImageJ to quantify the gray values of the Western blotting bands for the drug treatment, fitting the relationship curve between drug concentrations and gray values, and from the fitted curve, calculating the drug concentration corresponding to half of the gray value of the Western blotting band for the DMSO control.

IKZF1/3 Degradation effects of the compounds of the present invention based on lenalidomide were shown in FIG. 2. Compound SIAIS1213071, SIAIS1222187, SIAIS1224121, SIAIS1222161, and SIAIS1220009 showed significant degradation effects below 1 nM. Compounds SIAIS1220185, SIAIS1221003, SIAIS1221015, SIAIS1221019, SIAIS1222077, SIAIS1222085, SIAIS1222123, SIAIS1222159, SIAIS1224149, SIAIS1224153, SIAIS1227037, SIAIS1227043, SIAIS1227059, SIAIS1220193, SIAIS1220195, and SIAIS1221013 showed especially significant degradation effects below 0.1 nM. What's more, SIAIS1220033, SIAIS1220155, SIAIS1220165, SIAIS1221031, SIAIS1221069, SIAIS1221073, SIAIS1224155, and SIAIS287128 exhibited great degradation below 0.05 or 0.01 nM. Compared with lenalidomide, the compounds of the present invention significantly improves both proliferation inhibition and protein degradation activities in MM.1S cells (FIG. 2).

The basic principles, main features and advantages of the present disclosure are shown and described above. Those skilled in the art should understand that the present disclosure is not limited by the foregoing embodiments, and they can make various changes, substitutions and alterations herein without departing from the spirit and scope of the present disclosure. These changes, substitutions and alterations fall within the scope of the present disclosure. The claimed scope of the present disclosure is defined by the appended claims and their equivalents.

The invention claimed is:

1. A compound of Formula (Ia)

Formula (Ia)

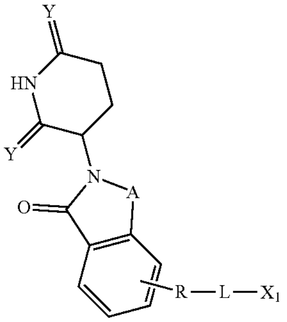

or a salt, a solvate, an isotopically enriched analog, a tautomer, a stereoisomer thereof, or a mixture of stereoisomers thereof, wherein A represents $CH_2$ or C(O);

Y represents O; and

R, L, and $X_1$ are as defined in the following (1) or (2);

(1) R represents S, S(O), or $S(O)_2$,

L represents a linear or branched $C_{1-40}$ alkylene group optionally substituted one or more substituent(s) selected from halogen, cyano, $C_{1-3}$ alkyl, $C_{1-3}$ alkoxy, trifluoromethyl, a 3- to 12-membered heterocyclyl, or any combination thereof, wherein the linear or branched $C_{1-40}$ alkylene group is optionally interrupted one or more times by one or more groups selected from: O, C(O), S, S(O), $S(O)_2$, $C(O)N(R_1)$, $N(R_2)C(O)$, $N(R_3)$, $N(R_4)C(O)N(R_5)$, wherein $R_1$, $R_2$, $R_3$, $R_4$, and $R_5$ each independently represent H or $C_{1-3}$ alkyl, cycloalkylene optionally substituted with substituent(s) selected from the group consisting of halogen, cyano, $C_{1-5}$ alkyl, $C_{1-3}$ alkoxy, halogenated $C_{1-3}$ alkyl, amino, hydroxyl, methanesulfonyloxy, trifluoromethanesulfonyloxy, p-toluenesulfonyloxy, oxo, and any combination thereof, arylene optionally substituted with substituent(s) selected from the group consisting of $C_{1-5}$ alkyl, halogenated $C_{1-3}$ alkoxy, cyano, $C_{1-3}$ alkoxy, halogenated $C_{1-3}$ alkyl, halogen, amino, hydroxyl, methanesulfonyloxy, trifluoromethanesulfonyloxy, and p-toluenesulfonyloxy, heterocyclylene optionally substituted with substituent (s) selected from the group consisting of $C_{1-5}$ alkyl, $C_{1-3}$ alkoxy, cyano, trifluoromethyl, halogen, amino, hydroxy, methanesulfonyloxy, trifluoromethanesulfonyloxy, p-toluenesulfonyloxy, and oxo, heteroarylene optionally substituted with substituent(s) selected from the group consisting of $C_{1-5}$ alkyl, $C_{1-3}$ alkoxy, cyano, trifluoromethyl, halogen, amino, hydroxy, methanesulfonyloxy, trifluoromethanesulfonyloxy, and p-toluenesulfonyloxy, or any combination thereof; and $X_1$ represents any one of (a1)-(a8) below:

(a1) $NR_6R_7$, $C(O)NR_eR_f$, $NHC(O)R_8$, $NHC(O)NR_9R_{10}$, $OR_h$, or SH, wherein $R_6$, $R_7$, $R_e$, $R_f$, $R_h$, $R_9$, and $R_{10}$ each independently represent: (i) H; (ii) linear or branched $C_{1-10}$ alkyl optionally substituted with one or more substituent(s) selected from halogen, cyano, $C_{1-3}$ alkyl, $C_{1-3}$ alkoxy, trifluoromethyl, a 3- to 12-membered heterocyclyl, or any combination thereof; (iii) cycloalkyl optionally substituted with substituent(s) selected from halogen, cyano, $C_{1-3}$ alkyl, $C_{1-3}$ alkoxy, halogenated $C_{1-3}$ alkyl, amino, hydroxyl, or any combination thereof; (iv) aryl optionally substituted with substituent(s) selected from $C_{1-5}$ alkyl, halogenated $C_{1-3}$ alkoxy, cyano, $C_{1-3}$ alkoxy, halogenated $C_{1-3}$ alkyl, halogen, amino, and hydroxyl; (v) heterocyclyl optionally substituted with substituent(s) selected from $C_{1-5}$ alkyl, $C_{1-3}$ alkoxy, cyano, trifluoromethyl, halogen, amino, and hydroxy; or (vi) heteroaryl optionally substituted with substituent(s) selected from $C_{1-3}$ alkyl, $C_{1-3}$ alkoxy, cyano, trifluoromethyl, halogen, amino, and hydroxy; wherein $R_6$ and $R_7$ are not H at the same time; and wherein $R_8$ represents a linear or branched $C_{1-8}$ alkyl, $C_5$-$C_{14}$ aryl, a 5- to 10-membered heteroaryl, or a 3- to 12-membered heterocyclyl; or wherein $R_e$ and $R_f$ together with the nitrogen atom to which they are attached form a 5- to 8-membered heterocyclyl; or wherein $R_6$ represents H, and $R_7$ represents ethyl which is substituted with 2,6-dichloro-3-fluorophenyl; or wherein $R_6$ represents H, and $R_7$ represents thiazolyl which is substituted with $C(O)NHR_d$, wherein $R_d$ represents $C_{1-5}$ alkyl or 2-chloro-6-methylphenyl; or wherein $R_6$ represents H or methyl; and $R_7$ represents a group of optionally substituted cycloalkyl, optionally substituted aryl, optionally substituted heterocyclyl, or optionally substituted heteroaryl, with each group being optionally substituted with substituent(s) selected from: (i) halogen, (ii) $C_{1-5}$ alkyl, (iii) di($C_{1-6}$ alkyl)phosphono, (iv) $C_{1-6}$ alkylsulfonyl, (v) oxo, (vi) cyano, (vii)$_6$-membered aryl optionally substituted with substituent(s) selected from $C_{1-6}$ alkyl, halogen and halogenated $C_{1-3}$ alkyl, (viii) 5- or 6-membered heterocyclyl optionally substituted with substituent(s) selected from $C_{1-6}$ alkyl and halogen, or (ix) 5- or 6-membered heteroaryl optionally substituted with substituent(s) selected from $C_{1-6}$ alkyl and halogen;

(a2) quaternary ammonium salt group having the Formula $N^+R_aR_bR_cX^-$, wherein $R_a$, $R_b$, and $R_c$ each independently represent $C_{1-20}$ alkyl group, and $X^-$ represents $F^-$, $Cl^-$, $Br^-$, or $I^-$; or wherein $R_a$ and $R_b$ together with the nitrogen atom to which they are attached form 5- to 8-membered heterocyclyl, and the ring atoms of the 5- to 8-membered heterocyclyl optionally comprise a heteroatom selected from oxygen, nitrogen, and sulfur, and $R_c$ represents $C_{1-20}$ alkyl; and $X^-$ represents $F^-$, $Cl^-$, $Br^-$, or $I^-$;

(a3) linear or branched $C_{1-10}$ alkyl optionally substituted with one or more fluorine;

(a4) cycloalkyl optionally substituted with substituent (s) selected from halogen, oxo, cyano, trifluoromethyl, amino, hydroxy, $C_{1-3}$ alkoxy, halogenated $C_{1-3}$ alkoxy, methanesulfonyloxy, trifluoromethanesulfonyloxy, p-toluenesulfonyloxy, $C_{1-6}$ alkyl, $C_{1-3}$ alkoxycarbonyl, or any combination thereof;

(a5) aryl substituted with substituent(s) selected from halogenated $C_{1-3}$ alkyl, amino, hydroxy, $C_{1-3}$ alkoxy, halogenated $C_{1-3}$ alkoxy, methanesulfonyloxy, trifluoromethanesulfonyloxy, p-toluenesulfonyloxy, $C_{1-6}$ alkyl, halogenated $C_{2-4}$ alkenyl, or any combination thereof;

(a6) 4-(bromomethyl)-2-fluorophenyl;

(a7) heteroaryl optionally substituted with substituent (s) selected from the group consisting of halogen, cyano, amino, hydroxy, $C_{1-3}$ alkoxy, halogenated $C_{1-3}$ alkoxy, halogenated $C_{1-3}$ alkyl, bis($C_{1-6}$ alkyl) phosphono, $C_{1-6}$ alkylsulfonyl, methanesulfonyloxy, trifluoromethanesulfonyloxy, p-toluenesulfonyloxy, $C_{1-6}$ alkyl, optionally substituted phenyl, optionally substituted 5- or 6-membered heterocyclyl, optionally substituted 5- or 6-membered heteroaryl, and any combination thereof, wherein said optionally substituted phenyl is optionally substituted with substituent(s) selected from the group consisting of $C_{1-6}$ alkyl, cyano, halogenated $C_{1-3}$ alkyl, amino, hydroxyl, halogen, and any combination thereof; and said optionally substituted 5- or 6-membered heterocyclyl is optionally substituted with substituent(s) selected from the group consisting of: $C_{1-6}$ alkyl, cyano, halogenated $C_{1-3}$ alkyl, amino, hydroxyl, halogen, and any combination thereof; and said optionally substituted 5- or 6-membered heteroaryl is optionally substituted with substituent(s) selected from the group consisting of: $C_{1-6}$ alkyl, halogenated $C_{1-3}$ alkyl, amino, hydroxyl, halogen, and any combination thereof; or (a8) a group represented by Formula ($G_2$):

Formula ($G_2$)

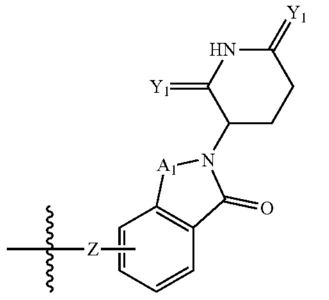

wherein, $A_1$ represents $CH_2$ or C(O);

$Y_1$ represents O; and

Z represents S, S(O), or $S(O)_2$;

or (2) R represents S,

L represents a linear or branched $C_{1-40}$ alkylene group optionally substituted with one or more substituent(s) selected from halogen, cyano, $C_{1-3}$ alkyl, $C_{1-3}$ alkoxy, trifluoromethyl, a 3- to 12-membered heterocyclyl, or any combination thereof, wherein the linear or branched $C_{1-40}$ alkylene group is optionally interrupted one or more times by one or more groups selected from:

O, C(O), S, S(O), $S(O)_2$, $C(O)N(R_1)$, $N(R_2)C(O)$, $N(R_3)$, $N(R_4)C(O)N(R_5)$, wherein $R_1$, $R_2$, $R_3$, $R_4$, and $R_5$ each independently represent H or $C_{1-3}$ alkyl, cycloalkylene optionally substituted with substituent(s) selected from halogen, cyano, $C_{1-5}$ alkyl, $C_{1-3}$ alkoxy, halogenated $C_{1-3}$ alkyl, amino, hydroxyl, methanesulfonyloxy, trifluoromethanesulfonyloxy, p-toluenesulfonyloxy, oxo, or any combination thereof, arylene optionally substituted with substituent(s) selected from $C_{1-5}$ alkyl, halogenated $C_{1-3}$ alkoxy, cyano, $C_{1-3}$ alkoxy, halogenated $C_{1-3}$ alkyl, halogen, amino, hydroxyl, methanesulfonyloxy, trifluoromethanesulfonyloxy, and p-toluenesulfonyloxy, heterocyclylene optionally substituted with substituent(s) selected from $C_{1-5}$ alkyl, $C_{1-3}$ alkoxy, cyano, trifluoromethyl, halogen, amino, hydroxy, methanesulfonyloxy, trifluoromethanesulfonyloxy, p-toluenesulfonyloxy, and oxo, heteroarylene optionally substituted with substituent(s) selected from $C_{1-5}$ alkyl, $C_{1-3}$ alkoxy, cyano, trifluoromethyl, halogen, amino, hydroxy, methanesulfonyloxy, trifluoromethanesulfonyloxy, and p-toluenesulfonyloxy, or any combination thereof; and $X_1$ represents:

heterocyclyl optionally substituted with substituent(s) selected from halogen, cyano, amino, hydroxy, $C_{1-3}$ alkoxy, halogenated $C_{1-3}$ alkoxy, halogenated $C_{1-3}$ alkyl, $C_{1-6}$ alkylsulfonyl, bis($C_{1-6}$ alkyl)phosphono, methanesulfonyloxy, trifluoromethanesulfonyloxy, p-toluenesulfonyloxy, oxo, optionally substituted 5- or 6-membered heterocyclyl, optionally substituted 5- or 6-membered heteroaryl, $C_{1-6}$ alkyl, or any combination thereof, wherein said optionally substituted 5- or 6-membered heterocyclyl is optionally substituted with substituent(s) selected from: $C_{1-6}$ alkyl, cyano, halogenated $C_{1-3}$ alkyl, amino, hydroxyl, halogen, or any combination thereof; and said optionally substituted 5- or 6-membered heteroaryl is optionally substituted with substituent(s) selected from: $C_{1-6}$ alkyl, halogenated $C_{1-3}$ alkyl, amino, hydroxyl, halogen, or any combination thereof.

2. The compound of Formula (Ia) or a salt, a solvate, an isotopically enriched analog, a tautomer, a stereoisomer thereof, or a mixture of stereoisomers thereof of claim 1, wherein R, L, and $X_1$ are as defined in the following (1') or (2'):

(1') R represents S, S(O) or $S(O)_2$;

L represents linear or branched $C_{1-30}$ alkylene group optionally substituted one or more substituent(s) selected from halogen, cyano, $C_{1-3}$ alkyl, $C_{1-3}$ alkoxy, trifluoromethyl, a 3- to 12-membered heterocyclyl, or any combination thereof, wherein the linear or branched $C_{1-30}$ alkylene group is optionally interrupted one or more times by one or more groups selected from:

O, C(O), S, S(O), $S(O)_2$, $C(O)N(R_1)$, $N(R_2)C(O)$, $N(R_3)$, $N(R_4)C(O)N(R_5)$, wherein $R_1$, $R_2$, $R_3$, $R_4$, and $R_5$ each independently represent H or $C_{1-3}$ alkyl, $C_3$-$C_{12}$ cycloalkylene optionally substituted with substituent(s) selected from the group consisting of halogen, cyano, $C_{1-5}$ alkyl, $C_{1-3}$ alkoxy, halogenated $C_{1-3}$ alkyl, amino, hydroxyl, methanesulfonyloxy, trifluoromethanesulfonyloxy, p-toluenesulfonyloxy, oxo, and any combination thereof, $C_5$-$C_{14}$ arylene optionally substituted with substituent(s) selected from the group consisting of $C_{1-5}$ alkyl, halogenated $C_{1-3}$ alkoxy, cyano, $C_{1-3}$ alkoxy, halogenated $C_{1-3}$ alkyl, halogen, amino, hydroxyl, methanesulfonyloxy, trifluoromethanesulfonyloxy, and p-toluenesulfonyloxy, 3- to 12-membered heterocyclylene optionally substituted with substituent(s) selected from the group consisting of $C_{1-5}$ alkyl, $C_{1-3}$ alkoxy, cyano, trifluoromethyl, halogen, amino, hydroxy, methanesulfonyloxy, trifluoromethanesulfonyloxy, p-toluenesulfonyloxy, and oxo, 5- to 10-membered heteroarylene optionally substituted with substituent(s) selected from the group consisting of $C_{1-5}$ alkyl, $C_{1-3}$ alkoxy, cyano, trifluoromethyl, halogen, amino, hydroxy, methanesulfonyloxy, trifluoromethanesulfonyloxy, and p-toluenesulfonyloxy, or any combination thereof; and $X_1$ represents any one of (b1)-(b7) below:

(b1) $NR_6R_7$, $C(O)NR_eR_f$, $NHC(O)R_8$, $NHC(O)NR_9R_{10}$, $OR_h$, or SH, wherein $R_6$, $R_7$, $R_e$, $R_f$, $R_h$, $R_9$, and $R_{10}$ each independently represent: H; linear or branched $C_{1-10}$ alkyl optionally substituted with one or more substituent(s) selected from halogen, cyano, $C_{1-3}$ alkyl, $C_{1-3}$ alkoxy, trifluoromethyl, a 3- to 12-membered heterocyclyl, or any combination thereof; $C_3$-$C_{12}$cycloalkyl optionally substituted with substituent(s) selected from halogen, cyano, $C_{1-3}$ alkyl, $C_{1-3}$ alkoxy, halogenated $C_{1-3}$ alkyl, amino, hydroxyl, or any combination thereof; $C_5$-$C_{14}$aryl optionally substituted with substituent(s) selected from $C_{1-5}$ alkyl, halogenated $C_{1-3}$ alkoxy, cyano, $C_{1-3}$ alkoxy, halogenated $C_{1-3}$ alkyl, halogen, amino, and hydroxyl; 3- to 12-membered heterocyclyl optionally substituted with substituent(s) selected from $C_{1-5}$ alkyl, $C_{1-3}$ alkoxy, cyano, trifluoromethyl, halogen, amino, and hydroxy; or 5- to 10-membered heteroaryl optionally substituted with substituent(s) selected from $C_{1-3}$ alkyl, $C_{1-3}$ alkoxy, cyano, trifluoromethyl, halogen, amino, and hydroxy; wherein $R_6$ and $R_7$ are not H at the same time; and wherein $R_8$ represents a linear or branched $C_{1-8}$ alkyl, $C_5$-$C_{14}$ aryl, a 5- to 10-membered heteroaryl, or a 3- to 12-membered heterocyclyl; or wherein $R_e$ and $R_f$ together with the nitrogen atom to which they are attached form a 5- to 8-membered heterocyclyl; or wherein $R_6$ represents H, and $R_7$ represents ethyl which is substituted with 2,6-dichloro-3-fluorophenyl; or wherein $R_6$ represents H, and $R_7$ represents thiazolyl which is substituted with the group of Formula $C(O)NHR_d$, wherein $R_d$ represents $C_{1-5}$ alkyl or 2-chloro-6-methylphenyl; or wherein $R_6$ represents H or methyl; and $R_7$ represents a group of optionally substituted $C_3$-$C_{12}$ cycloalkyl, optionally substituted $C_5$-$C_{14}$ aryl, optionally substituted 3- to 12-membered heterocyclyl, or optionally substituted 5- to 10-membered heteroaryl, with each group being optionally substituted with substituent(s) selected from: (i) halogen, (ii) $C_{1-5}$ alkyl, (iii) di($C_{1-6}$ alkyl)phosphono, (iv) $C_{1-6}$ alkylsulfonyl, (v) oxo, (vi) cyano, (vii) 6-membered aryl optionally substituted with substituent(s) selected from $C_{1-6}$ alkyl, halogen and halogenated $C_{1-3}$ alkyl, (viii) 5- or 6-membered heterocyclyl optionally substituted with substituent(s) selected from $C_{1-6}$ alkyl and halogen, or (ix) 5- or 6-membered heteroaryl optionally substituted with substituent(s) selected from $C_{1-6}$ alkyl and halogen;

(b2) quaternary ammonium salt group having the Formula $N^+R_aR_bR_cX^-$, wherein $R_a$, $R_b$, and $R_c$ each independently represent $C_{1-10}$ alkyl group, and $X^-$ represents $F^-$, $Cl^-$, $Br^-$, or $I^-$; or wherein $R_a$ and $R_b$ together with the nitrogen atom to which they are attached form 5- to 8-membered heterocyclyl, and the ring atoms of the 5- to 8-membered heterocyclyl optionally further comprise a heteroatom selected from the group consisting of oxygen, nitrogen, and sulfur, and $R_c$ represents $C_{1-20}$ alkyl; and $X^-$ represents $F^-$, $Cl^-$, $Br^-$, or $I^-$, (b3) linear or branched $C_{1-10}$ alkyl optionally substituted with one or more fluorine, (b4) $C_3$-$C_{12}$ cycloalkyl optionally substituted with substituent(s) selected from halogen, oxo, cyano, trifluoromethyl, amino, hydroxy, $C_{1-3}$ alkoxy, halogenated $C_{1-3}$ alkoxy, methanesulfonyloxy, trifluoromethanesulfonyloxy, p-toluenesulfonyloxy, $C_{1-6}$ alkyl, $C_{1-3}$ alkoxycarbonyl, or any combination thereof, (b5) $C_5$-$C_{14}$ aryl substituted with substituent(s) selected from halogenated $C_{1-3}$ alkyl, amino, hydroxy, $C_{1-3}$ alkoxy, halogenated $C_{1-3}$ alkoxy, methanesulfonyloxy, trifluoromethanesulfonyloxy, p-toluenesulfonyloxy, $C_{1-6}$ alkyl, halogenated $C_{2-4}$ alkenyl, or any combination thereof, (b6) 5- to 10-membered heteroaryl optionally substituted with substituent(s) selected from the group consisting of halogen, cyano, amino, hydroxy, $C_{1-3}$ alkoxy, halogenated $C_{1-3}$ alkoxy, halogenated $C_{1-3}$ alkyl, bis($C_{1-6}$ alkyl)phosphono, $C_{1-6}$ alkylsulfonyl, methanesulfonyloxy, trifluoromethanesulfonyloxy, p-toluenesulfonyloxy, $C_{1-6}$ alkyl, optionally substituted phenyl, optionally substituted 5- or 6-membered heterocyclyl, optionally substituted 5- or 6-membered heteroaryl, and any combination thereof, wherein said optionally substituted phenyl is optionally substituted with substituent(s) selected from the group consisting of $C_{1-6}$ alkyl, cyano, halogenated $C_{1-3}$ alkyl, amino, hydroxyl, halogen, and any combination thereof; and said optionally substituted 5- or 6-membered heterocyclyl is optionally substituted with substituent(s) selected from the group consisting of: $C_{1-6}$ alkyl, cyano, halogenated $C_{1-3}$ alkyl, amino, hydroxyl, halogen, and any combination thereof; and said optionally substituted 5- or 6-membered heteroaryl is optionally substituted with substituent(s) selected from the group consisting of: $C_{1-6}$ alkyl, halogenated $C_{1-3}$ alkyl, amino, hydroxyl, halogen, and any combination thereof; or (b7) a group represented by Formula ($G_2$):

Formula ($G_2$)

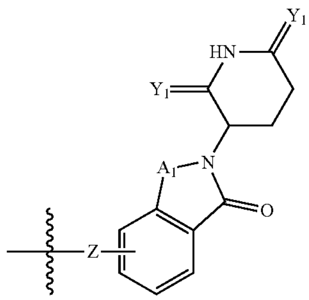

wherein, $A_1$ represents $CH_2$ or C(O);
$Y_1$ represents O; and
Z represents S, S(O), or $S(O)_2$;
or
(2') R represents S,
L represents linear or branched $C_{1-30}$ alkylene group optionally substituted with one or more substituent(s) selected from the group consisting of halogen, cyano, $C_{1-3}$ alkyl, $C_{1-3}$ alkoxy, trifluoromethyl, a 3- to 12-membered heterocyclyl, and any combination thereof, wherein the linear or branched $C_{1-30}$ alkylene group is optionally interrupted one or more times by one or more groups selected from the group consisting of:

O, C(O), S, S(O), $S(O)_2$, C(O)N($R_1$), N($R_2$)C(O), N($R_3$), N($R_4$)C(O)N($R_5$), wherein $R_1$, $R_2$, $R_3$, $R_4$, and $R_5$ each independently represent H or $C_{1-3}$ alkyl, $C_3$-$C_{12}$ cycloalkylene optionally substituted with substituent(s) selected from halogen, cyano, $C_{1-5}$ alkyl, $C_{1-3}$ alkoxy, halogenated $C_{1-3}$ alkyl, amino, hydroxyl, methanesulfonyloxy, trifluoromethanesulfonyloxy, p-toluenesulfonyloxy, oxo, and any combination thereof, $C_5$-$C_{14}$ arylene optionally substituted with substituent(s) selected from the group consisting of $C_{1-5}$ alkyl, halogenated $C_{1-3}$ alkoxy, cyano, $C_{1-3}$ alkoxy, halogenated $C_{1-3}$ alkyl, halogen, amino, hydroxyl, methanesulfonyloxy, trifluoromethanesulfonyloxy, and p-toluenesulfonyloxy, 3- to 12-membered heterocyclylene optionally substituted with substituent(s) selected from the group consisting of $C_{1-5}$ alkyl, $C_{1-3}$ alkoxy, cyano, trifluoromethyl, halogen, amino, hydroxy, methanesulfonyloxy, trifluoromethanesulfonyloxy, p-toluenesulfonyloxy, and oxo, 5- to 10-membered heteroarylene optionally substituted with substituent(s) selected from the group consisting of $C_{1-5}$ alkyl, $C_{1-3}$ alkoxy, cyano, trifluoromethyl, halogen, amino, hydroxy, methanesulfonyloxy, trifluoromethanesulfonyloxy, and p-toluenesulfonyloxy, and any combination thereof; and $X_1$ represents:

3- to 12-membered heterocyclyl optionally substituted with substituent(s) selected from the group consisting of halogen, cyano, amino, hydroxy, $C_{1-3}$ alkoxy, halogenated $C_{1-3}$ alkoxy, halogenated $C_{1-3}$ alkyl, $C_{1-6}$ alkylsulfonyl, bis($C_{1-6}$ alkyl)phosphono, methanesulfonyloxy, trifluoromethanesulfonyloxy, p-toluenesulfonyloxy, oxo, optionally substituted 5- or 6-membered heterocyclyl, optionally substituted 5- or 6-membered heteroaryl, $C_{1-6}$ alkyl, and any combination thereof, wherein said optionally substituted 5- or 6-membered heterocyclyl is optionally substituted with substituent(s) selected from the group consisting of: $C_{1-6}$ alkyl, cyano, halogenated $C_{1-3}$ alkyl, amino, hydroxyl, halogen, and any combination thereof; and said optionally substituted 5- or 6-membered heteroaryl is optionally substituted with substituent(s) selected from the group consisting of: $C_{1-6}$ alkyl, halogenated $C_{1-3}$ alkyl, amino, hydroxyl, halogen, and any combination thereof.

3. The compound of Formula (Ia) or a salt, a solvate, an isotopically enriched analog, a tautomer, a stereoisomer thereof, or a mixture of stereoisomers thereof of claim 1, which is also compound of Formula (Ib):

Formula (Ib)

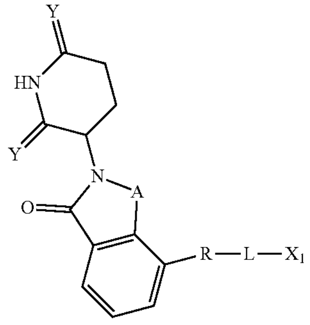

wherein A, R, L, $X_1$, and Y are as defined in claim 1.

4. The compound of Formula (Ia) or a salt, a solvate, an isotopically enriched analog, a tautomer, a stereoisomer thereof, or a mixture of stereoisomers thereof of claim 1, which is also compound of Formula (Ic):

(Ic)

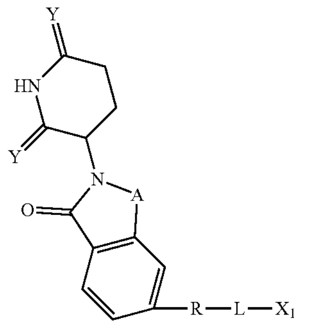

wherein A, R, L, $X_1$, and Y are as defined in claim 1.

5. The compound of Formula (Ia) or a salt, a solvate, an isotopically enriched analog, a tautomer, a stereoisomer thereof, or a mixture of stereoisomers thereof of claim 1, wherein L represents the following groups optionally substituted with substituent(s) selected from halogen, $C_{1-3}$ alkyl, or any combination thereof:

linear or branched $C_1$-$C_{40}$ alkylene; $*-((CH_2)_{n1}O)_{m1}-(CH_2)_{n2}-$; $*-((CH_2)_{n1}O)_{m1}-(CH_2)_{n2}-O-(CH_2)_{n3}-$; $*-(CH_2)_{n1}-O-(CH_2)_{n2}-$; $*-((CR_{11}R_{12})_{n1}O)_{m1}-(CR_{13}R_{14})_{n2}-$; $*-((CR_{15}R_{16})_{n1}O)_{m1}-(CR_{17}R_{18})_{n2}-O-(CR_{19}R_{20})_{n3}-$; $*-(CH_2)_{n1}-S-(CH_2)_{n2}-$; $*-(CH_2)_{n1}-S(O)-(CH_2)_{n2}-$; $*-(CH_2)_{n1}-S(O)_2-(CH_2)_{n2}-$; $*-(CH_2)_{n1}-N(R_{21})-(CH_2)_{n2}-$; $*-(CH_2)_{n1}-N(R_{22})C(O)-(CH_2)_{n2}-$; $*-(CH_2)_{n1}-C(O)N(R_{23})-(CH_2)_{n2}-$; $*-(CH_2)_{n1}-N(R_{24})C(O)N(R_{25})-(CH_2)_{n2}-$; $*-(CH_2)_{n1}-(N(R_{26})C(O)-(CH_2)_{n2})_{m1}-$; $*-(CH_2)_{n1}$-piperazinylene-$(CH_2)_{n2}-$; $*-(CH_2)_{n1}$-phenylene-$(CH_2)_{n2}-$; $*-(CH_2)_{n1}$-phenylene-$(CH_2)_{n2}-N(R_{21})-(CH_2)_{n3}-$; $*-(CH_2)_{n1}$-furanylene-$(CH_2)_{n2}-$; $*-(CH_2)_{n1}$-furanylene-$(CH_2)_{n2}-N(R_{21})-(CH_2)_{n3}-$; $*-(CH_2)_{n1}$-thiazolylene-$(CH_2)_{n2}-$; $*-(CH_2)_{n1}$-thiazolylene-$C(O)N(R_{23})-(CH_2)_{n2}-$; $*-(CH_2)_{n1}$-thiazolylene-$(CH_2)_{n2}-N(R_{21})-(CH_2)_{n3}-$; or linear or branched $C_1$-$C_{40}$ alkylene group optionally interrupted one or more times by one or more groups selected from: C(O); $N(R_{21})$; $C(O)N(R_{23})$; $N(R_{22})C(O)$; $C_3$-$C_{12}$ cycloalkylene optionally substituted with substituent(s) selected from halogen, cyano, $C_{1-5}$ alkyl, $C_{1-3}$ alkoxy, halogenated $C_{1-3}$ alkyl, amino, hydroxyl, methanesulfonyloxy, trifluoromethanesulfonyloxy, p-toluenesulfonyloxy, oxo, or any combination thereof; $C_5$-$C_{14}$ arylene optionally substituted with substituent(s) selected from $C_{1-5}$ alkyl, halogenated $C_{1-3}$ alkoxy, cyano, $C_{1-3}$ alkoxy, halogenated $C_{1-3}$ alkyl, halogen, amino, hydroxyl, methanesulfonyloxy, trifluoromethanesulfonyloxy, and p-toluenesulfonyloxy; 3- to 12-membered heterocyclylene optionally substituted with substituent(s) selected from $C_{1-5}$ alkyl, $C_{1-3}$ alkoxy, cyano, trifluoromethyl, halogen, amino, hydroxy, methanesulfonyloxy, trifluoromethanesulfonyloxy, p-toluenesulfonyloxy, and oxo; or 5- to 10-membered heteroarylene optionally substituted with substituent(s) selected from $C_{1-5}$ alkyl, $C_{1-3}$ alkoxy, cyano, trifluoromethyl, halogen, amino, hydroxy, methanesulfonyloxy, trifluoromethanesulfonyloxy, and p-toluenesulfonyloxy; or any combination thereof; or $*-((CH_2)_{n1}O)_{m1}-(CH_2)_{n2}-$, in which the backbone carbon chain is interrupted one or more times by one or more groups selected from: C(O); $C_3$-$C_{12}$ cycloalkylene optionally substituted with substituent(s) selected from the group consisting of halogen, cyano, $C_{1-5}$ alkyl, $C_{1-3}$ alkoxy, halogenated $C_{1-3}$ alkyl, amino, hydroxyl, methanesulfonyloxy, trifluoromethanesulfonyloxy, p-toluenesulfonyloxy, oxo, and any combination thereof; $C_5$-$C_{14}$ arylene optionally substituted with substituent(s) selected from the group consisting of $C_{1-5}$ alkyl, halogenated $C_{1-3}$ alkoxy, cyano, $C_{1-3}$ alkoxy, halogenated $C_{1-3}$ alkyl, halogen, amino, hydroxyl, methanesulfonyloxy, trifluoromethanesulfonyloxy, and p-toluenesulfonyloxy; 3- to 12-membered heterocyclylene optionally substituted with substituent(s) selected from the group consisting of $C_{1-5}$ alkyl, $C_{1-3}$ alkoxy, cyano, trifluoromethyl, halogen, amino, hydroxy, methanesulfonyloxy, trifluoromethanesulfonyloxy, p-toluenesulfonyloxy, and oxo; 5- to 10-membered heteroarylene optionally substituted with substituent(s) selected from the group consisting of $C_{1-5}$ alkyl, $C_{1-3}$ alkoxy, cyano, trifluoromethyl, halogen, amino, hydroxy, methanesulfonyloxy, trifluoromethanesulfonyloxy, and p-toluenesulfonyloxy; or any combination thereof, wherein * indicates the point of attachment to R;

$R_{21}$, $R_{22}$, $R_{23}$, $R_{24}$, $R_{25}$, and $R_{26}$ are each independently selected from H and $C_{1-3}$ alkyl;

$R_{11}$, $R_{12}$, $R_{13}$, $R_{14}$, $R_{15}$, $R_{16}$, $R_{17}$, $R_{18}$, $R_{19}$, and $R_{20}$ each independently represent H, a linear or branched $C_1$-$C_{10}$ alkyl, or $C_3$-$C_{10}$ cycloalkyl group, wherein in the same group L, $R_{11}$, $R_{12}$, $R_{13}$, and $R_{14}$, or $R_{15}$, $R_{16}$, $R_{17}$, $R_{18}$, $R_{19}$, and $R_{20}$ are not H at the same time; and n1, n2, n3, and m1 each independently represent an integer of 1, 2, 3, 4, 5, 6, 7, 8, 9, 10, 11, 12, 13, 14, 15, 16, 17, 18, 19, or 20.

6. The compound of Formula (Ia) or a salt, a solvate, an isotopically enriched analog, a tautomer, a stereoisomer thereof, or a mixture of stereoisomers thereof of claim 5, wherein L represents the following groups optionally substituted with substituent(s) selected from the group consisting of halogen, $C_{1-3}$ alkyl, and any combination thereof:

$-CH_2-$; $-(CH_2)_2-$; $-(CH_2)_3-$; $-(CH_2)_4-$; $-(CH_2)_5-$; $-(CH_2)_6-$; $-(CH_2)_7-$; $-(CH_2)_8-$; $-(CH_2)_9-$; $-(CH_2)_{10}-$; $-(CH_2)_{11}-$; $-(CH_2)_{12}-$; $-(CH_2)_{13}-$; $-(CH_2)_{14}-$; $-(CH_2)_{15}-$; $-(CH_2)_{16}-$; $-(CH_2)_{17}-$; $-(CH_2)_{18}-$; $-(CH_2)_{19}-$; or $-(CH_2)_{20}-$.

7. The compound of Formula (Ia) or a salt, a solvate, an isotopically enriched analog, a tautomer, a stereoisomer thereof, or a mixture of stereoisomers thereof of claim 5, wherein L represents the following groups optionally substituted with substituent(s) selected from the group consisting of halogen, $C_{1-3}$ alkyl, and any combination thereof:

$*-CH_2CH_2O(CH_2)_2-$; $*-(CH_2CH_2O)_2-(CH_2)_2-$; $*-(CH_2CH_2O)_3-(CH_2)_2-$; $*-(CH_2CH_2O)_4-(CH_2)_2-$; $*-(CH_2CH_2O)_5-(CH_2)_2-$; $*-(CH_2CH_2O)_6-(CH_2)_2-$; $*-(CH_2CH_2O)_7-(CH_2)_2-$; $*-(CH_2CH_2O)_8-(CH_2)_2-$; $*-(CH_2CH_2O)_9(CH_2)_2-$; $*-(CH_2CH_2O)_{10}(CH_2)_2-$; $*-CH_2CH_2OCH_2-$; $*-(CH_2CH_2O)_2-CH_2-$; $*-(CH_2CH_2O)_3-CH_2-$; $*-(CH_2CH_2O)_4-CH_2-$; $*-(CH_2CH_2O)_5-CH_2-$; $*-(CH_2CH_2O)_6-CH_2-$; $*-(CH_2CH_2O)_7-CH_2-$; $*-(CH_2CH_2O)_8-CH_2-$; $*-(CH_2CH_2O)_9-CH_2-$; $*-(CH_2CH_2O)_{10}-CH_2-$; $*-CH_2CH_2O(CH_2)_3-$; $*-(CH_2CH_2O)_2-(CH_2)_3-$; $*-(CH_2CH_2O)_3-(CH_2)_3-$; $*-(CH_2CH_2O)_4-(CH_2)_3-$; $*-(CH_2CH_2O)_5-(CH_2)_3-$; $*-(CH_2CH_2O)_6-(CH_2)_3-$; $*-(CH_2CH_2O)_7-(CH_2)_3-$; $*-(CH_2CH_2O)_8-(CH_2)_3-$; $*-(CH_2CH_2O)_9(CH_2)_3-$; $*-(CH_2CH_2O)_{10}(CH_2)_3-$; $*-CH_2CH_2OCH_2CH_2CH_2OCH_2-$; $*-CH_2CH_2OCH_2CH_2CH_2O-(CH_2)_2-$; $*-CH_2CH_2OCH_2CH_2CH_2O-(CH_2)_3-$; $*-(CH_2CH_2O)_2(CH_2CH_2CH_2O)(CH_2)_3-$; $*-(CH_2CH_2O)_2(CH_2CH_2CH_2O)_2(CH_2)_3-$; $*-(CH_2)_1O(CH_2)_1-$; $*-(CH_2)_1O(CH_2)_2-$; $*-(CH_2)_2O(CH_2)_4-$; $*-(CH_2)_2O(CH_2)_5-$; $*-(CH_2)_2O(CH_2)_6-$; $*-(CH_2)_3O(CH_2)_1-$; $*-(CH_2)_3O(CH_2)_2-$; $*-(CH_2)_3O(CH_2)_3-$; $*-(CH_2)_4O(CH_2)_1-$; $*-(CH_2)_4O(CH_2)_2-$; $*-(CH_2)_4O(CH_2)_3-$; $*-(CH_2)_5O(CH_2)_1-$; $*-(CH_2)_5O(CH_2)_2-$; $*-(CH_2)_5O(CH_2)_3-$; $*-(CH_2)_5O(CH_2)_4-$; or $*-(CH_2)_5O(CH_2)_5-$;

wherein * indicates the point of attachment to R.

8. The compound of Formula (Ia) or a salt, a solvate, an isotopically enriched analog, a tautomer, a stereoisomer thereof, or a mixture of stereoisomers thereof of claim 5, wherein L represents the following groups optionally substituted with substituent(s) selected from the group consisting of halogen, $C_{1-3}$ alkyl, and any combination thereof:

$*-(CH_2)_1-NH-(CH_2)_1-$; $*-(CH_2)_2-NH-(CH_2)_1-$; $*-(CH_2)_2-NH-(CH_2)_2-$; $*-(CH_2)_2-NH-(CH_2)_3-$; $*-(CH_2)_2-NH-(CH_2)_4-$; $*-(CH_2)_2-NH-(CH_2)_5-$; $*-(CH_2)_2-NH-(CH_2)_6-$; $*-(CH_2)_2-NH-(CH_2)_7-$; $*-(CH_2)_2-NH-(CH_2)_8-$; $*-(CH_2)_2-NH-(CH_2)_9-$; $*-(CH_2)_2-NH-(CH_2)_{10}-$; $*-(CH_2)_2-NH-(CH_2)_{11}-$; $*-(CH_2)_2-NH-(CH_2)_{12}-$; $*-(CH_2)_3-NH-(CH_2)_1-$; $*-(CH_2)_3-NH-(CH_2)_2-$; $*-(CH_2)_3-NH-(CH_2)_3-$; $*-(CH_2)_4-NH-(CH_2)_1-$; $*-(CH_2)_4-NH-(CH_2)_2-$; $*-(CH_2)_5-NH-(CH_2)_3-$; $*-(CH_2)_5-NH-(CH_2)_1-$; $*-(CH_2)_5-NH-(CH_2)_2-$; $*-(CH_2)_8-NH-(CH_2)_2-$; $*-(CH_2)_5-NH-(CH_2)_3-$; $*-(CH_2)_5-NH-(CH_2)_4-$; $*-(CH_2)_5-NH-(CH_2)_5-$; $*-(CH_2)_1-N(CH_3)-(CH_2)_8-$; $*-(CH_2)_2-N(CH_3)-(CH_2)_1-$; $*-(CH_2)_3-N(CH_3)-(CH_2)_1-$; $*-(CH_2)_4-N(CH_3)-(CH_2)_1-$; $*-(CH_2)_5-N(CH_3)-(CH_2)_1-$; $*-(CH_2)_6-N(CH_3)-(CH_2)_1-$; $*-(CH_2)_2-N(CH_3)-(CH_2)_2-$; $*-(CH_2)_2-N(CH_3)-(CH_2)_3-$; $*-(CH_2)_2-N(CH_3)-(CH_2)_4-$; $*-(CH_2)_2-N(CH_3)-(CH_2)_5-$; $*-(CH_2)_2-N(CH_3)-(CH_2)_6-$; $*-(CH_2)_2-N(CH_3)-(CH_2)_7-$; $*-(CH_2)_2-N(CH_3)-(CH_2)_8-$; $*-(CH_2)_2-N(CH_3)-(CH_2)_9-$; $*-(CH_2)_2-N(CH_3)-(CH_2)_{10}-$; $*-(CH_2)_2-N(CH_3)-(CH_2)_{11}-$; $*-(CH_2)_2-N(CH_3)-(CH_2)_{12}-$; $*-(CH_2)_2-NHC(O)-CH_2-$; $*-(CH_2)_2-NHC(O)-(CH_2)_2-$; $*-(CH_2)_2-NHC(O)-(CH_2)_3-$; $*-(CH_2)_2-NHC(O)-(CH_2)_4-$; $*-(CH_2)_2-NHC(O)-(CH_2)_5-$; $*-(CH_2)_2-NHC(O)-(CH_2)_6-$; $*-(CH_2)_2-NHC(O)-(CH_2)_7-$; $*-(CH_2)_2-NHC(O)-(CH_2)_8-$; $*-(CH_2)_2-NHC(O)-(CH_2)_9-$; $*-(CH_2)_2-NHC(O)-(CH_2)_{10}-$; $*-(CH_2)_2-NHC(O)-(CH_2)_{11}-$; $*-(CH_2)_2-NHC(O)-(CH_2)_{12}-$; $*-(CH_2)_2-NHC(O)-(CH_2)_{13}-$; $*-(CH_2)_2-NHC(O)-(CH_2)_{14}-$; $*-(CH_2)_2-NHC(O)-(CH_2)_{15}-$; $*-(CH_2)_3-NHC(O)-CH_2-$; $*-(CH_2)_3-NHC(O)-(CH_2)_2-$; $*-(CH_2)_3-NHC(O)-(CH_2)_3-$; $*-(CH_2)_3-NHC(O)-(CH_2)_4-$; $*-(CH_2)_3-NHC(O)-(CH_2)_5-$; $*-(CH_2)_3-NHC(O)-(CH_2)_6-$; $*-(CH_2)_3-NHC(O)-(CH_2)_7-$; $*-(CH_2)_3-NHC(O)-(CH_2)_8-$; $*-(CH_2)_3-NHC(O)-(CH_2)_9-$; $*-(CH_2)_3-NHC(O)-(CH_2)_{10}-$; $*-(CH_2)_3-NHC(O)-(CH_2)_{11}-$; $*-(CH_2)_3-NHC(O)-(CH_2)_{12}-$; $*-(CH_2)_3-NHC(O)-(CH_2)_{13}-$; $*-(CH_2)_3-NHC(O)-(CH_2)_{14}-$; $*-(CH_2)_3-NHC(O)-(CH_2)_{15}-$; $*-(CH_2)_4NHC(O)(CH_2)_1-$; $*-(CH_2)_4NHC(O)(CH_2)_2-$; $*-(CH_2)_4NHC(O)(CH_2)_3-$; $*-(CH_2)_4NHC(O)(CH_2)_4-$; $*-(CH_2)_4NHC(O)(CH_2)_5-$; $*-(CH_2)_4NHC(O)(CH_2)_6-$; $*-(CH_2)_4NHC(O)(CH_2)_7-$; $*-(CH_2)_4NHC(O)(CH_2)_8-$; $*-(CH_2)_4NHC(O)(CH_2)_9-$; $*-(CH_2)_4NHC(O)(CH_2)_{10}-$; $*-(CH_2)_5NHC(O)(CH_2)_1-$; $*-(CH_2)_8NHC(O)(CH_2)_2-$; $*-(CH_2)_2-N(CH_3)C(O)-CH_2-$; $*-(CH_2)_2-N(CH_3)C(O)-(CH_2)_2-$; $*-(CH_2)_2-N(CH_3)C(O)-(CH_2)_3-$; $*-(CH_2)_2-N(CH_3)C(O)-(CH_2)_4-$; $*-(CH_2)_2-N(CH_3)C(O)-(CH_2)_5-$; $*-(CH_2)_2-N(CH_3)C(O)-(CH_2)_6-$; $*-(CH_2)_2-N(CH_3)C(O)-(CH_2)_7-$; $*-(CH_2)_2-N(CH_3)C(O)-(CH_2)$; —; $*-(CH_2)_2-N(CH_3)C(O)-(CH_2)_9-$; $*-(CH_2)_2-N(CH_3)C(O)-(CH_2)_{10}-$; $*-(CH_2)_2-N(CH_3)C(O)-(CH_2)_{11}-$; $*-(CH_2)_2-N(CH_3)C(O)-(CH_2)_{12}-$; $*-(CH_2)_2-N(CH_3)C(O)-(CH_2)_{13}-$; $*-(CH_2)_2-N(CH_3)C(O)-(CH_2)_{14}-$; $*-(CH_2)_2-N(CH_3)C(O)-(CH_2)_{15}-$;

*—$(CH_2)_2$—C(O)NH—$CH_2$—; *—$(CH_2)_2$—C(O)NH—$(CH_2)_2$—; *—$(CH_2)_2$—C(O)NH—$(CH_2)_3$—; *—$(CH_2)_2$—C(O)NH—$(CH_2)_4$—; *—$(CH_2)_2$—C(O)NH—$(CH_2)_5$—; *—$(CH_2)_2$—C(O)NH—$(CH_2)_6$—; *—$(CH_2)_2$—C(O)NH—$(CH_2)_7$—; *—$(CH_2)_2$—C(O)NH—$(CH_2)_8$—; *—$(CH_2)_2$—C(O)NH—$(CH_2)_9$—; *—$(CH_2)_2$—C(O)NH—$(CH_2)_{10}$—; *—$(CH_2)_2$—C(O)NH—$(CH_2)_{11}$—; *—$(CH_2)_2$—C(O)NH—$(CH_2)_{12}$—; *—$(CH_2)_2$—C(O)NH—$(CH_2)_{13}$—; *—$(CH_2)_2$—C(O)NH—$(CH_2)_{14}$—; *—$(CH_2)_2$—C(O)NH—$(CH_2)_{15}$—; *—$(CH_2)_3$—C(O)NH—$CH_2$—; *—$(CH_2)_3$—C(O)NH—$(CH_2)_2$—; *—$(CH_2)_3$—C(O)NH—$(CH_2)_3$—; *—$(CH_2)_3$—C(O)NH—$(CH_2)_4$—; *—$(CH_2)_3$—C(O)NH—$(CH_2)_5$—; *—$(CH_2)_3$—C(O)NH—$(CH_2)_6$—; *—$(CH_2)_3$—C(O)NH—$(CH_2)_7$—; *—$(CH_2)_3$—C(O)NH—$(CH_2)_8$—; *—$(CH_2)_3$—C(O)NH—$(CH_2)_9$—; *—$(CH_2)_3$—C(O)NH—$(CH_2)_{10}$—; *—$(CH_2)_3$—C(O)NH—$(CH_2)_{11}$—; *—$(CH_2)_3$—C(O)NH—$(CH_2)_{12}$—; *—$(CH_2)_3$—C(O)NH—$(CH_2)_{13}$—; *—$(CH_2)_3$—C(O)NH—$(CH_2)_{14}$—; *—$(CH_2)_3$—C(O)NH—$(CH_2)_{15}$—; *—$(CH_2)_4$C(O)NH$(CH_2)_1$—; *—$(CH_2)_4$C(O)NH$(CH_2)_2$—; *—$(CH_2)_4$C(O)NH$(CH_2)_3$—; *—$(CH_2)_4$C(O)NH$(CH_2)_4$—; *—$(CH_2)_4$C(O)NH$(CH_2)_5$—; *—$(CH_2)_4$C(O)NH$(CH_2)_6$—; *—$(CH_2)_4$C(O)NH$(CH_2)_7$—; *—$(CH_2)_4$C(O)NH$(CH_2)_8$—; *—$(CH_2)_4$C(O)NH$(CH_2)_9$—; *—$(CH_2)_4$C(O)NH$(CH_2)_{10}$—; *—$(CH_2)_2$—C(O)N$(CH_3)$—$CH_2$—; *—$(CH_2)_2$—C(O)N$(CH_3)$—$(CH_2)_2$—; *—$(CH_2)_2$—C(O)N$(CH_3)$—$(CH_2)_3$—; *—$(CH_2)_2$—C(O)N$(CH_3)$—$(CH_2)_4$—; *—$(CH_2)_2$—C(O)N$(CH_3)$—$(CH_2)_5$—; *—$(CH_2)_2$—C(O)N$(CH_3)$—$(CH_2)_6$—; *—$(CH_2)_2$—C(O)N$(CH_3)$—$(CH_2)_7$—; *—$(CH_2)_2$—C(O)N$(CH_3)$—$(CH_2)_8$—; *—$(CH_2)_2$—C(O)N$(CH_3)$—$(CH_2)_9$—; *—$(CH_2)_2$—C(O)N$(CH_3)$—$(CH_2)_{10}$—; *—$(CH_2)_2$—C(O)N$(CH_3)$—$(CH_2)_{11}$—; *—$(CH_2)_2$—C(O)N$(CH_3)$—$(CH_2)_{12}$—; *—$(CH_2)_2$—C(O)N$(CH_3)$—$(CH_2)_{13}$—; *—$(CH_2)_2$—C(O)N$(CH_3)$—$(CH_2)_{14}$—; *—$(CH_2)_2$—C(O)N$(CH_3)$—$(CH_2)_{15}$—; *—$(CH_2)_2$—NHC(O)NH—$(CH_2)_4$—; *—$(CH_2)_4$—NHC(O)NH—$(CH_2)_2$—; *—$CH_2$—NHC(O)NH—$(CH_2)_2$—; *—$(CH_2)_2$—NHC(O)NH—$CH_2$—; *—$(CH_2)_2$—NHC(O)NH—$(CH_2)_2$—; *—$(CH_2)_2$—NHC(O)NH—$(CH_2)_3$—; *—$(CH_2)_3$—NHC(O)NH—$(CH_2)_2$—; *—$CH_2$-piperazinylene-$CH_2$—; *—$(CH_2)_2$-piperazinylene-$(CH_2)_2$—; *—$(CH_2)_2$-piperazinylene-$(CH_2)_3$—; *—$(CH_2)_2$-piperazinylene-$(CH_2)_4$—; *—$(CH_2)_2$-piperazinylene-$(CH_2)_5$—; *—$(CH_2)_3$-piperazinylene-$CH_2$—; *—$(CH_2)_3$-piperazinylene-$(CH_2)_2$—; *—$(CH_2)_3$-piperazinylene-$(CH_2)_3$—; *—$(CH_2)_4$-piperazinylene-$CH_2$—; *—$(CH_2)_4$-piperazinylene-$(CH_2)_2$—; *—$(CH_2)_4$-piperazinylene-$(CH_2)_3$—; *—$(CH_2)_8$-piperazinylene-$CH_2$—; *—$(CH_2)_8$-piperazinylene-$(CH_2)_2$—; *—$(CH_2)_8$-piperazinylene-$(CH_2)_3$—; *—$(CH_2)_8$-piperazinylene-$(CH_2)_4$—; *—$(CH_2)_8$-piperazinylene-$(CH_2)_5$—; *—$(CH_2)_8$-piperazinylene-$(CH_2)_6$—; *—$(CH_2)_8$-piperazinylene-$(CH_2)_7$—; *—$(CH_2)_8$-piperazinylene-$(CH_2)_8$—; *—$CH_2$-piperazinylene-$(CH_2)_8$—; *—$(CH_2)_2$-piperazinylene-$(CH_2)_8$—; *—$(CH_2)_3$-piperazinylene-$(CH_2)_8$—; *—$(CH_2)_4$-piperazinylene-*—$(CH_2)_5$-piperazinylene-$(CH_2)_8$—; *—$(CH_2)_6$-piperazinylene-$(CH_2)_8$—; *—$(CH_2)_7$—$(CH_2)_8$—; piperazinylene-$(CH_2)_8$—; *—$CH_2$-phenylene-$CH_2$—; *—$(CH_2)_2$-phenylene-$(CH_2)_2$—; *—$(CH_2)_2$-phenylene-$(CH_2)_3$—; *—$(CH_2)_2$-phenylene-$(CH_2)_4$—; *—$(CH_2)_2$-phenylene-$(CH_2)_5$—; *—$(CH_2)_3$-phenylene-$CH_2$—; *—$(CH_2)_3$-phenylene-$(CH_2)_2$—; *—$(CH_2)_3$-phenylene-$(CH_2)_3$—; *—$(CH_2)_4$-phenylene-$CH_2$—; *—$(CH_2)_4$-phenylene-$(CH_2)_2$—; *—$(CH_2)_4$-phenylene-$(CH_2)_3$—; *—$(CH_2)_5$-phenylene-$(CH_2)_3$—; *—$(CH_2)_6$-phenylene-$(CH_2)_3$—; *—$(CH_2)_7$-phenylene-$(CH_2)_3$—; *—$(CH_2)_8$-phenylene-$CH_2$—; *—$(CH_2)_8$-phenylene-$(CH_2)_5$—; *—$(CH_2)_8$-phenylene-$(CH_2)_6$—; *—$(CH_2)_8$-phenylene-$(CH_2)_4$—; *—$(CH_2)_8$-phenylene-$(CH_2)_5$—; *—$(CH_2)_8$-phenylene-$(CH_2)_6$—; *—$(CH_2)_8$-phenylene-$(CH_2)_7$—; *—$(CH_2)_8$-phenylene-$(CH_2)_8$—; *—$CH_2$-phenylene-$(CH_2)_8$—; *—$(CH_2)_2$-phenylene-$(CH_2)_8$—; *—$(CH_2)_3$ -phenylene-$(CH_2)_8$—; *—$(CH_2)_4$-phenylene-$(CH_2)_8$—; *—$(CH_2)_5$-phenylene-$(CH_2)_8$—; *—$(CH_2)_6$-phenylene-$(CH_2)_8$—; *—$(CH_2)_7$-phenylene-$(CH_2)_8$—; *—$(CH_2)_1$S$(CH_2)_1$—; *—$(CH_2)_2$S$(CH_2)_2$—; *—$(CH_2)_2$S$(CH_2)_1$—; *—$(CH_2)_1$S$(CH_2)_2$—; *—$(CH_2)_1$S$(CH_2)_3$—; *—$(CH_2)_1$S$(CH_2)_4$—; *—$(CH_2)_2$S$(CH_2)_3$—; *—$(CH_2)_2$S$(CH_2)_4$—; *—$(CH_2)_2$S$(CH_2)_5$—; *—$(CH_2)_3$S$(CH_2)_1$—; *—$(CH_2)_3$S$(CH_2)_2$—; *—$(CH_2)_3$S$(CH_2)_3$—; *—$(CH_2)_4$S$(CH_2)_1$—; *—$(CH_2)_4$S$(CH_2)_2$—; *—$(CH_2)_4$S$(CH_2)_3$—; *—$(CH_2)_5$S$(CH_2)_1$—; *—$(CH_2)_5$S$(CH_2)_2$—; *—$(CH_2)_5$S$(CH_2)_3$—; *—$(CH_2)_6$S$(CH_2)_1$—; *—$(CH_2)_6$S$(CH_2)_2$—; *—$(CH_2)_6$S$(CH_2)_3$—; *—$(CH_2)_7$S$(CH_2)_1$—; *—$(CH_2)_7$S$(CH_2)_2$—; *—$(CH_2)_7$S$(CH_2)_3$—; *—$(CH_2)_8$S$(CH_2)_1$—; *—$(CH_2)_8$S$(CH_2)_2$—; *—$(CH_2)_8$S$(CH_2)_3$—; *—$(CH_2)_9$S$(CH_2)_1$—; *—$(CH_2)_9$S$(CH_2)_2$—; *—$(CH_2)_9$S$(CH_2)_3$—; *—$(CH_2)_1$S(O)$(CH_2)_1$—; *—$(CH_2)_2$S(O)$(CH_2)_2$—; *—$(CH_2)_2$S(O)$(CH_2)_1$—; *—$(CH_2)_1$S(O)$(CH_2)_2$—; *—$(CH_2)_1$S(O)$(CH_2)_3$—; *—$(CH_2)_1$S(O)$(CH_2)_4$—; *—$(CH_2)_2$S(O)$(CH_2)_3$—; *—$(CH_2)_2$S(O)$(CH_2)_4$—; *—$(CH_2)_2$S(O)$(CH_2)_5$—; *—$(CH_2)_3$S(O)$(CH_2)_1$—; *—$(CH_2)_3$S(O)$(CH_2)_2$—; *—$(CH_2)_3$S(O)$(CH_2)_3$—; *—$(CH_2)_4$S(O)$(CH_2)_1$—; *—$(CH_2)_4$S(O)$(CH_2)_2$—; *—$(CH_2)_4$S(O)$(CH_2)_3$—; *—$(CH_2)_5$S(O)$(CH_2)_1$—; *—$(CH_2)_5$S(O)$(CH_2)_2$—; *—$(CH_2)_5$S(O)$(CH_2)_3$—; *—$(CH_2)_6$S(O)$(CH_2)_1$—; *—$(CH_2)_6$S(O)$(CH_2)_2$—; *—$(CH_2)_6$S(O)$(CH_2)_3$—; *—$(CH_2)_7$S(O)$(CH_2)_1$—; *—$(CH_2)_7$S(O)$(CH_2)_2$—; *—$(CH_2)_7$S(O)$(CH_2)_3$—; *—$(CH_2)_8$S(O)$(CH_2)_1$—; *—$(CH_2)_8$S(O)$(CH_2)_2$—; *—$(CH_2)_8$S(O)$(CH_2)_3$—; *—$(CH_2)_9$S(O)$(CH_2)_1$—; *—$(CH_2)_9$S(O)$(CH_2)_2$—; *—$(CH_2)_9$S(O)$(CH_2)_3$—; *—$(CH_2)_1$S$(O)_2$$(CH_2)_1$—; *—$(CH_2)_2$S$(O)_2$$(CH_2)_2$—; *—$(CH_2)_2$S$(O)_2$$(CH_2)_1$—; *—$(CH_2)_1$S$(O)_2$$(CH_2)_2$—; *—$(CH_2)_1$S$(O)_2$$(CH_2)_3$—; *—$(CH_2)_1$S$(O)_2$$(CH_2)_4$—; *—$(CH_2)_2$S$(O)_2$$(CH_2)_3$—; *—$(CH_2)_2$S$(O)_2$$(CH_2)_4$—; *—$(CH_2)_2$S$(O)_2$$(CH_2)_5$—; *—$(CH_2)_3$S$(O)_2$$(CH_2)_1$—; *—$(CH_2)_3$S$(O)_2$$(CH_2)_2$—; *—$(CH_2)_3$S$(O)_2$$(CH_2)_3$—; *—$(CH_2)_4$S$(O)_2$$(CH_2)_1$—; *—$(CH_2)_4$S$(O)_2$$(CH_2)_2$—; *—$(CH_2)_4$S$(O)_2$$(CH_2)_3$—; *—$(CH_2)_5$S$(O)_2$$(CH_2)_1$—; *—$(CH_2)_5$S$(O)_2$$(CH_2)_2$—; *—$(CH_2)_5$S(O)$(CH_2)_3$—; *—$(CH_2)_6$S$(O)_2$$(CH_2)_1$—; *—$(CH_2)_6$S$(O)_2$$(CH_2)_2$—; *—$(CH_2)_6$S$(O)_2$$(CH_2)_3$—; *—$(CH_2)_7$S$(O)_2$$(CH_2)_1$—; *—$(CH_2)_7$S$(O)_2$$(CH_2)_2$—; *—$(CH_2)_7$S$(O)_2$$(CH_2)_3$—; *—$(CH_2)_8$S$(O)_2$$(CH_2)_1$—; *—$(CH_2)_8$S$(O)_2$$(CH_2)_2$—; *—$(CH_2)_8$S$(O)_2$$(CH_2)_3$—; *—$(CH_2)_9$S$(O)_2$$(CH_2)_1$—; *—$(CH_2)_9$S$(O)_2$$(CH_2)_2$—; or *—$(CH_2)_9$S$(O)_2$$(CH_2)_3$—;

wherein * indicates the point of attachment to R.

9. The compound of Formula (Ia) or a salt, a solvate, an isotopically enriched analog, a tautomer, a stereoisomer thereof, or a mixture of stereoisomers thereof of claim 5, wherein L represents the following groups optionally substituted with substituent(s) selected from the group consisting of halogen, $C_{1-3}$ alkyl, and any combination thereof:

*—$(CH_2)_6$—NH—$(CH_2)_1$—; *—$(CH_2)_6$—NH—$(CH_2)_3$—; *—$(CH_2)_6$—NH—$(CH_2)_4$—; *—$(CH_2)_6$—NH—$(CH_2)_5$—; *—$(CH_2)_7$—NH—$(CH_2)_1$—; *—$(CH_2)_7$—NH—$(CH_2)_2$—; *—$(CH_2)_7$—NH—$(CH_2)_3$—; *—$(CH_2)_7$—NH—$(CH_2)_4$—; *—$(CH_2)_6$—NH—CH$(CH_3)$—; *—$(CH_2)_5$—NH—CH$(CH_3)$—; *—$(CH_2)_4$—NH—CH$(CH_3)$—; *—$(CH_2)_3$—NH—CH$(CH_3)$—; *—$(CH_2)_2$—NH—CH$(CH_3)$—; *—$(CH_2)_7$—NH—CH$(CH_3)$—; *—$(CH_2)_8$—NH—CH$(CH_3)$—; *—$(CH_2)_7$—NH—CH$(CF_3)$—; *—$(CH_2)_6$—NH—CH$(CF_3)$—; *—$(CH_2)_5$—NH—CH$(CF_3)$—; *—$(CH_2)_4$—NH—CH$(CF_3)$—; *—$(CH_2)_3$—NH—CH$(CF_3)$—; *—$(CH_2)_2$—NH—CH$(CF_3)$—; *—$(CH_2)_8$—NH—CH$(CF_3)$—; *—$CH_2$—C(O)NH—$(CH_2)_4$—; *—$CH_2$—C(O)NH—$(CH_2)_2$—; *—$CH_2$—C(O)NH—$(CH_2)_3$—; *—$CH_2$—C(O)NH—$(CH_2)_5$—; *—$(CH_2)_1$-phenylene-$(CH_2)_1$—; *—$(CH_2)_2$-phenylene-$(CH_2)_1$—; *—$(CH_2)_1$-phenylene-$(CH_2)_2$—; *—$(CH_2)_1$-phenylene-$(CH_2)_3$—; *—$(CH_2)_3$-phenylene-$(CH_2)_1$—; *—$(CH_2)_4$-phenylene-$(CH_2)_1$—; *—$(CH_2)_1$-phenylene-$(CH_2)_4$—; *—$(CH_2)_2$-phenylene-$(CH_2)_2$—; *—$CH_2$-phenylene-$CH_2$—NH—CH$(CH_3)$—; *—$CH_2$-phenylene-$(CH_2)_2$—NH—CH$(CH_3)$—; *—$CH_2$-phenylene-$CH_2$—NH—$CH_2$—; *—$CH_2$-phenylene-$(CH_2)_2$—NH—$CH_2$—; *—$(CH_2)_1$—C(O)NH—$(CH_2)_4$—; *—$(CH_2)_1$-furanylene-$(CH_2)_1$—; *—$(CH_2)_1$-furanylene-$(CH_2)_2$—; *—$(CH_2)_1$-furanylene-$(CH_2)_3$—; *—$(CH_2)_2$-furanylene-$(CH_2)_1$—; *—$(CH_2)_2$-furanylene-$(CH_2)_2$—; *—$(CH_2)_3$-furanylene-$(CH_2)_1$—; *—$(CH_2)_3$-furanylene-$(CH_2)_2$—; *—$(CH_2)_1$-thiazolylene-$(CH_2)_1$—; *—$(CH_2)_1$-thiazolylene-$(CH_2)_2$—; *—$(CH_2)_1$-thiazolylene-$(CH_2)_3$—; *—$(CH_2)_2$-thiazolylene-$(CH_2)_1$—; *—$(CH_2)_2$-thiazolylene-$(CH_2)_2$—; *—$(CH_2)_3$-thiazolylene-$(CH_2)_1$—; *—$(CH_2)_3$-thiazolylene-$(CH_2)_2$—; or *—$CH_2$-thiazolylene-$CH_2$—NH—$CH_2$—;

wherein * indicates the point of attachment to R.

10. The compound of Formula (Ia) or a salt, a solvate, an isotopically enriched analog, a tautomer, a stereoisomer thereof, or a mixture of stereoisomers thereof of claim 5, wherein L represents the following groups optionally substituted with substituent(s) selected from the group consisting of halogen, $C_{1-3}$ alkyl, and any combination thereof:

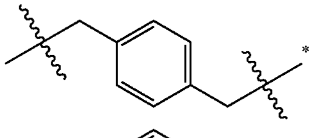

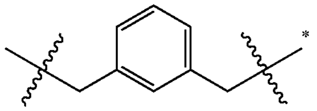

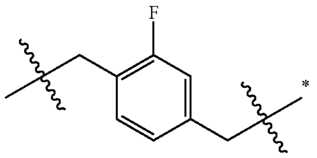

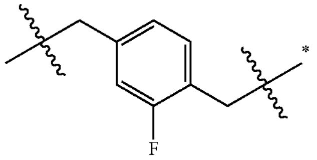

-continued

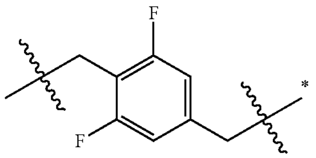

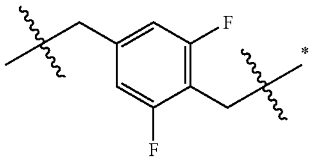

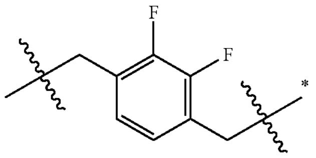

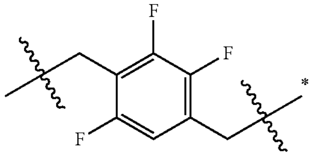

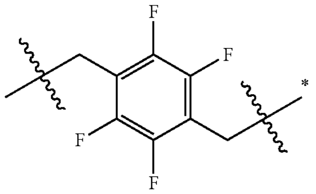

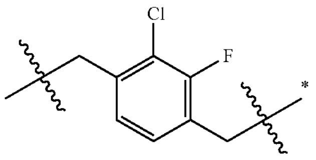

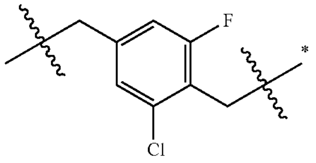

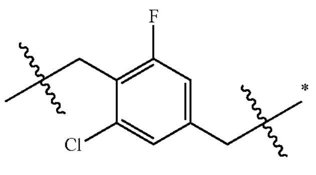

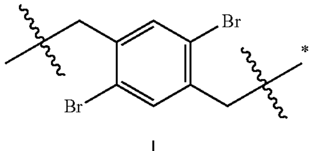

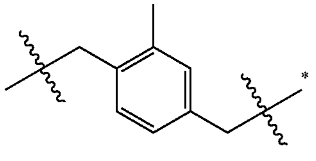

-continued
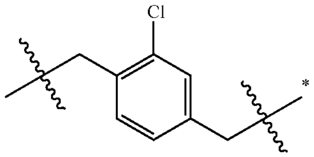
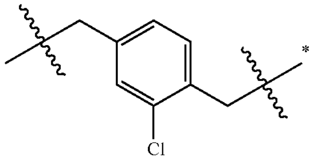
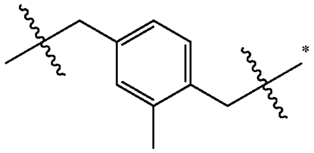
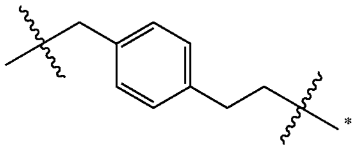
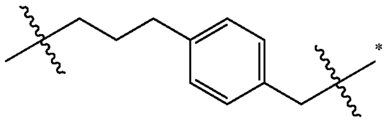
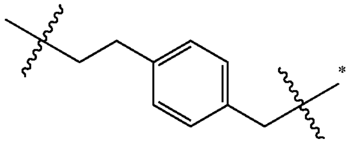
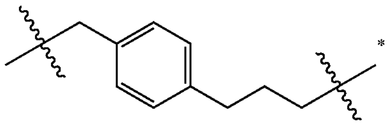
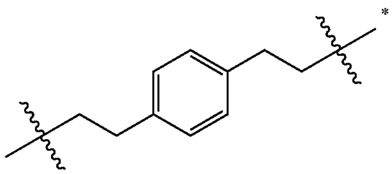
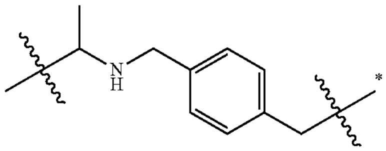
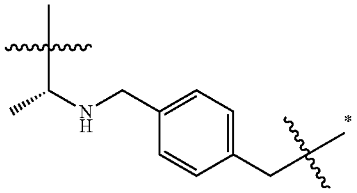
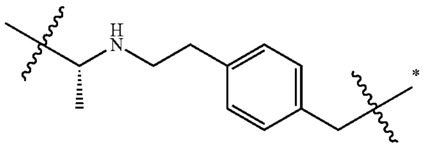
-continued
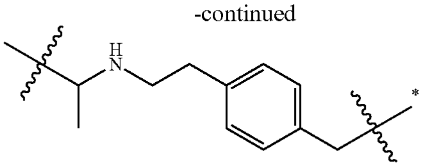
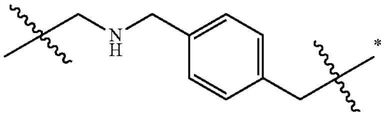
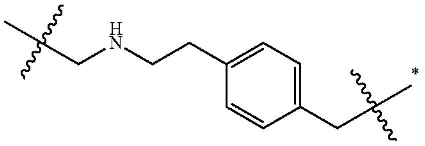
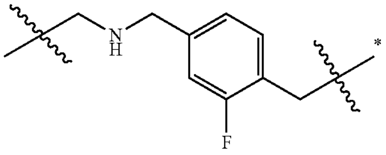
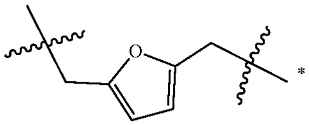
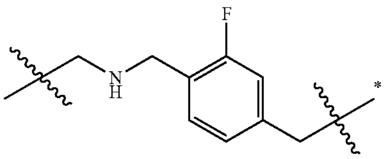
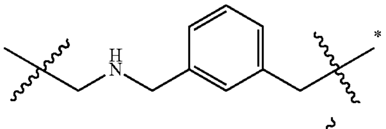
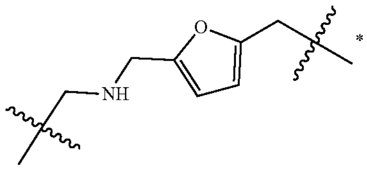
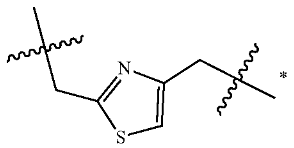
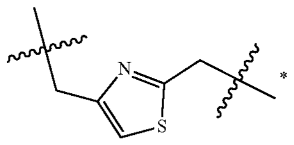
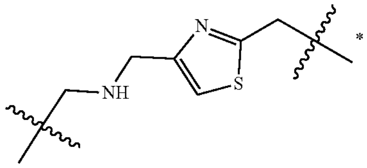
or
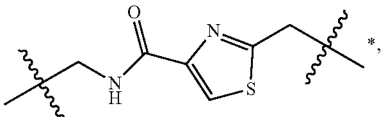
,
wherein * indicates the point of attachment to R.

11. The compound of Formula (Ia) or a salt, a solvate, an isotopically enriched analog, a tautomer, a stereoisomer thereof, or a mixture of stereoisomers thereof of claim 1, wherein $X_1$ represents:

$C(O)NH_2$, piperidine-1-carbonyl, N,N-diisopropylcarbamoyl, $NHC(O)CH_3$, OH, adamantanyl-O—, norcamphanyl-O—, 1,7,7-trimethyl-bicyclo[2.2.1]heptanyl-O—, or SH.

12. The compound of Formula (Ia) or a salt, a solvate, an isotopically enriched analog, a tautomer, a stereoisomer thereof, or a mixture of stereoisomers thereof of claim 1, wherein $X_1$ represents:

2-isopropyl-5-methylcyclohexyl-O—, adamantan-1-yl-O—, adamantan-2-yl-O—, adamantanyl-NHC(O)—, 3,5-dimethyladamantan-1-yl-NHC(O)—, adamantan-2-yl-NHC(O)—, or $NHC(O)CH_3$.

13. The compound of Formula (Ia) or a salt, a solvate, an isotopically enriched analog, a tautomer, a stereoisomer thereof, or a mixture of stereoisomers thereof of claim 1, wherein $X_1$ represents a linear or branched $C_{1-10}$ alkyl group optionally substituted with one or more fluorine.

14. The compound of Formula (Ia) or a salt, a solvate, an isotopically enriched analog, a tautomer, a stereoisomer thereof, or a mixture of stereoisomers thereof of claim 13, wherein $X_1$ represents $CF_2CF_3$, or $CF_3$.

15. The compound of Formula (Ia) or a salt, a solvate, an isotopically enriched analog, a tautomer, a stereoisomer thereof, or a mixture of stereoisomers thereof of claim 1, wherein $X_1$ represents $C_3$-$C_{12}$ cycloalkyl group optionally substituted with substituent(s) selected from halogen, oxo, cyano, $C_{1-3}$ alkoxy, trifluoromethyl, amino, hydroxy, halogenated $C_{1-3}$ alkoxy, methanesulfonyloxy, trifluoromethanesulfonyloxy, p-toluenesulfonyloxy, $C_{1-5}$ alkyl, or any combination thereof.

16. The compound of Formula (Ia) or a salt, a solvate, an isotopically enriched analog, a tautomer, a stereoisomer thereof, or a mixture of stereoisomers thereof of claim 15, wherein $X_1$ represents cyclobutyl, 3,3-difluorocyclobutyl, cyclopentyl, cyclohexyl, cycloheptyl, bicyclo[2.2.1]heptan-2-yl, or adamantanyl.

17. The compound of Formula (Ia) or a salt, a solvate, an isotopically enriched analog, a tautomer, a stereoisomer thereof, or a mixture of stereoisomers thereof of claim 15, wherein $X_1$ represents cyclopropyl, 2,3-dihydro-1H-indenyl, or 4-cyano-2,3-dihydro-1H-indenyl.

18. The compound of Formula (Ia) or a salt, a solvate, an isotopically enriched analog, a tautomer, a stereoisomer thereof, or a mixture of stereoisomers thereof of claim 15, wherein $X_1$ represents adamantan-1-yl, adamantan-2-yl, 3,5-dimethyladamantan-1-yl, or (1S,2R,4S)-1,7,7-trimethylbicyclo[2.2.1]heptan-2-yl.

19. The compound of Formula (Ia) or a salt, a solvate, an isotopically enriched analog, a tautomer, a stereoisomer thereof, or a mixture of stereoisomers thereof of claim 1, wherein $R_a$, $R_b$, and $R_c$ each independently represent a $C_{1-10}$ alkyl group.

20. The compound of Formula (Ia) or a salt, a solvate, an isotopically enriched analog, a tautomer, a stereoisomer thereof, or a mixture of stereoisomers thereof of claim 1, wherein $R_a$ and $R_b$ each independently represent methyl, ethyl, propyl, isopropyl or butyl; $R_c$ represents ethyl; and $X^-$ represents $Cl^-$.

21. The compound of Formula (Ia) or a salt, a solvate, an isotopically enriched analog, a tautomer, a stereoisomer thereof, or a mixture of stereoisomers thereof of claim 1, wherein $R_a$, $R_b$, and $R_c$ all represent ethyl, and $X^-$ represents $Cl^-$; or wherein $R_a$, $R_b$ and $R_c$ all represent methyl, and $X^-$ represents $Cl^-$.

22. The compound of Formula (Ia) or a salt, a solvate, an isotopically enriched analog, a tautomer, a stereoisomer thereof, or a mixture of stereoisomers thereof of claim 1, wherein $X_1$ represents:

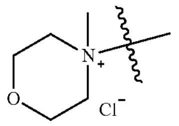
or
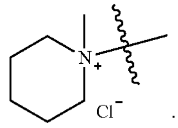
.

23. The compound of Formula (Ia) or a salt, a solvate, an isotopically enriched analog, a tautomer, a stereoisomer thereof, or a mixture of stereoisomers thereof of claim 1, wherein $X_1$ represents $C_5$-$C_{14}$ aryl group substituted with substituent(s) selected from halogenated $C_{1-3}$ alkyl, amino, hydroxy, $C_{1-3}$ alkoxy, halogenated $C_{1-3}$ alkoxy, methanesulfonyloxy, trifluoromethanesulfonyloxy, p-toluenesulfonyloxy, $C_{1-5}$ alkyl, halogenated $C_{2-4}$ alkenyl, or any combination thereof.

24. The compound of Formula (Ia) or a salt, a solvate, an isotopically enriched analog, a tautomer, a stereoisomer thereof, or a mixture of stereoisomers thereof of claim 23, wherein $X_1$ represents phenyl or naphthyl which are each independently substituted with substituent(s) selected from halogenated $C_{1-3}$ alkyl, amino, hydroxy, $C_{1-3}$ alkoxy, halogenated $C_{1-3}$ alkoxy, methanesulfonyloxy, trifluoromethanesulfonyloxy, p-toluenesulfonyloxy, $C_{1-5}$ alkyl, halogenated $C_{2-4}$ alkenyl, or any combination thereof.

25. The compound of Formula (Ia) or a salt, a solvate, an isotopically enriched analog, a tautomer, a stereoisomer thereof, or a mixture of stereoisomers thereof of claim 1, wherein under (2), $X_1$ represents optionally substituted 3- to 12-membered heterocyclyl, or under (1), $X_1$ represents optionally substituted 5- to 10-membered heteroaryl, wherein said optionally substituted 3- to 12-membered heterocyclyl is optionally substituted with substituent (s) selected from: $C_{1-6}$ alkyl, halogen, oxo, cyano, amino, hydroxy, $C_{1-3}$ alkoxy, halogenated $C_{1-3}$ alkoxy, halogenated $C_{1-3}$ alkyl, bis($C_{1-6}$ alkyl)phosphono, $C_{1-6}$ alkylsulfonyl, methanesulfonyloxy, trifluoromethanesulfonyloxy, p-toluenesulfonyloxy, optionally substituted 5- or 6-membered heterocyclyl, or optionally substituted 5- or 6-membered heteroaryl group, or any combination thereof, wherein said optionally substituted 5- or 6-membered heterocyclyl is optionally substituted with substituent(s) selected from the group consisting of: $C_{1-6}$ alkyl, cyano, halogenated $C_{1-3}$ alkyl, amino, hydroxyl, halogen, and any combination thereof; and said optionally substituted 5- or 6-membered heteroaryl is optionally substituted with substituent(s) selected from the group consisting of: $C_{1-6}$ alkyl, halogenated $C_{1-3}$ alkyl, amino, hydroxyl, halogen, and any combination thereof; and said optionally substituted 5- to 10-membered heteroaryl is optionally substituted with substituent(s) selected from: $C_{1-6}$ alkyl, halogen, cyano, amino, hydroxy, $C_{1-3}$ alkoxy, halogenated $C_{1-3}$ alkoxy, halogenated $C_{1-3}$ alkyl, bis($C_{1-6}$ alkyl)phosphono, $C_{1-6}$ alkylsulfonyl, methanesulfonyloxy, trifluoromethanesulfonyloxy, p-toluenesulfonyloxy, optionally substituted phenyl, optionally substituted 5- or 6-membered heterocyclyl, or optionally substituted 5- or 6-membered heteroaryl group, or any combination thereof, wherein said optionally substituted phenyl is optionally substituted with substituent(s) selected from $C_{1-6}$ alkyl, cyano, halogenated $C_{1-3}$ alkyl, amino, hydroxyl, halogen, or any combination thereof; and said optionally substituted 5- or 6-membered heterocyclyl is optionally substituted with substituent(s) selected from: $C_{1-6}$ alkyl, cyano, halogenated $C_{1-3}$ alkyl, amino, hydroxyl, halogen, or any combination thereof; and said optionally substituted 5- or 6-membered heteroaryl is optionally substituted with substituent(s) selected from: $C_{1-6}$ alkyl, halogenated $C_{1-3}$ alkyl, amino, hydroxyl, halogen, or any combination thereof.

26. The compound of Formula (Ia) or a salt, a solvate, an isotopically enriched analog, a tautomer, a stereoisomer thereof, or a mixture of stereoisomers thereof of claim 25, wherein the optionally substituted 3- to 12-membered heterocyclyl is optionally substituted morpholinyl; optionally substituted piperidinyl; optionally substituted piperazinyl; optionally substituted 1,4-diazepan-1-yl; optionally substituted 3,8-diazabicyclo[3.2.1]octan-3-yl; optionally substituted 2-azabicyclo[3.2.1]octanyl; optionally substituted 1,4-diazabicyclo[3.2.1]octanyl; optionally substituted 2,5-diazabicyclo[2.2.2]octan-2-yl; optionally substituted pyrrolidinyl; optionally substituted tetrahydro-2H-pyranyl; optionally substituted azacycloheptyl; optionally substituted azacyclooctyl; optionally substituted substituted 5-azaspiro[2.4]heptyl; optionally substituted 6-thiomorpholino; optionally azaspiro[2.5]octyl; optionally substituted 2-oxa-7-azaspiro[3.5]nonyl; optionally substituted 3-azabicyclo[3.1.0]hexyl; optionally substituted 3-azabicyclo[4.1.0]heptyl; optionally substituted 3-azaspiro[5.5]undecan-3-yl; optionally substituted hexahydro-1H-isoindol-2 (3H)-yl; optionally substituted (3aR,7aS)-hexahydro-1H-isoindol-2 (3H)-yl; optionally substituted (3aR,7aS)-octahydro-2H-isoindol-2-yl; optionally substituted azetidinyl; or [1,4'-dipiperidin]-1'-yl;

wherein the optionally substituted groups are each independently optionally substituted with substituent(s) selected from the group consisting of $C_{1-6}$ alkyl, halogen, cyano, amino, hydroxy, $C_{1-3}$ alkoxy, halogenated $C_{1-3}$ alkoxy, halogenated $C_{1-3}$ alkyl, di($C_{1-6}$ alkyl) phosphono, $C_{1-6}$ alkylsulfonyl, oxo, optionally substituted 5- or 6-membered heterocyclyl, optionally substituted 5- or 6-membered heteroaryl group, and any combination thereof, wherein said optionally substituted 5- or 6-membered heterocyclyl is optionally substituted with substituent(s) selected from the group consisting of: $C_{1-6}$ alkyl, cyano, halogenated $C_{1-3}$ alkyl, amino, hydroxyl, halogen, and any combination thereof; and said optionally substituted 5- or 6-membered heteroaryl is optionally substituted with substituent(s) selected from: $C_{1-6}$ alkyl, halogenated $C_{1-3}$ alkyl, amino, hydroxyl, halogen, and any combination thereof; and wherein the optionally substituted 5- to 10-membered heteroaryl is an optionally substituted quinazolinyl; optionally substituted pyridyl; optionally substituted pyrimidinyl; optionally substituted thiazolyl; optionally substituted quinolyl; optionally substituted indolyl; optionally substituted benzothienyl; optionally substituted isoindolyl; optionally substituted 5,7-dihydro-6H-pyrrolo[3,4-b]pyridyl; or optionally substituted benzofuranyl;

wherein the optionally substituted groups are each independently optionally substituted with substituent(s) selected from $C_{1-6}$ alkyl, halogen, cyano, amino, hydroxy, $C_{1-3}$ alkoxy, halogenated $C_{1-3}$ alkoxy, halogenated $C_{1-3}$ alkyl, di($C_{1-6}$ alkyl)phosphono, $C_{1-6}$ alkylsulfonyl, optionally substituted phenyl, optionally substituted 5- or 6-membered heterocyclyl, optionally substituted 5- or 6-membered heteroaryl group, or any combination thereof, wherein said optionally substituted phenyl is optionally substituted with substituent(s) selected from $C_{1-6}$ alkyl, cyano, halogenated $C_{1-3}$ alkyl, amino, hydroxyl, halogen, or any combination thereof; and said optionally substituted 5- or 6-membered heterocyclyl is optionally substituted with substituent(s) selected from: $C_{1-6}$ alkyl, cyano, halogenated $C_{1-3}$ alkyl, amino, hydroxyl, halogen, or any combination thereof; and said optionally substituted 5- or 6-membered heteroaryl is optionally substituted with substituent(s) selected from: $C_{1-6}$ alkyl, halogenated $C_{1-3}$ alkyl, amino, hydroxyl, halogen, or any combination thereof.

27. The compound of Formula (Ia) or a salt, a solvate, an isotopically enriched analog, a tautomer, a stereoisomer thereof, or a mixture of stereoisomers thereof of claim 26, wherein the optionally substituted 3- to 12-membered heterocyclyl or optionally substituted 5- to 10-membered heteroaryl is:

morpholinyl; piperidinyl; 2-oxopiperidin-1-yl; piperazinyl; N-methylpiperazinyl; 4-(methylsulfonyl)piperazin-1-yl; 4-(ethylsulfonyl)piperazin-1-yl; (N-methylpiperazinyl) piperidinyl; 3,5-dimethylpiperazinyl; 1,4-diazepan-1-yl; 4-methyl-1,4-diazepan-1-yl; 1-methyl-1,4-diazepan-1-yl; 8-methyl-3,8-diazabicyclo[3.2.1]octan-3-yl; 1,4-diazabicyclo[3.2.1]octan-4-yl; 5-methyl-2,5-diazabicyclo[2.2.2]octan-2-yl; 8,8-difluoro-2-azabicyclo[3.2.1]octan-2-yl; 2-oxopyrrolidin-1-yl; 3-fluoro-4-hydroxypyrrolidin-1-yl; 3-methyl-4-(trifluoromethyl) pyrrolidin-1-yl; 2,6-dioxopiperidin-3-yl; 4,4-dimethylpiperidin-1-yl; 3,5-dimethylpiperidin-1-yl; 4,4-difluoropiperidin-1-yl; 4-methylpiperazin-1-yl; tetrahydro-2H-pyran-2-yl; pyridyl; pyrimidinyl; thiazolyl; quinolyl; 6,7-difluoroquinazolin-4-yl; 3-cyano-quinolyl; indolyl; 1-methyl-1H-indol-7-yl; benzothienyl; benzofuranyl; quinazolinyl; 6,7-difluoroquinazolin-4-yl; pyrrolidinyl; pyrrolidin-1-yl; 4-(pyridin-3-yl)pyrimidin-2-yl; 3-cyanoazetidinyl; 3-hydroxyazetidinyl; 3-hydroxy-3-methylazetidinyl; 3-hydroxy-2-methylazetidin-1-yl; 3-(trifluoromethoxy) azetidin-1-yl; azepan-1-yl; azacyclooctan-1-yl; 7-fluoro-5-azaspiro[2.4]heptan-5-yl; 1,1-difluoro-5-azaspiro[2.4]heptan-5-yl; 1,1-difluoro-6-azaspiro[2.5]octan-6-yl; 6-azaspiro[2.5]octan-6-yl; 2-oxa-7-azaspiro[3.5]nonan-7-yl; 3-azabicyclo[3.1.0]hexan-3-yl; 6-(difluoromethyl)-3-azabicyclo[4.1.0]heptan-3-yl; 3-fluoro-5,7-dihydro-6H-pyrrolo[3,4-b]pyridin-6-yl; 3-(trifluoromethyl)-5,7-dihydro-6H-pyrrolo[3,4-b]pyridin-6-yl; isoindol-2-yl; thiomorpholino; [1,4'-dipiperidin]-1'-yl; 4,4-difluoropiperidinyl; or

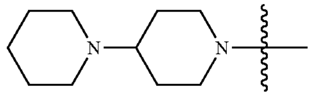

.

28. The compound of Formula (Ia) or a salt, a solvate, an isotopically enriched analog, a tautomer, a stereoisomer thereof, or a mixture of stereoisomers thereof of claim 1, wherein $X_1$ represents an optionally substituted $C_3$-$C_{12}$ cycloalkyl or substituted $C_5$-$C_{14}$ aryl, wherein said optionally substituted $C_3$-$C_{12}$ cycloalkyl is optionally substituted with substituent(s) selected from: $C_{1-6}$ alkyl, halogen, $C_{1-3}$ alkoxycarbonyl, or any combination thereof; and wherein said substituted $C_5$-$C_{14}$ aryl is substituted with substituent(s) selected from: halogenated $C_{2-4}$ alkenyl.

29. The compound of Formula (Ia) or a salt, a solvate, an isotopically enriched analog, a tautomer, a stereoisomer thereof, or a mixture of stereoisomers thereof of claim 28, wherein $X_1$ represents:

(2-bromovinyl)phenyl, or

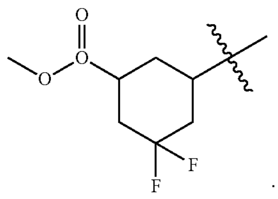

30. The compound of Formula (Ia) or a salt, a solvate, an isotopically enriched analog, a tautomer, a stereoisomer thereof, or a mixture of stereoisomers thereof of claim 1, wherein $X_1$ represents:

$NR_6R_7$, wherein $R_6$ and $R_7$ each independently represent H or a linear or branched $C_{1-10}$ alkyl group optionally substituted with one or more substituent(s) selected from halogen, cyano, $C_{1-3}$ alkyl, $C_{1-3}$ alkoxy, trifluoromethyl, a 3- to 12-membered heterocyclyl, or any combination thereof, provided that $R_6$ and $R_7$ are not H at the same time.

31. The compound of Formula (Ia) or a salt, a solvate, an isotopically enriched analog, a tautomer, a stereoisomer thereof, or a mixture of stereoisomers thereof of claim 30, wherein $X_1$ represents $NHCH_3$, $N(CH_3)_2$, $N(CH_2CH_3)_2$, or $N(CH(CH_3)_2)_2$.

32. The compound of Formula (Ia) or a salt, a solvate, an isotopically enriched analog, a tautomer, a stereoisomer thereof, or a mixture of stereoisomers thereof of claim 1, wherein $X_1$ represents:

$NR_6R_7$, wherein $R_6$ represents H or methyl; and $R_7$ represents pyrimidinyl, pyridyl, quinazolinyl, 6,7-difluoroquinazolin-4-yl, phenyl, 3-chloro-4-methylphenyl, 4-fluorophenyl, 3,5-difluorophenyl, 3,4,5-trifluorophenyl, 2-(dimethylphosphono)phenyl, 2-(isopropylsulfonyl)phenyl, 4-(pyridin-3-yl)pyrimidin-2-yl, indolyl, 1-methyl-1H-indol-7-yl, benzothienyl, benzo[b]thien-7-yl, benzofuran-7-yl, benzofuranyl, 3-cyano-quinol-4-yl, quinolyl, thiazolyl, adamantanyl, adamantan-1-yl, adamantan-2-yl, 3,5-dimethyladamantan-1-yl, 1,7,7-trimethylbicyclo[2.2.1]heptan-2-yl, 4-(4-methylpiperazin-1-yl) piperidin-1-yl, cyclohexyl, dimethylcyclohexyl, 4,4-dimethylcyclohexyl, spiro-cycloalkyl, spiro[5.5]undec-3-yl, spiro[3.3]heptyl, spiro[3.3]hept-2-yl, pyrrolidinyl, azepanyl, azacyclooctanyl, piperidinyl, dimethylpiperidinyl, or azaspirocycloalkyl.

33. The compound of Formula (Ia) or a salt, a solvate, an isotopically enriched analog, a tautomer, a stereoisomer thereof, or a mixture of stereoisomers thereof of claim 1, wherein $X_1$ represents:

$NR_6R_7$, wherein $R_6$ represents H, methyl, ethyl, isopropyl, or cyclohexyl; and $R_7$ represents the following groups:

adamantanyl, noradamantanyl, norcamphanyl, cyclohexyl, cyclopentyl, cyclopropyl, cyclobutyl, ethyl, isopropyl, tert-butyl, methyl, 2,4-dimethylpent-3-yl, dicyclopropylmethyl, spiro[3.3]heptyl, bicyclo[1.1.1]pentyl, bicyclo[2.2.2]octyl, 4,4-dimethylcyclohexyl, oxetanyl, oxazolyl, 2,3-dihydro-1H-indenyl, quinuclidinyl, 1,7,7-trimethylbicyclo[2.2.1]heptyl, 7,7-dimethylbicyclo[2.2.1]heptyl, bicyclo[2.2.1]heptyl, or 1-cyclopropylethyl.

34. The compound of Formula (Ia) or a salt, a solvate, an isotopically enriched analog, a tautomer, a stereoisomer thereof, or a mixture of stereoisomers thereof of claim 33, wherein $R_7$ represents:

bicyclo[1.1.1]pent-1-yl, 4,4-dimethylcyclohexyl, 2-methoxycyclopropyl, 3-fluorocyclobutyl, 3,3-difluorocyclobutyl, 3,3-difluoro-1-(2-(trifluoromethyl)phenyl)cyclobutyl, 3-(2-(trifluoromethyl)phenyl) oxetan-3-yl, 3,3-difluorocyclopentyl, 3-hydroxycyclohexyl, 3-hydroxycyclohexyl, 3-cyano-bicyclo[1.1.1]pent-1-yl, bicyclo[2.2.2]octan-1-yl, 4-hydroxybicyclo[2.2.2]octan-1-yl, 2-isopropyl-5-methylcyclohexyl, 5-methyloxazol-2-yl, 4-cyano-2,3-dihydro-1H-inden-1-yl, 2,4-dimethylpentan-3-yl, dicyclopropylmethyl, quinuclidin-3-yl, (S)-quinuclidin-3-yl, (R)-quinuclidin-3-yl, adamantan-1-yl, 3-hydroxyadamantanyl, 3-hydroxyadamantan-1-yl, 3-chloroadamantan-1-yl, 4-chloroadamantan-1-yl, 2-chloroadamantan-1-yl, adamantan-2-yl, 1,7,7-trimethylbicyclo[2.2.1]heptan-2-yl, 7,7-dimethylbicyclo[2.2.1]heptan-1-yl, 7,7-dimethyl-2-oxobicyclo[2.2.1]heptan-1-yl, 3,5-dimethyladamantanyl, 3,5-dimethyladamantan-1-yl, hexahydro-2,5-methanopentalen-3a (1H)-yl, bicyclo[2.2.1]heptyl, bicyclo[2.2.1]heptan-2-yl, 1-cyclopropylethyl, or

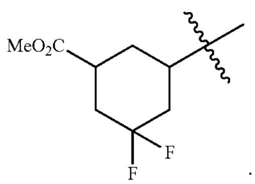

35. The compound of Formula (Ia) or a salt, a solvate, an isotopically enriched analog, a tautomer, a stereoisomer thereof, or a mixture of stereoisomers thereof of claim 1, wherein $X_1$ represents $NR_6R_7$, wherein $R_6$ represents H, and $R_7$ represents pyrimidin-4-yl, pyridin-4-yl, or quinazolin-4-yl; or wherein $X_1$ represents $NR_6R_7$, wherein $R_6$ and $R_7$ represent phenyl.

36. The compound of Formula (Ia) or a salt, a solvate, an isotopically enriched analog, a tautomer, a stereoisomer thereof, or a mixture of stereoisomers thereof of claim 1, wherein $X_1$ represents $NHC(O)NR_9R_{10}$, wherein $R_9$ represents H, and $R_{10}$ represents adamantanyl, adamantan-1-yl, adamantan-2-yl, 3,5-dimethyladamantan-1-yl, phenyl, or 3-chloro-4-methylphenyl.

37. The compound of Formula (Ia) or a salt, a solvate, an isotopically enriched analog, a tautomer, a stereoisomer thereof, or a mixture of stereoisomers thereof of claim 1, wherein the compound is selected from:
4-((6-(diethylamino)hexyl)thio)-2-(2,6-dioxopiperidin-3-yl)isoindoline-1,3-dione;
4-((6-(dimethylamino)hexyl)thio)-2-(2,6-dioxopiperidin-3-yl)isoindoline-1,3-dione;
2-(2,6-dioxopiperidin-3-yl)-4-((6-(methylamino)hexyl)thio)isoindoline-1,3-dione;
3-(4-((3-hydroxypropyl)thio)-1-oxoisoindolin-2-yl)piperidine-2,6-dione;
3-(4-((5-hydroxypentyl)thio)-1-oxoisoindolin-2-yl)piperidine-2,6-dione;
3-(4-((8-hydroxyoctyl)thio)-1-oxoisoindolin-2-yl)piperidine-2,6-dione;
2-((2-(2,6-dioxopiperidin-3-yl)-1-oxoisoindolin-4-yl)thio)acetamide;
3-(1-oxo-4-((9-((4,4,5,5,5-pentafluoropentyl)thio)nonyl)thio)isoindolin-2-yl)piperidine-2,6-dione;
3-(1-oxo-4-((9-((4,4,5,5,5-pentafluoropentyl)sulfinyl)nonyl)thio)isoindolin-2-yl)piperidine-2,6-dione;
3-(1-oxo-4-((9-((4,4,5,5,5-pentafluoropentyl) sulfonyl)nonyl)thio)isoindolin-2-yl)piperidine-2,6-dione;
3-(1-oxo-4-((9,9,10,10,10-pentafluorodecyl)thio)isoindolin-2-yl)piperidine-2,6-dione;
3-(4-((2-morpholinoethyl)thio)-1-oxoisoindolin-2-yl)piperidine-2,6-dione;
3-(1-oxo-4-((2-(piperazin-1-yl)ethyl)thio)isoindolin-2-yl)piperidine-2,6-dione;
3-(1-oxo-4-((2-(piperidin-1-yl)ethyl)thio)isoindolin-2-yl)piperidine-2,6-dione;
3-(4-((2-(diethylamino)ethyl)thio)-1-oxoisoindolin-2-yl)piperidine-2,6-dione;
3-(4-((2-(diisopropylamino)ethyl)thio)-1-oxoisoindolin-2-yl)piperidine-2,6-dione;
3-(4-((3-morpholinopropyl)thio)-1-oxoisoindolin-2-yl)piperidine-2,6-dione;
3-(1-oxo-4-((3-(piperazin-1-yl)propyl)thio)isoindolin-2-yl)piperidine-2,6-dione;
3-(1-oxo-4-((3-(piperidin-1-yl)propyl)thio)isoindolin-2-yl)piperidine-2,6-dione;
3-(4-((3-(diethylamino)propyl)thio)-1-oxoisoindolin-2-yl)piperidine-2,6-dione;
3-(4-((3-(diisopropylamino)propyl)thio)-1-oxoisoindolin-2-yl)piperidine-2,6-dione;
3-(4-((4-morpholinobutyl)thio)-1-oxoisoindolin-2-yl)piperidine-2,6-dione;
3-(1-oxo-4-((4-(piperazin-1-yl)butyl)thio)isoindolin-2-yl)piperidine-2,6-dione;
3-(1-oxo-4-((4-(piperidin-1-yl)butyl)thio)isoindolin-2-yl)piperidine-2,6-dione;
3-(4-((4-(diethylamino)butyl)thio)-1-oxoisoindolin-2-yl)piperidine-2,6-dione;
3-(4-((4-(diisopropylamino)butyl)thio)-1-oxoisoindolin-2-yl)piperidine-2,6-dione;
3-(4-((5-morpholinopentyl)thio)-1-oxoisoindolin-2-yl)piperidine-2,6-dione;
3-(1-oxo-4-((5-(piperazin-1-yl)pentyl)thio)isoindolin-2-yl)piperidine-2,6-dione;
3-(1-oxo-4-((5-(piperidin-1-yl)pentyl)thio)isoindolin-2-yl)piperidine-2,6-dione;
3-(4-((5-(diethylamino)pentyl)thio)-1-oxoisoindolin-2-yl)piperidine-2,6-dione;
3-(4-((5-(diisopropylamino)pentyl)thio)-1-oxoisoindolin-2-yl)piperidine-2,6-dione;
3-(4-((5-(dimethylamino)pentyl)thio)-1-oxoisoindolin-2-yl)piperidine-2,6-dione;
3-(4-((5-(methylamino)pentyl)thio)-1-oxoisoindolin-2-yl)piperidine-2,6-dione;
N-(5-((2-(2,6-dioxopiperidin-3-yl)-1-oxoisoindolin-4-yl)thio)pentyl)acetamide;
3-(4-((6-morpholinohexyl)thio)-1-oxoisoindolin-2-yl)piperidine-2,6-dione;
3-(1-oxo-4-((6-(piperazin-1-yl)hexyl)thio)isoindolin-2-yl)piperidine-2,6-dione;
3-(1-oxo-4-((6-(piperidin-1-yl)hexyl)thio)isoindolin-2-yl)piperidine-2,6-dione;
3-(4-((6-(diethylamino)hexyl)thio)-1-oxoisoindolin-2-yl)piperidine-2,6-dione;
3-(4-((6-(diisopropylamino)hexyl)thio)-1-oxoisoindolin-2-yl)piperidine-2,6-dione;
3-(4-((6-(dimethylamino)hexyl)thio)-1-oxoisoindolin-2-yl)piperidine-2,6-dione;
3-(4-((6-(methylamino)hexyl)thio)-1-oxoisoindolin-2-yl)piperidine-2,6-dione;
3-(4-((7-morpholinoheptyl)thio)-1-oxoisoindolin-2-yl)piperidine-2,6-dione;
3-(1-oxo-4-((7-(piperazin-1-yl)heptyl)thio)isoindolin-2-yl)piperidine-2,6-dione;
3-(1-oxo-4-((7-(piperidin-1-yl)heptyl)thio)isoindolin-2-yl)piperidine-2,6-dione;
3-(4-((7-(diethylamino)heptyl)thio)-1-oxoisoindolin-2-yl)piperidine-2,6-dione;
3-(4-((7-(diisopropylamino)heptyl)thio)-1-oxoisoindolin-2-yl)piperidine-2,6-dione;
3-(4-((8-morpholinooctyl)thio)-1-oxoisoindolin-2-yl)piperidine-2,6-dione;
3-(1-oxo-4-((8-(piperazin-1-yl)octyl)thio)isoindolin-2-yl)piperidine-2,6-dione;
3-(4-((8-(4-methylpiperazin-1-yl)octyl)thio)-1-oxoisoindolin-2-yl)piperidine-2,6-dione;
3-(4-((8-(3,5-dimethylpiperazin-1-yl)octyl)thio)-1-oxoisoindolin-2-yl)piperidine-2,6-dione;
3-(1-oxo-4-((8-(piperidin-1-yl)octyl)thio)isoindolin-2-yl)piperidine-2,6-dione;
3-(4-((8-(4,4-difluoropiperidin-1-yl)octyl)thio)-1-oxoisoindolin-2-yl)piperidine-2,6-dione;
3-(4-((8-(1,4-diazepan-1-yl)octyl)thio)-1-oxoisoindolin-2-yl)piperidine-2,6-dione;
3-(4-((8-(4-methyl-1,4-diazepan-1-yl)octyl)thio)-1-oxoisoindolin-2-yl)piperidine-2,6-dione;
3-(1-oxo-4-((8-(4-(piperazin-1-yl) piperidin-1-yl)octyl)thio)isoindolin-2-yl)piperidine-2,6-dione;
3-(4-((8-(4-(4-methylpiperazin-1-yl) piperidin-1-yl)octyl)thio)-1-oxoisoindolin-2-yl)piperidine-2,6-dione;
3-(4-((8-(diisopropylamino)octyl)thio)-1-oxoisoindolin-2-yl)piperidine-2,6-dione;
3-(4-((5-((2-(diethylamino)ethyl)amino)pentyl)thio)-1-oxoisoindolin-2-yl)piperidine-2,6-dione;
5-((2-(2,6-dioxopiperidin-3-yl)-1-oxoisoindolin-4-yl)thio)-N-(2-morpholinoethyl) pentanamide;
N-(4-((2-(2,6-dioxopiperidin-3-yl)-1-oxoisoindolin-4-yl)thio)butyl)-3-morpholinopropanamide;
3-(4-((8-(diethylamino)octyl)thio)-1-oxoisoindolin-2-yl)piperidine-2,6-dione;
3-(4-((8-(dimethylamino)octyl)thio)-1-oxoisoindolin-2-yl)piperidine-2,6-dione;
3-(4-((8-(methylamino)octyl)thio)-1-oxoisoindolin-2-yl)piperidine-2,6-dione;
3-(4-((9-morpholinononyl)thio)-1-oxoisoindolin-2-yl)piperidine-2,6-dione;

3-(1-oxo-4-((9-(piperazin-1-yl)nonyl)thio)isoindolin-2-yl)piperidine-2,6-dione;

3-(1-oxo-4-((9-(piperidin-1-yl)nonyl)thio)isoindolin-2-yl)piperidine-2,6-dione;

3-(4-((9-(diethylamino)nonyl)thio)-1-oxoisoindolin-2-yl)piperidine-2,6-dione;

3-(4-((9-(diisopropylamino)nonyl)thio)-1-oxoisoindolin-2-yl)piperidine-2,6-dione;

3-(4-((10-morpholinodecyl)thio)-1-oxoisoindolin-2-yl)piperidine-2,6-dione;

3-(1-oxo-4-((10-(piperazin-1-yl)decyl)thio)isoindolin-2-yl)piperidine-2,6-dione;

3-(1-oxo-4-((10-(piperidin-1-yl)decyl)thio)isoindolin-2-yl)piperidine-2,6-dione;

3-(4-((10-(diethylamino)decyl)thio)-1-oxoisoindolin-2-yl)piperidine-2,6-dione;

3-(4-((10-(diisopropylamino)decyl)thio)-1-oxoisoindolin-2-yl)piperidine-2,6-dione;

3-(4-((11-morpholinoundecyl)thio)-1-oxoisoindolin-2-yl)piperidine-2,6-dione;

3-(1-oxo-4-((11-(piperazin-1-yl)undecyl)thio)isoindolin-2-yl)piperidine-2,6-dione;

3-(1-oxo-4-((11-(piperidin-1-yl)undecyl)thio)isoindolin-2-yl)piperidine-2,6-dione;

3-(4-((11-(diethylamino)undecyl)thio)-1-oxoisoindolin-2-yl)piperidine-2,6-dione;

3-(4-((11-(diisopropylamino)undecyl)thio)-1-oxoisoindolin-2-yl)piperidine-2,6-dione;

3-(4-((8-((2-(diethylamino)ethyl)amino)octyl)thio)-1-oxoisoindolin-2-yl)piperidine-2,6-dione;

3-(4-((12-morpholinododecyl)thio)-1-oxoisoindolin-2-yl)piperidine-2,6-dione;

3-(1-oxo-4-((12-(piperazin-1-yl) dodecyl)thio)isoindolin-2-yl)piperidine-2,6-dione;

3-(1-oxo-4-((12-(piperidin-1-yl) dodecyl)thio)isoindolin-2-yl)piperidine-2,6-dione;

3-(4-((12-(diethylamino) dodecyl)thio)-1-oxoisoindolin-2-yl)piperidine-2,6-dione;

3-(4-((12-(diisopropylamino) dodecyl)thio)-1-oxoisoindolin-2-yl)piperidine-2,6-dione;

N-(8-((2-(2,6-dioxopiperidin-3-yl)-1-oxoisoindolin-4-yl)thio)octyl)-3-morpholinopropanamide;

3-(4-((15-morpholinopentadecyl)thio)-1-oxoisoindolin-2-yl)piperidine-2,6-dione;

3-(1-oxo-4-((15-(piperidin-1-yl)pentadecyl)thio)isoindolin-2-yl)piperidine-2,6-dione;

3-(4-((8-(8-methyl-3,8-diazabicyclo[3.2.1]octan-3-yl)octyl)thio)-1-oxoisoindolin-2-yl)piperidine-2,6-dione;

3-(4-((8-(5-methyl-2,5-diazabicyclo[2.2.2]octan-2-yl)octyl)thio)-1-oxoisoindolin-2-yl)piperidine-2,6-dione;

3-(4-((4-(4-(2-morpholinoethyl)phenyl)butyl)thio)-1-oxoisoindolin-2-yl)piperidine-2,6-dione;

3-(4-((8-(4-((3,3-difluorocyclobutyl)methyl)piperazin-1-yl)octyl)thio)-1-oxoisoindolin-2-yl)piperidine-2,6-dione;

3-(4-((5-((2-hydroxyethyl)amino)pentyl)thio)-1-oxoisoindolin-2-yl)piperidine-2,6-dione;

3-(1-oxo-4-((8-(2-oxopiperidin-1-yl)octyl)thio)isoindolin-2-yl)piperidine-2,6-dione;

3-(1-oxo-4-((8-(2-oxopyrrolidin-1-yl)octyl)thio)isoindolin-2-yl)piperidine-2,6-dione;

1-(8-((2-(2,6-dioxopiperidin-3-yl)-1-oxoisoindolin-4-yl)thio)octyl)piperidine-2,6-dione;

3-(1-oxo-4-((8-(pyrimidin-4-ylamino)octyl)thio)isoindolin-2-yl)piperidine-2,6-dione;

3-(1-oxo-4-((8-(pyridin-4-ylamino)octyl)thio)isoindolin-2-yl)piperidine-2,6-dione;

3-(1-oxo-4-((8-(quinazolin-4-ylamino)octyl)thio)isoindolin-2-yl)piperidine-2,6-dione;

3-(4-((8-((6,7-difluoroquinazolin-4-yl)amino)octyl)thio)-1-oxoisoindolin-2-yl)piperidine-2,6-dione;

3-(4-((8-((4-fluorophenyl)amino)octyl)thio)-1-oxoisoindolin-2-yl)piperidine-2,6-dione;

3-(4-((8-((3,5-difluorophenyl)amino)octyl)thio)-1-oxoisoindolin-2-yl)piperidine-2,6-dione;

3-(1-oxo-4-((8-((3,4,5-trifluorophenyl)amino)octyl)thio)isoindolin-2-yl)piperidine-2,6-dione;

3-(4-((8-((2-(dimethylphosphoryl)phenyl)amino)octyl)thio)-1-oxoisoindolin-2-yl)piperidine-2,6-dione;

3-(4-((8-((2-(isopropylsulfonyl)phenyl)amino)octyl)thio)-1-oxoisoindolin-2-yl)piperidine-2,6-dione;

3-(1-oxo-4-((8-((4-(pyridin-3-yl)pyrimidin-2-yl)amino)octyl)thio)isoindolin-2-yl)piperidine-2,6-dione;

N-(2-chloro-6-methylphenyl)-2-((8-((2-(2,6-dioxopiperidin-3-yl)-1-oxoisoindolin-4-yl)thio)octyl)amino)thiazole-5-carboxamide;

3-(4-((8-((1-(2,6-dichloro-3-fluorophenyl)ethyl)amino)octyl)thio)-1-oxoisoindolin-2-yl)piperidine-2,6-dione;

3-(4-((8-((1-methyl-1H-indol-7-yl)amino)octyl)thio)-1-oxoisoindolin-2-yl)piperidine-2,6-dione;

3-(4-((8-(benzo[b]thiophen-7-ylamino)octyl)thio)-1-oxoisoindolin-2-yl)piperidine-2,6-dione;

3-(4-((8-(benzofuran-7-ylamino)octyl)thio)-1-oxoisoindolin-2-yl)piperidine-2,6-dione;

4-((8-((2-(2,6-dioxopiperidin-3-yl)-1-oxoisoindolin-4-yl)thio)octyl)amino) quinoline-3-carbonitrile;

8-((2-(2,6-dioxopiperidin-3-yl)-1-oxoisoindolin-4-yl)thio)-N-ethyl-N,N-diisopropyloctan-1-aminium chloride;

8-((2-(2,6-dioxopiperidin-3-yl)-1-oxoisoindolin-4-yl)thio)-N,N,N-triethyloctan-1-aminium chloride;

8-((2-(2,6-dioxopiperidin-3-yl)-1-oxoisoindolin-4-yl)thio)-N,N,N-trimethyloctan-1-aminium chloride;

4-(8-((2-(2,6-dioxopiperidin-3-yl)-1-oxoisoindolin-4-yl)thio)octyl)-4-methylmorpholin-4-ium chloride;

1-(8-((2-(2,6-dioxopiperidin-3-yl)-1-oxoisoindolin-4-yl)thio)octyl)-1-methylpiperidin-1-ium chloride;

3-(4-((4-((adamantan-1-yl)amino)butyl)thio)-1-oxoisoindolin-2-yl)piperidine-2,6-dione;

3-(4-((5-((adamantan-1-yl)amino)pentyl)thio)-1-oxoisoindolin-2-yl)piperidine-2,6-dione;

3-(4-((6-((adamantan-1-yl)amino)hexyl)thio)-1-oxoisoindolin-2-yl)piperidine-2,6-dione;

3-(4-((7-((adamantan-1-yl)amino)heptyl)thio)-1-oxoisoindolin-2-yl)piperidine-2,6-dione;

3-(4-((8-((adamantan-1-yl)amino)octyl)thio)-1-oxoisoindolin-2-yl)piperidine-2,6-dione;

3-(4-((4-((adamantan-2-yl)amino)butyl)thio)-1-oxoisoindolin-2-yl)piperidine-2,6-dione;

3-(4-((5-((adamantan-2-yl)amino)pentyl)thio)-1-oxoisoindolin-2-yl)piperidine-2,6-dione;

3-(4-((6-((adamantan-2-yl)amino)hexyl)thio)-1-oxoisoindolin-2-yl)piperidine-2,6-dione;

3-(4-((7-((adamantan-2-yl)amino)heptyl)thio)-1-oxoisoindolin-2-yl)piperidine-2,6-dione;

3-(4-((8-((adamantan-2-yl)amino)octyl)thio)-1-oxoisoindolin-2-yl)piperidine-2,6-dione;

3-(4-((2-(2-((adamantan-2-yl)amino)ethoxy)ethyl)thio)-1-oxoisoindolin-2-yl)piperidine-2,6-dione;

3-(4-((2-(2-(2-((adamantan-2-yl)amino)ethoxy)ethoxy)ethyl)thio)-1-oxoisoindolin-2-yl)piperidine-2,6-dione;

1-(adamantan-1-yl)-3-(6-((2-(2,6-dioxopiperidin-3-yl)-1-oxoisoindolin-4-yl)thio)hexyl)urea;

1-(4-(adamantan-1-yl)butyl)-3-(2-((2-(2,6-dioxopiperidin-3-yl)-1-oxoisoindolin-4-yl)thio)ethyl)urea;
3-(4-((8-((adamantan-1-yl)(methyl)amino)octyl)thio)-1-oxoisoindolin-2-yl)piperidine-2,6-dione;
3-(4-((8-((3,5-dimethyladamantan-1-yl)amino)octyl)thio)-1-oxoisoindolin-2-yl)piperidine-2,6-dione;
3-(4-((9-(adamantan-1-yl)nonyl)thio)-1-oxoisoindolin-2-yl)piperidine-2,6-dione;
2-((adamantan-1-yl)amino)-N-(5-((2-(2,6-dioxopiperidin-3-yl)-1-oxoisoindolin-4-yl)thio)pentyl)acetamide;
3-(1-oxo-4-((8-(((1S,2R,4S)-1,7,7-trimethylbicyclo[2.2.1]heptan-2-yl)amino)octyl)thio)isoindolin-2-yl)piperidine-2,6-dione;
3-(4-((2-(2-morpholinoethoxy)ethyl)thio)-1-oxoisoindolin-2-yl)piperidine-2,6-dione;
3-(1-oxo-4-((2-(2-(piperazin-1-yl)ethoxy)ethyl)thio)isoindolin-2-yl)piperidine-2,6-dione;
3-(4-((2-(2-(diethylamino)ethoxy)ethyl)thio)-1-oxoisoindolin-2-yl)piperidine-2,6-dione;
3-(4-((2-(2-(dimethylamino)ethoxy)ethyl)thio)-1-oxoisoindolin-2-yl)piperidine-2,6-dione;
3-(4-((2-(2-(methylamino)ethoxy)ethyl)thio)-1-oxoisoindolin-2-yl)piperidine-2,6-dione;
3-(4-((2-(3-morpholinopropoxy)ethyl)thio)-1-oxoisoindolin-2-yl)piperidine-2,6-dione;
3-(1-oxo-4-((2-(3-(piperazin-1-yl)propoxy)ethyl)thio)isoindolin-2-yl)piperidine-2,6-dione;
3-(4-((2-(2-(2-morpholinoethoxy)ethoxy)ethyl)thio)-1-oxoisoindolin-2-yl)piperidine-2,6-dione;
3-(1-oxo-4-((2-(2-(2-(piperazin-1-yl)ethoxy)ethoxy)ethyl)thio)isoindolin-2-yl)piperidine-2,6-dione;
3-(4-((2-(2-(2-(diethylamino)ethoxy)ethoxy)ethyl)thio)-1-oxoisoindolin-2-yl)piperidine-2,6-dione;
3-(4-((2-(2-(2-(dimethylamino)ethoxy)ethoxy)ethyl)thio)-1-oxoisoindolin-2-yl)piperidine-2,6-dione;
3-(4-((2-(2-(2-(methylamino)ethoxy)ethoxy)ethyl)thio)-1-oxoisoindolin-2-yl)piperidine-2,6-dione;
3-(4-((2-(3-(3-morpholinopropoxy)propoxy)ethyl)thio)-1-oxoisoindolin-2-yl)piperidine-2,6-dione;
3-(1-oxo-4-((2-(3-(3-(piperazin-1-yl)propoxy)propoxy)ethyl)thio)isoindolin-2-yl)piperidine-2,6-dione;
3-(4-((5-(2-morpholinoethoxy)pentyl)thio)-1-oxoisoindolin-2-yl)piperidine-2,6-dione;
3-(4-((2-((5-morpholinopentyl)oxy)ethyl)thio)-1-oxoisoindolin-2-yl)piperidine-2,6-dione;
1-(3-chloro-4-methylphenyl)-3-(2-((2-(2,6-dioxopiperidin-3-yl)-1-oxoisoindolin-4-yl)thio)ethyl)urea;
1-(3-chloro-4-methylphenyl)-3-(3-((2-(2,6-dioxopiperidin-3-yl)-1-oxoisoindolin-4-yl)thio)propyl)urea;
1-(3-chloro-4-methylphenyl)-3-(4-((2-(2,6-dioxopiperidin-3-yl)-1-oxoisoindolin-4-yl)thio)butyl)urea;
1-(3-chloro-4-methylphenyl)-3-(5-((2-(2,6-dioxopiperidin-3-yl)-1-oxoisoindolin-4-yl)thio)pentyl)urea;
1-(3-chloro-4-methylphenyl)-3-(6-((2-(2,6-dioxopiperidin-3-yl)-1-oxoisoindolin-4-yl)thio)hexyl)urea;
1-(3-chloro-4-methylphenyl)-3-(7-((2-(2,6-dioxopiperidin-3-yl)-1-oxoisoindolin-4-yl)thio)heptyl)urea;
1-(3-chloro-4-methylphenyl)-3-(8-((2-(2,6-dioxopiperidin-3-yl)-1-oxoisoindolin-4-yl)thio)octyl)urea;
1-(3-chloro-4-methylphenyl)-3-(9-((2-(2,6-dioxopiperidin-3-yl)-1-oxoisoindolin-4-yl)thio)nonyl)urea;
1-(3-chloro-4-methylphenyl)-3-(10-((2-(2,6-dioxopiperidin-3-yl)-1-oxoisoindolin-4-yl)thio)decyl)urea;
1-(3-chloro-4-methylphenyl)-3-(11-((2-(2,6-dioxopiperidin-3-yl)-1-oxoisoindolin-4-yl)thio)undecyl)urea;
3,3'-((octane-1,8-diylbis(sulfanediyl))bis(1-oxoisoindoline-4,2-diyl))bis(piperidine-2,6-dione);
3,3'-((nonane-1,9-diylbis(sulfanediyl))bis(1-oxoisoindoline-4,2-diyl))bis(piperidine-2,6-dione);
3,3'-(((piperazine-1,4-diylbis(octane-8,1-diyl))bis(sulfanediyl))bis(1-oxoisoindoline-4,2-diyl))bis(piperidine-2,6-dione);
3-(5-((5-morpholinopentyl)thio)-1-oxoisoindolin-2-yl)piperidine-2,6-dione;
3-(5-((6-morpholinohexyl)thio)-1-oxoisoindolin-2-yl)piperidine-2,6-dione;
3-(5-((7-morpholinoheptyl)thio)-1-oxoisoindolin-2-yl)piperidine-2,6-dione;
3-(5-((8-morpholinooctyl)thio)-1-oxoisoindolin-2-yl)piperidine-2,6-dione;
3-(1-oxo-5-((8-(piperazin-1-yl)octyl)thio)isoindolin-2-yl)piperidine-2,6-dione;
3-(5-((8-(4-methylpiperazin-1-yl)octyl)thio)-1-oxoisoindolin-2-yl)piperidine-2,6-dione;
3-(5-((8-(4-(4-methylpiperazin-1-yl) piperidin-1-yl)octyl)thio)-1-oxoisoindolin-2-yl)piperidine-2,6-dione;
3-(1-oxo-5-((8-(piperidin-1-yl)octyl)thio)isoindolin-2-yl)piperidine-2,6-dione;
3-(5-((8-(diethylamino)octyl)thio)-1-oxoisoindolin-2-yl)piperidine-2,6-dione;
3-(5-((8-(diisopropylamino)octyl)thio)-1-oxoisoindolin-2-yl)piperidine-2,6-dione;
3-(5-((8-(dimethylamino)octyl)thio)-1-oxoisoindolin-2-yl)piperidine-2,6-dione;
3-(5-((8-(methylamino)octyl)thio)-1-oxoisoindolin-2-yl)piperidine-2,6-dione;
1-(3-chloro-4-methylphenyl)-3-(2-((2-(2,6-dioxopiperidin-3-yl)-1-oxoisoindolin-5-yl)thio)ethyl)urea;
1-(3-chloro-4-methylphenyl)-3-(3-((2-(2,6-dioxopiperidin-3-yl)-1-oxoisoindolin-5-yl)thio)propyl)urea;
1-(3-chloro-4-methylphenyl)-3-(4-((2-(2,6-dioxopiperidin-3-yl)-1-oxoisoindolin-5-yl)thio)butyl)urea;
1-(3-chloro-4-methylphenyl)-3-(5-((2-(2,6-dioxopiperidin-3-yl)-1-oxoisoindolin-5-yl)thio)pentyl)urea;
1-(3-chloro-4-methylphenyl)-3-(6-((2-(2,6-dioxopiperidin-3-yl)-1-oxoisoindolin-5-yl)thio)hexyl)urea;
1-(3-chloro-4-methylphenyl)-3-(7-((2-(2,6-dioxopiperidin-3-yl)-1-oxoisoindolin-5-yl)thio)heptyl)urea;
3-(4-((8-mercaptooctyl)thio)-1-oxoisoindolin-2-yl)piperidine-2,6-dione;
3-(1-oxo-4-((4,4,5,5,5-pentafluoropentyl)thio)isoindolin-2-yl)piperidine-2,6-dione;
3-(4-((6-(cyclohexylamino)hexyl)thio)-1-oxoisoindolin-2-yl)piperidine-2,6-dione;
3-(4-((6-((4,4-dimethylcyclohexyl)amino)hexyl)thio)-1-oxoisoindolin-2-yl)piperidine-2,6-dione;
3-(1-oxo-4-((6-(spiro[5.5]undecan-3-ylamino)hexyl)thio)isoindolin-2-yl)piperidine-2,6-dione;
3-(1-oxo-4-((6-(spiro[3.3]heptan-2-ylamino)hexyl)thio)isoindolin-2-yl)piperidine-2,6-dione;
3-(1-oxo-4-((7-(pyrrolidin-1-yl)heptyl)thio)isoindolin-2-yl)piperidine-2,6-dione;
3-(4-((7-(azepan-1-yl)heptyl)thio)-1-oxoisoindolin-2-yl)piperidine-2,6-dione;
3-(4-((7-(azocan-1-yl)heptyl)thio)-1-oxoisoindolin-2-yl)piperidine-2,6-dione;
3-(4-((7-(4,4-dimethylpiperidin-1-yl)heptyl)thio)-1-oxoisoindolin-2-yl)piperidine-2,6-dione;
3-(4-((7-(3,5-dimethylpiperidin-1-yl)heptyl)thio)-1-oxoisoindolin-2-yl)piperidine-2,6-dione;
3-(4-((7-(3-azaspiro[5.5]undecan-3-yl)heptyl)thio)-1-oxoisoindolin-2-yl)piperidine-2,6-dione;
3-(4-((7-(cyclohexylamino)heptyl)thio)-1-oxoisoindolin-2-yl)piperidine-2,6-dione;

3-(4-((7-((4,4-dimethylcyclohexyl)amino)heptyl)thio)-1-oxoisoindolin-2-yl)piperidine-2,6-dione;

3-(1-oxo-4-((7-(spiro[3.3]heptan-2-ylamino)heptyl)thio)isoindolin-2-yl)piperidine-2,6-dione;

3-(1-oxo-4-((7-oxo-7-(piperidin-1-yl)heptyl)thio)isoindolin-2-yl)piperidine-2,6-dione;

7-((2-(2,6-dioxopiperidin-3-yl)-1-oxoisoindolin-4-yl)thio)-N,N-diisopropylheptanamide;

3-(1-oxo-4-((7-(phenylamino)heptyl)thio)isoindolin-2-yl)piperidine-2,6-dione;

3-(4-((7-(methyl(phenyl)amino)heptyl)thio)-1-oxoisoindolin-2-yl)piperidine-2,6-dione;

3-(4-((7-(diphenylamino)heptyl)thio)-1-oxoisoindolin-2-yl)piperidine-2,6-dione;

3-(4-((6-(benzyl(methyl)amino)hexyl)thio)-1-oxoisoindolin-2-yl)piperidine-2,6-dione;

N-(2-((2-(2,6-dioxopiperidin-3-yl)-1-oxoisoindolin-4-yl)thio)ethyl)-5-(piperidin-1-yl) pentanamide;

3-(1-oxo-4-((8-oxo-8-(piperidin-1-yl)octyl)thio)isoindolin-2-yl)piperidine-2,6-dione;

8-((2-(2,6-dioxopiperidin-3-yl)-1-oxoisoindolin-4-yl)thio)-N,N-diisopropyloctanamide;

3-(4-((7-((3,5-dimethyladamantan-1-yl)amino)heptyl)thio)-1-oxoisoindolin-2-yl)piperidine-2,6-dione;

3-(4-((7-((adamantan-1-yl)oxy)heptyl)thio)-1-oxoisoindolin-2-yl)piperidine-2,6-dione;

3-(4-((7-((adamantan-2-yl)oxy)heptyl)thio)-1-oxoisoindolin-2-yl)piperidine-2,6-dione;

3-(1-oxo-4-((7-(((1S,2R,4S)-1,7,7-trimethylbicyclo[2.2.1]heptan-2-yl)oxy)heptyl)thio)isoindolin-2-yl)piperidine-2,6-dione;

3-(4-((4-(morpholinomethyl)benzyl)thio)-1-oxoisoindolin-2-yl)piperidine-2,6-dione;

3-(1-oxo-4-((4-(piperidin-1-ylmethyl)benzyl)thio)isoindolin-2-yl)piperidine-2,6-dione;

3-(4-((4-((diisopropylamino)methyl)benzyl)thio)-1-oxoisoindolin-2-yl)piperidine-2,6-dione;

3-(4-((4-(((adamantan-1-yl)amino)methyl)benzyl)thio)-1-oxoisoindolin-2-yl)piperidine-2,6-dione; and 1-(3-chloro-4-methylphenyl)-3-(8-((2-(2,6-dioxopiperidin-3-yl)-1-oxoisoindolin-5-yl)thio)octyl)urea.

38. The compound of Formula (Ia) or a salt, a solvate, an isotopically enriched analog, a tautomer, a stereoisomer thereof, or a mixture of stereoisomers thereof of claim 1, wherein the compound is selected from:

2-(2,6-dioxopiperidin-3-yl)-4-((7-(piperidin-1-yl)heptyl)thio)isoindoline-1,3-dione;

4-((5-((adamantan-1-yl)amino)pentyl)thio)-2-(2,6-dioxopiperidin-3-yl)isoindoline-1,3-dione;

4-((6-((adamantan-1-yl)amino)hexyl)thio)-2-(2,6-dioxopiperidin-3-yl)isoindoline-1,3-dione;

4-((7-((adamantan-1-yl)amino)heptyl)thio)-2-(2,6-dioxopiperidin-3-yl)isoindoline-1,3-dione;

4-((7-((adamantan-1-yl)(methyl)amino)heptyl)thio)-2-(2,6-dioxopiperidin-3-yl)isoindoline-1,3-dione;

4-((6-(((adamantan-1-yl)methyl)amino)hexyl)thio)-2-(2,6-dioxopiperidin-3-yl)isoindoline-1,3-dione;

4-((4-(((adamantan-1-yl)amino)methyl)benzyl)thio)-2-(2,6-dioxopiperidin-3-yl)isoindoline-1,3-dione;

2-(2,6-dioxopiperidin-3-yl)-4-((7-(((1R,2S,4R)-1,7,7-trimethylbicyclo[2.2.1]heptan-2-yl)amino)heptyl)thio)isoindoline-1,3-dione;

2-(2,6-dioxopiperidin-3-yl)-4-((4-((((1R,2S,4R)-1,7,7-trimethylbicyclo[2.2.1]heptan-2-yl)amino)methyl)benzyl)thio)isoindoline-1,3-dione;

4-((7-(cyclohexylamino)heptyl)thio)-2-(2,6-dioxopiperidin-3-yl)isoindoline-1,3-dione;

2-(2,6-dioxopiperidin-3-yl)-4-((7-(spiro[3.3]heptan-2-ylamino)heptyl)thio)isoindoline-1,3-dione;

4-((4-(((adamantan-1-yl)amino)methyl) phenethyl)thio)-2-(2,6-dioxopiperidin-3-yl)isoindoline-1,3-dione;

2-(2,6-dioxopiperidin-3-yl)-4-((4-(piperidin-1-ylmethyl)phenethyl)thio)isoindoline-1,3-dione;

4-((4-((cyclohexylamino)methyl) phenethyl)thio)-2-(2,6-dioxopiperidin-3-yl)isoindoline-1,3-dione;

2-(2,6-dioxopiperidin-3-yl)-4-((4-(3-(piperidin-1-yl)propyl)benzyl)thio)isoindoline-1,3-dione;

4-((4-(3-(cyclohexylamino)propyl)benzyl)thio)-2-(2,6-dioxopiperidin-3-yl)isoindoline-1,3-dione;

2-(2,6-dioxopiperidin-3-yl)-4-((4-(3-morpholinopropyl)benzyl)thio)isoindoline-1,3-dione;

2-(2,6-dioxopiperidin-3-yl)-4-((3-(4-(piperidin-1-ylmethyl)phenyl)propyl)thio)isoindoline-1,3-dione;

4-((3-(4-((cyclohexylamino)methyl)phenyl)propyl)thio)-2-(2,6-dioxopiperidin-3-yl)isoindoline-1,3-dione;

4-((3-(4-(((adamantan-1-yl)amino)methyl)phenyl)propyl)thio)-2-(2,6-dioxopiperidin-3-yl)isoindoline-1,3-dione;

4-((8-((adamantan-1-yl)amino)octyl)thio)-2-(2,6-dioxopiperidin-3-yl)isoindoline-1,3-dione;

3-(4-((5-(3-azaspiro[5.5]undecan-3-yl)pentyl)thio)-1-oxoisoindolin-2-yl)piperidine-2,6-dione;

3-(4-((6-(3-azaspiro[5.5]undecan-3-yl)hexyl)thio)-1-oxoisoindolin-2-yl)piperidine-2,6-dione;

3-(4-((7-((cyclohexylmethyl)amino)heptyl)thio)-1-oxoisoindolin-2-yl)piperidine-2,6-dione;

3-(4-((7-(cyclopropylamino)heptyl)thio)-1-oxoisoindolin-2-yl)piperidine-2,6-dione;

3-(4-((7-(cyclopropyl(methyl)amino)heptyl)thio)-1-oxoisoindolin-2-yl)piperidine-2,6-dione;

3-(4-((7-(cyclobutylamino)heptyl)thio)-1-oxoisoindolin-2-yl)piperidine-2,6-dione;

3-(4-((7-(bicyclo[1.1.1]pentan-1-ylamino)heptyl)thio)-1-oxoisoindolin-2-yl)piperidine-2,6-dione;

3-(4-((7-(cyclopentylamino)heptyl)thio)-1-oxoisoindolin-2-yl)piperidine-2,6-dione;

3-(4-((7-((4,4-dimethylcyclohexyl)(methyl)amino)heptyl)thio)-1-oxoisoindolin-2-yl)piperidine-2,6-dione;

3-(4-((6-((cyclohexylmethyl)amino)hexyl)thio)-1-oxoisoindolin-2-yl)piperidine-2,6-dione;

3-(4-((7-((3aR,7aS)-hexahydro-1H-isoindol-2 (3H)-yl)heptyl)thio)-1-oxoisoindolin-2-yl)piperidine-2,6-dione;

3-(4-((7-(tert-butylamino)heptyl)thio)-1-oxoisoindolin-2-yl)piperidine-2,6-dione;

3-(4-((7-(((1R,2R)-2-methoxycyclopropyl)amino)heptyl)thio)-1-oxoisoindolin-2-yl)piperidine-2,6-dione;

3-(4-((7-((1-cyclopropyl-2,2,2-trifluoroethyl)amino)heptyl)thio)-1-oxoisoindolin-2-yl)piperidine-2,6-dione;

1-(7-((2-(2,6-dioxopiperidin-3-yl)-1-oxoisoindolin-4-yl)thio)heptyl) azetidine-3-carbonitrile;

3-(4-((7-(3-hydroxyazetidin-1-yl)heptyl)thio)-1-oxoisoindolin-2-yl)piperidine-2,6-dione;

3-(4-((7-(3-hydroxy-3-methylazetidin-1-yl)heptyl)thio)-1-oxoisoindolin-2-yl)piperidine-2,6-dione;

3-(4-((7-(oxetan-3-ylamino)heptyl)thio)-1-oxoisoindolin-2-yl)piperidine-2,6-dione;

3-(4-((7-((3-fluorocyclobutyl)amino)heptyl)thio)-1-oxoisoindolin-2-yl)piperidine-2,6-dione;

3-(4-((7-((3,3-difluorocyclobutyl)amino)heptyl)thio)-1-oxoisoindolin-2-yl)piperidine-2,6-dione;

3-(4-((7-((2S,3R)-3-hydroxy-2-methylazetidin-1-yl)heptyl)thio)-1-oxoisoindolin-2-yl)piperidine-2,6-dione;

3-(1-oxo-4-((7-(3-(trifluoromethoxy) azetidin-1-yl)heptyl)thio)isoindolin-2-yl)piperidine-2,6-dione;
3-(4-((7-((3,3-difluoro-1-(2-(trifluoromethyl)phenyl)cyclobutyl)amino)heptyl)thio)-1-oxoisoindolin-2-yl)piperidine-2,6-dione;
3-(1-oxo-4-((7-((3-(2-(trifluoromethyl)phenyl) oxetan-3-yl)amino)heptyl)thio)isoindolin-2-yl)piperidine-2,6-dione;
3-(4-((7-((3,3-difluorocyclopentyl)amino)heptyl)thio)-1-oxoisoindolin-2-yl)piperidine-2,6-dione;
3-(4-((7-((3R,4R)-3-fluoro-4-hydroxypyrrolidin-1-yl) heptyl)thio)-1-oxoisoindolin-2-yl)piperidine-2,6-dione;
3-(4-((7-((3S,4S)-3-methyl-4-(trifluoromethyl) pyrrolidin-1-yl)heptyl)thio)-1-oxoisoindolin-2-yl)piperidine-2,6-dione;
3-(4-((7-(7-fluoro-5-azaspiro[2.4]heptan-5-yl)heptyl) thio)-1-oxoisoindolin-2-yl)piperidine-2,6-dione;
3-(4-((7-((3-hydroxycyclohexyl)amino)heptyl)thio)-1-oxoisoindolin-2-yl)piperidine-2,6-dione;
methyl 5-((7-((2-(2,6-dioxopiperidin-3-yl)-1-oxoisoindolin-4-yl)thio)heptyl)amino)-3,3-difluorocyclohexane-1-carboxylate;
3-(4-((7-(3-azabicyclo[3.1.0]hexan-3-yl)heptyl)thio)-1-oxoisoindolin-2-yl)piperidine-2,6-dione;
3-(4-((7-(6-(difluoromethyl)-3-azabicyclo[4.1.0]heptan-3-yl)heptyl)thio)-1-oxoisoindolin-2-yl)piperidine-2,6-dione;
3-(4-((7-(3-fluoro-5,7-dihydro-6H-pyrrolo[3,4-b]pyridin-6-yl)heptyl)thio)-1-oxoisoindolin-2-yl)piperidine-2,6-dione;
3-(1-oxo-4-((7-(3-(trifluoromethyl)-5,7-dihydro-6H-pyrrolo[3,4-b]pyridin-6-yl)heptyl)thio)isoindolin-2-yl)piperidine-2,6-dione;
3-(4-((7-(1,1-difluoro-5-azaspiro[2.4]heptan-5-yl)heptyl) thio)-1-oxoisoindolin-2-yl)piperidine-2,6-dione;
3-(4-((7-(1,1-difluoro-6-azaspiro[2.5]octan-6-yl)heptyl) thio)-1-oxoisoindolin-2-yl)piperidine-2,6-dione;
3-(4-((7-(2-oxa-7-azaspiro[3.5]nonan-7-yl)heptyl)thio)-1-oxoisoindolin-2-yl)piperidine-2,6-dione;
3-((7-((2-(2,6-dioxopiperidin-3-yl)-1-oxoisoindolin-4-yl) thio)heptyl)amino)bicyclo[1.1.1]pentane-1-carbonitrile;
3-(4-((7-(bicyclo[2.2.2]octan-1-ylamino)heptyl)thio)-1-oxoisoindolin-2-yl)piperidine-2,6-dione;
3-(4-((7-((4-hydroxybicyclo[2.2.2]octan-1-yl)amino)heptyl)thio)-1-oxoisoindolin-2-yl)piperidine-2,6-dione;
3-(4-((7-(((1S,2R,5S)-2-isopropyl-5-methylcyclohexyl) oxy)heptyl)thio)-1-oxoisoindolin-2-yl)piperidine-2,6-dione;
3-(4-((7-(((1S,2R,5S)-2-isopropyl-5-methylcyclohexyl) amino)heptyl)thio)-1-oxoisoindolin-2-yl)piperidine-2,6-dione;
3-(4-((7-(8,8-difluoro-2-azabicyclo[3.2.1]octan-2-yl)heptyl)thio)-1-oxoisoindolin-2-yl)piperidine-2,6-dione;
3-(4-((7-(1,4-diazabicyclo[3.2.1]octan-4-yl)heptyl)thio)-1-oxoisoindolin-2-yl)piperidine-2,6-dione;
3-(4-((7-(((5-methyloxazol-2-yl)methyl)amino)heptyl) thio)-1-oxoisoindolin-2-yl)piperidine-2,6-dione;
(1R)-1-((7-((2-(2,6-dioxopiperidin-3-yl)-1-oxoisoindolin-4-yl)thio)heptyl)amino)-2,3-dihydro-1H-indene-4-carbonitrile;
3-(4-((7-((2,4-dimethylpentan-3-yl)amino)heptyl)thio)-1-oxoisoindolin-2-yl)piperidine-2,6-dione;
3-(4-((7-((dicyclopropylmethyl)amino)heptyl)thio)-1-oxoisoindolin-2-yl)piperidine-2,6-dione;
3-(4-((7-(((R)-1-cyclopropylethyl)amino)heptyl)thio)-1-oxoisoindolin-2-yl)piperidine-2,6-dione;
3-(4-((7-(6-azaspiro[2.5]octan-6-yl)heptyl)thio)-1-oxoisoindolin-2-yl)piperidine-2,6-dione;
3-(4-((7-(isoindolin-2-yl)heptyl)thio)-1-oxoisoindolin-2-yl)piperidine-2,6-dione;
3-(1-oxo-4-((7-(((S)-quinuclidin-3-yl)amino)heptyl)thio) isoindolin-2-yl)piperidine-2,6-dione;
3-(1-oxo-4-((7-(((R)-quinuclidin-3-yl)amino)heptyl)thio) isoindolin-2-yl)piperidine-2,6-dione;
3-(1-oxo-4-((7-thiomorpholinoheptyl)thio)isoindolin-2-yl)piperidine-2,6-dione;
3-(4-((7-(4-(methylsulfonyl)piperazin-1-yl)heptyl)thio)-1-oxoisoindolin-2-yl)piperidine-2,6-dione;
3-(4-((7-(4-(ethylsulfonyl)piperazin-1-yl)heptyl)thio)-1-oxoisoindolin-2-yl)piperidine-2,6-dione;
3-(1-oxo-4-((7-(2-oxopiperidin-1-yl)heptyl)thio)isoindolin-2-yl)piperidine-2,6-dione;
3-(4-((2-(adamantan-1-yl)ethyl)thio)-1-oxoisoindolin-2-yl)piperidine-2,6-dione;
3-(4-((2-(adamantan-1-ylamino)ethyl)thio)-1-oxoisoindolin-2-yl)piperidine-2,6-dione;
3-(4-((3-(adamantan-1-ylamino)propyl)thio)-1-oxoisoindolin-2-yl)piperidine-2,6-dione;
(3S)-3-(4-((7-((adamantan-1-yl)amino)heptyl)thio)-1-oxoisoindolin-2-yl)piperidine-2,6-dione;
(3R)-3-(4-((7-((adamantan-1-yl)amino)heptyl)thio)-1-oxoisoindolin-2-yl)piperidine-2,6-dione;
3-(4-((7-((adamantan-1-yl)(methyl)amino)heptyl)thio)-1-oxoisoindolin-2-yl)piperidine-2,6-dione;
3-(4-((4-(2-(adamantan-1-yl(methyl)amino)ethoxy)butyl) thio)-1-oxoisoindolin-2-yl)piperidine-2,6-dione;
3-(4-((7-(3-hydroxyadamantan-1-yl)amino)heptyl)thio)-1-oxoisoindolin-2-yl)piperidine-2,6-dione;
3-(4-((6-((adamantan-1-ylmethyl)amino)hexyl)thio)-1-oxoisoindolin-2-yl)piperidine-2,6-dione;
3-(4-((6-((adamantan-1-ylmethyl)(methyl)amino)hexyl) thio)-1-oxoisoindolin-2-yl)piperidine-2,6-dione;
3-(4-((6-((1-(adamantan-1-yl)ethyl)amino)hexyl)thio)-1-oxoisoindolin-2-yl)piperidine-2,6-dione;
3-(4-((5-((2-(adamantan-1-yl)ethyl)amino)pentyl)thio)-1-oxoisoindolin-2-yl)piperidine-2,6-dione;
3-(4-((7-(((adamantan-1-yl)methyl)amino)heptyl)thio)-1-oxoisoindolin-2-yl)piperidine-2,6-dione;
N-(adamantan-1-yl)-7-((2-(2,6-dioxopiperidin-3-yl)-1-oxoisoindolin-4-yl)thio)heptanamide;
N-(3,5-dimethyladamantan-1-yl)-7-((2-(2,6-dioxopiperidin-3-yl)-1-oxoisoindolin-4-yl)thio)heptanamide;
N-(adamantan-2-yl)-7-((2-(2,6-dioxopiperidin-3-yl)-1-oxoisoindolin-4-yl)thio)heptanamide;
3-(4-((7-((3-chloroadamantan-1-yl)amino)heptyl)thio)-1-oxoisoindolin-2-yl)piperidine-2,6-dione;
3-(4-((7-((4-chloroadamantan-1-yl)amino)heptyl)thio)-1-oxoisoindolin-2-yl)piperidine-2,6-dione;
3-(4-((7-((2-chloroadamantan-1-yl)amino)heptyl)thio)-1-oxoisoindolin-2-yl)piperidine-2,6-dione;
3-(4-((7-(adamantan-1-yloxy)heptyl)thio)-1-oxoisoindolin-2-yl)piperidine-2,6-dione;
3-(4-((7-(adamantan-2-yloxy)heptyl)thio)-1-oxoisoindolin-2-yl)piperidine-2,6-dione;
3-(4-((4-((adamantan-2-ylamino)methyl)benzyl)thio)-1-oxoisoindolin-2-yl)piperidine-2,6-dione;
3-(4-((4-(((1-(adamantan-1-yl)ethyl)amino)methyl)benzyl)thio)-1-oxoisoindolin-2-yl)piperidine-2,6-dione;
3-(4-((4-(((adamantan-1-ylmethyl)amino)methyl)benzyl) thio)-1-oxoisoindolin-2-yl)piperidine-2,6-dione;

3-(4-((4-(2-(adamantan-1-ylamino)ethyl)benzyl)thio)-1-oxoisoindolin-2-yl)piperidine-2,6-dione;

N-(4-(adamantan-1-yl(methyl)amino)butyl)-2-((2-(2,6-dioxopiperidin-3-yl)-1-oxoisoindolin-4-yl)thio)acetamide;

3-(1-oxo-4-((5-(((1R,2S,4R)-1,7,7-trimethylbicyclo[2.2.1]heptan-2-yl)amino)pentyl)thio)isoindolin-2-yl)piperidine-2,6-dione;

3-(1-oxo-4-((6-(((1R,2S,4R)-1,7,7-trimethylbicyclo[2.2.1]heptan-2-yl)amino)hexyl)thio)isoindolin-2-yl)piperidine-2,6-dione;

3-(1-oxo-4-((7-(((1R,2S,4R)-1,7,7-trimethylbicyclo[2.2.1]heptan-2-yl)amino)heptyl)thio)isoindolin-2-yl)piperidine-2,6-dione;

3-(4-((7-(methyl((1R,2S,4R)-1,7,7-trimethylbicyclo[2.2.1]heptan-2-yl)amino)heptyl)thio)-1-oxoisoindolin-2-yl)piperidine-2,6-dione;

3-(1-oxo-4-((4-((((1R,2S,4R)-1,7,7-trimethylbicyclo[2.2.1]heptan-2-yl)amino)methyl)benzyl)thio)isoindolin-2-yl)piperidine-2,6-dione;

(S)-3-(1-oxo-4-((4-(piperidin-1-ylmethyl)benzyl)thio)isoindolin-2-yl)piperidine-2,6-dione;

(R)-3-(1-oxo-4-((4-(piperidin-1-ylmethyl)benzyl)thio)isoindolin-2-yl)piperidine-2,6-dione;

3-(1-oxo-4-((3-(piperidin-1-ylmethyl)benzyl)thio)isoindolin-2-yl)piperidine-2,6-dione;

3-(4-((3-((cyclohexylamino)methyl)benzyl)thio)-1-oxoisoindolin-2-yl)piperidine-2,6-dione;

3-(4-((3-(((adamantan-1-yl)amino)methyl)benzyl)thio)-1-oxoisoindolin-2-yl)piperidine-2,6-dione;

3-(4-((3-(morpholinomethyl)benzyl)thio)-1-oxoisoindolin-2-yl)piperidine-2,6-dione;

3-(4-((2,5-dibromo-4-(piperidin-1-ylmethyl)benzyl)thio)-1-oxoisoindolin-2-yl)piperidine-2,6-dione;

3-(4-((2,5-dibromo-4-((cyclohexylamino)methyl)benzyl)thio)-1-oxoisoindolin-2-yl)piperidine-2,6-dione;

3-(4-((4-(((adamantan-1-yl)amino)methyl)-2,5-dibromobenzyl)thio)-1-oxoisoindolin-2-yl)piperidine-2,6-dione;

3-(4-((4-(2-(azocan-1-yl)ethyl)benzyl)thio)-1-oxoisoindolin-2-yl)piperidine-2,6-dione;

3-(4-((4-(2-(4,4-difluoropiperidin-1-yl)ethyl)benzyl)thio)-1-oxoisoindolin-2-yl)piperidine-2,6-dione;

3-(4-((4-(2-(6-azaspiro[2.5]octan-6-yl)ethyl)benzyl)thio)-1-oxoisoindolin-2-yl)piperidine-2,6-dione;

3-(4-((4-(2-(3,5-dimethylpiperidin-1-yl)ethyl)benzyl)thio)-1-oxoisoindolin-2-yl)piperidine-2,6-dione;

3-(4-((4-((4,4-difluoropiperidin-1-yl)methyl)benzyl)thio)-1-oxoisoindolin-2-yl)piperidine-2,6-dione;

3-(4-((4-((4-methylpiperazin-1-yl)methyl)benzyl)thio)-1-oxoisoindolin-2-yl)piperidine-2,6-dione;

3-(4-((4-(((3aR,7aS)-octahydro-2H-isoindol-2-yl)methyl)benzyl)thio)-1-oxoisoindolin-2-yl)piperidine-2,6-dione;

3-(4-((4-((((R)-1-cyclopropylethyl)amino)methyl)benzyl)thio)-1-oxoisoindolin-2-yl)piperidine-2,6-dione;

3-(4-((4-(bromomethyl)-2-fluorobenzyl)thio)-1-oxoisoindolin-2-yl)piperidine-2,6-dione;

3-(4-((3-fluoro-4-(piperidin-1-ylmethyl)benzyl)thio)-1-oxoisoindolin-2-yl)piperidine-2,6-dione;

3-(4-((3,5-difluoro-4-(piperidin-1-ylmethyl)benzyl)thio)-1-oxoisoindolin-2-yl)piperidine-2,6-dione;

3-(4-((2-fluoro-4-(piperidin-1-ylmethyl)benzyl)thio)-1-oxoisoindolin-2-yl)piperidine-2,6-dione;

3-(4-((2,6-difluoro-4-(piperidin-1-ylmethyl)benzyl)thio)-1-oxoisoindolin-2-yl)piperidine-2,6-dione;

3-(4-((2,3-difluoro-4-(piperidin-1-ylmethyl)benzyl)thio)-1-oxoisoindolin-2-yl)piperidine-2,6-dione;

3-(1-oxo-4-((2,3,5-trifluoro-4-(piperidin-1-ylmethyl)benzyl)thio)isoindolin-2-yl)piperidine-2,6-dione;

3-(1-oxo-4-((2,3,5,6-tetrafluoro-4-(piperidin-1-ylmethyl)benzyl)thio)isoindolin-2-yl)piperidine-2,6-dione;

3-(4-((3-chloro-2-fluoro-4-(piperidin-1-ylmethyl)benzyl)thio)-1-oxoisoindolin-2-yl)piperidine-2,6-dione;

3-(4-((2-chloro-6-fluoro-4-(piperidin-1-ylmethyl)benzyl)thio)-1-oxoisoindolin-2-yl)piperidine-2,6-dione;

3-(4-((3-chloro-5-fluoro-4-(piperidin-1-ylmethyl)benzyl)thio)-1-oxoisoindolin-2-yl)piperidine-2,6-dione;

3-(4-((4-((cyclohexylamino)methyl)-2-fluorobenzyl)thio)-1-oxoisoindolin-2-yl)piperidine-2,6-dione;

3-(4-((4-(((adamantan-1-yl)amino)methyl)-2-fluorobenzyl)thio)-1-oxoisoindolin-2-yl)piperidine-2,6-dione;

3-(4-((2-fluoro-4-(morpholinomethyl)benzyl)thio)-1-oxoisoindolin-2-yl)piperidine-2,6-dione;

3-(4-((4-(((dicyclopropylmethyl)amino)methyl)benzyl)thio)-1-oxoisoindolin-2-yl)piperidine-2,6-dione;

3-(4-((4-((cyclopropylamino)methyl)benzyl)thio)-1-oxoisoindolin-2-yl)piperidine-2,6-dione;

3-(4-((4-((bicyclo[1.1.1]pentan-1-ylamino)methyl)benzyl)thio)-1-oxoisoindolin-2-yl)piperidine-2,6-dione;

3-(1-oxo-4-((4-((spiro[3.3]heptan-2-ylamino)methyl)benzyl)thio)isoindolin-2-yl)piperidine-2,6-dione;

3-(4-((4-((cyclohexylamino)methyl)benzyl)thio)-1-oxoisoindolin-2-yl)piperidine-2,6-dione;

3-(4-((4-(((cyclohexylmethyl)amino)methyl)benzyl)thio)-1-oxoisoindolin-2-yl)piperidine-2,6-dione;

3-(1-oxo-4-((4-((((tetrahydro-2H-pyran-2-yl)methyl)amino)methyl)benzyl)thio)isoindolin-2-yl)piperidine-2,6-dione;

3-(1-oxo-4-((4-(thiomorpholinomethyl)benzyl)thio)isoindolin-2-yl)piperidine-2,6-dione;

3-(4-((4-((diethylamino)methyl)benzyl)thio)-1-oxoisoindolin-2-yl)piperidine-2,6-dione;

3-(4-((4-((dicyclohexylamino)methyl)benzyl)thio)-1-oxoisoindolin-2-yl)piperidine-2,6-dione;

3-(4-((4-(((3-hydroxyadamantan-1-yl)amino)methyl)benzyl)thio)-1-oxoisoindolin-2-yl)piperidine-2,6-dione;

3-(4-((4-(2-((4,4-dimethylcyclohexyl)amino)ethyl)benzyl)thio)-1-oxoisoindolin-2-yl)piperidine-2,6-dione;

3-(4-((4-(((4,4-dimethylcyclohexyl)amino)methyl)benzyl)thio)-1-oxoisoindolin-2-yl)piperidine-2,6-dione;

3-(4-((4-((4,4-dimethylpiperidin-1-yl)methyl)benzyl)thio)-1-oxoisoindolin-2-yl)piperidine-2,6-dione;

3-(4-((4-((6-azaspiro[2.5]octan-6-yl)methyl)benzyl)thio)-1-oxoisoindolin-2-yl)piperidine-2,6-dione;

3-(4-((4-((3,5-dimethylpiperidin-1-yl)methyl)benzyl)thio)-1-oxoisoindolin-2-yl)piperidine-2,6-dione;

3-(4-((4-((3-azaspiro[5.5]undecan-3-yl)methyl)benzyl)thio)-1-oxoisoindolin-2-yl)piperidine-2,6-dione;

3-(4-((4-((tert-butylamino)methyl)benzyl)thio)-1-oxoisoindolin-2-yl)piperidine-2,6-dione;

3-(4-((4-(azocan-1-ylmethyl)benzyl)thio)-1-oxoisoindolin-2-yl)piperidine-2,6-dione;

3-(1-oxo-4-((4-(2-(piperidin-1-yl)ethyl)benzyl)thio)isoindolin-2-yl)piperidine-2,6-dione;

3-(4-((4-(2-(cyclohexylamino)ethyl)benzyl)thio)-1-oxoisoindolin-2-yl)piperidine-2,6-dione;

3-(4-((4-(2-morpholinoethyl)benzyl)thio)-1-oxoisoindolin-2-yl)piperidine-2,6-dione;

3-(4-((4-(2-(diethylamino)ethyl)benzyl)thio)-1-oxoisoindolin-2-yl)piperidine-2,6-dione;

3-(4-((4-(2-(4-methylpiperazin-1-yl)ethyl)benzyl)thio)-1-oxoisoindolin-2-yl)piperidine-2,6-dione;

3-(1-oxo-4-((4-(2-thiomorpholinoethyl)benzyl)thio) isoindolin-2-yl)piperidine-2,6-dione;
3-(4-((4-(((adamantan-1-yl)amino)methyl) phenethyl) thio)-1-oxoisoindolin-2-yl)piperidine-2,6-dione;
3-(1-oxo-4-((4-(piperidin-1-ylmethyl) phenethyl)thio) isoindolin-2-yl)piperidine-2,6-dione;
3-(4-((4-((cyclohexylamino)methyl) phenethyl)thio)-1-oxoisoindolin-2-yl)piperidine-2,6-dione;
3-(1-oxo-4-((4-(3-(piperidin-1-yl)propyl)benzyl)thio) isoindolin-2-yl)piperidine-2,6-dione;
3-(4-((4-(3-(cyclohexylamino)propyl)benzyl)thio)-1-oxoisoindolin-2-yl)piperidine-2,6-dione;
3-(4-((4-(3-((adamantan-1-yl)amino)propyl)benzyl)thio)-1-oxoisoindolin-2-yl)piperidine-2,6-dione;
3-(4-((4-(3-morpholinopropyl)benzyl)thio)-1-oxoisoindolin-2-yl)piperidine-2,6-dione;
3-(1-oxo-4-((4-(2-(piperidin-1-yl)ethyl) phenethyl)thio) isoindolin-2-yl)piperidine-2,6-dione;
3-(4-((4-(2-((adamantan-1-yl)amino)ethyl) phenethyl) thio)-1-oxoisoindolin-2-yl)piperidine-2,6-dione;
3-(1-oxo-4-((3-(4-(piperidin-1-ylmethyl)phenyl)propyl) thio)isoindolin-2-yl)piperidine-2,6-dione;
3-(4-((3-(4-((cyclohexylamino)methyl)phenyl)propyl) thio)-1-oxoisoindolin-2-yl)piperidine-2,6-dione;
3-(4-((3-(4-(((adamantan-1-yl)amino)methyl)phenyl)propyl)thio)-1-oxoisoindolin-2-yl)piperidine-2,6-dione;
3-(4-((3-(4-(morpholinomethyl)phenyl)propyl)thio)-1-oxoisoindolin-2-yl)piperidine-2,6-dione;
3-(4-((4-(2-(diisopropylamino)ethyl)benzyl)thio)-1-oxoisoindolin-2-yl)piperidine-2,6-dione;
3-(4-((4-(2-((2,4-dimethylpentan-3-yl)amino)ethyl)benzyl)thio)-1-oxoisoindolin-2-yl)piperidine-2,6-dione;
3-(4-((4-(2-(dimethylamino)ethyl)benzyl)thio)-1-oxoisoindolin-2-yl)piperidine-2,6-dione;
3-(4-((4-(2-(methylamino)ethyl)benzyl)thio)-1-oxoisoindolin-2-yl)piperidine-2,6-dione;
3-(4-((4-(2-(tert-butylamino)ethyl)benzyl)thio)-1-oxoisoindolin-2-yl)piperidine-2,6-dione;
N-(4-(((2-(2,6-dioxopiperidin-3-yl)-1-oxoisoindolin-4-yl)thio)methyl) phenethyl)acetamide;
3-(1-oxo-4-((4-(2-(pyrrolidin-1-yl)ethyl)benzyl)thio) isoindolin-2-yl)piperidine-2,6-dione;
3-(4-((4-(2-(azepan-1-yl)ethyl)benzyl)thio)-1-oxoisoindolin-2-yl)piperidine-2,6-dione;
3-(4-((4-(2-(4,4-dimethylpiperidin-1-yl)ethyl)benzyl) thio)-1-oxoisoindolin-2-yl)piperidine-2,6-dione;
3-(4-((4-(2-(3-azaspiro[5.5]undecan-3-yl)ethyl)benzyl) thio)-1-oxoisoindolin-2-yl)piperidine-2,6-dione;
3-(4-((4-(2-((3aR,7aS)-octahydro-2H-isoindol-2-yl) ethyl)benzyl)thio)-1-oxoisoindolin-2-yl)piperidine-2,6-dione;
3-(4-((4-(2-(4-(methylsulfonyl)piperazin-1-yl)ethyl)benzyl)thio)-1-oxoisoindolin-2-yl)piperidine-2,6-dione;
3-(4-((4-(2-([1,4'-bipiperidin]-1'-yl)ethyl)benzyl)thio)-1-oxoisoindolin-2-yl)piperidine-2,6-dione;
3-(4-((4-(2-(cyclopropylamino)ethyl)benzyl)thio)-1-oxoisoindolin-2-yl)piperidine-2,6-dione;
3-(4-((4-(2-(cyclobutylamino)ethyl)benzyl)thio)-1-oxoisoindolin-2-yl)piperidine-2,6-dione;
3-(4-((4-(2-(cyclopentylamino)ethyl)benzyl)thio)-1-oxoisoindolin-2-yl)piperidine-2,6-dione;
3-(4-((4-(2-((dicyclopropylmethyl)amino)ethyl)benzyl) thio)-1-oxoisoindolin-2-yl)piperidine-2,6-dione;
3-(4-((4-(2-(((R)-1-cyclopropylethyl)amino)ethyl)benzyl)thio)-1-oxoisoindolin-2-yl)piperidine-2,6-dione;
3-(4-((4-(2-(bicyclo[1.1.1]pentan-1-ylamino)ethyl)benzyl)thio)-1-oxoisoindolin-2-yl)piperidine-2,6-dione;
3-(1-oxo-4-((4-(2-(spiro[3.3]heptan-2-ylamino)ethyl) benzyl)thio)isoindolin-2-yl)piperidine-2,6-dione;
3-(4-((4-(2-((cyclohexylmethyl)amino)ethyl)benzyl) thio)-1-oxoisoindolin-2-yl)piperidine-2,6-dione;
3-(4-((4-(2-(dicyclohexylamino)ethyl)benzyl)thio)-1-oxoisoindolin-2-yl)piperidine-2,6-dione;
3-(4-((4-(2-((hexahydro-2,5-methanopentalen-3a (1H)-yl)amino)ethyl)benzyl)thio)-1-oxoisoindolin-2-yl)piperidine-2,6-dione;
3-(4-((4-(2-((adamantan-2-yl)amino)ethyl)benzyl)thio)-1-oxoisoindolin-2-yl)piperidine-2,6-dione;
3-(4-((4-(2-((3,5-dimethyladamantan-1-yl)amino)ethyl) benzyl)thio)-1-oxoisoindolin-2-yl)piperidine-2,6-dione;
3-(4-((4-(2-((3-hydroxyadamantan-1-yl)amino)ethyl) benzyl)thio)-1-oxoisoindolin-2-yl)piperidine-2,6-dione;
3-(4-((4-(2-(((adamantan-1-yl)methyl)amino)ethyl)benzyl)thio)-1-oxoisoindolin-2-yl)piperidine-2,6-dione;
3-(4-((4-(2-((1-(adamantan-1-yl)ethyl)amino)ethyl)benzyl)thio)-1-oxoisoindolin-2-yl)piperidine-2,6-dione;
3-(4-((4-(2-(((1R,2S,4S)-bicyclo[2.2.1]heptan-2-yl) amino)ethyl)benzyl)thio)-1-oxoisoindolin-2-yl)piperidine-2,6-dione;
3-(1-oxo-4-((4-(2-(((1R,2S,4R)-1,7,7-trimethylbicyclo [2.2.1]heptan-2-yl)amino)ethyl)benzyl)thio)isoindolin-2-yl)piperidine-2,6-dione;
3-(4-((3-(azocan-1-ylmethyl)benzyl)thio)-1-oxoisoindolin-2-yl)piperidine-2,6-dione;
3-(4-((3-((dicyclohexylamino)methyl)benzyl)thio)-1-oxoisoindolin-2-yl)piperidine-2,6-dione;
3-(4-((3-(((2,4-dimethylpentan-3-yl)amino)methyl)benzyl)thio)-1-oxoisoindolin-2-yl)piperidine-2,6-dione;
3-(4-((3-(((4,4-dimethylcyclohexyl)amino)methyl)benzyl)thio)-1-oxoisoindolin-2-yl)piperidine-2,6-dione;
3-(1-oxo-4-((3-((spiro[3.3]heptan-2-ylamino)methyl) benzyl)thio)isoindolin-2-yl)piperidine-2,6-dione;
3-(4-((3-(((3,5-dimethyladamantan-1-yl)amino)methyl) benzyl)thio)-1-oxoisoindolin-2-yl)piperidine-2,6-dione;
3-(4-((3-((((adamantan-1-yl)methyl)amino)methyl)benzyl)thio)-1-oxoisoindolin-2-yl)piperidine-2,6-dione;
3-(1-oxo-4-((3-((((1R,2S,4R)-1,7,7-trimethylbicyclo [2.2.1]heptan-2-yl)amino)methyl)benzyl)thio)isoindolin-2-yl)piperidine-2,6-dione;
3-(4-((4-((diisopropylamino)methyl)-2-fluorobenzyl) thio)-1-oxoisoindolin-2-yl)piperidine-2,6-dione;
3-(4-((4-((diisopropylamino)methyl)-3-fluorobenzyl) thio)-1-oxoisoindolin-2-yl)piperidine-2,6-dione;
3-(4-((4-(azocan-1-ylmethyl)-2-fluorobenzyl)thio)-1-oxoisoindolin-2-yl)piperidine-2,6-dione;
3-(4-((4-(azocan-1-ylmethyl)-3-fluorobenzyl)thio)-1-oxoisoindolin-2-yl)piperidine-2,6-dione;
3-(4-((4-(((4,4-dimethylcyclohexyl)amino)methyl)-2-fluorobenzyl)thio)-1-oxoisoindolin-2-yl)piperidine-2,6-dione;
3-(4-((4-(((4,4-dimethylcyclohexyl)amino)methyl)-3-fluorobenzyl)thio)-1-oxoisoindolin-2-yl)piperidine-2,6-dione;
3-(4-((2-fluoro-4-((spiro[3.3]heptan-2-ylamino)methyl) benzyl)thio)-1-oxoisoindolin-2-yl)piperidine-2,6-dione;
3-(4-((3-fluoro-4-((spiro[3.3]heptan-2-ylamino)methyl) benzyl)thio)-1-oxoisoindolin-2-yl)piperidine-2,6-dione;

3-(4-((4-(((3,5-dimethyladamantan-1-yl)amino)methyl)-2-fluorobenzyl)thio)-1-oxoisoindolin-2-yl)piperidine-2,6-dione;

3-(4-((4-(((3,5-dimethyladamantan-1-yl)amino)methyl)-3-fluorobenzyl)thio)-1-oxoisoindolin-2-yl)piperidine-2,6-dione;

3-(4-((4-((((adamantan-1-yl)methyl)amino)methyl)-2-fluorobenzyl)thio)-1-oxoisoindolin-2-yl)piperidine-2,6-dione;

3-(4-((4-((((adamantan-1-yl)methyl)amino)methyl)-3-fluorobenzyl)thio)-1-oxoisoindolin-2-yl)piperidine-2,6-dione;

3-(4-((2-fluoro-4-((((1R,2S,4R)-1,7,7-trimethylbicyclo[2.2.1]heptan-2-yl)amino)methyl)benzyl)thio)-1-oxoisoindolin-2-yl)piperidine-2,6-dione;

3-(4-((3-fluoro-4-((((1R,2S,4R)-1,7,7-trimethylbicyclo[2.2.1]heptan-2-yl)amino)methyl)benzyl)thio)-1-oxoisoindolin-2-yl)piperidine-2,6-dione;

3-(4-((4-(((adamantan-1-yl)amino)methyl)-2-chlorobenzyl)thio)-1-oxoisoindolin-2-yl)piperidine-2,6-dione;

3-(4-((4-(((adamantan-1-yl)amino)methyl)-3-chlorobenzyl)thio)-1-oxoisoindolin-2-yl)piperidine-2,6-dione;

3-(4-((4-(((adamantan-1-yl)amino)methyl)-2-methylbenzyl)thio)-1-oxoisoindolin-2-yl)piperidine-2,6-dione;

3-(4-((4-(((adamantan-1-yl)amino)methyl)-3-methylbenzyl)thio)-1-oxoisoindolin-2-yl)piperidine-2,6-dione;

3-(1-oxo-5-((7-(((1R,2S,4R)-1,7,7-trimethylbicyclo[2.2.1]heptan-2-yl)amino)heptyl)thio)isoindolin-2-yl)piperidine-2,6-dione;

3-(1-oxo-5-((7-(((1R,2S,4R)-1,7,7-trimethylbicyclo[2.2.1]heptan-2-yl)oxy)heptyl)thio)isoindolin-2-yl)piperidine-2,6-dione;

3-(1-oxo-5-((4-((((1R,2S,4R)-1,7,7-trimethylbicyclo[2.2.1]heptan-2-yl)amino)methyl)benzyl)thio)isoindolin-2-yl)piperidine-2,6-dione;

3-(5-((7-((adamantan-1-yl)amino)heptyl)thio)-1-oxoisoindolin-2-yl)piperidine-2,6-dione;

3-(5-((7-((adamantan-1-yl)(methyl)amino)heptyl)thio)-1-oxoisoindolin-2-yl)piperidine-2,6-dione;

3-(5-((7-((3-hydroxyadamantan-1-yl)amino)heptyl)thio)-1-oxoisoindolin-2-yl)piperidine-2,6-dione;

3-(5-((7-((adamantan-2-yl)amino)heptyl)thio)-1-oxoisoindolin-2-yl)piperidine-2,6-dione;

3-(5-((7-((adamantan-2-yl)(methyl)amino)heptyl)thio)-1-oxoisoindolin-2-yl)piperidine-2,6-dione;

3-(5-((7-((1-(adamantan-1-yl)ethyl)amino)heptyl)thio)-1-oxoisoindolin-2-yl)piperidine-2,6-dione;

N-(4-((adamantan-1-yl)(methyl)amino)butyl)-2-((2-(2,6-dioxopiperidin-3-yl)-1-oxoisoindolin-5-yl)thio)acetamide;

3-(5-((4-(((adamantan-1-yl)amino)methyl)benzyl)thio)-1-oxoisoindolin-2-yl)piperidine-2,6-dione;

3-(5-((4-(((adamantan-1-yl)(methyl)amino)methyl)benzyl)thio)-1-oxoisoindolin-2-yl)piperidine-2,6-dione;

1-(((adamantan-1-yl)amino)methyl)-3-(2-((2-(2,6-dioxopiperidin-3-yl)-1-oxoisoindolin-5-yl)thio)ethyl)urea;

3-(5-((7-(cyclopropylamino)heptyl)thio)-1-oxoisoindolin-2-yl)piperidine-2,6-dione;

3-(5-((7-(cyclobutylamino)heptyl)thio)-1-oxoisoindolin-2-yl)piperidine-2,6-dione;

3-(1-oxo-5-((7-(spiro[3.3]heptan-2-ylamino)heptyl)thio)isoindolin-2-yl)piperidine-2,6-dione;

3-(5-((7-(cyclopentylamino)heptyl)thio)-1-oxoisoindolin-2-yl)piperidine-2,6-dione;

3-(5-((7-(cyclohexylamino)heptyl)thio)-1-oxoisoindolin-2-yl)piperidine-2,6-dione;

3-(5-((7-(3-azaspiro[5.5]undecan-3-yl)heptyl)thio)-1-oxoisoindolin-2-yl)piperidine-2,6-dione;

3-(5-((7-((4,4-dimethylcyclohexyl)amino)heptyl)thio)-1-oxoisoindolin-2-yl)piperidine-2,6-dione;

3-(5-((7-((3aR,7aS)-octahydro-2H-isoindol-2-yl)heptyl)thio)-1-oxoisoindolin-2-yl)piperidine-2,6-dione;

5-((7-((adamantan-1-yl)amino)heptyl)thio)-2-(2,6-dioxopiperidin-3-yl)isoindoline-1,3-dione;

3-(5-((7-((adamantan-1-yl)amino)heptyl)thio)-1-oxoisoindolin-2-yl)piperidine-2,6-dione;

3-(1-oxo-4-(((5-(piperidin-1-ylmethyl) furan-2-yl)methyl)thio)isoindolin-2-yl)piperidine-2,6-dione;

3-(4-(((5-(morpholinomethyl) furan-2-yl)methyl)thio)-1-oxoisoindolin-2-yl)piperidine-2,6-dione;

3-(4-(((5-((((S)-1-cyclopropylethyl)amino)methyl) furan-2-yl)methyl)thio)-1-oxoisoindolin-2-yl)piperidine-2,6-dione;

3-(4-(((5-(azepan-1-ylmethyl) furan-2-yl)methyl)thio)-1-oxoisoindolin-2-yl)piperidine-2,6-dione;

3-(4-(((5-((cyclopentylamino)methyl) furan-2-yl)methyl)thio)-1-oxoisoindolin-2-yl)piperidine-2,6-dione;

3-(1-oxo-4-(((5-((((tetrahydro-2H-pyran-2-yl)methyl)amino)methyl) furan-2-yl)methyl)thio)isoindolin-2-yl)piperidine-2,6-dione;

3-(4-(((5-(((dicyclopropylmethyl)amino)methyl) furan-2-yl)methyl)thio)-1-oxoisoindolin-2-yl)piperidine-2,6-dione;

3-(4-(((2-(morpholinomethyl)thiazol-4-yl)methyl)thio)-1-oxoisoindolin-2-yl)piperidine-2,6-dione;

3-(1-oxo-4-(((2-(piperidin-1-ylmethyl)thiazol-4-yl)methyl)thio)isoindolin-2-yl)piperidine-2,6-dione;

3-(4-(((2-(azepan-1-ylmethyl)thiazol-4-yl)methyl)thio)-1-oxoisoindolin-2-yl)piperidine-2,6-dione;

3-(4-(((2-((cyclopentylamino)methyl)thiazol-4-yl)methyl)thio)-1-oxoisoindolin-2-yl)piperidine-2,6-dione;

3-(4-(((4-(morpholinomethyl)thiazol-2-yl)methyl)thio)-1-oxoisoindolin-2-yl)piperidine-2,6-dione;

3-(1-oxo-4-(((4-(piperidin-1-ylmethyl)thiazol-2-yl)methyl)thio)isoindolin-2-yl)piperidine-2,6-dione;

3-(4-(((4-(azepan-1-ylmethyl)thiazol-2-yl)methyl)thio)-1-oxoisoindolin-2-yl)piperidine-2,6-dione;

3-(4-(((4-((3,5-dimethylpiperidin-1-yl)methyl)thiazol-2-yl)methyl)thio)-1-oxoisoindolin-2-yl)piperidine-2,6-dione;

3-(4-(((4-((hexahydro-1H-isoindol-2 (3H)-yl)methyl)thiazol-2-yl)methyl)thio)-1-oxoisoindolin-2-yl)piperidine-2,6-dione;

3-(1-oxo-4-(((4-(thiomorpholinomethyl)thiazol-2-yl)methyl)thio)isoindolin-2-yl)piperidine-2,6-dione;

3-(4-(((4-((diethylamino)methyl)thiazol-2-yl)methyl)thio)-1-oxoisoindolin-2-yl)piperidine-2,6-dione;

3-(4-(((4-((cyclohexylamino)methyl)thiazol-2-yl)methyl)thio)-1-oxoisoindolin-2-yl)piperidine-2,6-dione;

3-(4-(((4-(((cyclohexylmethyl)amino)methyl)thiazol-2-yl)methyl)thio)-1-oxoisoindolin-2-yl)piperidine-2,6-dione;

N-(cyclohexylmethyl)-4-(((2-(2,6-dioxopiperidin-3-yl)-1-oxoisoindolin-4-yl)thio)methyl)thiazole-2-carboxamide;

3-(4-((7-((hexahydro-2,5-methanopentalen-3a (1H)-yl)amino)heptyl)thio)-1-oxoisoindolin-2-yl)piperidine-2,6-dione;

3-(4-((4-(((hexahydro-2,5-methanopentalen-3a (1H)-yl)amino)methyl)benzyl)thio)-1-oxoisoindolin-2-yl)piperidine-2,6-dione;

(E)-3-(4-((4-(2-bromovinyl)benzyl)thio)-1-oxoisoindolin-2-yl)piperidine-2,6-dione; and 3-(4-((7-(((1R,2S,4S)-bicyclo[2.2.1]heptan-2-yl)amino)heptyl)thio)-1-oxoisoindolin-2-yl)piperidine-2,6-dione.

39. A compound of Formula (I')

Formula (I')

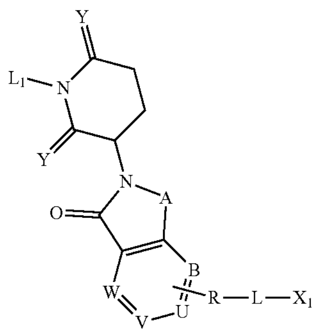

or a salt, a solvate, an isotopically enriched analog, a tautomer, a stereoisomer thereof, or a mixture of stereoisomers thereof, wherein A represents $CH_2$ or C(O);

B, U, V, and W represent CH;

Y represents O;

R represents S, S(O), or $S(O)_2$;

L represents a linear or branched $C_{1-40}$ alkylene group optionally substituted with one or more substituent(s) selected from halogen, cyano, $C_{1-3}$ alkyl, $C_{1-3}$ alkoxy, trifluoromethyl, a 3- to 12-membered heterocyclyl, or any combination thereof, wherein the linear or branched $C_{1-40}$ alkylene group is optionally interrupted one or more times by one or more groups selected from:

O, C(O), S, S(O), $S(O)_2$, $S(O)_2N(R_1)$, $N(R_2)$ $S(O)_2$, $C(O)N(R_1)$, $N(R_2)C(O)$, $N(R_3)$, or $N(R_4)C(O)N(R_5)$, wherein $R_1$, $R_2$, $R_3$, $R_4$, and $R_5$ each independently represent H or $C_{1-3}$ alkyl, cycloalkylene optionally substituted with substituent(s) selected from the group consisting of halogen, $C_{1-5}$ alkyl, methanesulfonyloxy, trifluoromethanesulfonyloxy, p-toluenesulfonyloxy, and oxo, arylene optionally substituted with substituent(s) selected from the group consisting of halogen, $C_{1-5}$ alkyl, methanesulfonyloxy, trifluoromethanesulfonyloxy, and p-toluenesulfonyloxy, heterocyclylene optionally substituted with substituent (s) selected from the group consisting of halogen, $C_{1-5}$ alkyl, methanesulfonyloxy, trifluoromethanesulfonyloxy, p-toluenesulfonyloxy, and oxo, heteroarylene optionally substituted with substituent(s) selected from the group consisting of halogen, $C_{1-5}$ alkyl, methanesulfonyloxy, trifluoromethanesulfonyloxy, and p-toluenesulfonyloxy, or any combination thereof; and $L_1$ represents H or $C_{1-3}$ alkyl; and wherein when $L_1$ represents H, $X_1$ represents $NHC(O)R_i$ or $SR_j$, wherein $R_i$ and $R_j$ each independently represent cycloalkyl optionally substituted with substituent(s) selected from $C_{1-6}$ alkyl, oxo, halogen, cyano, trifluoromethyl, amino, hydroxy, $C_{1-3}$ alkoxy, halogenated $C_{1-3}$ alkoxy, methanesulfonyloxy, trifluoromethanesulfonyloxy, p-toluenesulfonyloxy, or any combination thereof, or $X_1$ represents cycloalkyl optionally substituted with substituent(s) selected from $C_{1-6}$ alkyl, oxo, halogen, cyano, trifluoromethyl, amino, hydroxy, $C_{1-3}$ alkoxy, halogenated $C_{1-3}$ alkoxy, methanesulfonyloxy, trifluoromethanesulfonyloxy, p-toluenesulfonyloxy, or any combination thereof; or when $L_1$ represents $C_{1-3}$ alkyl, $X_1$ represents:

$NR_6R_7$, wherein $R_6$ represents H or $C_{1-6}$ alkyl, and $R_7$ represents cycloalkyl optionally substituted with substituent(s) selected from $C_{1-6}$ alkyl, oxo, halogen, cyano, trifluoromethyl, amino, hydroxy, $C_{1-3}$ alkoxy, $C_{1-3}$ halogenated alkoxy, methanesulfonyloxy, trifluoromethanesulfonyloxy, p-toluenesulfonyloxy, or any combination thereof; or heterocyclyl, optionally substituted with substituent(s) selected from $C_{1-6}$ alkyl, oxo, halogen, cyano, trifluoromethyl, amino, hydroxy, $C_{1-3}$ alkoxy, halogenated $C_{1-3}$ alkoxy, methanesulfonyloxy, trifluoromethanesulfonyloxy, p-toluenesulfonyloxy, or any combination thereof.

40. The compound of Formula (I') or a salt, a solvate, an isotopically enriched analog, a tautomer, a stereoisomer thereof, or a mixture of stereoisomers thereof of claim 39, wherein L represents a linear or branched $C_{1-40}$ alkylene group optionally substituted with one or more substituents selected from the group consisting of halogen, cyano, $C_{1-3}$ alkyl, $C_{1-3}$ alkoxy, trifluoromethyl, a 3- to 12-membered heterocyclyl, and any combination thereof, wherein the linear or branched $C_{1-40}$ alkylene group is optionally interrupted one or more times by one or more groups selected from:

O; C(O); S; S(O); $S(O)_2$; $S(O)_2N(R_1)$; $N(R_2)$ $S(O)_2$; $C(O)N(R_1)$; $N(R_2)C(O)$; $N(R_3)$; $N(R_4)C(O)N(R_5)$; wherein $R_1$, $R_2$, $R_3$, $R_4$, and $R_5$ each independently represent H or $C_{1-3}$ alkyl;

$C_5$-$C_{14}$ arylene group optionally substituted with substituent(s) selected from halogen, methanesulfonyloxy, trifluoromethanesulfonyloxy, p-toluenesulfonyloxy, or $C_{1-5}$ alkyl, 3- to 12-membered heterocyclylene group optionally substituted with substituent(s) selected from halogen, methanesulfonyloxy, trifluoromethanesulfonyloxy, p-toluenesulfonyloxy, oxo, or $C_{1-5}$ alkyl;

5- to 10-membered heteroarylene group optionally substituted with substituent(s) selected from halogen, methanesulfonyloxy, trifluoromethanesulfonyloxy, p-toluenesulfonyloxy, or $C_{1-5}$ alkyl;

$C_3$-$C_{12}$ cycloalkylene group optionally substituted with substituent(s) selected from halogen, methanesulfonyloxy, trifluoromethanesulfonyloxy, p-toluenesulfonyloxy, oxo, or $C_{1-5}$ alkyl, or any combination thereof;

wherein $R_1$, $R_2$, $R_3$, $R_4$, and $R_5$ each independently represent H or $C_{1-3}$ alkyl.

41. The compound of Formula (I') or a salt, a solvate, an isotopically enriched analog, a tautomer, a stereoisomer thereof, or a mixture of stereoisomers thereof of claim 39, wherein L represents the following groups optionally substituted with one or more substituent(s) selected from halogen, cyano, $C_{1-3}$ alkyl, $C_{1-3}$ alkoxy, trifluoromethyl, a 3- to 12-membered heterocyclyl, or any combination thereof:

linear or branched $C_1$-$C_{40}$ alkylene; *—$(CH_2)_{n1}$—$N(R_{22})$ $S(O)_2$—$(CH_2)_{n2}$—; *—$(CH_2)_{n1}$—$S(O)_2N(R_{23})$—$(CH_2)_{n2}$—; or *—$(CH_2)_{n1}$-phenylene-$(CH_2)_{n2}$—;

wherein * indicates the point of attachment to R;

$R_{22}$ and $R_{23}$ are each independently selected from H and $C_{1-3}$ alkyl;

n1 and n2 each independently represent an integer of 1, 2, 3, 4, 5, 6, 7, 8, 9, 10, 11, 12, 13, 14, 15, 16, 17, 18, 19, or 20.

42. The compound of Formula (I') or a salt, a solvate, an isotopically enriched analog, a tautomer, a stereoisomer thereof, or a mixture of stereoisomers thereof of claim 39, wherein L represents the following groups optionally substituted with one or more substituent(s) selected from halogen, cyano, $C_{1-3}$ alkyl, $C_{1-3}$ alkoxy, trifluoromethyl, a 3- to 12-membered heterocyclyl, or any combination thereof:

$-CH_2-$; $-(CH_2)_2-$; $-(CH_2)_3-$; $-(CH_2)_4-$; $-(CH_2)_5-$; $-(CH_2)_6-$; $-(CH_2)_7-$; $-(CH_2)_8-$; $-(CH_2)_9-$; $-(CH_2)_{10}-$; $-(CH_2)_{11}-$; $-(CH_2)_{12}-$; $-(CH_2)_{13}-$; $-(CH_2)_{14}-$; $-(CH_2)_{15}-$; $-(CH_2)_{16}-$; $-(CH_2)_{17}-$; $-(CH_2)_{18}-$; $-(CH_2)_{19}-$; $-(CH_2)_{20}-$; $*-(CH_2)_2-NHS(O)_2-CH_2-$; $*-(CH_2)_2-NHS(O)_2-(CH_2)_2-$; $*-(CH_2)_2-NHS(O)_2-(CH_2)_3-$; $*-(CH_2)_2-NHS(O)_2-(CH_2)_4-$; $*-(CH_2)_2-NHS(O)_2-(CH_2)_5-$; $*-(CH_2)_2-NHS(O)_2-(CH_2)_6-$; $*-(CH_2)_2-NHS(O)_2-(CH_2)_7-$; $*-(CH_2)_2-NHS(O)_2-(CH_2)_8-$; $*-(CH_2)_2-NHS(O)_2-(CH_2)_9-$; $*-(CH_2)_2-NHS(O)_2-(CH_2)_{10}-$; $*-(CH_2)_2-NHS(O)_2-(CH_2)_{11}-$; $*-(CH_2)_2-NHS(O)_2-(CH_2)_{12}-$; $*-(CH_2)_2-NHS(O)_2-(CH_2)_{13}-$; $*-(CH_2)_2-NHS(O)_2-(CH_2)_{14}-$; $*-(CH_2)_2-NHS(O)_2-(CH_2)_{15}-$; $*-(CH_2)_3-NHS(O)_2-CH_2-$; $*-(CH_2)_3-NHS(O)_2-(CH_2)_2-$; $*-(CH_2)_3-NHS(O)_2-(CH_2)_3-$; $*-(CH_2)_3-NHS(O)_2-(CH_2)_4-$; $*-(CH_2)_3-NHS(O)_2-(CH_2)_5-$; $*-(CH_2)_3-NHS(O)_2-(CH_2)_6-$; $*-(CH_2)_3-NHS(O)_2-(CH_2)_7-$; $*-(CH_2)_3-NHS(O)_2-(CH_2)_8-$; $*-(CH_2)_3-NHS(O)_2-(CH_2)_9-$; $*-(CH_2)_3-NHS(O)_2-(CH_2)_{10}-$; $*-(CH_2)_3-NHS(O)_2-(CH_2)_{11}-$; $*-(CH_2)_3-NHS(O)_2-(CH_2)_{12}-$; $*-(CH_2)_3-NHS(O)_2-(CH_2)_{13}-$; $*-(CH_2)_3-NHS(O)_2-(CH_2)_{14}-$; $*-(CH_2)_3-NHS(O)_2-(CH_2)_{15}-$; $*-(CH_2)_4NHS(O)_2(CH_2)_1-$; $*-(CH_2)_4NHS(O)_2(CH_2)_2-$; $*-(CH_2)_4NHS(O)_2(CH_2)_3-$; $*-(CH_2)_4NHS(O)_2(CH_2)_4-$; $*-(CH_2)_4NHS(O)_2(CH_2)_5-$; $*-(CH_2)_4NHS(O)_2(CH_2)_6-$; $*-(CH_2)_4NHS(O)_2(CH_2)_7-$; $*-(CH_2)_4NHS(O)_2(CH_2)_8-$; $*-(CH_2)_4NHS(O)_2(CH_2)_9-$; $*-(CH_2)_4NHS(O)_2(CH_2)_{10}-$; $*-(CH_2)_5NHS(O)_2(CH_2)_1-$; $*-(CH_2)_6NHS(O)_2(CH_2)_1-$; $*-(CH_2)_7NHS(O)_2(CH_2)_1-$; $*-(CH_2)_8NHS(O)_2(CH_2)_1-$; $*-(CH_2)_8NHS(O)_2(CH_2)_2-$; $*-(CH_2)_9NHS(O)_2(CH_2)_1-$; $*-(CH_2)_{10}NHS(O)_2(CH_2)_1-$; $*-(CH_2)_5NHS(O)_2(CH_2)_2-$; $*-(CH_2)_6NHS(O)_2(CH_2)_2-$; $*-(CH_2)_7NHS(O)_2(CH_2)_2-$; $*-(CH_2)_8NHS(O)_2(CH_2)_3-$; * (CH$_2$) NHS(O)$_2$(CH$_2$)$_2$—; $*-(CH_2)_{10}NHS(O)_2(CH_2)_2-$; $*-CH_2\text{-phenylene-}CH_2-$; $*-(CH_2)_1\text{-phenylene-}(CH_2)_2-$; $*-(CH_2)_1\text{-phenylene-}(CH_2)_3-$; $*-(CH_2)_1\text{-phenylene-}(CH_2)_4-$; $*-(CH_2)_2\text{-phenylene-}(CH_2)_1-$; $*-(CH_2)_2\text{-phenylene-}(CH_2)_2-$; $*-(CH_2)_2\text{-phenylene-}(CH_2)_3-$; $*-(CH_2)_2\text{-phenylene-}(CH_2)_4-$; $*-(CH_2)_2\text{-phenylene-}(CH_2)_5-$; $*-(CH_2)_3\text{-phenylene-}(CH_2)_1-$; $*-(CH_2)_3\text{-phenylene-}CH_2-$; $*-(CH_2)_3\text{-phenylene-}(CH_2)_2-$; $*-(CH_2)_3\text{-phenylene-}(CH_2)_3-$; $*-(CH_2)_4$ -phenylene-$CH_2-$; $*-(CH_2)_4\text{-phenylene-}(CH_2)_2-$; $*-(CH_2)_4\text{-phenylene-}(CH_2)_3-$; $*-(CH_2)_5\text{-phenylene-}(CH_2)_3-$; $*-(CH_2)_6\text{-phenylene-}(CH_2)_3-$; $*-(CH_2)_7\text{-phenylene-}(CH_2)_3-$; $*-(CH_2)_8\text{-phenylene-}CH_2-$; $*-(CH_2)_8\text{-phenylene-}(CH_2)_2-$; $*-(CH_2)_8\text{-phenylene-}(CH_2)_3-$; $*-(CH_2)_8\text{-phenylene-}(CH_2)_4-$; $*-(CH_2)_8\text{-phenylene-}(CH_2)_5-$; $*-(CH_2)_8\text{-phenylene-}(CH_2)_6-$; $*-(CH_2)_8\text{-phenylene-}(CH_2)_7-$; $*-(CH_2)_8\text{-phenylene-}(CH_2)_8-$; $*-CH_2\text{-phenylene-}(CH_2)_8-$; $*-(CH_2)_2\text{-phenylene-}(CH_2)_8-$; $*-(CH_2)_3\text{-phenylene-}(CH_2)_8-$; $*-(CH_2)_4\text{-phenylene-}(CH_2)_8-$; $*-(CH_2)_5\text{-phenylene-}(CH_2)_8-$; $*-(CH_2)_6\text{-phenylene-}(CH_2)_8-$; or $*-(CH_2)_7\text{-phenylene-}(CH_2)_8-$;

wherein * indicates the point of attachment to R.

43. The compound of Formula (I') or a salt, a solvate, an isotopically enriched analog, a tautomer, a stereoisomer thereof, or a mixture of stereoisomers thereof of claim 39, wherein L represents the following groups optionally substituted with one or more substituent(s) selected from halogen, cyano, $C_{1-3}$ alkyl, $C_{1-3}$ alkoxy, trifluoromethyl, a 3- to 12-membered heterocyclyl, or any combination thereof:

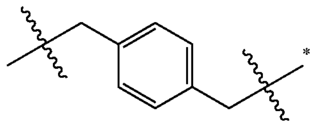

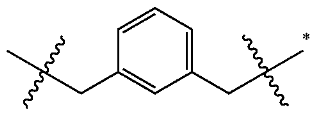

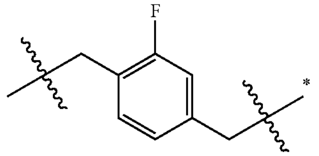

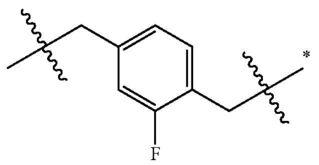

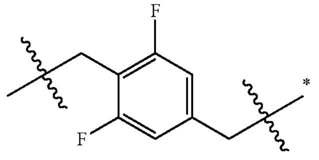

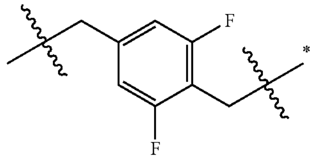

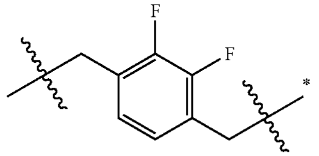

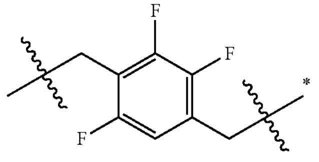

-continued

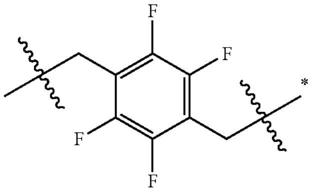

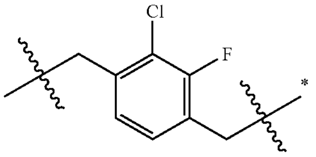

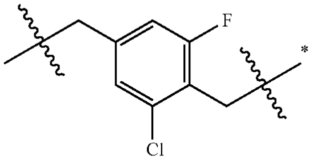

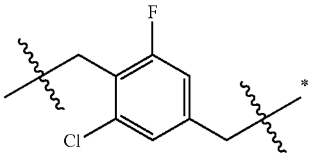

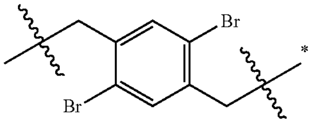

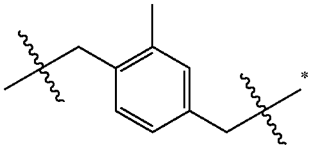

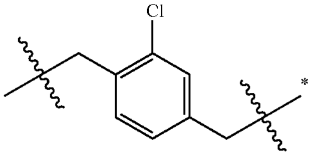

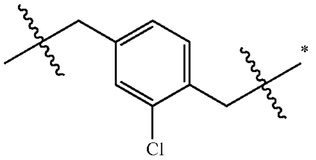

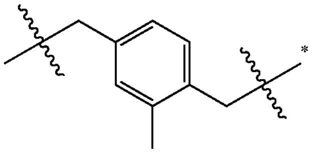

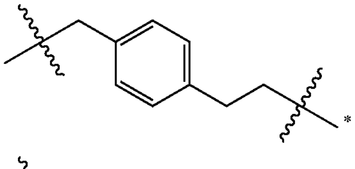

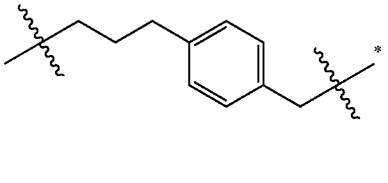

-continued

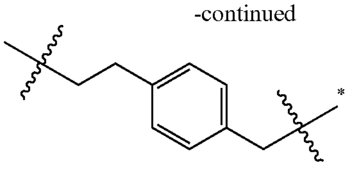

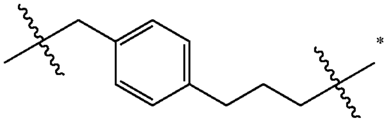

or

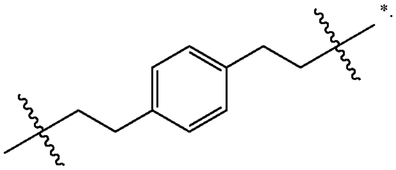

44. The compound of Formula (I') or a salt, a solvate, an isotopically enriched analog, a tautomer, a stereoisomer thereof, or a mixture of stereoisomers thereof of claim 39, wherein $L_1$ represents H, and $X_1$ represents the following optionally substituted groups: adamantanyl-C(O)NH—, adamantanyl-S—, or norcamphanyl, wherein the optional substituent(s) of the optionally substituted group is selected from $C_{1-6}$ alkyl, oxo, halogen, cyano, trifluoromethyl, amino, hydroxy, $C_{1-3}$ alkoxy, halogenated $C_{1-3}$ alkoxy, methanesulfonyloxy, trifluoromethanesulfonyloxy, p-toluenesulfonyloxy, or any combination thereof.

45. The compound of Formula (I') or a salt, a solvate, an isotopically enriched analog, a tautomer, a stereoisomer thereof, or a mixture of stereoisomers thereof of claim 44, wherein $X_1$ represents:

adamantan-1-yl-C(O)NH—, 3-hydroxyadamantanyl-C(O)NH—, 3-hydroxyadamantan-1-yl-C(O)NH—, 3-chloro-adamantan-1-yl-C(O)NH—, 4-chloroadamantan-1-yl-C(O)NH—, 2-chloroadamantan-1-yl-C(O)NH—, adamantan-2-yl-C(O)NH—, adamantan-1-yl-S—, 3-hydroxyadamantanyl-S—, 3-hydroxyadamantan-1-yl-S—, 3-chloroadamantan-1-yl-S—, 4-chloroadamantan-1-yl-S—, 2-chloroadamantan-1-yl-S—, adamantan-2-yl-S—, bicyclo[2.2.1]heptan-2-yl, 1,7,7-trimethylbicyclo[2.2.1]heptan-2-yl, 7,7-dimethylbicyclo[2.2.1]heptan-1-yl, or 7,7-dimethyl-2-oxobicyclo[2.2.1]heptan-1-yl.

46. The compound of Formula (I') or a salt, a solvate, an isotopically enriched analog, a tautomer, a stereoisomer thereof, or a mixture of stereoisomers thereof of claim 39, wherein when $L_1$ represents $C_{1-3}$ alkyl, $X_1$ represents $NR_6R_7$, wherein $R_6$ represents H or $C_{1-3}$ alkyl, and $R_7$ represents: adamantanyl, cyclohexyl, spiro-cycloalkyl, or norcamphanyl;

wherein the adamantanyl, cyclohexyl, spiro-cycloalkyl and norcamphanyl are optionally substituted with a substituent(s) selected from $C_{1-6}$ alkyl, oxo, halogen, cyano, trifluoromethyl, amino, hydroxy, $C_{1-3}$ alkoxy, halogenated $C_{1-3}$ alkoxy, methanesulfonyloxy, trifluoromethanesulfonyloxy, p-toluenesulfonyloxy, or any combination thereof.

47. The compound of Formula (I') or a salt, a solvate, an isotopically enriched analog, a tautomer, a stereoisomer thereof, or a mixture of stereoisomers thereof of claim 46, wherein $R_7$ represents:

adamantan-1-yl, 3-hydroxyadamantanyl, 3-hydroxyadamantan-1-yl, 3-chloroadamantan-1-yl, 4-chloroadamantan-1-yl, 2-chloroadamantan-1-yl, adamantan-2-yl, bicyclo[2.2.1]heptan-2-yl, 1,7,7-trimethylbicyclo[2.2.1]heptan-2-yl, 7,7-dimethylbicyclo[2.2.1]heptan-1-yl, or 7,7-dimethyl-2-oxobicyclo[2.2.1]heptan-1-yl.

48. The compound of Formula (I') or a salt, a solvate, an isotopically enriched analog, a tautomer, a stereoisomer thereof, or a mixture of stereoisomers thereof of claim 39, wherein when $L_1$ represents $C_{1-3}$ alkyl, $X_1$ represents an optionally substituted piperidinyl, wherein the optional substituent(s) of said optionally substituted piperidinyl is selected from: $C_{1-6}$ alkyl, halogen, oxo, cyano, amino, hydroxy, $C_{1-3}$ alkoxy, halogenated $C_{1-3}$ alkoxy, halogenated $C_{1-3}$ alkyl, di($C_{1-6}$ alkyl) phosphono, $C_{1-6}$ alkylsulfonyl, or any combination thereof.

49. The compound of F Formula (I') or a salt, a solvate, an isotopically enriched analog, a tautomer, a stereoisomer thereof, or a mixture of stereoisomers thereof of claim 39, wherein the compound is selected from:

N-(6-((2-(2,6-dioxopiperidin-3-yl)-1-oxoisoindolin-4-yl) thio)hexyl) adamantane-1-carboxamide;

3-chloro-N-(6-((2-(2,6-dioxopiperidin-3-yl)-1-oxoisoindolin-4-yl)thio)hexyl) adamantane-1-carboxamide;

3-(4-((7-(adamantan-1-ylthio)heptyl)thio)-1-oxoisoindolin-2-yl)piperidine-2,6-dione;

1-((1R,4S)-7,7-dimethyl-2-oxobicyclo[2.2.1]heptan-1-yl)-N-(6-((2-(2,6-dioxopiperidin-3-yl)-1-oxoisoindolin-4-yl)thio)hexyl)methanesulfonamide;

1-((1R,4S)-7,7-dimethyl-2-oxobicyclo[2.2.1]heptan-1-yl)-N-(7-((2-(2,6-dioxopiperidin-3-yl)-1-oxoisoindolin-4-yl)thio)heptyl)methanesulfonamide;

3-(4-((7-(adamantan-1-ylamino)heptyl)thio)-1-oxoisoindolin-2-yl)-1-methylpiperidine-2,6-dione;

1-methyl-3-(1-oxo-4-((7-(((1R,2S,4R)-1,7,7-trimethylbicyclo[2.2.1]heptan-2-yl)amino)heptyl)thio)isoindolin-2-yl)piperidine-2,6-dione;

1-methyl-3-(1-oxo-4-((4-((((1R,2S,4R)-1,7,7-trimethylbicyclo[2.2.1]heptan-2-yl)amino)methyl)benzyl)thio) isoindolin-2-yl)piperidine-2,6-dione;

3-(4-((7-(cyclohexylamino)heptyl)thio)-1-oxoisoindolin-2-yl)-1-methylpiperidine-2,6-dione;

1-methyl-3-(1-oxo-4-((4-(piperidin-1-ylmethyl)benzyl) thio)isoindolin-2-yl)piperidine-2,6-dione;

3-(4-((4-(((adamantan-1-yl)amino)methyl)benzyl)thio)-1-oxoisoindolin-2-yl)-1-methylpiperidine-2,6-dione; or 1-methyl-3-(1-oxo-4-((7-(spiro[3.3]heptan-2-ylamino) heptyl)thio)isoindolin-2-yl)piperidine-2,6-dione.

50. A pharmaceutical composition comprising, as an active ingredient, the compound of Formula (I) of claim 1 or a pharmaceutically acceptable salt thereof, and at least one pharmaceutically acceptable carrier.

51. The pharmaceutical composition of claim 50, further comprising at least one additional therapeutic agent.

52. A pharmaceutical composition comprising, as an active ingredient, the compound of Formula (I') of claim 39 or a pharmaceutically acceptable salt thereof, and at least one pharmaceutically acceptable carrier.

53. The pharmaceutical composition of claim 52, further comprising at least one additional therapeutic agent.

* * * * *